(12) United States Patent
Seitzberg et al.

(10) Patent No.: US 10,752,640 B2
(45) Date of Patent: Aug. 25, 2020

(54) COMPOUNDS ACTIVE TOWARDS BROMODOMAINS

(71) Applicant: NUEVOLUTION A/S, Copenhagen (DK)

(72) Inventors: Jimmi Gerner Seitzberg, Malmö (SE); Tine Titilola Akinlemnu Kronborg, Værløse (DK); Visnja Poljak, Copenhagen (DK); Gitte Friberg, Albertslund (DK); Lene Teuber, Værløse (DK)

(73) Assignee: NUEVOLUTION A/S, Copenhagen (DK)

( * ) Notice: Subject to any disclaimer, the term of this patent is extended or adjusted under 35 U.S.C. 154(b) by 0 days.

(21) Appl. No.: 15/501,058

(22) PCT Filed: Jul. 29, 2015

(86) PCT No.: PCT/EP2015/067400
§ 371 (c)(1),
(2) Date: Feb. 1, 2017

(87) PCT Pub. No.: WO2016/016316
PCT Pub. Date: Feb. 4, 2016

(65) Prior Publication Data
US 2017/0349607 A1    Dec. 7, 2017

(30) Foreign Application Priority Data
Aug. 1, 2014  (SE) ........................... 1450919

(51) Int. Cl.
| | | |
|---|---|---|
| C07D 498/08 | (2006.01) | |
| C07D 401/14 | (2006.01) | |
| C07D 405/14 | (2006.01) | |
| C07D 413/14 | (2006.01) | |
| C07D 401/12 | (2006.01) | |
| C07D 471/04 | (2006.01) | |
| C07D 487/04 | (2006.01) | |
| C07D 498/04 | (2006.01) | |
| C07D 215/22 | (2006.01) | |
| C07D 491/10 | (2006.01) | |
| C07D 215/227 | (2006.01) | |
| C07D 405/12 | (2006.01) | |
| C07D 413/02 | (2006.01) | |
| C07D 491/107 | (2006.01) | |

(52) U.S. Cl.
CPC ......... *C07D 498/08* (2013.01); *C07D 215/22* (2013.01); *C07D 215/227* (2013.01); *C07D 401/12* (2013.01); *C07D 401/14* (2013.01); *C07D 405/12* (2013.01); *C07D 405/14* (2013.01); *C07D 413/02* (2013.01); *C07D 413/14* (2013.01); *C07D 471/04* (2013.01); *C07D 487/04* (2013.01); *C07D 491/10* (2013.01); *C07D 491/107* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 4,327,173 A | 4/1982 | Aoki et al. | |
| 4,810,801 A | 3/1989 | Mertens et al. | |
| 4,879,206 A | 11/1989 | Asami | |
| 4,962,014 A | 10/1990 | Ishikawa et al. | |
| 5,756,502 A | 5/1998 | Padia | |
| 5,780,480 A | 7/1998 | Wai et al. | |
| 2004/0092535 A1 | 5/2004 | Barsanti et al. | |
| 2004/0142950 A1 | 7/2004 | Bunker et al. | |
| 2004/0157866 A1* | 8/2004 | Takasugi | C07C 271/24 514/266.2 |
| 2005/0261307 A1 | 11/2005 | Cai et al. | |
| 2006/0014956 A1 | 1/2006 | Deng et al. | |

(Continued)

FOREIGN PATENT DOCUMENTS

| | | |
|---|---|---|
| CN | 102887895 A | 1/2013 |
| DE | 3626465 A1 | 2/1987 |

(Continued)

OTHER PUBLICATIONS

Nishi et al., CAS SciFinder abstract of WO 9703070 A1 (Jan. 30, 1997) (CAPLUS Acc. No. 1997:204148).*

(Continued)

*Primary Examiner* — Brian J Davis
(74) *Attorney, Agent, or Firm* — Merchant & Gould P.C.

(57) ABSTRACT

Disclosed are compounds towards bromodomains, pharmaceutical compositions containing the compounds and use of the compounds in therapy.

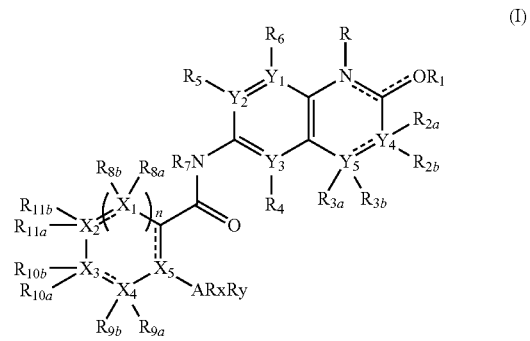

(I)

38 Claims, No Drawings

(56) References Cited

U.S. PATENT DOCUMENTS

| | | |
|---|---|---|
| 2008/0293739 A1 | 11/2008 | Trede |
| 2010/0068204 A1 | 3/2010 | Tsou et al. |
| 2010/0160373 A1 | 6/2010 | Berger et al. |
| 2010/0261687 A1 | 10/2010 | Grundl et al. |
| 2010/0273781 A1 | 10/2010 | Ginn et al. |
| 2011/0281865 A1 | 11/2011 | Muthuppalaniappan et al. |
| 2014/0039006 A1 | 2/2014 | Amans et al. |

FOREIGN PATENT DOCUMENTS

| | | |
|---|---|---|
| DE | 3803775 A1 | 8/1989 |
| DE | 3925584 A1 | 2/1991 |
| DE | 4027592 A1 | 3/1992 |
| DE | 19839499 A1 | 3/2000 |
| EA | 201101398 A1 | 4/2012 |
| EA | 201391285 A1 | 4/2014 |
| EP | 244697 A2 | 11/1987 |
| EP | 254280 A2 | 1/1988 |
| EP | 386669 A2 | 9/1990 |
| EP | 392481 A2 | 10/1991 |
| EP | 598216 A1 | 5/1994 |
| EP | 786690 A2 | 7/1997 |
| EP | 1388342 A1 | 2/2004 |
| EP | 1655295 A1 | 5/2006 |
| JP | 48-78229 A | 10/1973 |
| JP | 56-104333 A | 8/1981 |
| JP | 62-38463 A | 2/1987 |
| JP | 62-92939 A | 4/1987 |
| JP | 62-115157 A | 5/1987 |
| JP | 62-129853 A | 6/1987 |
| JP | 62-153953 A | 7/1987 |
| JP | 62-173466 A | 7/1987 |
| JP | 62-222251 A | 9/1987 |
| JP | 02-264946 A | 10/1990 |
| JP | 04-315148 A | 11/1992 |
| JP | 2002-296731 A | 10/2002 |
| JP | 2002-341484 A | 11/2002 |
| JP | 2003-321472 A | 11/2003 |
| JP | 2012-232930 A | 11/2012 |
| WO | 93/18769 A2 | 9/1993 |
| WO | 95/32710 A1 | 12/1995 |
| WO | 97/03070 A1 | 1/1997 |
| WO | WO 9703070 A1 * | 1/1997 ........... C07D 403/12 |
| WO | 97/31910 A1 | 9/1997 |
| WO | 98/28980 A1 | 7/1998 |
| WO | 99/17759 A2 | 4/1999 |
| WO | 99/31086 A1 | 6/1999 |
| WO | 99/32436 A1 | 7/1999 |
| WO | 2001/057021 A2 | 8/2001 |
| WO | 02/091830 A1 | 11/2002 |
| WO | 2002/090347 A1 | 11/2002 |
| WO | 2004/018419 A2 | 3/2004 |
| WO | 2004/026794 A2 | 4/2004 |
| WO | 2004/052370 A2 | 6/2004 |
| WO | 2004/082687 A1 | 9/2004 |
| WO | 2004/110350 A2 | 12/2004 |
| WO | 2004/113330 A1 | 12/2004 |
| WO | 2005047244 A2 | 5/2005 |
| WO | 2005/087742 A1 | 9/2005 |
| WO | 2005/094805 A1 | 10/2005 |
| WO | 2005/121137 A1 | 12/2005 |
| WO | 2006/010591 A2 | 2/2006 |
| WO | 2006/051290 A2 | 5/2006 |
| WO | 2006/105222 A2 | 10/2006 |
| WO | 2006/117552 A1 | 11/2006 |
| WO | 2006/117570 A1 | 11/2006 |
| WO | 2006/130437 A2 | 12/2006 |
| WO | 2007/035935 A1 | 3/2007 |
| WO | 2007/093402 A1 | 8/2007 |
| WO | 2007/109251 A2 | 9/2007 |
| WO | 2007/130468 A2 | 11/2007 |
| WO | 2008/029152 A2 | 3/2008 |
| WO | 2008/040778 A2 | 4/2008 |
| WO | 2008/048375 A1 | 4/2008 |
| WO | 2008/097428 A2 | 8/2008 |
| WO | 2008/103277 A2 | 8/2008 |
| WO | WO 2008/109180 A2 * | 9/2008 |
| WO | 2008/130021 A2 | 10/2008 |
| WO | 2009/000558 A1 | 12/2008 |
| WO | 2009/020677 A2 | 2/2009 |
| WO | 2009/039127 A1 | 3/2009 |
| WO | 2009/152356 A2 | 12/2009 |
| WO | 2010/045374 A1 | 4/2010 |
| WO | 2010/101949 A1 | 9/2010 |
| WO | 2010/126851 A1 | 11/2010 |
| WO | 2011/017561 A1 | 2/2011 |
| WO | 2011/137089 A1 | 11/2011 |
| WO | 2011/156632 A2 | 12/2011 |
| WO | 2012/020820 A1 | 2/2012 |
| WO | 2012/080284 A2 | 6/2012 |
| WO | 2012/111995 A1 | 8/2012 |
| WO | 2012/125668 A1 | 9/2012 |
| WO | 2012/143415 A1 | 10/2012 |
| WO | 2012/166951 A1 | 12/2012 |
| WO | 2013/019682 A1 | 2/2013 |
| WO | 2013/027168 A1 | 2/2013 |
| WO | 2013/055984 A1 | 4/2013 |
| WO | 2013/063462 A2 | 5/2013 |
| WO | 2013/161308 A1 | 10/2013 |
| WO | 2014/034719 A1 | 3/2014 |
| WO | 2014/095774 A1 | 6/2014 |
| WO | 2014/095775 A1 | 6/2014 |

OTHER PUBLICATIONS

Takasugi et al., CAS SciFinder abstract (Database CAPLUS, Acc. No. 2002:868923) of US 2004/0157866 A1 (Aug. 121, 2004).*
Office Action for Swedish Patent Application No. 1450919-4, dated Feb. 17, 2015.
Office Action for Swedish Patent Application No. 1450920-2, dated Feb. 17, 2015.
Office Action for Swedish Patent Application No. 1451406-1, dated May 29, 2015.
International Search Report for PCT/EP2015/067400, dated Oct. 22, 2015.
Belkina et al., "BET domain co-regulators in obesity, inflammation and cancer", Nature Reviews, Cancer, vol. 12: 465-477 (2012).
Felisbino et al., "Epigenetics in Cardiac Fibrosis, Emphasis on Inflammation and Fibroblast Activation", JACC: Basic to Translational Science, vol. 3(5): 704-715 (2018).
Ghosh et al., "Suppression of TH 17-mediated pathology through BET bromodomain inhibition", Drug Discovery Today: Technologies, vol. 19: 39-44 (2016).
Hajmirza et al., "BET Family Protein BRD4: An Emerging Actor in NFKB Signaling in Inflammation and Center", Biomedicines, 6, 16: 1-9 (2018).
Klein, "Bromodomain protein inhibition: a novel therapeutic strategy in rheumatic diseases", RMD Open, Animal models, 4:e000744: 1-10 (2018).
Kumar et al., "BET inhibitors block pancreatic stellate cell collagen I production and attenuate fibrosis in vivo", JCI Insight, 2(3):e88032: 1-15 (2017).
Shu et al., "BET Bromodomain Proteins as Cancer Therapeutic Targets", Cold Spring Harbor Symposia on Quantitative Biology, vol. LXXXI: 123-129 (2016).
Tang et al., "BET Bromodomain Proteins Mediate Downstream Signaling Events following Growth Factor Stimulation in Human Lung Fibroblasts and Are Involved in Bleomycin-Induced Pulmonary Fibrosis", Molecular Pharmacology, 83: 283-293 (2013).
Xu et al., "Targeting Cancer Cells with BET Bromodomain Inhibitors", Cold Spring Harbor Perspective in Medicine, 7: a026674: 1-18 (2017).
Communication Pursuant to Article 94(3) for European Patent Application No. 15744908.3, dated Mar. 5, 2020.

* cited by examiner

COMPOUNDS ACTIVE TOWARDS BROMODOMAINS

CROSS-REFERENCE TO RELATED APPLICATIONS

This application claims priority to the PCT Application PCT/EP2015/067400 filed on 29 Jul. 2015 which further claims the priority of Swedish Patent No. SE 1450919-4 filed on 1 Aug. 2014 in the Swedish Patent and Trademark Office. The specifications of the above referenced patent applications are incorporated herein by reference in their entireties.

FIELD

The present application relates to compounds active towards bromodomains, pharmaceutical compositions comprising the compounds, and methods of treating diseases or disorders using the compounds.

BACKGROUND

Bromodomains are protein domains of biological and pharmaceutical interest, for example as components of transcription factor complexes and determinants of epigenetic memory. The human genome codes for 61 bromodomains that are present in 46 human proteins, and which may be categorized into 8 distinct bromodomain families based on primary sequence conservation (Nat Rev Drug Discov. 2014 May; 13(5):337-56). One such family, the BET family, or bromodomain and extraterminal domain family, includes BRD2, BRD3, BRD4 and BRDT all of which are found in humans. Bromodomains are capable of recognizing acetylated histones. The BET family has a common domain architecture featuring two amino-terminal bromodomains that exhibit high levels of sequence conservation, and a more divergent carboxy-terminal recruitment domain (Filippakopoulos, P. et al., *Nature* 2010, 468, 1067-1073). BRD2 and BRD3 are reported to associate with histones along actively transcribed genes and may be involved in facilitating transcriptional elongation (Leroy et al, *Mol. Cell.* 2008, 30, 51-60). It has also been reported that BRD4 or BRD3 may fuse with NUT (nuclear protein in testis) forming novel fusion oncogenes in a highly malignant form of epithelial neoplasia called NUT-midline carcinoma. It has been suggested that BRD-NUT fusion proteins contribute to carcinogenesis (*Oncogene* 2008, 27, 2237-2242). BRDT is uniquely expressed in the testes and ovary.

All BET family members have been reported to have some involvement in aspects of the cell cycle. In addition, some viruses make use of these proteins to tether their genomes to the host cell chromatin, as part of the process of viral replication (You et al. *Cell* 2004 117, 349-60). BRD4 appears to be involved in the recruitment of the pTEF-P complex to inducible genes resulting in phosphorylation of RNA polymerase and increased transcriptional output (Hargreaves et al, *Cell* 2009 138, 129-145).

In recent years, proteins containing bromodomains have attracted much interest and bromodomain binding agents have been reported in WO2009084693, WO2012075383, WO2011054553, WO2011054841, WO2011054844, WO2011054845, WO2011054846, WO2011054848, WO2011143669, WO2011161031, WO2013027168, WO2014095774, and WO2014095775.

Thus proteins containing bromodomains have been reported to be involved in transcription, DNA repair, replication, and chromosome condensation. Filippakopoulos, P. et al. recently published a review summarizing many findings related to proteins containing bromodomains (Filippakopoulos, P. et al., *Nature Reviews Drug Discovery*, 2014, doi:10.1038/nrd4286).

Despite the progress in the field of molecules that modulate the function of bromodomains there is a need for further bromodomain inhibitors.

SUMMARY

An aspect disclosed herein relates to a compound of Formula (I)

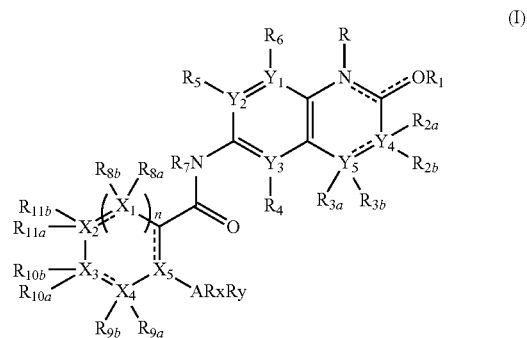

or pharmaceutically acceptable salts, hydrates, solvates, polymorphs, stereoisomers, and tautomers thereof, wherein $Y_1$, $Y_2$, $Y_3$, and $Y_4$ are independently of each other selected from the group consisting of N or C;

$Y_5$ is selected from C or O;

$X_1$, $X_2$, $X_3$, $X_4$, and $X_5$ are independently of each other selected from the group consisting of N, O, S or C;

n is an integer selected from 0 or 1;

R is absent or selected from the group of hydrogen, unsubstituted or substituted $C_{1-4}$ alkyl;

$R_1$ is absent, or selected from the group consisting of hydrogen, unsubstituted or substituted $C_{1-4}$ alkyl;

$R_{2a}$, $R_{2b}$, $R_{3a}$, and $R_{3b}$ are independently of each other either absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$OR_{31}$, or $R_{2a}$ and $R_{2b}$ taken together with $Y_4$, and/or $R_{3a}$ and $R_{3b}$ taken together with $Y_5$ form a ring selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl;

$R_4$, $R_5$, $R_6$, $R_{8a}$, $R_{8b}$, $R_{9a}$, $R_{9b}$, $R_{10a}$, $R_{10b}$, $R_{11a}$, $R_{11b}$ and $R_{32}$ are independently of each other absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, —$NO_2$, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$NR_{12}R_{13}$, —$NR_{14}C(=O)$ R$_{15}$, —NR$_{16}$C(=O)NR$_{17}$R$_{18}$, —NR$_{28}$C(=O)OR$_{19}$, —C(=O)R$_{20}$, —C(=O)OR$_{21}$, —OC(=O)R$_{21}$, —C(=O)NR$_{22}$R$_{23}$, —S(=O)R$_{24}$, —SO$_2$R$_{25}$, —SO$_2$NR$_{26}$R$_{27}$, and —OR$_{31}$; or R$_5$, R$_6$, R$_{8a}$, R$_{8b}$, R$_{9a}$, R$_{9b}$, R$_{10a}$, R$_{10b}$, R$_{11a}$, R$_{11b}$ are taken together with an adjacent R$_5$, R$_6$, R$_{8a}$, R$_{8b}$, R$_{9a}$, R$_{9b}$, R$_{10a}$, R$_{10b}$, R$_{11a}$, R$_{11b}$ group to form a ring system selected from the group consisting of unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl; or R$_{8a}$, R$_{8b}$ and X$_1$; R$_{9a}$, R$_{9b}$ and X$_4$; R$_{10a}$, R$_{10b}$ and X$_3$; R$_{11a}$, R$_{11b}$ and X$_2$ are taken together to form a ring system selected from the group consisting of unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl;

R$_7$ is selected from the group consisting of hydrogen, —OH, unsubstituted or substituted C$_{1-6}$ alkyl, unsubstituted or substituted C$_{3-8}$ cycloalkyl, unsubstituted or substituted C$_{3-8}$ cycloalkenyl;

R$_{12}$, R$_{13}$, R$_{16}$, R$_{17}$, R$_{18}$, R$_{22}$, R$_{23}$, R$_{26}$, and R$_{27}$ are independently of each other absent or selected from hydrogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, or R$_{12}$ and R$_{13}$, R$_{16}$ and R$_{17}$, R$_{17}$ and R$_{18}$, R$_{22}$ and R$_{23}$, R$_{26}$ and R$_{27}$ are taken together with the atom to which they are attached form a ring selected from the group consisting of unsubstituted or substituted C$_{2-9}$ heteroalicyclyl and unsubstituted or substituted heteroaryl;

R$_{14}$, R$_{15}$, R$_{19}$, R$_{20}$, R$_{21}$, R$_{24}$, R$_{25}$, R$_{28}$, R$_{29}$, R$_{30}$, and R$_{31}$ are independently of each other absent or selected from hydrogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl;

A is selected from CR$_{32}$ or N;

R$_x$ and R$_y$ are independently of each other selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$; or R$_x$ and R$_y$ are both taken together with A to form a ring system selected from the group consisting of unsubstituted or substituted C$_{3-8}$ cycloalkyl, unsubstituted or substituted C$_{3-8}$ cycloalkenyl, and unsubstituted or substituted C$_{2-9}$ heteroalicyclyl or unsubstituted or substituted heteroaryl, unsubstituted or substituted aryl; or one of R$_x$ or R$_y$ is taken together with A to form a ring system selected from the group consisting of unsubstituted or substituted C$_{3-8}$ cycloalkyl, unsubstituted or substituted C$_{3-8}$ cycloalkenyl, and unsubstituted or substituted C$_{2-9}$ heteroalicyclyl or unsubstituted or substituted heteroaryl, unsubstituted or substituted aryl; and whenever R$_x$ and R$_y$ independently of each other are selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, and, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$, then both R$_{11a}$ and R$_{11b}$ cannot be hydrogen;

whenever one or more heteroatom(s) is/are present it is/they are selected from O, N and S; and with the proviso that the compound of Formula (I) is not

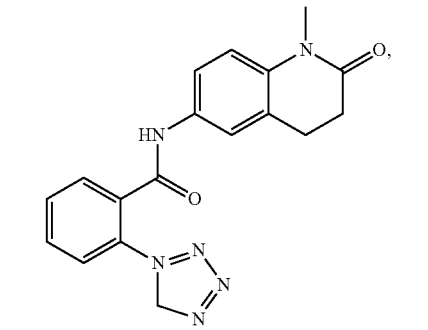

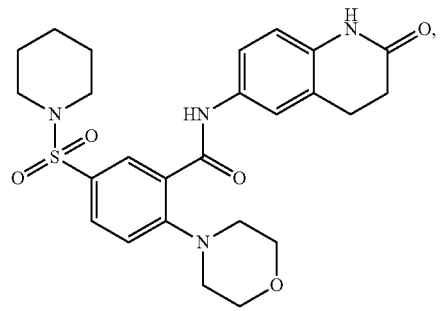

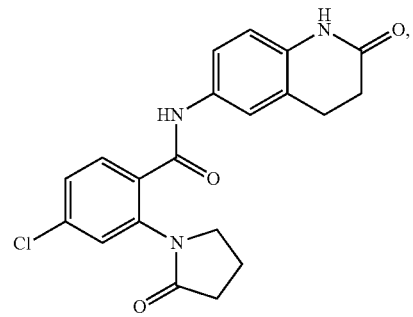

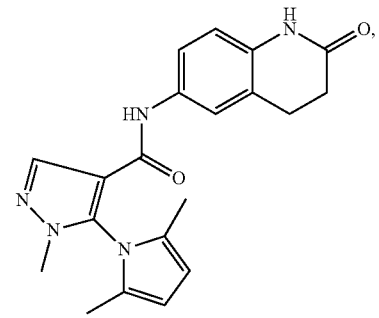

-continued

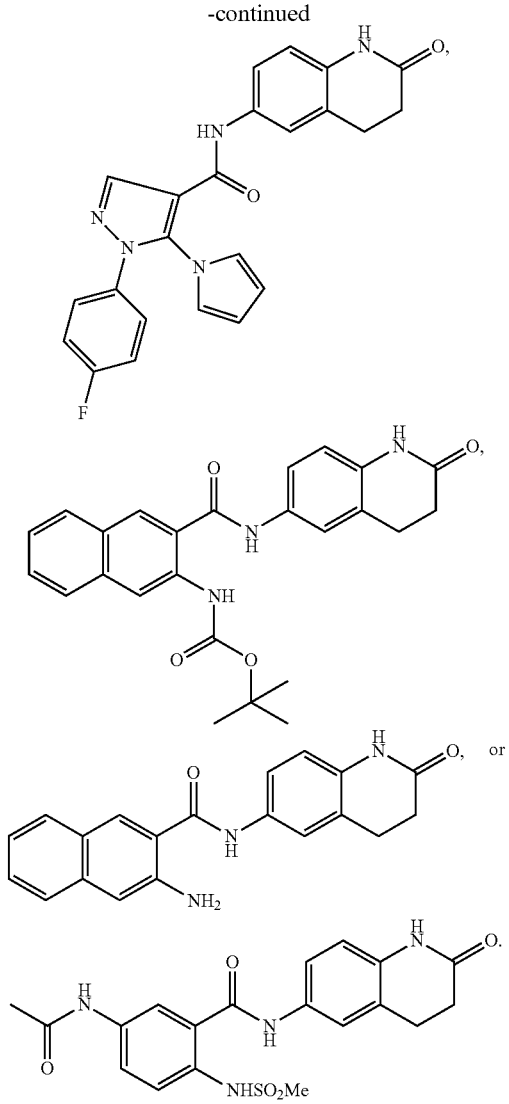

An aspect relates to pharmaceutical compositions comprising the compound according to formula (I).

An aspect relates to the compounds according to formula (I) or pharmaceutical compositions comprising the compound according to formula (I) for modulating, such as inhibiting at least one bromodomain. An aspect relates to the bromodomain being a member of the BET family.

An aspect relates to the compounds according to formula (I) or pharmaceutical compositions comprising the compound according to formula (I) for treating diseases or conditions related to systemic or tissue inflammation, inflammatory responses to infection or hypoxia, cellular activation and proliferation, lipid metabolism, fibrosis and in the prevention and treatment of viral infections; or chronic autoimmune and inflammatory diseases or conditions such as rheumatoid arthritis, osteoarthritis, acute gout, psoriasis, psoriatic arthritis, systemic lupus erythematosus, multiple sclerosis, inflammatory bowel disease, inflammatory bowel syndrome, Crohn's disease, ulcerative colitis, colitis, asthma, chronic obstructive airways disease, pneumonitis, myocarditis, pericarditis, myositis, eczema, dermatitis, atopic dermatitis, allergy, ankylosing spondylitis, lupus erythematosus, Hashimoto's disease, pancreatitis, autoimmune ocular disease, Sjögren's disease, optic neuritis, neuromyelitis optica, Myasthenia Gravis, Guillain Barre syndrome, Graves' disease, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, hypophysitis, thyroiditis, Addison's disease, type I diabetes and acute rejection of transplanted organs; or treating an acute inflammatory diseases or conditions such as acute gout, giant cell arteritis, nephritis including lupus nephritis, vasculitis with organ involvement such as glomerulonephritis, vasculitis including giant cell arteritis, Polyarteritis nodosa, Behcet's disease, Wegener's granulomatosis, Kawasaki disease, Takayasu's Arteritis, vasculitis with organ involvement and acute rejection of transplanted organs; or treating inflammatory responses to infections caused by bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus; or treating ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism; or treating disorders or conditions of lipid metabolism such as hypercholesterolemia, atherosclerosis and Alzheimer's disease; or treating fibrotic disorders or conditions such as idiopathic pulmonary fibrosis, renal fibrosis, post-operative stricture, keloid formation, scleroderma and cardiac fibrosis; or viral infections such as herpes virus, human papilloma virus, human immunodeficiency virus (HIV), adenovirus and poxvirus; or treating cancer, including hematological, epithelial including lung, breast and colon carcinomas, midline carcinomas, sarcomas, mesenchymal, hepatic, renal and neurological tumours; such as adenocarcinoma, acute lymphoblastic leukemia, acute myelogenous leukemia, adult T-cell leukemia/lymphoma, bladder cancer, blastoma, bone cancer, breast cancer, brain cancer, burkitts lymphoma, carcinoma, myeloid sarcoma, cervical cancer, chronic lymphocytic leukemia, chronic myelogenous leukemia, colorectal cancer, diffuse large B-cell lymphoma, endometrial cancer, esophageal cancer, follicular lymphoma, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, melanoma, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor; or treating obesity, such as obesity associated with cancer treatment or obesity associated with diabetes and cardiac hypertrophy.

Further, advantageous features of various aspects and embodiments are defined in the dependent claims and within the detailed description below.

DETAILED DESCRIPTION OF EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there is a plurality of definitions for a term herein, those in this section prevail unless stated otherwise.

As used herein, any "R" group(s) such as, without limitation, $R_1$, $R_2$, $R_3$, $R_4$, $R_5$, $R_8$, $R_9$, and $R_{10}$, represent substituents that can be attached to the indicated atom. A non-limiting list of R groups include but are not limited to hydrogen, alkyl, alkenyl, alkynyl, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined to" as defined herein to form a cycloalkyl, aryl, heteroaryl or heteroalicyclyl group. For example, without limitation, if $R_a$ and $R_b$ of an $NR_aR_b$ group are indicated to be "taken together" or "combined to", it means that they are covalently bonded to one another at their terminal atoms to form a ring that includes the nitrogen:

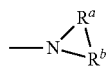

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

When a substituent is deemed to be "substituted," the substitutent itself is substituted with one ore more of the indicated substitutents. When the referenced substituent is substituted, it is meant that one or more hydrogen atoms on the referenced group may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, $3^{rd}$ Ed., John Wiley & Sons, New York, N.Y., 1999, which is hereby incorporated by reference in its entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH_3)CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atom, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "alkynyl" refers to an alkyl group that contains in the straight or branched hydrocarbon chain one or more triple bonds The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atom, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replaced may be in the middle or at the end of the alkyl group. Examples of heteroalkyl include, but are not limited to, —S-alkyl, —O-alkyl, —NH-alkyl, alkyl-O-alkyl, etc.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. Examples of "heteroaryl" include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine, tetrazole, and triazine. A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_1$-6". The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, —$CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, 1-methylethoxy (isopropoxy), cyclopropoxy, n-butoxy, isobutoxy, sec-butoxy, tert-butoxy, amoxy, tert-amoxy and the like. An alkoxy may be substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO— and RS—, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, in other embodiments it may range from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in other embodiments it may range from $C_2$ to $C_9$ and in other embodiments it may range from $C_2$ to $C_8$. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, azetidinyl, dioxolanyl, imidazolinyl, imidazolinolyl morpholinyl, oxetanyl, oxiranyl, piperidinyl N-Oxide, piperidinyl (e.g. 1-piperidinyl, 2-piperidinyl, 3-piperidinyl and 4-piperidinyl), pyrrolidinyl, (e.g. 1-pyrrolidinyl, 2-pyrrolidinyl and 3-pyrrolidinyl), piperazinyl, pyranyl, 4-piperidonyl, tetrahydrofuranyl, tetrahydropyranyl, pyrazolidinyl, 2-oxopyrrolidinyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "X₃CSO₂—" group" wherein X is a halogen.

A dashed bond, - - - -, represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

A "nitro" group refers to a "—NO₂" group

A "cyano" group refers to a "—CN" group.

A "cyanato" group refers to an "—OCN" group.

An "isocyanato" group refers to a "—NCO" group.

A "thiocyanato" group refers to a "—SCN" group.

A "carbonyl" group refers to a "—C(=O)—" group.

A "thiocarbonyl" group refers to a "—C(=S)—" group.

An "oxo" group refers to a "=O" group.

An "isothiocyanato" group refers to an "—NCS" group.

A "sulfinyl" group refers to an "—S(=O)—R" group in which R can be the same as defined with respect to O-carboxy. A sulfinyl may be substituted.

A "sulfonyl" group refers to an "SO₂R" group in which R can be the same as defined with respect to O-carboxy. A sulfonyl may be substituted.

An "S-sulfonamido" group refers to a "—SO₂NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted C$_{3-8}$ cycloalkyl, substituted or unsubstituted C$_{3-8}$ cycloalkenyl, substituted or unsubstituted heteroalicyclyl, substituted or unsubstituted aryl, and substituted or unsubstituted heteroaryl. A S-sulfonamido may be substituted.

An "N-sulfonamido" group refers to a "RSO₂N(R$_A$)—" group in which R and R$_A$ independently of each other can be the same as defined with respect to the R group as defined for O-carboxy. An N-sulfonamido may be substituted.

A "trihalomethanesulfonamido" group refers to an "X₃CSO₂N(R)—" group with X as halogen and R can be the same as defined with respect to O-carboxy. A trihalomethanesulfonamido may be substituted.

A "C-amido" group refers to a "—C(=O)NR$_A$R$_B$" group in which R$_A$ and R$_B$ independently of each other can be the same as defined with respect to the R group as defined for O-carboxy, or combined to form a ring system selected from the group consisting of substituted or unsubstituted C$_{3-8}$ cycloalkyl, substituted or unsubstituted C$_{3-8}$ cycloalkenyl, substituted or unsubstituted C$_{3-8}$ cycloalkyl, substituted or unsubstituted C$_{3-8}$ cycloalkenyl, substituted or unsubstituted heteroalicyclyl, substituted or unsubstituted aryl, and substituted or unsubstituted heteroaryl. A C-amido may be substituted.

An "N-amido" group refers to a "RC(=O)NR$_A$—" group in which R and R$_A$ independently of each other can be the same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amino" refers to "RNH₂" (primary amines), "R₂NH" (secondary amines), and "R₃N" (tertiary amines). An amino group may be substituted.

An aminoalkyl refers to an amino group connected via a alkylene group. A aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As employed herein, the following terms have their accepted meaning in the chemical literature.

| | |
|---|---|
| AcOH | Acetic acid |
| BrettPhos | dicyclohexyl-[3,6-dimethoxy-2-(2,4,6-triisopropylphenyl)phenyl]phosphane |
| CHAPS | 3-[(3-Cholamidopropyl)dimethylammonio]-1-propanesulfonate hydrate |
| Cs₂CO₃ | Cesium carbonate, 99% |
| DCM | Methylene chloride, dichloromethane |
| DIC | (3-Dimethylamino-propyl)-ethyl-carbodiimide |
| DIPEA | N,N-Diisopropylethylamine |
| DIEA | N,N-Diisopropylethylamine |
| DMAP | 4-Dimethylaminopyridine |
| DMF | N,N-dimethylformamide |
| DMSO | Dimethylsulfoxide |
| Dppf | Diphenylphosphinoferrocene |
| EDC | (3-Dimethylamino-propyl)-ethyl-carbodiimide |
| EtOAc | Ethyl acetate |
| EtOH | Ethanol |
| Fe | Iron |
| H₂ | Hydrogen |
| H₂SO₄ | Sulfuric acid |
| HCl | Hydrochloric acid |
| HEPES | 4-(2-Hydroxyethyl)piperazine-1-ethanesulfonic acid, N-(2-Hydroxyethyl)piperazine-N'-(2-ethanesulfonic acid) |
| HOAt | [1,2,3]Triazolo[4,5-b]pyridin-3-ol |
| HOBt | 1-Hydroxy-benzotriazole |
| K₂CO₃ | Potassium carbonate |
| LCMS | Liquid Chromatography - Mass spectrometry |
| LiI | Lithium Iodide |
| LiOH | Lithium hydroxide |
| mAb | Monoclonal antibody |
| MeCN | Acetonitrile |
| MeOH | Methanol |
| MgSO₄ | Magnesium sulfate |
| Na₂CO₃ | Sodium Carbonate |
| Na₂SO₄ | Sodium Sulfate, anhydrous |
| NaBH(OAc)₃ | Sodium triacetoxyborohydride |
| NaH | Sodium hydride |
| NaHCO₃ | sodium hydrogen carbonate |
| NaOH | Sodium hydroxide |
| NaOtBu | Sodium-tert-butylat |
| NH₃-aq | ammonium hydroxide |
| NH₄Cl | Ammonium chloride |
| NMP | 1-methylpyrrolidin-2-one |
| NT | Not Tested |
| Pd(OAc)₂ | Palladium acetate |
| Pd(PPh₃)₄ | Tetrakis(triphenylphosphine)palladium |
| Pd(dppf)Cl₂ | 1'-Bis(diphenylphosphino)-ferrocene]dichloropalladium(II) |
| Pd/C | Palladium on activated charcoal |
| PtO₂ | Platinum(IV) oxide |
| Rt | room temperature |
| RuPhos | Dicyclohexyl-[2-(2,6-diisopropoxyphenyl)- |

| | |
|---|---|
| | phenyl]phosphane |
| t-BuOH | Tert-Butanol |
| t-But-phos-pd(o) | Palladium(0) and tri-tert-butylphospine. |
| TEA | Triethylamine |
| TFA | Trifluoroacetic acid |
| THF | Tetrahydrofuran |
| TMS | Trimethylsilyl |
| TPP | Triphenylphosphine |
| TrixiePhos | Di-tert-butyl-[1-(1-naphthyl)-2-naphthyl]phosphane |
| $Zn(CN)_2$ | zinc dicyanide |

It is understood that, in any compound disclosed herein having one or more chiral centers, if an absolute stereochemistry is not expressly indicated, then each center may independently be of R-configuration or S-configuration or a mixture thereof. Thus, the compounds provided herein may be enatiomerically pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

"Tautomers" refer to compounds that are interchangeable forms of a particular compound structure which vary in the displacement of hydrogen atoms and electrons, a typical example is the "enol"-"keto" forms:

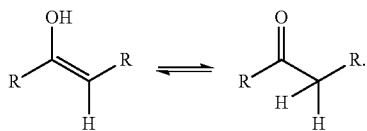

"Enol"-"keto" tautomerism may be exemplified by compound 1 of the present application:

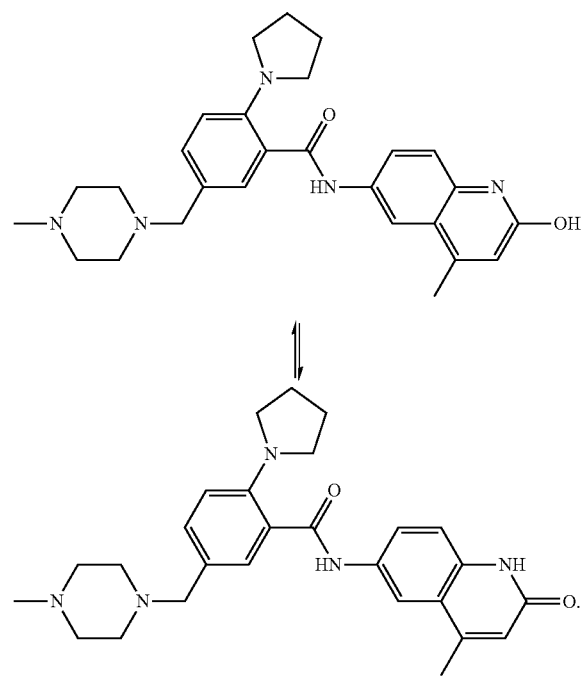

Additional non-limiting examples of tautomers include imine-enamine tautomers (—$CH_2$—CH=NH and —CH=CH—$NH_2$), or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, hydrochlorides, hydrobromides, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985)

*Medicinal Chemistry A Biochemical Approach*, Oxford University Press, New York, pages 388-392).

"Anti-drug" refers to a compound or composition acting against or opposing illicit drugs or their use. Compounds of the present application may act as anti-drugs.

As used herein, to "modulate" the function of a bromodomain or a bromodomain containing protein means either to increase its cellular function over the base level measured in the particular environment in which it is found, or decrease its cellular function to less than the measured base level in the environment in which it is found and/or render it unable to perform its cellular function at all.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor. "Ligand" is intended to include any substance that binds to or interacts with a bromodomain or a bromodomain containing protein.

"Selective" or "selectivity" is defined as a compound's ability to bind or inhibit preferentially a particular protein or specific domain of a protein over other proteins or other domains. "Selective" or "selectivity" of a bromodomain binding compound or inhibitor may refer to a compound being able to bind preferentially a bromodomain of the BET family over non-BET family bromodomain containing proteins. It may also refer to a compound being able to bind preferentially to the N-terminal bromodomain of a BET family protein over the C-terminal bromodomain or the compound being able to preferentially bind the C-terminal bromodomain over the N-terminal domain As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

An aspect disclosed herein relates to compounds of Formula (I)

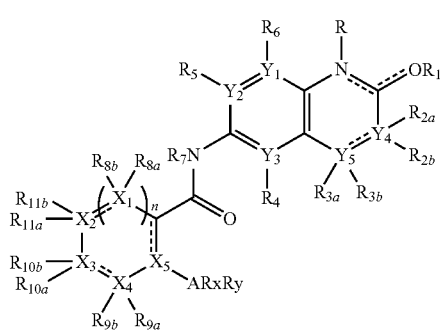

(I)

or pharmaceutically acceptable salts, hydrates, solvates, polymorphs, stereoisomers, and tautomers thereof, wherein $Y_1$, $Y_2$, $Y_3$, and $Y_4$ are independently of each other selected from the group consisting of N or C;

$Y_5$ is selected from C or O;

$X_1$, $X_2$, $X_3$, $X_4$, and $X_5$ are independently of each other selected from the group consisting of N, O, S or C;

n is an integer selected from 0 or 1;

R is absent or selected from the group of hydrogen, unsubstituted or substituted $C_{1-4}$ alkyl;

$R_1$ is absent, or selected from the group consisting of hydrogen, unsubstituted or substituted $C_{1-4}$ alkyl;

$R_{2a}$, $R_{2b}$, $R_{3a}$, and $R_{3b}$ are independently of each other either absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$OR_{31}$, or $R_{2a}$ and $R_{2b}$ taken together with $Y_4$, and/or $R_{3a}$ and $R_{3b}$ taken together with $Y_5$ form a ring selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl;

$R_4$, $R_5$, $R_6$, $R_{8a}$, $R_{8b}$, $R_{9a}$, $R_{9b}$, $R_{10a}$, $R_{10b}$, $R_{11a}$, $R_{11b}$ and $R_{32}$ are independently of each other absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, —$NO_2$, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$NR_{12}R_{13}$, —$NR_{14}C(=O)R_{15}$, —$NR_{16}C(=O)NR_{17}R_{18}$, —$NR_{28}C(=O)OR_{19}$, —$C(=O)R_{20}$, —$C(=O)OR_{21}$, —$OC(=O)R_{21}$, —$C(=O)NR_{22}R_{23}$, —$S(=O)R_{24}$, —$SO_2R_{25}$, —$SO_2NR_{26}R_{27}$, and —$OR_{31}$; or $R_5$, $R_6$, $R_{8a}$, $R_{8b}$, $R_{9a}$, $R_{9b}$, $R_{10a}$, $R_{10b}$, $R_{11a}$, $R_{11b}$ are taken together with an adjacent $R_5$, $R_6$, $R_{8a}$, $R_{8b}$, $R_{9a}$, $R_{9b}$, $R_{10a}$, $R_{10b}$, $R_{11a}$, $R_{11b}$ group to form a ring system selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl; or $R_{8a}$, $R_{8b}$ and $X_1$; $R_{9a}$, $R_{9b}$ and $X_4$; $R_{10a}$, $R_{10b}$ and $X_3$; $R_{11a}$, $R_{11b}$ and $X_2$ are taken together to form a ring system selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl;

$R_7$ is selected from the group consisting of hydrogen, —OH, unsubstituted or substituted $C_{1-6}$ alkyl, unsubstituted or substituted $C_{3-8}$ cycloalkyl, unsubstituted or substituted $C_{3-8}$ cycloalkenyl;

$R_{12}$, $R_{13}$, $R_{16}$, $R_{17}$, $R_{18}$, $R_{22}$, $R_{23}$, $R_{26}$, and $R_{27}$ are independently of each other absent or selected from hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, or $R_{12}$ and $R_{13}$, $R_{16}$ and $R_{17}$, $R_{17}$ and $R_{18}$, $R_{22}$ and $R_{23}$, $R_{26}$ and $R_{27}$ are taken together with the atom to which they are attached form a ring selected from the group consisting of unsubstituted or substituted $C_{2-9}$ heteroalicyclyl and unsubstituted or substituted heteroaryl;

$R_{14}$, $R_{15}$, $R_{19}$, $R_{20}$, $R_{21}$, $R_{24}$, $R_{25}$, $R_{28}$, $R_{29}$, $R_{30}$, and $R_{31}$ are independently of each other absent or selected from hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl;

A is selected from $CR_{32}$ or N;

$R_x$ and $R_y$ are independently of each other selected from hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$C(=O)R_{20}$ and —$SO_2R_{25}$; or $R_x$ and $R_y$ are both taken together with A to form a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, unsubstituted or substituted aryl; or one of $R_x$ or $R_y$ is taken together with A to form a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, unsubstituted or substituted aryl; and whenever $R_x$ and $R_y$ independently of each other are selected from hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, and, unsubstituted or substituted $C_{2-9}$ heteroalicyclyl, unsubstituted or substituted aryl, unsubstituted or substituted heteroaryl, —$C(=O)R_{20}$ and —$SO_2R_{25}$, then both $R_{11a}$ and $R_{11b}$ cannot be hydrogen;

whenever one or more heteroatom(s) is/are present it is/they are selected from O, N and S; and with the proviso that the compound of Formula (I) is not

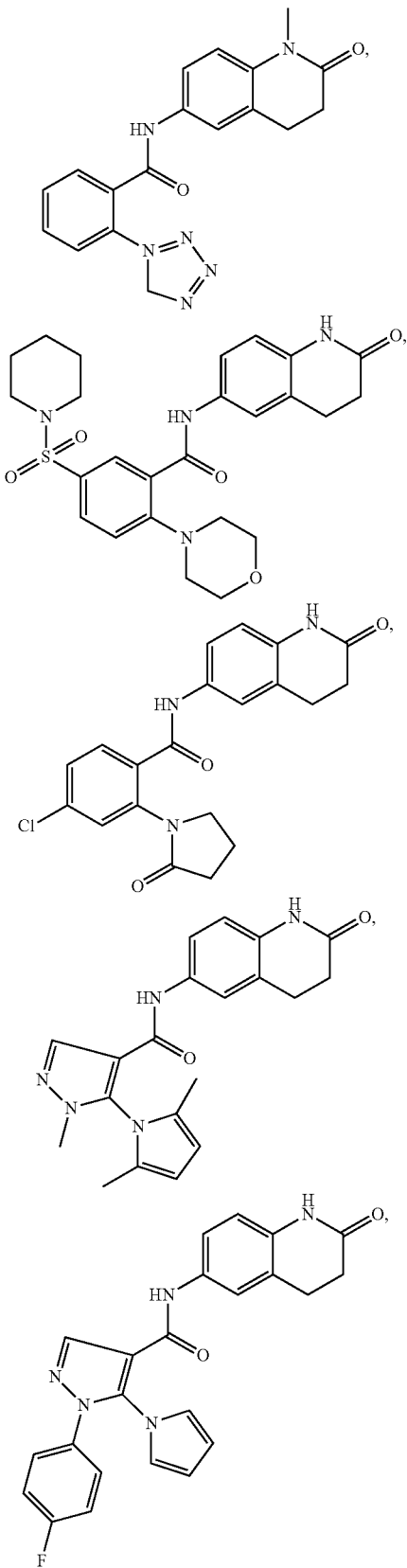

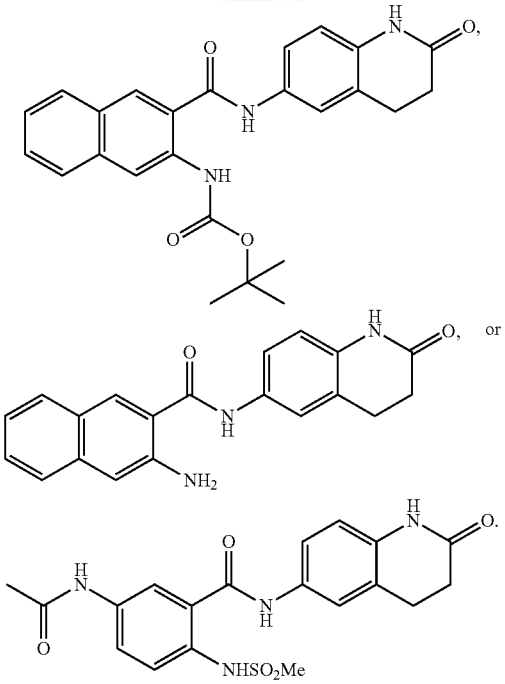

An aspect disclosed herein relates to compounds of Formula (I)

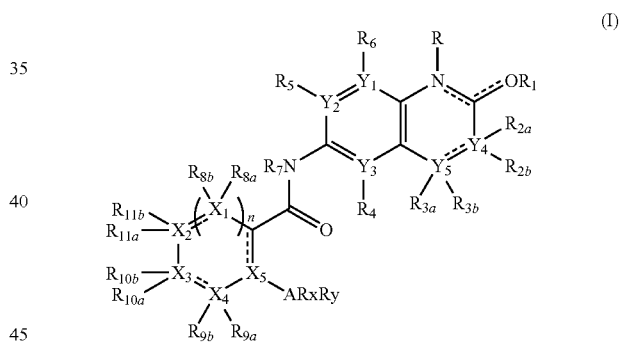

or pharmaceutically acceptable salts, hydrates, solvates, polymorphs, stereoisomers, and tautomers thereof, wherein $Y_1$, $Y_2$, $Y_3$, and $Y_4$ are independently of each other selected from the group consisting of N or C;

$Y_5$ is selected from C or O;

$X_1$, $X_2$, $X_3$, $X_4$, and $X_5$ are independently of each other selected from the group consisting of N, O, S or C;

n is an integer selected from 0 or 1;

R is absent or selected from the group of hydrogen, unsubstituted or substituted $C_{1-4}$ alkyl;

$R_1$ is absent, or selected from the group consisting of hydrogen, unsubstituted or substituted $C_{1-4}$ alkyl;

$R_{2a}$, $R_{2b}$, $R_{3a}$, and $R_{3b}$ are independently of each other either absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —OR$_{31}$, or R$_{2a}$ and R$_{2b}$ taken together with Y$_4$, and/or R$_{3a}$ and R$_{3b}$ taken together with Y$_5$ form a ring selected from the group consisting of unsubstituted or substituted C$_{3-8}$ cycloalkyl, unsubstituted or substituted C$_{3-8}$ cycloalkenyl, unsubstituted or substituted C$_{2-9}$ heteroalicyclyl;

R$_4$, R$_5$, R$_6$, R$_{8a}$, R$_{8b}$, R$_{9a}$, R$_{9b}$, R$_{10a}$, R$_{10b}$, R$_{11a}$, R$_{11b}$ and R$_{32}$ are independently of each other absent or selected from the group consisting of hydrogen, halogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, —OH, —CN, —NO$_2$, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —NR$_{12}$R$_{13}$, —NR$_{14}$C(=O)R$_{15}$, —NR$_{16}$C(=O)NR$_{17}$R$_{18}$, —NR$_{28}$C(=O)OR$_{19}$, —C(=O)R$_{20}$, —C(=O)OR$_{21}$, —OC(=O)R$_{21}$, —C(=O)NR$_{22}$R$_{23}$, —S(=O)R$_{24}$, —SO$_2$R$_{25}$, —SO$_2$NR$_{26}$R$_{27}$, and —OR$_{31}$; or R$_5$, R$_6$, R$_{8a}$, R$_{8b}$, R$_{9a}$, R$_{9b}$, R$_{10a}$, R$_{10b}$, R$_{11a}$, R$_{11b}$ are taken together with an adjacent R$_5$, R$_6$, R$_{8a}$, R$_{8b}$, R$_{9a}$, R$_{9b}$, R$_{10a}$, R$_{10b}$, R$_{11a}$, R$_{11b}$ group to form a ring system selected from the group consisting of unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl; or R$_{8a}$, R$_{8b}$ and X$_1$; R$_{9a}$, R$_{9b}$ and X$_4$; R$_{10a}$, R$_{10b}$ and X$_3$; R$_{11a}$, R$_{11b}$ and X$_2$ are taken together to form a ring system selected from the group consisting of unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl;

R$_7$ is selected from the group consisting of hydrogen, —OH, unsubstituted or substituted C$_{1-6}$ alkyl, unsubstituted or substituted C$_{3-8}$ cycloalkyl, unsubstituted or substituted C$_{3-8}$ cycloalkenyl;

R$_{12}$, R$_{13}$, R$_{16}$, R$_{17}$, R$_{18}$, R$_{22}$, R$_{23}$, R$_{26}$, and R$_{27}$ are independently of each other absent or selected from hydrogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, or R$_{12}$ and R$_{13}$, R$_{16}$ and R$_{17}$, R$_{17}$ and R$_{18}$, R$_{22}$ and R$_{23}$, R$_{26}$ and R$_{27}$ are taken together with the atom to which they are attached form a ring selected from the group consisting of unsubstituted or substituted C$_{2-9}$ heteroalicyclyl and unsubstituted or substituted heteroaryl;

R$_{14}$, R$_{15}$, R$_{19}$, R$_{20}$, R$_{21}$, R$_{24}$, R$_{25}$, R$_{28}$, R$_{29}$, R$_{30}$, and R$_{31}$ are independently of each other absent or selected from hydrogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl; A is selected from CR$_{32}$ or N;

R$_x$ and R$_y$ are independently of each other selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$; or R$_x$ and R$_y$ are both taken together with A to form a ring system selected from the group consisting of unsubstituted or substituted C$_{3-8}$ cycloalkyl, unsubstituted or substituted C$_{3-8}$ cycloalkenyl, and unsubstituted or substituted C$_{2-9}$ heteroalicyclyl or unsubstituted or substituted heteroaryl, unsubstituted or substituted aryl; or one of R$_x$ or R$_y$ is taken together with A to form a ring system selected from the group consisting of unsubstituted or substituted C$_{3-8}$ cycloalkyl, unsubstituted or substituted C$_{3-8}$ cycloalkenyl, and unsubstituted or substituted C$_{2-9}$ heteroalicyclyl or unsubstituted or substituted heteroaryl, unsubstituted or substituted aryl; and whenever R$_x$ and R$_y$ independently of each other are selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, and, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$, then both R$_{11a}$ and R$_{11b}$ cannot be hydrogen;

whenever one or more heteroatom(s) is/are present it is/they are selected from O, N and S; and with the proviso that the compound of Formula (I) is not

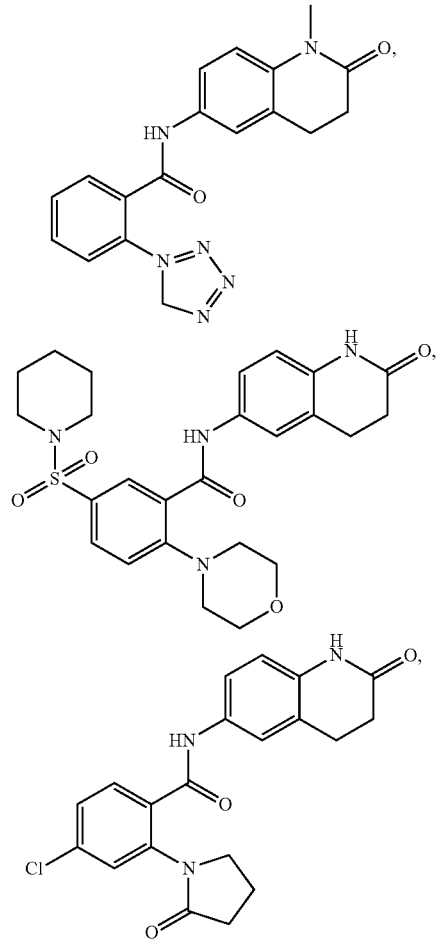

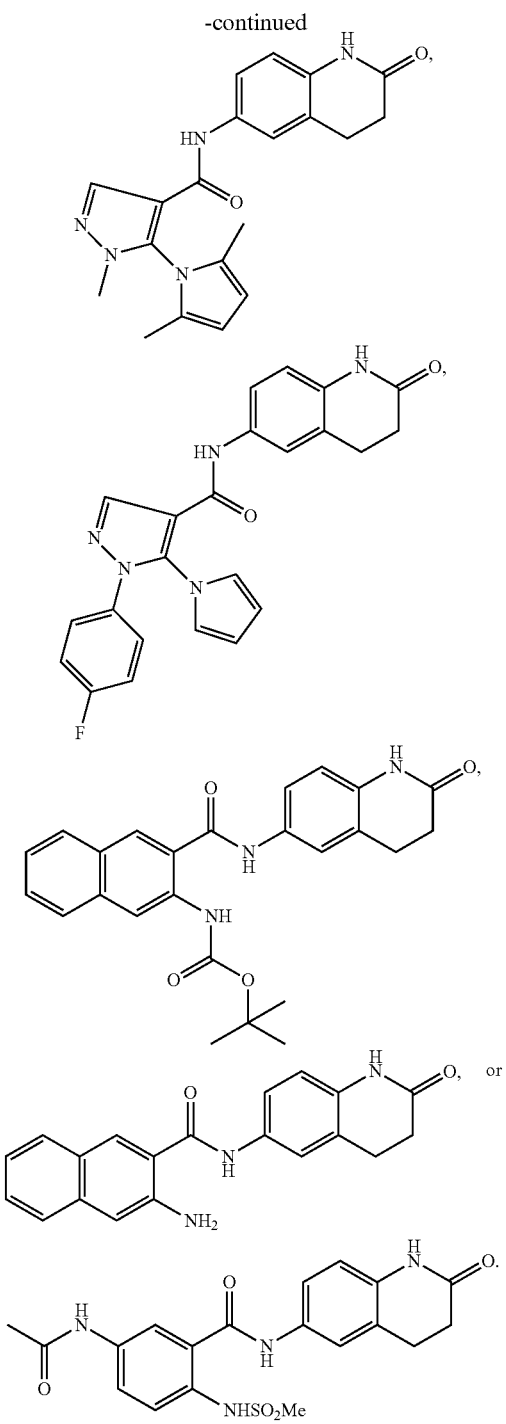

tuted $C_{1-6}$ alkyl, unsubstituted or substituted $C_{3-6}$ cycloalkyl and unsubstituted or substituted $C_{1-6}$ alkoxy.

Whenever the designated substitutent, e.g. $R_{2a}$, $R_{2b}$, $R_{3a}$ and/or $R_{3b}$, is deemed absent it may mean the formation of a double bond (as exemplified by Formula (III) where $R_{2b}$ and $R_{3b}$ are absent and a double bond is present).

Some aspects relates to a compound according to Formulae (II)-(VI):

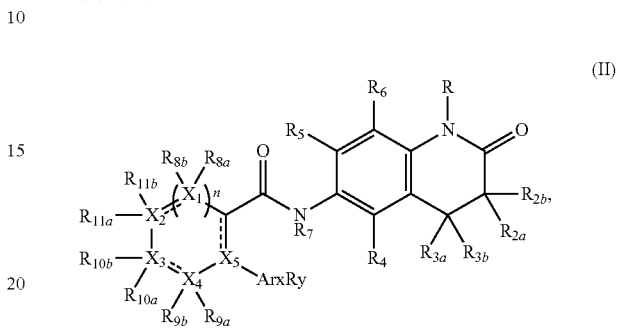

(II)

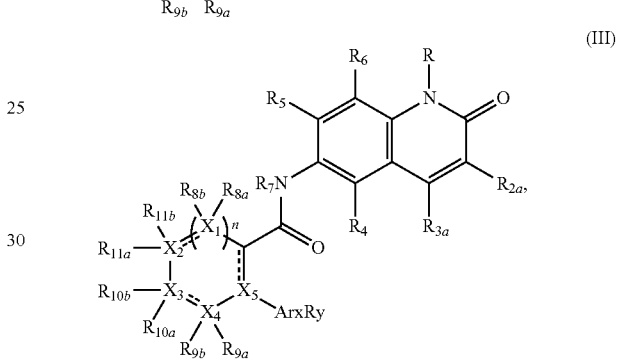

(III)

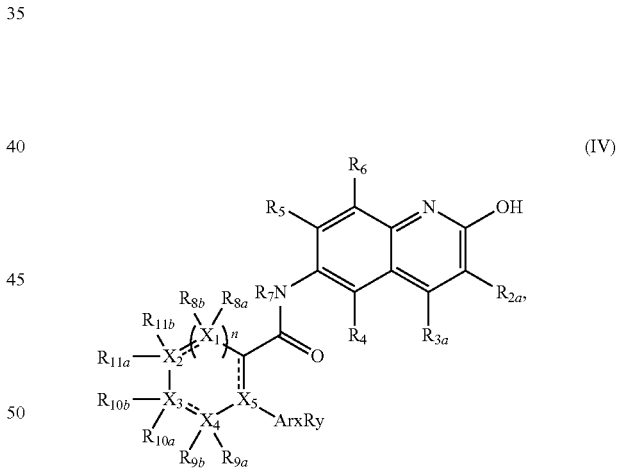

(IV)

Some embodiments relate to a compound according to any of the Formulae presented herein and wherein $R_{2a}$ and $R_{2b}$ independently of each other are absent or $R_{2a}$ and $R_{2b}$ independently of each other are selected from the group consisting of hydrogen, halogen, unsubstituted or substituted $C_{1-6}$ alkyl, unsubstituted or substituted $C_{3-6}$ cycloalkyl and unsubstituted or substituted $C_{1-6}$ alkoxy.

Some embodiments relate to a compound according to any of the Formulae presented herein and wherein $R_{3a}$ and $R_{3b}$ independently of each other are absent or $R_{3a}$ and $R_{3b}$ independently of each other are selected from the group consisting of hydrogen, halogen, unsubstituted or substi-

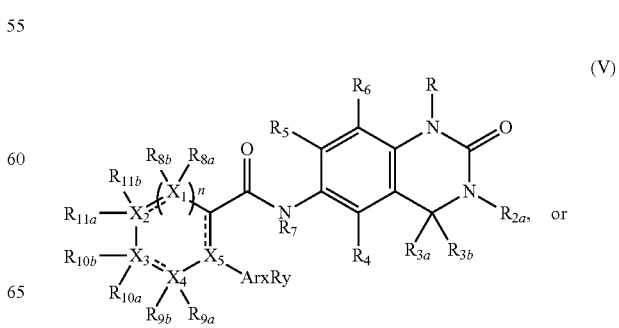

(V)

27
-continued (VI)

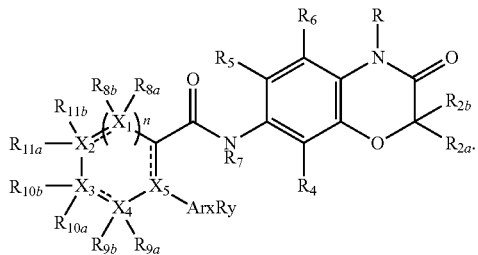

Some aspects relates to a compound according to Formulae (IIb)-(VIb):

(IIb)

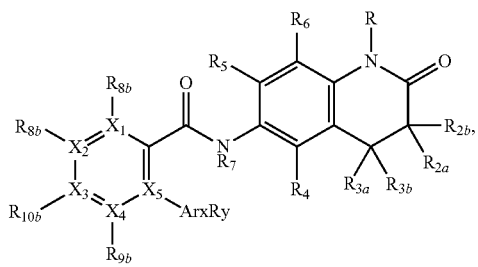

(IIIb)

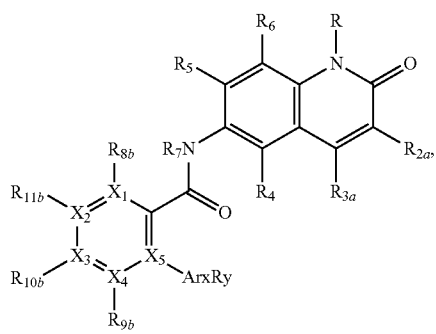

(IVb)

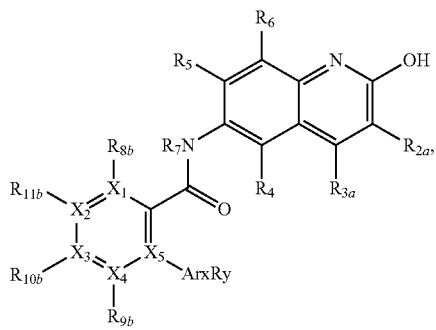

(Vb)

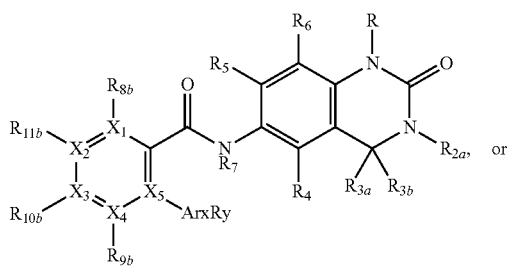

or

28
-continued (VIb)

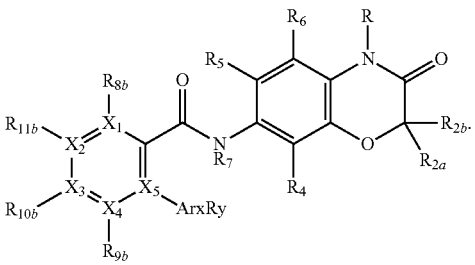

Some embodiment relate to a compound being selected from a compound according to any of the Formulae (II), (IIb), (III), (IIIb), (IV) or (IVb).

In embodiments wherein the integer "n" is 0, and the ring comprising $X_1$, $X_2$, $X_3$, $X_4$ and $X_5$ is a 5 membered ring.

Some embodiments relate to a compound as described herein wherein $X_1$, $X_2$, $X_3$ and $X_4$ independently of each other are selected from the group consisting of N or C, and $X_5$ is C.

Some embodiments relate to the integer "n" being 1, the ring comprising $X_1$, $X_2$, $X_3$, $X_4$ and $X_5$ thus being a 6 membered ring that may or may not comprise nitrogen atom(s). An example thereof is when $X_1$, $X_2$, $X_3$ and $X_4$ independently of each other are selected from the group consisting of N or C, and $X_5$ is C. Further, examples include one nitrogen atom being present in the ring comprising $X_1$, $X_2$, $X_3$, $X_4$ and $X_5$ i.e. in such embodiments one of $X_1$, $X_2$, $X_3$ and $X_4$ may be N (nitrogen) the others being C (carbon). Other examples relate to the ring comprising $X_1$, $X_2$, $X_3$, $X_4$ and $X_5$ wherein all are C, i.e. a phenyl ring.

Some embodiments relates to $R_{8b}$, $R_{11b}$, $X_1$ and $X_2$; $R_{10b}$, $R_{11b}$, $X_2$ and $X_3$; and/or $R_{9b}$, $R_{10b}$, $X_3$ and $X_4$ are taken together to form a fused ring system selected from the group consisting of unsubstituted or substituted aryl, unsubstituted or substituted heteroaryl, unsubstituted or substituted heteroalicyclyl, unsubstituted or substituted cycloalkyl, and unsubstituted or substituted cycloalkenyl. Such embodiments relates to the ring comprising $X_1$, $X_2$, $X_3$, $X_4$ and $X_5$ having substituents that taken together form a fused ring system, i.e. the ring comprising $X_1$, $X_2$, $X_3$, $X_4$ and $X_5$ is part of the fused ring system.

According to some embodiments the compound of Formulae IIb, IIIb, IVb, Vb, and VIb are selected from a compound wherein $X_5$ is C (carbon atom).

Some embodiments relate to a compound as described herein and wherein A is selected from $CR_{32}$ or N, and $R_x$ and $R_y$ are independently of each other selected from hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —C(═O)$R_{20}$ and —SO$_2$$R_{25}$. According to these embodiments both $R_{11a}$ and $R_{11b}$ cannot be hydrogen. According to these embodiments $R_{11a}$ is absent and $R_{11b}$ is selected from the group consisting of halogen, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{1-6}$ cyanoalkyl, unsubstituted or substituted $C_{1-6}$ alkoxy-$C_{1-6}$ alkyl, unsubstituted or substituted $C_{1-6}$ alkoxy, unsubstituted or substituted $C_{1-6}$ haloalkoxy, —OH, —CN, —NO$_2$, unsubstituted or substituted $C_{2-9}$ heteroalicyclyl, unsubstituted or substituted aryl, unsubstituted or substituted heteroaryl, —NR$_{12}$R$_{13}$, —C(=O)NR$_{22}$R$_{23}$, —SO$_2$R$_{25}$, —SO$_2$NR$_{26}$R$_{27}$, —NR$_{33}$(CR$_{34}$R$_{35}$)$_m$C(=O)NR$_{36}$R$_{37}$, —(CR$_{38}$R$_{39}$)$_m$NR$_{40}$R$_{41}$, and —(CR$_{42}$R$_{43}$)$_m$C(=O)NR$_{44}$R$_{45}$, wherein R$_{12}$, R$_{13}$, R$_{22}$, R$_{23}$, R$_{25}$, R$_{26}$, R$_{27}$, R$_{36}$, R$_{37}$, R$_{40}$, R$_{41}$, R$_{44}$, R$_{45}$ independently of each other are selected from the group consisting of hydrogen, unsubstituted or substituted C$_{1-6}$ alkyl, unsubstituted or substituted C$_{1-6}$ alkoxy, unsubstituted or substituted C$_{3-8}$ cycloalkyl, unsubstituted or substituted C$_{2-9}$ heteroalicyclyl, unsubstituted or substituted aryl, unsubstituted or substituted heteroaryl; or R$_{12}$, R$_{13}$; R$_{22}$, R$_{23}$; R$_{26}$, R$_{27}$; R$_{36}$, R$_{37}$; R$_{40}$, R$_{41}$; and R$_{44}$, R$_{45}$ together with the nitrogen atom to which they are attached form a ring selected from the group consisting of unsubstituted or substituted C$_{3-8}$ cycloalkyl, unsubstituted or substituted C$_{2-9}$ heteroalicyclyl, unsubstituted or substituted aryl, unsubstituted or substituted heteroaryl, R$_{33}$, R$_{34}$, R$_{35}$, R$_{38}$, R$_{39}$, R$_{42}$, and R$_{43}$ independently are selected from the group consisting of hydrogen and C$_{1-6}$ alkyl, and m is an integer selected from the group consisting of 0, 1, 2, 3 and 4. Some embodiments relate to R$_{11a}$ being absent and R$_{11b}$ selected from:

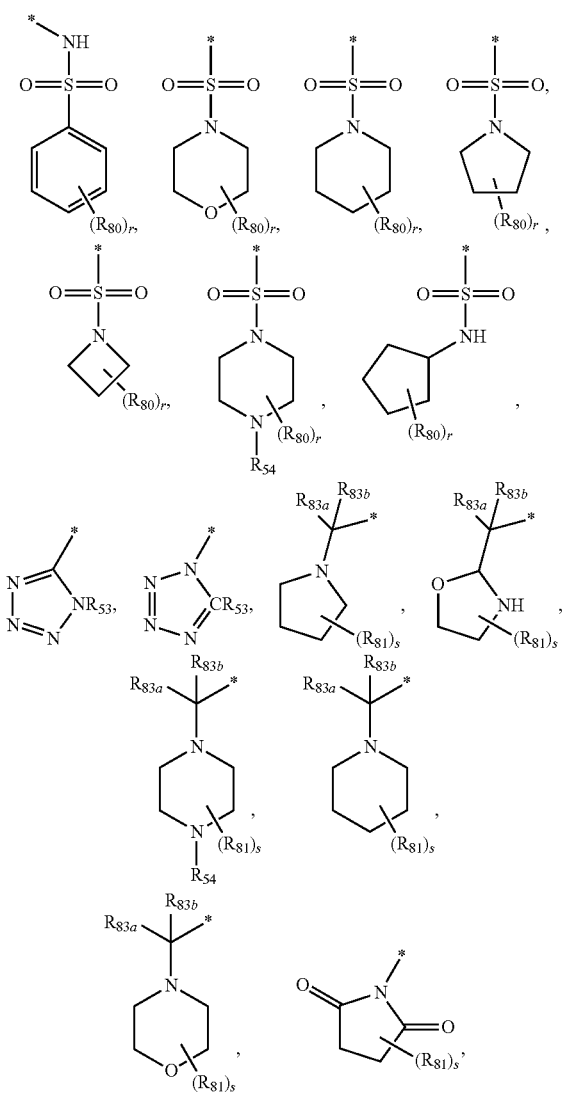

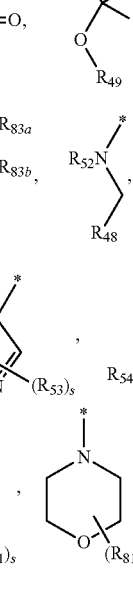

halogen
wherein R$_{83a}$ and R$_{83b}$ are independently of each other selected from the group consisting of hydrogen, fluoro, C$_{1-6}$ alkyl, or R$_{83a}$ and R$_{83b}$ taken together with the carbon atom to which they are attached form a C$_{3-8}$ cycloalkyl; R$_{80}$ and R$_{81}$ independently of each other are selected from the group consisting of hydrogen, halogen, —CN, —OH, C$_{1-4}$ alkyl, C$_{1-4}$ haloalkyl, C$_{1-4}$ hydroxyalkyl, C$_{1-4}$ aminoalkyl, —CF$_3$, C$_{1-4}$ alkoxy, C$_{1-4}$ alkoxy-C$_{1-4}$ alkyl, —OCF$_3$, —NR$_{52}$R$_{53}$, —C(=O)NR$_{52}$R$_{53}$, —C(=O)OR$_{52}$; r and s are integers selected from 0, 1 or 2; R$_{47}$, R$_{48}$, R$_{49}$, and R$_{50}$ and R$_{82}$ independently of each other are selected from the group consisting of hydrogen, C$_{1-6}$ alkyl, C$_{1-6}$ alkoxy-C$_{1-6}$ alkyl, —NR$_{52}$R$_{53}$, C$_{1-6}$ aminoalkyl, —OH, —C(=O)NR$_{55}$R$_{56}$; R$_{82}$ is selected from the group consisting of C$_{1-6}$ alkyl, C$_{1-6}$ alkoxy, —NR$_{85}$R$_{86}$, and —OH; R$_{52}$, R$_{53}$, and R$_{54}$ independently of each other are selected from the group consisting of hydrogen, C$_{1-6}$ alkyl, C$_{1-6}$ haloalkyl, C$_{1-6}$ hydroxyalkyl, C$_{1-6}$ aminoalkyl, C$_{1-6}$ alkoxy, C$_{1-4}$ alkoxy-C$_{1-4}$ alkyl, C$_{3-8}$ cycloalkyl, and —C(=O)R$_{82}$; R$_{55}$ and R$_{56}$ independently of each other are selected from the group consisting of C$_{1-6}$ alkyl, unsubstituted or substituted C$_{3-8}$ cycloalkyl, unsubstituted or substituted C$_{2-9}$ heteroalicyclyl, unsubstituted or substituted aryl, unsubstituted or substituted heteroaryl, and R$_{85}$ and R$_{86}$ independently of each other are selected from the group consisting of hydrogen, C$_{1-6}$ alkyl, and C$_{3-8}$ cycloalkyl or R$_{85}$ and R$_{86}$ taken together with the nitrogen atom form a ring system selected from unsubstituted or substituted heteroalicyclyl.

The asterisk denotes the radical forming a bond to the general formula, e.g. in this particular example the ring system comprising X$_1$, X$_2$, X$_3$, X$_4$ and X$_5$. In order to further illustrate the asterisk the following example structurally discloses the replacement of R$_{11b}$ by the —CR$_{44a}$R$_{44b}$-morpholinyl:

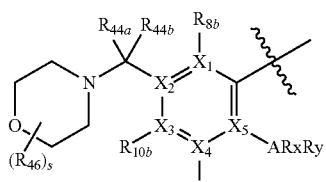

Some embodiments relate to $AR_xR_y$ forming a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, unsubstituted or substituted aryl. In some related embodiments $R_x$ or $R_y$ together with A form a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, unsubstituted or substituted aryl. Consequently according to these embodiments, the ring comprising $X_1$, $X_2$, $X_3$, $X_4$ and $X_5$ is substituted in position 2 by a ring system comprising A and at least one of $R_x$ and $R_y$. Some embodiments relate to the ring system comprising A and at least one of $R_x$ and $R_y$ is a ring system selected from unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl. Some embodiments relate to A being a nitrogen atom and accordingly the ring system formed selected from unsubstituted or substituted $C_{2-9}$ heteroalicyclyl or unsubstituted or substituted heteroaryl. In some embodiments the ring system is described as being substituted, the substituent is not intended to be particularly limited and may when present be present 1, 2, 3, or 4 times, and there may be different substitutents on the ring system, all within the capacity of those skilled in the art to synthesize. Examples of substituents on the ring system are unsubstituted or substituted $C_{1-6}$ alkyl, unsubstituted or substituted $C_{1-6}$ alkoxy, halogen, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted heteroaryl, —$NR_{62}R_{63}$, —$NR_{64}C(=O)NR_{65}R_{66}$, —$C(=O)NR_{67}R_{68}$, and —$C(=O)OR_{69}$, wherein $R_{60}$, $R_{61}$, $R_{62}$, $R_{63}$, $R_{64}$, $R_{65}$, $R_{66}$, $R_{67}$, $R_{68}$ and $R_{69}$ are independently of each other selected from the group consisting of hydrogen, unsubstituted or substituted $C_{1-6}$ alkyl. Examples of unsubstituted or substituted $C_{1-6}$ alkyl are selected from the group consisting of methyl, ethyl, propyl, isopropyl, butyl, tert-butyl, $C_{1-6}$ haloalkyl, $C_{1-6}$ aminoalkyl, —$CH_2NR_{70}R_{71}$, $C_{1-6}$ hydroxyalkyl, $C_{1-6}$ alkoxy-$C_{1-6}$ alkyl, aryl-$C_{1-6}$alkyl, wherein $R_{70}$ and $R_{71}$ independently of each other are selected from hydrogen or $C_{1-4}$ alkyl. Examples of unsubstituted or substituted $C_{2-9}$ heteroalicyclyl are unsubstituted or substituted pyrrolidinyl, and unsubstituted or substituted pyrrolidinyl-2-one. Examples of unsubstituted or substituted heteroaryl are unsubstituted or substituted imidazolyl, unsubstituted or substituted pyrrolyl, unsubstituted or substituted pyrazolyl, unsubstituted or substituted tetrazolyl, and unsubstituted or substituted pyridyl. Examples of unsubstituted or substituted aryl are unsubstituted or substituted phenyl.

Some embodiments relate to $AR_xR_y$ forming a ring system as disclosed above, $R_{11a}$ being absent and $R_{11b}$ selected as disclosed above from a non hydrogen substitutent.

Some embodiments relate to $AR_xR_y$ forming a ring system as disclosed above, $R_{11b}$ selected as disclosed above from a non hydrogen substitutent, and and $R_{8a}$, $R_{9a}$, $R_{10a}$ and $R_{11a}$ are absent and $R_{8b}$, $R_{9b}$, and $R_{10b}$ are hydrogen.

Some embodiments relate to $AR_xR_y$ forming a ring system as disclosed above and $R_{8a}$, $R_{9a}$, $R_{10a}$ and $R_{11a}$ are absent and $R_{8b}$, $R_{9b}$, $R_{10b}$, and $R_{11b}$ are hydrogen.

Some examples of $AR_xR_y$ forming a ring system are shown in Formulae (VII, VIII, IX, and X):

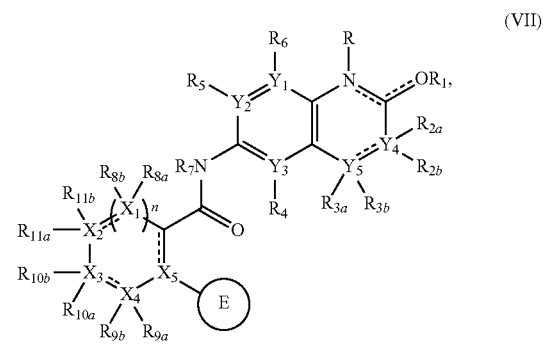

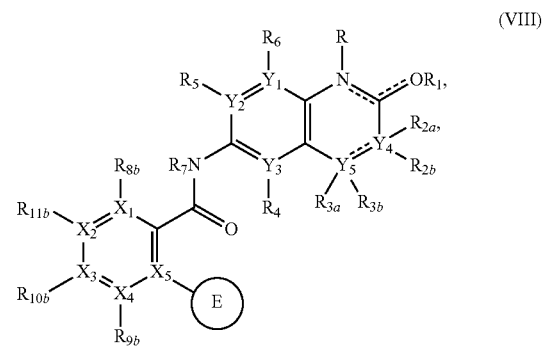

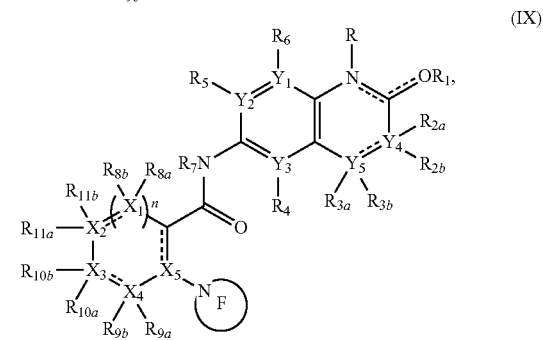

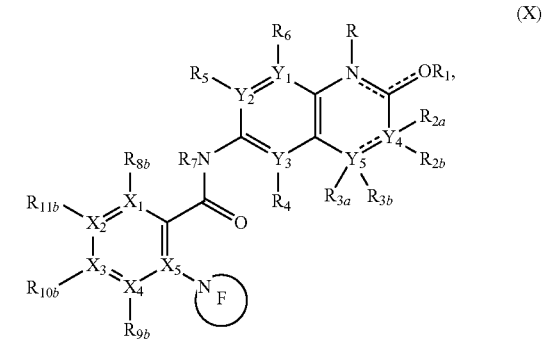

wherein the substituents are selected as described herein above.

According to some embodiments the compound of Formulae VII, VIII, IX, and X are selected from a compound wherein $X_5$ is C (carbon atom).

Examples of ring systems E and F are:

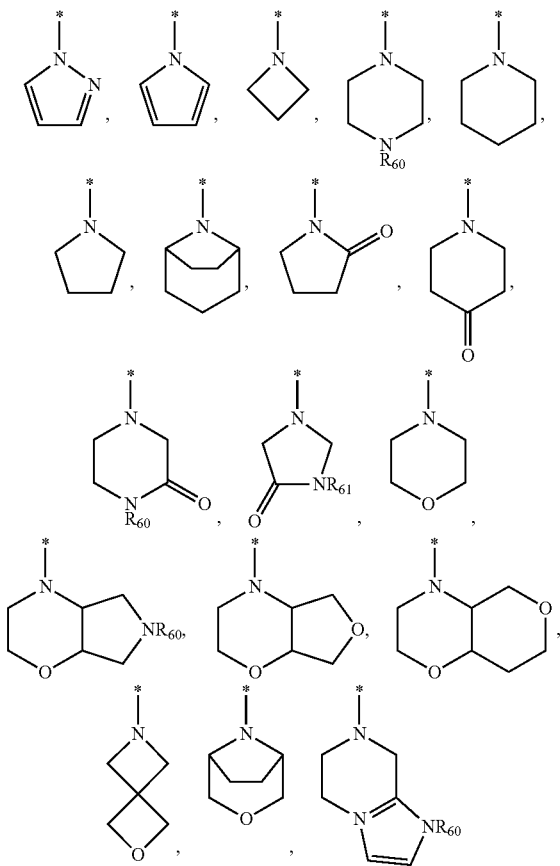

which may be unsubstituted or substituted with 1, 2, 3, or 4 substituents selected from the group consisting of unsubstituted or substituted $C_{1-6}$ alkyl, unsubstituted or substituted $C_{1-6}$ alkoxy, halogen, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted heteroaryl, —NR$_{62}$R$_{63}$, —NR$_{64}$C(=O)NR$_{65}$R$_{66}$, —C(=O)NR$_{67}$R$_{68}$, and —C(=O)OR$_{69}$, wherein R$_{60}$, R$_{61}$, R$_{62}$, R$_{63}$, R$_{64}$, R$_{65}$, R$_{66}$, R$_{67}$, R$_{68}$ and R$_{69}$ are independently of each other selected from the group consisting of hydrogen, unsubstituted or substituted $C_{1-6}$ alkyl.

In some of the above described embodiments whenever a ring system, for example a cycloalkyl, heteroalicyclyl, aryl, or heteroaryl is deemed substituted examples of suitable substituents are halogen, —CN, —OH, oxo, $C_{1-4}$ alkyl, $C_{1-4}$ haloalkyl, $C_{1-4}$ hydroxyalkyl, $C_{1-4}$ alkoxy, $C_{1-4}$ haloalkoxy-$C_{1-4}$ alkyl, $C_{1-4}$ alkoxy-$C_{1-4}$ alkyl, —NR$_{52}$R$_{53}$, —C(=O)NR$_{52}$R$_{53}$, —C(=O)OR$_{52}$, —C(=O)R$_{82}$, and $C_{1-4}$ aminoalkyl, wherein R$_{82}$ is selected from the group consisting of $C_{1-6}$ alkyl, $C_{1-6}$ alkoxy, —NR$_{85}$R$_{86}$, and —OH; R$_{52}$, R$_{53}$, and R$_{54}$ independently of each other are selected from the group consisting of hydrogen, $C_{1-6}$ alkyl, $C_{3-8}$ cycloalkyl, and —C(=O)R$_{82}$; R$_{55}$ and R$_{56}$ independently of each other are selected from the group consisting of $C_{1-6}$ alkyl, unsubstituted or substituted $C_{3-8}$ cycloalkyl, unsubstituted or substituted $C_{2-9}$ heteroalicyclyl, unsubstituted or substituted aryl, unsubstituted or substituted heteroaryl, and R$_{85}$ and R$_{86}$ independently of each other are selected from the group consisting of hydrogen, $C_{1-6}$ alkyl, and $C_{3-8}$ cycloalkyl or R$_{85}$ and R$_{86}$ taken together with the nitrogen atom form a ring system selected from unsubstituted or substituted heteroalicyclyl.

In some embodiments whenever a halogen is specified to be a substituent the halogen is selected from fluoro or chloro.

Some embodiments relate to a compound of formula XI

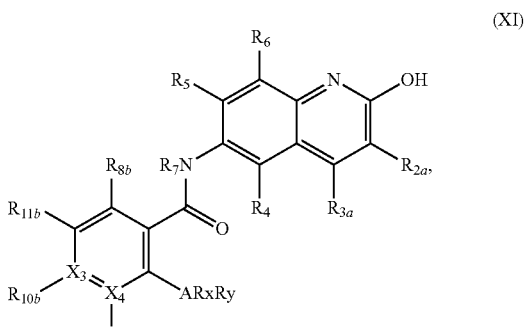

(XI)

wherein R$_{2a}$ is hydrogen or methyl; R$_{3a}$ is hydrogen or methyl; R$_7$ is hydrogen;

R$_4$, R$_5$, R$_6$ and R$_{8b}$ independently of each other are selected from the group consisting of hydrogen, halogen, $C_{1-4}$ alkyl, $C_{1-4}$ alkoxy, $C_{3-5}$ cycloalkyl, —CN, —OH, —CF$_3$, and —OCF$_3$;

$X_3$ and $X_4$ independently of each other are selected from the group consisting of N and C;

when $X_4$ is N, R$_{9b}$ is absent, when $X_4$ is C, R$_{9b}$ is selected from the group consisting of hydrogen, halogen, $C_{1-4}$ alkyl, $C_{1-4}$ alkoxy, $C_{3-5}$ cycloalkyl, —CN, —OH, —CF$_3$, and —OCF$_3$;

when $X_3$ is N, R$_{10b}$ is absent, when $X_3$ is C, R$_{10b}$ is selected from the group consisting of hydrogen, halogen, $C_{1-4}$ alkyl, $C_{1-4}$ alkoxy, $C_{3-5}$ cycloalkyl, —CN, —OH, —CF$_3$, and —OCF$_3$;

R$_{11b}$ is selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, —NO$_2$, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —NR$_{12}$R$_{13}$, —NR$_{14}$C(=O)R$_{15}$, —NR$_{16}$C(=O)NR$_{17}$R$_{18}$, —NR$_{28}$C(=O)OR$_{19}$, —C(=O)R$_{20}$, —C(=O)OR$_{21}$, —OC(=O)R$_{21}$, —C(=O)NR$_{22}$R$_{23}$, —S(=O)R$_{24}$, —SO$_2$R$_{25}$, —SO$_2$NR$_{26}$R$_{27}$, and —OR$_{31}$;

A is selected from CR$_{32}$ or N;

R$_x$ and R$_y$ are independently of each other selected from hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —C(=O)R$_{20}$ and —SO$_2$R$_{25}$; or R$_x$ and R$_y$ are both taken together with A to form a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, and unsubstituted or substituted aryl; or one of $R_x$ or $R_y$ is taken together with A to form a ring system selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl or unsubstituted or substituted heteroaryl, and unsubstituted or substituted aryl; and whenever $R_x$ and $R_y$ independently of each other are selected from hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, and, unsubstituted or substituted $C_{2-9}$ heteroalicyclyl, unsubstituted or substituted aryl, unsubstituted or substituted heteroaryl, —C(=O)$R_{20}$ and —SO$_2$$R_{25}$, then $R_{11b}$ cannot be hydrogen;

whenever one or more heteroatom(s) is/are present it is/they are selected from O, N and S.

In some embodiments the compound of formula (XI) is selected from compounds wherein $R_x$ and $R_y$ are both taken together with A to form a ring system selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted heteroaryl, and unsubstituted or substituted aryl; or $R_{11b}$ is selected from the group consisting of unsubstituted or substituted $C_{2-9}$ heteroalicyclyl and unsubstituted or substituted heteroaryl, or selected from the group consisting of:

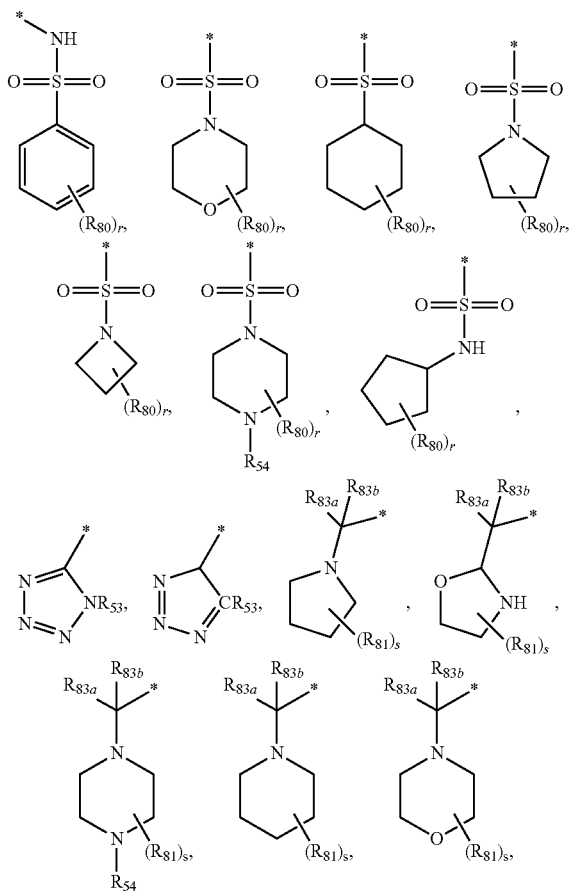

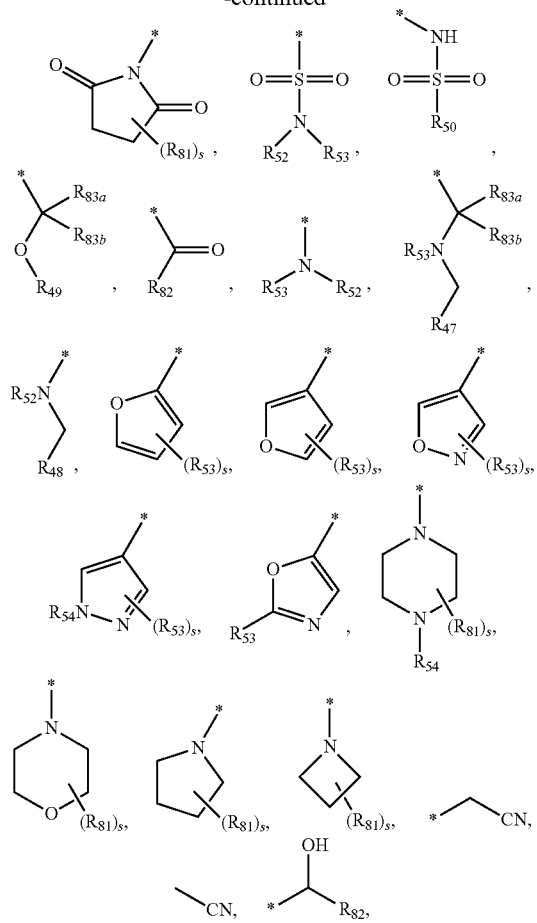

and halogen wherein $R_{83a}$ and $R_{83b}$ are independently of each other selected from the group consisting of hydrogen, fluoro, and $C_{1-6}$ alkyl, or $R_{83a}$ and $R_{83b}$ taken together with the carbon atom to which they are attached form a $C_{3-8}$ cycloalkyl;

$R_{80}$ and $R_{81}$ independently of each other are selected from the group consisting of hydrogen, halogen, —CN, —OH, $C_{1-4}$ alkyl, $C_{1-4}$ haloalkyl, $C_{1-4}$ hydroxyalkyl, $C_{1-4}$ aminoalkyl, —CF$_3$, $C_{1-4}$ alkoxy, $C_{1-4}$ alkoxy-$C_{1-4}$ alkyl, —OCF$_3$, —NR$_{52}$R$_{53}$, —C(=O)NR$_{52}$R$_{53}$, and —C(=O)OR$_{52}$;

r and s are integers selected from 0, 1 or 2;

$R_{47}$, $R_{48}$, $R_{49}$, and $R_{50}$ independently of each other are selected from the group consisting of hydrogen, $C_{1-6}$ alkyl, $C_{1-6}$ alkoxy-$C_{1-6}$ alkyl, —NR$_{52}$R$_{53}$, $C_{1-6}$ aminoalkyl, —OH, and —C(=O)NR$_{55}$R$_{56}$;

$R_{82}$ is selected from the group consisting of $C_{1-6}$ alkyl, $C_{1-6}$ alkoxy, —NR$_{85}$R$_{86}$, and —OH;

$R_{52}$, $R_{53}$, and $R_{54}$ independently of each other are selected from the group consisting of hydrogen, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-4}$ alkoxy-$C_{1-4}$ alkyl, $C_{3-8}$ cycloalkyl, and —C(=O)$R_{82}$;

$R_{55}$ and $R_{56}$ independently of each other are selected from the group consisting of $C_{1-6}$ alkyl, unsubstituted or substituted $C_{3-8}$ cycloalkyl, unsubstituted or substituted $C_{2-9}$ heteroalicyclyl, unsubstituted or substituted aryl, and unsubstituted or substituted heteroaryl; and $R_{85}$ and $R_{86}$ independently of each other are selected from the group consisting of hydrogen, $C_{1-6}$ alkyl, and $C_{3-8}$ cycloalkyl or $R_{85}$ and $R_{86}$ taken together with the nitrogen atom form a ring system selected from unsubstituted or substituted heteroalicyclyl.

In some embodiments the compound of formula (XI) is selected from compounds wherein $R_x$ and $R_y$ taken together with A form a ring system selected from the group consisting of:

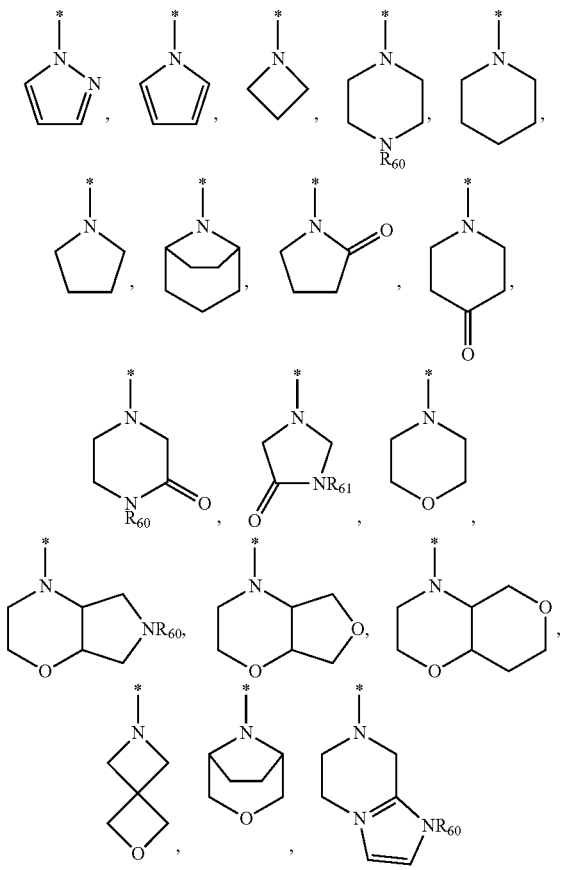

which ring system is unsubstituted or substituted with 1, 2, 3 or 4 substituents selected from the group consisting of unsubstituted or substituted $C_{1-6}$ alkyl, unsubstituted or substituted $C_{1-6}$ alkoxy, unsubstituted or substituted $C_{1-6}$ haloalkyl, unsubstituted or substituted $C_{1-6}$ hydroxyalkyl, unsubstituted or substituted $C_{1-6}$ aminoalkyl, halogen, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted $C_{2-9}$ heteroalicyclyl-$C_{1-6}$ alkyl, unsubstituted or substituted heteroaryl, unsubstituted or substituted heteroaryl-$C_{1-6}$ alkyl, —$(CR_{64}R_{65})_tNR_{62}R_{63}$, —$NR_{64}C(=O)NR_{65}R_{66}$, —$C(=O)NR_{67}R_{68}$, and —$C(=O)OR_{69}$;

wherein $R_{60}$, $R_{61}$, $R_{62}$, $R_{63}$, $R_{64}$, $R_{65}$, $R_{66}$, $R_{67}$, $R_{68}$ and $R_{69}$ are independently of each other selected from the group consisting of hydrogen, and unsubstituted or substituted $C_{1-6}$ alkyl; or the ring system is part of a bicyclic ring system; and t is selected from an integer selected from 0, 1, 2 and 3.

In some embodiment the compound of formula (XI) is selected from compounds wherein $R_{2a}$ is hydrogen or methyl; $R_{3a}$ is hydrogen or methyl; $R_7$ is hydrogen; $R_4$, $R_5$, $R_6$ independently of each other are selected from the group consisting of hydrogen, methyl, and methoxy;

$X_3$ and $X_4$ independently of each other are selected from the group consisting of N and C, wherein $R_{8b}$, $R_{9b}$, and $R_{10b}$ are hydrogen or in case of $X_3$ or $X_4$ being N, $R_{9b}$, and $R_{10b}$ are absent.

In some embodiments the compound of formula (XI) is selected from compounds wherein $R_x$ and $R_y$ taken together with A form a ring system selected from the group consisting of:

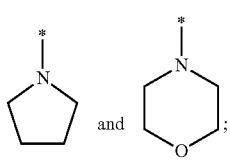

and $R_{11b}$ is selected from the group consisting of

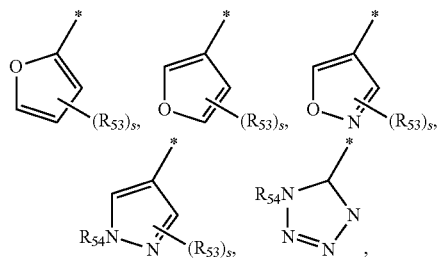

wherein s is selected from 0, 1 or 2 and $R_{53}$ when present is methyl; $R_{54}$ is selected from hydrogen and methyl.

Additional aspects and embodiments are included in the accompanying claims.

In related aspects and embodiments disclosed herein, there are provided a prodrug of a compound of Formulae (I)-(XI) or (Ib)-(IVb) as described herein.

In some embodiments, the compounds as disclosed herein are selectively binding any one of the bromodomains in the BET family of proteins compared to bromodomains not in the BET family. In some embodiments the compounds as disclosed herein selectively bind to the N-terminal bromodomain (BD1) over the C-terminal bromodomain (BD2) in any of the BET family of proteins.

Pharmaceutical Composition

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae (I)-(XI) or (Ib)-(VIIIb) as disclosed herein. The compound of Formula (I) included in the pharmaceutical composition may also be any compound of the preferred embodiments described above. In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae I-XI or Ib-VIb as disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds disclosed herein may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Uses

The compounds or pharmaceutical compositions as described herein may be used to modulate, such as inhibiting, the function of at least one bromodomain. The at least one bromodomain may be selected from the group consisting of BAZ2A, BAZ2B, CECR2, BAZ1A, TRIM66, TRIM24, TRIM33-1, TRIM33-2, TRIM28, SP100, SP140, SP140L, SP110-1, SP110-6, BAZ1B, BRD8(2), BRD8(1), BRWD1(2), BRWD3(2), PHIP(2), MLL, EP300, CREBBP, ATAD2, ATAD2B, BRD7, BRD9, BRPF3, BRD1, BRPF1-1, BRPF1-2, SMARCA2-2, SMARCA2-1, SMARCA4, PBRM1(6), PBRM1(4), PBRM1(5), PBRM1(3), PBRM1(1), ASH1L, PBRM1(2), TAF1L(2), TAF1(2), TAF1L(1), TAF1(1), ZMYND11, ZMYND8, KAT2B, KAT2A, BPTF, BRD3(2), BRD2(2), BRD4(2), BRDT(2), BRWD1(1), BRWD3(1), PHIP(1), BRDT(1), BRD3(1), BRD2(1), BRD4(1). The bromodomain may be a member of the BET (bromodomain and extraterminal domain) family. The compounds or pharmaceutical compositions as described herein may be used to inhibit the function of BRD4. The compounds or pharmaceutical compositions as described herein may modulate, such as inhibit, more than one bromodomain simultaneously. The bromodomain may be contained in a human protein.

The compounds or pharmaceutical compositions as described herein may be used to treat, prevent or ameliorate disease or conditions related to at least one bromodomain.

The compounds or pharmaceutical compositions as described herein may be used to treat, prevent or ameliorate disease or conditions related to at least one bromodomain contained in a human protein.

The compounds or pharmaceutical compositions as described herein and above may also be used in therapy or may be used to treat, prevent or ameliorate a variety of diseases or conditions, e.g. related to systemic or tissue inflammation, inflammatory responses to infection or hypoxia, cellular activation and proliferation, lipid metabolism, fibrosis and in the prevention, e.g. prophylactic treatment, and treatment of viral infections.

More specific examples of diseases, disorders or conditions which may be treated, prevented or ameliorated by compounds disclosed herein include chronic autoimmune and/or inflammatory diseases, or diseases or conditions associated with chronic autoimmune and/or inflammatory diseases such as rheumatoid arthritis, osteoarthritis, acute gout, psoriasis, psoriatric arthritis, systemic lupus erythematosus, multiple sclerosis, inflammatory bowel disease, inflammatory bowel syndrome, Crohn's disease, ulcerative colitis, colitis, asthma, chronic obstructive airways disease, pneumonitis, myocarditis, pericarditis, myositis, eczema, dermatitis, atopic dermatitis, allergy, ankylosing spondylitis, lupus erythematosus, Hashimoto's disease, pancreatitis, autoimmune ocular disease, Sjögren's disease, optic neuritis, neuromyelitis optica, Myasthenia Gravis, Guillain Barre syndrome, Graves' disease, alopecia, vitiligo, bullous skin diseases, asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, hypophysitis, thyroiditis, Addison's disease, type I diabetes and acute rejection of transplanted organs.

Additional examples of diseases, disorders or conditions include acute inflammatory diseases or conditions such as acute gout, giant cell arteritis, nephritis including lupus nephritis, vasculitis with organ involvement such as glomerulonephritis, vasculitis including giant cell arteritis, Polyarteritis nodosa, Behcet's disease, Wegener's granulomatosis, Kawasaki disease, Takayasu's Arteritis, vasculitis with organ involvement and acute rejection of transplanted organs.

Additional examples of diseases, disorders or conditions include inflammatory responses to infections caused by bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Additional examples of diseases, disorders or conditions include ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures, heart failure, cardiac hypertrophy, pulmonary, renal, hepatic, gastro-intestinal or peripheral limb embolism.

Additional examples of diseases, disorders or conditions include treating disorders or conditions of lipid metabolism such as hypercholesterolemia, atherosclerosis and Alzheimer's disease.

Additional examples of diseases, disorders or conditions include fibrotic disorders or conditions such as idiopathic pulmonary fibrosis, renal fibrosis, post-operative stricture, keloid formation, scleroderma and cardiac fibrosis.

Additional examples of diseases, disorders or conditions include viral infections such as herpes virus, human papilloma virus, human immunodeficiency virus (HIV), adenovirus and poxvirus.

Additional examples of diseases, disorders or conditions include cancer, including hematological, epithelial including lung, breast and colon carcinomas, midline carcinomas, sarcomas, mesenchymal, hepatic, renal and neurological tumours; such as adenocarcinoma, acute lymphoblastic leukemia, acute myelogenous leukemia, adult T-cell leukemia/lymphoma, bladder cancer, blastoma, bone cancer, breast cancer, brain cancer, burkitts lymphoma, carcinoma, myeloid sarcoma, cervical cancer, chronic lymphocytic leukemia, chronic myelogenous leukemia, colorectal cancer, diffuse large B-cell lymphoma, endometrial cancer, esophageal cancer, follicular lymphoma, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, melanoma, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

Additional examples of diseases, disorders or conditions include obesity, such as obesity associated with cancer treatment or obesity associated with diabetes and cardiac hypertrophy.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation by intratumoral injection, or by intra-lymph node injection; as well as (e) administration topically; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage administered to a human or non-human subject may range broadly, depending upon the desired effects and the therapeutic indication. Typically, dosages may be between about 10 microgram/kg and 1000 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

Additional uses, formulations and methods of administration may be disclosed in Nat Rev Drug Discov. 2014 May; 13(5):337-56, Nature 2010, 468, 1067-1073, Mol. Cell. 2008, 30, 51-60, Oncogene 2008, 27, 2237-2242, Cell 2004 117, 349-60, Cell 2009 138, 129-145, Nature Review Drug Discovery, 2014, doi:10.1038/nrd4286, WO2009084693, WO2012075383, WO2011054553, WO2011054841, WO2011054844, WO2011054845, WO2011054846, WO2011054848, WO2011143669, WO2011161031, WO2013027168, WO2014095774, and WO2014095775, all of which are incorporated herein by reference in their entirety.

General Remarks

As described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality.

The phrases "at least one" and "one or more" refer to 1 or a number greater than 1, such as to 1, 2, 3, 4, 5, 6, 7, 8, 9, or 10.

EXPERIMENTAL

The following examples are mere examples and should by no means be interpreted to limit the scope of the invention. Rather, the invention is limited only by the accompanying claims.

The compounds described below have, unless specifically stated, been prepared using commercially available starting materials. The following is a non-comprehensive list of starting materials used for the synthesis of compounds prepared herein.

| IUPAC_NAME | Structure | SUPPLIER |
|---|---|---|
| 2-morpholinobenzoic acid | 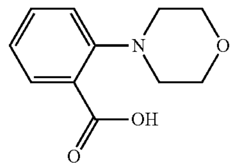 [SMILES: O=C(O)c1ccccc1N1CCOCC1] | Enamine-BB |
| 2-morpholinopyridine-3-carboxylic acid | 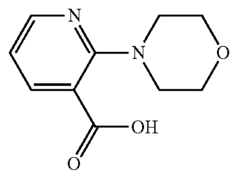 [SMILES: O=C(O)c1cccnc1N1CCOCC1] | Enamine-BB |
| 2-(methylamino)ethanol | 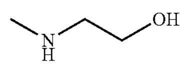 | Sigma-Aldrich |
| pyrrolidine | 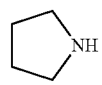 | Sigma-Aldrich |
| tetrahydrofuran-2-ylmethanamine | 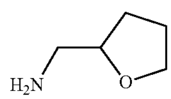 | Sigma-Aldrich |
| 4-amino-3-nitro-benzoic acid | 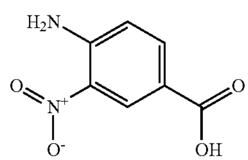 [SMILES: Nc1ccc(C(=O)O)cc1[N+](=O)[O-]] | Sigma-Aldrich |
| 1H-indole-6-carboxylic acid | 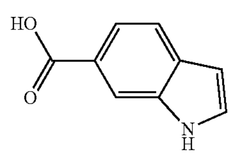 [SMILES: O=C(O)c1ccc2cc[nH]c2c1] | Fluka |
| 2-(4-methylpiperazin-1-yl)benzoic acid | 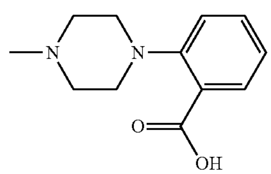 [SMILES: CN1CCN(c2ccccc2C(=O)O)CC1] | Maybridge |
| N,N-dimethylpyrrolidin-3-amine | 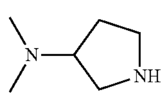 | Fluorochem |
| (2R)-2-(methoxymethyl)pyrrolidine | 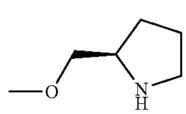 | Fluka |
| pyrrolidin-3-ol | 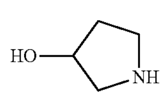 | Sigma-Aldrich |
| (2S)-2-(methoxymethyl)pyrrolidine | 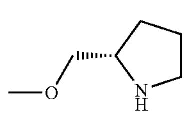 | Sigma-Aldrich |

-continued

| IUPAC_NAME | Structure | SUPPLIER |
|---|---|---|
| 2-piperazin-1-ylethanol | 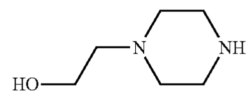 | Sigma-Aldrich |
| 1-methyl-1,4-diazepane | 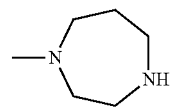 | Sigma-Aldrich |
| 3-[(4-tert-butoxycarbonylpiperazin-1-yl)methyl]benzoic acid | 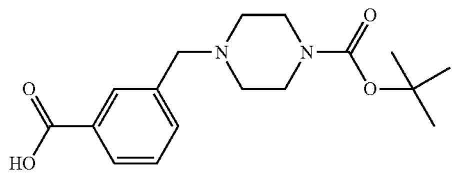 [SMILES: CC(C)(C)OC(=O)N1CCN(Cc2cccc(C(=O)O)c2)CC1] | Maybridge |
| 3-methoxypyrrolidine | 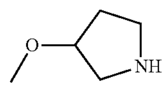 | Matrix |
| 4-pyrrolidin-3-ylpyridine | 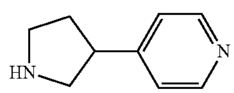 [SMILES: c1cc(C2CCNC2)ccn1] | Matrix |
| azetidin-3-ol | 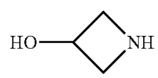 | Sigma-Aldrich |
| N,N-dimethylpyrrolidine-2-carboxamide | 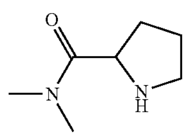 | Enamine-BB |
| 2-isobutylpyrrolidine | 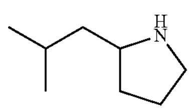 | ASDI-Inter |
| 1-pyrrolidin-3-ylpyrrolidine | 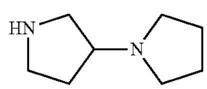 | TCI |
| 3-methylpyrrolidine | 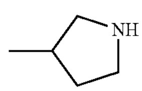 | Astatech |
| 3-(methoxymethyl)azetidine | 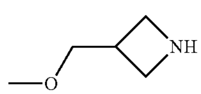 | Ace-Synthesis |
| 3-(methoxymethyl)piperidine | 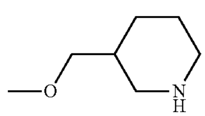 | Fluorochem |
| 2-bromo-5-morpholinosulfonyl-benzoic acid | 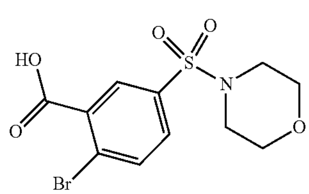 [SMILES: O=C(O)c1cc(S(=O)(=O)N2CCOCC2)ccc1Br] | Enamine-BB |

-continued

| IUPAC_NAME | Structure | SUPPLIER |
|---|---|---|
| 4-chloro-3-nitro-benzoic acid | 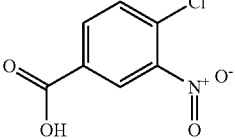 | Enamine-BB |
| 2-(dimethylamino)-5-nitro-benzoic acid | 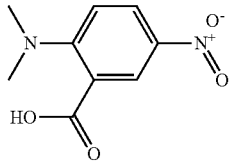 | Enamine-BB |
| 3-(methylsulfamoyl)benzoic acid | 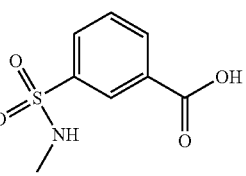 | Enamine-BB |
| 3-[(2-oxopyrrolidin-1-yl)methyl]benzoic acid | 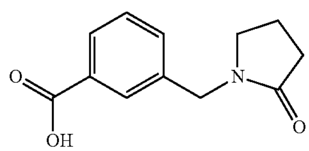 [SMILES: O=C(O)c1cccc(CN2CCCC2=O)c1] | Enamine-BB |
| 5-nitro-2-pyrrolidin-1-yl-benzoic acid | 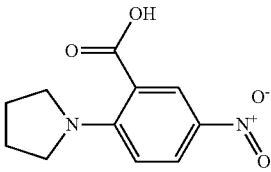 | Enamine-BB |
| 5-(dimethylsulfamoyl)-2-fluoro-benzoic acid | 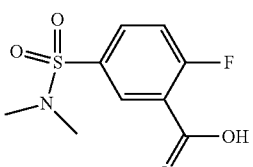 | Enamine-BB |
| 2-morpholino-5-nitro-benzoic acid | 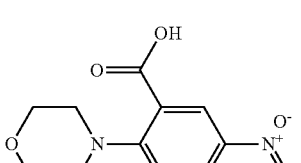 | Enamine-BB |
| 3-[(2-amino-2-oxo-ethyl)sulfamoyl]benzoic acid | 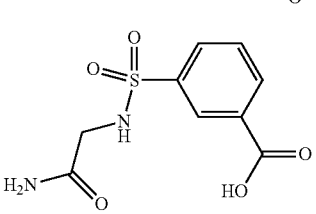 | Enamine-BB |
| 2-(4-pyrazin-2-ylpiperazin-1-yl)benzoic acid | 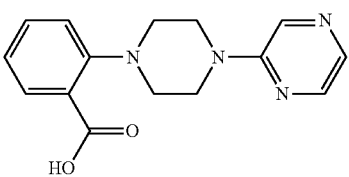 [SMILES: O=C(O)c1ccccc1N1CCN(c2cnccn2)CC1] | Enamine-BB |

-continued

| IUPAC_NAME | Structure | SUPPLIER |
|---|---|---|
| 3-(4-methylpiperazin-1-yl)sulfonylbenzoic acid | 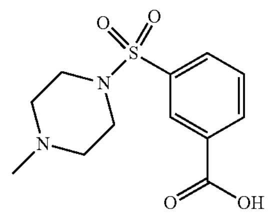 [SMILES: CN1CCN(S(=O)(=O)c2cccc(C(=O)O)c2)CC1] | Enamine-BB |
| 2-morpholino-5-sulfamoyl-benzoic acid | 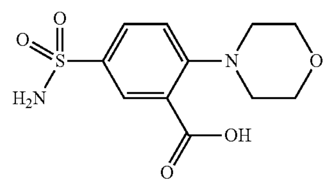 [SMILES: NS(=O)(=O)c1ccc(N2CCOCC2)c(C(=O)O)c1] | Enamine-BB |
| 5-(dimethylsulfamoyl)-2-pyrrolidin-1-yl-benzoic acid | 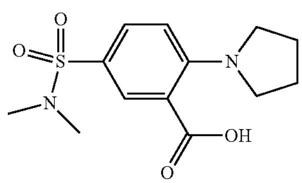 [SMILES: CN(C)S(=O)(=O)c1ccc(N2CCCC2)c(C(=O)O)c1] | Enamine-BB |
| 5-(dimethylsulfamoyl)-2-morpholino-benzoic acid | 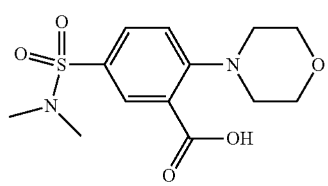 [SMILES: CN(C)S(=O)(=O)c1ccc(N2CCOCC2)c(C(=O)O)c1] | Enamine-BB |
| 5-(diethylsulfamoyl)-2-pyrrolidin-1-yl-benzoic acid | 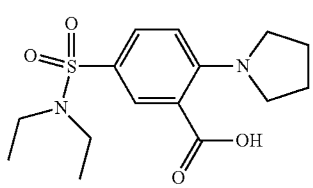 [SMILES: CCN(CC)S(=O)(=O)c1ccc(N2CCCC2)c(C(=O)O)c1] | Enamine-BB |
| 5-morpholinosulfonyl-2-pyrrolidin-1-yl-benzoic acid | 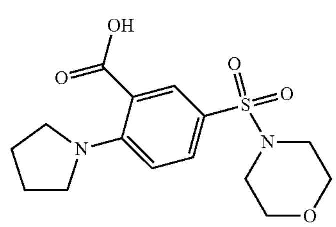 [SMILES: O=C(O)c1cc(S(=O)(=O)N2CCOCC2)ccc1N1CCCC1] | Enamine-BB |
| 5-(diethylsulfamoyl)-2-(1-piperidyl)benzoic acid | 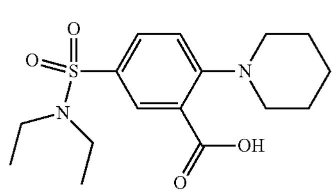 [SMILES: CCN(CC)S(=O)(=O)c1ccc(N2CCCCC2)c(C(=O)O)c1] | Enamine-BB |

-continued

| IUPAC_NAME | Structure | SUPPLIER |
|---|---|---|
| 2-morpholino-5-(1-piperidylsulfonyl)benzoic acid | 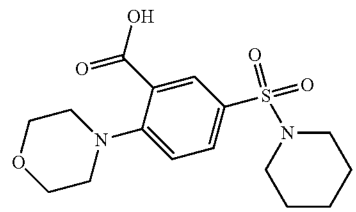 [SMILES: O=C(O)c1cc(S(=O)(=O)N2CCCCC2)ccc1N1CCOCC1] | Enamine-BB |
| 2-morpholino-5-morpholinosulfonyl-benzoic acid | 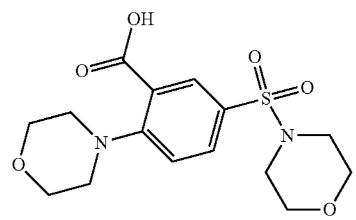 [SMILES: O=C(O)c1cc(S(=O)(=O)N2CCOCC2)ccc1N1CCOCC1] | Enamine-BB |
| 3-pyrrolidin-1-ylbenzoic acid | 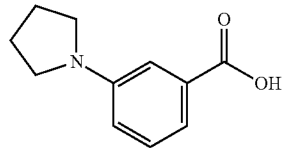 [SMILES: O=C(O)c1cccc(N2CCCC2)c1] | Specs |
| 5-(2,5-dioxopyrrolidin-1-yl)-2-morpholino-benzoic acid | 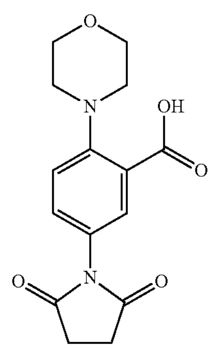 [SMILES: O=C(O)c1cc(N2C(=O)CCC2=O)ccc1N1CCOCC1] | Chembridge |
| 6-amino-3,4-dihydro-1H-quinolin-2-one | 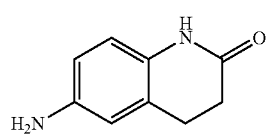 [SMILES: Nc1ccc2c(c1)CCC(=O)N2] | Enamine-BB |
| 4-(1-tert-butoxycarbonyl-4-piperidyl)-2-morpholino-pyrimidine-5-carboxylic acid | 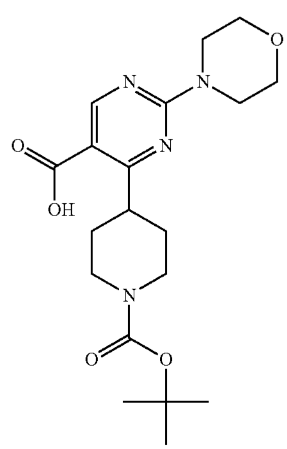 [SMILES: CC(C)(C)OC(=O)N1CCC(c2nc(N3CCOCC3)ncc2C(=O)O)CC1] | ChemDiv |

| IUPAC_NAME | Structure | SUPPLIER |
|---|---|---|
| 5-(benzenesulfonamido)-2-(4-methylpiperazin-1-yl)benzoic acid | 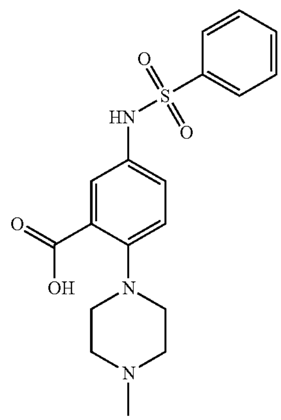 [SMILES: CN1CCN(c2ccc(NS(=O)(=O)c3ccccc3)cc2C(=O)O)CC1] | ChemDiv |
| 5-(ethylsulfonylamino)-2-(4-methylpiperazin-1-yl)benzoic acid | 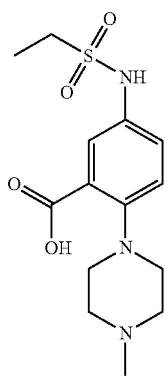 [SMILES: CCS(=O)(=O)Nc1ccc(N2CCN(C)CC2)c(C(=O)O)c1] | ChemDiv |
| 2-(methanesulfonamido)-5-morpholino-benzoic acid | 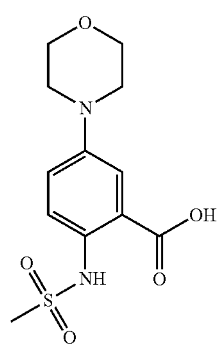 [SMILES: CS(=O)(=O)Nc1ccc(N2CCOCC2)cc1C(=O)O] | ChemDiv |
| 6-amino-1-methyl-3,4-dihydroquinolin-2-one | 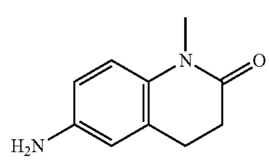 | Enamine-BB |
| 2,5-dimethylpiperidin-4-ol | 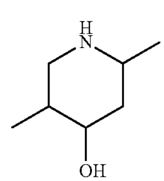 | InterBioScreen |

-continued

| IUPAC_NAME | Structure | SUPPLIER |
|---|---|---|
| 7-amino-4-methyl-1,4-benzoxazin-3-one | 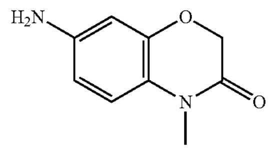 | Chembridge |
| 6-amino-1H-quinazoline-2,4-dione | 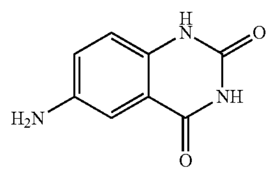 [SMILES: Nc1ccc2[nH]c(=O)[nH]c(=O)c2c1] | PrincetonBio |
| 6-amino-4-methyl-quinolin-2-ol | 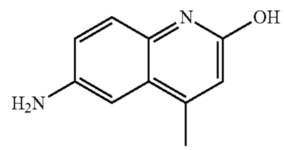 | PrincetonBio |
| 4-hydroxypyrrolidine-2-carboxamide | 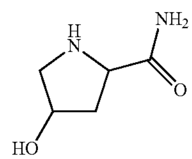 | Enamine-BB |
| 7-amino-4H-1,4-benzoxazin-3-one | 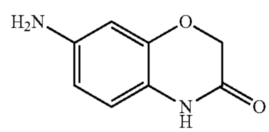 [SMILES: Nc1ccc2c(c1)OCC(=O)N2] | Enamine-BB |
| 3-pyrrolidin-2-ylpyridine | 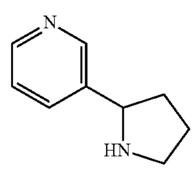 [SMILES: c1cncc(C2CCCN2)c1] | Enamine-BB |
| 3-(dimethylaminomethyl)-1H-indole-6-carboxylic acid | 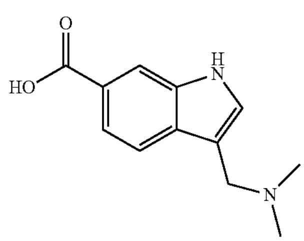 [SMILES: CN(C)Cc1c[nH]c2cc(C(=O)O)ccc12] | InterBioScreen |
| 2-phenylpiperidine | 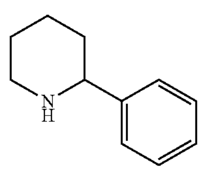 [SMILES: c1ccc(C2CCCCN2)cc1] | Sigma-Aldrich |
| morpholin-2-ylmethanol | 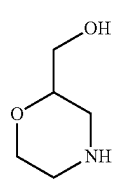 | Enamine-BB |

-continued

| IUPAC_NAME | Structure | SUPPLIER |
|---|---|---|
| 3-(cyclopentylsulfamoyl)-4-methyl-benzoic acid | 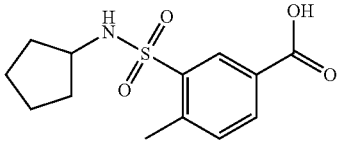 [SMILES: Cc1ccc(C(=O)O)cc1S(=O)(=O)NC1CCCC1] | Enamine-BB |
| 2-methylpyrrolidine | 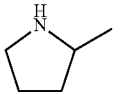 | Enamine-BB |
| 3-fluoropyrrolidine | 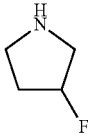 | Enamine-BB |
| pyrrolidin-3-ylmethanol | 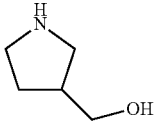 | Enamine-BB |
| 3-fluoro-3-methyl-pyrrolidine | 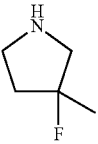 | Enamine-BB |
| pyrrolidine-3-carboxamide | 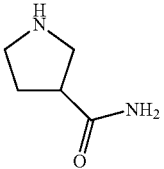 | Enamine-BB |
| 3-(methoxymethyl)pyrrolidine | 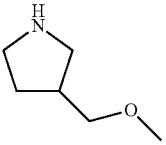 | Enamine-BB |
| 5-methyl-2,3,3a,4,6,6a-hexahydro-1H-pyrrolo[2,3-c]pyrrole | 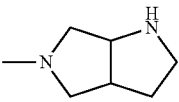 | Enamine-BB |
| 3-isobutylpyrrolidine | 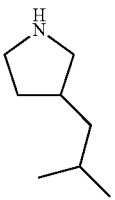 | Enamine-BB |
| N,N-dimethyl-1-pyrrolidin-2-yl-methanamine | 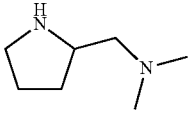 | Enamine-BB |

-continued

| IUPAC_NAME | Structure | SUPPLIER |
|---|---|---|
| N,N-dimethyl-1-pyrrolidin-3-yl-methanamine | 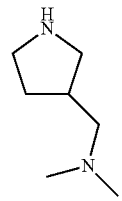 | Enamine-BB |
| 2-pyrrolidin-2-ylacetic acid | 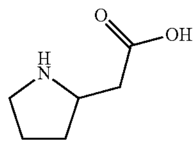 | Enamine-BB |
| pyrrolidin-3-ylurea | 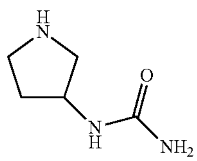 | Enamine-BB |
| 2-pyrrolidin-2-ylpropan-2-ol | 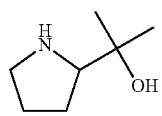 | Enamine-BB |
| (5-methylmorpholin-2-yl)methanol | 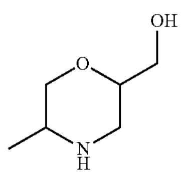 | Enamine-BB |
| 2-(methoxymethyl)morpholine | 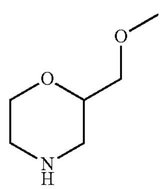 | Enamine-BB |
| 2-pyrrolidin-2-yl-1H-imidazole | 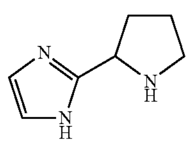 | Enamine-BB |
| 3-pyrrolidin-2-yl-1H-pyrazole | 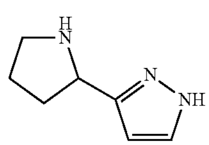 | Enamine-BB |
| 5-pyrrolidin-2-yl-1H-tetrazole | 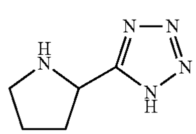 | Enamine-BB |

-continued

| IUPAC_NAME | Structure | SUPPLIER |
|---|---|---|
| 3-methyl-8-azabicyclo[3.2.1]octan-3-ol | 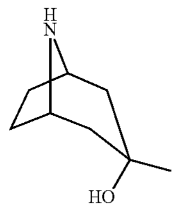 | Enamine-BB |
| 2,3,4,4a,5,7,8,8a-octahydro-1H-pyrano[4,3-b]pyridine | 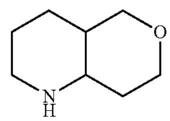 | Enamine-BB |
| 4-methyl-3,4a,5,6,7,7a-hexahydro-2H-pyrrolo[3,4-b][1,4]oxazine | 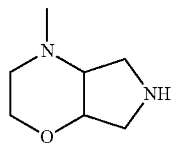 | Enamine-BB |
| 2-pyrrolidin-3-yloxyacetamide | 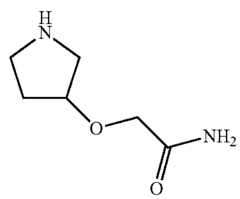 | Enamine-BB |
| N,N-dimethyl-1-morpholin-2-yl-methanamine | 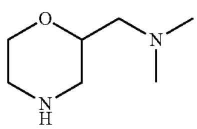 | Enamine-BB |
| 3-phenylpyrrolidine | 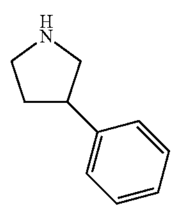 [SMILES: c1ccc(C2CCNC2)cc1] | Enamine-BB |
| 4-(2-piperidyl)pyrrolidin-2-one | 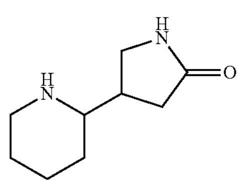 [SMILES: O=C1CC(C2CCCCN2)CN1] | Enamine-BB |
| 1-(pyrrolidin-2-ylmethyl)imidazole | 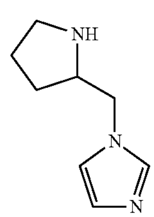 [SMILES: c1cn(CC2CCCN2)cn1] | Enamine-BB |

| IUPAC_NAME | Structure | SUPPLIER |
|---|---|---|
| 1-(pyrrolidin-2-ylmethyl)pyrazole | 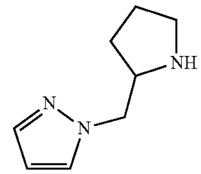 [SMILES: c1cnn(CC2CCCN2)c1] | Enamine-BB |
| 6-amino-4-hydroxy-1H-quinolin-2-one | 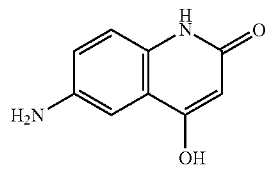 [SMILES: Nc1ccc2[nH]c(=O)cc(O)c2c1] | Accel Pharmtech |
| 6-amino-4-(trifluoromethyl)-1H-quinolin-2-one | 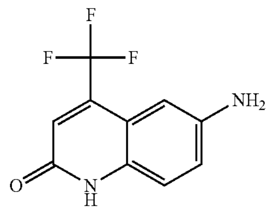 [SMILES: Nc1ccc2[nH]c(=O)cc(C(F)(F)F)c2c1] | Accel Pharmtech |
| 6-amino-3-methyl-1,4-dihydroquinazolin-2-one | 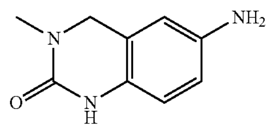 | Ukrorgsyn_BB |

Detailed description of the preparation of individual compounds according to formula (I) are described herein below.

Compound names were generated using Accelrys Draw 4.1, or Chemdraw Ultra 11.0.1.

Compounds were characterized using LC-MS analysis and/or $^1$H-Nuclear Magnetic Resonance (NMR) and were in all cases consistent with the proposed structures. Chemical shifts relating to NMR are reported in parts-per-million (ppm) and referenced from non-deuterated solvent residues. Conventional abbreviations for designation of major peaks were used, e.g. s, singlet; d, doublet; t, triplet; q, quartet; m, multiplet; br, broad. Abbreviations for common solvents are: Chloroform-d or CDCl$_3$, deuterochloroform; DMSO-d$_6$, hexadeuterodimethylsulfoxide; CD$_3$COOD, deuteroacetic acid; and CD$_3$OD, deuteromethanol.

Synthesis of Compound-1, Compound-2, Compound-3, and Compound-4

Compound-1

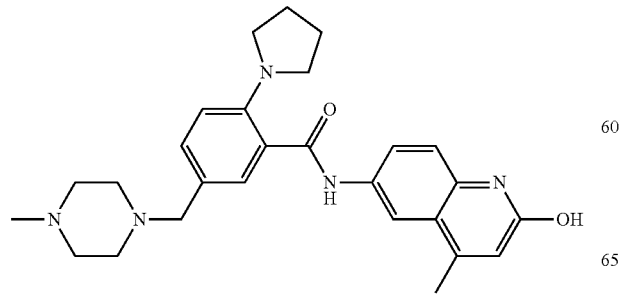

Compound-2

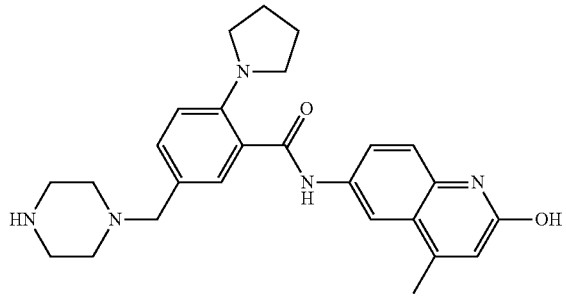

Compound-3

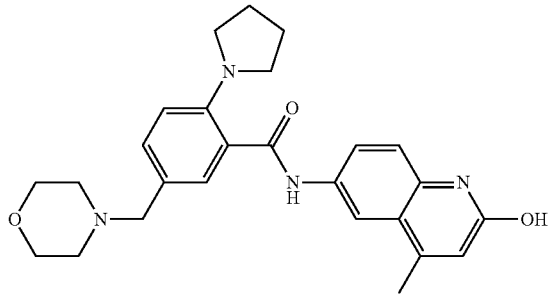

-continued

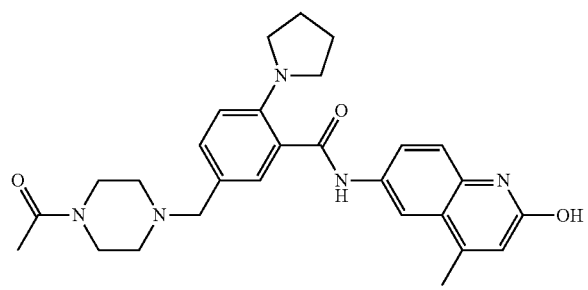
Compound-4

Synthesis of Compound-1:

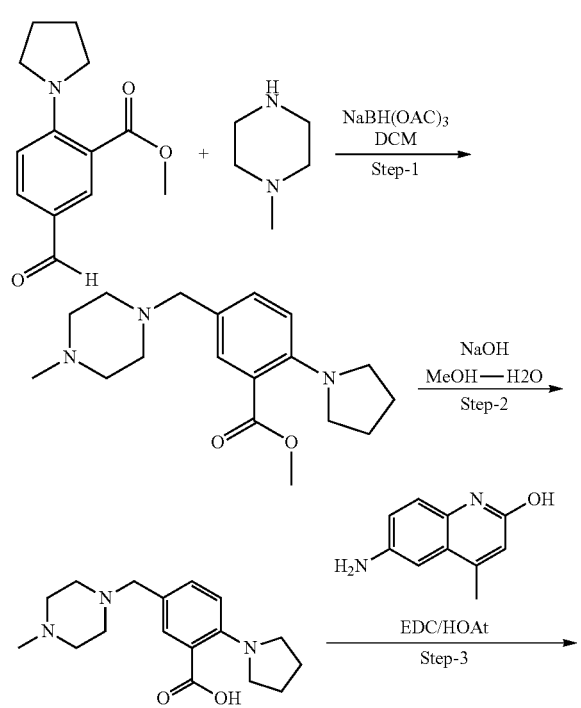

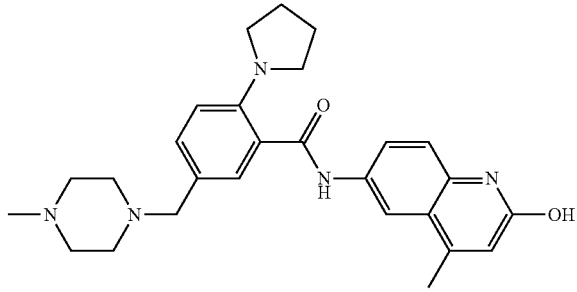
Compound-1

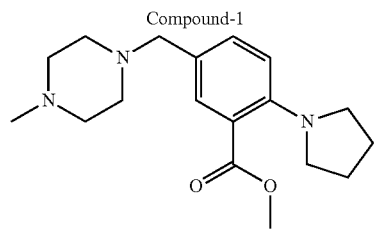
Compound-1

Preparation of methyl 5-((4-methylpiperazin-1-yl) methyl)-2-(pyrrolidin-1-yl) benzoate: to a solution of methyl 5-formyl-2-(pyrrolidin-1-yl)benzoate (600 mg, 2.575 mmol, 1 eq) in DCM (10 mL) at RT, was added molecular sieves powder (100 mg), 1-methylpiperazine (257 mg, 2.575 mmol, 1 eq), acetic acid (0.3 ml) followed by Sodium triacetoxy borohydride (1.08 g, 5.15 mmol, 2 eq) and stirred at RT for 16 h. After completion, the reaction mixture was filtered through celite pad, the filtrate was diluted with DCM (10 mL), washed with NaHCO$_3$ solution (10 mL), water (10 ml), brine (10 ml), dried over anhydrous Na$_2$SO$_4$, filtered and evaporated. The crude compound was purified by column chromatography using (SiO$_2$) by eluting MeOH:DCM (1:9) to afford methyl 5-((4-methylpiperazin-1-yl) methyl)-2-(pyrrolidin-1-yl) benzoate (450 mg, 55%) as off white solid.

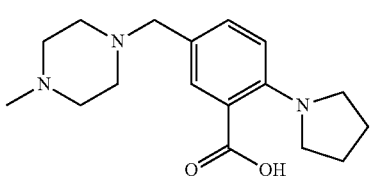 [SMILES: CN1CCN(Cc2ccc(N3CCCC3)c(C(=O)O)c2)CC1]

Preparation of 5-((4-methylpiperazin-1-yl) methyl)-2-(pyrrolidin-1-yl) benzoic acid: to a solution of methyl 5-((4-methylpiperazin-1-yl)methyl)-2-(pyrrolidin-1-yl)benzoate (450 mg, 1.419 mmol, 1 eq) in MeOH—H$_2$O (3:1, 10 mL) at 0° C. added NaOH (170 mg, 4.258 mmol, 3 eq) and stirred at 60° C. for 5 h. After completion, the solvent was evaporated, the reaction mixture was acidified by using 1 N HCl and the solvent was evaporated. The residue was dissolved in MeOH, the insoluble inorganic material was filtered and the filtrate was evaporated to afford 5-((4-methylpiperazin-1-yl) methyl)-2-(pyrrolidin-1-yl) benzoic acid 280 mg (65%) as off white solid. LCMS analysis indicated 97.95% desired product.

$^1$H NMR (400 MHz, CD$_3$OD) δ 8.46 (d, J=2.1 Hz, 1H), 8.13 (dd, J=8.3, 2.2 Hz, 1H), 7.97 (d, J=8.5 Hz, 1H), 4.52 (s, 2H), 3.98-3.83 (m, 4H), 3.55 (d, J=56.3 Hz, 8H), 3.00 (s, 3H), 2.42-2.30 (m, 4H).

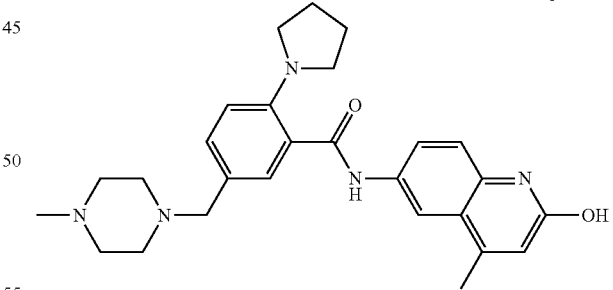
Compound-1

Preparation of N-(2-hydroxy-4-methylquinolin-6-yl)-5-((4-methylpiperazin-1-yl)methyl)-2-(pyrrolidin-1-yl)benzamide (Compound-1): to a solution of 5-((4-methylpiperazin-1-yl)methyl)-2-(pyrrolidin-1-yl) benzoic acid (150 mg, 0.495 mmol, 1 eq) in DMF (3 mL) added HOAT (67.3 MG, 0.495 mmol, 1 eq), EDC (94.5 mg, 0.495 mmol, 1 eq), DIPEA (0.17 ml, 0.99 mmol, 2 eq) and 6-amino-4-methylquinolin-2-ol (86.1 mg, 0.495 mmol, 1 eq) and stirred at RT for 16 h. After completion, the reaction mixture was poured into ice water and extracted with EtOAc (3×10 mL). The combined extracts were washed with water (10 mL), brine (10 mL), dried over anhydrous $Na_2SO_4$, filtered and evaporated The crude compound was purified by Prep HPLC to afford N-(2-hydroxy-4-methylquinolin-6-yl)-5-((4-methylpiperazin-1-yl)methyl)-2-(pyrrolidin-1-yl)benzamide (Compound-1) (10 mg) as off white solid. LCMS analysis indicated 97.36% desired product.

$^1$H NMR (400 MHz, DMSO-$d_6$) δ 11.54 (s, 1H), 10.44 (s, 1H), 8.15 (d, J=2.2 Hz, 1H), 7.81 (dd, J=8.8, 2.3 Hz, 1H), 7.27 (d, J=8.9 Hz, 1H), 7.24-7.14 (m, 2H), 6.76 (d, J=8.3 Hz, 1H), 6.41 (s, 1H), 3.36 (s, 2H), 3.25-3.16 (m, 4H), 2.44-2.23 (m, 11H), 2.14 (s, 3H), 1.85 (q, J=3.3 Hz, 4H).

Compound-3 was made according to the above procedure using morpholine instead of 1-methylpiperazine in step-1:

$^1$H NMR (400 MHz, DMSO-$d_6$) δ 11.55 (s, 1H), 10.44 (s, 1H), 8.15 (d, J=2.2 Hz, 1H), 7.81 (dd, J=8.9, 2.2 Hz, 1H), 7.27 (d, J=8.8 Hz, 1H), 7.24-7.18 (m, 2H), 6.76 (d, J=8.3 Hz, 1H), 6.42 (d, J=1.9 Hz, 1H), 3.56 (t, J=4.5 Hz, 4H), 3.37 (s, 2H), 3.26-3.13 (m, 4H), 2.43-2.30 (m, 7H), 1.92-1.79 (m, 4H).

Compound-2 was made using tert-butoxycarbonyl piperazine in step-1 and a deprotection step following step-3:

5-[(4-tert-butoxycarbonylpiperazin-1-yl)methyl]-2-pyrrolidin-1-yl-benzoic acid $^1$H NMR (400 MHz, DMSO-$d_6$) δ 13.66 (s, 1H), 7.47 (d, J=2.2 Hz, 1H), 7.27 (dd, J=8.4, 2.2 Hz, 1H), 6.92 (d, J=8.5 Hz, 1H), 3.38 (s, 2H), 3.32-3.24 (m, 4H), 3.23-3.13 (m, 4H), 2.27 (t, J=4.9 Hz, 4H), 1.90 (p, J=3.7 Hz, 4H), 1.38 (s, 9H).

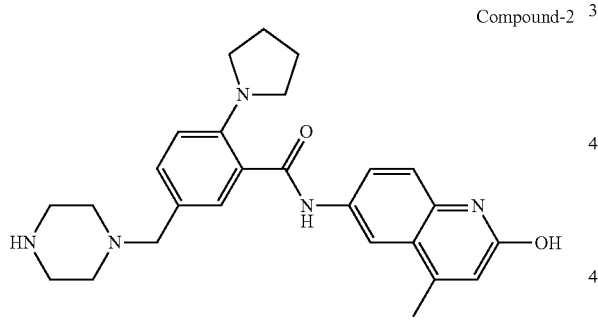

Compound-2

Preparation of N-(2-hydroxy-4-methylquinolin-6-yl)-5-(piperazin-1-ylmethyl)-2-(pyrrolidin-1-yl)benzamide (Compound-2): to a solution of tert-butyl 4-(3-(2-hydroxy-4-methylquinolin-6-ylcarbamoyl)-4-(pyrrolidin-1-yl)benzyl)piperazine-1-carboxylate (25 mg, 0.0458 mmol, 1 eq) in 1,4-Dioxane (3 mL), added HCl in dioxane (2 ml), and stirred at RT for 16 h. After completion, the solvent was evaporated. The crude compound was washed with diethyl ether to afford N-(2-hydroxy-4-methylquinolin-6-yl)-5-(piperazin-1-ylmethyl)-2-(pyrrolidin-1-yl)benzamide (Compound-2) (18 mg, 90%) as HCl salt as an off white solid.

$^1$H NMR (400 MHz, DMSO-$d_6$) δ 11.60 (s, 1H), 11.39 (s, 1H), 10.46 (s, 1H), 9.47 (s, 2H), 8.18 (s, 1H), 7.86 (d, J=8.7 Hz, 1H), 7.57 (s, 1H), 7.49 (d, J=8.2 Hz, 1H), 7.28 (d, J=8.6 Hz, 1H), 6.81 (d, J=8.4 Hz, 1H), 6.43 (s, 1H), 4.28 (s, 1H), 3.51 (s, 4H), 3.39 (s, 2H), 3.32-3.09 (m, 6H), 2.39 (s, 3H), 1.88 (d, J=5.9 Hz, 4H).

Synthesis of Compound-3 and Compound-4:

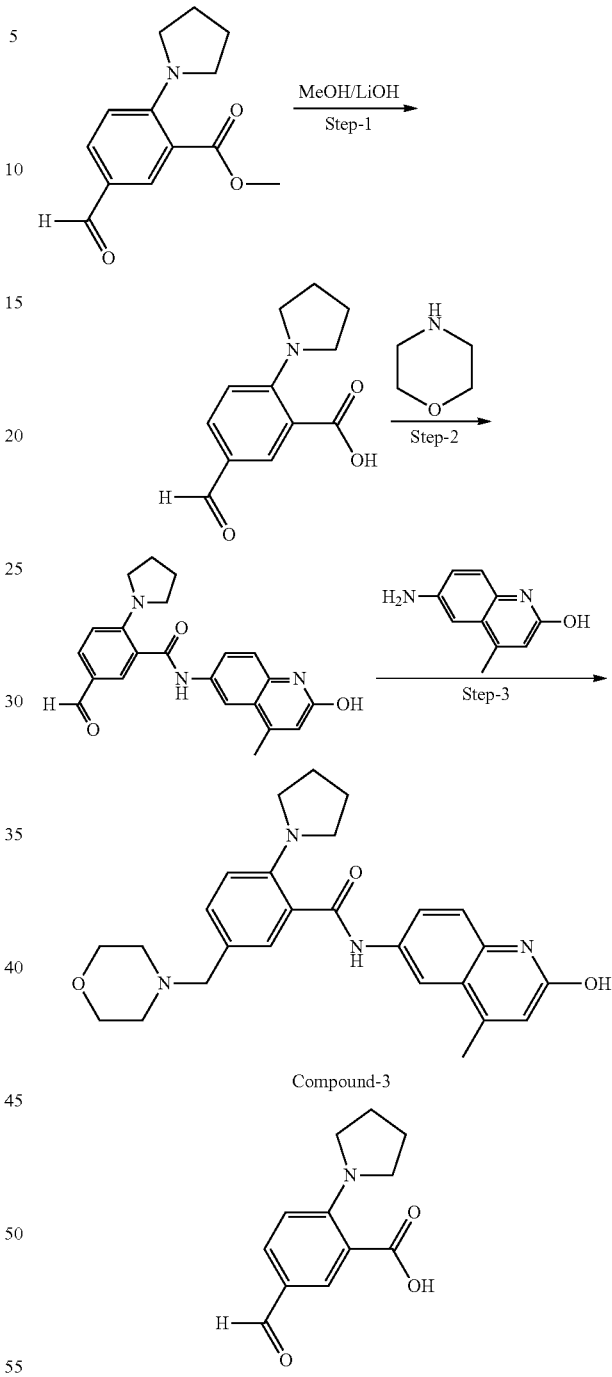

Preparation of 5-formyl-2-(pyrrolidin-1-yl) benzoic acid: to a solution of methyl 5-formyl-2-(pyrrolidin-1-yl)benzoate (1.1 g, 4.71 mmol, 1 eq) in MeOH (11 mL) at RT, added 4N NaOH (377 mg, 9.42 mmol, 2 eq) and stirred at 75° C. for 16 h. After completion, the solvent was evaporated, diluted with water and pH was adjusted to acidic using 1N HCl solution and extracted with EtOAc (3×30 mL). The combined extracts were dried over anhydrous $Na_2SO_4$, filtered and evaporated to afford 5-formyl-2-(pyrrolidin-1-yl) benzoic acid (900 mg, 87.3%) as pale yellow color solid.

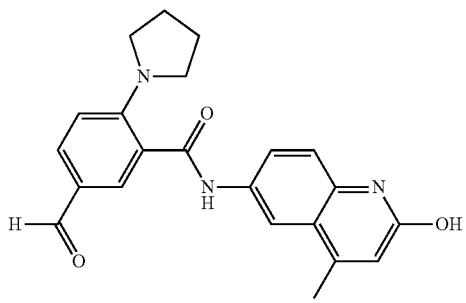 [SMILES: Cc1cc(O)nc2ccc(NC(=O)c3cc(C=O)ccc3N3CCCC3)cc12]

Preparation of 5-formyl-N-(2-hydroxy-4-methylquinolin-6-yl)-2-(pyrrolidin-1-yl) benzamide: to a solution of 5-formyl-2-(pyrrolidin-1-yl)benzoic acid (900 mg, 4.109 mmol, 1 eq) in DMF (9 ml) added HOAt (558.8 mg, 4.109 mmol, 1 eq), DIPEA (1.59 g, 12.327 mmol, 3 eq), morpholine (715 mg, 4.109 mmol, 1 eq) and EDC (784.8 mg, 4.109 mmol, 1 eq) at room temperature and stirred at 90° C. for 48 h. After completion, the reaction mixture was poured into water solid that precipitated was separated by filtration. The crude compound was purified by preparative HPLC to afford 5-formyl-N-(2-hydroxy-4-methylquinolin-6-yl)-2-(pyrrolidin-1-yl)benzamide (350 mg, 22.7%) as off white solid. LCMS analysis indicated 98.1% desired product.

$^1$H NMR (400 MHz, DMSO-$d_6$) δ 11.57 (s, 1H), 10.58 (s, 1H), 9.74 (s, 1H), 8.13 (d, J=2.3 Hz, 1H), 7.88-7.80 (m, 2H), 7.77 (dd, J=8.8, 2.1 Hz, 1H), 7.29 (d, J=8.8 Hz, 1H), 6.87 (d, J=8.8 Hz, 1H), 3.45-3.35 (m, 4H), 2.39 (d, J=1.3 Hz, 3H), 1.97-1.84 (m, 4H).

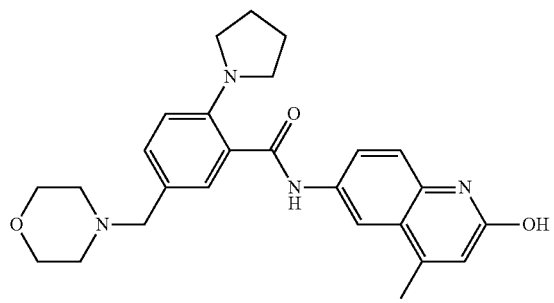 [SMILES: Cc1cc(O)nc2ccc(NC(=O)c3cc(CN4CCOCC4)ccc3N3CCCC3)cc12]

Preparation of N-(2-hydroxy-4-methylquinolin-6-yl)-5-(morpholinomethyl)-2-(pyrrolidin-1-yl)benzamide (Compound-3): to a solution of 5-formyl-N-(2-hydroxy-4-methylquinolin-6-yl)-2-(pyrrolidin-1-yl) benzamide (95 mg, 0.253 mmol, 1 eq) in DMSO (0.95 mL), added morpholine (22.04 mg, 0.253 mmol, 1 eq), NaBH(OAc)$_3$ (107.2 mg, 0.506 mmol, 2 eq), molecular sieves powder and AcOH (catalytic) and stirred at room temperature for 16 h. After completion, the reaction mixture was poured into water, unwanted salts were separated by filtering through celite bed and extracted with EtOAc (2×1 mL). The combined extracts were dried over anhydrous Na$_2$SO$_4$, filtered and evaporated. The crude compound was purified by preparative HPLC to afford N-(2-hydroxy-4-methylquinolin-6-yl)-5-(morpholinomethyl)-2-(pyrrolidin-1-yl) benzamide (Compound-3) (35 mg, 31.5%) as off white solid. LCMS analysis indicated 99.7% desired product.

$^1$H NMR (400 MHz, DMSO-$d_6$) δ 11.55 (s, 1H), 10.44 (s, 1H), 8.15 (d, J=2.2 Hz, 1H), 7.81 (dd, J=8.9, 2.2 Hz, 1H), 7.27 (d, J=8.8 Hz, 1H), 7.24-7.18 (m, 2H), 6.76 (d, J=8.3 Hz, 1H), 6.42 (d, J=1.9 Hz, 1H), 3.56 (t, J=4.5 Hz, 4H), 3.37 (s, 2H), 3.26-3.13 (m, 4H), 2.43-2.30 (m, 7H), 1.92-1.79 (m, 4H).

Compound-4 was made using acetyl piperazine in step-2:
$^1$H NMR (400 MHz, DMSO-$d_6$) δ 11.55 (s, 1H), 10.44 (s, 1H), 8.15 (d, J=2.3 Hz, 1H), 7.81 (dd, J=8.9, 2.3 Hz, 1H), 7.32-7.18 (m, 3H), 6.77 (d, J=8.2 Hz, 1H), 6.41 (s, 1H), 3.41 (d, J=4.5 Hz, 6H), 3.23 (d, J=6.4 Hz, 4H), 2.43-2.26 (m, 7H), 1.97 (s, 3H), 1.85 (q, J=3.3 Hz, 4H).

Synthesis of Compound-5, Compound-6, Compound-7, and Compound-8:

Compound-5

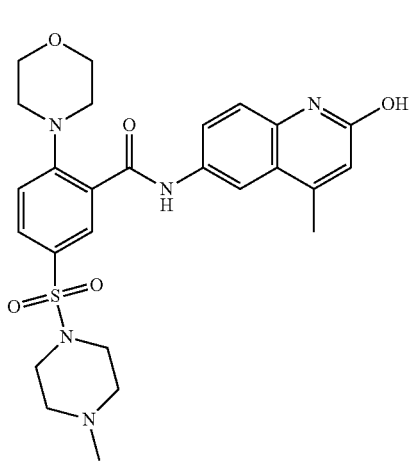

Compound-6

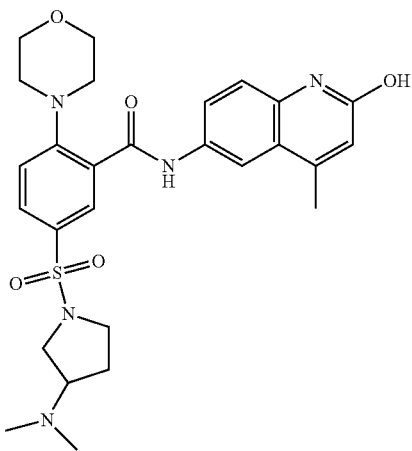

Compound-7

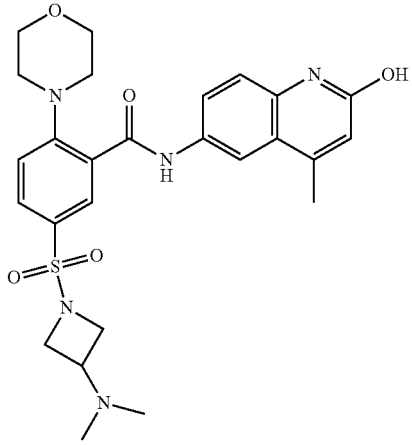

77

-continued

Compound-8

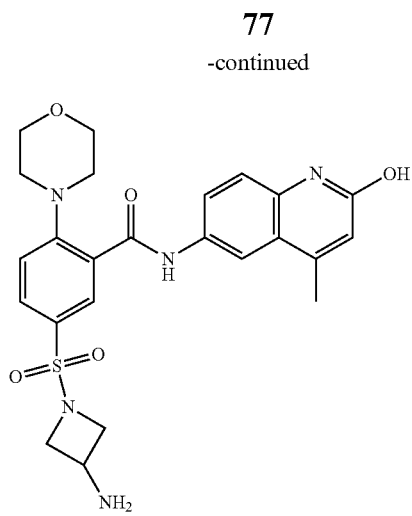

Scheme:

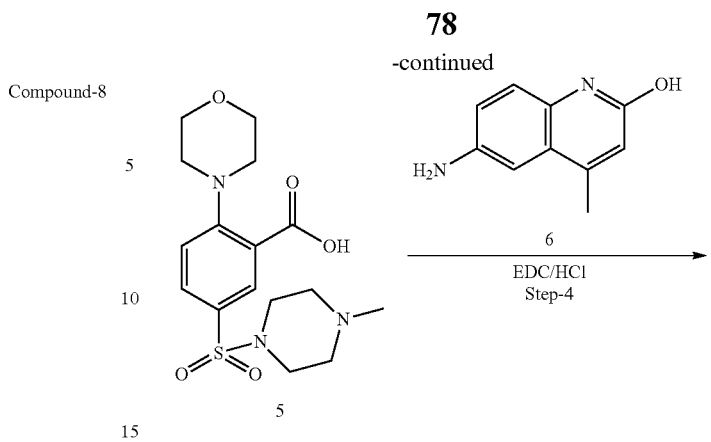

78

-continued

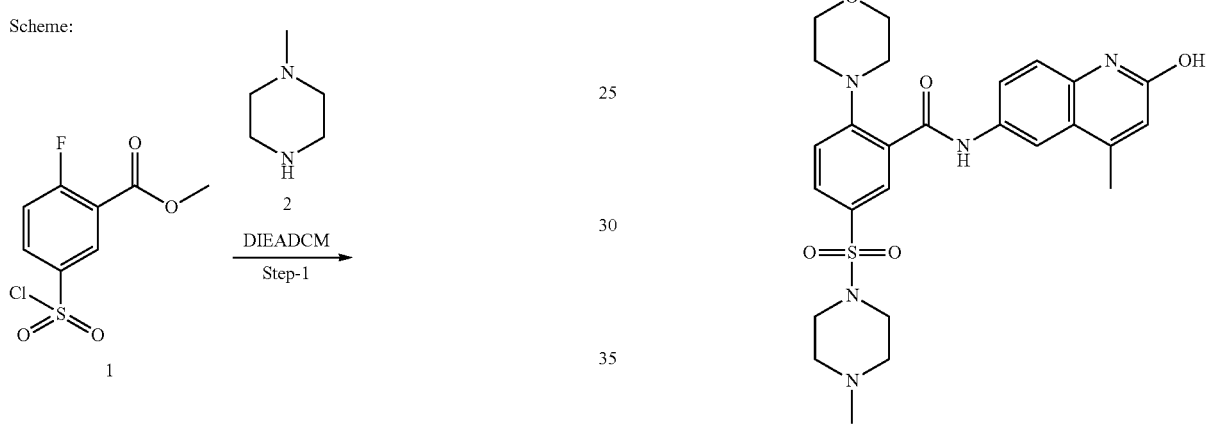

Compound-5

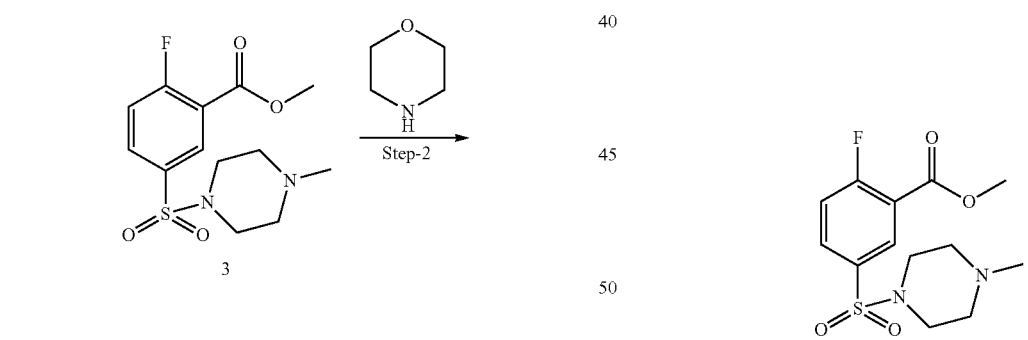

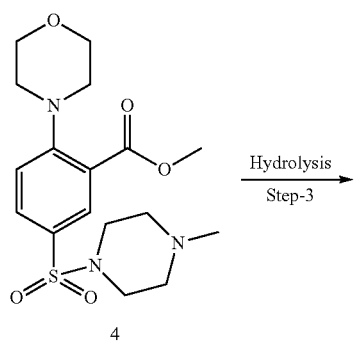

Preparation of methyl 2-fluoro-5-(4-methylpiperazin-1-ylsulfonyl) benzoate: to a solution of methyl 5-(chlorosulfonyl)-2-fluorobenzoate (150 mg, 0.59 mmol, 1 eq) in dry DCM (3 mL) added DIEA (304 mg, 2.36 mmol, 4 eq), then added N-Methyl Piperazine (59 mg, 0.59 mmol, 1 eq) and stirred at RT for 16 h. After completion, the reaction mixture was poured into water and extracted with DCM (2×15 mL). The combined extracts were washed with water (15 mL), brine (15 mL), dried over anhydrous $Na_2SO_4$, filtered and evaporated. The crude was purified by column chromatography using ($SiO_2$) by eluting (4:6) (EtOAc:Pet ether) to afford methyl 2-fluoro-5-(4-methylpiperazin-1-ylsulfonyl) benzoate (150 mg, 79.7%).

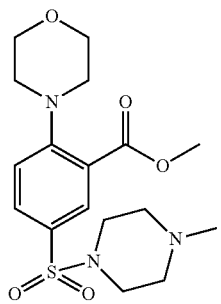 [SMILES: COC(=O)c1cc(S(=O)(=O)N2CCN(C)CC2)ccc1N1CCOCC1]

Preparation of methyl 5-(4-methylpiperazin-1-ylsulfonyl)-2-morpholinobenzoate

To a solution of methyl 2-fluoro-5-(4-methylpiperazin-1-ylsulfonyl) benzoate (140 mg, 0.44 mmol, 1 eq), in dry DMSO (3 mL) added DIPEA (170 mg, 1.32 mmol, 3 eq) and morpholine (38 mg, 0.44 mmol, 1 eq) and stirred at RT for 3 h. After completion, the reaction mixture was poured into water and extracted with EtOAc (2×15 mL). The combined extracts were washed with water (2×15 mL), brine (15 mL), dried over anhydrous Na$_2$SO$_4$, filtered and evaporated to afford methyl 5-(4-methylpiperazin-1-ylsulfonyl)-2-morpholinobenzoate (130 mg, 76%).

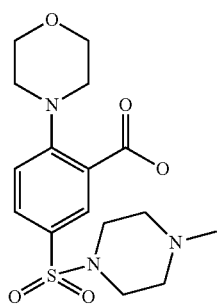 [SMILES: CN1CCN(S(=O)(=O)c2ccc(N3CCOCC3)c(C(=O)O)c2)CC1]

Preparation of 5-(4-methylpiperazin-1-ylsulfonyl)-2-morpholinobenzoic acid: to a solution of methyl 5-(4-methylpiperazin-1-ylsulfonyl)-2-morpholinobenzoate (50 mg, 0.13 mmol, 1 eq) in MeOH (2 mL) added LiOH.H$_2$O (10.9 mg, 0.26 mmol, 2 eq) and stirred at RT for 16 h. After completion, the solvent was evaporated, the solid residue was taken in 1, 4-Dioxane (1 mL) added HCl in 1, 4-Dioxane (0.5 mL) stirred at RT for 30 min. After completion, the solvent was evaporated to afford 5-(4-methylpiperazin-1-ylsulfonyl)-2-morpholinobenzoic acid (40 mg) as HCl salt.

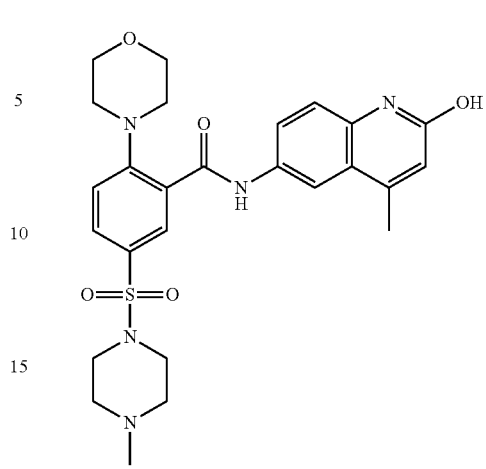

Compound-5

Preparation of N-(2-hydroxy-4-methyl quinolin-6-yl)-5-(4-methyl piperazin-1-ylsulfonyl)-2-morpholino benzamide (Compound-5): to a solution of 5-(4-methylpiperazin-1-ylsulfonyl)-2-morpholinobenzoic acid (30 mg, 0.0813 mmol, 1 eq) in dry DMF (1 mL) added DIPEA (31.4 mg, 0.243 mmol, 3 eq), HOAt (11 mg, 0.0813 mmol, 1 eq), (14 mg, 0.0813 mmol, 1 eq) then added EDC (15 mg, 0.0813 mmol, 1 eq) and stirred at RT for 48 h. After completion, the reaction mixture was poured into water and extracted with EtOAc (2×10 mL). The combined extracts were washed with water (2×10 mL), brine (10 mL), dried over anhydrous Na$_2$SO$_4$, filtered and evaporated. The crude compound was purified by preparative HPLC to afford N-(2-hydroxy-4-methyl quinolin-6-yl)-5-(4-methylpiperazin-1-ylsulfonyl)-2-morpholino benzamide (Compound-5) (13 mg, 30.9%) as off white solid. LCMS analysis indicated 93.7% desired product.

$^1$H NMR (400 MHz, DMSO-d$_6$) δ 11.59 (s, 1H), 10.67 (s, 1H), 8.22 (d, J=2.3 Hz, 1H), 7.83-7.73 (m, 3H), 7.32 (d, J=8.6 Hz, 2H), 6.44 (s, 1H), 3.66 (t, J=4.4 Hz, 4H), 3.20-3.09 (m, 4H), 2.89 (s, 4H), 2.43-2.30 (m, 7H), 2.14 (s, 3H).

Compound-6 was made according to the above procedure using 3-dimethylaminopyrrolidine instead of N-Methyl Piperazine in step-1:

$^1$H NMR (400 MHz, CD$_3$COOD) δ 8.60 (d, J=2.4 Hz, 1H), 8.37 (d, J=2.3 Hz, 1H), 8.04 (dd, J=8.6, 2.4 Hz, 1H), 7.98 (dd, J=8.9, 2.2 Hz, 1H), 7.56 (d, J=8.8 Hz, 1H), 7.47 (d, J=8.7 Hz, 1H), 6.89 (s, 1H), 4.07-3.92 (m, 5H), 3.77-3.53 (m, 3H), 3.38-3.25 (m, 5H), 2.95 (s, 6H), 2.67 (s, 3H), 2.48-2.22 (m, 2H).

Compound-7 was made using dimethylaminoazetidine in step-1:

$^1$H NMR (400 MHz, DMSO-d$_6$) δ 11.58 (s, 1H), 10.69 (s, 1H), 8.22 (d, J=2.3 Hz, 1H), 7.87-7.78 (m, 3H), 7.34 (dd, J=10.0, 8.5 Hz, 2H), 6.43 (s, 1H), 3.74 (t, J=7.4 Hz, 2H), 3.68 (t, J=4.4 Hz, 4H), 3.42 (dd, J=8.1, 6.2 Hz, 2H), 3.16 (q, J=5.2, 4.6 Hz, 4H), 2.96 (q, J=6.7 Hz, 1H), 2.41 (d, J=1.4 Hz, 3H), 1.91 (s, 6H).

Compound-8 was made using tert-butyl azetidin-3-ylcarbamate in step-1 followed by a deprotection step:

Compound-8

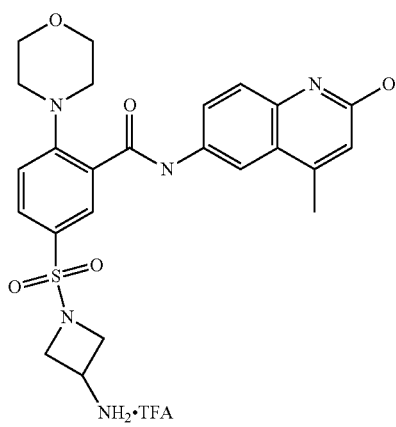

Compound-10

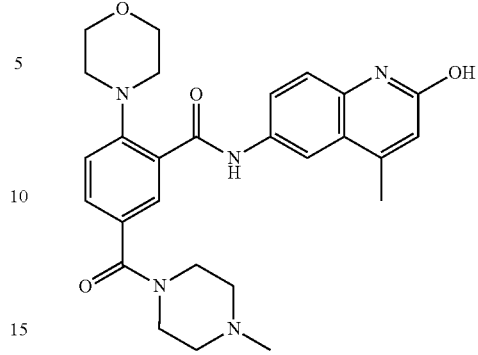

Compound-11

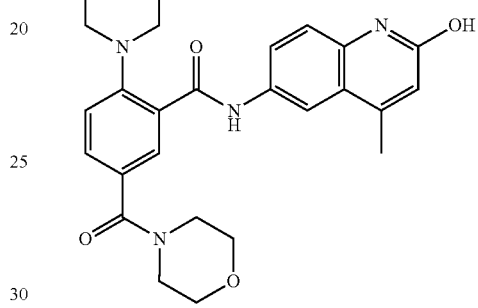

Compound-12

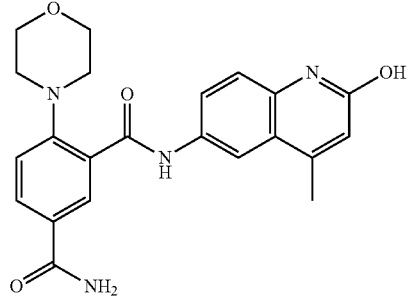

Preparation of 1-(3-(2-hydroxy-4-methylquinolin-6-yl-carbamoyl)-4-morpholinophenylsulfonyl) azetidin-3-aminium 2, 2, 2-trifluoroacetate (Compound-8): to a solution of tert-butyl 1-(3-(2-hydroxy-4-methylquinolin-6-ylcarbamoyl)-4-morpholinophenylsulfonyl) azetidin-3-ylcarbamate (25 mg, 0.0418 mmol, 1 eq) in DCM (0.5 mL) added TFA (19 mg, 0.167 mmol, 4 eq) in DCM (0.5 mL) at 0° C. and stirred at RT for 16 h. After completion, the solvent was evaporated. The solid residue was triturated with Et₂O and dried to afford 1-(3-(2-hydroxy-4-methylquinolin-6-ylcarbamoyl)-4-morpholinophenylsulfonyl) azetidin-3-aminium 2, 2, 2-trifluoroacetate (Compound-8) (21 mg, 82.3%) as off-white solid. LCMS analysis indicated 99.07% of desired product.

¹H NMR (400 MHz, DMSO-d6) δ 11.60 (s, 1H), 10.67 (s, 1H), 8.33-8.16 (m, 4H), 7.90-7.76 (m, 3H), 7.33 (dd, J=8.7, 5.3 Hz, 2H), 6.44 (s, 1H), 3.97-3.83 (m, 3H), 3.76 (dd, J=8.3, 4.0 Hz, 2H), 3.69 (t, J=4.5 Hz, 4H), 3.17 (t, J=4.5 Hz, 4H), 2.41 (s, 3H).

Synthesis of Compound-9, Compound-11, Compound-10, Compound-12:

Compound-9

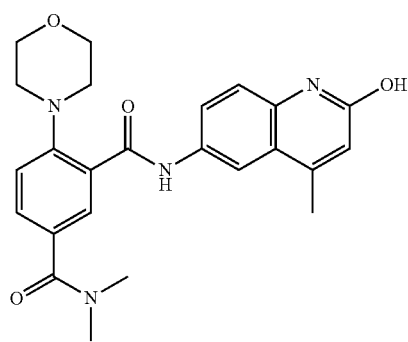

Scheme:

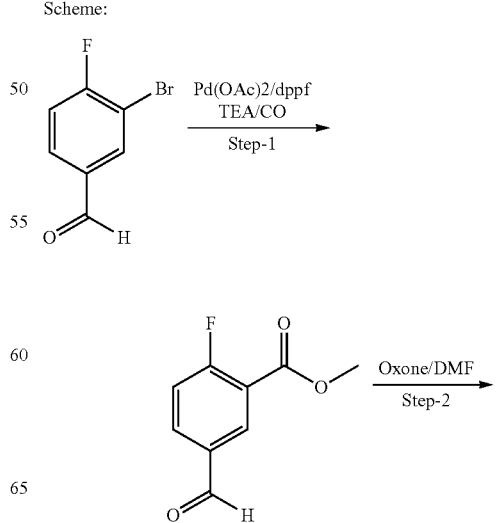

-continued

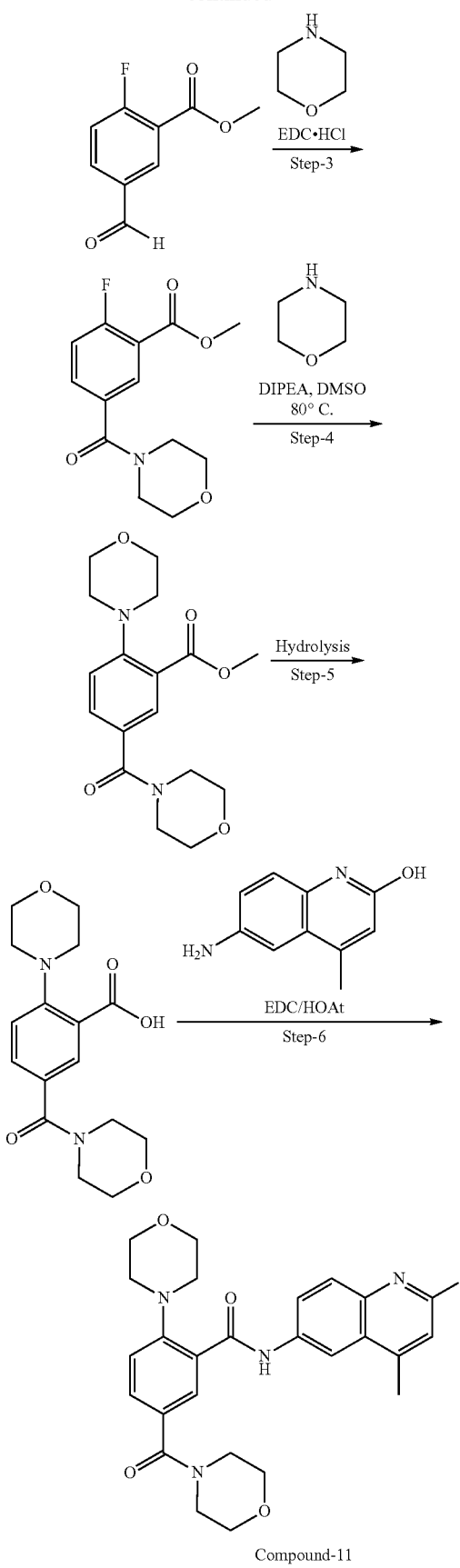

Compound-11

-continued

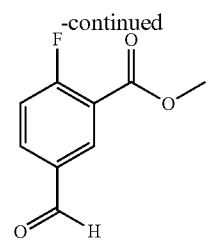

Preparation of methyl 2-fluoro-5-formylbenzoate: to a solution of 3-bromo-4-fluorobenzaldehyde (10 g, 49.26 mmol, 1 eq) in dry MeOH (25 ml) and Dry DMF (45 ml) at RT, added dppf (1.36 g, 2.463 mmol, 0.05 eq), Palladium acetate (0.31 g, 1.379 mmol, 0.028 eq) followed by Triethyl amine (9.95 g, 98.52 mmol, 2.0 eq) in steel pressure reactor (autoclave) with 80 Psi of CO gas and stirred at 80° C. for 24 h. After completion, solvent was evaporated. The reaction mixture was poured into water and extracted with EtOAc (3×100 mL). The combined extracts were washed with water (1 L), brine (1 L), dried over anhydrous $Na_2SO_4$, filtered and evaporated. The crude compound was purified by flash column chromatography using ($SiO_2$) by eluting EtOAc:Pet ether (6:94) to afford methyl 2-fluoro-5-formylbenzoate (6 g, 66.9%) as an off white solid. LCMS analysis indicated 98% desired product.

Preparation of 4-fluoro-3-(methoxycarbonyl) benzoic acid: to a solution of methyl 2-fluoro-5-formylbenzoate (6 g, 32.96 mmol, 1 eq) in Dry DMF (60 mL), added Oxone (20.23 g, 32.96 mmol, 1 eq) and stirred at RT for 3 h. After completion, the reaction mixture was acidified with 1N HCl and extracted with EtOAc (3×100 mL). The combined extracts were washed with water (3×100 mL), brine (1×100 mL), dried over anhydrous $Na_2SO_4$, filtered and evaporated to afford 4-fluoro-3-(methoxycarbonyl)benzoic acid (6 g, 92%) as an off white solid. LCMS analysis indicated 99% desired product.

Preparation of methyl 2-fluoro-5-(morpholine-4-carbonyl) benzoate: to a solution of 4-fluoro-3-(methoxycarbonyl)benzoic acid (500 mg, 2.52 mmol, 1 eq) in Dry DMF (10 mL), added HOAt (685 mg, 5.04 mmol, 2 eq), EDC (966 mg, 5.04 mmol, 2 eq), DIPEA (0.86 mL, 5.04 mmol, 2 eq), morpholine (263 mg, 3.02 mmol, 1.2 eq) and stirred at RT for 16 h. After completion, the reaction mixture was poured into ice water and extracted with EtOAc (2×20 mL). The combined extracts were washed with water (30 mL), brine (30 mL), dried over anhydrous Na₂SO₄, filtered and evaporated. The crude compound was purified by flash column chromatography using (SiO₂) by eluting EtOAc:Pet ether (25:75) to afford methyl 2-fluoro-5-(morpholine-4-carbonyl) benzoate (400 mg, 59%) as an off white solid. LCMS analysis indicated 95% desired product.

$^1$H NMR (400 MHz, DMSO-d6) δ 7.90 (dd, J=7.0, 2.3 Hz, 1H), 7.78-7.69 (m, 1H), 7.44 (dd, J=10.8, 8.5 Hz, 1H), 3.87 (s, 3H), 3.59 (brs, 8H).

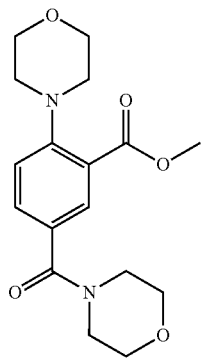 [SMILES: COC(=O)c1cc(C(=O)N2CCOCC2)ccc1N1CCOCC1]

Preparation of methyl 5-(morpholine-4-carbonyl)-2-morpholinobenzoate: to a solution of 2-fluoro-5-(morpholine-4-carbonyl) benzoate (400 mg, 1.872 mmol, 1 eq) in DMSO (10 vol), added morpholine (245 mg, 2.808 mmol, 1.5 eq), DIPEA (0.96 mL, 5.61 mmol, 3 eq) and stirred at 80° C. for 18 h. After completion, the reaction mixture was poured into ice water and extracted with EtOAc (2×20 mL). The combined extracts were washed with water (30 mL), brine (30 mL), dried over anhydrous Na₂SO₄, filtered and evaporated. The crude compound was purified by column chromatography using (SiO₂) by eluting EtOAc:Pet ether (50:50) to afford methyl 5-(morpholine-4-carbonyl)-2-morpholinobenzoate (300 mg, 60%) as pale yellow solid. LCMS analysis indicated 95% desired product.

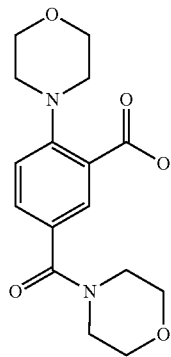 [SMILES: O=C(O)c1cc(C(=O)N2CCOCC2)ccc1N1CCOCC1]

Preparation of 5-(morpholine-4-carbonyl)-2-morpholinobenzoic acid: to a solution of methyl 5-(morpholine-4-carbonyl)-2-morpholinobenzoate (300 mg, 1.136 mmol, 1 eq) in MeOH:H₂O (3:1) (9 ml) at RT added LiOH (142.9 mg, 3.408 mmol, 3.0 eq) and stirred at RT for 5 h. After completion, solvent was evaporated. The crude acidified with 1N HCl and extracted with EtOAc (2×20 mL). The combined extracts were washed with water (20 mL), brine (20 mL), dried over anhydrous Na₂SO₄, filtered and evaporated to afford 5-(morpholine-4-carbonyl)-2-morpholinobenzoic acid (200 mg 69%) as brown solid. The crude was carried to next step without further purification.

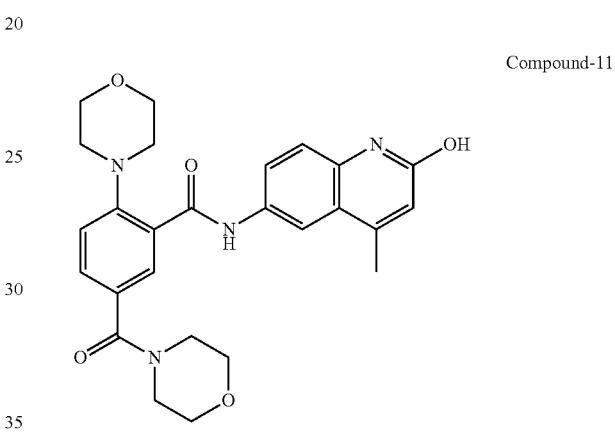

Compound-11

Preparation of N-(2-hydroxy-4-methyl quinolin-6-yl)-5-(morpholine-4-carbonyl)-2-morpholinobenzamide (Compound-11): to a solution of 5-(morpholine-4-carbonyl)-2-morpholinobenzoic acid (200 mg, 0.625 mmol, 1 eq) in Dry DMF (10 mL) at RT added 6-amino-4-methyl-quinolin-2-ol (108.8 mg, 0.625 mmol, 1 eq), HOAt (85 mg, 0.625 mmol, 1 eq), EDC (119.8 mg, 0.625 mmol, 1 eq), DIPEA (322.5 mg, 2.5 mmol, 4 eq) and stirred at RT for 16 h. After completion, the reaction mixture poured into ice water, solid obtained was filtered, washed with DMSO and Ether to afford N-(2-hydroxy-4-methylquinolin-6-yl)-5-(morpholine-4-carbonyl)-2-morpholinobenzamide (Compound-11) (45 mg, 22.5%) as off white solid. LCMS analysis indicated 96.9% desired product.

$^1$H NMR (400 MHz, DMSO-d₆) δ 11.59 (s, 1H), 10.89 (s, 1H), 8.24 (d, J=2.3 Hz, 1H), 7.81 (dd, J=8.8, 2.3 Hz, 1H), 7.68 (d, J=2.2 Hz, 1H), 7.54 (dd, J=8.4, 2.2 Hz, 1H), 7.29 (dd, J=25.0, 8.6 Hz, 2H), 6.44 (s, 1H), 3.69 (s, 4H), 3.61 (s, 4H), 3.51 (s, 4H), 3.04 (br s, 4H), 2.41 (s, 3H).

Compounds Compound-9, Compound-10, Compound-12 were made according to the above procedures used for the synthesis of Compound-11 using the following intermediates:

| Amide | Reagents & conditions | Result |
|---|---|---|
| 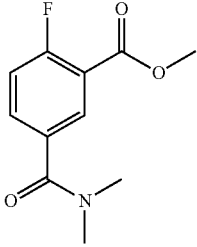 [SMILES: COC(=O)c1cc(C(=O)N(C)C)ccc1F] | Acid (500 mg, 2.52 mmol, 1 eq) Dry DCM:DMF(50:50) (10 mL), Dimethyl amine•HCl (1.2 eq), HOAt (685 mg, 5.04 mmol, 2 eq), EDC (966 mg, 5.04 mmol, 2 eq), DIPEA (1.73 mL, 10.08 mmol, 4 eq) RT for 16 h. | 350 mg (61.6%) $^1$H NMR (400 MHz, CD$_3$COOD) δ 8.61 (d, J = 2.3 Hz, 1H), 8.22 (d, J = 2.2 Hz, 1H), 7.97 (dd, J = 9.2, 2.2 Hz, 1H), 7.80 (dd, J = 8.6, 2.1 Hz, 1H), 7.57 (d, J = 8.8 Hz, 1H), 7.47 (d, J = 8.3 Hz, 1H), 6.89 (s, 1H), 4.03 (t, J = 4.3 Hz, 4H), 3.26 (t, J = 4.4 Hz, 4H), 3.22 (s, 3H), 3.16 (s, 3H), 2.68 (s, 3H). |
| 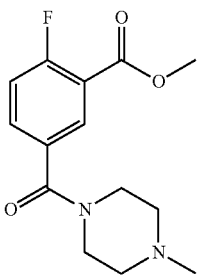 [SMILES: COC(=O)c1cc(C(=O)N2CCN(C)CC2)ccc1F] | Acid (500 mg, 2.52 mmol, 1 eq), Dry DMF (10 mL), HOAt (685 mg, 5.04 mmol, 2 eq), EDC (966 mg, 5.04 mmol, 2 eq), DIPEA (1.7 mL, 10.08 mmol, 4 eq), N-Methyl piperazine (302.9 mg, 3.02 mmol, 1.2 eq) RT for 16 h. | 380 mg (53.7%) $^1$H NMR (400 MHz, CD$_3$COOD) δ 8.60 (s, 1H), 8.23 (s, 1H), 7.96 (d, J = 9.0 Hz, 1H), 7.81 (d, J = 8.5 Hz, 1H), 7.57 (d, J = 8.8 Hz, 1H), 7.47 (d, J = 8.3 Hz, 1H), 6.90 (s, 1H), 4.02 (t, J = 4.5 Hz, 4H), 3.77 (brs, 4H), 3.26 (t, J = 4.6 Hz, 4H), 3.01 (s, 4H), 2.83 (s, 3H), 2.67 (s, 3H). |
| 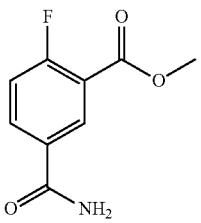 | Acid (500 mg, 2.52 mmol, 1 eq), Dry DMF (10 mL), HATU(1.91 g, 5.04 mmol, 2 eq), NH$_4$Cl (202.1 mg, 3.78 mmol, 1.5 eq), DIPEA (1.73 mL, 10.08 mmol, 4 eq), RT for 16 h. | 250 mg (49.7%) $^1$H NMR (400 MHz, CD$_3$COOD) δ 8.70 (d, J = 2.3 Hz, 1H), 8.62 (d, J = 2.3 Hz, 1H), 8.25 (dd, J = 8.4, 2.4 Hz, 1H), 7.96 (dd, J = 8.8, 2.2 Hz, 1H), 7.57 (d, J = 8.8 Hz, 1H), 7.47 (d, J = 8.5 Hz, 1H), 6.90 (s, 1H), 4.03 (t, J = 4.6 Hz, 4H), 3.28 (t, J = 4.4 Hz, 4H), 2.68 (s, 3H). |

Synthesis of Compound-13 and Compound-14:

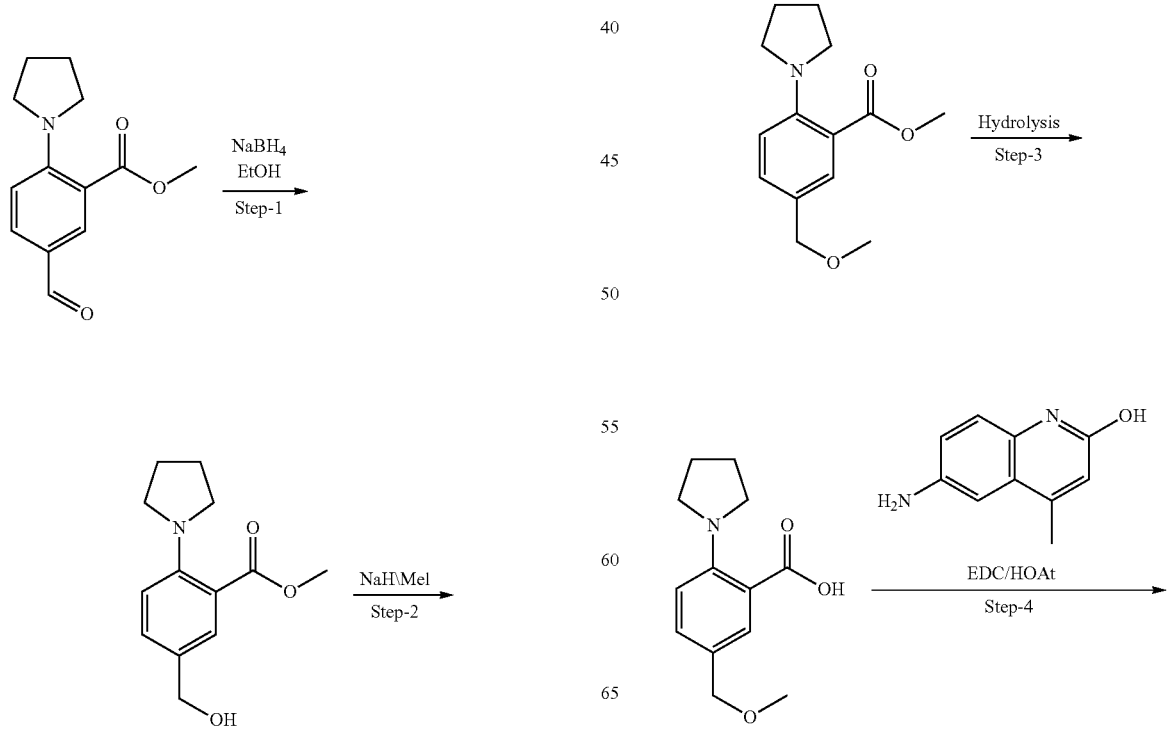

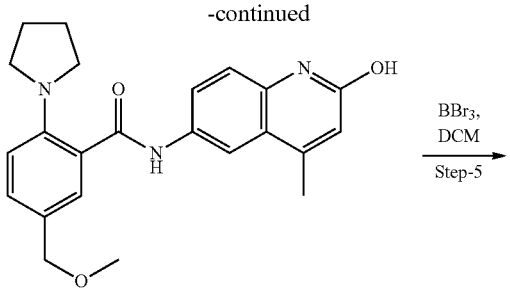

Compound-13

$\xrightarrow{\text{BBr}_3, \text{DCM}}$ Step-5

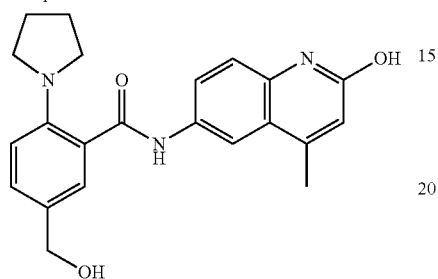

Compound-14

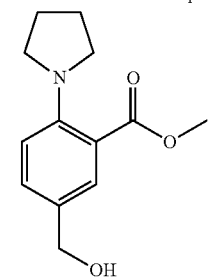

Preparation of methyl 5-(hydroxymethyl)-2-(pyrrolidin-1-yl) benzoate: to a solution of methyl 5-formyl-2-(pyrrolidin-1-yl) benzoate (1 g, 4.28 mmol, 1 eq) in ethanol (10 mL) at 0° C. added NaBH4 (480 mg, 12.86 mmol, 3 eq) over a period of 10 min's, and stirred at RT for 1 h. After completion reaction mixture was quenched with sat NH4Cl solution and solvent was evaporated. The reaction mixture was poured into water and extracted with EtOAc (3×20 mL). The combined extracts were washed with water (20 mL), brine (20 mL), dried over anhydrous Na2SO4, filtered and evaporated to afford methyl 5-(hydroxymethyl)-2-(pyrrolidin-1-yl) benzoate (1 g) a pale yellow liquid. The crude compound was carried to next step without further purification. LCMS analysis indicated 98% desired product.

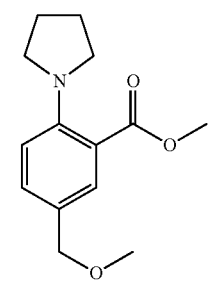 [SMILES: COCc1ccc(N2CCCC2)c(C(=O)OC)c1]

Preparation of methyl 5-(methoxymethyl)-2-(pyrrolidin-1-yl) benzoate: to a solution of methyl 5-(hydroxymethyl)-2-(pyrrolidin-1-yl) benzoate (1 g, 4.25 mmol, 1 eq) in DMF added NaH (0.036 g, 12.75 mmol, 3 eq) at 0° C. over a period of 10 min's then added MeI (0.906 mg, 6.38 mmol, 1.5 eq), and stirred at RT for 16 h. After completion reaction mixture was quenched with ice cold water, the reaction mixture was poured into water and extracted with EtOAc (3×20 mL). The combined extracts were washed with water (20 mL), brine (20 mL), dried over anhydrous Na2SO4, filtered and evaporated. The crude product was purified by column chromatography to afford methyl 5-(methoxymethyl)-2-(pyrrolidin-1-yl) benzoate (800 mg, 75.5%) as a pale yellow liquid. LCMS analysis indicated 79% desired product.

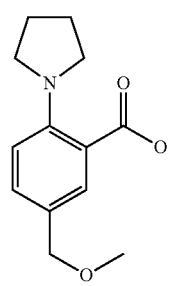 [SMILES: COCc1ccc(N2CCCC2)c(C(=O)O)c1]

Preparation of 5-(methoxymethyl)-2-(pyrrolidin-1-yl) benzoic acid: to a solution of methyl 5-(methoxymethyl)-2-(pyrrolidin-1-yl) benzoate (800 mg, 3.2 mmol, 1 eq) in MeOH (5 mL) and water (5 mL) added NaOH (0.38 g, 9.6 mmol, 3 eq) and stirred at 60° C. for 16 h. After completion solvent was evaporated and poured into water acidified with 1N HCl (up to PH=2) and extracted with EtOAc (3×20 mL). The combined extracts were washed with water (20 mL), brine (20 mL), dried over anhydrous Na2SO4, filtered and evaporated to afford to 5-(methoxymethyl)-2-(pyrrolidin-1-yl) benzoic acid (600 mg, 80%) as pale brown color liquid. LCMS analysis indicated 81% desired product.

Compound-13

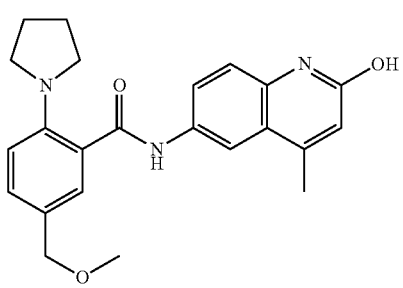

Preparation of N-(2-hydroxy-4-methylquinlin-6-yl)-5-(methoxymethyl)-2-(pyrrolidin-1-yl) benzamide (Compound-13): to a solution of 5-(methoxymethyl)-2-(pyrrolidin-1-yl) benzoic acid (600 mg, 2.55 mmol, 1 eq) in DMF added EDC.HCl (0.975 g, 5.10 mmol, 2 eq), HOAt (0.694 g, 5.10 mmol, 2 eq) and DIPEA (4 eq) allowed to stir at RT for 15 mins 6-amino-4-methylquinlin-2-ol (0.533 g, 3.06 mmol, 1.2 eq) and stirred at RT for 48 h. After completion, the reaction mixture is poured into water and extracted with EtOAc (3×20 mL). The combined extracts were washed with water (20 mL) brine (20 mL), dried over anhydrous Na2SO4, filtered and evaporated. The crude was purified by column chromatography using 4% MeOH/DCM to afford to N-(2-hyroxy-4-methylquinlin-6-yl)-5-(methoxymethyl)-2-

(pyrrolidin-1-yl) benzamide (Compound-13) (600 mg, 60%) as off white solid. LCMS analysis indicated 97% desired product.

$^1$H NMR (400 MHz, DMSO-d6) δ 11.54 (s, 1H), 10.44 (s, 1H), 8.14 (d, J=2.2 Hz, 1H), 7.82 (dd, J=8.8, 2.2 Hz, 1H), 7.32-7.19 (m, 3H), 6.76 (d, J=8.5 Hz, 1H), 6.41 (s, 1H), 4.31 (s, 2H), 3.24 (d, J=7.2 Hz, 7H), 2.39 (s, 3H), 1.95-1.79 (m, 4H).

Compound-14

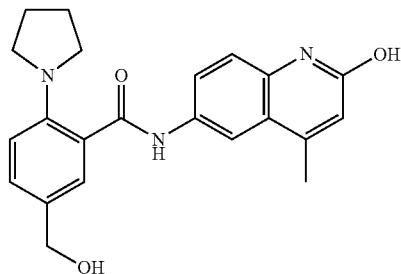

Preparation of N-(2-hydroxy-4-methylquinlin-6-yl)-5-(hydroxymethyl)-2-(pyrrolidin-1-yl) benzamide (Compound-14): to a solution of N-(2-hydroxy-4-methylquinlin-6-yl)-5-(methoxymethyl)-2-(pyrrolidin-1-yl)benzamide (Compound-13) (600 mg, 1.53 mmol, 1 eq) in DCM added BBr3 at 0° C., and stirred at RT for 3 h. After completion reaction mixture was quenched with sat NaHCO3 solution and stirred for 1 h and precipitated solid was filtered washed with diethyl ether, total crude was purified by preparative HPLC to afford N-(2-hydroxy-4-methylquinlin-6-yl)-5-(hydroxymethyl)-2-(pyrrolidin-1-yl)benzamide (Compound-14) (160 mg, 28%) as white solid. LCMS analysis indicated 96.2% desired product.

$^1$H NMR (400 MHz, DMSO-d6) δ 11.54 (s, 1H), 10.47 (s, 1H), 8.14 (d, J=2.2 Hz, 1H), 7.82 (dd, J=8.8, 2.2 Hz, 1H), 7.32-7.20 (m, 3H), 6.77 (d, J=8.5 Hz, 1H), 6.41 (s, 1H), 5.01 (t, J=5.6 Hz, 1H), 4.41 (d, J=5.6 Hz, 2H), 3.25-3.16 (m, 4H), 2.39 (S, 3H), 1.91-1.80 (m, 4H).

Synthesis of Compound-15, Compound-16, Compound-17, Compound-18, Compound-19, Compound-20

Compound-15

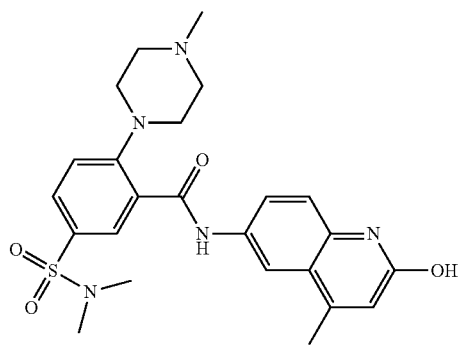

Compound-16

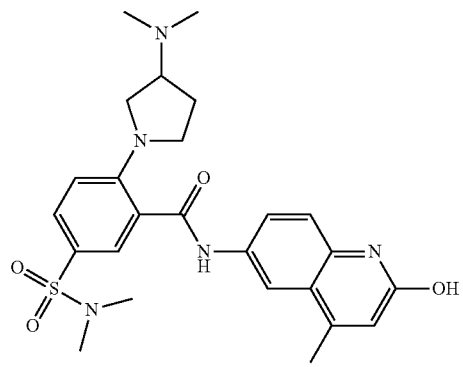

Compound-17

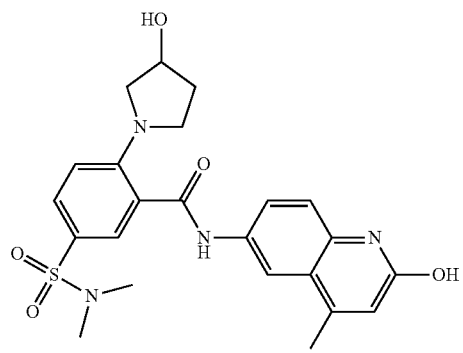

Compound-18

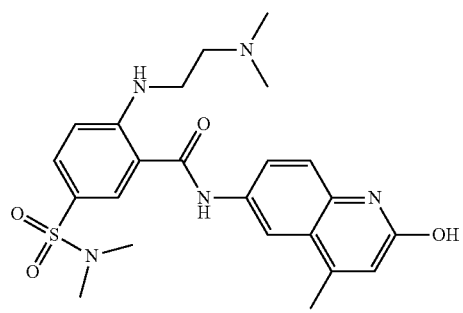

Compound-19

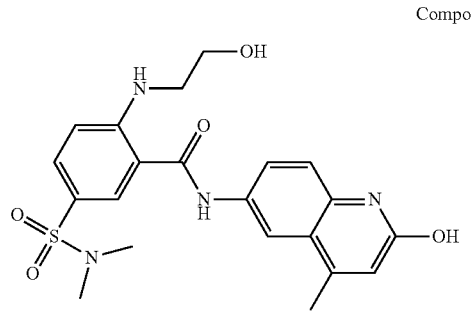

Compound-20

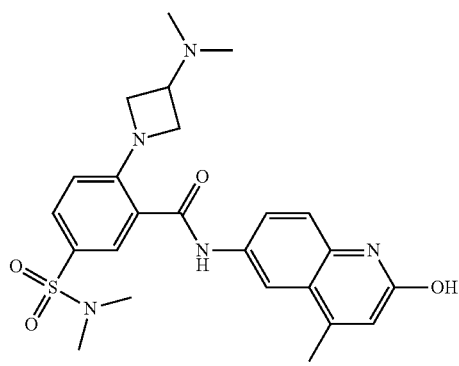

Scheme:

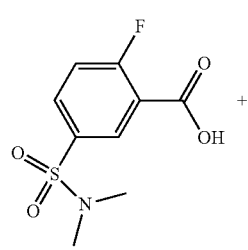
+

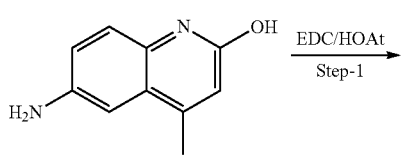
EDC/HOAt
Step-1

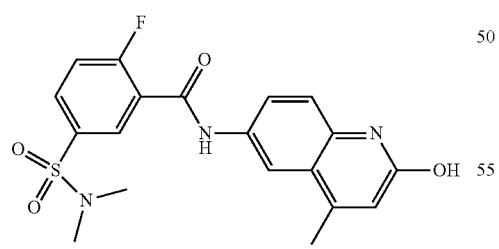

Step-2
DMSO/DIEA

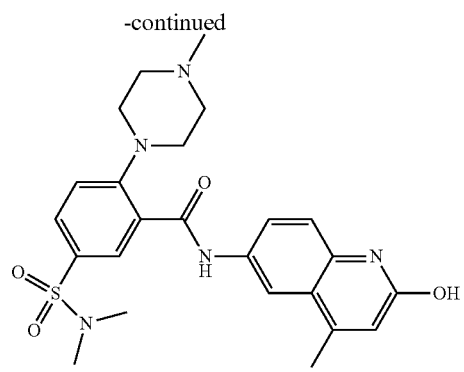

Compound-15

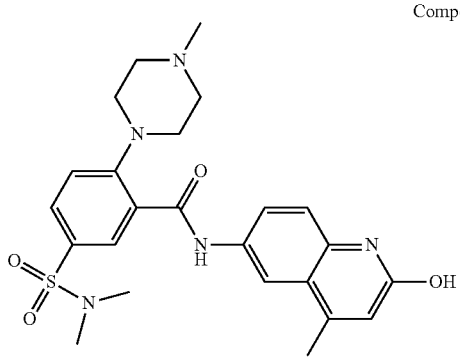

Preparation of 5-(N, N-dimethylsulfamoyl)-2-fluoro-N-(2-hydroxy-4-methylquinolin-6-yl) benzamide: to a solution of 6-amino-4-methylquinolin-2-ol (70.2 mg, 0.404 mmol, 1 eq), added a solution of 5-(N, N-dimethylsulfamoyl)-2-fluorobenzoic acid (100 mg, 0.404 mmol, 1 eq) in dry DMF (2 mL) added DIPEA (104 mg, 0.808 mmol, 1 eq), HOAt (54.9 mg, 0.404 mmol, 1 eq), followed by EDC (77 mg, 0.404, 1 eq) and stirred at RT for 16 h. After completion, the reaction mixture was poured into water and extracted with DCM (2×15 mL). The combined extracts were washed with water (15 mL), brine (15 mL), dried over anhydrous Na$_2$SO$_4$, filtered and evaporated. The crude was purified by flash column chromatography by eluting with EtOAc:Pet ether (4:6) to afford 5-(N, N-dimethylsulfamoyl)-2-fluoro-N-(2-hydroxy-4-methylquinolin-6-yl) benzamide (110 mg, 49.7%).

$^1$H NMR (400 MHz, DMSO-d$_6$) δ 11.63 (s, 1H), 10.71 (s, 1H), 8.13 (d, J=2.3 Hz, 1H), 8.05-7.93 (m, 2H), 7.79 (dd, J=8.8, 2.3 Hz, 1H), 7.66 (t, J=9.1 Hz, 1H), 7.31 (d, J=8.8 Hz, 1H), 6.44 (s, 1H), 2.67 (s, 6H), 2.41 (d, J=1.4 Hz, 3H).

Preparation of 5-(N, N-dimethylsulfamoyl)-N-(2-hydroxy-4-methylquinolin-6-yl)-2-(4-methylpiperazin-1-yl) benzamide (Compound-15): to a solution of 5-(N,N-dimethylsulfamoyl)-2-fluoro-N-(2-hydroxy-4-methylquinolin- 6-yl)benzamide (50 mg, 0.124 mmol, 1 eq) in dry DMSO (1 mL) added DIPEA (31.9 mg, 0.248 mmol, 2 eq) and 1-methylpiperazine (12.2 mg, 0.124 mmol, 1 eq) and stirred at RT for 24 h. After completion, the reaction mixture was poured into ice water and extracted with EtOAc (2×15 mL). The combined extracts were washed with water (2×15 mL), brine (15 mL), dried over anhydrous Na$_2$SO$_4$, filtered and evaporated to afford 5-(N, N-dimethylsulfamoyl)-N-(2-hydroxy-4-methylquinolin-6-yl)-2-(4-methylpiperazin-1-yl) benzamide (Compound-15) (45 mg, 83.48%). LCMS analysis indicated 96.9% desired product.

1H NMR (400 MHz, DMSO-d6) δ 11.61 (s, 1H), 10.71 (s, 1H), 8.19 (d, J=2.4 Hz, 1H), 7.89-7.72 (m, 3H), 7.33 (t, J=8.8 Hz, 2H), 6.44 (s, 1H), 3.13 (t, J=4.7 Hz, 4H), 2.62 (s, 6H), 2.41 (s, 7H), 2.15 (s, 3H).

Compounds Compound-16, Compound-17, Compound-18, Compound-19, and Compound-20 were made according to the same procedure.

Compound-20:
$^1$H NMR (400 MHz, DMSO-d6) δ 11.59 (s, 1H), 10.54 (s, 1H), 8.08 (s, 1H), 7.81 (d, J=8.8, 2.4 Hz, 1H), 7.63-7.54 (m, 2H), 7.29 (d, J=8.8 Hz, 1H), 6.65 (d, J=8.7 Hz, 1H), 6.43 (s, 1H), 4.01 (t, J=8.0 Hz, 2H), 3.75 (dd, J=8.4, 4.9 Hz, 2H), 3.19-3.11 (m, 1H), 2.59 (s, 6H), 2.40 (s, 3H), 2.06 (s, 6H).

Compound-16:
$^1$H NMR (400 MHz, CD3COOD) δ 8.43 (s, 1H), 8.06-7.95 (m, 2H), 7.81 (d, J=9.0, 2.4 Hz, 1H), 7.52 (d, J=8.8 Hz, 1H), 7.02 (d, J=9.0 Hz, 1H), 6.89 (s, 1H), 4.10 (p, J=7.2 Hz, 1H), 4.03-3.90 (m, 2H), 3.79-3.62 (m, 2H), 2.98 (s, 6H), 2.75 (s, 6H), 2.64 (s, 3H), 2.52 (q, J=7.1 Hz, 2H).

Compound-17:
$^1$H NMR (400 MHz, CD3COOD) δ 8.47 (d, J=2.2 Hz, 1H), 8.01 (dd, J=8.8, 2.2 Hz, 1H), 7.97 (d, J=2.2 Hz, 1H), 7.78 (dd, J=8.9, 2.3 Hz, 1H), 7.52 (d, J=8.7 Hz, 1H), 6.98 (d, J=9.0 Hz, 1H), 6.88 (s, 1H), 4.67 (s, 1H), 3.87-3.72 (m, 2H), 3.54 (t, J=7.9 Hz, 1H), 3.44 (d, J=11.2 Hz, 1H), 2.74 (s, 6H), 2.64 (s, 3H), 2.19 (t, J=10.4 Hz, 2H).

Compound-18:
$^1$H NMR (400 MHz, DMSO-d6) δ 11.61 (s, 1H), 10.47 (s, 1H), 8.07 (t, J=4.8 Hz, 1H), 8.00 (d, J=2.3 Hz, 1H), 7.92 (d, J=2.3 Hz, 1H), 7.77 (dd, J=8.9, 2.2 Hz, 1H), 7.64 (dd, J=8.9, 2.2 Hz, 1H), 7.30 (d, J=8.8 Hz, 1H), 6.90 (d, J=8.9 Hz, 1H), 6.43 (s, 1H), 3.29-3.23 (m, 2H), 2.60 (s, 6H), 2.49 (s, 2H), 2.41 (s, 3H), 2.18 (s, 6H).

Compound-19:
$^1$H NMR (400 MHz, CD3COOD) δ 8.33 (d, J=2.3 Hz, 1H), 8.24 (d, J=2.2 Hz, 1H), 8.02 (dd, J=9.0, 2.2 Hz, 1H), 7.80 (dd, J=9.0, 2.2 Hz, 1H), 7.52 (d, J=8.9 Hz, 1H), 7.01 (d, J=9.1 Hz, 1H), 6.87 (s, 1H), 3.98 (t, J=5.5 Hz, 2H), 3.57 (t, J=5.6 Hz, 2H), 2.74 (s, 6H), 2.65 (s, 3H).

Synthesis of Compound-21:

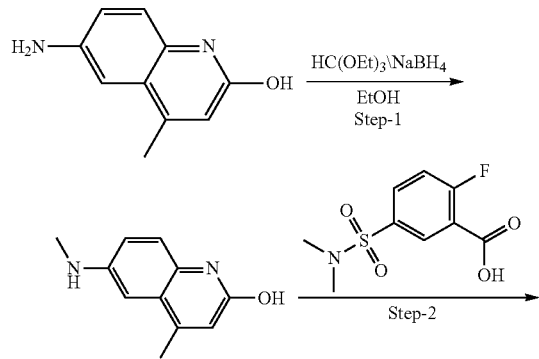

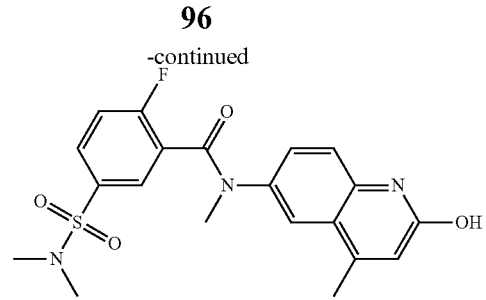

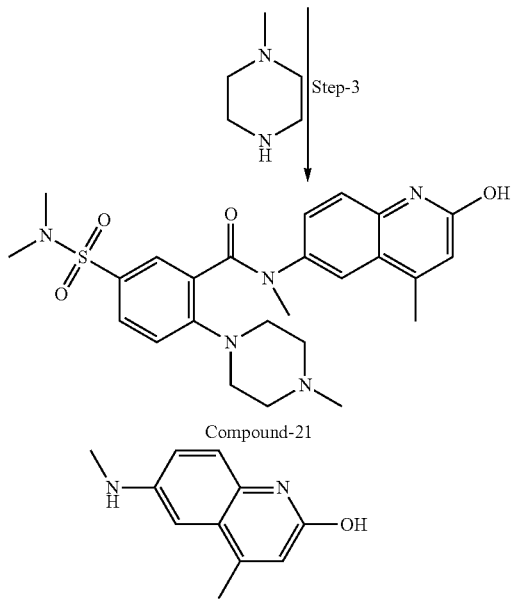

Preparation of 4-methyl-6-(methylamino) quinolin-2-ol: a mixture of 6-amino-4-methylquinolin-2-ol (500 mg, 2.87 mmol, 1 eq) and triethylorthoformate (8.5 g, 57.47 mmol, 20 eq) was stirred at 130° C. for 48 h. then the solvent was evaporated, the residue was dissolved in Ethanol (5 mL), added NaBH$_4$ (531 mg, 14.36 mmol, 5.0 eq) at 0° C. in small portions and stirred at RT for 2 h. After completion, the solvent was evaporated. The reaction mixture was poured into water and extracted with EtOAc (3×10 mL). The combined extracts were washed with water (5 mL), brine (5 mL), dried over anhydrous Na$_2$SO$_4$, filtered and evaporated to afford 4-methyl-6-(methylamino) quinolin-2-ol (450 mg) as a pale yellow solid.

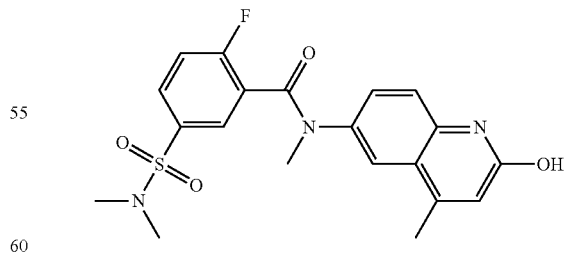

Preparation of 5-(N,N-dimethylsulfamoyl)-2-fluoro-N-(2-hydroxy-4-methylquinolin-6-yl)-N-methylbenzamide: to a solution of 5-(N,N-dimethylsulfamoyl)-2-fluorobenzoic acid (142 mg, 0.574 mmol, 1 eq) in Dry DMF (5 mL) at RT added 4-methyl-6-(methylamino) quinolin-2-ol (100 mg, 0.574 mmol, 1 eq), HOAt (78.06 mg, 0.574 mmol, 1 eq), EDC (109.6 mg, 0.574 mmol, 1 eq), DIPEA (74.04 mg, 1.724 mmol, 3 eq) and stirred at RT for 16 h. After completion, the reaction mixture was poured into ice water and extracted with EtOAc (3×10 mL). The combined extracts were washed with cold water (2×5 mL), brine (5 mL), dried over anhydrous Na$_2$SO$_4$, filtered and evaporated to Afford 4-(N,N-dimethyl sulfamoyl)-2-fluoro-N-(2-hydroxy-4-methyl quinolin-6-yl)-N-methylbenzamide (66 mg) as a pale yellow solid.

$^1$H NMR (300 MHz, DMSO-d6) δ 11.58 (s, 1H), 7.75 (dd, J=6.2, 2.4 Hz, 1H), 7.68-7.56 (m, 2H), 7.44-7.27 (m, 2H), 7.13 (d, J=8.6 Hz, 1H), 6.36 (s, 1H), 3.43 (s, 3H), 2.35 (s, 6H), 2.26 (s, 3H).

Preparation of 5-(N, N-dimethylsulfamoyl)-N-(2-hydroxy-4-methylquinolin-6-yl)-N-methyl-2-(4-methylpiperazin-1-yl) benzamide (Compound-21): to a solution of 5-(N, N-dimethylsulfamoyl)-2-fluoro-N-(2-hydroxy-4-methylquinolin-6-yl)-N-methylbenzamide (66 mg, 0.158 mmol, 1 eq) in DMSO (10 vol) added 1-methylpiperazine (15 mg, 0.158 mmol, 1 eq), DIPEA (40.7 mg, 0.316 mmol, 2.0 eq) and stirred at 130° C. for 16 h. After completion, the reaction mixture was poured into water and extracted with EtOAc (3×5 mL). The combined extracts were washed with water (2×5 mL), brine (5 mL), dried over anhydrous Na$_2$SO$_4$, filtered and evaporated. The crude compound was purified by column chromatography using (SiO$_2$) by eluting DCM: Methanol (95:5) to afford 4-(N, N-dimethylsulfamoyl)-N-(2-hydroxy-4-methyl quinolin-6-yl)-N-methyl-2-(4-methylpiperazin-1-yl) benzamide (Compound-21) (16 mg) as a white solid.

$^1$H NMR (300 MHz, DMSO-d$_6$) δ 11.52 (S, 1H), 7.60 (d, J=2.5 Hz, 1H), 7.50-7.27 (m, 3H), 7.06 (d, J=8.5 Hz, 1H), 6.84 (d, J=8.6 Hz, 1H), 6.32 (s, 1H), 3.41 (s, 3H), 3.26-3.04 (m, 4H), 2.59 (d, J=18.9 Hz, 4H), 2.47 (s, 6H), 2.28 (s, 3H), 2.21 (s, 3H).

Compound-21

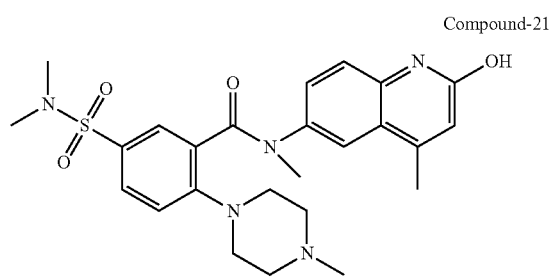 [SMILES: Cc1cc(O)nc2ccc(N(C)C(=O)c3cc(S(=O)(=O)N(C)C)ccc3N3CCN(C)CC3)cc12]

Synthesis of Compound-22:

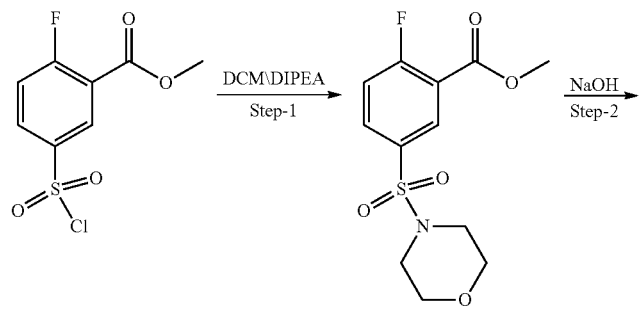

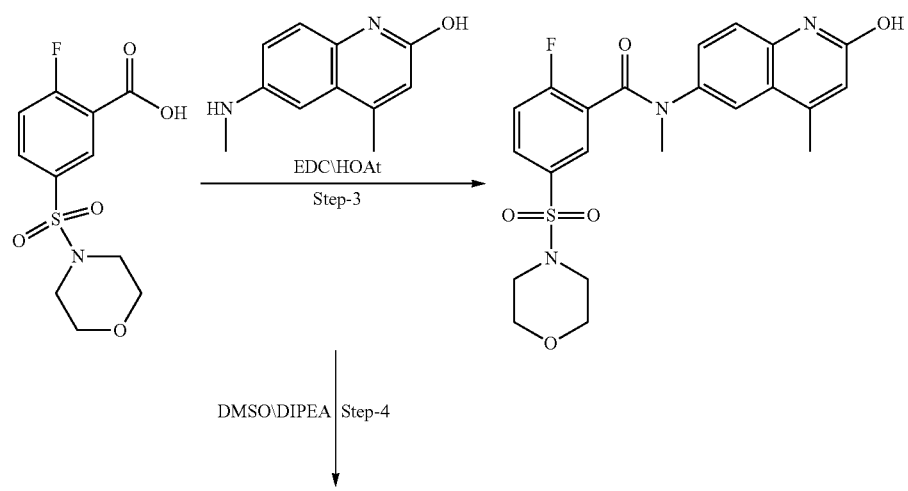

-continued

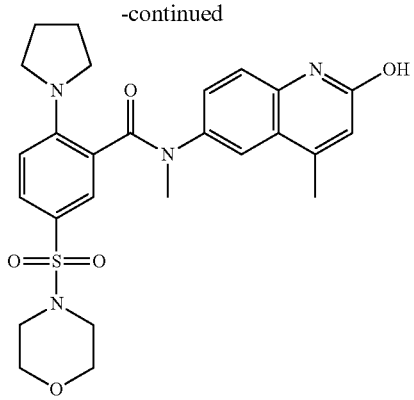

Compound-22

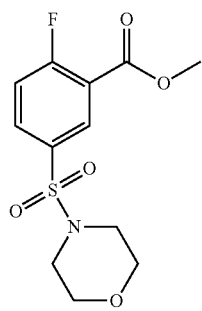

Preparation of methyl 2-fluoro-5-(morpholinosulfonyl) benzoate: to a solution of methyl 5-(chlorosulfonyl)-2-fluorobenzoate (500 mg, 1.99 mmol, 1 eq) in dry DCM (5 ml) at RT was added DIPEA (641.7 mg, 4.975 mmol, 2.5 eq) followed by morpholine (207.7 mg, 2.38 mmol, 1.2 eq) and stirred at RT for 4 h. After completion, The reaction mixture was washed with water (2×10 mL), dried over anhydrous Na$_2$SO$_4$, filtered and evaporated to afford 2-fluoro-5-(morpholinosulfonyl)benzoate (580 mg) as an off white solid.

Preparation of 2-fluoro-5-(morpholinosulfonyl) benzoic acid: to a solution of methyl 2-fluoro-5-(morpholinosulfonyl) benzoate (580 mg, 1.91 mmol, 1 eq) in MeOH:H$_2$O (3:1) (6 mL) was added NaOH (306 mg, 7.65 mmol, 4.0 eq) at 0° C. and stirred at RT for 4 h. After completion, the solvent was evaporated, the residue was taken in water adjusted the pH to acidic with 1N HCl and extracted with EtOAc (3×20 mL). The combined extracts were washed with water (10 mL), dried over anhydrous Na$_2$SO$_4$, filtered and evaporated to afford 2-fluoro-5-(morpholinosulfonyl) benzoic acid (400 mg) as an off white solid.

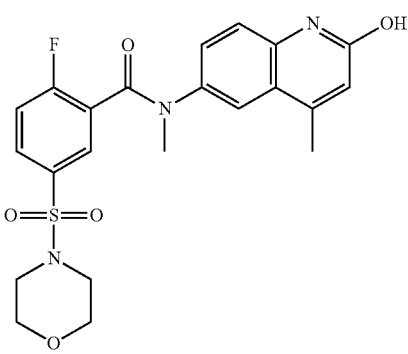 [SMILES: Cc1cc(O)nc2ccc(N(C)C(=O)c3cc(S(=O)(=O)N4CCOCC4)ccc3F)cc12]

Preparation of 2-fluoro-N-(2-hydroxy-4-methylquinolin-6-yl)-N-methyl-5-(morpholinosulfonyl) benzamide: to a solution of 2-fluoro-5-(morpholinosulfonyl)benzoic acid (380 mg, 1.31 mmol, 1 eq) in Dry DMF (5 mL) at RT was added 6-amino-4-methyl-quinolin-2-ol (247.1 mg, 1.31 mmol, 1 eq), HOAt (178.1 mg, 1.31 mmol, 1 eq), EDC (250.2 mg, 1.31 mmol, 1 eq), DIPEA (506.9 mg, 3.93 mmol, 3 eq) and stirred at RT for 16 h. After completion, the reaction mixture poured into ice water and extracted with EtOAc (3×10 mL). The combined extracts were washed with cold water (2×5 mL), brine (5 mL), dried over anhydrous Na$_2$SO$_4$, filtered and evaporated. The crude compound was purified by column chromatography (SiO$_2$) using DCM: Methanol (95:4) to afford 2-fluoro-N-(2-hydroxy-4-methylquinolin-6-yl)-N-methyl-5-(morpholinosulfonyl) benzamide (85 mg) as a pale yellow solid.

Compound-22

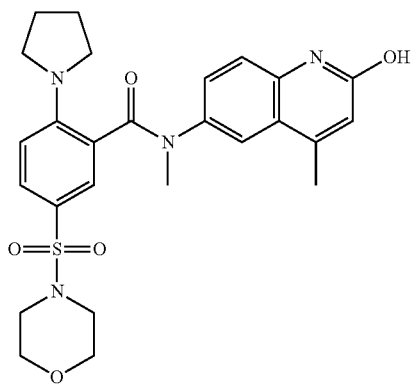

Preparation of N-(2-hydroxy-4-methylquinolin-6-yl)-N-methyl-5-(morpholinosulfonyl)-2-(pyrrolidin-1-yl) benzamide (Compound-22): to a solution of 2-fluoro-N-(2-hydroxy-4-methylquinolin-6-yl)-N-methyl-5-(morpholinosulfonyl) benzamide (85 mg, 0.185 mmol, 1 eq) in DMSO (10 vol) was added Pyrrolidine (13.1 mg, 0.185 mmol, 1 eq) and DIPEA (71.5 mg, 0.55 mmol, 3 eq) and stirred at 120° C. for 16 h. After completion, the reaction mixture was poured into ice water and extracted with EtOAc (3×10 mL). The combined extracts were washed with cold water (2×5 mL), brine (5 mL), dried over anhydrous $Na_2SO_4$, filtered and evaporated. The crude compound was purified by column chromatography ($SiO_2$) using DCM:Methanol (95:5) to afford N-(2-hydroxy-4-methylquinolin-6-yl)-N-methyl-5-(morpholinosulfonyl)-2-(pyrrolidin-1-yl) benzamide (Compound-22) (13 mg) as an off white solid.

$^1$H NMR (300 MHz, DMSO-$d_6$) δ 11.52 (S, 1H), 7.60 (d, J=2.5 Hz, 1H), 7.50-7.27 (m, 3H), 7.06 (d, J=8.5 Hz, 1H), 6.84 (d, J=8.6 Hz, 1H), 6.32 (s, 1H), 3.41 (s, 3H), 3.26-3.04 (m, 4H), 2.59 (d, J=18.9 Hz, 4H), 2.47 (s, 6H), 2.28 (s, 3H), 2.21 (s, 3H).

Synthesis of Compound-23 and Compound-24

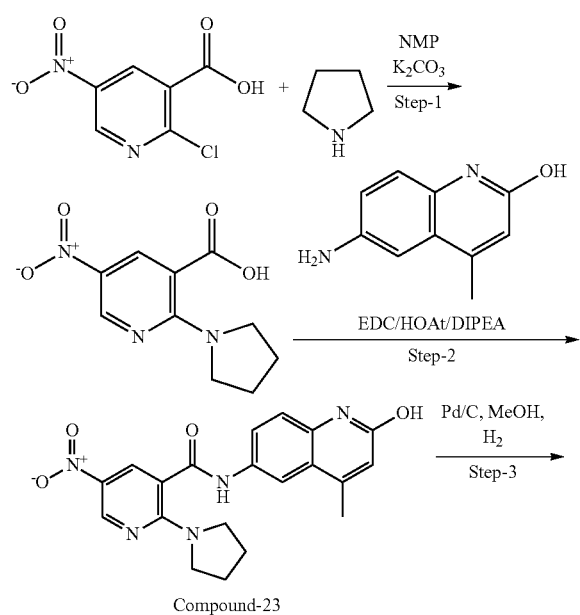

Compound-24

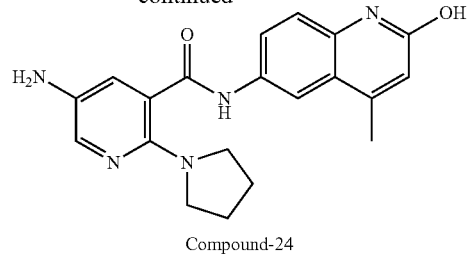

Preparation of 5-nitro-2-pyrrolidin-1-yl-pyridine-3-carboxylic acid

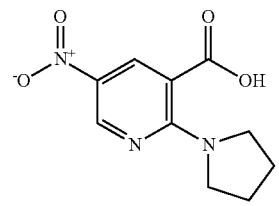

2-Chloro-5-nitro-pyridine-3-carboxylic acid (1.018 g, 5 mmol, 1 eq) is dissolved in 15 mL NMP. Potassium carbonate (1.382 g, 10 mmol, 2.0 eg) is added to the solution. Pyrrolidine (630 μL, 7.5 mmol, 1.5 eq) is added. The reaction mixture is heated for 60 minutes at 80° C. Crude is filtered and solvent is removed by air-flow. Working up with water:EtOAc. Solvent is removed by rotavap. Yield of 5-nitro-2-pyrrolidin-1-yl-pyridine-3-carboxylic acid (0.861 g, 3.63 mmol, 0.66 eq). LCMS: 97% pure.

$^1$H NMR (300 MHz, DMSO-$d_6$) δ 13.49 (s, 1H), 9.03 (d, J=2.7 Hz, 1H), 8.48 (d, J=2.7 Hz, 1H), 3.61-3.47 (m, 4H), 1.99-1.84 (m, 4H).

Preparation of N-(2-hydroxy-4-methyl-6-quinolyl)-5-nitro-2-pyrrolidin-1-yl-pyridine-3-carboxamide (Compound-23)

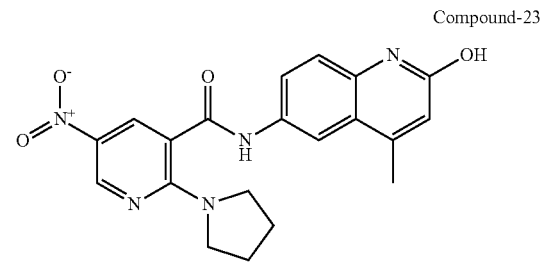 [SMILES: Cc1cc(O)nc2ccc(NC(=O)c3cc([N+](=O)[O-])cnc3N3CCCC3)cc12]

Compound-23

5-nitro-2-pyrrolidin-1-yl-pyridine-3-carboxylic acid (0.861 g, 3.63 mmol, 1 eq) is weighed out in a 100 mL flask. EDC ((3-Dimethylamino-propyl)-ethyl-carbodiimide) (0.767 g, 4.0 mmol, 1.1 eq) and HOAt ([1,2,3]Triazolo[4,5-b]pyridin-3-ol) is dissolved in 10 mL DMF with 1900 μL DIPEA. The solution is added to the flask. 6-amino-4-methyl-quinolin-2-ol (0.697 g, 4.0 mmol, 1.1 eq) is added. Total volume of DMF is 25 mL. The reaction is stirred over night at room temperature. Precipitation is filtered off and solvent is removed by rotavap. Working up with $H_2O$:

EtOAc. The organic phase is dried with MgSO₄ and solvent is removed by rotavap. Crude is purified by CombiFlash DCM:MeOH gradient 0%→10% MeOH. Isolated product is dried overnight. Yield of N-(2-hydroxy-4-methyl-6-quinolyl)-5-nitro-2-pyrrolidin-1-yl-pyridine-3-carboxamide (0.951 g, 2.41 mmol, 0.67 eq). LCMS: 99% pure.

¹H NMR (300 MHz, DMSO-d₆) δ 11.61 (s, 1H), 10.75 (s, 1H), 9.06 (d, J=2.7 Hz, 1H), 8.42 (d, J=2.7 Hz, 1H), 8.09 (d, J=2.2 Hz, 1H), 7.81 (dd, J=8.9, 2.2 Hz, 1H), 7.31 (d, J=8.8 Hz, 1H), 6.43 (s, 1H), 3.63-3.47 (m, 4H), 2.40 (d, J=1.2 Hz, 3H), 1.97-1.86 (m, 4H), 1.34-1.20 (m, 1H).

Preparation of 5-amino-N-(2-hydroxy-4-methyl-6-quinolyl)-2-pyrrolidin-1-yl-pyridine-3-carboxamide (Compound-24)

Compound-24

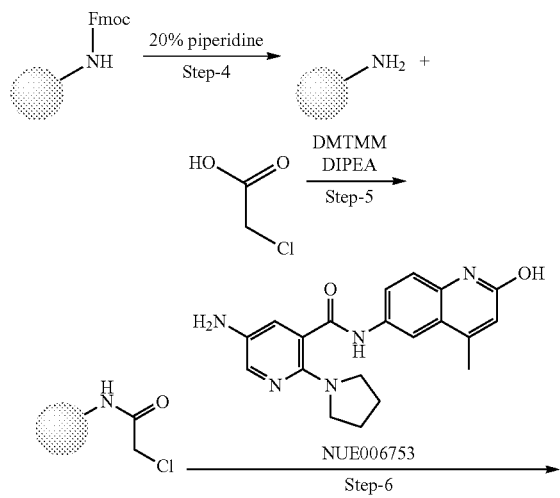

N-(2-hydroxy-4-methyl-6-quinolyl)-5-nitro-2-pyrrolidin-1-yl-pyridine-3-carboxamide (0.203 g, 0.515 mmol, 1.0 eq) is dissolved/suspended in 5 mL dry MeOH. Pd/C (ca. 5 mg) is added. The flask is evacuated and filled with argon 3 times. H₂ gas is added with a balloon. The reaction is stirred overnight at room temperature. Crude is filtered by 22 μm filter. Solvent is removed by rotavap to form 5-amino-N-(2-hydroxy-4-methyl-6-quinolyl)-2-pyrrolidin-1-yl-pyridine-3-carboxamide (0.111 g, 0.31 mmol, 0.59 eq). Purification by preparative HPLC. Relevant fractions are collected and solvent is removed by rotavap. LCMS 93% pure.

Synthesis of Compound-25

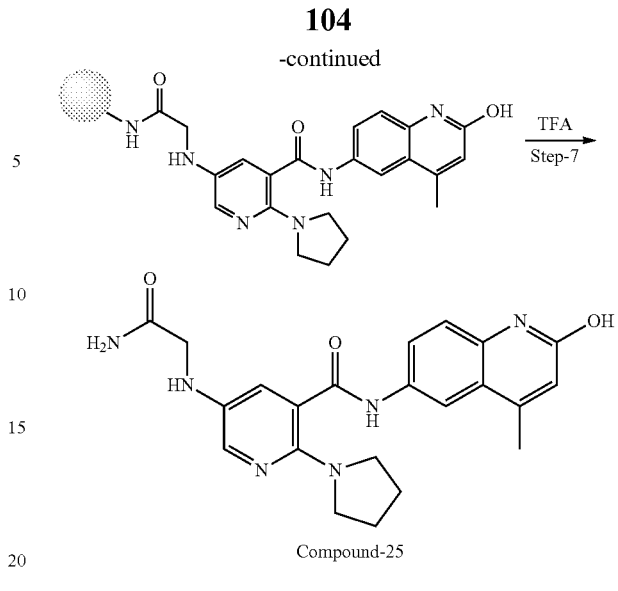

Preparation of 5-[(2-amino-2-oxo-ethyl)amino]-N-(2-hydroxy-4-methyl-6-quinolyl)-2-pyrrolidin-1-yl-pyridine-3-carboxamide (Compound-25)

Compound-25

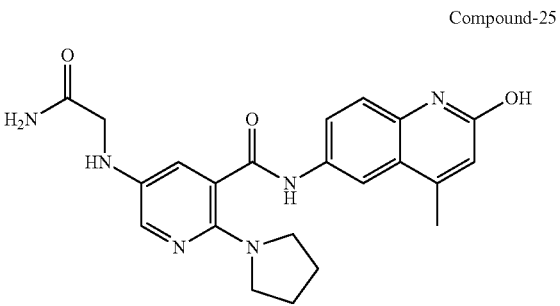 [SMILES: Cc1cc(O)nc2ccc(NC(=O)c3cc(NCC(N)=O)cnc3N3CCCC3)cc12]

The resin (SpheriTide amide, 0.060 mmol/g, 0.1 mmol 1.0 eq) is dried on oil pump overnight. The resin is washed 2 times with dry DMF. The resin swells in dry DMF for 15 minutes and drained. Approx. 2 mL of a 20% piperidine solution in dry DMF is added to the resin, and the resin is shaken for 20 minutes. The solvent is drained and the resin is washed with DMF (3×), MeOH (3×), DMF (3×), DCM (3×).

The resin is washed with 2 times dry DMF and swells in dry DMF for 15 minutes. 2-chloroacetic acid (0.0382 g, 0.4 mmol, 4.0 eq) and DIPEA (N,N-Diisopropylethylamine) (140 μL, 0.8 mmol, 8.0 eq) are dissolved in approx. 1 mL dry DMF and the solution is added to the resin. DMTMM (4-(4,6-dimethoxy-1,3,5-triazin-2-yl)-4-methyl-morpholin-4-ium tetrafluoroborate) (0.1304 g, 0.4 mmol, 4.0 eq) is dissolved in aprox. 1 mL dry DMF and added to the resin. The reaction is shaken over night at room temperature. The solvent is drained and the resin is washed with DMF (3×), DMF (3×), DCM (3×).

The resin is washed with 2 times dry DMSO. 5-amino-N-(2-hydroxy-4-methyl-6-quinolyl)-2-pyrrolidin-1-yl-pyridine-3-carboxamide (0.0729 g, 0.20 mmol, 2.0 eq) is dissolved in approx. 1 mL dry DMSO and added to the resin. DIPEA (N,N-Diisopropylethylamine) (70 μL, 0.4 mmol, 4.0 eq) is added to the resin. The mixture is shaken over night at 80° C. The resin is drained and washed with DMF (3×), IPA (2×), DMF (3×), DCM (3×). 5-[(2-amino-2-oxo-ethyl)amino]-N-(2-hydroxy-4-methyl-6-quinolyl)-2-pyrrolidin-1-yl-pyridine-3-carboxamide (0.0388 g, 0.092 mmol, 0.92 eq) is cleaved from the resin with 80 W/W % TFA in DCM. Solvent is removed by rotavap. Crude is purified by CombiFlash DCM:MeOH gradient 0%→10% MeOH. Relevant fractions are collected and solvent is removed by rotavap to form 5-[(2-amino-2-oxo-ethyl)amino]-N-(2-hydroxy-4-methyl-6-quinolyl)-2-pyrrolidin-1-yl-pyridine-3-carboxamide (Compound-25, 0.017 g, 0.041 mmol, 0.41 eq). LCMS: 82% pure.

Synthesis of Compound-26

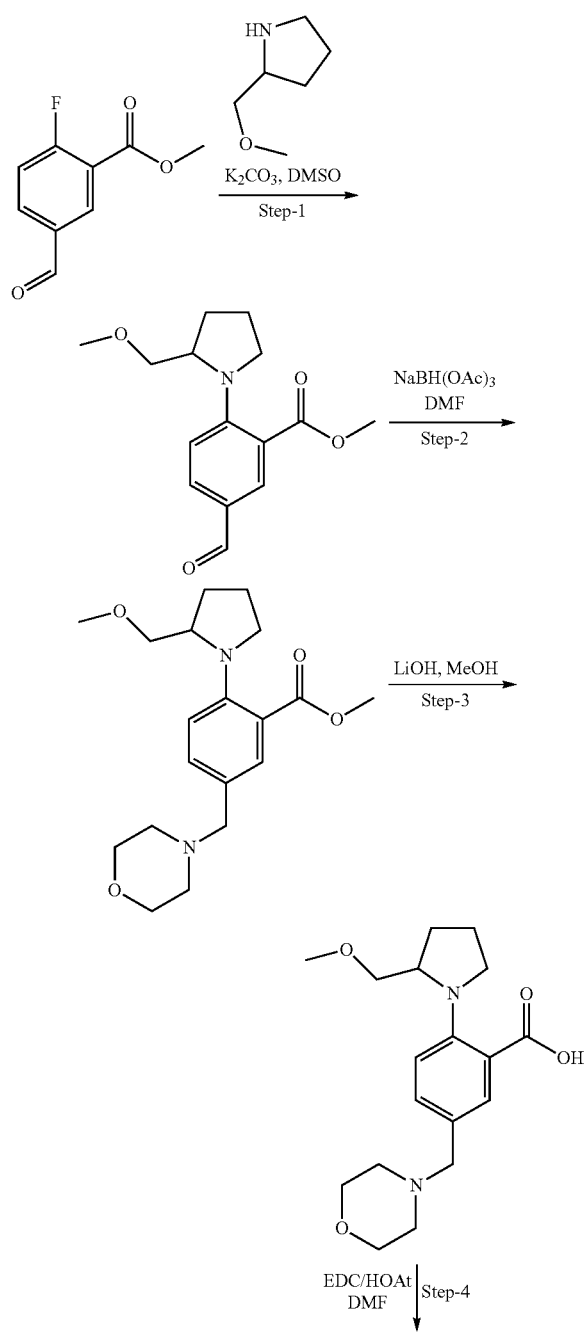

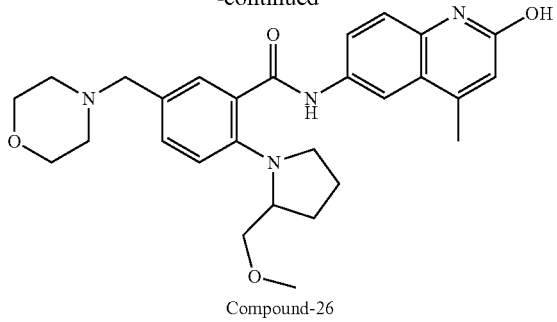

Compound-26

Preparation of methyl 5-formyl-2-(2-(methoxymethyl) pyrrolidin-1-yl) benzoate: to a solution of methyl 2-fluoro-5-formylbenzoate (200 mg, 1.098 mmol, 1 eq) in DMSO (10 vol) was added 2-(methoxymethyl) pyrrolidine (126.46 mg, 1.098 mmol, 1.5 eq), $K_2CO_3$ (303.04 mg, 2.196 mmol, 2 eq) and stirred at 120° C. for 18 h. After completion, the reaction mixture was poured into ice water and extracted with EtOAc (2×20 mL). The combined extracts were washed with water (30 mL), brine (30 mL), dried over anhydrous $Na_2SO_4$, filtered and evaporated. The crude compound was purified by column chromatography ($SiO_2$) using EtOAc:Pet ether (20:80) to afford methyl 5-formyl-2-(2-(methoxymethyl) pyrrolidin-1-yl)benzoate (220 mg) as pale yellow solid.

Preparation of methyl 2-(2-(methoxymethyl) pyrrolidin-1-yl)-5-(morpholinomethyl) benzoate: to a solution of methyl 5-formyl-2-(2-(methoxymethyl)pyrrolidin-1-yl)benzoate (220 mg, 0.794 mmol, 1 eq) in Dry DCM (5 mL) was added morpholine (69.17 mg, 0.794 mmol, 1.0 eq), Na(OAC)$_3$BH (336.65 mg, 1.588 mmol, 1 eq), $CH_3COOH$ (Catalytic) and molecular sieves, stirred at RT for 16 h. After completion, the reaction mixture was poured into water and extracted with DCM (3×30 mL). The combined extracts were washed with water (20 mL), brine (20 mL), dried over anhydrous $Na_2SO_4$, filtered and evaporated to afford methyl 2-(2-(methoxymethyl)pyrrolidin-1-yl)-5-(morpholinomethyl)benzoate (215 g) as an off white solid.

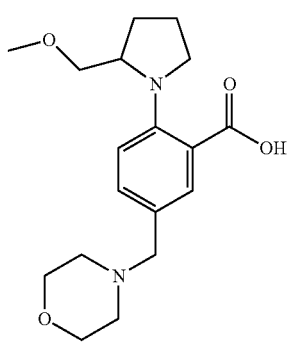 [SMILES: COCC1CCCN1c1ccc(CN2CCOCC2)cc1C(=O)O]

Preparation of 2-(2-(methoxymethyl)pyrrolidin-1-yl)-5-(morpholinomethyl)benzoic acid: to a solution of methyl 2-(2-(methoxymethyl)pyrrolidin-1-yl)-5-(morpholinomethyl)benzoate (215 mg, 0.617 mmol, 1 eq) in MeOH:H$_2$O (3:1)(9 mL) at RT was added LiOH (77.6 mg, 1.851 mmol, 3.0 eq) and stirred for 5 h. After completion, the solvent was evaporated the crude was taken water and acidified with 1N HCl, evaporated to afford 2-(2-(methoxymethyl)pyrrolidin-1-yl)-5-(morpholinomethyl)benzoic acid (Compound-5) (180 mg) as brown solid. The crude was carried to next step without further purification.

Compound-26

Preparation of N-(2-hydroxy-4-methylquinolin-6-yl)-2-(2-(methoxymethyl) pyrrolidin-1-yl)-5-(morpholinomethyl) benzamide (Compound-26): to a solution of 2-(2-(methoxymethyl)pyrrolidin-1-yl)-5-(morpholinomethyl) benzoic acid (180 mg, 0.485 mmol, 1 eq) in Dry DMF (5 mL) at RT was added 6-amino-4-methyl-quinolin-2-ol (84.39 mg, 0.485 mmol, 1 eq), HOAt (65.96 mg, 0.485 mmol, 1 eq), EDC (92.97 mg, 0.485 mmol, 1 eq), DIPEA (187.6 mg, 1.455 mmol, 3 eq) and stirred for 16 h. After completion, the reaction mixture was poured into ice water, The crude compound was purified by column chromatography (SiO$_2$) using MeOH:DCM (3:97) to afford N-(2-hydroxy-4-methylquinolin-6-yl)-2-(2-(methoxy methyl) pyrrolidin-1-yl)-5-(morpholinomethyl) benzamide (Compound-26) (45 mg) as an off white solid.

$^1$H NMR (400 MHz, CD3COOD) δ 8.44 (d, J=2.2 Hz, 1H), 8.21 (d, J=2.3 Hz, 1H), 7.99 (dd, J=8.9, 2.2 Hz, 1H), 7.83-7.72 (m, 1H), 7.46 (t, J=7.7 Hz, 2H), 6.81 (s, 1H), 4.38 (s, 2H), 4.09 (s, 1H), 3.99 (t, J=4.9 Hz, 4H), 3.66 (d, J=8.3 Hz, 1H), 3.59-3.46 (m, 2H), 3.35 (s, 4H), 3.28 (s, 3H), 3.16 (d, J=8.4 Hz, 1H), 2.59 (s, 3H), 2.28 (d, J=7.3 Hz, 1H), 2.15-2.05 (m, 1H).

Synthesis of Compound-27

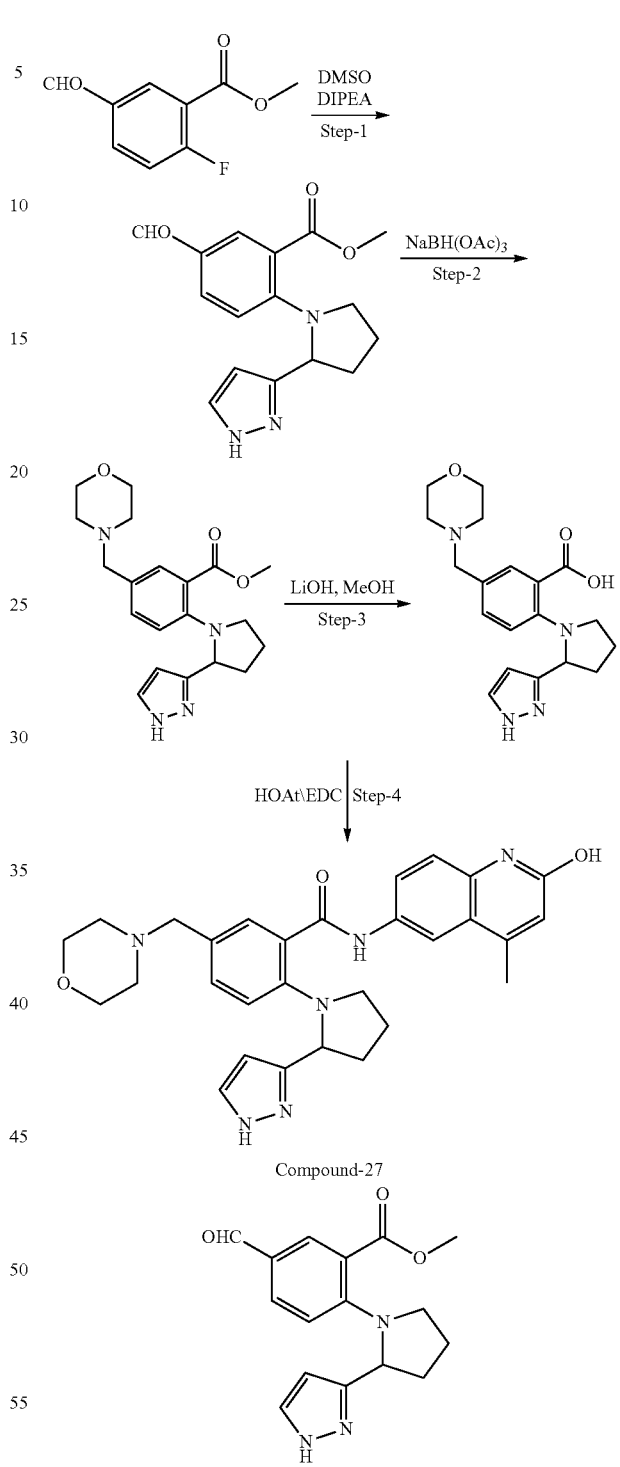

Compound-27

Preparation of methyl 2-(2-(1H-pyrazol-3-yl)pyrrolidin-1-yl)-5-(morpholinomethyl) benzoate: to a solution of methyl 2-fluoro-5-formylbenzoate (500 mg, 2.74 mmol, 1 eq) in DMSO (10 vol) was added (376.83 mg, 2.74 mmol, 1.5 eq), DIPEA (708.72 mg, 5.494 mmol, 2 eq) and stirred at 120° C. for 18 h. After completion, the reaction mixture was poured into ice water and extracted with EtOAc (2×20 mL). The combined extracts were washed with water (30 mL), brine (30 mL), dried over anhydrous Na₂SO₄, filtered and evaporated. The crude compound was purified by column chromatography (SiO₂) using EtOAc:Pet ether (50:50) to afford methyl 2-(2-(1H-pyrazol-3-yl) pyrrolidin-1-yl)-5-(morpholinomethyl) benzoate (480 mg) as pale yellow solid.

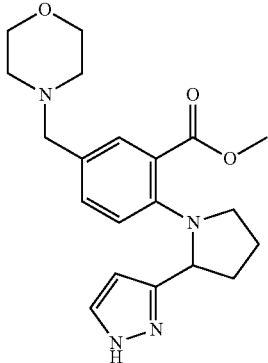 [SMILES: COC(=O)c1cc(CN2CCOCC2)ccc1N1CCCC1c1cc[nH]n1]

Preparation of methyl 2-(2-(1H-pyrazol-3-yl) pyrrolidin-1-yl)-5-(morpholinomethyl) benzoate: to a solution of methyl 2-(2-(1H-pyrazol-3-yl) pyrrolidin-1-yl)-5-formyl-benzoate (240 mg, 0.802 mmol, 1 eq) in Dry DCM (5 mL) was added morpholine (69.8 mg, 0.802 mmol, 1.0 eq), Na(OAC)₃BH (340.04 mg, 1.604 mmol, 1 eq), CH₃COOH (Catalytic) and molecular sieves, stirred at RT for 16 h. After completion, the reaction mixture was poured into water and extracted with DCM (3×30 mL). The combined extracts were washed with water (20 mL), brine (20 mL), dried over anhydrous Na₂SO₄, filtered and evaporated to afford methyl 2-(2-(1H-pyrazol-3-yl)pyrrolidin-1-yl)-5-(morpholinomethyl)benzoate (225 mg) as a brown liquid.

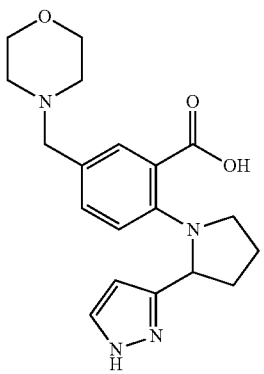 [SMILES: O=C(O)c1cc(CN2CCOCC2)ccc1N1CCCC1c1cc[nH]n1]

Preparation of 2-(2-(1H-pyrazol-3-yl) pyrrolidin-1-yl)-5-(morpholinomethyl) benzoic acid: to a solution of methyl 2-(2-(1H-pyrazol-3-yl) pyrrolidin-1-yl)-5-(morpholinomethyl) benzoate (215 mg, 0.608 mmol, 1 eq) in MeOH:H₂O (3:1) (9 mL) at RT was added LiOH (76.5 mg, 1.824 mmol, 3.0 eq) and stirred at RT for 5 h. After completion, the solvent was evaporated, the crude was acidified with 1N HCl and evaporated to afford 2-(2-(1H-pyrazol-3-yl) pyrrolidin-1-yl)-5-(morpholinomethyl) benzoic acid (170 mg) as a brown solid. The crude was carried to next step without further purification.

Compound-27

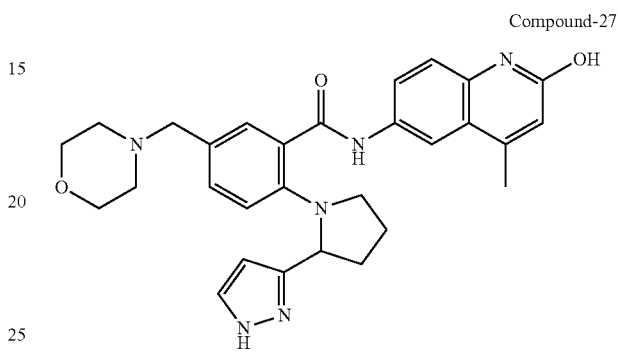

Preparation of 2-(2-(1H-pyrazol-3-yl) pyrrolidin-1-yl)-N-(2-hydroxy-4-methylquinolin-6-yl)-5-(morpholinomethyl) benzamide (Compound-27): to a solution of 2-(2-(methoxymethyl)pyrrolidin-1-yl)-5-(morpholinomethyl) benzoic acid (90 mg, 0.252 mmol, 1 eq) in Dry DMF (5 mL) at RT was added 6-amino-4-methyl-quinolin-2-ol (43.8 mg, 0.252 mmol, 1 eq), HOAt (34.27 mg, 0.252 mmol, 1 eq), EDC (48.30 mg, 0.252 mmol, 1 eq), DIPEA (97.5 mg, 0.756 mmol, 3 eq) and stirred at RT for 16 h. After completion, the reaction mixture poured into ice water and extracted with MeOH:DCM (1:9) (3×20 mL). The combined extracts were washed with water (20 mL), brine (20 mL), dried over anhydrous Na₂SO₄, filtered and evaporated. The crude compound was purified by column chromatography (SiO₂) using MeOH:DCM (5:95) to afford 2-(2-(1H-pyrazol-3-yl) pyrrolidin-1-yl)-N-(2-hydroxy-4-methylquinolin-6-yl)-5-(morpholinomethyl) benzamide (Compound-27) (30 mg) as an off white solid.

¹H NMR (400 MHz, CF₃COOD) δ 8.58 (brs, 1H), 8.33-8.05 (m, 4H), 8.04-7.90 (m, 2H), 7.83 (s, 1H), 7.32 (s, 1H), 6.78 (s, 1H), 5.10 (brs, 1H), 4.72 (s, 2H), 4.48-4.33 (m, 2H), 4.25-4.07 (m, 2H), 3.89-3.47 (m, 6H), 2.90 (s, 3H), 2.69-2.50 (m, 1H), 2.50-2.16 (m, 3H).

Synthesis of Compound-28 and Compound-29:

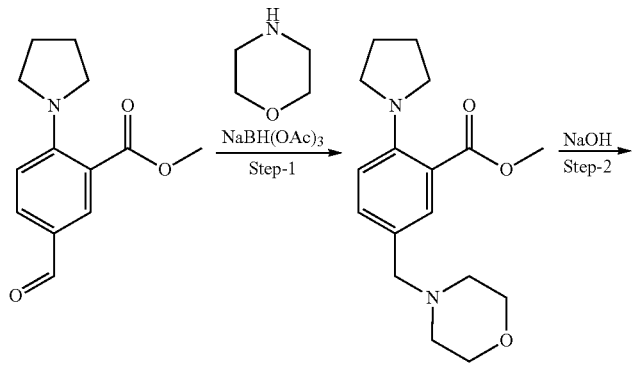

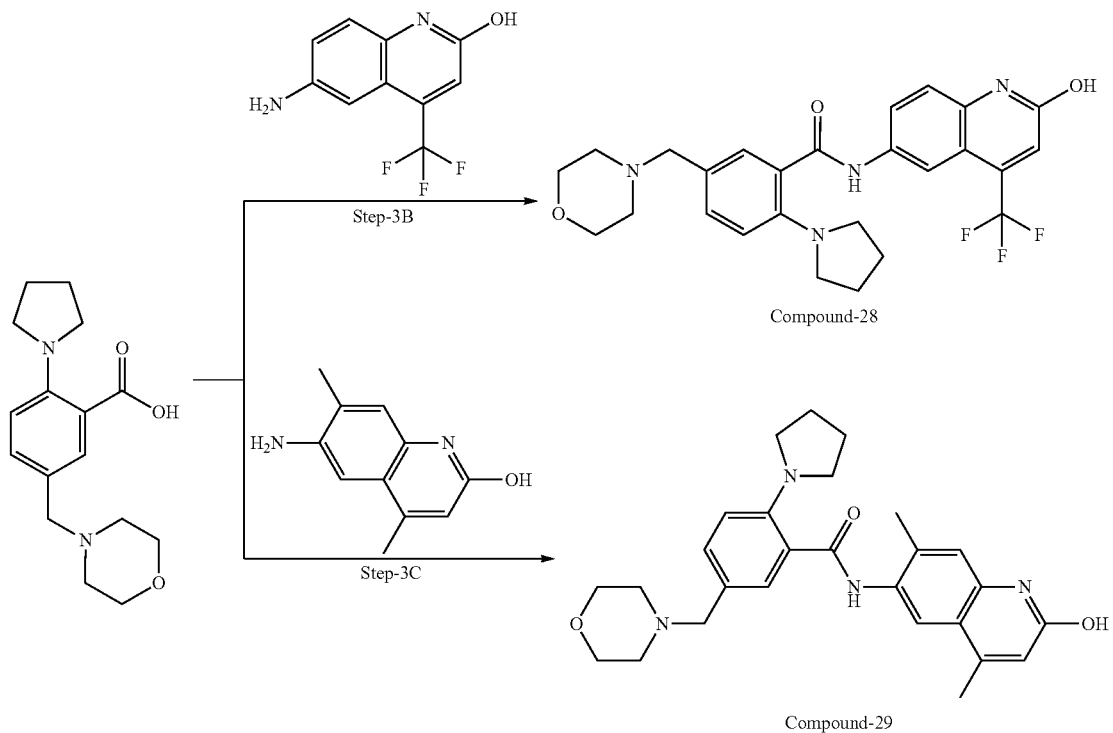

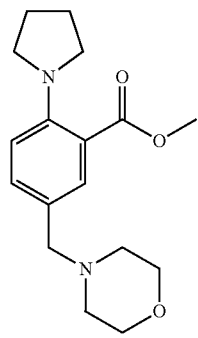

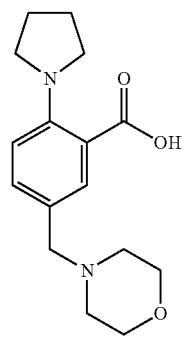 [SMILES: O=C(O)c1cc(CN2CCOCC2)ccc1N1CCCC1]

Preparation of methyl 5-(morpholinomethyl)-2-(pyrrolidin-1-yl) benzoate: to a solution of methyl 5-formyl-2-(pyrrolidin-1-yl)benzoate (1.7 g, 7.29 mmol, 1 eq) in dry DCM (25 mL) was added morpholine (0.63 g, 7.29 mmol, 1 eq), sodium triacetoxy borohydride (3.03 g, 14.59 mmol, 2 eq) and stirred at RT for 2 h. After completion, the reaction mixture was basified with NaHCO$_3$ solution and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) using EtOAc:Pet ether (40:60) to afford methyl 5-(morpholinomethyl)-2-(pyrrolidin-1-yl) benzoate (1.5 g) as an off white solid.

Preparation of 5-(morpholinomethyl)-2-(pyrrolidin-1-yl) benzoic acid: to a solution of methyl 5-(morpholinomethyl)-2-(pyrrolidin-1-yl) benzoate (1.5 g, 4.93 mmol, 1 eq) in MeOH:H$_2$O (3:1) (15 mL) at RT was added NaOH (0.79 g, 4.93 mmol, 4 eq) and stirred at RT for 5 h. After completion, the solvent was evaporated, the crude was taken in water, acidified with 1N HCl and evaporated to afford 5-(morpholinomethyl)-2-(pyrrolidin-1-yl) benzoic acid (900 mg) as off white solid.

$^1$H NMR (300 MHz, DMSO-d$_6$) δ 11.18 (s, 1H), 7.67 (d, J=2.2 Hz, 1H), 7.55 (dd, J=9.0, 2.1 Hz, 1H), 6.85 (d, J=8.7 Hz, 1H), 4.20 (d, J=5.0 Hz, 2H), 3.92 (dd, J=12.5, 3.5 Hz, 2H), 3.86-3.70 (m, 2H), 3.18 (m, 6H), 3.10-2.92 (m, 2H), 1.98-1.81 (m, 4H)

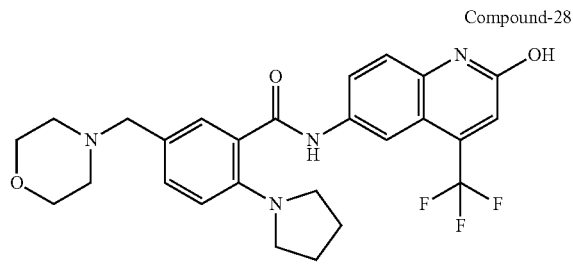 [SMILES: O=C(Nc1ccc2nc(O)cc(C(F)(F)F)c2c1)c1cc(CN2CCOCC2)ccc1N1CCCC1]

Compound-28

Preparation of N-(2-hydroxy-4-(trifluoromethyl) quinolin-6-yl)-5-(morpholinomethyl)-2-(pyrrolidin-1-yl) benzamide (Compound-28): to a solution of 5-(morpholinomethyl)-2-(pyrrolidin-1-yl)benzoic acid (100 mg, 0.34 mmol, 1 eq) in Dry DMF (1 mL) at RT was added 6-amino-4-(trifluoromethyl)-1H-quinolin-2-one (79 mg, 0.34 mmol, 1 eq), HOAt (71 mg, 0.51 mmol, 1.5 eq), EDC (99 mg, 0.51 mmol, 1.5 eq), DIPEA (133 mg, 1.03 mmol, 3 eq) and stirred for 16 h. After completion, the reaction mixture poured into ice water and extracted with EtOAc (2×30 mL). The combined extracts were washed with water (20 mL), brine (20 mL), dried over anhydrous Na$_2$SO$_4$, filtered and evaporated. The crude compound was purified by column chromatography (SiO$_2$) using MeOH:DCM (10:90) to afford N-(2-hydroxy-4-(trifluoromethyl) quinolin-6-yl)-5-(morpholinomethyl)-2-(pyrrolidin-1-yl) benzamide (Compound-28) (31 mg) as an off white solid.

$^1$H NMR (400 MHz, DMSO-d$_6$) δ 11.55 (s, 1H), 10.44 (s, 1H), 8.15 (d, J=2.3 Hz, 1H), 7.81 (dd, J=8.9, 2.3 Hz, 1H), 7.32-7.18 (m, 3H), 6.77 (d, J=8.2 Hz, 1H), 6.41 (s, 1H), 3.41 (d, J=4.5 Hz, 6H), 3.23 (d, J=6.4 Hz, 4H), 2.43-2.26 (m, 7H), 1.97 (s, 3H), 1.85 (q, J=3.3 Hz, 4H).

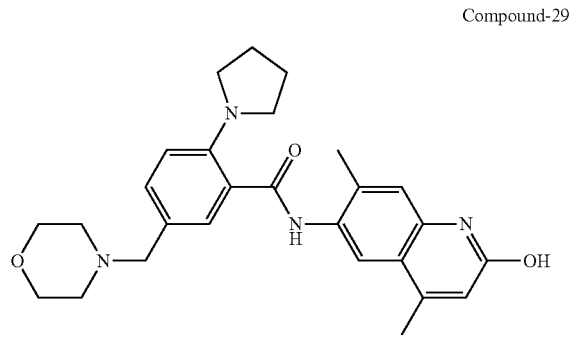 [SMILES: Cc1cc2nc(O)cc(C)c2cc1NC(=O)c1cc(CN2CCOCC2)ccc1N1CCCC1]

Compound-29

Preparation of N-(2-hydroxy-4,7-dimethylquinolin-6-yl)-5-(morpholinomethyl)-2-(pyrrolidin-1-yl)benzamide (Compound-29): to a solution of 5-(morpholinomethyl)-2-(pyrrolidin-1-yl)benzoic acid (100 mg, 0.34 mmol, 1 eq) in Dry DMF (1 mL) at RT was added 6-amino-4,7-dimethyl-1H-quinolin-2-one (65 mg, 0.34 mmol, 1 eq), HOAt (71 mg, 0.51 mmol, 1.5 eq), EDC (99 mg, 0.51 mmol, 1.5 eq), DIPEA (133 mg, 1.03 mmol, 3 eq) and stirred at RT for 16 h. After completion, the reaction mixture poured into ice water and extracted with EtOAc (2×30 mL). The combined extracts were washed with water (20 mL), brine (20 mL), dried over anhydrous Na$_2$SO$_4$, filtered and evaporated. The crude compound was purified by column chromatography (SiO$_2$) using MeOH:DCM (10:90) to afford N-(2-hydroxy-4, 7-dimethylquinolin-6-yl)-5-(morpholinomethyl)-2-(pyrrolidin-1-yl) benzamide (Compound-29) (13 mg) as an off white solid.

$^1$H NMR (300 MHz, DMSO-D6) δ 11.52 (s, 1H), 10.02 (s, 1H), 8.18 (s, 1H), 7.88 (s, 1H), 7.41 (d, J=2.2 Hz, 1H), 7.24 (d, J=8.2 Hz, 1H), 7.16 (s, 1H), 6.83 (d, J=8.6 Hz, 1H), 6.36 (s, 1H), 3.57 (t, J=4.6 Hz, 4H), 3.39 (s, 2H), 3.29-3.20 (m, 3H), 2.54 (s, 3H), 2.41-2.31 (m, 9H), 1.96-1.84 (m, 4H).

Synthesis Compound-30

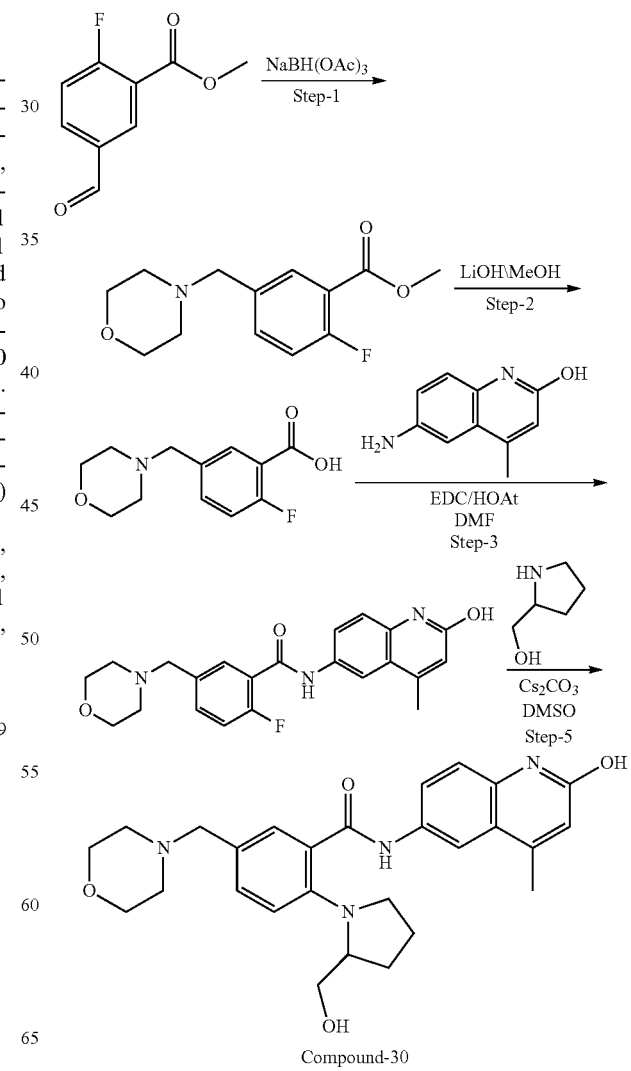

Compound-30

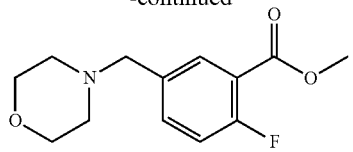

Preparation of methyl 2-fluoro-5-(morpholinomethyl) benzoate: to a solution of methyl 2-fluoro-5-formylbenzoate (1 g, 5.494 mmol, 1 eq) in Dry DCM (5 mL) was added morpholine (478.63 mg, 5.494 mmol, 1.0 eq), Na(OAC)$_3$BH (2.32 g, 10.988 mmol, 2 eq), CH$_3$COOH (catalytic) and molecular sieves, stirred at RT for 16 h. After completion, the reaction mixture was poured into water and extracted with DCM (3×50 mL). The combined extracts were washed with water (20 mL), brine (20 mL), dried over anhydrous Na$_2$SO$_4$, filtered and evaporated to afford methyl 2-fluoro-5-(morpholinomethyl)benzoate (1.1 g) as an pale yellow liquid.

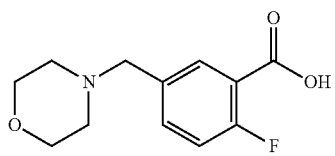 [SMILES: O=C(O)c1cc(CN2CCOCC2)ccc1F]

Preparation of 2-fluoro-5-(morpholinomethyl)benzoic acid: to a solution of methyl 2-fluoro-5-(morpholinomethyl) benzoate (1.1 g, 4.347 mmol, 1 eq) in MeOH:H$_2$O (3:1) (9 mL) at RT added LiOH (547.2 mg, 13.041 mmol, 3.0 eq) and stirred at RT for 5 h. After completion, the solvent was evaporated, the crude was taken in water and neutralized with 1N HCl and extracted with EtOAc (2×50 mL). The combined extracts were washed with water (30 mL), brine (30 mL), dried over anhydrous Na$_2$SO$_4$, filtered and evaporated to afford 2-fluoro-5-(morpholinomethyl)benzoic acid (850 mg) as an off white solid.

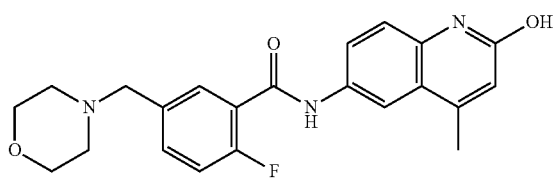 [SMILES: Cc1cc(O)nc2ccc(NC(=O)c3cc(CN4CCOCC4)ccc3F)cc12]

Preparation of 2-fluoro-N-(2-hydroxy-4-methylquinolin-6-yl)-5-(morpholinomethyl) benzamide To a solution of 2-fluoro-5-(morpholinomethyl)benzoic acid (850 mg, 3.556 mmol, 1 eq) in Dry DMF (10 mL) at RT was added 6-amino-4-methyl-quinolin-2-ol (618.7 mg, 3.556 mmol, 1 eq), HOAt (483.6 mg, 3.556 mmol, 1 eq), EDC (681.6 mg, 3.556 mmol, 1 eq), DIPEA (1.37 g, 10.668 mmol, 3 eq) and stirred for 16 h. After completion, the reaction mixture was poured into ice water and extracted with MeOH:DCM (1:9) (2×50 mL). The combined extracts were washed with water (50 mL), brine (50 mL), dried over anhydrous Na$_2$SO$_4$, filtered and evaporated. The crude compound was purified by column chromatography (SiO$_2$) using MeOH:DCM (3:97) to afford 2-fluoro-N-(2-hydroxy-4-methyl quinolin-6-yl)-5-(morpholinomethyl) benzamide (640 mg) as a pale yellow solid.

Compound-30

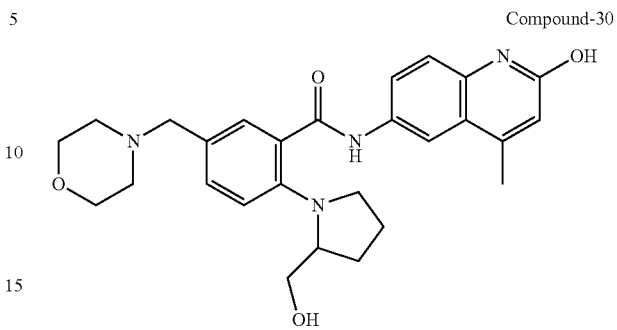

Preparation of N-(2-hydroxy-4-methylquinolin-6-yl)-2-(2-(hydroxymethyl) pyrrolidin-1-yl)-5-(morpholinomethyl) benzamide (Compound-30): to a solution of 2-fluoro-N-(2-hydroxy-4-methylquinolin-6-yl)-5-(morpholinomethyl)benzamide (200 mg, 0.5 mmol, 1 eq) in DMSO (10 vol) was added pyrrolidin-2-yl-methanol (50.55 mg, 0.5 mmol, 1.0 eq), KotBu (281.55 mg, 2.5 mmol, 5 eq) and stirred at 130° C. for 2 h in Microwave. After completion, the reaction mixture was poured into ice water and extracted with MeOH:DCM (1:9) (2×30 mL). The combined extracts were washed with water (50 mL), brine (50 mL), dried over anhydrous Na$_2$SO$_4$, filtered and evaporated. The crude compound was purified by column chromatography (SiO$_2$) using MeOH:DCM (5:95) to afford N-(2-hydroxy-4-methylquinolin-6-yl)-2-(2-(hydroxymethyl) pyrrolidin-1-yl)-5-(morpholinomethyl) benzamide (Compound-30) (20 mg) as an off white solid.

$^1$H NMR (300 MHz, DMSO-d6) δ 11.55 (s, 1H), 11.34 (s, 1H), 8.18 (d, J=2.2 Hz, 1H), 7.80 (dd, J=8.9, 2.3 Hz, 1H), 7.60 (d, J=2.2 Hz, 1H), 7.34 (dd, J=8.3, 2.3 Hz, 1H), 7.28 (d, J=8.8 Hz, 1H), 7.19 (d, J=8.4 Hz, 1H), 6.42 (s, 1H), 4.90-4.84 (m, 1H), 3.87-3.76 (m, 1H), 3.57 (t, J=4.6 Hz, 4H), 3.49-3.35 (m, 5H), 2.99-2.88 (m, 1H), 2.42-2.30 (m, 7H), 2.10-1.90 (m, 2H), 1.90-1.71 (m, 2H).

Synthesis of Compound-31

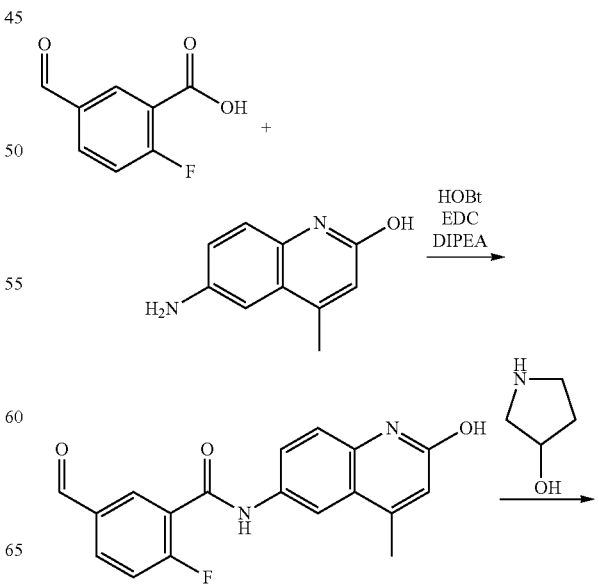

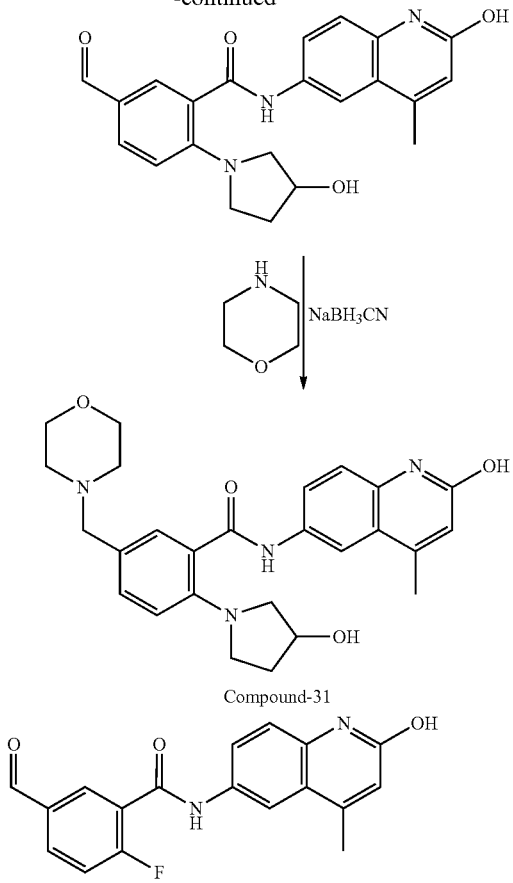

Compound-31

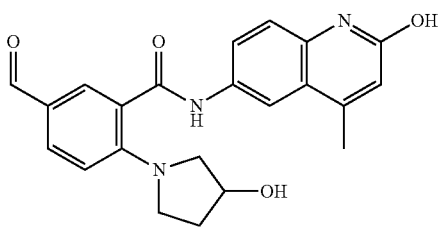 [SMILES: Cc1cc(O)nc2ccc(NC(=O)c3cc(C=O)ccc3N3CCC(O)C3)cc12]

Preparation of 2-fluoro-5-formyl-N-(2-hydroxy-4-methyl-6-quinolyl)benzamide: to a solution of 2-fluoro-5-formyl-benzoic acid (1.0 g, 5.95 mmol, 1 eq) in DMF (15 mL), HOAt (810 mg, 5.95 mmol, 1 eq), EDC (1.14 mg, 5.95 mmol, 1 eq) and DIPEA (2.07 mL, 11.9 mmol, 2 eq) were added, followed by addition of 6-amino-4-methyl-quinolin-2-ol (1.036 mg, 5.95 mmol) and the reaction stirred in DMF overnight at 70° C. TLC showed complete conversion of starting material.

Reaction mixture was diluted with 20 mL EtOAC and 20 mL water and extracted. The organic layer was washed with water and evaporated under reduced pressure to give 200 mg of 2-fluoro-5-formyl-N-(2-hydroxy-4-methyl-6-quinolyl)benzamide. Precipitate that remained in the water extract was filtered off, washed with water and dried to give an additional 1.17 g of title product in the mixture.

1H NMR (300 MHz, DMSO-d6) δ 11.63 (s, 1H), 10.69 (s, 1H), 10.06 (s, 1H), 8.35-8.08 (m, 3H), 7.81 (dd, J=8.9, 2.3 Hz, 1H), 7.74-7.55 (m, 1H), 7.31 (d, J=8.8 Hz, 1H), 6.44 (s, 1H), 2.41 (d, J=1.2 Hz, 3H).

Preparation of 5-formyl-N-(2-hydroxy-4-methyl-6-quinolyl)-2-(3-hydroxypyrrolidin-1-yl)benzamide: to a solution of 2-fluoro-5-formyl-N-(2-hydroxy-4-methyl-6-quinolyl)benzamide (200 mg, 0.62 mmol, 1 eq) in NMP (5 mL), pyrrolidin-3-ol (215 mg, 2.47 mmol, 4 eq) was added and the reaction mixture heated with stirring in microwave reactor at 120° C. for 40 min.

HPLC-MS showed complete conversion. Reaction mixture was diluted with 20 mL EtOAC and 20 mL water and extracted. The organic layer was washed with water and evaporated to give 132 mg of 5-formyl-N-(2-hydroxy-4-methyl-6-quinolyl)-2-(3-hydroxypyrrolidin-1-yl)benzamide. MS: m/z (M+H)+ 392

$^1$H NMR (300 MHz, DMSO-d$_6$) δ 11.58 (s, 1H), 10.61 (s, 1H), 9.74 (s, 1H), 8.14 (d, J=2.1 Hz, 1H), 7.97-7.67 (m, 2H), 7.29 (d, J=8.9 Hz, 1H), 6.87 (d, J=8.9 Hz, 1H), 6.43 (s, 1H), 5.00 (d, J=3.2 Hz, 1H), 4.33 (s, 1H), 3.65-3.48 (m, 1H), 3.46-3.33 (m, 3H), 3.14 (d, J=11.2 Hz, 1H), 2.39 (s, 3H), 2.06-1.75 (m, 2H).

Compound-31

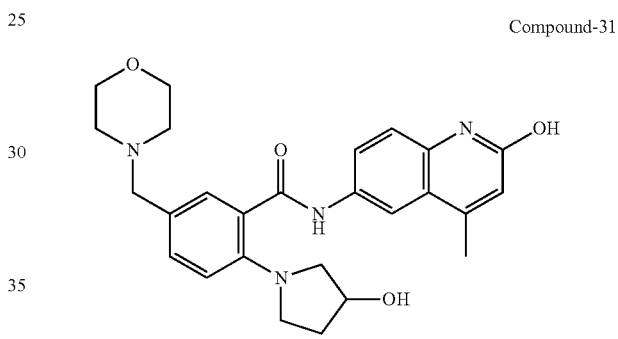

Preparation of N-(2-hydroxy-4-methyl-6-quinolyl)-2-(3-hydroxypyrrolidin-1-yl)-5-(morpholinomethyl)benzamide (Compound-31): to a solution of 5-formyl-N-(2-hydroxy-4-methyl-6-quinolyl)-2-(3-hydroxypyrrolidin-1-yl)benzamide (65 mg, 0.1 mmol, 1 eq) in THF (5 mL), morpholine (29 mg, 0.34 mmol, 2 eq) cyanoborohydride (1.0 M in THF, 0.51 mL, 0.51 mmol, 3 eq) and acetic acid (1 drop, cat. amount) were added and the reaction mixture stirred at room temperature for 20 h. Reaction mixture was diluted with 20 mL EtOAC and 20 mL water and extracted. The organic layer was washed with water and concentrated under reduced pressure to give 25 mg of crude product. Crude product was purified by CombiFlash DCM:MeOH gradient 0%→10% MeOH. Relevant fractions were collected and solvent removed in vacuo to form N-(2-hydroxy-4-methyl-6-quinolyl)-2-(3-hydroxypyrrolidin-1-yl)-5-(morpholinomethyl)benzamide (Compound-31, 28 mg, 36% yield). MS(MH+)= 463.2.

$^1$H NMR (300 MHz, DMSO-d$_6$) δ 11.55 (s, 1H), 10.54 (s, 1H), 8.16 (d, J=2.2 Hz, 1H), 7.84 (dd, J=8.9, 2.2 Hz, 1H), 7.32-7.17 (m, 3H), 6.76 (d, J=8.4 Hz, 1H), 6.41 (s, 1H), 4.90 (d, J=3.4 Hz, 1H), 4.29 (s, 1H), 3.61-3.51 (m, 4H), 3.49-3.32 (m, 4H), 3.28-3.13 (m, 2H), 3.00 (d, J=10.1 Hz, 1H), 2.42-2.30 (m, 7H), 2.05-1.93 (m, 1H), 1.87-1.78 (m, 1H).

Synthesis of Compound-32

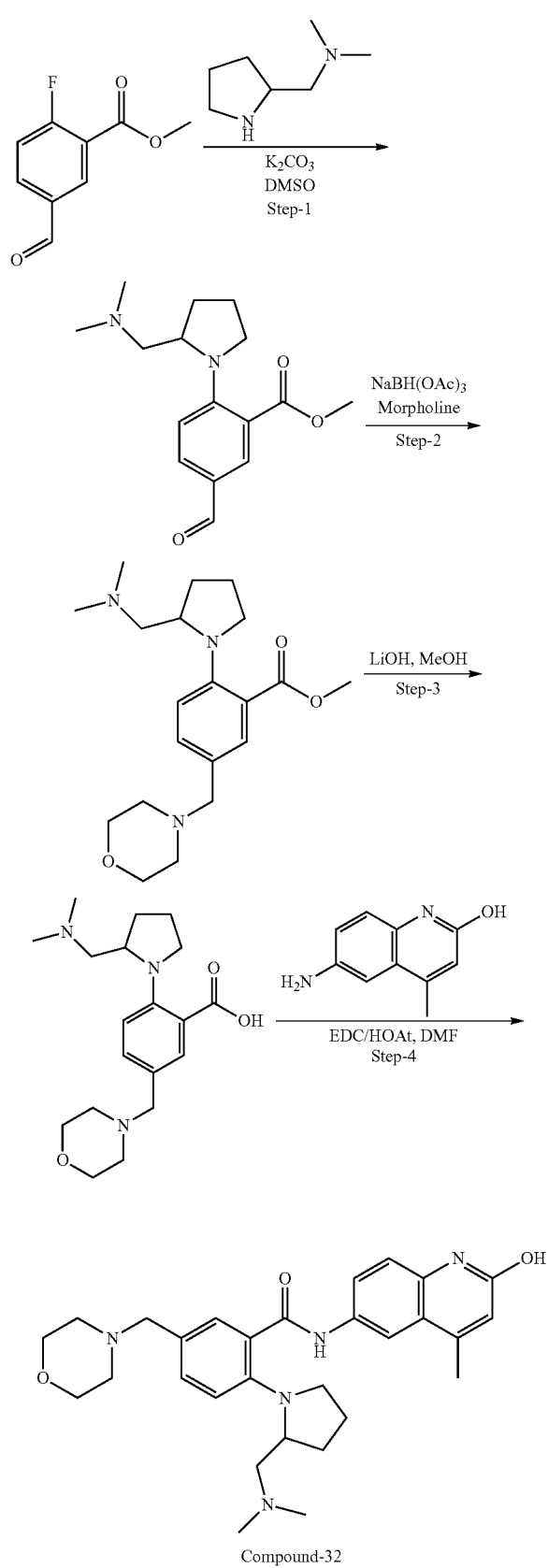

Preparation of methyl 2-(2-((dimethylamino) methyl) pyrrolidin-1-yl)-5-formylbenzoate: to a solution of methyl 2-fluoro-5-formylbenzoate (200 mg, 1.098 mmol, 1 eq) in DMSO (10 vol) was added N,N-dimethyl-1-pyrrolidin-2-yl-methanamine (221.02 mg, 1.098 mmol, 1.0 eq), $K_2CO_3$ (303.04 mg, 2.19 mmol, 2 eq) and stirred at 120° C. for 18 h. After completion, the reaction mixture was poured into ice water and extracted with EtOAc (2×30 mL). The combined extracts were washed with water (20 mL), brine (30 mL), dried over anhydrous $Na_2SO_4$, filtered and evaporated. The crude compound was purified by column chromatography ($SiO_2$) using MeOH:DCM (2:98) to afford methyl 2-(2-((dimethylamino)methyl)pyrrolidin-1-yl)-5-formylbenzoate (180 mg) as a brown liquid.

Preparation of methyl 2-(2-((dimethylamino)methyl)pyrrolidin-1-yl)-5-(morpholinomethyl) benzoate: to a solution of methyl 2-(2-((dimethylamino)methyl)-pyrrolidin-1-yl)-5-formylbenzoate (180 mg, 0.62 mmol, 1 eq) in Dry DCM (5 mL) was added morpholine (54.01 mg, 0.62 mmol, 1.0 eq), $Na(OAC)_3BH$ (262.8 mg, 1.604 mmol, 1 eq), $CH_3COOH$ (Catalytic) and molecular sieves, stirred at RT for 16 h. After completion, the reaction mixture was poured into ice water and extracted with DCM (3×30 mL). The combined extracts were washed with water (20 mL), brine (20 mL), dried over anhydrous $Na_2SO_4$, filtered and evaporated to afford methyl 2-(2-((dimethylamino)methyl)pyrrolidin-1-yl)-5-(morpholinomethyl)benzoate (170 mg) as a pale yellow liquid.

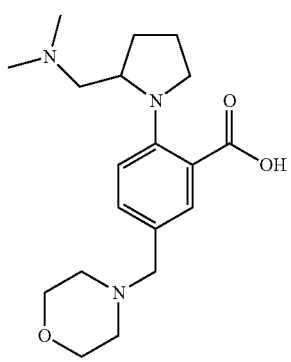 [SMILES: CN(C)CC1CCCN1c1ccc(CN2CCOCC2)cc1C(=O)O]

Preparation of 2-(2-(((dimethylamino) methyl) pyrrolidin-1-yl)-5-(morpholinomethyl) benzoic acid: to a solution of methyl 2-(2-(((dimethylamino) methyl) pyrrolidin-1-yl)-5-(morpholinomethyl) benzoate (170 mg, 0.47 mmol, 1 eq) in MeOH:$H_2O$ (3:1) (6 mL) at RT was added LiOH (59.16 mg, 1.41 mmol, 3.0 eq) and stirred for 5 h. After completion, the solvent was evaporated, the crude was taken in water, acidified with 1N HCl and evaporated to afford 2-(2-(((dimethylamino) methyl) pyrrolidin-1-yl)-5-(morpholinomethyl) benzoic acid (130 mg) as brown solid. The crude was carried to next step without further purification.

Compound-32

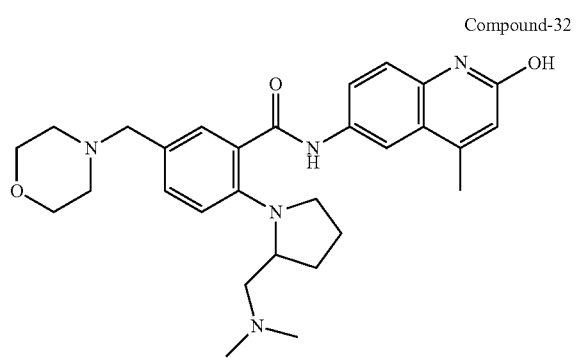 [SMILES: Cc1cc(O)nc2ccc(NC(=O)c3cc(CN4CCOCC4)ccc3N3CCCC3CN(C)C)cc12]

Preparation of 2-(2-(((dimethylamino) methyl) pyrrolidin-1-yl)-N-(2-hydroxy-4-methylquinolin-6-yl)-5-(morpholinomethyl) benzamide (Compound-32): to a solution of 2-(2-(((dimethylamino)methyl)pyrrolidin-1-yl)-5-(morpholinomethyl)benzoic acid (130 mg, 0.373 mmol, 1 eq) in Dry DMF (5 mL) at RT was added 6-amino-4-methyl-quinolin-2-ol (64.9 mg, 0.373 mmol, 1 eq), HOAt (50.72 mg, 0.373 mmol, 1 eq), EDC (71.5 mg, 0.373 mmol, 1 eq), DIPEA (144.3 mg, 1.119 mmol, 3 eq) and stirred for 16 h. After completion, the reaction mixture poured into ice water, extracted with MeoH:DCM (1:9) (3×20 mL). The combined extracts were washed with water (20 mL), brine (20 mL), dried over anhydrous $Na_2SO_4$, filtered and evaporated. The crude compound was purified by column chromatography ($SiO_2$) using MeOH:DCM (5:95) to afford 2-(2-(((dimethylamino)methyl)pyrrolidin-1-yl)-N-(2-hydroxy-4-methylquinolin-6-yl)-5-(morpholinomethyl)benzamide (Compound-32) (20 mg) as an off white solid.

$^1$H NMR (400 MHz, dmso) δ11.56 (s, 1H), 11.30 (s, 1H), 8.16 (d, J=2.4 Hz, 1H), 7.74 (dd, J=8.8, 2.4 Hz, 1H), 7.52 (d, J=1.5 Hz, 1H), 7.33-7.26 (m, 2H), 7.10 (d, J=8.6 Hz, 1H), 6.42 (s, 1H), 3.86 (s, 1H), 3.57 (t, J=4.6 Hz, 4H), 3.42 (s, 3H), 3.02-2.94 (m, 1H), 2.38 (d, J=15.9 Hz, 7H), 2.09 (s, 7H), 1.94-1.73 (m, 3H)

Synthesis of Compound-33:

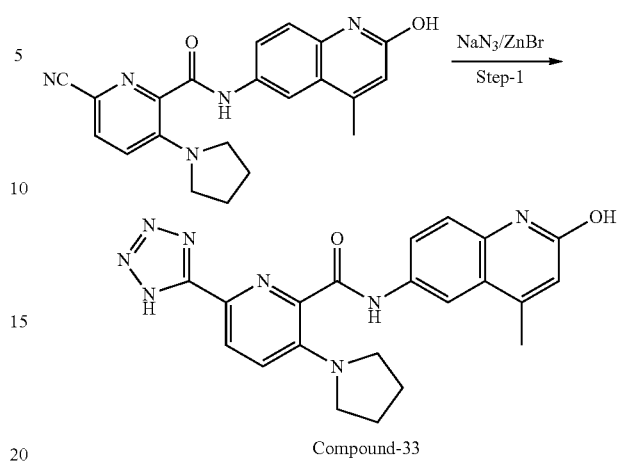

Compound-33

Preparation of N-(2-hydroxy-4-methylquinolin-6-yl)-3-(pyrrolidin-1-yl)-6-(1H-tetrazol-5-yl) picolinamide (Compound-33): to a solution of 6-Cyano-N-(2-hydroxy-4-methylquinolin-6-yl)-3-(pyrrolidin-1-yl) picolinamide (Compound-35) (40 mg, 0.107 mmol, 1 eq) in IPA:$H_2O$ (10 vol) was added $NaN_3$ (3 eq), $ZnBr_2$ (1 eq) and stirred at 100° C. for 20 h. After completion, the reaction mixture was poured into water and precipitated solid was filtered. The crude product was triturated with diethyl ether and pentane to afford N-(2-hydroxy-4-methylquinolin-6-yl)-3-(pyrrolidin-1-yl)-6-(1H-tetrazol-5-yl) picolinamide (Compound-33, 22 mg) as Pale yellow solid.

$^1$H NMR (300 MHz, DMSO-d6) δ 16.66 (s, 1H), 11.60 (s, 1H), 10.63 (s, 1H), 8.16 (s, 1H), 8.07 (d, J=8.8 Hz, 1H), 7.91-7.83 (m, 1H), 7.40 (d, J=8.9 Hz, 1H), 7.32 (d, J=8.8 Hz, 1H), 6.44 (s, 1H), 3.35 (s, 4H), 2.42 (s, 3H), 1.91 (s, 4H).

Synthesis of Compound-34

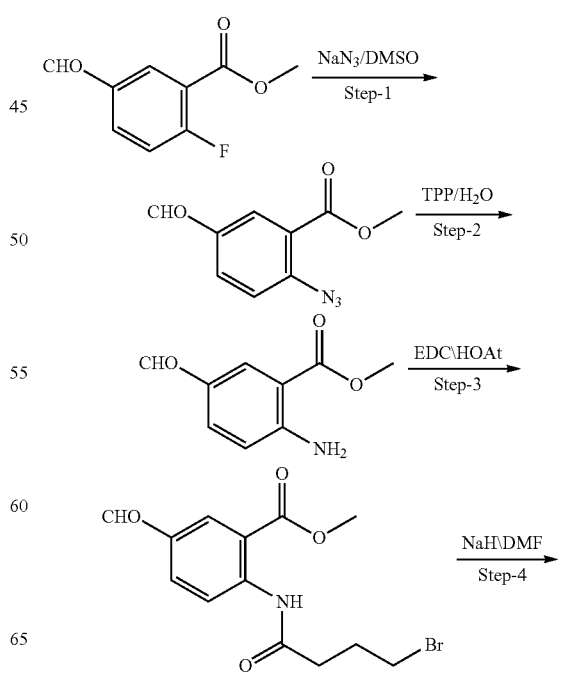

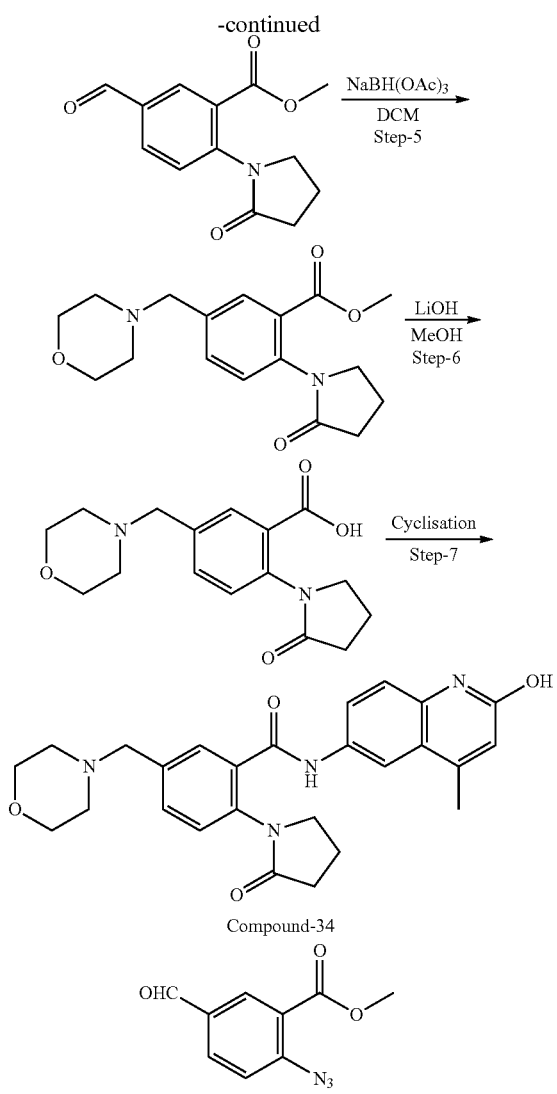

Compound-34

Preparation of methyl 2-azido-5-formylbenzoate: to a solution of methyl 2-fluoro-5-formylbenzoate (5 g, 27.47 mmol, 1 eq) in dry DMSO (50 mL) at 80° C. was added NaN$_3$ (1.78 g, 27.47 mmol, 0.05 eq) and stirred at 70° C. for 5 h. After completion, the solvent was evaporated. The reaction mixture was poured into water and extracted with EtOAc (3×50 mL). The combined extracts were washed with water (200 mL), brine (200 mL), dried over anhydrous Na$_2$SO$_4$, filtered and evaporated. The crude compound was purified by column chromatography using (SiO$_2$) by eluting EtOAc:Pet ether (10:90) to afford methyl 2-azido-5-formylbenzoate (4 g) as an off white solid.

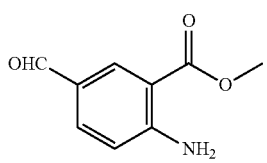

Preparation of methyl 2-amino-5-formylbenzoate: to a solution of methyl 2-azido-5-formylbenzoate (4 g, 19.41 mmol, 1 eq) in THF:H$_2$O (1:1)(40 mL) was added Triphenylphosphine (5 g, 19.41 mmol, 1 eq) and stirred at RT for 2 h. After completion, the reaction mixture was poured into water and extracted with EtOAc (2×100 mL). The combined extracts were washed with water (2×50 mL), brine (50 mL), dried over anhydrous Na$_2$SO$_4$, filtered and evaporated. The crude compound was purified by column chromatography (SiO$_2$) using EtOAc:Pet ether (15:85) to afford methyl 2-amino-5-formylbenzoate (3 g) as a pale yellow solid.

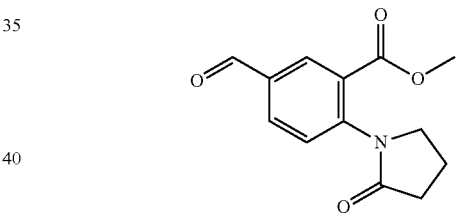

Preparation of methyl 2-(4-bromobutanamido)-5-formylbenzoate: to a solution of methyl 2-amino-5-formylbenzoate (3 g, 16.75 mmol, 1 eq) in Dry DCM (30 mL) was added 4-Bromo buteryl chloride (9.2 g, 50.27 mmol, 3 eq), pyridine (1.3 g, 16.75 mmol, 1 eq), and stirred at RT for 5 h. After completion, the reaction mixture was poured into ice water and extracted with DCM (2×50 mL). The combined extracts were washed with water (50 mL), brine (50 mL), dried over anhydrous Na$_2$SO$_4$, filtered and evaporated. The crude compound was purified by column chromatography using (SiO$_2$) by eluting EtOAc:Pet ether (12:87) to afford methyl 2-(4-bromobutanamido)-5-formylbenzoate (2.8 g) as pale yellow solid.

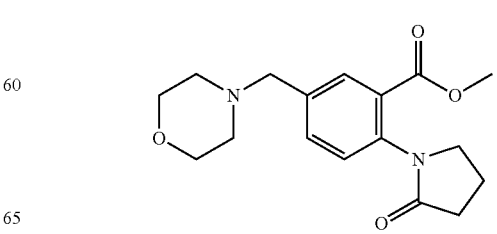

Preparation of methyl 5-formyl-2-(2-oxopyrrolidin-1-yl) benzoate: to a solution of methyl 2-(4-bromobutanamido)-5-formylbenzoate (2.8 g, 8.56 mmol, 1 eq) in Dry THF (10 vol) was added 60% NaH (246 mg, 10.27 mmol, 1.2 eq) and stirred at RT for 2 h. After completion, the reaction mixture was poured into ice water and extracted with EtOAc (2×50 mL). The combined extracts were washed with water (50 mL), brine (50 mL), dried over anhydrous Na$_2$SO$_4$, filtered and evaporated. The crude compound was purified by column chromatography (SiO$_2$) using EtOAc:Pet ether (25:75) to afford methyl 5-formyl-2-(2-oxopyrrolidin-1-yl) benzoate (910 mg) as pale yellow liquid.

Preparation of methyl 5-(morpholinomethyl)-2-(2-oxopyrrolidin-1-yl) benzoate: to a solution of methyl 5-formyl-2-(2-oxopyrrolidin-1-yl)benzoate (910 mg, 3.68 mmol, 1 eq) in Dry DCM (10 mL) was added morpholine (320.6 mg, 3.68 mmol, 1.0 eq), Na(OAC)$_3$BH (1.55 g, 7.36 mmol, 1 eq), CH$_3$COOH (Catalytic) with molecular sieves and stirred at RT for 16 h. After completion, the reaction mixture was added water and extracted with DCM (3×30 mL). The combined extracts were washed with water (3×20 mL), brine (1×20 mL), dried over anhydrous Na$_2$SO$_4$, filtered and evaporated. The crude compound was purified by column chromatography (SiO$_2$) using MeOH:DCM (4:96) to afford methyl 5-(morpholinomethyl)-2-(2-oxopyrrolidin-1-yl) benzoate (800 mg) as a pale yellow liquid.

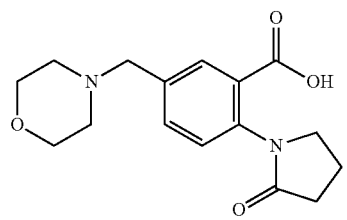 [SMILES: O=C(O)c1cc(CN2CCOCC2)ccc1N1CCCC1=O]

Preparation of 5-(morpholinomethyl)-2-(2-oxopyrrolidin-1-yl) benzoic acid: to a solution of methyl 5-(morpholinomethyl)-2-(2-oxopyrrolidin-1-yl) benzoate (800 mg, 2.51 mmol, 1 eq) in MeOH:H$_2$O (3:1) (12 mL) at RT added LiOH (210 mg, 5.02 mmol, 2.0 eq) and stirred at RT for 5 h. After completion, the solvent was evaporated. The crude residue was washed with di ethyl ether and dried to afford 5-(morpholinomethyl)-2-(2-oxopyrrolidin-1-yl) benzoic acid as Li salt (600 mg) as an off white solid. The crude was carried to next step without further purification.

Compound-34

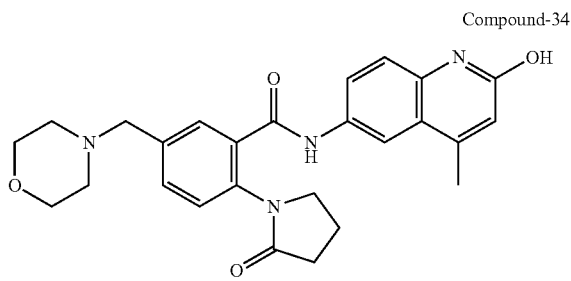 [SMILES: Cc1cc(O)nc2ccc(NC(=O)c3cc(CN4CCOCC4)ccc3N3CCCC3=O)cc12]

Preparation of N-(2-hydroxy-4-methylquinolin-6-yl)-5-(morpholinomethyl)-2-(2-oxopyrrolidin-1-yl) benzamide (Compound-34): to a solution of 5-(morpholinomethyl)-2-(2-oxopyrrolidin-1-yl)benzoic acid (600 mg, 1.97 mmol, 1 eq) in Dry DMF (6 mL) at RT was added Compound-7a (342.7 mg, 1.97 mmol, 1 eq), HOAt (267.9 mg, 1.97 mmol, 1 eq), EDC (377.6 mg, 1.97 mmol, 1 eq), DIPEA (762.3 mg, 5.91 mmol, 3 eq) and stirred at RT for 16 h. After completion, the reaction mixture was poured into ice water and extracted with MeOH:DCM (1:9) (3×30 mL). The combined extracts were washed with water (3×20 mL), brine (1×20 mL), dried over anhydrous Na$_2$SO$_4$, filtered and evaporated. The crude compound was purified by column chromatography (SiO$_2$) using MeOH:DCM (5:95) to afford N-(2-hydroxy-4-methylquinolin-6-yl)-5-(morpholinomethyl)-2-(2-oxopyrrolidin-1-yl) benzamide (Compound-34) (75 mg) as an off white solid.

$^1$H NMR (300 MHz, DMSO-d6) δ 11.56 (s, 1H), 10.33 (s, 1H), 8.05 (s, 1H), 7.77 (d, J=8.7 Hz, 1H), 7.57-7.44 (m, 2H), 7.36 (d, J=8.1 Hz, 1H), 7.27 (d, J=8.9 Hz, 1H), 6.42 (s, 1H), 3.83 (t, J=6.9 Hz, 2H), 3.59-3.52 (m, 6H), 2.46-2.23 (m, 10H), 2.13-2.00 (m, 2H).

Synthesis of Compound-35, Compound-36, Compound-37, Compound-38, Compound-39, and Compound-40:

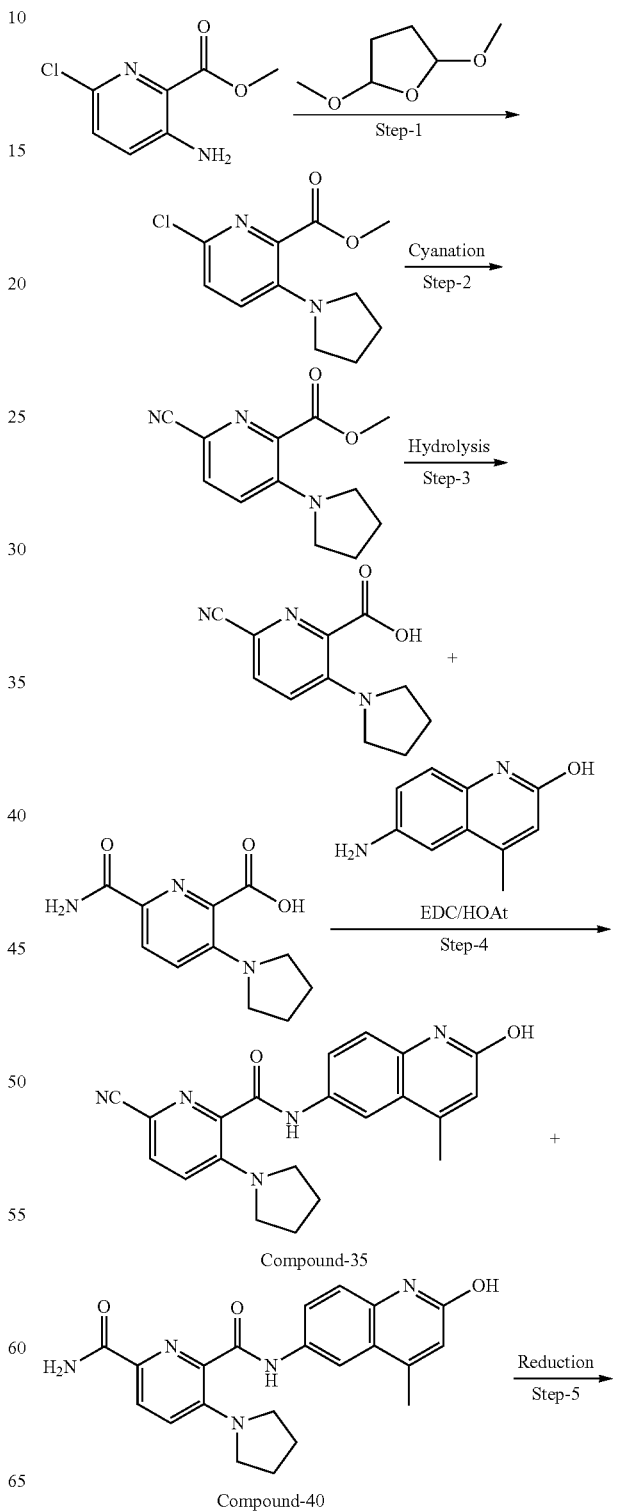

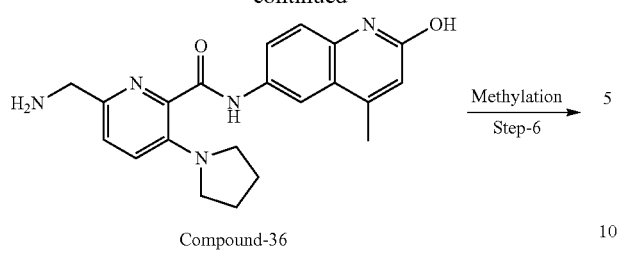

Compound-36

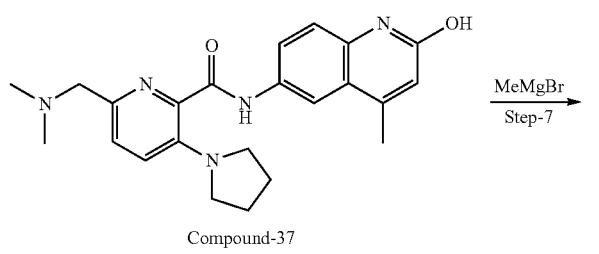

Compound-37

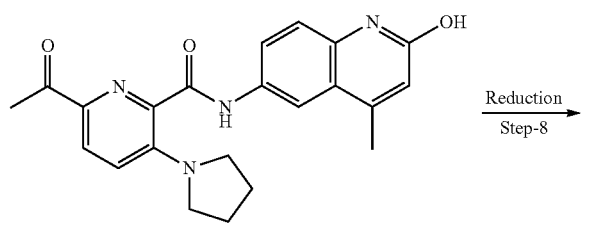

Compound-38

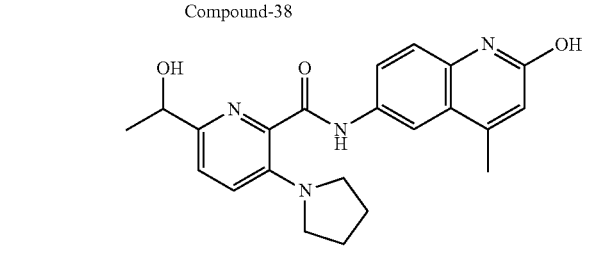

Compound-39

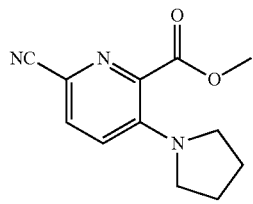 [SMILES: COC(=O)c1nc(C#N)ccc1N1CCCC1]

Preparation of methyl 6-chloro-3-(pyrrolidin-1-yl) picolinate

To a solution of methyl 3-amino-6-chloro picolinate (2 g, 10.6 mmol, 1 eq) in MeOH:THF (1:1) (80 mL), 4N $H_2SO_4$ (20 mL) added 2,5-dimethoxytetrahydrofuran (4.19 g, 31.8 mmol, 3 eq) and $NaBH_4$ (1.2 g, 31.8 mmol, 3 eq) at 0° C. over a period of 30 min's, and stirred at RT for 48 h. After completion, the reaction mixture was poured into water (100 mL), neutralized with $NaHCO_3$ and extracted with EtOAc (3×20 mL). The combined extracts were washed with water (20 mL) followed by brine solution (20 mL), dried over anhydrous $Na_2SO_4$, filtered and evaporated. The crude residue was purified by column chromatography (100-200 mesh silica, EtOAc:Hexane (5:95)) to afford to 6-chloro-3-(pyrrolidin-1-yl) picolinate (760 mg) as off white solid.

Preparation of methyl 6-cyano-3 (pyrrolidin-1-yl) picolinate: to a solution of 6-chloro-3-(pyrrolidin-1-yl)picolinate (600 mg, 2.5 mmol, 1 eq) in DMF (12 mL) was added $ZnCN_2$ (351 mg, 3.0 mmol, 3 eq), degassed with $N_2$ gas for 15 min. Then added Tetrakis (triphenylphosphine) palladium (289 mg, 0.25 mmol, 0.1 eq) and heated at 120° C. for 16 h. After completion, the reaction mixture was poured into water and extracted with EtOAc (3×20 mL). The combined extracts were washed with water (20 mL), brine (20 mL), dried over anhydrous $Na_2SO_4$, filtered and evaporated. The crude residue was purified by column chromatography (100-200 mesh, silica, EtOAc:Hexane (4:6)) to afford to methyl 6-cyano-3(pyrrolidin-1-yl) picolinate (500 mg) as a pale yellow solid.

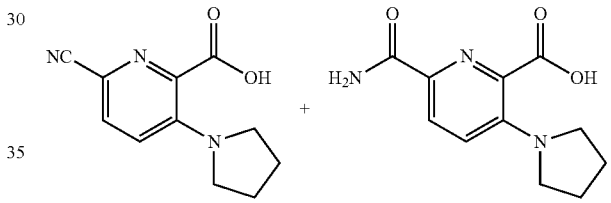

Preparation of 6-cyano-3(pyrrolidin-1-yl) picolinic acid and 6-carbamoyl-3-(pyrrolidin-1-yl) picolinic acid: to a solution of methyl 6-cyano-3(pyrrolidin-1-yl) picolinate (500 mg, 2.16 mmol, 1 eq) in MeOH:$H_2O$ (1:1) (5 mL) added NaOH (259 mg, 6.49 mg, 3 eq) and stirred at RT for 16 h. After completion reaction mixture was poured into water (15 mL), acidified with 1N HCl and extracted with EtOAc (3×20 mL). The combined extracts were washed with water (20 mL), brine solution (20 mL), dried over anhydrous $Na_2SO_4$, filtered and evaporated to afford mixture of 6-cyano-3(pyrrolidin-1-yl) picolinic acid and 6-carbmoyl-3-(pyrrolidin-1-yl)picolinic acid (350 mg).

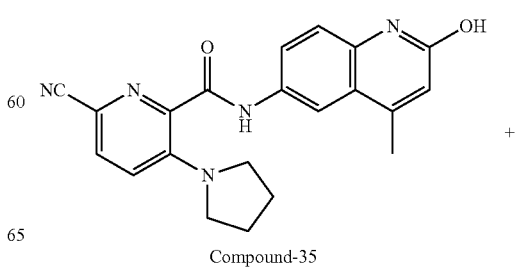

Compound-35

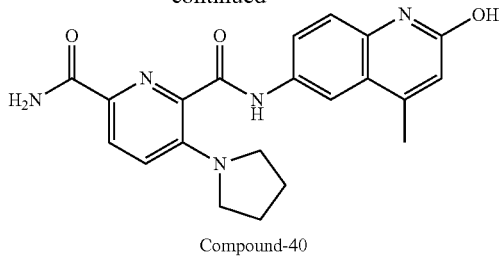

Compound-40

Preparation of 6-Cyano-N-(2-hydroxy-4-methylquinolin-6-yl)-3-(pyrrolidin-1-yl)picolinamide (Compound-35) and N2-(2-hydroxy-4-methylquinolin-6-yl)-3-(pyrrolidin-1-yl) pyridine-2,6-dicarboxamide (Compound-40): to a solution of 6-cyano-3-(pyrrolidin-1-yl) picolinic acid and 6-carbamoyl-3-(pyrrolidin-1-yl) picolinic acid (350 mg, 1.61 mmol, 1 eq) in DMF added EDC.HCl (578 mg, 3.0 mmol, 2 eq), HOAt (412 g, 3.0 mmol, 2 eq) and DIPEA (3 eq) allowed to stir at RT for 15 min's. Then added 6-amino-4-methylquinlin-2-ol (316 mg, 1.81 mmol, 1.2 eq) and stirred at RT for 16 h. After completion, the reaction mixture was poured into water and precipitated solid was filtered. The crude product was purified by column chromatography (100-200 mesh silica, MeOH:DCM (4:96)), to afford to 6-Cyano-N-(2-hydroxy-4-methylquinolin-6-yl)-3-(pyrrolidin-1-yl)picolinamide (Compound-35) (250 mg) as pale yellow solid and $N^2$-(2-hydroxy-4-methyl quinolin-6-yl)-3-(pyrrolidin-1-yl) pyridine-2,6-dicarboxamide (Compound-40) (23 mg) as pale yellow solid.

Compound-40:
$^1$H NMR (300 MHz, dmso) δ 11.59 (s, 1H), 10.60 (s, 1H), 8.17-8.06 (m, 2H), 7.91 (dd, J=8.8, 3.0 Hz, 2H), 7.38-7.27 (m, 3H), 6.43 (s, 1H), 3.31-3.25 (m, 4H), 2.42 (s, 3H), 1.96-1.85 (m, 4H).

Compound-35:
$^1$H NMR (300 MHz, DMSO-$d_6$) δ 11.59 (s, 1H), 10.74 (s, 1H), 8.12 (d, J=2.2 Hz, 1H), 7.89-7.80 (m, 2H), 7.27 (dd, J=19.2, 8.9 Hz, 2H), 6.43 (d, J=2.1 Hz, 1H), 3.40-3.33 (m, 4H), 2.40 (s, 3H), 1.96-1.84 (m, 4H).

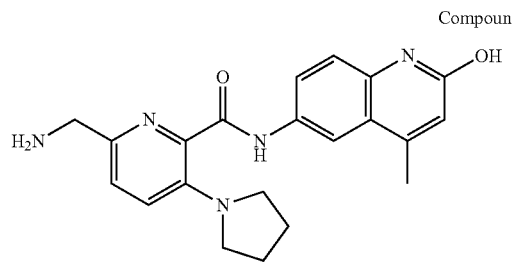

Compound-36

Preparation of 6-(aminomethyl)-N-(2-hydroxy-4-methylqunolin-6-yl)-3-(pyrrolidin-1-yl)picolinamide (Compound-36): to a solution of 6-Cyano-N-(2-hydroxy-4-methylquinolin-6-yl)-3-(pyrrolidin-1-yl)picolinamide (Compound-35) (100 mg, 0.26 mmol, 1 eq) in EtOH:Conc HCl (10:1) (10 vol) was added 10% Pd/C (20 mg) and hydrogenated (50 psi) at RT for 8 h. After completion, the reaction mixture was filtered through a pad of celite, washed with EtOH (50 mL). The combined filtrate was evaporated and washed with diethylether to afford 6-(aminomethyl)-N-(2-hydroxy-4-methylqunolin-6-yl)-3-(pyrrolidin-1-yl)picolinamide (Compound-36) (80 mg) as brown solid.

$^1$H NMR (300 MHz, dmso) δ 11.59 (s, 1H), 10.72 (s, 1H), 8.52 (brs, 3H), 8.29 (s, 1H), 8.04 (d, J=7.0 Hz, 1H), 7.47-7.21 (m, 4H), 6.43 (s, 1H), 4.10 (s, 2H), 3.27 (s, 4H), 2.41 (s, 3H), 1.90 (s, 4H).

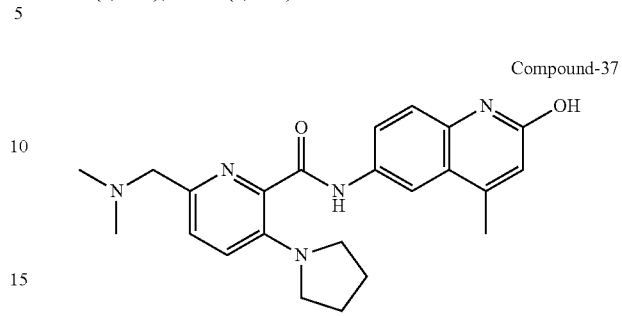

Compound-37

Preparation of 6-((dimethylamino) methyl-N-(2-hydroxy-4-methylqunolin-6-yl)-3-(pyrrolidin-1-yl) picolinamide (Compound-37): to a solution of 6-(aminomethyl)-N-(2-hydroxy-4-methylqunolin-6-yl)-3-(pyrrolidin-1-yl)picolinamide (Compound-36) (50 mg, 0.13 mmol, 1 eq) in ACN was added 37% of formaldehyde (5 mL), acetic acid (cat) and stirred at RT for 15 min. Then added NaBH$_3$CN (24.18 mg, 0.39 mmol, 3 eq) and stirred at RT for 16 h. After completion, the reaction mixture quenched with ice water and evaporated the solvent to dryness. The residue was purified on Prep HPLC to afford 6-((dimethylamino)methyl-N-(2-hydroxy-4-methylqunolin-6-yl)-3-(pyrrolidin-1-yl)picolinamide (Compound-37) (8 mg) as off white thick liquid.

1H NMR (300 MHz, CDCl3) δ 10.00 (s, 1H), 9.07 (s, 1H), 8.29 (s, 1H), 7.84 (d, J=8.7 Hz, 1H), 7.29 (d, J=8.5 Hz, 1H), 7.22 (s, 1H), 7.14 (d, J=8.8 Hz, 1H), 6.55 (s, 1H), 3.69 (s, 2H), 3.43-3.30 (m, 5H), 2.52 (d, J=1.3 Hz, 3H), 2.44 (s, 6H), 1.99 (d, J=6.5 Hz, 3H).

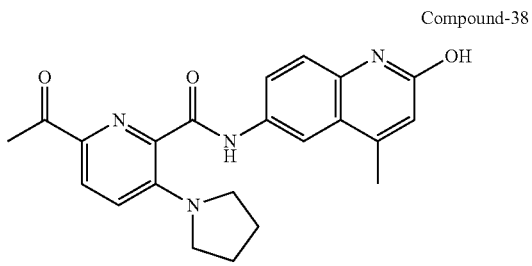 [SMILES: CC(=O)c1ccc(N2CCCC2)c(C(=O)Nc2ccc3nc(O)cc(C)c3c2)n1]

Compound-38

Preparation of 6-acetyl-N-(2-hydroxy-4-methylquinolin-6-yl)-3(pyrrolidin-1-yl)picolinamide (Compound-38): to a solution of 6-Cyano-N-(2-hydroxy-4-methylquinolin-6-yl)-3-(pyrrolidin-1-yl)picolinamide (Compound-37) (60 mg, 0.156 mmol, 1 eq) in Dry THF (10 vol) was added MeMgBr (5 eq) at 0° C. and allowed to stir at RT for 16 h. The reaction was monitored by LCMS, After completion reaction mixture was quenched with ice water (15 mL) and extracted with EtOAc (3×10 mL). The combined extracts were washed with water (20 mL), brine (20 mL), dried over anhydrous Na$_2$SO$_4$, filtered and evaporated. The crude product was purified by combiflash using DCM:MeOH (5:95) to afford 6-acetyl-N-(2-hydroxy-4-methylquinolin-6-yl)-3(pyrrolidin-1-yl)picolinamide (Compound-38) (45 mg) as pale yellow solid.

$^1$H NMR (400 MHz, dmso) δ 11.58 (s, 1H), 10.66 (s, 1H), 8.18 (d, J=2.2 Hz, 1H), 7.94-7.84 (m, 2H), 7.28 (dd, J=22.1,

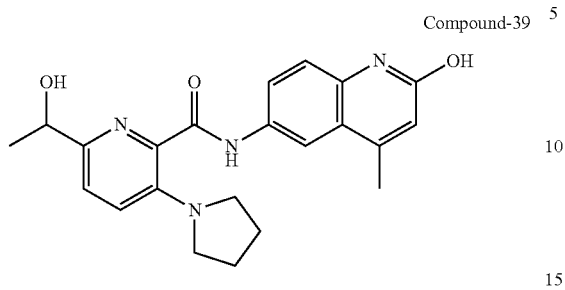

Compound-39

Preparation of N-(2-hydroxy4-methylquinolin-6-yl)-6-(1-hydroxymethyl)-3-(pyrrolidin-1-yl)picolinamide (Compound-39): to a solution of 6-acetyl-N-(2-hydroxy-4-methylquinolin-6-yl)-3(pyrrolidin-1-yl) picolinamide (Compound-38) (45 mg, 0.115 mmol, 1 eq) in MeOH (10 vol) was added NaBH$_4$ (13.15 mg, 0.346 mmol, 3 eq) at 0° C. and stirred at RT for 16 h. After completion, the reaction mixture was quenched with NH$_4$Cl solution (15 mL) and extracted with EtOAc (3×20 mL). The combined extracts were washed with water (20 mL), brine (20 mL), dried over anhydrous Na$_2$SO$_4$, filtered and evaporated. The crude residue was purified by combiflash using DCM:MeOH (92:8) to afford N-(2-hydroxy4-methylquinolin-6-yl)-6-(1-hydroxymethyl)-3-(pyrrolidin-1-yl) picolinamide (Compound-39) (22 mg) as pale yellow solid.

$^1$H NMR (400 MHz, cdcl$_3$) δ 10.77 (s, 1H), 9.28 (s, 1H), 8.25 (d, J=2.4 Hz, 1H), 7.71 (dd, J=8.8, 2.4 Hz, 1H), 7.34-7.26 (m, 3H), 6.59 (s, 1H), 4.91 (q, J=6.1 Hz, 1H), 3.44-3.29 (m, 4H), 2.53 (s, 3H), 2.04-1.92 (m, 4H), 1.54 (d, J=6.6 Hz, 3H).

Synthesis of Compound-41, Compound-42, Compound-43, Compound-44, and Compound-45:

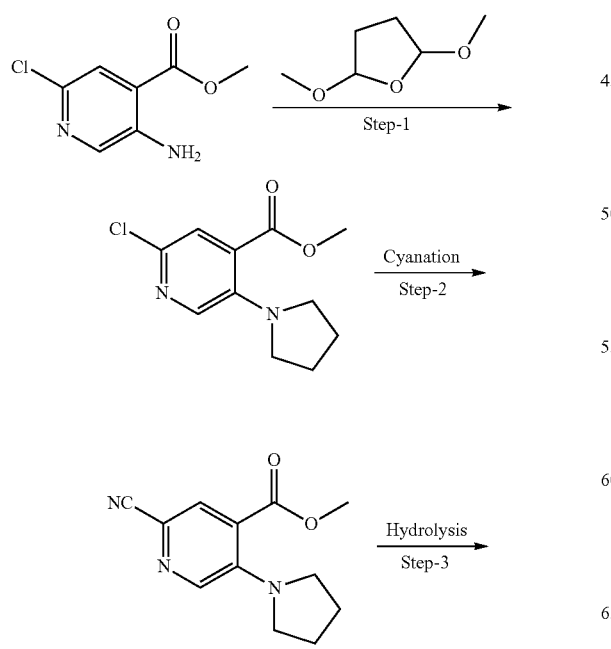

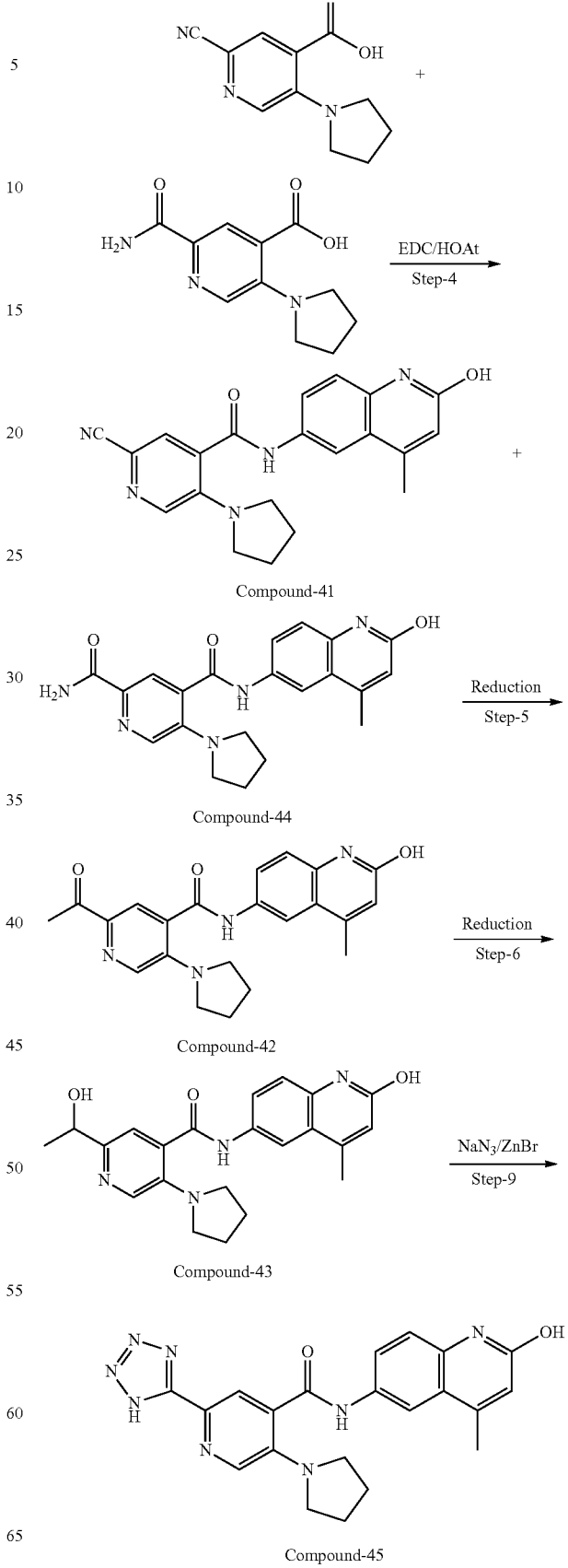

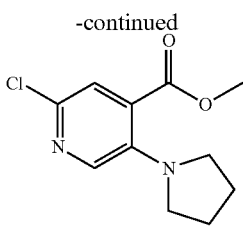

Preparation of methyl 2-chloro-5-(pyrrolidin-1-yl) isonicotinate: to a solution of methyl 5-amino-2-chloroisonicotinate (2 g, 10.6 mmol, 1 eq) in MeOH:THF (1:1) (80 mL), 4N $H_2SO_4$ (20 mL) was added 2,5-dimethoxytetrahydrofuran (4.19 g, 31.8 mmol, 3 eq) and $NaBH_4$ (1.2 g, 31.8 mmol, 3 eq) at 0° C. over a period of 30 min and stirred at RT for 48 h. After completion, the reaction mixture was poured into water (50 mL), neutralized with $NaHCO_3$ and extracted with EtOAc (3×25 mL). The combined extracts were washed with water (20 mL), brine (20 mL), dried over anhydrous $Na_2SO_4$, filtered and evaporated. The crude residue was purified by column chromatography (100-200 mesh silica EtOAc:Hexane (10:90)), to afford to 2-chloro-5-(pyrrolidin-1-yl) isonicotinate (1 g) as off white solid.

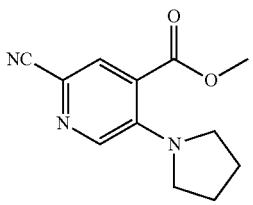 [SMILES: COC(=O)c1cc(C#N)ncc1N1CCCC1]

Preparation of methyl 2-cyano-5(pyrrolidin-1-yl) isonicotinate: to a solution of 2-chloro-5-(pyrrolidin-1-yl) isonicotinate (2 g, 8.3 mmol, 1 eq) in DMF was added $ZnCN_2$ (2.92 g, 25.2 mmol, 3 eq) and the suspension was degassed for 15 min. Then added Tetrakis (triphenylphosphine) palladium(0) (2.87 g, 2.49 mmol, 0.3 eq) and stirred at 120° C. for 16 h. After completion, the reaction mixture was poured into water and extracted with EtOAc (3×20 mL). The combined extracts were washed with water (20 mL), brine (20 mL), dried over anhydrous $Na_2SO_4$, filtered and evaporated. The crude residue was purified by column chromatography (100-200 mesh, silica EtOAc:Hexane (4:6)) to afford to methyl 2-cyano-5(pyrrolidin-1-yl) isonicotinate (1.3 g) as a pale yellow liquid.

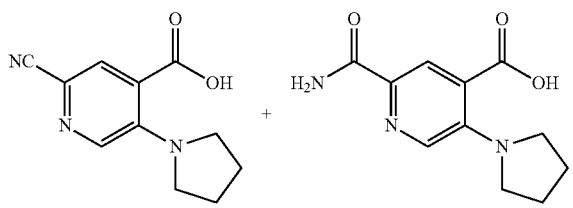 [SMILES: N#Cc1cc(C(=O)O)c(N2CCCC2)cn1 ; NC(=O)c1cc(C(=O)O)c(N2CCCC2)cn1]

Preparation of 2-cyano-5(pyrrolidin-1-yl) isonicotinic acid and 2-carbmoyl-5-(pyrrolidin-1-yl) isonicotinic acid: to a solution of methyl 2-cyano-3(pyrrolidin-1-yl) isonicotinate (800 mg, 3.46 mmol, 1 eq) in MeOH:$H_2O$ (1:1) (5 mL) was added NaOH (259 mg, 6.49 mg, 3 eq) and stirred at RT for 16 h. After completion, the reaction mixture was poured into water (15 mL), acidified with 1N HCl and extracted with EtOAc (3×20 mL). The combined extracts were washed with water (20 mL), brine (20 mL), dried over anhydrous $Na_2SO_4$, filtered and evaporated to afford a mixture of 2-cyano-5(pyrrolidin-1-yl)isonicotinic acid and 2-carbmoyl-5-(pyrrolidin-1-yl)isonicotinic acid (700 mg).

Compound-41

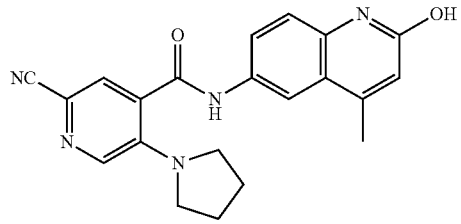

Preparation of 2-Cyano-N-(2-hydroxy-4-methylquinolin-6-yl)-5-(pyrrolidin-1-yl) isonicotinamide (Compound-41): to a solution of 2-cyano-5(pyrrolidin-1-yl)isonicotinic acid and 2-carbmoyl-5-(pyrrolidin-1-yl)isonicotinic acid (700 mg, 3.22 mmol, 1 eq) in DMF (7 mL) was added EDC.HCl (578 mg, 3.0 mmol, 2 eq), HOAT (412 g, 3.0 mmol, 2 eq) and DIPEA (3 eq) followed by 6-amino-4-methylquinlin-2-ol (316 mg, 1.81 mmol, 1.2 eq), and stirred at RT for 16 h. After completion, The reaction mixture was poured into water and precipitated solid was filtered. The crude was purified by column chromatography (100-200 mesh silica, MeOH:DCM (4:96)) to afford 2-Cyano-N-(2-hydroxy-4-methylquinolin-6-yl)-5-(pyrrolidin-1-yl)isonicotinamide (Compound-41) (120 mg) as Pale yellow solid.

$^1$H NMR (300 MHz, dmso) δ 11.60 (s, 1H), 10.67 (s, 1H), 8.25 (s, 1H), 8.08 (d, J=2.3 Hz, 1H), 7.88 (s, 1H), 7.78 (dd, J=8.8, 2.2 Hz, 1H), 7.30 (d, J=8.8 Hz, 1H), 6.43 (s, 1H), 3.46-3.36 (m, 4H), 2.39 (s, 3H), 1.97-1.85 (m, 4H).

Compound-42

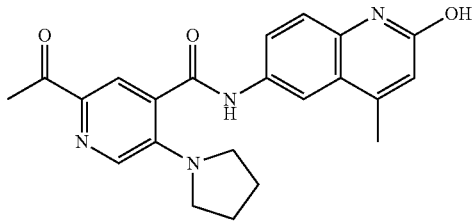

Preparation of 2-acetyl-N-(2-hydroxy-4-methylquinolin-6-yl)-5 (pyrrolidin-1-yl)isonicotinamide (Compound-42): to a solution of 2-Cyano-N-(2-hydroxy-4-methylquinolin-6-yl)-5-(pyrrolidin-1-yl) isonicotinamide (Compound-41) (100 mg, 0.26 mmol, 1 eq) in Dry THF (2 mL) was added MeMgBr (5 eq) at 0° C. and stirred at RT for 16 h. The reaction was monitored by LCMS. After completion, the reaction mixture was poured into ice-water (15 mL) and extracted with EtOAc (3×10 mL). The combined extracts were washed with water (20 mL), brine (20 mL), dried over anhydrous $Na_2SO_4$, filtered and evaporated. The crude residue was purified by combiflash to afford 2-acetyl-N-(2-hydroxy-4-methylquinolin-6-yl)-5 (pyrrolidin-1-yl)isonicotinamide (Compound-42) (70 mg) as pale yellow solid.

$^1$H NMR (300 MHz, DMSO-d6) δ 11.59 (s, 1H), 10.69 (s, 1H), 8.22 (s, 1H), 8.09 (d, J=2.3 Hz, 1H), 7.88-7.71 (m, 2H), 7.30 (d, J=8.8 Hz, 1H), 6.43 (s, 1H), 3.43 (s, 4H), 2.55 (s, 3H), 2.40 (d, J=1.3 Hz, 3H), 1.92 (s, 4H).

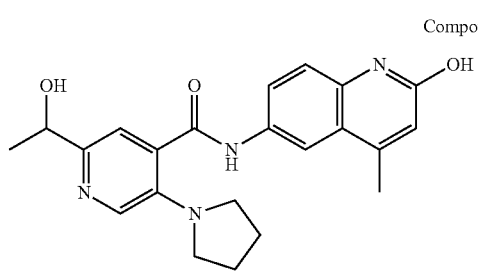
Compound-43

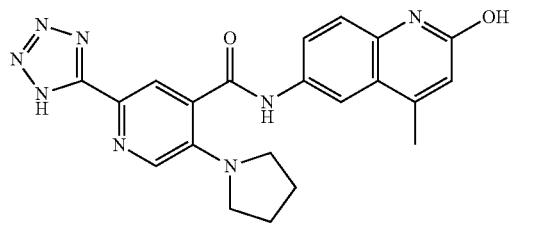
Compound-45

Preparation of N-(2-hydroxy4-methylquinolin-6-yl)-2-(1-hydroxymethyl)-5-(pyrrolidin-1-yl) isonicotinamide (Compound-43)

To a solution of 6-acetyl-N-(2-hydroxy-4-methylquinolin-6-yl)-3(pyrrolidin-1-yl)picolinamide (Compound-42) (40 mg, 0.115 mmol, 1 eq) in MeOH (2 mL) added NaBH$_4$(3 eq) at 0° C. allowed to stir at RT for 16 h. After completion, the reaction mixture was quenched with NH$_4$Cl solution (15 mL) and extracted with EtOAc (3×20 mL). The combined extracts were washed with water (20 mL), brine (20 mL), dried over anhydrous Na$_2$SO$_4$, filtered and evaporated. The crude product was purified by combiflash to afford N-(2-hydroxy-4-methylquinolin-6-yl)-6-(1-hydroxymethyl)-3-(pyrrolidin-1-yl) picolinamide (Compound-43) (16 mg) as pale yellow solid.

$^1$H NMR (400 MHz, cd$_3$od) δ 8.23 (d, J=2.4 Hz, 1H), 8.07 (s, 1H), 7.83 (dd, J=8.7, 2.4 Hz, 1H), 7.47 (s, 1H), 7.38 (d, J=8.8 Hz, 1H), 6.55 (s, 1H), 3.38 (d, J=6.3 Hz, 5H), 2.53 (s, 3H), 2.03-1.93 (m, 4H), 1.47 (d, J=6.6 Hz, 3H).

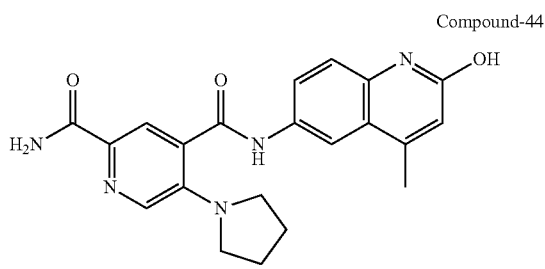 [SMILES: Cc1cc(O)nc2ccc(NC(=O)c3cc(C(N)=O)ncc3N3CCCC3)cc12]
Compound-44

Preparation of N4-(2-hydroxy-4-methylquinolin-6-yl)-5-(pyrrolidin-1-yl)pyridine-2,4-dicarboxamide (Compound-44): to a solution of 2-carbamoyl-5-(pyrrolidin-1-yl)isonicotinic acid (100 mg, 0.425 mmol, 1 eq) in DMF (2 mL) was added EDC.HCl (162 mg, 0.85 mmol, 2 eq), HOAT (115 mg, 0.85 mmol, 2 eq), DIPEA (3 eq), followed by 6-amino-4-methylquinlin-2-ol (88 mg, 0.51 mmol, 1.2 eq) and stirred at RT for 16 h. After completion, the reaction mixture was poured into water and precipitated solid was filtered. The crude residue was purified by column chromatography (100-200 mesh silica, MeOH:DCM (4:96)) to afford N$^4$-(2-hydroxy-4-methylquinolin-6-yl)-5-(pyrrolidin-1-yl) pyridine-2,4-dicarboxamide (Compound-44) (24 mg) as Pale yellow solid.

$^1$H NMR (300 MHz, DMSO-d$_6$) δ 11.59 (s, 1H), 10.68 (s, 1H), 8.13-8.07 (m, 2H), 7.87-7.74 (m, 2H), 7.30 (d, J=9.2 Hz, 2H), 6.43 (s, 1H), 3.49-3.34 (m, 4H), 2.40 (s, 3H), 1.98-1.86 (m, 4H).

Preparation of N-(2-hydroxy-4-methylquinolin-6-yl)-5-(pyrrolidin-1-yl)-2-(1H-tetrazol-5-yl) isonicotinamide (Compound-45)

To a solution of 2-Cyano-N-(2-hydroxy-4-methylquinolin-6-yl)-5-(pyrrolidin-1-yl) isonicotinamide, Compound-41 (60 mg, 0.16 mmol, 1 eq) in IPA:H$_2$O (10 vol) was added NaN$_3$ (3 eq), ZnBr$_2$ (1 eq) and stirred at 100° C. for 20 h. After completion, the reaction mixture was poured into water and precipitated solid was filtered. The crude residue was triturated with diethyl ether and pentane to afford to N-(2-hydroxy-4-methylquinolin-6-yl)-3-(pyrrolidin-1-yl)-6-(1H-tetrazol-5-yl) picolinamide (Compound-45) (22 mg) as Pale yellow solid.

$^1$H NMR (400 MHz, DMSO-d$_6$) δ 11.60 (s, 1H), 10.74 (m, 1H), 8.08 (s, 1H), 7.92 (s, 1H), 7.80 (d, J=8.9 Hz, 1H), 7.56-7.40 (m, 1H), 7.31 (d, J=8.8 Hz, 1H), 6.43 (s, 1H), 3.26-3.15 (m, 4H), 2.40 (s, 3H), 1.96-1.85 (m, 4H).

Synthesis of Compound-46 and Compound-47:

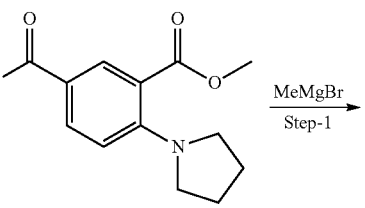
MeMgBr
Step-1

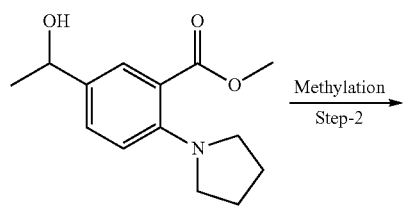
Methylation
Step-2

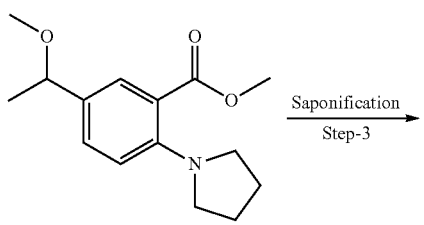
Saponification
Step-3

-continued

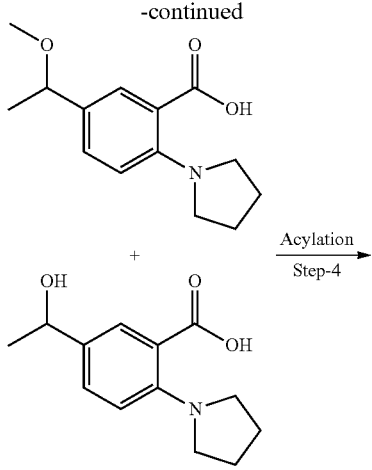

Acylation
Step-4

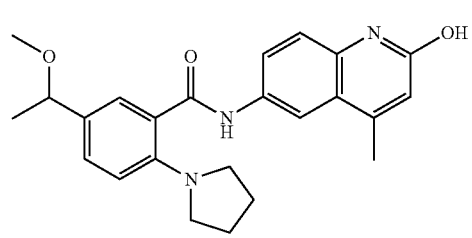

Compound-46

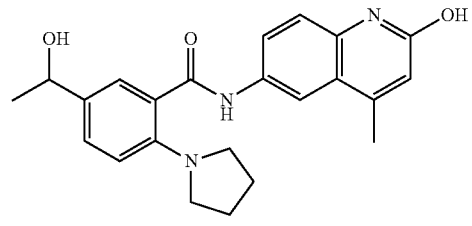

Compound-47

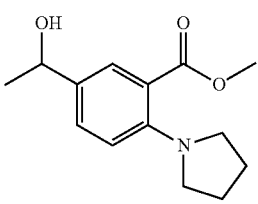 [SMILES: COC(=O)c1cc(C(C)O)ccc1N1CCCC1]

Preparation of methyl
5-(1-hydroxyethyl)-2-(pyrrolidin-1-yl)benzoate

To a solution of methyl 5-formyl-2-(pyrrolidin-1-yl) benzoate (1 g, 4.28 mmol, 1 eq) in dry THF (25 mL) at −78° C. was added MeMgBr (510.3 mg, 4.28 mmol, 1 eq) and stirred at RT for 16 h. After completion, the reaction mixture was quenched with saturated NH₄Cl solution and extracted with EtOAc (3×30 mL). The combined extracts were washed with water (50 mL), brine (50 mL), dried over anhydrous Na₂SO₄, filtered and evaporated. The crude product was purified by column chromatography (SiO₂) using EtOAc:Pet ether (15:85) to afford methyl 5-(1-hydroxyethyl)-2-(pyrrolidin-1-yl) benzoate (600 mg) as a pale yellow liquid.

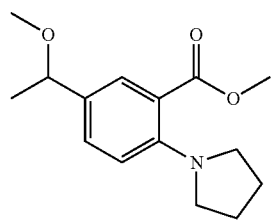 [SMILES: COC(=O)c1cc(C(C)OC)ccc1N1CCCC1]

Preparation of methyl 5-(1-methoxyethyl)-2-(pyrrolidin-1-yl) benzoate: to a solution of methyl 5-(1-hydroxyethyl)-2-(pyrrolidin-1-yl)benzoate (600 mg, 2.4 mmol, 1 eq) in Dry DMF (6 mL) added 50% NaH (172.8 mg, 7.2 mmol, 3 eq) MeI (511.2 mg, 3.6 mmol, 1.5 eq) and stirred at RT for 4 h. After completion, the reaction mixture was poured into ice water and extracted with EtOAc (3×50 mL). The combined extracts were washed with water (3×30 mL), brine (1×30 mL), dried over anhydrous Na₂SO₄, filtered and evaporated to afford methyl 5-(1-methoxyethyl)-2-(pyrrolidin-1-yl)benzoate (510 mg) as an off white solid.

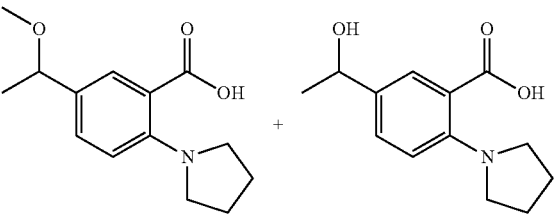 [SMILES: COC(C)c1ccc(N2CCCC2)c(C(=O)O)c1 ; CC(O)c1ccc(N2CCCC2)c(C(=O)O)c1]

Preparation of 5-(1-methoxyethyl)-2-(pyrrolidin-1-yl) benzoic acid and 5-(1-methoxyethyl)-2-(pyrrolidin-1-yl) benzoic acid: to a solution of methyl 5-(1-methoxyethyl)-2-(pyrrolidin-1-yl) benzoate (510 mg, 1.939 mmol, 1 eq) in MeOH:H₂O (3:1) (9 mL) at RT and added LiOH (244 mg, 5.817 mmol, 3.0 eq) and stirred at RT for 5 h. After completion, the solvent was evaporated. The crude was acidified with 1N HCl and the water layer was evaporated. The crude product was dissolved in MeOH and filtered the inorganic salts and evaporated the filtrate to afford 5-(1-methoxyethyl)-2-(pyrrolidin-1-yl) benzoic acid and 5-(1-methoxyethyl)-2-(pyrrolidin-1-yl) benzoic acid (350 mg) as a brown solid.

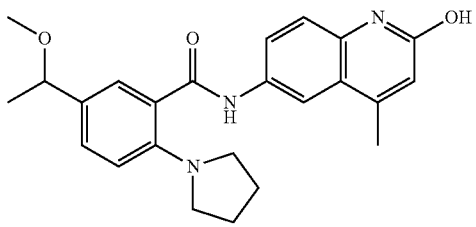

Compound-46

-continued

Compound-47

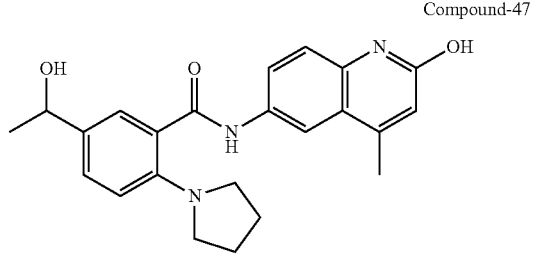

Preparation of N-(2-hydroxy-4-methylquinolin-6-yl)-5-(1-methoxyethyl)-2-(pyrrolidin-1-yl) benzamide (Compound-46) and N-(2-hydroxy-4-methylquinolin-6-yl)-5-(1-hydroxyethyl)-2-(pyrrolidin-1-yl) benzamide (Compound-47): to a solution of 5-(1-methoxyethyl)-2-(pyrrolidin-1-yl) benzoic acid and 5-(1-methoxyethyl)-2-(pyrrolidin-1-yl) benzoic acid (350 mg, 1.93 mmol, 1 eq) in Dry DMF (10 mL) at RT was added 6-amino-4-methyl-quinolin-2-ol (335.8 mg, 1.93 mmol, 1 eq), HOAt (262.4 mg, 1.93 mmol, 1 eq), EDC (369.9 mg, 1.93 mmol, 1 eq), DIPEA (746.9 mg, 5.79 mmol, 3 eq) and stirred at RT for 16 h. After completion, the reaction mixture was poured into ice water and extracted with 10% MeOH:DCM (3×20 mL). The combined extracts were washed with water (2×30 mL), brine (30 mL), dried over anhydrous $Na_2SO_4$, filtered and evaporated. The crude compound was purified by column chromatography ($SiO_2$) using MeOH:DCM (3:97) to afford N-(2-hydroxy-4-methylquinolin-6-yl)-5-(1-methoxyethyl)-2-(pyrrolidin-1-yl) benzamide (Compound-47) (100 mg) as off white solid and N-(2-hydroxy-4-methylquinolin-6-yl)-5-(1-hydroxyethyl)-2-(pyrrolidin-1-yl) benzamide (Compound-46) (22 mg) as off white solids.

Compound-46:
$^1$H NMR (300 MHz, DMSO-d6) δ 11.54 (s, 1H), 10.47 (s, 1H), 8.15 (d, J=2.2 Hz, 1H), 7.81 (dd, J=8.8, 2.2 Hz, 1H), 7.32-7.21 (m, 2H), 6.77 (d, J=8.6 Hz, 1H), 6.41 (s, 1H), 4.99 (d, J=4.4 Hz, 1H), 4.70-4.61 (m, 1H), 3.25-3.14 (m, 4H), 2.39 (d, J=1.3 Hz, 2H), 1.89-1.80 (m, 4H), 1.32 (d, J=6.4 Hz, 3H).

Compound-47:
1H NMR (400 MHz, DMSO-d6) δ 11.55 (s, 1H), 10.43 (s, 1H), 8.15 (d, J=2.3 Hz, 1H), 7.82 (dd, J=8.8, 2.2 Hz, 1H), 7.32-7.17 (m, 3H), 6.79 (d, J=8.6 Hz, 1H), 6.41 (s, 1H), 4.24 (q, J=6.3 Hz, 1H), 3.27-3.18 (m, 4H), 3.11 (s, 3H), 2.39 (d, J=1.3 Hz, 3H), 1.91-1.80 (m, 4H), 1.33 (d, J=6.4 Hz, 3H).

Synthesis of Compound-48:

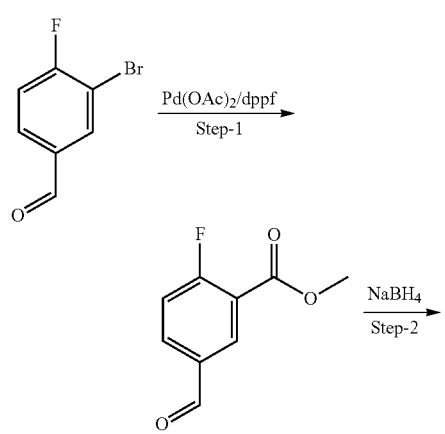

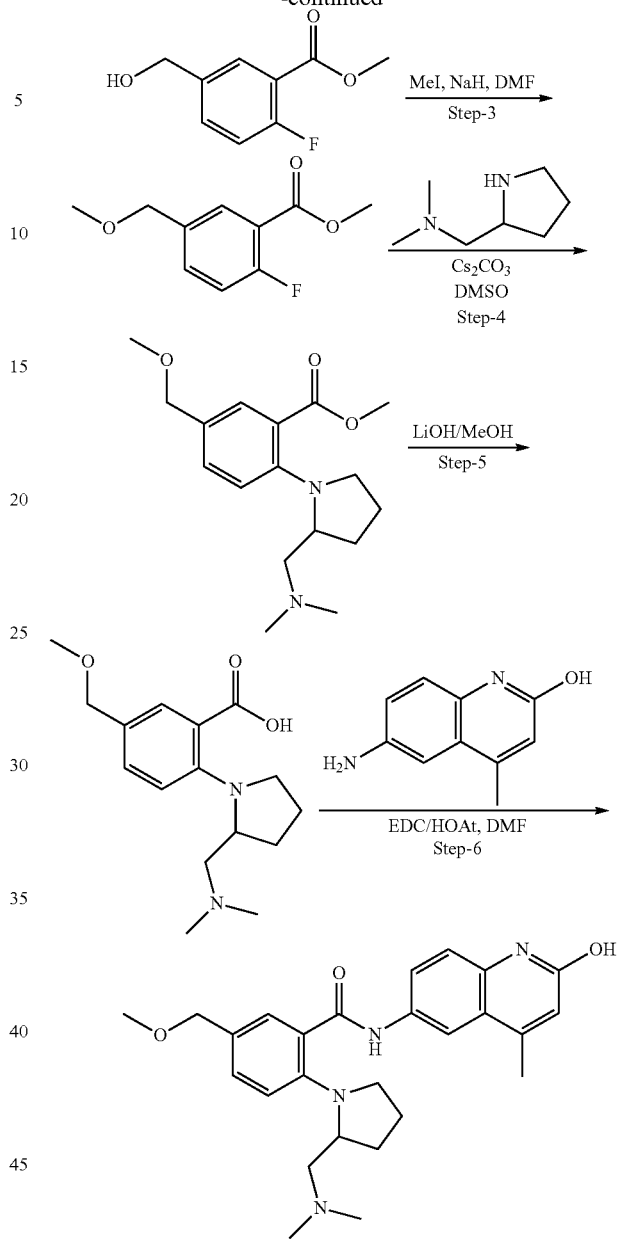

Preparation of methyl 2-fluoro-5-formylbenzoate: to a solution of 3-bromo-4-fluorobenzaldehyde (20 g, 98.52 mmol, 1 eq) in dry MeOH (50 mL) and Dry DMF (80 mL) at RT was added dppf (2.73 g, 4.926 mmol, 0.05 eq), Palladium acetate (1.85 g, 2.758 mmol, 0.028 eq) followed by Triethyl amine (19.9 g, 197.04 mmol, 2.0 eq) in a steel reactor with 80 psi of CO gas and stirred at 80° C. for 24 h. After completion, the solvent was evaporated and the residue was taken in water and extracted with EtOAc (3×200 mL). The combined extracts were washed with water (500 mL), brine (500 mL), dried over anhydrous $Na_2SO_4$, filtered and evaporated. The crude compound was purified by column chromatography using ($SiO_2$) by eluting EtOAc:Pet ether (5:95) to afford methyl 2-fluoro-5-formylbenzoate (12 g, 67%) as an off white solid.

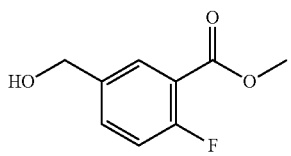

Preparation of methyl 2-fluoro-5-(hydroxymethyl)benzoate: to a solution of methyl 2-fluoro-5-formylbenzoate (500 mg, 2.747 mmol, 1 eq) in EtOH (5 mL) was added $NaBH_4$ (207.3 mg 5.48 mmol, 2.0 eq) and stirred at RT for 1 h. After completion, the solvent was evaporated, the residue was taken in water and extracted with EtOAc (3×20 mL). The combined extracts were washed with water (3×50 mL), brine (1×50 mL), dried over anhydrous $Na_2SO_4$, filtered and evaporated to afford methyl 2-fluoro-5-(hydroxymethyl) benzoate (450 mg, 89%) as an pale yellow liquid.

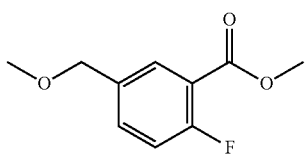

Preparation of methyl 2-fluoro-5-(methoxymethyl)benzoate: to a solution of methyl 2-fluoro-5-(hydroxymethyl) benzoate (450 mg, 2.445 mmol, 1 eq) in DMF (10 vol) was added NaH (176.04 mg, 7.335 mmol, 1.0 eq) and stirred at 0° C. to RT for 4 h. After completion, the reaction mixture quenched with 1N HCl and extracted with EtOAc (2×50 mL). The combined extracts were washed with water (30 mL), brine (30 mL), dried over anhydrous $Na_2SO_4$, filtered and evaporated. The crude compound was purified by combiflash chromatography using EtOAc:Pet ether (1:1) to afford methyl 2-fluoro-5-(methoxymethyl) benzoate (160 mg, 33%) as a brown liquid.

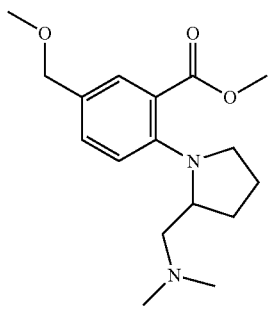

Preparation of methyl 2-(2-((dimethylamino) methyl) pyrrolidin-1-yl)-5-(methoxymethyl) benzoate: to a solution of methyl 2-fluoro-5-(methoxymethyl) benzoate (160 mg, 0.808 mmol, 1 eq) in DMSO (10 vol) was added N,N-dimethyl-1-pyrrolidin-2-yl-methanamine (162.5 mg, 0.808 mmol, 1.0 eq), $Cs_2CO_3$ (525.2 mg, 1.616 mmol, 2 eq) and stirred at 130° C. for 2 h in Microwave. After completion, the reaction mixture was poured into ice water and extracted with EtOAc (2×30 mL). The combined extracts were washed with water (30 mL), brine (30 mL), dried over anhydrous $Na_2SO_4$, filtered and evaporated. The crude compound was purified by combiflash chromatography using MeOH:DCM (3:97) to afford methyl 2-(2-((dimethylamino)methyl) pyrrolidin-1-yl)-5-(methoxymethyl) benzoate (20 mg) as a brown liquid.

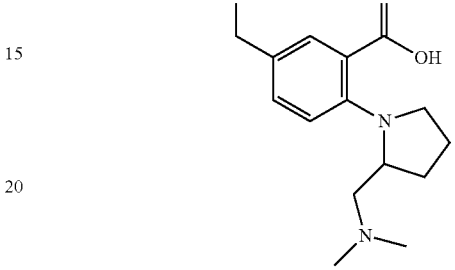

Preparation of 2-(2-((dimethylamino)methyl)pyrrolidin-1-yl)-5-(methoxymethyl)benzoic acid: to a solution of methyl 2-(2-((dimethylamino)methyl)pyrrolidin-1-yl)-5-(methoxymethyl)benzoate (20 mg, 0.065 mmol, 1 eq) in MeOH:$H_2O$ (3:1) (9 mL) at RT added LiOH (8.18 mg, 0.195 mmol, 3.0 eq) and stirred at RT for 5 h. After completion, the solvent was evaporated and the crude acidified with Dioxane HCl and evaporated to afford 2-(2-((dimethylamino) methyl) pyrrolidin-1-yl)-5-(methoxymethyl) benzoic acid Hydrochloride (15 mg) as brown solid. The crude was carried to next step without further purification.

Compound-48

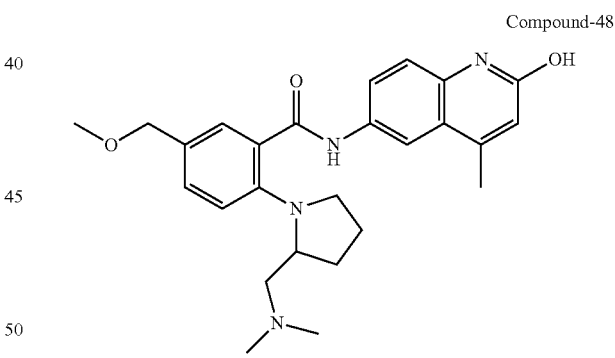

Preparation of 2-(2-((dimethylamino)methyl)pyrrolidin-1-yl)-N-(2-hydroxy-4-methylquinolin-6-yl)-5-(methoxymethyl)benzamide (Compound-48): to a solution of 2-(2-((dimethylamino)methyl)pyrrolidin-1-yl)-5-(methoxymethyl)benzoic acid (15 mg, 0.05 mmol, 1 eq) in Dry DMF (1 mL) at RT was added 6-amino-4-methylquinolin-2-ol (8.7 mg, 0.05 mmol, 1 eq), HOAt (6.8 mg, 0.05 mmol, 1 eq), EDC (9.58 mg, 0.05 mmol, 1 eq), DIPEA (19.35 mg, 0.05 mmol, 3 eq) and stirred at RT for 16 h. After completion, the reaction mixture was poured into ice water and extracted with 10% MeOH:DCM (4×20 mL). The combined extracts were washed with water (30 mL), brine (30 mL), dried over anhydrous $Na_2SO_4$, filtered and evaporated. The crude compound was purified by combiflash chromatography ($SiO_2$) using MeOH:DCM (3:97) to afford 2-(2-((dimethylamino) methyl)pyrrolidin-1-yl)-N-(2-hydroxy-4-methylquinolin-6-yl)-5-(methoxymethyl)benzamide (Compound-48) (2 mg) as brown solid.

Synthesis of Compound-49:

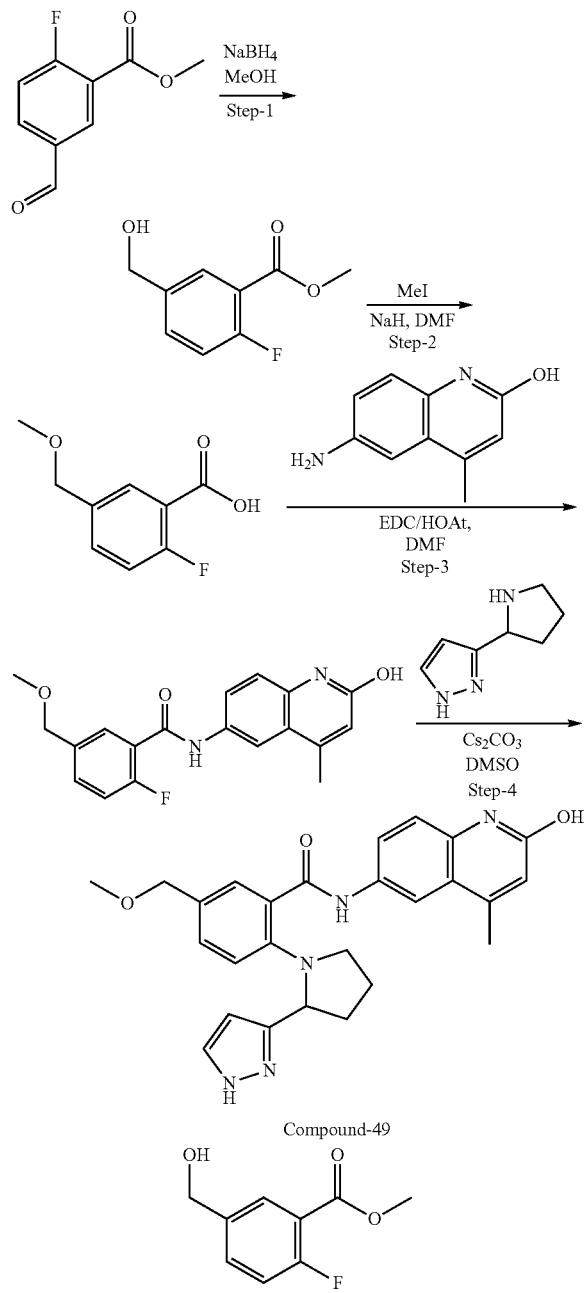

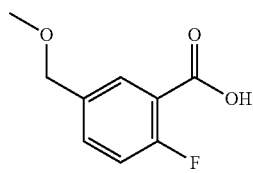

Preparation of 2-fluoro-5-(methoxymethyl) benzoic acid: to a solution of methyl 2-fluoro-5-(hydroxymethyl) benzoate (490 mg, 2.66 mmol, 1 eq) in DMF (10 vol) was added NaH (191.73 mg, 7.989 mmol, 1.5 eq) and stirred at 0° C. for 1 h. Then added MeI (567.73 mg, 3.994 mmol, 3.0 eq) and stirred at 0° C. to RT for 4 h. After completion, the reaction mixture quenched with 1N HCl and extracted with EtOAc (2×50 mL). The combined extracts were washed with water (30 mL), brine (30 mL), dried over anhydrous $Na_2SO_4$, filtered and evaporated to afford 2-fluoro-5-(methoxymethyl)benzoic acid (200 mg) as an off white solid.

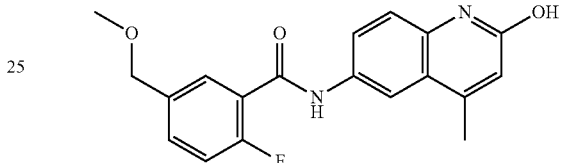

Preparation of 2-fluoro-N-(2-hydroxy-4-methylquinolin-6-yl)-5-(methoxymethyl) benzamide: to a solution of 2-fluoro-5-(methoxymethyl)benzoic acid (200 mg, 1.086 mmol, 1 eq) in Dry DMF (1 mL) at RT was added 6-amino-4-methyl-quinolin-2-ol (188.9 mg, 1.086 mmol, 1 eq), HOAt (147.69 mg, 1.086 mmol, 1 eq), EDC (208.1 mg, 1.086 mmol, 1 eq), DIPEA (280.1 mg, 2.172 mmol, 2 eq) and stirred at RT for 16 h. After completion, the reaction mixture was poured into ice water, filtered the solid formed. The crude solid was washed with water and diethyl ether to afford 2-fluoro-N-(2-hydroxy-4-methylquinolin-6-yl)-5-(methoxymethyl) benzamide (150 mg) as pale yellow solid.

Compound-49

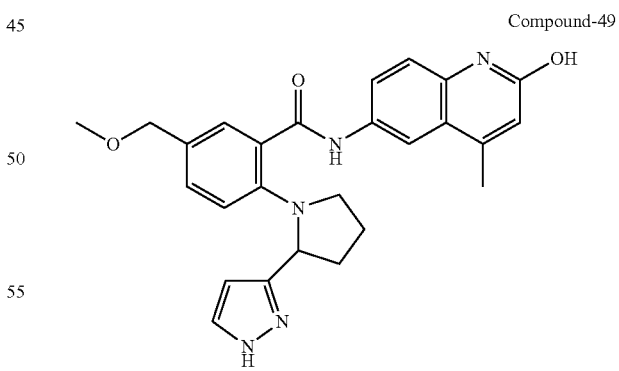

Preparation of methyl 2-fluoro-5-(hydroxymethyl) benzoate: to a solution of methyl 2-fluoro-5-formylbenzoate (500 mg, 2.747 mmol, 1 eq) in EtOH (5 mL) was added $NaBH_4$ (207.3 mg 5.48 mmol, 2.0 eq) and stirred at RT for 1 h. After completion, the solvent was evaporated, the residue was taken in water and extracted with EtOAc (3×20 mL). The combined extracts were washed with water (3×50 mL), brine (1×50 mL), dried over anhydrous $Na_2SO_4$, filtered and evaporated to afford methyl 2-fluoro-5-(hydroxymethyl) benzoate (490 mg) as a pale yellow liquid.

Preparation of 2-(2-(1H-pyrazol-3-yl)pyrrolidin-1-yl)-N-(2-hydroxy-4-methylquinolin-6-yl)-5-(methoxymethyl)benzamide (Compound-49): to a solution of 2-fluoro-N-(2-hydroxy-4-methylquinolin-6-yl)-5-(methoxymethyl) benzamide (100 mg, 0.294 mmol, 1 eq) in DMSO (10 vol) was added 3-pyrrolidin-2-yl-1H-pyrazole (40.33 mg, 0.294 mmol, 1.0 eq), $Cs_2CO_3$ (191.57 mg, 0.588 mmol, 2 eq) and stirred at 130° C. for 2 h in Microwave. After completion, the reaction mixture was poured into ice water and extracted with MeOH:DCM (1:9) (2×50 mL). The combined extracts were washed with water (30 mL), brine (30 mL), dried over anhydrous Na₂SO₄, filtered and evaporated. The crude compound was purified by column chromatography using (SiO₂) by eluting MeOH:DCM (3:97) to afford 2-(2-(1H-pyrazol-3-yl) pyrrolidin-1-yl)-N-(2-hydroxy-4-methylquinolin-6-yl)-5-(methoxymethyl) benzamide (Compound-49) (8 mg) as an off white solid.

Synthesis of Compound-50:

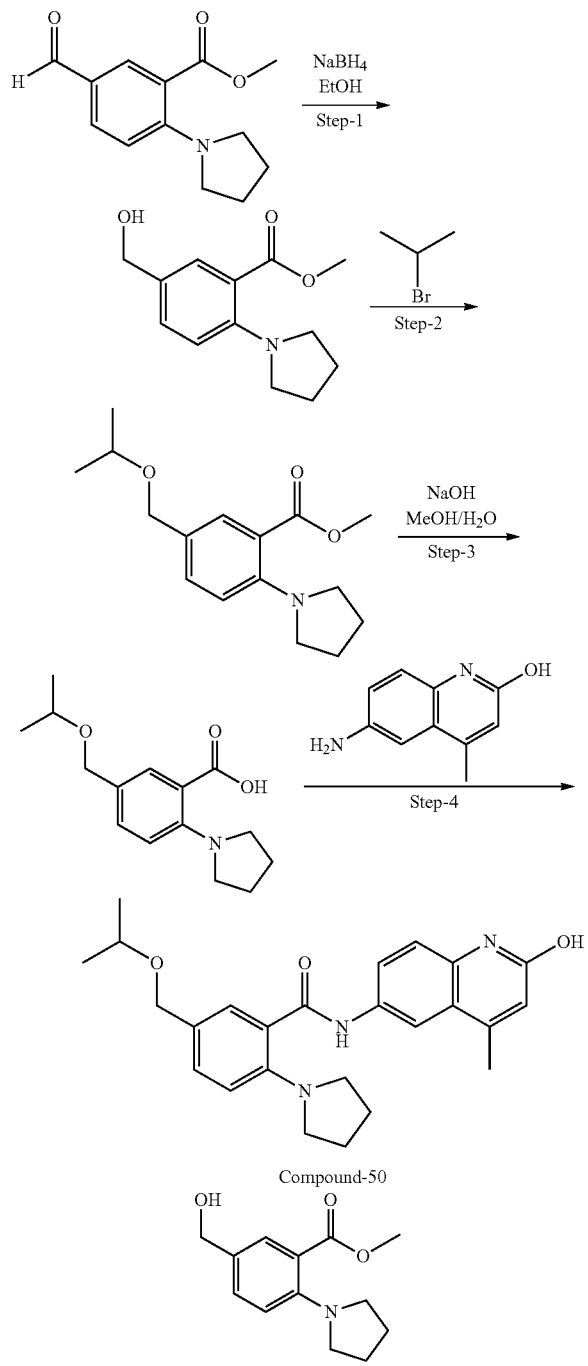

Preparation of methyl 5-(hydroxymethyl)-2-(pyrrolidin-1-yl) benzoate: to a solution of methyl 5-formyl-2-(pyrrolidin-1-yl) benzoate (2.0 g, 8.58 mmol, 1 eq) in Ethanol (10 mL) was added NaBH₄ (0.49 g, 12.87 mmol, 1.5 eq) at 0° C. and stirred at RT for 1 h. After completion, the reaction mixture was poured into ice water and extracted with EtOAc (2×30 mL). The combined extracts were washed with water (2×40 mL), brine (40 mL), dried over anhydrous Na₂SO₄, filtered and evaporated. The crude compound was purified by column chromatography using (SiO₂) by eluting EtOAc: Pet ether (40:60) to afford methyl 5-(hydroxymethyl)-2-(pyrrolidin-1-yl) benzoate (2 g) as a pale yellow liquid.

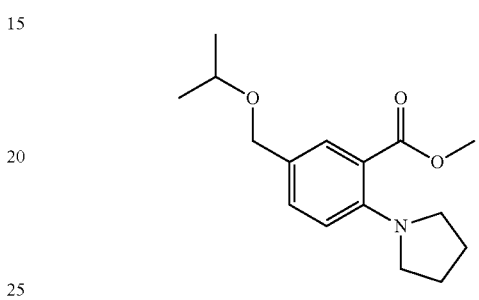

Preparation of methyl 5-(isopropoxymethyl)-2-(pyrrolidin-1-yl) benzoate: To a solution of methyl 5-(hydroxymethyl)-2-(pyrrolidin-1-yl) benzoate (500 mg, 2.12 mmol, 1 eq) in Dry DMF (3 mL) at RT added NaH (147 mg, 6.38 mmol, 3.0 eq), isopropyl bromide (523 mg, 4.25 mmol, 2 eq) and stirred at RT for 24 h. After completion, the reaction mixture was poured into ice water and extracted with EtOAc (2×30 mL). The combined extracts were washed with water (2×40 mL), brine (40 mL), dried over anhydrous Na₂SO₄, filtered and evaporated. The crude compound was purified by column chromatography using (SiO₂) by eluting EtOAc: Pet ether (40:60) to afford methyl 5-(isopropoxymethyl)-2-(pyrrolidin-1-yl) benzoate (200 mg) as a pale yellow liquid.

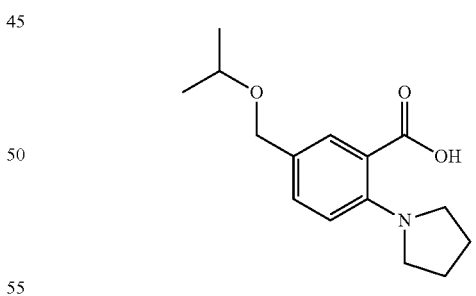

Preparation of 5-(isopropoxymethyl)-2-(pyrrolidin-1-yl) benzoic acid: to a solution of methyl 5-(isopropoxymethyl)-2-(pyrrolidin-1-yl) benzoate (200 mg, 0.72 mmol, 1 eq) in MeOH:H₂O (3:1) (8 mL) at RT was added NaOH (115 mg, 2.88 mmol, 4 eq) and stirred at RT for 24 h. After completion, the solvent was evaporated and the residue was evaporated to afford 5-(isopropoxymethyl)-2-(pyrrolidin-1-yl) benzoic acid sodium salt (150 mg) as an off white solid.

Compound-50

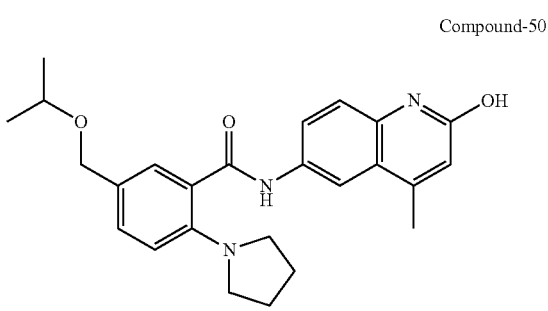 [SMILES: Cc1cc(O)nc2ccc(NC(=O)c3cc(COC(C)C)ccc3N3CCCC3)cc12]

Preparation of N-(2-hydroxy-4-methylquinolin-6-yl)-5-(isopropoxymethyl)-2-(pyrrolidin-1-yl) benzamide (Compound-50): to a solution of 5-(isopropoxymethyl)-2-(pyrrolidin-1-yl)benzoic acid sodium salt (150 mg, 0.57 mmol, 1 eq) in Dry DMF (2 mL) at RT added 6-amino-4-methylquinolin-2-ol (100 mg, 0.57 mmol, 1 eq), HOAt (117 mg, 0.85 mmol, 1.5 eq), EDC (163 mg, 0.85 mmol, 1.5 eq), DIPEA (220 mg, 1.71 mmol, 3 eq) and stirred at RT for 16 h. After completion, the reaction mixture poured into ice water and extracted with EtOAc (2×30 mL). The combined extracts were washed with water (2×40 mL), brine (40 mL), dried over anhydrous $Na_2SO_4$, filtered and evaporated. The crude compound was purified by column chromatography using ($SiO_2$) by eluting MeOH:DCM (10:90) to afford N-(2-hydroxy-4-methylquinolin-6-yl)-5-(isopropoxymethyl)-2-(pyrrolidin-1-yl) benzamide (Compound-50) (9 mg) as an off white solid.

$^1$H NMR (300 MHz, dmso) δ 11.58-11.52 (m, 1H), 10.46 (s, 1H), 8.15 (s, 1H), 7.85-7.79 (m, 1H), 7.30-7.20 (m, 2H), 6.76 (d, J=8.0 Hz, 1H), 6.41 (s, 1H), 4.36 (s, 2H), 3.71-3.56 (m, 1H), 3.27-3.18 (m, 4H), 2.39 (s, 3H), 1.91-1.80 (m, 4H), 1.13 (dd, J=6.1, 1.5 Hz, 6H).

Synthesis of 2-fluoro-5-formyl-N-(2-hydroxy-4-methylquinolin-6-yl) benzamide

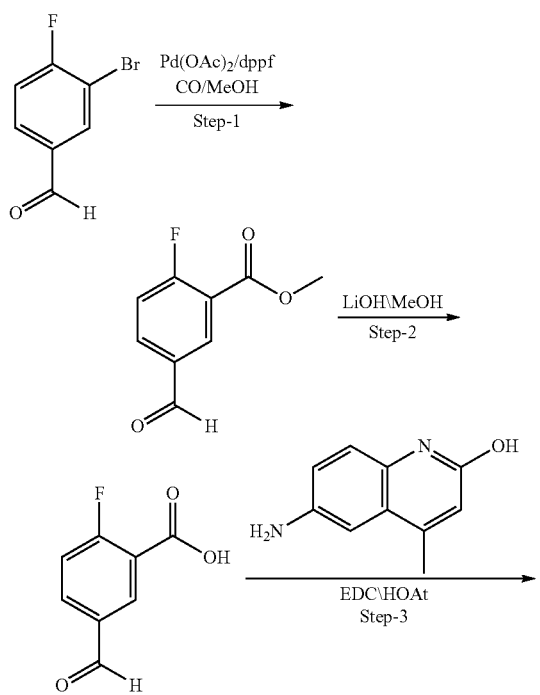

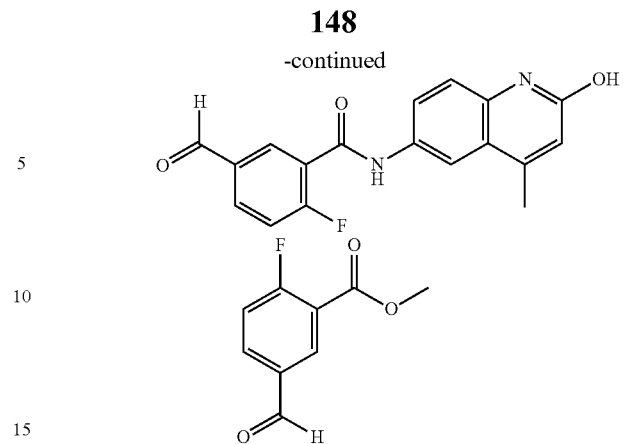

Preparation of methyl 2-fluoro-5-formylbenzoate: to a solution of 3-bromo-4-fluorobenzaldehyde (20 g, 98.5 mmol, 1 eq) in dry MeOH (50 ml) and Dry DMF (80 ml) was added dppf (2.72 g, 4.92 mmol, 0.05 eq), Palladium acetate (1.32 g, 1.97 mmol, 0.028 eq) followed by triethyl amine (19.89 g, 197 mmol, 2.0 eq) in pressure reactor and stirred at 80° C. under 80 Psi of CO gas for 24 h. After completion, solvent was evaporated. The reaction mixture was poured into water and extracted with EtOAc (3×200 mL). The combined extracts were washed with water (1 L), brine (1 L), dried over anhydrous $Na_2SO_4$, filtered and evaporated. The crude compound was purified by column chromatography ($SiO_2$) using EtOAc:Pet ether (6:94) to afford methyl 2-fluoro-5-formylbenzoate (12 g) as an off white solid.

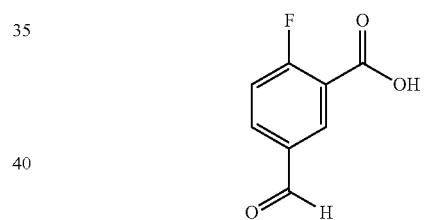

Preparation of 2-fluoro-5-formylbenzoic acid: to a solution of methyl 5-(morpholine-4-carbonyl)-2-morpholinobenzoate (10 g, 54.9 mmol, 1 eq) in MeOH:$H_2O$ (3:1) (100 mL) at RT was added LiOH (6.91 g, 164.7 mmol, 3.0 eq) and stirred at RT for 5 h. After completion, the solvent was evaporated. The crude compound was acidified with 1N HCl and extracted with EtOAc washed with water (200 mL), brine (200 mL), dried over anhydrous $Na_2SO_4$, filtered and evaporated to afford 2-fluoro-5-formylbenzoic acid (6 g) as off white solid.

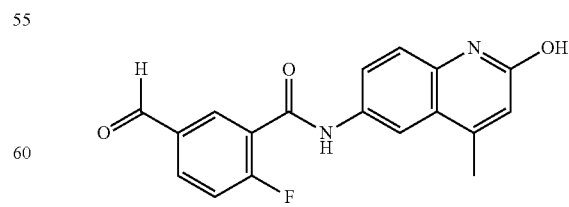

Preparation of 2-fluoro-5-formyl-N-(2-hydroxy-4-methylquinolin-6-yl) benzamide: to a solution of 2-fluoro-5-formylbenzoic acid (6 g, 35.71 mmol, 1 eq) in Dry DMF (60 mL) at RT was added 6-amino-4-methylquinolin-2-ol (6.21 g, 35.71 mmol, 1 eq), HOAt (4.85 g, 35.71 mmol, 1 eq), EDC (6.84 g, 35.71 mmol, 1 eq), DIPEA (13.81 g, 107.13 mmol, 3 eq) and stirred at RT for 16 h. After completion, the reaction mixture poured into ice water, the solid obtained was filtered. The crude compound was taken in 4N HCl (80 mL), stirred at RT for 4 h, filtered and washed with Ether to afford 2-fluoro-5-formyl-N-(2-hydroxy-4-methylquinolin-6-yl)benzamide (5.2 g) as a pale yellow solid.

$^1$H NMR (300 MHz, DMSO-d$_6$) δ 11.65 (s, 1H), 10.70 (s, 1H), 10.06 (s, 1H), 8.27 (dd, J=6.8, 2.2 Hz, 1H), 8.18-8.10 (m, 2H), 7.82 (dd, J=8.8, 2.2 Hz, 1H), 7.62 (dd, J=9.9, 8.5 Hz, 1H), 7.32 (d, J=8.8 Hz, 1H), 6.48-6.43 (m, 1H), 2.41 (d, J=1.4 Hz, 3H).

Synthesis of Compound-51.

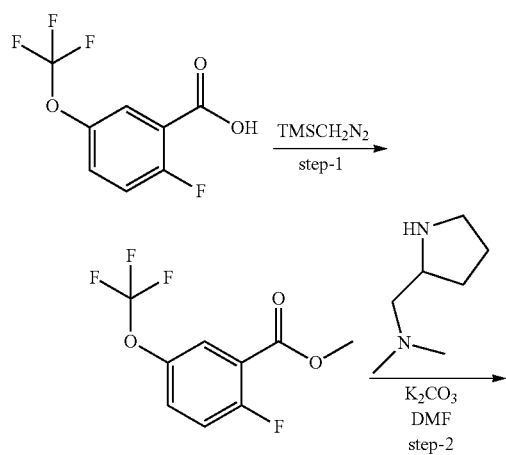

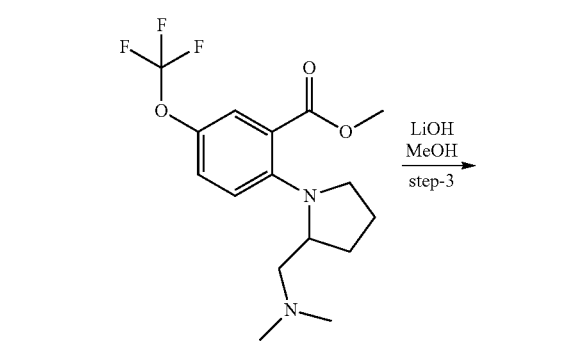

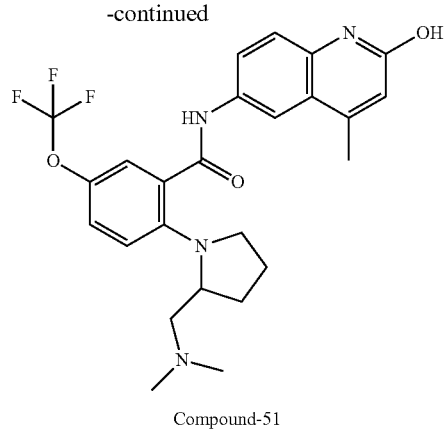

Compound-51

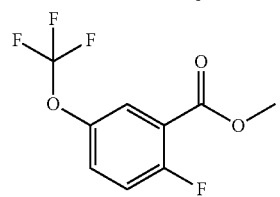

Preparation of methyl 2-fluoro-5-(trifluoromethoxy) benzoate: to a solution of 2-fluoro-5-(trifluoromethoxy)benzoic acid (1 g, 4.464 mmol, 1 eq) in MeOH:Toluene (1:1) (10 mL) added TMS diazomethane (2M in Hexane) (2.63 mL, 5.35 mmol, 1.2 eq) at 0° C. and stirred at RT for 3 h. After completion, the solvent was evaporated under reduced pressure to get methyl 2-fluoro-5-(trifluoromethoxy) benzoate (1 g crude) as a pale yellow liquid.

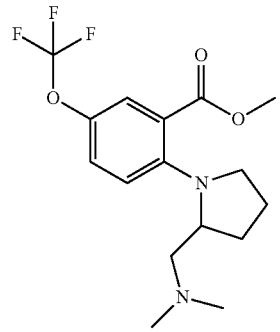 [SMILES: COC(=O)c1cc(OC(F)(F)F)ccc1N1CCCC1CN(C)C]

Preparation of methyl 2-(2-((dimethylamino)methyl)pyrrolidin-1-yl)-5-(trifluoromethoxy) benzoate: to a solution of methyl 2-fluoro-5-(trifluoromethoxy) benzoate (500 mg, 2.10 mmol, 1 eq) in DMSO (5 ml) was added K$_2$CO$_3$ (870 mg, 6.3 mmol, 3 eq), N,N-dimethyl-1-(pyrrolidin-2-yl)methanamine (507 mg, 2.52 mmol, 1.2 eq) and stirred at RT for 16 h. After completion, the reaction mixture was poured into water (10 mL) and extracted with EtOAc (2×10 mL). The combined extracts were washed with water (20 mL), brine (10 mL), dried over anhydrous Na$_2$SO$_4$, filtered and evaporated. The crude residue was purified by washing with n-pentane to get methyl 2-(2-((dimethylamino) methyl) pyrrolidin-1-yl)-5-(trifluoromethoxy) benzoate (450 mg).

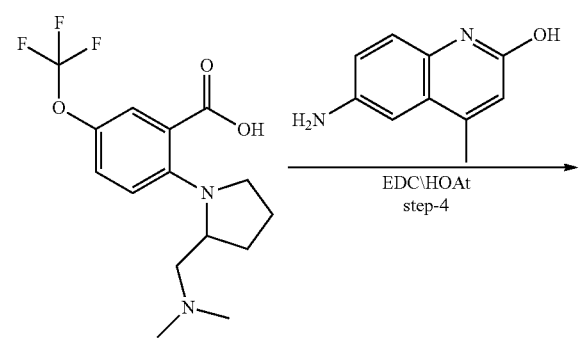

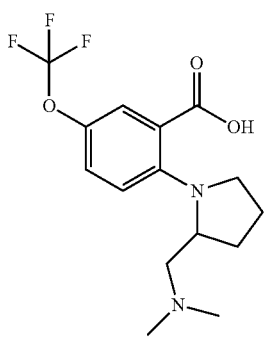 [SMILES: CN(C)CC1CCCN1c1ccc(OC(F)(F)F)cc1C(=O)O]

Preparation of 2-(2-((dimethylamino) methyl) pyrrolidin-1-yl)-5-(trifluoromethoxy)benzoic acid: to a solution of methyl 2-(2-((dimethylamino) methyl) pyrrolidin-1-yl)-5-(trifluoromethoxy) benzoate (450 mg, 1.30 mmol, 1 eq) in MeOH:H$_2$O (1:1) (10 mL) added LiOH.H$_2$O (163 mg, 3.90 mmol, 3 eq) and stirred at RT for 16 h. After completion, reaction mixture was poured into water (15 mL) acidified with 1N HCl and extracted with MeOH:DCM (1:9) (3×15 mL). The combined extracts were washed with water (20 mL), dried over anhydrous Na$_2$SO$_4$, filtered and evaporated. The residue was purified by combiflash to get title compound of 2-(2-((dimethylamino) methyl) pyrrolidin-1-yl)-5-(trifluoromethoxy) benzoic acid (320 mg) as pale yellow liquid.

Compound-51

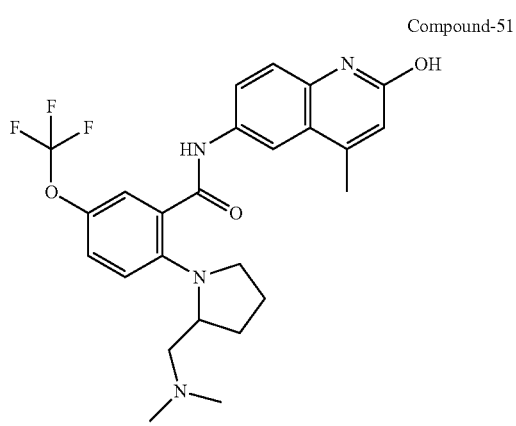 [SMILES: Cc1cc(O)nc2ccc(NC(=O)c3cc(OC(F)(F)F)ccc3N3CCCC3CN(C)C)cc12]

Preparation of 2-(2-((dimethylamino) methyl) pyrrolidin-1-yl)-N-(2-hydroxy-4-methylquinolin-6-yl)-5-(trifluoromethoxy) benzamide (Compound-51)

To a solution of 2-(2-((dimethylamino)methyl)pyrrolidin-1-yl)-5-(trifluoromethoxy)benzoic acid (320 mg, 0.963 mmol, 1 eq) in DMF was added EDC.HCl (367 mg, 1.92 mmol, 2 eq), HOAt (261 mg, 1.92 mmol, 2 eq), DIPEA (3 eq) followed by 6-amino-4-methylquinlin-2-ol (201 mg, 1.15 mmol, 1.2 eq) and stirred at RT for 16 h. After completion, The reaction mixture was poured into water and precipitated solid was filtered. The crude product was purified by column chromatography (100-200 mesh silica MeOH:DCM (4:96)) to afford to 2-(2-((dimethylamino) methyl) pyrrolidin-1-yl)-N-(2-hydroxy-4-methylquinolin-6-yl)-5-(trifluoromethoxy)benzamide (Compound-51) (90 mg) as Pale yellow solid.

$^1$H NMR (300 MHz, DMSO-d6) δ 11.58 (s, 1H), 10.94 (s, 1H), 8.14 (d, J=2.4 Hz, 1H), 7.75 (dd, J=8.5, 2.4 Hz, 1H), 7.60-7.19 (m, 3H), 7.10 (d, J=9.0 Hz, 1H), 6.43 (s, 1H), 3.92 (s, 1H), 3.43-3.40 (m, 1H), 3.06 (s, 1H), 2.39 (s, 3H), 2.12 (s, 7H), 1.94-1.68 (m, 3H).

Synthesis of Compound-54 and Compound-55

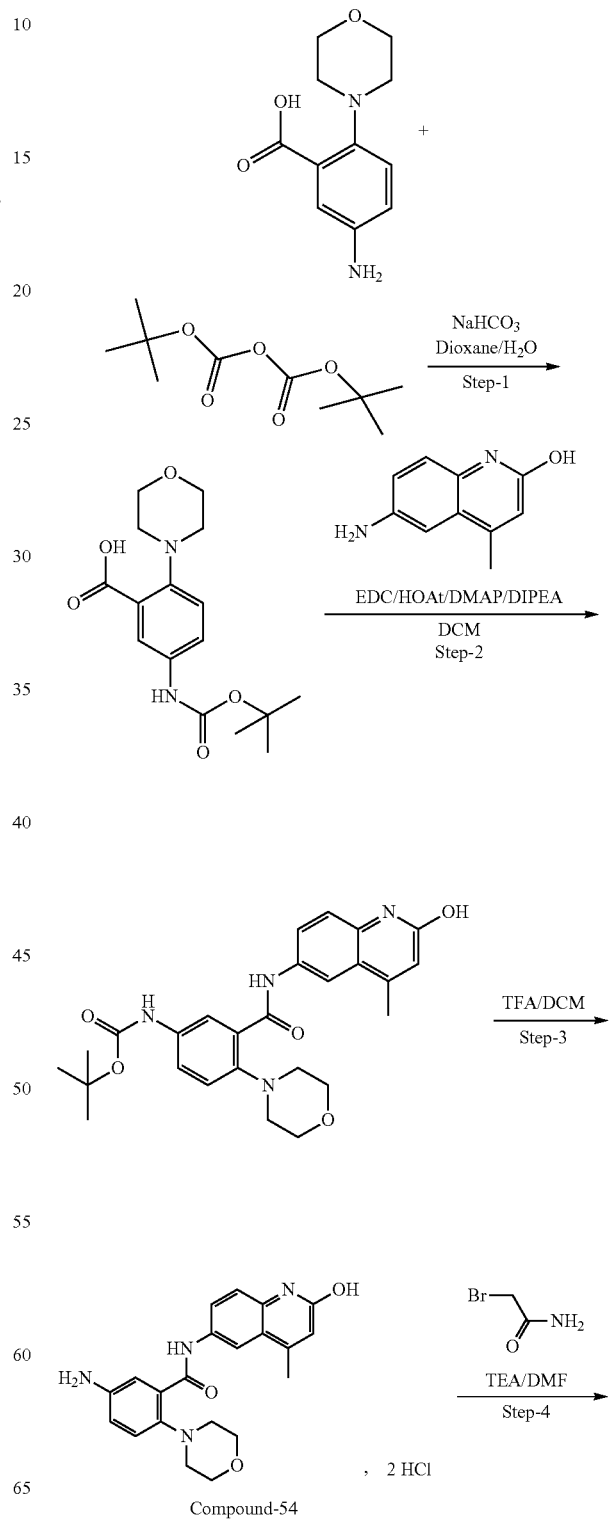

Compound-54

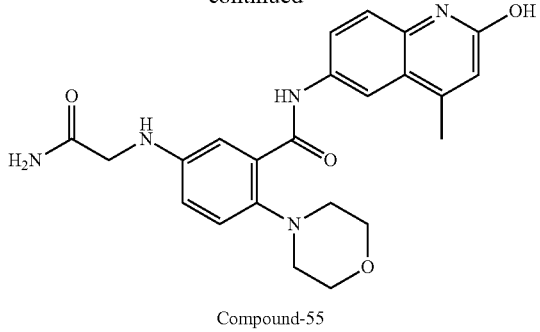

Compound-55

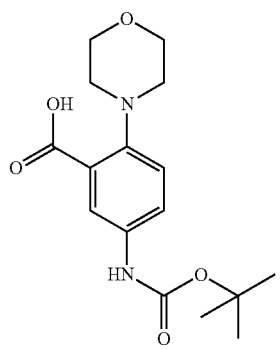 [SMILES: CC(C)(C)OC(=O)Nc1ccc(N2CCOCC2)c(C(=O)O)c1]

Preparation of 5-(tert-butoxycarbonylamino)-2-morpholino-benzoic acid: to a slurry of 5-Amino-2-morpholin-4-yl-benzoic acid (390 mg, 1.75 mmol, 1 eq) and di-tert-butyl bicarbonate (574 mg, 2.63 mmol, 1.5 eq) in dioxane (3 mL) and water (3 mL) were added sodium hydrogen carbonate (588 mg, 7.0 mmol, 4 eq). The reaction mixture was stirred overnight at room temperature. Water was added and the mixture extracted with EtOAc (3×10 mL). The combined extracts were dried over anhydrous $Na_2SO_4$, and evaporated. The crude compound was stirred in diethyl ether for 30 min, filtered and dried on the filter to afford 5-(tert-butoxycarbonylamino)-2-morpholino-benzoic acid (400 mg, 70%) as a white solid. LCMS: (M+H)=323, UV=85%.

$^1$H NMR (300 MHz, Methanol-$d_4$) δ 8.19-8.11 (m, 2H), 7.84 (dd, J=9.1, 2.8 Hz, 1H), 7.62 (d, J=8.8, 0.9 Hz, 1H), 4.00-3.90 (m, 4H), 3.25-3.15 (m, 4H), 1.54 (s, 9H).

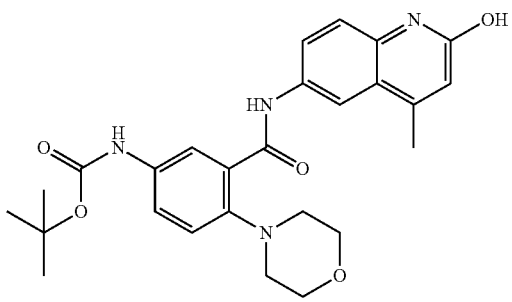 [SMILES: Cc1cc(O)nc2ccc(NC(=O)c3cc(NC(=O)OC(C)(C)C)ccc3N3CCOCC3)cc12]

Preparation of tert-butyl N-[3-[(2-hydroxy-4-methyl-6-quinolyl)carbamoyl]-4-morpholino-phenyl]carbamate: to a solution of 5-(tert-butoxycarbonylamino)-2-morpholino-benzoic acid (350 mg, 1.09 mmol, 1 eq) in DCM (6 mL) were added 6-amino-4-methyl-quinolin-2-ol (322 mg, 1.85 mmol, 1.7 eq), HOAt (252 mg, 1.85 mmol, 1.7 eq), EDC (355 mg, 1.85 mmol, 1.7 eq), DMAP (24 mg, 0.19 mmol, 0.2 eq) and DIPEA (568 µL, 3.27 mL, 3 eq). The reaction mixture was stirred at room temperature for 72 hours. After completion the reaction mixture was added water. The precipitated product was filtered off and washed with water and DCM. The crude compound was recrystallized from MeOH yielding tert-butyl N-[3-[(2-hydroxy-4-methyl-6-quinolyl)carbamoyl]-4-morpholino-phenyl]carbamate (285 mg, 55% yield) as a grayish solid. LCMS: (M+H)=479, UV=98%.

$^1$H NMR (300 MHz, DMSO-$d_6$) δ 11.72 (s, 1H), 11.63 (s, 1H), 9.48 (s, 1H), 8.29 (d, J=2.2 Hz, 1H), 8.02 (d, J=2.6 Hz, 1H), 7.80 (dd, J=8.9, 2.2 Hz, 1H), 7.56 (dd, J=8.8, 2.8 Hz, 1H), 7.35 (d, J=8.8 Hz, 1H), 7.28 (d, J=8.7 Hz, 1H), 6.43 (s, 1H), 3.86-3.63 (m, 4H), 2.99-2.85 (m, 4H), 2.46-2.35 (m, 3H), 1.48 (s, 9H).

Compound-54

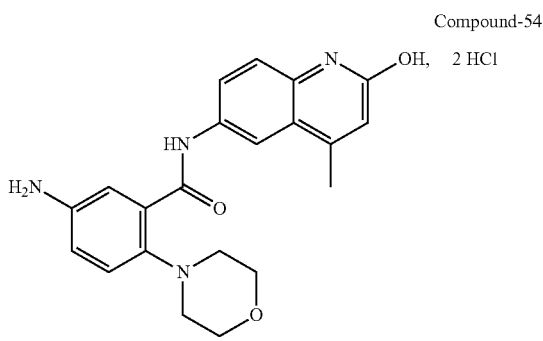 [SMILES: Cc1cc(O)nc2ccc(NC(=O)c3cc(N)ccc3N3CCOCC3)cc12 ; "2 HCl"]

Preparation of 5-amino-N-(2-hydroxy-4-methyl-6-quinolyl)-2-morpholino-benzamide (Compound-54): Tert-butyl N-[3-[(2-hydroxy-4-methyl-6-quinolyl)carbamoyl]-4-morpholino-phenyl]carbamate (285 mg, 0.60 mmol, 1 eq) was dissolved in DCM (3 mL) and added a solution of TFA in DCM (50%)(3 mL). The reaction mixture was stirred at room temperature for 4 h and evaporated to dryness. The residue was evaporated from toluene twice to remove water. 4 M HCl in Dioxane (3 mL) was added and evaporated to give the hydrochloric salt. The residue was stirred in diethyl ether (10 mL), filtered, washed with diethyl ether and dried to yield 5-amino-N-(2-hydroxy-4-methyl-6-quinolyl)-2-morpholino-benzamide (Compound-54) (281 mg, 98% yield) as a pink solid. LCMS: (M+H)=379, UV=93%.

$δ_H$ (300 MHz, DMSO-$d_6$): 11.69 (1H, s), 11.20 (1H, s), 8.26 (1H, d, J=2 Hz), 7.83 (1H, dd, J=9, 2 Hz), 7.72 (1H, d, J=3 Hz), 7.50 (1H, dd, J=9, 3 Hz), 7.42-7.28 (2H, m), 6.46 (1H, s), 3.85-3.61 (4H, m), 3.09-2.94 (4H, m), 2.42 (3H, s)

Compound-55

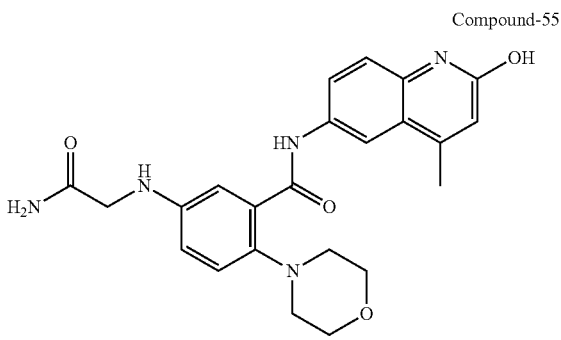 [SMILES: Cc1cc(O)nc2ccc(NC(=O)c3cc(NCC(N)=O)ccc3N3CCOCC3)cc12]

Preparation of 5-[(2-amino-2-oxo-ethyl)amino]-N-(2-hydroxy-4-methyl-6-quinolyl)-2-morpholino-benzamide (Compound-55): 5-amino-N-(2-hydroxy-4-methyl-6-quinolyl)-2-morpholino-benzamide (50 mg, 0.11 mmol, 1 eq) was dissolved in DMF (1 mL). 2-bromoacetamide (15 µL, 0.55 mmol, 5 eq) and TEA (45 µL, 0.33 mmol, 6 eq) were added and the mixture was heated in a microwave oven at 80° C. for 60 min. The mixture was poured into water, extracted with EtOAc (5×2 mL). The combined extracts were dried over MgSO₄, filtered and concentrated in vacuo. The crude product was purified by flash chromatography (Eluent: DCM/MeOH 10%/NH₃-aq 1%) yielding 5-[(2-amino-2-oxo-ethyl)amino]-N-(2-hydroxy-4-methyl-6-quinolyl)-2-morpholino-benzamide (Compound-55) (2.7 mg, 6% yield) as a pink solid.

LCMS: (M+H)=436, UV=95%

¹H-NMR (300 MHz, Methanol-d₄): δ$_H$ 8.38 (1H, d, J=2 Hz), 7.86 (1H, dd, J=9, 2 Hz), 7.48-7.38 (2H, m), 7.33 (1H, d, J=9 Hz), 6.83 (1H, dd, J=9, 3 Hz), 6.58 (1H, s), 3.97 (2H, d, J=1 Hz), 3.94-3.88 (4H, m), 3.81 (2H, s), 3.08-2.99 (4H, m), 2.57 (3H, s)

Synthesis of Compound-66

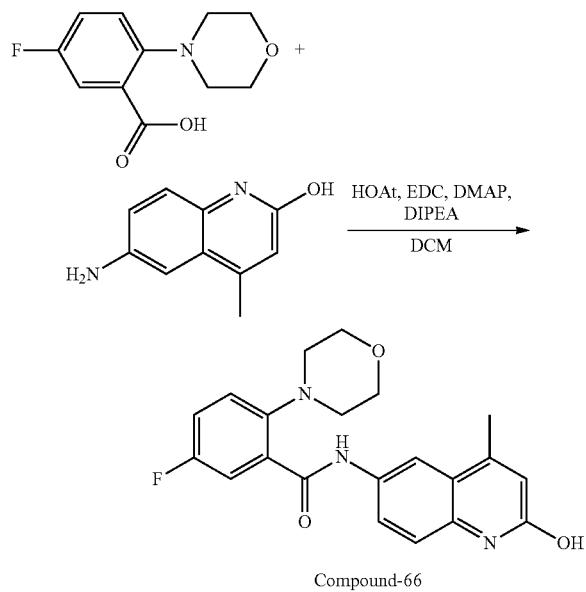

Compound-66

Preparation of 5-fluoro-N-(2-hydroxy-4-methyl-6-quinolyl)-2-morpholino-benzamide (Compound-66): to a solution of 5-fluoro-2-morpholino-benzoic acid (29 mg, 0.13 mmol, 1 eq) in DCM (0.5 mL) were added 6-amino-4-methyl-quinolin-2-ol (57 mg, 0.33 mmol, 2.5 eq), HOAt (44 mg, 0.33 mmol, 2.5 eq), EDC (62 mg, 0.33 mmol, 2.5 eq), DMAP (6 mg, 0.05 mmol, 0.4 eq) and DIPEA (73 µL, 0.39 mmol, 3 eq). The reaction mixture was stirred at room temperature overnight. Water was added and the precipitated product collected by filtration. The crude product was heated at reflux in MeOH for 5 minutes, filtered, washed with MeOH and dried yielding 5-fluoro-N-(2-hydroxy-4-methyl-6-quinolyl)-2-morpholino-benzamide (Compound-66) (24 mg, 48% yield) as a gray solid. LCMS: (M+H)=382, UV=98%.

¹H-NMR (300 MHz, DMSO-d₆): δ$_H$ 11.61 (1H, s), 11.54 (1H, s), 8.39-8.18 (1H, m), 7.92-7.70 (1H, m), 7.67-7.51 (1H, m), 7.47-7.24 (3H, m), 6.44 (1H, s), 3.87-3.63 (4H, m), 3.06-2.89 (4H, m), 2.41 (3H, s)

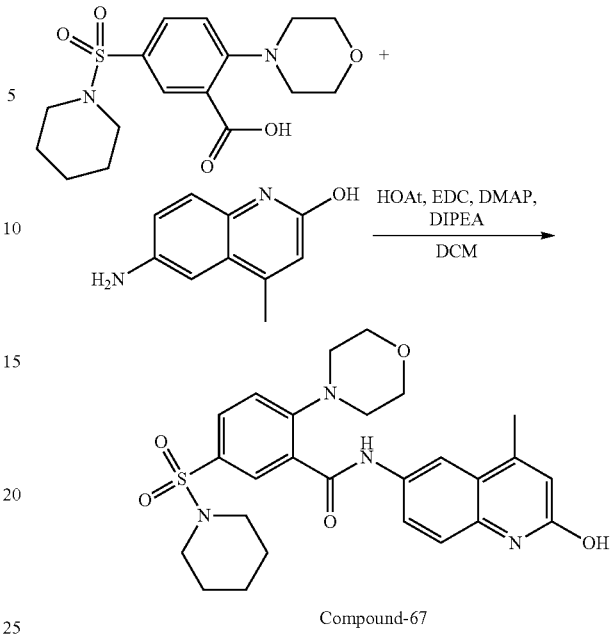

Compound-67

Synthesis of Compound-67

Preparation of N-(2-hydroxy-4-methyl-6-quinolyl)-2-morpholino-5-(1-piperidylsulfonyl)benzamide (Compound-67): to a solution of 2-morpholino-5-(1-piperidylsulfonyl) benzoic acid (46 mg, 0.13 mmol, 1 eq) in DCM (0.5 ml) were added 6-amino-4-methyl-quinolin-2-ol (57 mg, 0.33 mmol, 2.5 eq), HOAt (44 mg, 0.33 mmol, 2.5 eq), EDC (62 mg, 0.33 mmol, 2.5 eq), DMAP (6 mg, 0.05 mmol, 0.4 eq) and DIPEA (73 µL, 0.39 mmol, 3 eq). The reaction mixture was stirred at room temperature overnight. Water was added and the mixture was extracted with DCM (4×1.5 mL), dried over MgSO₄, filtered and evaporated under reduced pressure. The residue was purified by flash chromatography (Eluent: DCM/MeOH 10%/NH₃-aq 1%) yielding N-(2-hydroxy-4-methyl-6-quinolyl)-2-morpholino-5-(1-piperidylsulfonyl)benzamide (Compound-67)(32 mg, 48% yield) as a pink solid. LCMS: (M+H)=511, UV=98% pure.

¹H-NMR (300 MHz, Chloroform-d): δ$_H$ 12.70 (1H, s), 10.93 (1H, s), 8.52-8.21 (2H, m), 7.72 (1H, dd, J=9, 2 Hz), 7.63 (1H, dd, J=9, 2 Hz), 7.47 (1H, d, J=9 Hz), 7.33-7.20 (1H, m), 6.61 (1H, s), 4.03-3.80 (4H, m), 3.25-3.11 (4H, m), 3.06-2.94 (4H, m), 2.55 (3H, s), 1.74-1.56 (4H, m), 1.52-1.29 (2H, m).

Synthesis of Compound-68

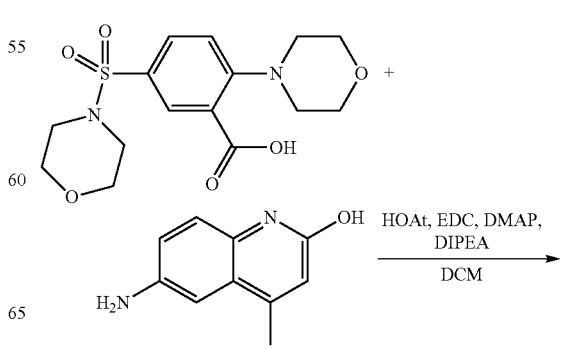

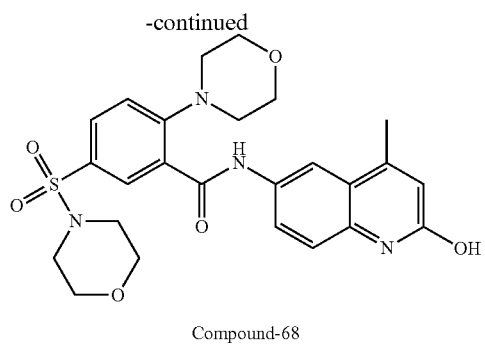

Compound-68

Preparation of N-(2-hydroxy-4-methyl-6-quinolyl)-2-morpholino-5-morpholinosulfonyl-benzamide (Compound-68): to a solution of 2-morpholino-5-morpholinosulfonyl-benzoic acid (46 mg, 0.13 mmol, 1 eq) in DCM (0.5 mL) were added 6-amino-4-methyl-quinolin-2-ol (57 mg, 0.33 mmol, 2.5 eq), HOAt (44 mg, 0.33 mmol, 2.5 eq), EDC (62 mg, 0.33 mmol, 2.5 eq), DMAP (6 mg, 0.05 mmol, 0.4 eq) and DIPEA (73 µL, 0.39 mmol, 3 eq). The reaction mixture was heated overnight at 45° C. Water was added and the mixture was extracted with DCM (4×2 mL), dried over MgSO$_4$, filtered and evaporated under reduced pressure. The residue was purified by flash chromatography (Eluent: DCM/MeOH 10%/NH$_3$-aq 1%) yielding N-(2-hydroxy-4-methyl-6-quinolyl)-2-morpholino-5-morpholinosulfonyl-benzamide (Compound-68) (20 mg, 30% yield) as a pink solid. LCMS: (M+H)=513, 98% pure.

$^1$H-NMR (300 MHz, Chloroform-d): δ$_H$ 12.60 (1H, s), 10.99 (1H, s), 8.64-8.23 (2H, m), 7.80 (1H, dd, J=8, 2 Hz), 7.61 (1H, dd, J=9, 2 Hz), 7.49 (1H, d, J=9 Hz), 7.35 (1H, d, J=9 Hz), 6.64 (1H, s), 4.02-3.86 (4H, m), 3.82-3.68 (4H, m), 3.25-3.11 (4H, m), 3.10-2.98 (4H, m), 2.58 (3H, s).

Synthesis of Compound-69 (Comparative)

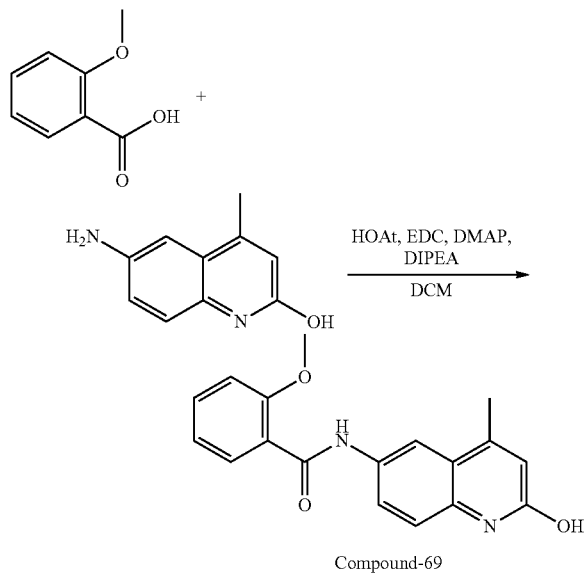

Compound-69

Preparation of N-(2-hydroxy-4-methyl-6-quinolyl)-2-methoxy-benzamide (Compound-69): To a solution of 2-methoxybenzoic acid (32 mg, 0.21 mmol, 1 eq) in DCM (0.5 mL) were added 6-amino-4-methyl-quinolin-2-ol (40 mg, 0.23 mmol, 1.1 eq), HOAt (42 mg, 0.31 mmol, 1.5 eq), EDC (60 mg, 0.32 mmol, 1.5 eq), DMAP (8 mg, 0.06 mmol, 0.3 eq) and DIPEA (110 µL, 0.63 mmol, 3 eq). The reaction mixture was stirred overnight at room temperature. Water was added and the reaction mixture extracted with DCM (4×5 mL), dried over MgSO$_4$, filtered and evaporated under reduced pressure. The residue was purified by flash chromatography (Eluent: DCM/MeOH 10%/NH$_3$-aq 1%) yielding N-(2-hydroxy-4-methyl-6-quinolyl)-2-methoxy-benzamide (Compound-69) (39 mg, 61% yield) as a pink solid. LCMS: (M+H)=309, UV=98%.

$^1$H-NMR (300 MHz, DMSO-d$_6$): δ$_H$ 11.57 (1H, s), 10.20 (1H, s), 8.20 (1H, d, J=2 Hz), 7.80 (1H, dd, J=9, 2 Hz), 7.65 (1H, dd, J=8, 2 Hz), 7.51 (1H, td, J=9, 7, 2 Hz), 7.27 (1H, d, J=9 Hz), 7.18 (1H, d), 7.07 (1H, td, J=7, 1 Hz), 6.42 (1H, s), 3.91 (3H, s), 2.41 (3H, s)

Synthesis of Compound-70

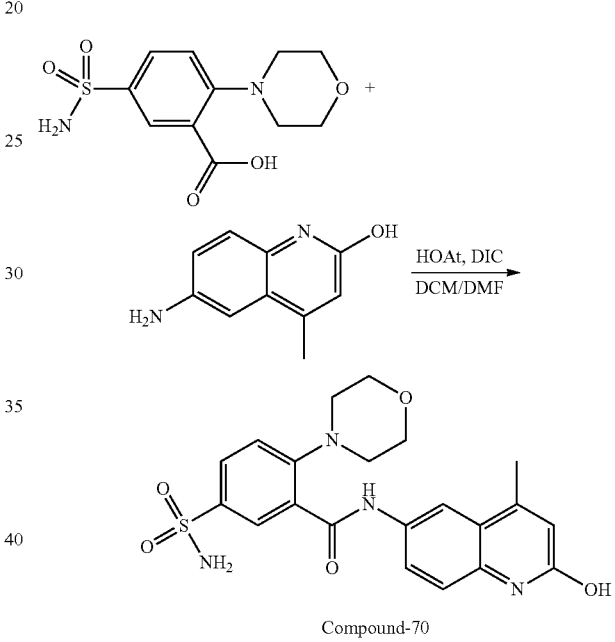

Compound-70

Preparation of N-(2-hydroxy-4-methyl-6-quinolyl)-2-morpholino-5-sulfamoyl-benzamide (Compound-70): to a slurry of 2-morpholino-5-sulfamoyl-benzoic acid (45 mg, 0.16 mmol, 1 eq) and 6-amino-4-methyl-quinolin-2-ol (27 mg, 0.16 mmol, 1 eq), in DCM/DMF (50:50, 1.0 mL) were added HOAt (24 mg, 0.17 mmol, 1.1 eq) and DIC (22 mg, 0.17 mmol, 1.1 eq). The reaction mixture was stirred overnight at room temperature. Water was added and the mixture was extracted with DCM/MeOH (9/1) (3×5 ml), dried over MgSO$_4$, filtered and evaporated under reduced pressure. The residue was heated at reflux in MeOH (5 mL) for 5 minutes, cooled at room temperature, filtered, washed with MeOH and dried yielding N-(2-hydroxy-4-methyl-6-quinolyl)-2-morpholino-5-sulfamoyl-benzamide (18 mg, 26% yield) as a pink solid. LCMS: (M+H)=443, UV=98% pure.

$^1$H-NMR (300 MHz, DMSO-d$_6$): δ$_H$ 11.60 (1H, s), 10.75 (1H, s), 8.21 (1H, d, J=2 Hz), 8.01 (1H, d, J=2 Hz), 7.90-7.76 (2H, m), 7.39-7.25 (3H, m), 6.44 (1H, s), 3.73-3.63 (4H, m), 3.13-3.02 (4H, m), 2.41 (3H, s)

Synthesis of Compound-71

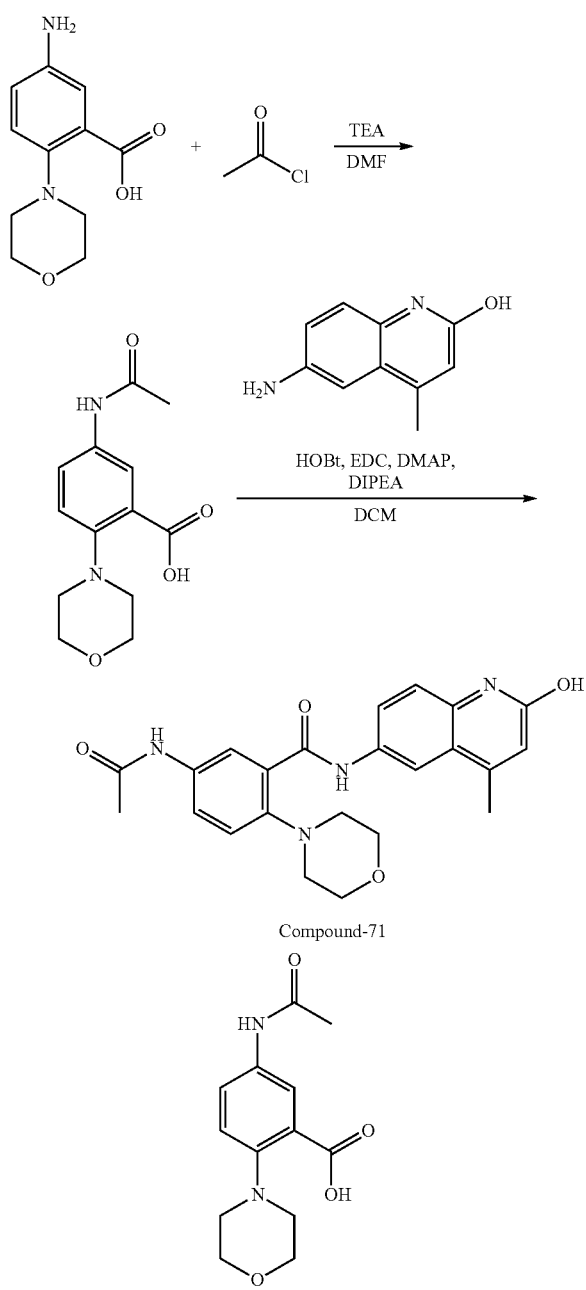

Compound-71

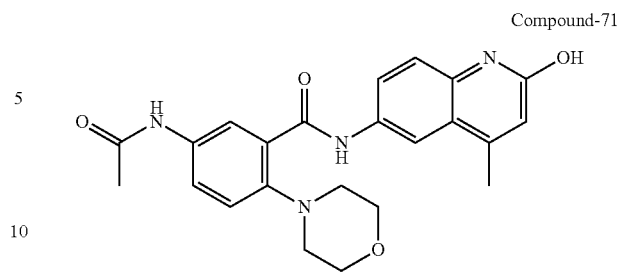

Preparation of 5-acetamido-N-(2-hydroxy-4-methyl-6-quinolyl)-2-morpholino-benzamide (Compound-71): a mixture of 5-acetamido-2-morpholino-benzoic acid (50 mg, 0.19 mmol, 1 eq) and 6-amino-4-methyl-quinolin-2-ol (33 mg, 0.19 mmol, 1 eq) in DCM (2 ml) were added HOBt (52 mg, 0.38 mmol, 2 eq), EDC (73 mg, 0.38 mmol, 2 eq), DMAP (8 mg, 0.07 mmol, 0.4 eq) and DIPEA (196 μL, 1.14 mmol, 6 eq). The reaction mixture was stirred at room temperature overnight. Water was added and the precipitated solid was filtered off and wash with water. The crude product was stirred in DCM (2 mL), filtered and dried yielding 5-acetamido-N-(2-hydroxy-4-methyl-6-quinolyl)-2-morpholino-benzamide (Compound-71) (23 mg, 29% yield) as a pink solid. LCMS: (M+H)=421, UV=98%

$^1$H-NMR (300 MHz, DMSO-d$_6$): δ$_H$ 11.65 (1H, s), 11.59 (1H, s), 10.05 (1H, s), 8.25 (1H, s), 8.06 (1H, s), 7.94-7.68 (2H, m), 7.50-7.22 (2H, m), 6.43 (1H, s), 4.09-3.58 (4H, m), 3.17-2.73 (4H, m), 2.42 (3H, s), 2.05 (3H, s).

Synthesis of Compound-72

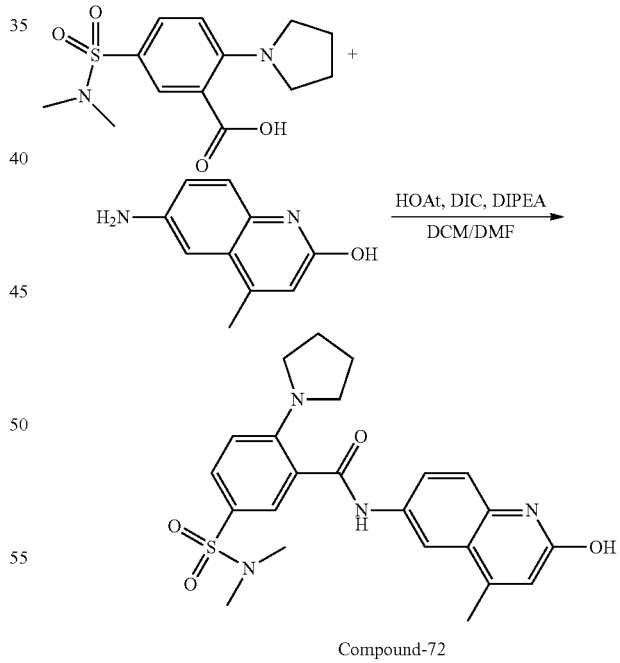

Compound-72

Preparation of 5-(dimethylsulfamoyl)-N-(2-hydroxy-4-methyl-6-quinolyl)-2-pyrrolidin-1-yl-benzamide (Compound-72): to a slurry of 5-(dimethylsulfamoyl)-2-pyrrolidin-1-yl-benzoic acid (75 mg, 0.25 mmol, 1 eq) and 6-amino-4-methyl-quinolin-2-ol (44 mg, 0.25 mmol, 1 eg) in DCM/DMF 50:50 (1 mL) were added HOAt (37 mg, 0.28 mmol, 1.1 eq), DIC (52 μl, 0.28 mmol, 1.1 eq) and DIPEA Preparation of 5-acetamido-2-morpholino-benzoic acid: to a slurry of 5-amino-2-morpholino-benzoic acid (105 mg, 0.47 mmol, 1 eq) in DMF (1 mL) were added acetyl chloride (41 μL, 0.47 mmol, 1.5 eq) and TEA (196 μL, 1.41 mmol, 3 eq). The reaction mixture was stirred at room temperature overnight, evaporated to dryness and the resultant residue was purified by flash chromatography (Eluent: DCM/MeOH 10%/NH$_3$-aq 1%) yielding 5-acetamido-2-morpholino-benzoic acid (109 mg, 88%) as a white solid. LCMS: (M+H)= 265, UV=98%.

$^1$H-NMR (300 MHz, DMSO-d$_6$): δ$_H$ 10.18 (1H, s), 8.20 (1H, d, J=3 Hz), 7.88 (1H, dd, J=9, 3 Hz), 7.65 (1H, d, J=9 Hz), 3.86-3.73 (4H, m), 3.11-2.96 (4H, m), 2.05 (3H, s).

(90 µL, 0.50 mmol, 2 eq). The reaction mixture was heated at 80° C. for 5 h and poured into water (10 mL). The precipitated solid was filtered off, washed with water, dried and purified by flash chromatography (Eluent: DCM/MeOH 10%/NH$_3$-aq 1%) to yield 5-(dimethylsulfamoyl)-N-(2-hydroxy-4-methyl-6-quinolyl)-2-pyrrolidin-1-yl-benzamide (Compound-72) (56 mg, 50% yield) as a pink solid. LCMS: (M+H)=455, UV=98% pure.

$^1$H-NMR (300 MHz, DMSO-d$_6$): δ$_H$ 11.59 (1H, s), 10.58 (1H, s), 8.11 (1H, d, J=2 Hz), 7.80 (1H, dd, J=9, 2 Hz), 7.68-7.48 (2H, m), 7.29 (1H, d, J=9 Hz), 6.89 (1H, d, J=9 Hz), 6.42 (1H, s), 3.46-3.33 (4H, m), 2.59 (6H, s), 2.40 (3H, d, J=1 Hz), 1.95-1.84 (4H, m)

Synthesis of Compound-73

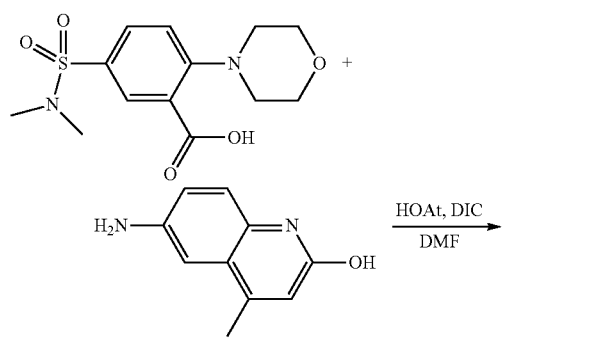

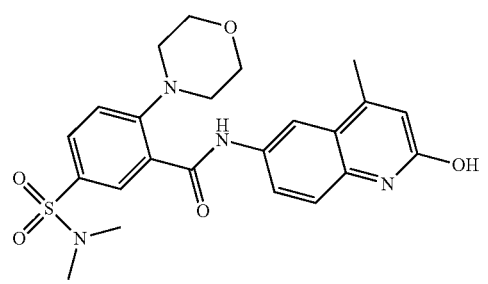

Compound-73

Preparation of 5-(dimethylsulfamoyl)-N-(2-hydroxy-4-methyl-6-quinolyl)-2-morpholino-benzamide (Compound-73): to a solution of 5-(dimethylsulfamoyl)-2-morpholino-benzoic acid (94 mg, 0.30 mmol, 1 eq) and 6-amino-4-methyl-quinolin-2-ol (52 mg, 0.30 mmol, 1 eq) in DMF (1.5 mL) were added HOAt (45 mg, 0.33 mmol, 1.1 eq) and DIC (51 mg, 1.1 mmol, 1.1 eq). The reaction mixture was stirred at room temperature for 72 h and poured into water (10 mL). The precipitated solid was filtered off, washed with water and dried. The crude product was added THF (1 mL) and the slurry was stirred overnight, filtered, washed with THF and dried giving 5-(dimethylsulfamoyl)-N-(2-hydroxy-4-methyl-6-quinolyl)-2-morpholino-benzamide (Compound-73) (45 mg, 32%) as a grayish solid. LCMS: (M+H)=471, UV=99%.

$^1$H-NMR (300 MHz, DMSO-d$_6$): δ$_H$ 11.61 (1H, s), 10.68 (1H, s), 8.23 (1H, s), 7.92-7.66 (3H, m), 7.32 (2H, d, J=9 Hz), 6.44 (1H, s), 3.72-3.63 (4H, m), 3.19-3.03 (4H, m), 2.62 (6H, s), 2.40 (3H, s)

Synthesis of Compound-74

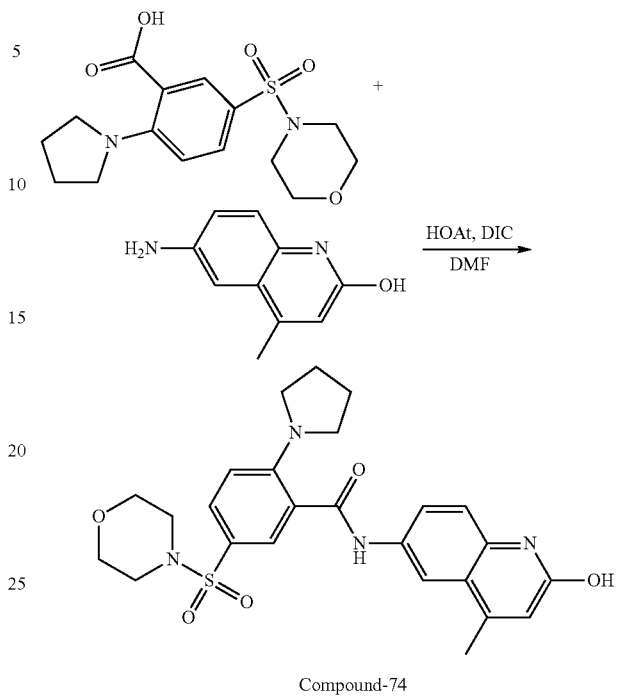

Compound-74

Preparation of N-(2-hydroxy-4-methyl-6-quinolyl)-5-morpholinosulfonyl-2-pyrrolidin-1-yl-benzamide (Compound-74): to a solution of 5-morpholinosulfonyl-2-pyrrolidin-1-yl-benzoic acid (103 mg, 0.30 mmol, 1 eq) and 6-amino-4-methyl-quinolin-2-ol (52 mg, 0.30 mmol, 1 eq) in DMF (1.5 mL) was added HOAt (45 mg, 0.33 mmol, 1.1 eq) and DIC (51 mg, 1.1 mmol, 1.1 eq). The reaction mixture was stirred at room temperature for 72 h and poured into water (10 mL). The precipitated solid was filtered off and purified by flash chromatography (Eluent: DCM/MeOH 10%/NH$_3$-aq 1%) giving N-(2-hydroxy-4-methyl-6-quinolyl)-5-morpholino sulfonyl-2-pyrrolidin-1-yl-benzamide (Compound-74) (67 mg, 45%), as a pink solid. LCMS: (M+H)=497, UV=99%.

$^1$H-NMR (300 MHz, DMSO-d$_6$): δ$_H$ 11.59 (1H, s), 10.60 (1H, s), 8.12 (1H, d, J=2 Hz), 7.80 (1H, dd, J=9, 2 Hz), 7.63-7.46 (2H, m), 7.29 (1H, d, J=9 Hz), 6.90 (1H, d, J=9 Hz), 6.43 (1H, s), 3.75-3.57 (4H, m), 3.40-3.33 (4H, m), 2.93-2.78 (4H, m), 2.40 (3H, s), 1.98-1.66 (4H, m)

Synthesis of Compound-76 and Compound-77 (Comparative)

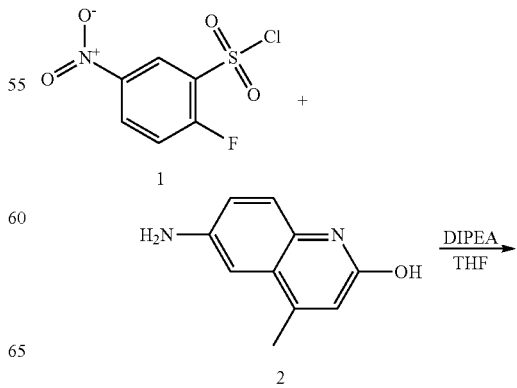

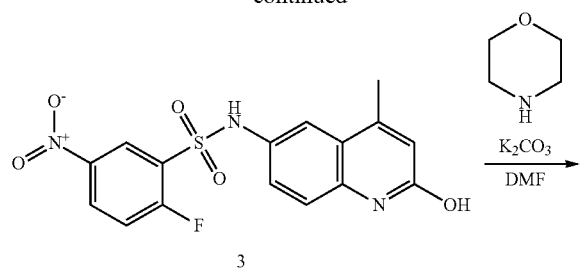

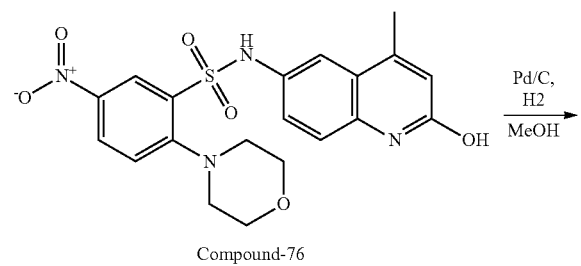

Compound-76

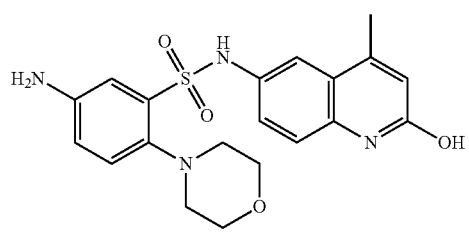

Compound-77

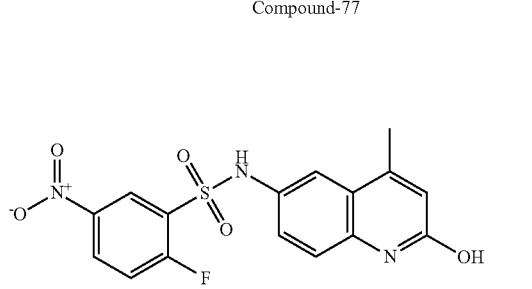

Preparation of 2-fluoro-N-(2-hydroxy-4-methyl-6-quinolyl)-5-nitro-benzenesulfonamide: to a solution of 2-fluoro-5-nitro-benzenesulfonyl chloride (320 mg, 1.33 mmol, 1 eq) in THF (5 mL) were added 6-amino-4-methylquinolin-2-ol (239 mg, 1.33 mmol, 1 eq) and DIPEA (700 μL, 3.99 mmol, 3 eq). The mixture was heated at 80° C. for 5 h, poured into water (15 mL) and extracted with EtOAc (3×5 mL). The combined extracts were washed with water and dried over MgSO$_4$, filtered and evaporated under reduced pressure. The residue was purified by flash chromatography (Eluent: DCM/MeOH 10%/NH$_3$-aq 1%) yielding 2-fluoro-N-(2-hydroxy-4-methyl-6-quinolyl)-5-nitro-benzenesulfonamide (74 mg, 15% yield) as a yellow solid. LCMS: (M+H)=379, UV=99%

$^1$H-NMR (300 MHz, DMSO-d$_6$): δ$_H$ 11.59 (1H, s), 10.90 (1H, s), 8.68-8.31 (2H, m), 7.74 (1H, t, J=9 Hz), 7.39 (1H, d, J=2 Hz), 7.26 (1H, dd, J=9, 2 Hz), 7.20 (1H, d, J=9 Hz), 6.39 (1H, s), 2.30 (3H, s)

Compound-76

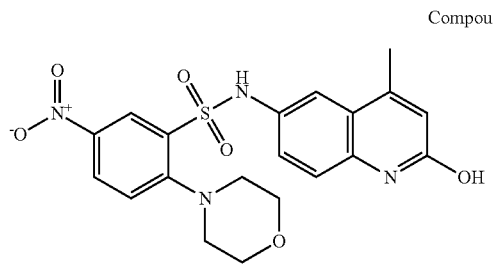

Preparation of N-(2-hydroxy-4-methyl-6-quinolyl)-2-morpholino-5-nitro-benzenesulfonamide (Compound-76) (comparative): to a solution of 2-fluoro-N-(2-hydroxy-4-methyl-6-quinolyl)-5-nitro-benzenesulfonamide (74 mg, 0.20 mmol, 1.0 eq) in NMP (1 mL) were added morpholine (26 μl, 0.30 mmol, 1.5 eq) and potassium carbonate (83 mg, 0.60 mmol, 3 eq). The mixture was heated at 80° C. for 40 min. Water (5 m) was added and the mixture extracted with EtOAc (5×3 mL). The combined extracts were dried over MgSO$_4$, filtered and evaporated under reduced pressure. The residue was added water (3 mL) and stirred for 1 h, filtered, washed with water and dried to afford N-(2-hydroxy-4-methyl-6-quinolyl)-2-morpholino-5-nitro-benzenesulfonamide (Compound-76) (23 mg, 26% yield) as a yellowish solid. LCMS: (M+H)=445, UV=91%

$^1$H-NMR (300 MHz, DMSO-d$_6$): δ$_H$ 11.54 (1H, s), 10.24 (1H, s), 8.66 (1H, d, J=3 Hz), 8.30 (1H, dd, J=9, 3 Hz), 7.46 (1H, d, J=9 Hz), 7.25 (1H, d, J=2 Hz), 7.21-7.09 (2H, m), 6.37 (1H, s), 3.84-3.71 (4H, m), 3.18-3.02 (4H, m), 2.24 (3H, s).

Compound-77

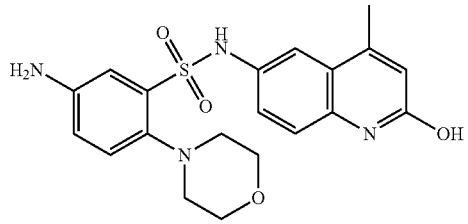

Preparation of 5-amino-N-(2-hydroxy-4-methyl-6-quinolyl)-2-morpholino-benzenesulfonamide (Compound-77) (comparative): N-(2-hydroxy-4-methyl-6-quinolyl)-2-morpholino-5-nitro-benzenesulfonamide (25 mg, 0.056 mmol, 1 eq) in MeOH (0.5 mL) were added Pd/C 5% (5 mg). The mixture was stirred under an atmosphere of hydrogen at room temperature for 2 h, filtered through a pad of celite and the filtrate evaporated under reduced pressure. The crude compound was purified by flash chromatography (Eluent: DCM/MeOH 10%/NH$_3$-aq 1%) yielding 5-amino-N-(2-hydroxy-4-methyl-6-quinolyl)-2-morpholino-benzenesulfonamide (Compound-77) (7.2 mg, 31%) as a white solid. LCMS: (M+H)=415, UV=96%

$^1$H-NMR (300 MHz, DMSO-d$_6$): δ$_H$ 11.49 (1H, s), 9.25 (1H, s), 7.26 (1H, s), 7.22-7.06 (4H, m), 6.69 (1H, dd, J=9, 3 Hz), 6.35 (1H, s), 5.38 (2H, s), 3.91-3.68 (4H, m), 2.80-2.63 (4H, m), 2.25 (3H, s).

Synthesis of Compound-79

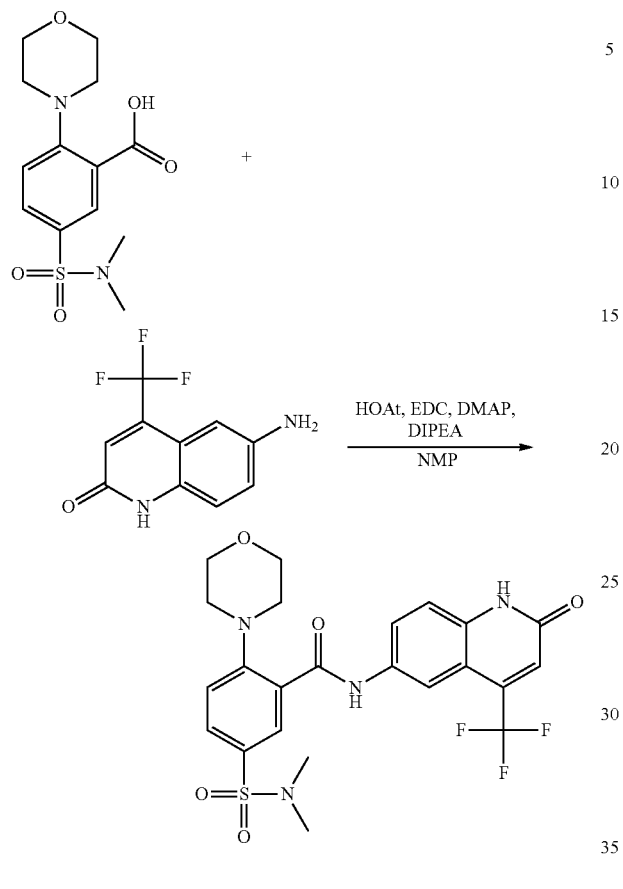

Compound-79

Preparation 5-(dimethylsulfamoyl)-2-morpholino-N-[2-oxo-4-(trifluoromethyl)-1H-quinolin-6-yl]benzamide (Compound-79): to a mixture of 5-(dimethylsulfamoyl)-2-morpholino-benzoic acid (50 mg, 0.22 mmol, 1 eq) in NMP (1 mL) were added 6-amino-4-(trifluoromethyl)-1H-quinolin-2-one (83 mg, 0.26 mmol, 1.2 eq), HOAt (70 mg, 0.53 mmol, 2.4 eq), EDC (101 mg, 0.53 mmol, 2.4 eq), DMAP (10 mg, 0.08 mmol, 0.4 eq), DIPEA (73 µL, 0.66 mmol, 6 eq). The reaction mixture was stirred overnight at room temperature and poured into water. The precipitated compound was filtered off and washed with water. The residue was stirred in diethyl ether, filtered and dried to yield 5-(dimethylsulfamoyl)-2-morpholino-N-[2-oxo-4-(trifluoromethyl)-1H-quinolin-6-yl]benzamide (Compound-79) (92 mg, 80% yield) as a yellowish solid. LCMS: (M+H)=525, UV=98%.

$^1$H-NMR (300 MHz, DMSO-$d_6$): $\delta_H$ 12.34 (1H, s), 10.82 (1H, s), 8.38 (1H, s), 7.99 (1H, dd, J=9, 2 Hz), 7.90-7.66 (2H, m), 7.46 (1H, d, J=9 Hz), 7.33 (1H, d, J=8 Hz), 7.01 (1H, s), 3.86-3.51 (4H, m), 3.23-2.91 (4H, m), 2.62 (6H, s).

Synthesis of Compound-80

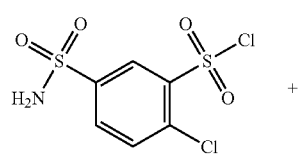

+

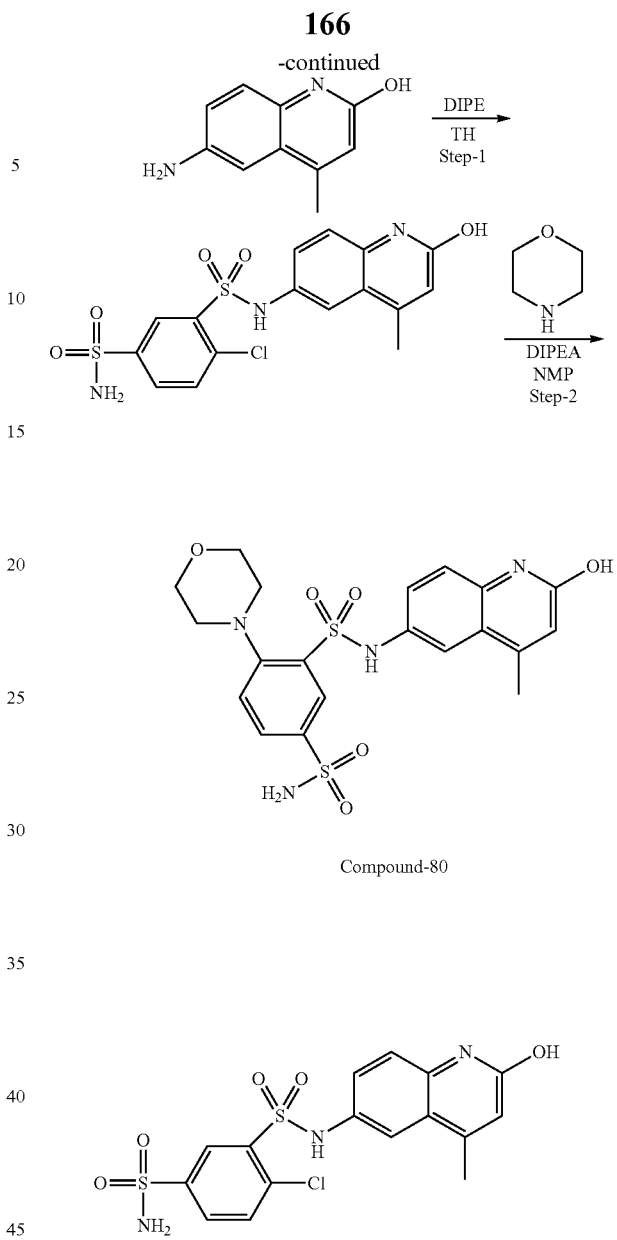

Compound-80

Preparation of 4-chloro-N3-(2-hydroxy-4-methyl-6-quinolyl)benzene-1,3-disulfonamide: to a solution of 2-chloro-5-sulfamoyl-benzenesulfonyl chloride (290 mg, 1.0 mmol, 1 eq) in THF (5 mL) were added 6-amino-4-methyl-quinolin-2-ol (174 mg, 1.0 mmol, 1 eq) and DIPEA (521 µL, 3.0 mmol, 3 eq). The mixture was heated at 70° C. for 4 h, poured into water (10 mL) and extracted with EtOAc (3×4 mL). The combined extracts were washed with 0.4 M HCl (2×4 mL), water (4 mL), sat. NaHCO$_3$ (4 mL) and brine (4 mL). Dried over MgSO$_4$, filtered and evaporated under reduced pressure. The crude product was purified by flash chromatography (Eluent: DCM/MeOH 10%/NH$_3$-aq 1%) to afford 4-chloro-N3-(2-hydroxy-4-methyl-6-quinolyl)benzene-1,3-disulfonamide (50 mg, 12%) as a solid. LCMS: (M+H)=428, UV=99%.

$^1$H-NMR (300 MHz, Methanol-$d_4$): $\delta_H$ 8.55 (1H, d, J=2 Hz), 8.01 (1H, dd, J=8, 2 Hz), 7.76 (1H, d, J=8 Hz), 7.53 (1H, d, J=2 Hz), 7.37 (1H, dd, J=9, 2 Hz), 7.24 (1H, d, J=9 Hz), 6.48 (1H, s), 2.42 (3H, s).

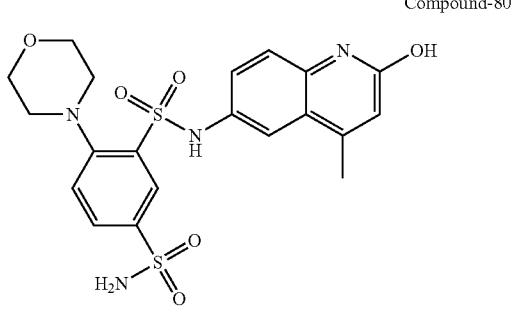

Compound-80

Preparation of N3-(2-hydroxy-4-methyl-6-quinolyl)-4-morpholino-benzene-1,3-disulfonamide (Compound-80) (comparative): to a solution of 4-chloro-N3-(2-hydroxy-4-methyl-6-quinolyl)benzene-1,3-disulfonamide (15 mg, 0.035 mmol, 1 eq) in NMP (0.5 mL) were added morpholine (12 µL, 0.14 mmol, 4 eq) and DIPEA (18 µL), 0.105 mmol, 3 eq). The mixture was heated in a microwave oven at 120° C. for 5 h. Water was added (2 ml) and the mixture was extracted with EtOAc (4×2 mL), washed with brine and dried over MgSO$_4$, filtered and evaporated under reduced pressure. The residue was purified by flash chromatography (Eluent: DCM/MeOH 10%/NH$_3$-aq 1%) yielding N3-(2-hydroxy-4-methyl-6-quinolyl)-4-morpholino-benzene-1,3-disulfonamide (Compound-80) (5.3 mg, 32%). LCMS: (M+H)=479, UV=97%

$^1$H-NMR (300 MHz, Methanol-d$_4$): δ$_H$ 8.51 (1H, t, J=2 Hz), 8.01 (1H, dt, J=8, 2 Hz), 7.52 (1H, dd, J=8, 1 Hz), 7.39 (1H, t, J=2 Hz), 7.28 (1H, dt, J=9, 2 Hz), 7.20 (1H, dd, J=9, 1 Hz), 6.47 (1H, s), 4.05-3.88 (4H, m), 3.15-2.99 (4H, m), 2.39 (3H, s).

Synthesis of Compound-81

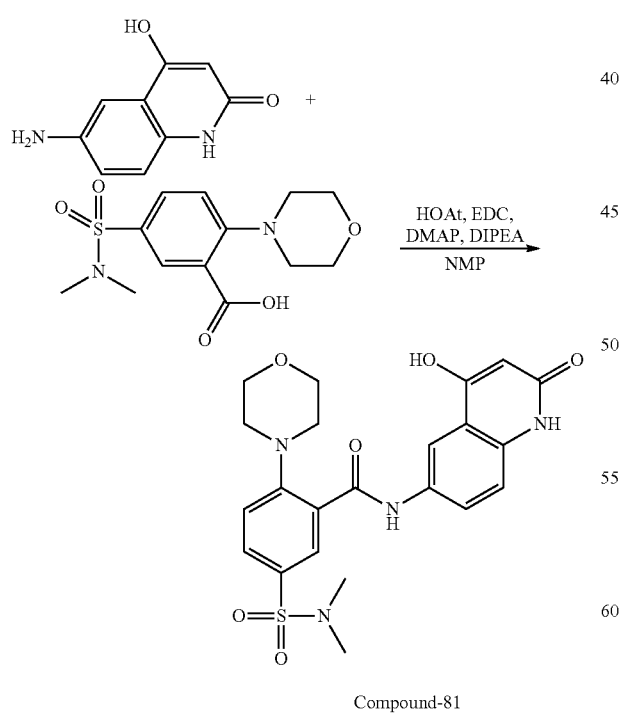

Compound-81

Preparation of 5-(dimethylsulfamoyl)-N-(4-hydroxy-2-oxo-1H-quinolin-6-yl)-2-morpholino-benzamide (Compound-81): to a mixture of 6-amino-4-hydroxy-1H-quinolin-2-one (35 mg, 0.20 mmol, 1 eq) and 5-(dimethylsulfamoyl)-2-morpholino-benzoic acid (76 mg, 0.24 mmol, 1.2 eq) in NMP (1 mL) were added HOAt (32 mg, 0.24 mmol, 1.2 eq), EDC (37 mg, 0.24 mmol, 0.24 mmol), DMAP (5 mg, 0.04 mmol, 0.2 eq) and DIPEA (104 µL, 0.6 mmol, 3 eq). The reaction mixture was heated at 50° C. for 2 h and poured into water. The water phase was washed with EtOAc and evaporated to dryness. The crude product was purified by flash chromatography (Eluent: DCM/MeOH 10%/NH$_3$-aq 1%) yielding 5-(dimethylsulfamoyl)-N-(4-hydroxy-2-oxo-1H-quinolin-6-yl)-2-morpholino-benzamide (Compound-81) (12 mg, 13%) as a white solid. LCMS: (M+H)=473, UV=95%.

$^1$H-NMR (300 MHz, DMSO-d$_6$): δ$_H$ 11.36 (1H, s), 11.17 (1H, s), 10.63 (1H, s), 8.33 (1H, d, J=2 Hz), 7.96-7.61 (3H, m), 7.31 (1H, d, J=9 Hz), 7.25 (1H, d, J=9 Hz), 5.74 (1H, s), 3.85-3.48 (4H, m), 3.15-3.07 (4H, m), 2.62 (6H, s).

Synthesis of Compound-82

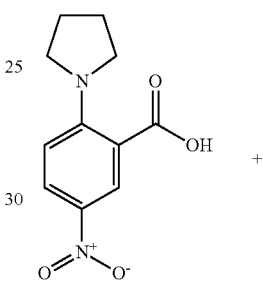

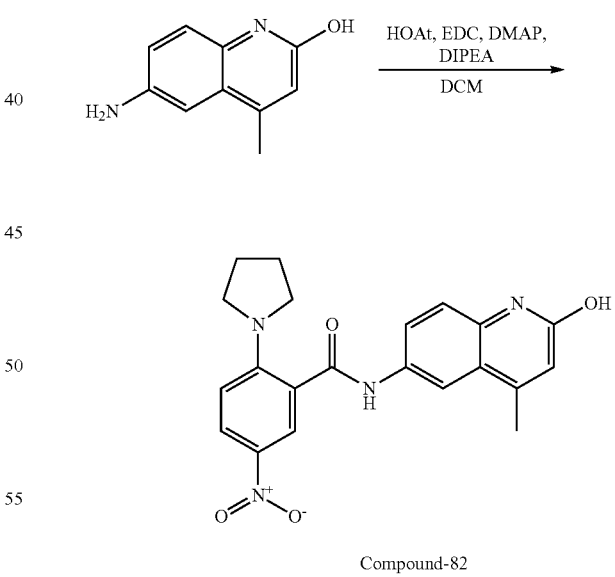

Compound-82

Preparation of N-(2-hydroxy-4-methyl-6-quinolyl)-5-nitro-2-pyrrolidin-1-yl-benzamide (Compound-82): LCMS: (M+H)=393, UV=95%

$^1$H-NMR (300 MHz, DMSO-d$_6$): δ$_H$ 7.52 (1H, d, J=3 Hz), 7.45 (1H, d, J=2 Hz), 7.38 (1H, dd, J=9, 3 Hz), 7.06 (1H, dd, J=9, 2 Hz), 6.60 (1H, d, J=9 Hz), 6.09 (1H, d, J=9 Hz), 5.77 (1H, s), 2.87-2.61 (4H, m), 1.75 (3H, s), 1.37-1.07 (4H, m).

Synthesis of Compound-83 and Compound-84

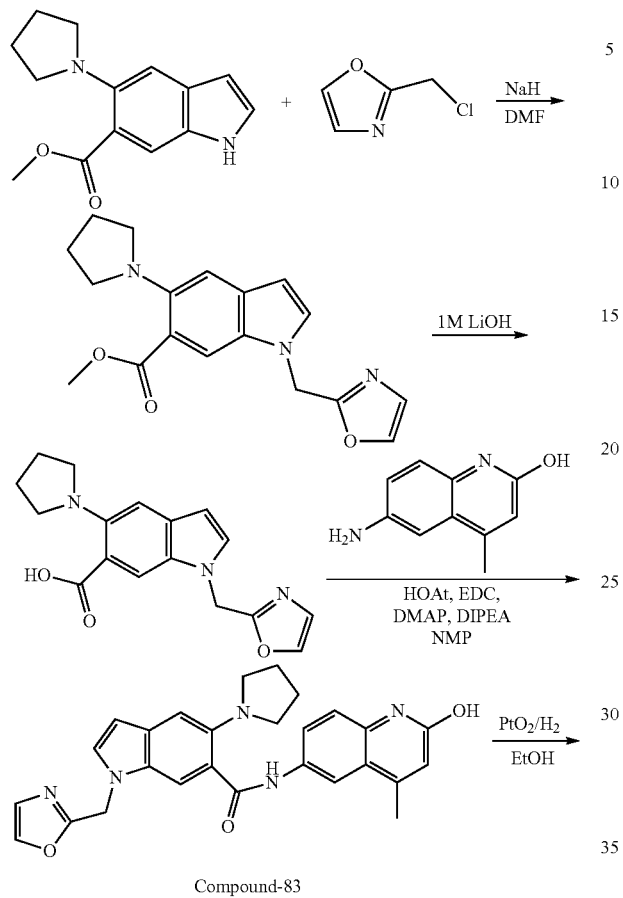

Compound-83

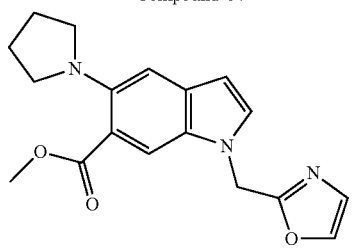

Compound-84

Preparation of methyl 1-(oxazol-2-ylmethyl)-5-pyrrolidin-1-yl-indole-6-carboxylate: methyl 5-pyrrolidin-1-yl-1H-indole-6-carboxylate (200 mg, 0.82 mmol, 1 eq) was dissolved in DMF (1.5 mL). NaH 60% (163 mg, 4.1 mmol, 5 eqv) was added and the mixture stirred at room temperature for 90 min. 2-(chloromethyl)oxazole (186 μL, 2.05 mmol, 2.5 eq) was added and the mixture stirred at room temperature overnight. Additional NaH (98 mg, 2.46 mmol, 3 eq) was added. After 2 h, additional 2-(chloromethyl)oxazole (90 μL, 0.98 mmol, 1.2 eq) was added. The reaction mixture was stirred for 2 h and quenched with water (3 mL), extracted with EtOAc (4×3 mL), washed with water and brine, dried over $Na_2SO_4$, filtered and evaporated under reduced pressure. The residue was purified by flash chromatography (Eluent: DCM/MeOH 10%/$NH_3$-aq 1%) yielding methyl 1-(oxazol-2-ylmethyl)-5-pyrrolidin-1-yl-indole-6-carboxylate (124 mg, 47%). LCMS: (M+H)=326.

$^1$H-NMR $\delta_H$ (300 MHz, DMSO-$d_6$): $\delta_H$ 8.05 (1H, d, J=1 Hz), 7.66 (1H, s), 7.48 (1H, d, J=3 Hz), 7.17 (1H, d, J=1 Hz), 6.94 (1H, s), 6.36 (1H, dd, J=3, 1 Hz), 5.57 (2H, s), 3.80 (3H, s), 3.22-2.93 (5H, m), 1.94-1.71 (2H, m).

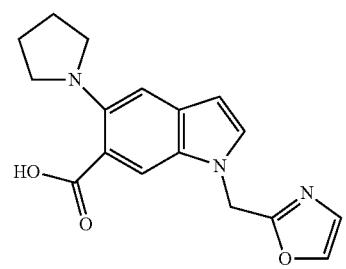 [SMILES: O=C(O)c1cc2c(ccn2Cc2ncco2)cc1N1CCCC1]

Preparation of 1-(oxazol-2-ylmethyl)-5-pyrrolidin-1-yl-indole-6-carboxylic acid: methyl 1-(oxazol-2-ylmethyl)-5-pyrrolidin-1-yl-indole-6-carboxylate (124 mg, 0.38 mmol, 1 eq) in 1M LiOH (2 mL, 2 mmol, 5 eq) was stirred at 100° C. overnight, neutralized with 1M HCl and evaporated under reduced pressure to yield 1-(oxazol-2-ylmethyl)-5-pyrrolidin-1-yl-indole-6-carboxylic acid. LCMS: (M+H)=312, UV=60%. Used without purification in the next step.

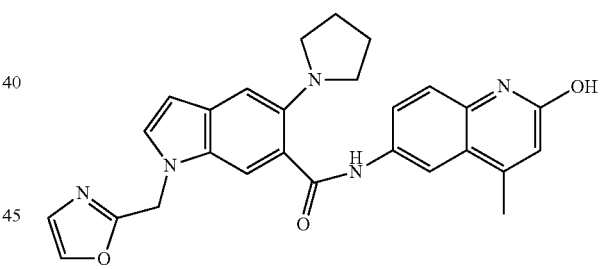

Compound-83

Preparation of N-(2-hydroxy-4-methyl-6-quinolyl)-1-(oxazol-2-ylmethyl)-5-pyrrolidin-1-yl-indole-6-carboxamide (Compound-83): to a solution of 1-(oxazol-2-ylmethyl)-5-pyrrolidin-1-yl-indole-6-carboxylic acid (crude product) (0.38 mmol, 1 eq) in NMP (2 ml) were added 6-amino-4-methyl-quinolin-2-ol (132 mg, 0.76 mmol, 2 eq), HOAt (155 mg, 1.14 mmol, 3 eq), EDC (219 mg, 1.14 mmol, 3 eq), DMAP (18 mg, 0.15 mmol, 0.4 eq) and DIPEA (330 μL, 1.9 mmol, 5 eq). The reaction mixture was heated at 80° for 90 min and poured into water. Precipitated solid were filtered off. The crude product was slurred in MeOH and heated at reflux. After cooling the solid was filtered off and dried yielding N-(2-hydroxy-4-methyl-6-quinolyl)-1-(oxazol-2-ylmethyl)-5-pyrrolidin-1-yl-indole-6-carboxamide (Compound-83) (30 mg, 17%), as a brown solid. LCMS: (M+H)=468, UV=95%.

$^1$H-NMR (300 MHz, DMSO-$d_6$): $\delta_H$ 12.39 (1H, s), 11.59 (1H, s), 8.21 (1H, d, J=2 Hz), 8.07 (2H, s), 7.72 (1H, dd, J=9, 2 Hz), 7.58 (1H, d, J=3 Hz), 7.48 (1H, s), 7.30 (1H, d, J=9

Hz), 7.18 (1H, s), 6.48 (1H, d, J=3 Hz), 6.43 (1H, s), 5.66 (2H, s), 3.21-3.07 (4H, m), 2.41 (3H, s), 2.07-1.89 (4H, m).

Compound-84

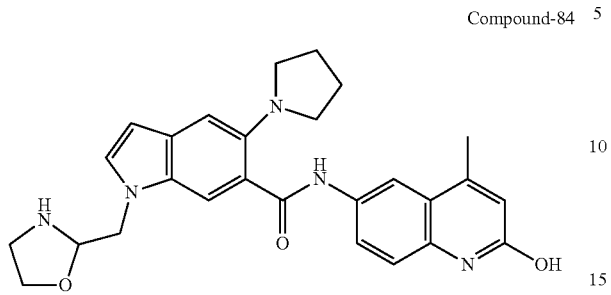

Preparation of N-(2-hydroxy-4-methyl-6-quinolyl)-1-(oxazolidin-2-ylmethyl)-5-pyrrolidin-1-yl-indole-6-carboxamide (Compound-84): to a slurry of N-(2-hydroxy-4-methyl-6-quinolyl)-1-(oxazol-2-ylmethyl)-5-pyrrolidin-1-yl-indole-6-carboxamide (10 mg, 0.021 mmol, 1 eq) in EtOH (1 mL) was added PtO$_2$ (2 mg). The mixture was stirred under an atmosphere of hydrogen for 48 h. Filtered through celite and evaporated to yield N-(2-hydroxy-4-methyl-6-quinolyl)-1-(oxazolidin-2-ylmethyl)-5-pyrrolidin-1-yl-indole-6-carboxamide (Compound-84) (5 mg, 50%) as a solid. LCMS: (M+H)=472, UV=64%.

Synthesis of Compound-85

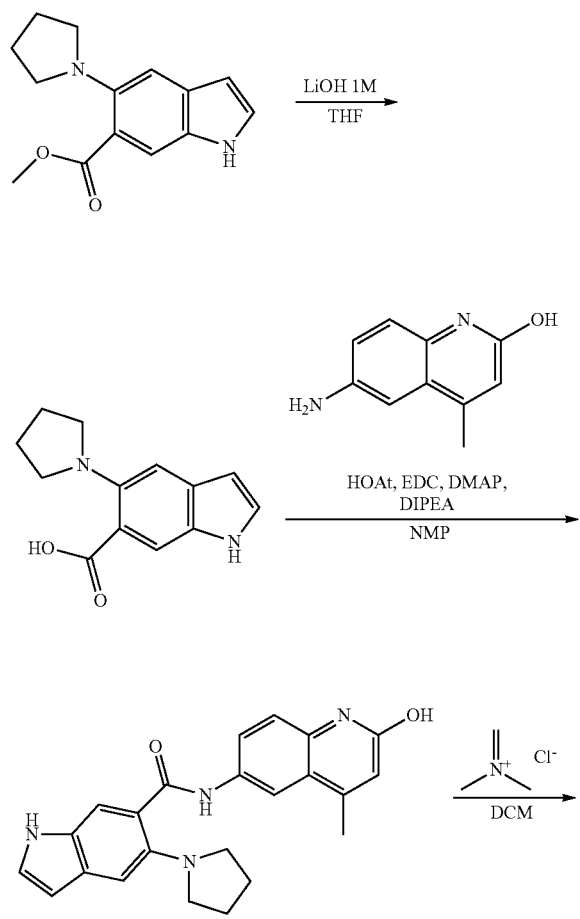

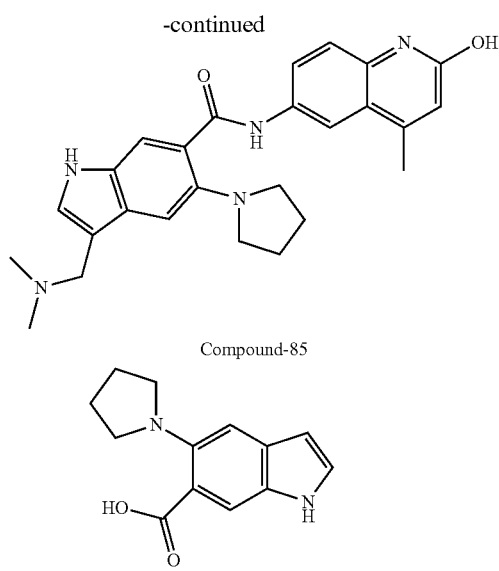

Compound-85

Preparation of 5-pyrrolidin-1-yl-1H-indole-6-carboxylic acid: a solution of methyl 5-pyrrolidin-1-yl-1H-indole-6-carboxylate in THF (1 mL) was added 1M LiOH (0.75 mL) and heated at 100° C. for 6 h. The mixture was poured into water and unreacted starting material was removed by extraction with EtOAc. The water phase was evaporated under reduced pressure yielding 5-pyrrolidin-1-yl-1H-indole-6-carboxylic acid. The crude product was used without purification in the next step. LCMS: (M+H)=231

Preparation of N-(2-hydroxy-4-methyl-6-quinolyl)-5-pyrrolidin-1-yl-1H-indole-6-carboxamide: to a mixture of 5-pyrrolidin-1-yl-1H-indole-6-carboxylic acid (crude product) (0.21 mmol, 1 eq) in NMP (0.5 mL) were added 6-amino-4-methyl-quinolin-2-ol (52 mg, 0.32 mmol, 1.5 eq), HOAt (41 mg, 0.32 mmol, 1.5 eq), EDC (58 mg, 0.32 mmol, 1.5 eq), DMAP (5 mg, 0.04 mmol, 0.2 eq) and DIPEA (104 μL, 0.63 mmol, 3 eq). The reaction mixture was heated at 60° for 4 h, poured into water and extracted with EtOAc. The combined organic phases were dried over Na2SO4, filtered and evaporated to dryness. The crude product was purified by flash chromatography (Eluent: DCM/MeOH 10%/NH$_3$-aq 1%) yielding N-(2-hydroxy-4-methyl-6-quinolyl)-5-pyrrolidin-1-yl-1H-indole-6-carboxamide (6.2 mg, 7%, over two steps). LCMS: (M+H)=387, UV=98%.

$^1$H-NMR (300 MHz, DMSO-d$_6$): δ$_H$ 12.78 (1H, s), 11.58 (1H, s), 11.31 (1H, s), 8.17 (1H, d, J=2 Hz), 8.06 (1H, s), 7.75 (1H, dd, J=9, 2 Hz), 7.53 (1H, s), 7.50 (1H, t, J=3 Hz), 7.31 (1H, d, J=9 Hz), 6.43 (2H, s), 3.23-3.07 (4H, m), 2.43 (3H, s), 2.10-1.87 (4H, m).

Compound-85

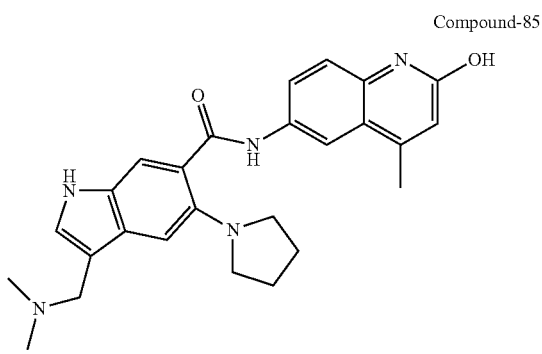 [SMILES: Cc1cc(O)nc2ccc(NC(=O)c3cc4[nH]cc(CN(C)C)c4cc3N3CCCC3)cc12]

Preparation of 3-(dimethylaminomethyl)-N-(2-hydroxy-4-methyl-6-quinolyl)-5-pyrrolidin-1-yl-1H-indole-6-carboxamide (Compound-85): the crude product of (N-(2-hydroxy-4-methyl-6-quinolyl)-5-pyrrolidin-1-yl-1H-indole-6-carboxamide) in dioxane (1 mL) was added dimethyl (methylene)ammonium chloride (13.5 mg, 0.132 mmol, 3.3 eq) and the reaction mixture was heated at 75° C. for 10 h. Water was added and the mixture made slightly basic by adding 4 M NaOH. Precipitated compound was filtered off and washed with MeOH yielding 3-(dimethylaminomethyl)-N-(2-hydroxy-4-methyl-6-quinolyl)-5-pyrrolidin-1-yl-1H-indole-6-carboxamide (Compound-85)(4.2 mg, 22%). LCMS: (M+H)=444, UV=80%.

$^1$H-NMR (300 MHz, DMSO-d$_6$): δ$_H$ 12.76 (1H, s), 11.58 (1H, s), 11.15 (1H, s), 8.17 (1H, d, J=2 Hz), 8.02 (1H, s), 7.74 (1H, dd, J=9, 2 Hz), 7.54 (1H, s), 7.37 (1H, d, J=2 Hz), 7.31 (1H, d, J=9 Hz), 6.43 (1H, s), 3.53 (2H, s), 3.20-3.09 (4H, m), 2.42 (3H, s), 2.15 (6H, s), 2.08-1.96 (4H, m).

Synthesis of Compound-86

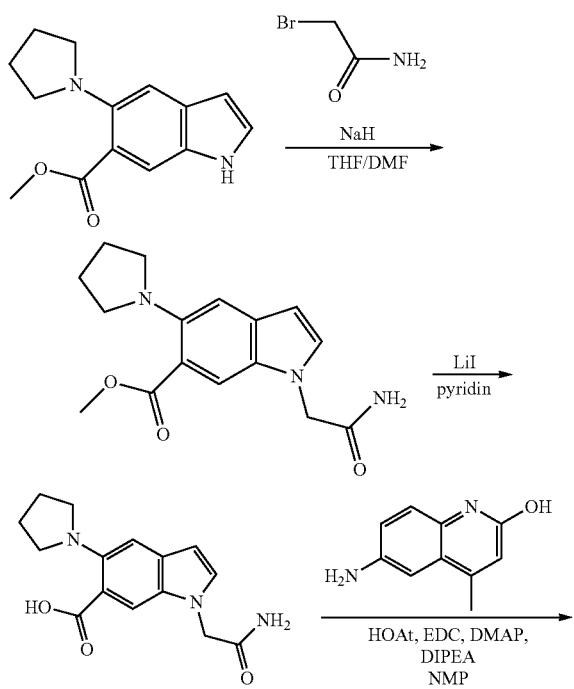

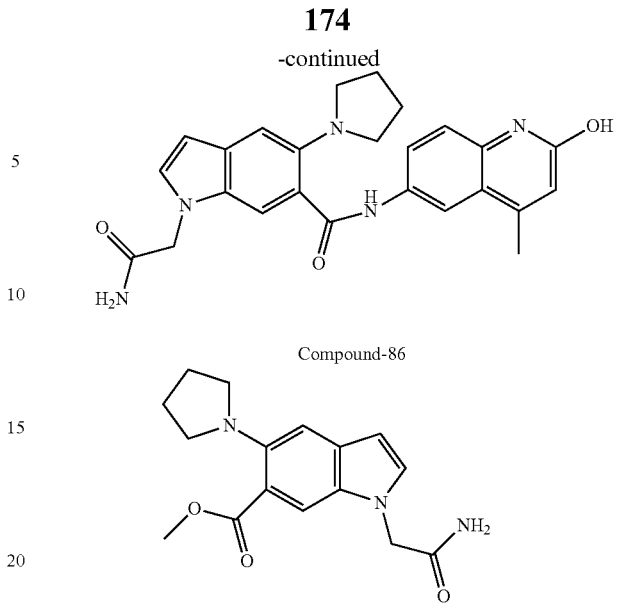

Preparation of methyl 1-(2-amino-2-oxo-ethyl)-5-pyrrolidin-1-yl-indole-6-carboxylate: a solution of methyl 5-pyrrolidin-1-yl-1H-indole-6-carboxylate (300 mg, 1.22 mmol, 1 eq) in DMF (4 mL) was added sodium hydride (60%) (245 mg, 6.1 mmol, 5 eq) in small portions. After 50 min of stirring at room temperature 2-bromoacetamide was added and the reaction mixture stirred for 2 h. Quenched with water and extracted with EtOAc, dried over Na$_2$SO$_4$, filtered and evaporated under reduced pressure. Purified by flash chromatography (Eluent: DCM/MeOH 10%/NH$_3$-aq 1%) yielding methyl 1-(2-amino-2-oxo-ethyl)-5-pyrrolidin-1-yl-indole-6-carboxylate (252 mg, 69%) as a yellowish solid. LCMS: (M+H)=302, UV=95%.

$^1$H NMR (300 MHz, Chloroform-d) δ 7.68 (s, 1H), 7.17 (s, 1H), 6.51 (d, J=3.1 Hz, 1H), 5.47 (s, 1H), 4.79 (s, 2H), 3.95 (s, 3H), 3.46-3.10 (m, 4H), 2.11-1.87 (m, 4H).

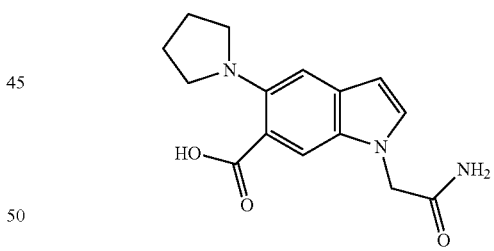

Preparation of 1-(2-amino-2-oxo-ethyl)-5-pyrrolidin-1-yl-indole-6-carboxylic acid: a mixture of methyl 1-(2-amino-2-oxo-ethyl)-5-pyrrolidin-1-yl-indole-6-carboxylate (138 mg, 0.46 mmol, 1 eq), LiI (613 mg, 4.6 mmol, 10 eq) in pyridine (2 mL) was heated in microwave oven at 150 C for 1 h. Evaporated under reduced pressure and purified by flash chromatography (Eluent: DCM/MeOH 10%/NH$_3$-aq 1%) yielding 1-(2-amino-2-oxo-ethyl)-5-pyrrolidin-1-yl-indole-6-carboxylic acid (107 mg, 81%) as a solid. LCMS: (M+H)=288, UV=95%.

$^1$H NMR (300 MHz, DMSO-d$_6$) δ 8.05 (s, 1H), 7.92 (s, 1H), 7.69 (s, 1H), 7.58 (d, J=3.1 Hz, 1H), 7.29 (s, 1H), 6.51 (dd, J=3.1, 0.9 Hz, 1H), 4.89 (s, 2H), 3.32-3.22 (m, 4H), 2.19-1.98 (m, 4H).

Compound-86

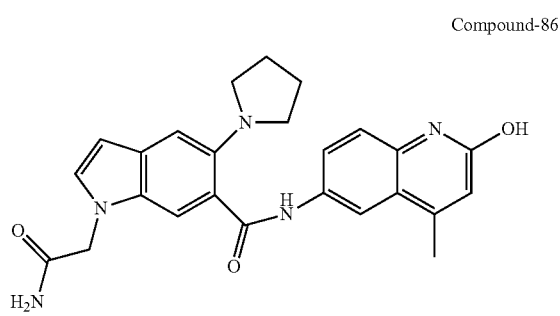 [SMILES: Cc1cc(O)nc2ccc(NC(=O)c3cc4c(ccn4CC(N)=O)cc3N3CCCC3)cc12]

Preparation of 1-(2-amino-2-oxo-ethyl)-N-(2-hydroxy-4-methyl-6-quinolyl)-5-pyrrolidin-1-yl-indole-6-carboxamide (Compound-86): to a mixture of 1-(2-amino-2-oxo-ethyl)-5-pyrrolidin-1-yl-indole-6-carboxylic acid (107 mg, 0.37 mmol, 1 eq) in NMP (2 mL) was added 6-amino-4-methyl-quinolin-2-ol (129 mg, 0.74 mmol, 2 eq), HOAt (151 mg, 1.11 mmol, 3 eq), EDC (213 mg, 1.11 mmol, 3 eq), DMAP (18 mg, 0.15 mmol, 0.4 eq) and DIPEA (321 µL, 1.85 mmol, 5 eq). The reaction mixture was heated at 80° C. for 2 h, poured into water. Precipitated product was filtered of yielding 1-(2-amino-2-oxo-ethyl)-N-(2-hydroxy-4-methyl-6-quinolyl)-5-pyrrolidin-1-yl-indole-6-carboxamide (Compound-86) (8 mg, 5%) as a brownish solid. LCMS: (M+H)=444, UV=98%.

$^1$H NMR (300 MHz, DMSO-d$_6$) δ 12.64 (s, 1H), 11.59 (s, 1H), 8.22 (d, J=2.2 Hz, 1H), 7.97 (s, 1H), 7.71 (dd, J=8.8, 2.2 Hz, 1H), 7.67-7.60 (m, 1H), 7.51 (s, 1H), 7.46 (d, J=3.1 Hz, 1H), 7.31 (d, J=8.8 Hz, 1H), 7.27 (s, 1H), 6.48-6.35 (m, 2H), 4.84 (s, 2H), 3.24-3.04 (m, 4H), 2.45-2.36 (m, 3H), 2.08-1.87 (m, 4H), 1.35 (s, 4H).

Synthesis of Compound-87

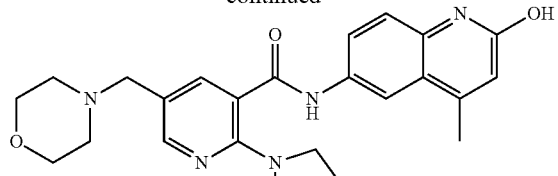

Compound-87

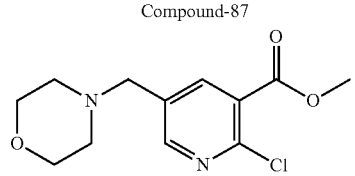

Preparation of methyl 2-chloro-5-(morpholinomethyl)pyridine-3-carboxylate: to a solution of methyl 2-chloro-5-formyl-pyridine-3-carboxylate (200 mg, 1.0 mmol, 1 eq) in DCM (4 mL) were added molecular sieves (40 mg), morpholine (87 µl, 1.0 mmol, 1 eq), acetic acid (120 µL, 2.1 mmol, 2.1 eq) and NaBH(OAc)$_3$ (423 mg, 2.0 mmol, 2.0 eq). The mixture was stirred at room temperature overnight and filtered through a pad of celite. The filtrate was washed with NaHCO$_3$, water and brine, dried over Na$_2$SO$_4$, filtrated and evaporated under reduced pressure to dryness. The crude product was purified by flash chromatography yielding methyl 2-chloro-5-(morpholinomethyl)pyridine-3-carboxylate (129 mg, 48%) as colorless oil. LCMS: (M+H)=270, UV=95%.

1H-NMR δ$_H$ (300 MHz, Chloroform-d): 8.38 (1H, d, J=2 Hz), 8.07 (1H, d, J=2 Hz), 3.90 (3H, s), 3.72-3.55 (4H, m), 3.46 (2H, s), 2.49-2.25 (4H, m).

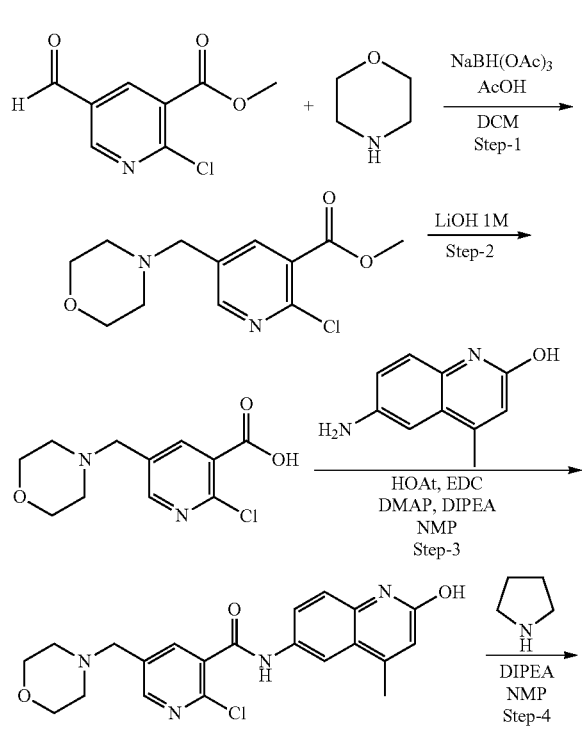

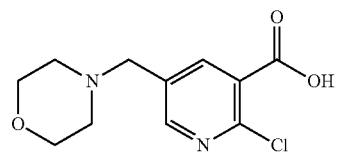 [SMILES: O=C(O)c1cc(CN2CCOCC2)cnc1Cl]

Preparation of 2-chloro-5-(morpholinomethyl)pyridine-3-carboxylic acid: a mixture of methyl 2-chloro-5-(morpholinomethyl)pyridine-3-carboxylate (129 mg, 0.48 mmol, 1 eq) in 1 M LiOH (2 mL, 2 mmol, 4 eq) was stirred at 80° C. for 1 h. Evaporated under reduced pressure, slurred in toluene and evaporated to dryness. The crude product was used without purification in the next step. LCMS: (M+H)=257, UV=95%.

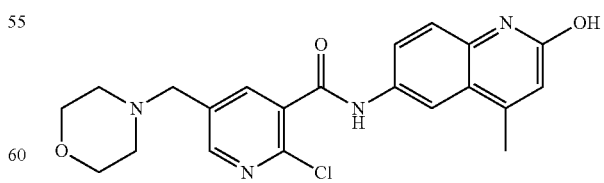

Preparation of 2-chloro-N-(2-hydroxy-4-methyl-6-quinolyl)-5-(morpholinomethyl)pyridine-3-carboxamide: to a solution of 2-chloro-5-(morpholinomethyl)pyridine-3-carboxylic acid (0.48 mmol, 1 eq) (crude product containing LiOH) in NMP (1.5 mL) were added 6-amino-4-methylquinolin-2-ol (93 mg, 0.53 mmol, 1.1 eq), (HOAt 98 mg, 0.72 mmol, 1.5 eq), EDC (138 mg, 0.72 mmol, 1.5 eq), DMAP (12 mg, 0.1 mmol, 0.2 eq) and DIPEA (251 µL, 1.44 mmol, 3 eq). The reaction mixture was stirred at 60° C. for 30 min. Water was added and the mixture extracted with ethyl acetate (8×15 mL), dried over Na$_2$SO$_4$, filtered and evaporated under reduced pressure. The crude product was purified by flash chromatography yielding 2-chloro-N-(2-hydroxy-4-methyl-6-quinolyl)-5-(morpholinomethyl)pyridine-3-carboxamide (123 mg, 62%). LCMS: (M+H)=257, UV=95% pure.

$^1$H NMR (300 MHz, DMSO-d$_6$) δ 11.63 (s, 1H), 10.74 (s, 1H), 8.46 (d, J=2.3 Hz, 1H), 8.12 (d, J=2.2 Hz, 1H), 7.98 (d, J=2.3 Hz, 1H), 7.76 (dd, J=8.8, 2.3 Hz, 1H), 7.31 (d, J=8.8 Hz, 1H), 6.44 (s, 1H), 3.68-3.48 (m, 6H), 2.45-2.31 (m, 7H).

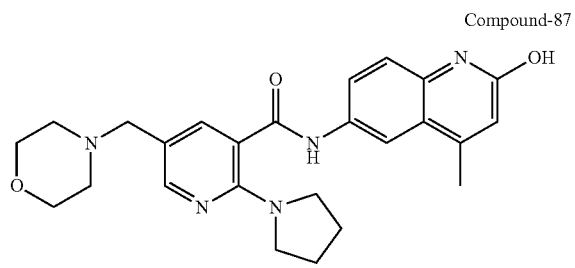 [SMILES: Cc1cc(O)nc2ccc(NC(=O)c3cc(CN4CCOCC4)cnc3N3CCCC3)cc12]

Compound-87

Preparation of N-(2-hydroxy-4-methyl-6-quinolyl)-5-(morpholinomethyl)-2-pyrrolidin-1-yl-pyridine-3-carboxamide (Compound-87): to a solution of 2-chloro-N-(2-hydroxy-4-methyl-6-quinolyl)-5-(morpholinomethyl)pyridine-3-carboxamide (50 mg, 0.12 mmol, 1 eq) in NMP (0.3 mL) were added pyrrolidine (30 µL, 0.36 mmol, 3 eq) and DIPEA (63 µL, 0.36 mmol, 3 eq). The reaction mixture was heated overnight at 95° C., poured into water, extracted with EtOAc (5×15 mL), dried over Na$_2$SO$_4$, filtered and evaporated. The crude product was purified by flash chromatography (DCM+(MeOH/NH3-aq 9/1)) to afford N-(2-hydroxy-4-methyl-6-quinolyl)-5-(morpholinomethyl)-2-pyrrolidin-1-yl-pyridine-3-carboxamide (Compound-87) (3.9 mg, 7%) as a white solid. LCMS: (M+H)=448, UV=95% pure.

$^1$H NMR (300 MHz, Methanol-d$_4$) δ 8.23 (dd, J=2.3, 1.0 Hz, 1H), 8.12 (dd, J=2.3, 1.0 Hz, 1H), 7.85 (ddd, J=8.8, 2.3, 1.1 Hz, 1H), 7.74 (dd, J=2.4, 1.1 Hz, 1H), 7.39 (dd, J=8.9, 1.0 Hz, 1H), 6.57 (t, J=1.2 Hz, 1H), 3.80-3.63 (m, 4H), 3.61-3.43 (m, 6H), 2.64-2.44 (m, 7H), 1.98-1.90 (m, 4H).

Synthesis of Compound-88

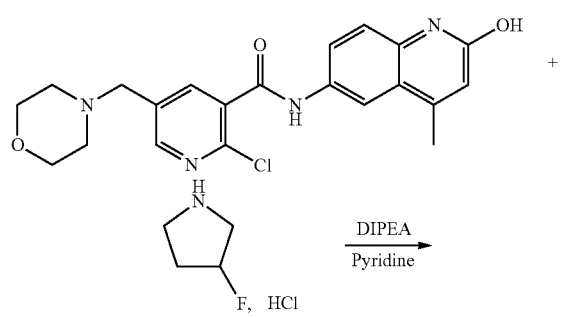

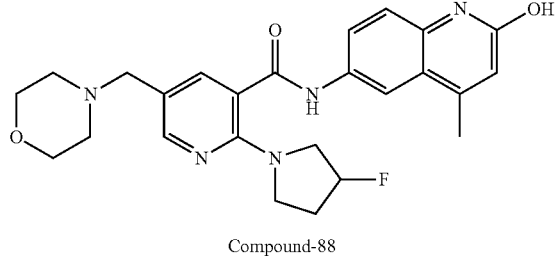

Compound-88

Preparation of 2-(3-fluoropyrrolidin-1-yl)-N-(2-hydroxy-4-methyl-6-quinolyl)-5-(morpholinomethyl)pyridine-3-carboxamide (Compound-88): to a solution of 2-chloro-N-(2-hydroxy-4-methyl-6-quinolyl)-5-(morpholinomethyl)pyridine-3-carboxamide (50 mg, 0.12 mmol, 1 eq) in pyridine (500 µL) was added 3-fluoropyrrolidine hydrochloride (45 mg, 0.36 mmol, 3 eq). The mixture was heated in a micro wave oven at 150° C. for 5 hours, evaporated to dryness, purified by flash chromatography (DCM+(MeOH/NH3-aq 9/1)) and recrystallized from MeOH yielding 2-(3-fluoropyrrolidin-1-yl)-N-(2-hydroxy-4-methyl-6-quinolyl)-5-(morpholinomethyl)pyridine-3-carboxamide (Compound-88) (7.0 mg, 12%) as an off-white solid. LCMS: (M+H)=466, UV=95%.

$^1$H NMR (300 MHz, DMSO-d$_6$) δ 11.58 (s, 1H), 10.56 (s, 1H), 8.11 (dd, J=4.1, 2.2 Hz, 2H), 7.81 (dd, J=8.9, 2.2 Hz, 1H), 7.59 (d, J=2.3 Hz, 1H), 7.29 (d, J=8.8 Hz, 1H), 6.42 (s, 1H), 5.54-5.19 (m, 1H), 3.88-3.43 (m, 7H), 3.39 (s, 2H), 2.45-2.30 (m, 7H), 2.25-1.93 (m, 2H).

Synthesis of Compound-89

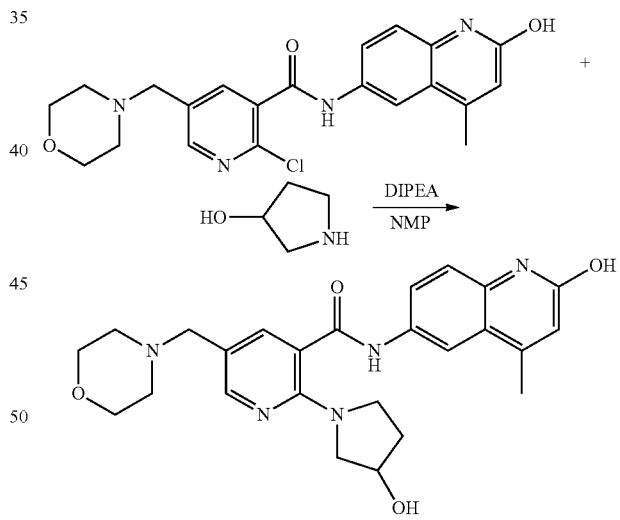

Compound-89

Preparation of N-(2-hydroxy-4-methyl-6-quinolyl)-2-(3-hydroxypyrrolidin-1-yl)-5-(morpholinomethyl)pyridine-3-carboxamide (Compound-89): to a solution of 2-chloro-N-(2-hydroxy-4-methyl-6-quinolyl)-5-(morpholinomethyl)pyridine-3-carboxamide (75 mg, 0.18 mmol, 1 eq) in NMP (1 mL) were added motpholin-3-ylmethanol (48 mg, 0.54 mmol, 3 eq) and DIPEA (94 µL, 0.54 mmol, 3 eq). Water was added to the reaction mixture which was extracted with EtOAc (5×15 mL), dried over Na$_2$SO$_4$ filtered and evaporated. The crude product was purified by flash chromatography (DCM+(MeOH/NH₃-aq 9/1)) and recrystallized from MeOH yielding N-(2-hydroxy-4-methyl-6-quinolyl)-2-(3-hydroxypyrrolidin-1-yl)-5-(morpholinomethyl)pyridine-3-carboxamide (Compound-89) (23 mg, 28%) as an off-white solid. LCMS: (M+H)=464, 98%.

¹H NMR (300 MHz, DMSO-d₆) δ 11.58 (s, 1H), 10.50 (s, 1H), 8.12 (d, J=2.2 Hz, 1H), 8.07 (d, J=2.2 Hz, 1H), 7.81 (dd, J=8.8, 2.2 Hz, 1H), 7.54 (d, J=2.2 Hz, 1H), 7.28 (d, J=8.8 Hz, 1H), 6.42 (s, 1H), 4.88 (d, J=3.3 Hz, 1H), 4.28 (s, 1H), 3.63-3.39 (m, 6H), 3.37 (s, 2H), 3.20-3.11 (m, 1H), 2.43-2.29 (m, 7H), 2.00-1.70 (m, 2H).

Synthesis of Compound-90 and Compound-91

Preparation of methyl 2-morpholino-5-(morpholinomethyl)pyridine-3-carboxylate: to a solution of methyl 2-chloro-5-formyl-pyridine-3-carboxylate (1.5 g, 7.5 mmol, 1 eq) in DCM (25 mL) were added molecular sieves (300 mg), morpholine (0.64 ml, 7.5 mmol, 1 eq), acetic acid (1 mL) and sodium triacetoxyborhydride (3.2 g, 15 mmol, 2 eq). The mixture was stirred at room temperature for three days and filtered through a pad of celite. The filtrate was washed with Saturated NaHCO₃, water and brine, dried over Na₂SO₄, filtered and evaporated. The crude product was purified by flash chromatography (DCM/MeOH/NH3-aq)

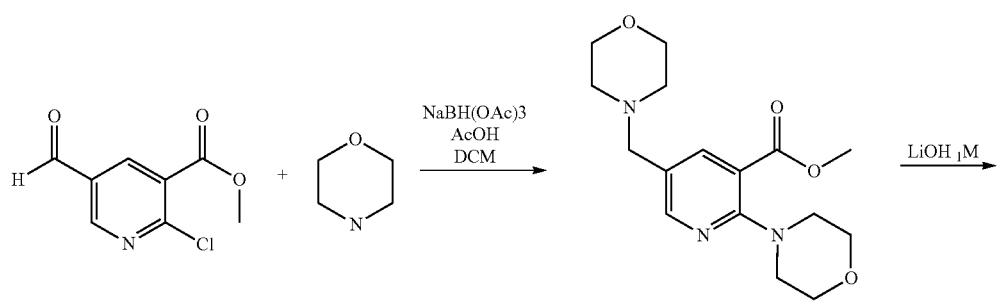

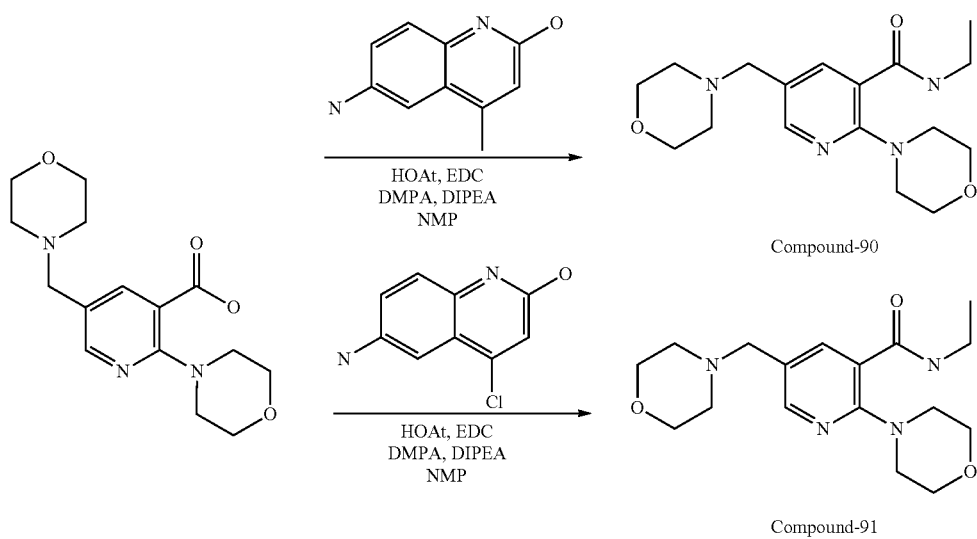

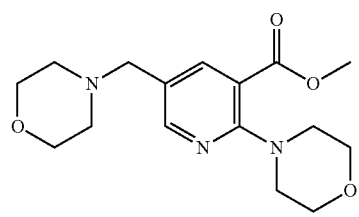

yielding methyl 2-morpholino-5-(morpholinomethyl)pyridine-3-carboxylate (0.15 mg, 7.5%). LCMS: (M+H)=322, UV=100%.

¹H NMR (300 MHz, Chloroform-d) δ 8.24 (d, J=2.3 Hz, 1H), 8.01 (s, 1H), 3.91 (s, 3H), 3.87-3.77 (m, 4H), 3.77-3.65 (m, 4H), 3.54-3.33 (m, 6H), 2.60-2.32 (m, 4H).

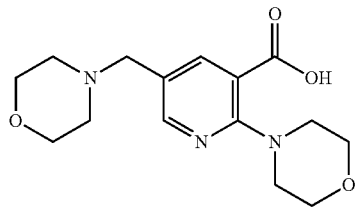 [SMILES: O=C(O)c1cc(CN2CCOCC2)cnc1N1CCOCC1]

Preparation of 2-morpholino-5-(morpholinomethyl)pyridine-3-carboxylic acid: methyl 2-morpholino-5-(morpholinomethyl)pyridine-3-carboxylate (150 mg, 0.47 mmol, 1 eq) in 1 M LiOH (2 ml, 2 mmol, 4 eq) was stirred at 80° C. for 1 h. Evaporated under reduced pressure. The crude product was slurred in toluene, evaporated to dryness. LCMS: (M+H)=308, UV=95%.

The crude product was used without purification in the synthesis of Compound-90 and Compound-91.

Compound-90

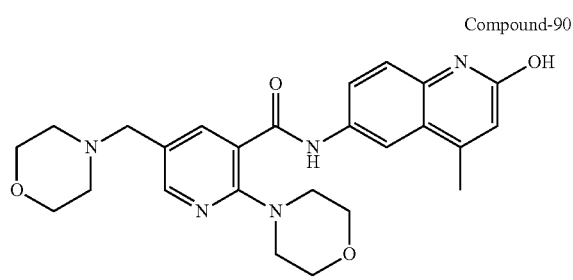 [SMILES: Cc1cc(O)nc2ccc(NC(=O)c3cc(CN4CCOCC4)cnc3N3CCOCC3)cc12]

Preparation of (N-(2-hydroxy-4-methyl-6-quinolyl)-2-morpholino-5-(morpholinomethyl)pyridine-3-carboxamide) (Compound-90): to a suspension of 2-morpholino-5-(morpholinomethyl)pyridine-3-carboxylic acid (0.47 mmol, 1.0 eq) (crude product containing LiOH) in NMP (0.5 ml) were added 6-amino-4-methyl-quinolin-2-ol (82 mg, 0.47 mmol, 1.0 eq), HOAt (71 mg, 0.71 mmol, 1.5 eq), EDC (135 mg, 0.71 mmol, 1.5 eq), DMAP (11 mg, 0.1 mmol, 0.2 eq) and DIPEA (245 µL, 1.41 mmol, 3 eq). The reaction mixture was stirred at 80° C. for 30 min. Water was added and the mixture extracted with ethyl acetate (8×15 mL), dried over Na₂SO₄, filtrated and evaporated under reduced pressure. The crude product was purified by flash chromatography (DCM+(MeOH/NH3-aq 9/1)) yielding (N-(2-hydroxy-4-methyl-6-quinolyl)-2-morpholino-5-(morpholinomethyl)pyridine-3-carboxamide) (Compound-90) (48 mg, 22%) as a purple colored solid. LCMS: (M+H)=464, UV=100%.

¹H NMR (300 MHz, DMSO-d₆) δ 11.60 (s, 1H), 10.61 (s, 1H), 8.23 (d, J=2.3 Hz, 1H), 8.19 (d, J=2.3 Hz, 1H), 7.84-7.74 (m, 2H), 7.30 (d, J=8.8 Hz, 1H), 6.43 (s, 1H), 3.65 (t, J=4.6 Hz, 4H), 3.57 (t, J=4.6 Hz, 4H), 3.45 (s, 2H), 3.26 (t, J=4.6 Hz, 4H), 2.40 (s, 3H), 2.37 (d, J=4.4 Hz, 4H).

Compound-91

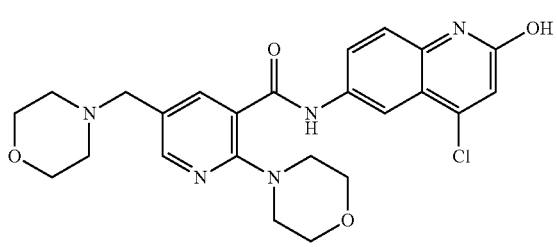

Preparation of N-(4-chloro-2-hydroxy-6-quinolyl)-2-morpholino-5-(morpholinomethyl)pyridine-3-carboxamide (Compound-91): to a suspension of 2-morpholino-5-(morpholinomethyl)pyridine-3-carboxylic acid (0.11 mmol, 1.0 eq) (crude product containing LiOH) in NMP (2 mL) were added 6-amino-4-chloro-1H-quinolin-2-one (30 mg, 0.15 mmol, 1.4 eq), HOAt (45 mg, 0.3 mmol, 3 eq), EDC (63 mg, 0.33 mmol, 3 eq), DMAP (5 mg, 0.04 mmol, 0.4 eq) and DIPEA (115 µL, 0.66 mmol, 6 eq). The reaction mixture was stirred at 80° C. for 1 h and left over night at room temperature. The reaction mixture was evaporated to dryness and purified by flash chromatography (DCM+(MeOH/NH3-aq 9/1)) yielding N-(4-chloro-2-hydroxy-6-quinolyl)-2-morpholino-5-(morpholinomethyl)pyridine-3-carboxamide (Compound-91) (3.6 mg, 6.8%) as a white solid. LCMS: (M+H)=484, UV=98%.

¹H NMR (300 MHz, DMSO-d₆) δ 12.04 (s, 1H), 10.74 (s, 1H), 8.48 (d, J=2.2 Hz, 1H), 8.23 (d, J=2.3 Hz, 1H), 7.87 (dd, J=8.9, 2.3 Hz, 1H), 7.78 (d, J=2.3 Hz, 1H), 7.39 (d, J=8.9 Hz, 1H), 6.85 (s, 1H), 3.69-3.60 (m, 4H), 3.61-3.52 (m, 4H), 3.45 (s, 2H), 3.29-3.19 (m, 4H), 2.41-2.33 (m, 4H).

Synthesis of Compound-92

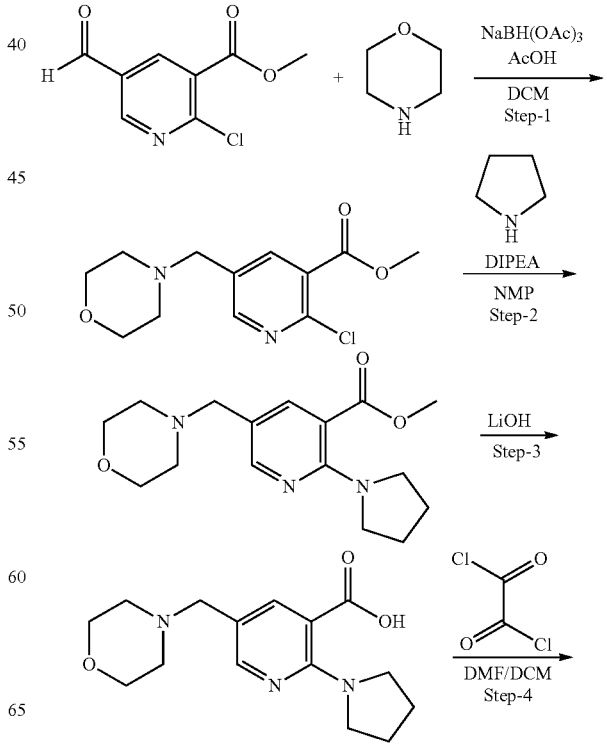

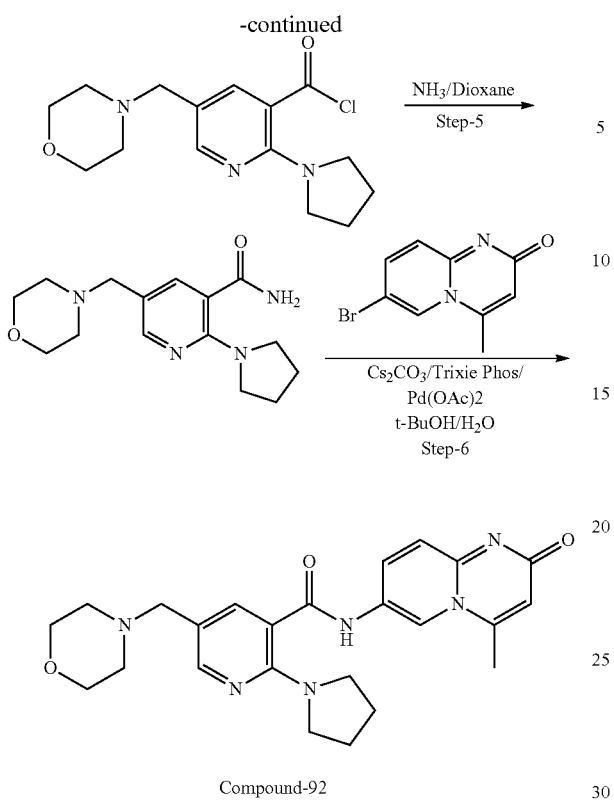

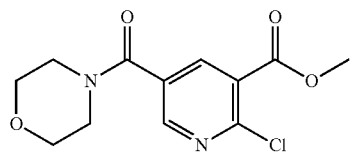 [SMILES: COC(=O)c1cc(C(=O)N2CCOCC2)cnc1Cl]

Preparation of methyl 2-chloro-5-(morpholinomethyl)pyridine-3-carboxylate

Synthesis was made according to the procedure used in step 1 in the synthesis of Compound-87. LCMS: (M+H)=271, UV=98%.

1H-NMR $\delta_H$ (300 MHz, Chloroform-d): 8.38 (1H, d, J=2 Hz), 8.07 (1H, d, J=2 Hz), 3.90 (3H, s), 3.72-3.55 (4H, m), 3.46 (2H, s), 2.49-2.25 (4H, m)

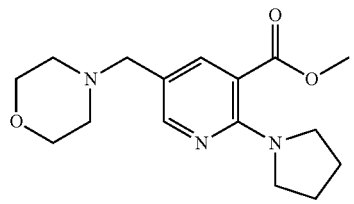 [SMILES: COC(=O)c1cc(CN2CCOCC2)cnc1N1CCCC1]

Preparation of methyl 5-(morpholinomethyl)-2-pyrrolidin-1-yl-pyridine-3-carboxylate: to a solution of methyl 2-chloro-5-(morpholinomethyl)pyridine-3-carboxylate (300 mg, 1.11 mmol, 1 eq) in NMP (1.5 mL) were added pyrrolidine (182 μL, 2.22 mmol, 2 eq) and DIPEA (579 μL, 3.33 mmol, 3 eq). The reaction mixture was heated overnight at 70° C. Water was added and the reaction mixture extracted with EtOAc, dried over Na$_2$SO$_4$, filtered and evaporated. The crude product was purified by flash chromatography (DCM+(MeOH/NH3-aq 9/1)) to afford methyl 5-(morpholinomethyl)-2-pyrrolidin-1-yl-pyridine-3-carboxylate (225 mg, 67%) as an yellow oil. LCMS: (M+H)=306, UV=98%.

$^1$H NMR (300 MHz, Chloroform-d) δ 8.17 (d, J=2.3 Hz, 1H), 7.85 (d, J=2.4 Hz, 1H), 3.90 (s, 3H), 3.82-3.65 (m, 4H), 3.50-3.39 (m, 4H), 2.90-2.83 (m, 2H), 2.56-2.42 (m, 4H), 2.00-1.87 (m, 4H).

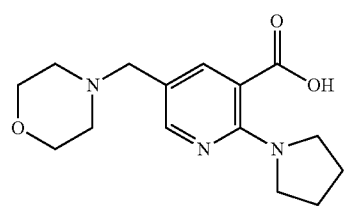 [SMILES: O=C(O)c1cc(CN2CCOCC2)cnc1N1CCCC1]

Preparation of 5-(morpholinomethyl)-2-pyrrolidin-1-yl-pyridine-3-carboxylic acid: a mixture of methyl 5-(morpholinomethyl)-2-pyrrolidin-1-yl-pyridine-3-carboxylate (225 mg, 0.74 mmol, 1 eq) in 1 M LiOH (2 mL, 2 mmol, 2.7 eq) was heated at 90° C. for 3 h. Evaporated under reduced pressure, slurred in toluene and evaporated to dryness. LCMS: (M+H)=292, UV=93%. The crude product was used without purification in the next step.

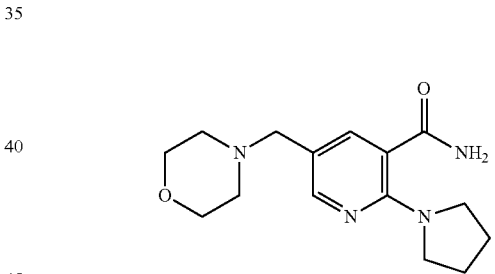

Preparation of 5-(morpholinomethyl)-2-pyrrolidin-1-yl-pyridine-3-carbonyl chloride and 5-(morpholinomethyl)-2-pyrrolidin-1-yl-pyridine-3-carboxamide: to a solution 5-(morpholinomethyl)-2-pyrrolidin-1-yl-pyridine-3-carboxylic acid (0.74 mmol, 1 eq) in DCM (2 mL) were slowly added oxalyl dichloride (375 μL, 4.44 mmol, 6 eq) and two drops of DMF. The reaction mixture was stirred at room temperature for one hour. A small sample was added MeOH and LCMS showed full conversion to the ester methyl 5-(morpholinomethyl)-2-pyrrolidin-1-yl-pyridine-3-carboxylate indicating full conversion to 5-(morpholinomethyl)-2-pyrrolidin-1-yl-pyridine-3-carbonyl chloride. Ammonia in dioxane (15 ml, 7.4 mmol, 10 eq) was added and the mixture stirred at room temperature overnight, evaporated and purified by flash chromatography (DCM+(MeOH/NH3-aq 9/1)) yielding 5-(morpholinomethyl)-2-pyrrolidin-1-yl-pyridine-3-carboxamide (88 mg, 41%). LCMS: (M+H)=291, UV=90%.

$^1$H NMR (300 MHz, Chloroform-d) δ 8.12 (d, J=2.4 Hz, 1H), 7.73 (d, J=2.4 Hz, 1H), 6.32 (s, 2H), 3.84-3.60 (m, 4H), 3.54-3.43 (m, 4H), 3.40 (s, 2H), 2.51-2.37 (m, 4H), 1.98-1.87 (m, 4H).

Compound-92

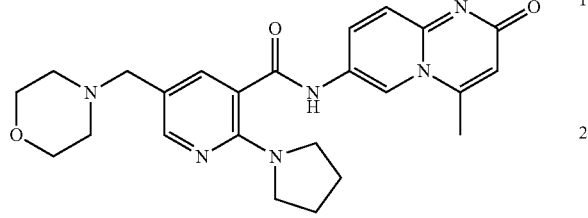

Preparation of N-(4-methyl-2-oxo-pyrido[1,2-a]pyrimidin-7-yl)-5-(morpholinomethyl)-2-pyrrolidin-1-yl-pyridine-3-carboxamide (Compound-92): a suspension of 5-(morpholinomethyl)-2-pyrrolidin-1-yl-pyridine-3-carboxamide (30 mg, 0.10 mmol, 1 eq), 7-bromo-4-methyl-pyrido[1,2-a]pyrimidin-2-one (24 mg, 0.10 mmol, 1 eq) and cesium carbonate (46 mg, 0.14 mmol, 1.4 eq) in tert butanol/water (2 mL/2 drops) was evaporated and filled with argon three times. TrixiePhos (6 mg, 0.15 eq) and Palladium(II) acetate (2 mg, 0.07 eq) were added and the reaction mixture heated at 90° C. overnight, evaporated to dryness and purified by flash chromatography (DCM+(MeOH/NH3-aq 9/1)) yielding N-(4-methyl-2-oxo-pyrido[1,2-a]pyrimidin-7-yl)-5-(morpholinomethyl)-2-pyrrolidin-1-yl-pyridine-3-carboxamide (Compound-92) (4.0 mg, 9%). LCMS: (M+H)=449, UV=100%.

$^1$H NMR (300 MHz, Methanol-d$_4$) δ 9.80 (s, 1H), 8.23-8.03 (m, 2H), 7.78 (s, 1H), 7.68 (d, J=9.6 Hz, 1H), 6.38 (s, 1H), 3.80-3.63 (m, 4H), 3.54-3.42 (m, 6H), 2.56-2.38 (m, 7H), 2.02-1.84 (m, 4H).

Synthesis of Compound-93

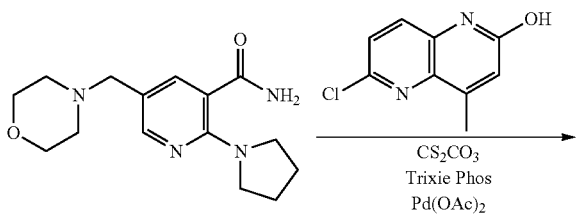

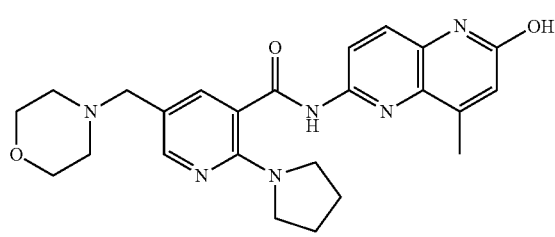

Compound-93

Preparation of N-(8-methyl-6-oxo-5H-1,5-naphthyridin-2-yl)-5-(morpholinomethyl)-2-pyrrolidin-1-yl-pyridine-3-carboxamide (Compound-93): 5-(morpholinomethyl)-2-pyrrolidin-1-yl-pyridine-3-carboxamide (58 mg, 0.16 mmol, 1 eq), 6-chloro-4-methyl-1H-1,5-naphthyridin-2-one (24 mg, 0.19 mmol, 1 eq) and Cs$_2$CO$_3$ (73 mg, 0.22 mmol, 1.4 eq) were suspended in t-BuOH/water (2 mL/2 drops). The reaction was heated at 90° C. for two days, water was added and the mixture extracted with EtOAc, dried over Na$_2$SO$_4$, filtered and evaporated to dryness. The crude product was purified by flash chromatography yielding N-(8-methyl-6-oxo-5H-1,5-naphthyridin-2-yl)-5-(morpholinomethyl)-2-pyrrolidin-1-yl-pyridine-3-carboxamide (Compound-93) (4.6 mg, 6.4%) as an off-white solid. LCMS: (M+H)=449, UV=95%.

$^1$H NMR (300 MHz, DMSO-d$_6$) δ 11.69 (s, 1H), 10.94 (s, 1H), 8.26 (s, 1H), 8.06 (s, 1H), 7.71 (d, J=9.0 Hz, 1H), 7.55 (s, 1H), 6.62 (s, 1H), 3.75-3.00 (m, 13H), 2.46-2.16 (m, 4H), 1.94-1.73 (m, 4H).

Synthesis of Compound-94

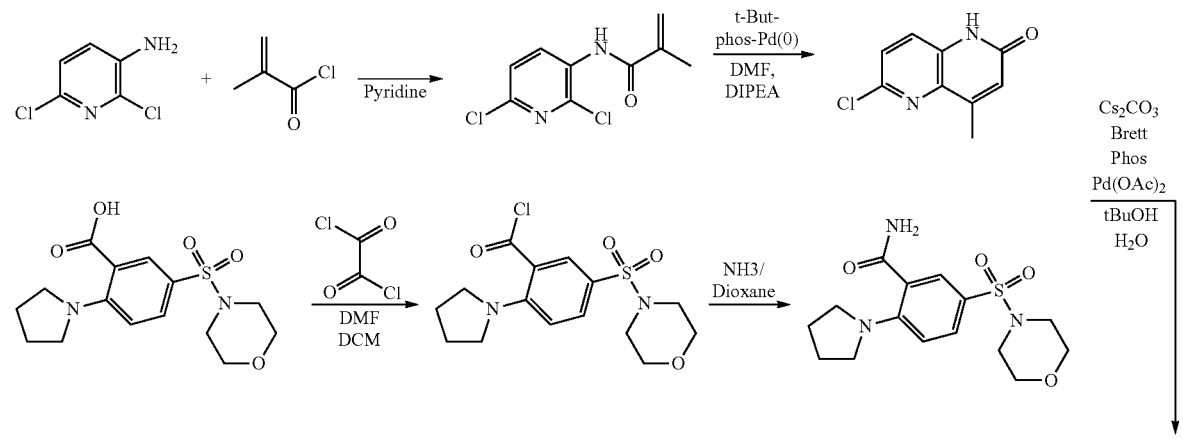

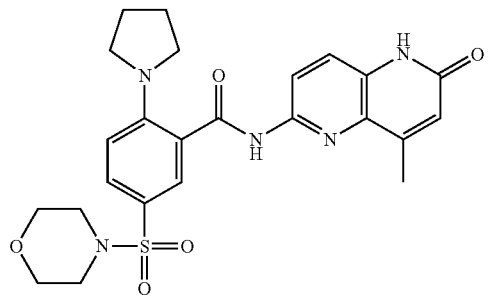

Compound-94

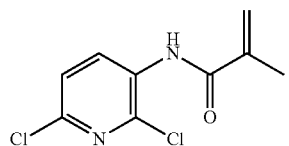

Preparation of N-(2,6-dichloro-3-pyridyl)-2-methyl-prop-2-enamide: 2,6-dichloropyridin-3-amine (1 g 6.1 mmol, 1 eq) was dissolved in pyridine (5 mL) and cooled at 0° on an is bath. 2-methylprop-2-enoyl chloride (610 μL, 6.1 mmol, 1 eq) was added and the reaction mixture stirred for 2 h. Another portion of 2-methylprop-2-enoyl chloride (400 μL, 4.0 mmol, 0.74 eq) was added and the reaction mixture stirred for 30 min. Water was added and the reaction mixture was extracted with EtOAc, washed with water and brine, dried over Na$_2$SO$_4$ filtered and evaporated to dryness. The crude product as purified by flash chromatography (Heptan/EtOAc 1/1) yielding N-(2,6-dichloro-3-pyridyl)-2-methyl-prop-2-enamide (633 mg, 45%). LCMS: (M+H)=231, UV=100%.

$^1$H NMR (300 MHz, Chloroform-d) δ 8.83 (d, J=8.5 Hz, 1H), 8.07 (s, 1H), 7.33 (dd, J=8.6, 0.6 Hz, 1H), 5.95 (d, J=1.0 Hz, 1H), 5.62 (q, J=1.6 Hz, 1H), 2.12 (dd, J=1.6, 0.9 Hz, 3H).

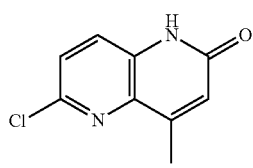

Preparation of 6-chloro-4-methyl-1H-1,5-naphthyridin-2-one: N-(2,6-dichloro-3-pyridyl)-2-methyl-prop-2-enamide (633 mg, 2.74 mmol, 1 eq) and DIPEA (0.95 mL, 5.48 mmol, 2 eq) were dissolved in DMF (6 mL). tBut-Phos-Pd (0) (3×60 mg, 0.36 mmol, 0.13 eq) was divided into three portions and added every 2 h. The flask was wrapped in tinfoil and heated for eight hours at 110° C. and poured into water (100 mL). The precipitated crude product was collected by filtration and purified by flash chromatography (DCM/MeOH/NH3-aq) yielding 6-chloro-4-methyl-1H-1,5-naphthyridin-2-one (129 mg, 24%) as a solid. LCMS: (M+H)=195, UV=90%

$^1$H NMR (300 MHz, DMSO-d$_6$) δ 11.87 (s, 1H), 7.70 (d, J=8.7 Hz, 1H), 7.61 (d, J=8.6 Hz, 1H), 6.70 (d, J=1.4 Hz, 1H), 2.41 (d, J=1.3 Hz, 3H).

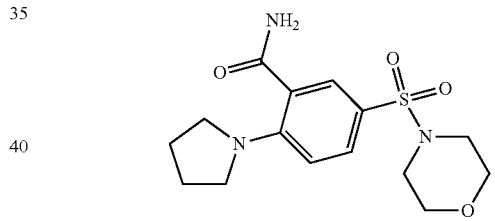

Preparation of 5-morpholinosulfonyl-2-pyrrolidin-1-yl-benzoyl chloride and 5-morpholinosulfonyl-2-pyrrolidin-1-yl-benzamide: to a solution of 5-morpholinosulfonyl-2-pyrrolidin-1-yl-benzoic acid (100 mg, 0.294 mmol, 1 eq) in DCM (1 ml) were added oxalyl dichloride (62 μl, 0.735 mmol, 2.5 eq) and two drops of DMF. The reaction mixture was stirred at room temperature for one hour. When all of the starting material had been converted to 5-morpholinosulfonyl-2-pyrrolidin-1-yl-benzoyl chloride, ammonia in dioxane (5 mL, 2.5 mmol, 8.5 eq) was added and the mixture stirred at room temperature overnight. Water was added and the reaction mixture extracted with EtOAc, dried over Na$_2$SO$_4$, filtered and evaporated. The crude product was purified by flash chromatography to yield 5-morpholinosulfonyl-2-pyrrolidin-1-yl-benzamide (50 mg, 50%) as a white solid. LCMS: (M+H)=340, UV=95%.

$^1$H NMR (300 MHz, DMSO-d$_6$) δ 7.94 (s, 1H), 7.48 (dd, J=8.9, 2.3 Hz, 1H), 7.43 (d, J=2.4 Hz, 2H), 6.81 (d, J=8.9 Hz, 1H), 3.69-3.58 (m, 4H), 3.39-3.27 (m, 4H), 2.87-2.77 (m, 4H), 2.02-1.77 (m, 4H).

Compound-94

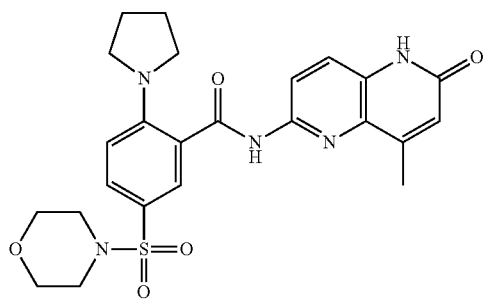

Preparation of N-(8-methyl-6-oxo-5H-1,5-naphthyridin-2-yl)-5-morpholino sulfonyl-2-pyrrolidin-1-yl-benzamide (Compound-94): a suspension of 5-morpholinosulfonyl-2-pyrrolidin-1-yl-benzamide (62 mg, 0.183 mmol, 1 eq), 6-chloro-4-methyl-1H-1,5-naphthyridin-2-one (36 mg, 0.183 mmol, 1 eq) and cesium carbonate (59 mg, 0.256 mmol, 1.4 eq) in tert butanol/water (2 mL/2 drops) was evaporated and filled with argon. Brett Phos (15 mg, 0.15 eq) and Palladium(II) acetate (3 mg, 0.07 eq) were added and the reaction mixture heated at 95° C. for three days, evaporated to dryness and purified by flash chromatography (DCM/MeOH/NH3-aq) to yield N-(8-methyl-6-oxo-5H-1,5-naphthyridin-2-yl)-5-morpholinosulfonyl-2-pyrrolidin-1-yl-benzamide (Compound-94) (4.5 mg, 5%) as a yellowish solid. LCMS: (M+H)=498, UV=80%.

$^1$H NMR (300 MHz, Chloroform-d) δ 12.27 (s, 1H), 8.95 (s, 1H), 8.58 (d, J=8.9 Hz, 1H), 7.96 (d, J=2.2 Hz, 1H), 7.83 (d, J=9.0 Hz, 1H), 7.69 (dd, 1H), 6.91 (d, J=9.0 Hz, 1H), 6.82 (s, 1H), 3.83-3.71 (m, 4H), 3.49-3.36 (m, 4H), 3.11-2.95 (m, 4H), 2.57 (s, 3H), 2.09-1.96 (m, 4H).

Synthesis of Compound-95

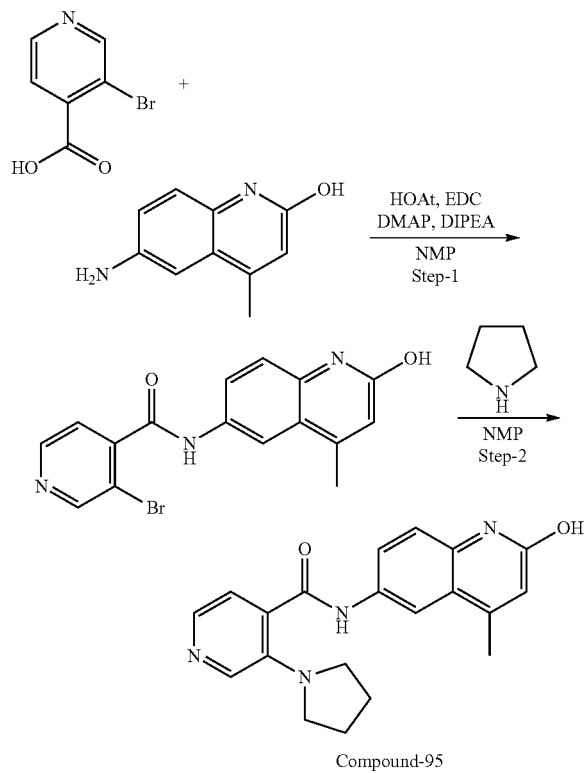

Compound-95

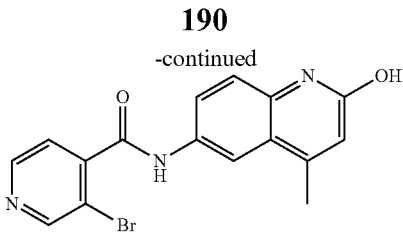

Preparation of 3-bromo-N-(2-hydroxy-4-methyl-6-quinolyl)pyridine-4-carboxamide: to a solution of 3-bromopyridine-4-carboxylic acid (150 mg, 0.74 mmol, 1 eq) in NMP (2 mL) were added 6-amino-4-methyl-quinolin-2-ol (128 mg, 0.74, 1.0 eq), HOAt (151 mg, 1.11 mmol, 1.5 eq), EDC (213 mg, 1.11 mmol, 1.5 eq), DMAP (18 mg, 0.15 mmol, 0.2 eq) and DIPEA (386 µL, 2.22 mmol, 3 eq). The mixture was heated at 80° C. for 1 h. Water (75 mL) was added to the reaction mixture and the precipitated solid was filtered of, washed with water and EtOAc. The product was dried on the filter to yield 3-bromo-N-(2-hydroxy-4-methyl-6-quinolyl)pyridine-4-carboxamide (200 mg, 78%) as a grayish/pink colored solid. LCMS: (M+H)=358, UV=100% pure.

$^1$H NMR (300 MHz, DMSO-d$_6$) δ 11.63 (s, 1H), 10.77 (s, 1H), 8.88 (s, 1H), 8.69 (d, J=4.8 Hz, 1H), 8.12 (d, J=2.2 Hz, 1H), 7.76 (dd, J=8.8, 2.3 Hz, 1H), 7.64 (d, 1H), 7.31 (d, J=8.8 Hz, 1H), 6.44 (s, 1H), 2.40 (d, J=1.2 Hz, 3H).

Compound-95

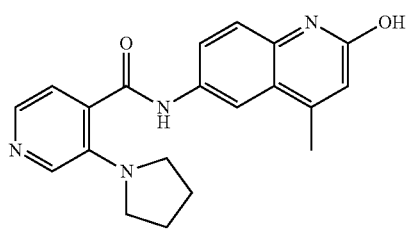

Preparation of N-(2-hydroxy-4-methyl-6-quinolyl)-3-pyrrolidin-1-yl-pyridine-4-carboxamide (Compound-95): a solution of 3-bromo-N-(2-hydroxy-4-methyl-6-quinolyl)pyridine-4-carboxamide (100 mg, 0.28 mmol, 1 eq) in NMP (1 mL) were added pyrrolidine (100 µL, 1.4 mmol, 5 eq) and DIPEA (146 µL, 0.84 mmol, 3 eq). The reaction mixture was heated at 150° C. in a microwave oven for 1 h. The reaction mixture was poured into water and the precipitated solid was filtered off and purified by flash chromatography to yield N-(2-hydroxy-4-methyl-6-quinolyl)-3-pyrrolidin-1-yl-pyridine-4-carboxamide (Compound-95) (19 mg, 20%). LCMS: (M+H)=349, UV=97%.

$^1$H NMR (300 MHz, DMSO-d$_6$) δ 11.57 (s, 1H), 10.56 (s, 1H), 8.27-8.03 (m, 2H), 7.93 (d, J=4.7 Hz, 1H), 7.79 (dd, J=8.8, 2.3 Hz, 1H), 7.29 (d, J=8.5 Hz, 1H), 7.22 (d, J=4.7 Hz, 1H), 6.42 (s, 1H), 3.30-3.26 (m, 4H), 2.39 (d, J=1.6 Hz, 3H), 1.95-1.72 (m, 4H).

Synthesis of Compound-96

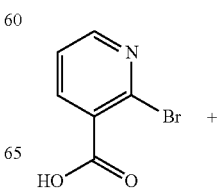

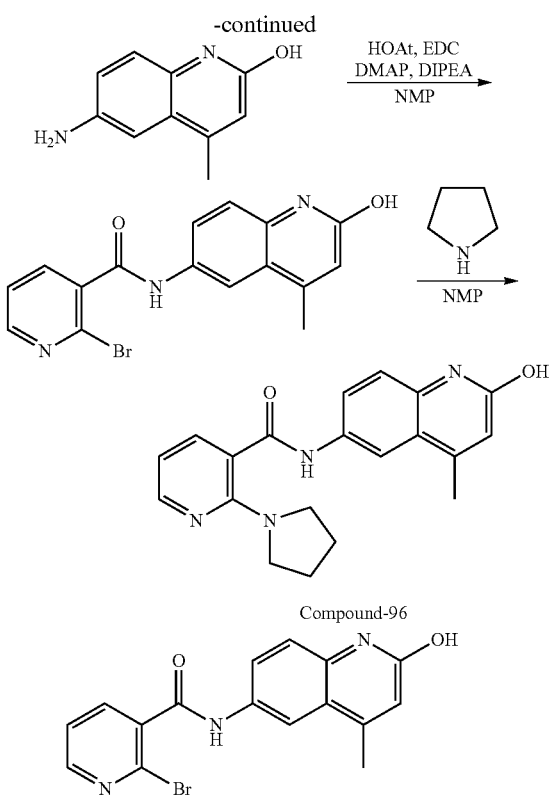

Compound-96

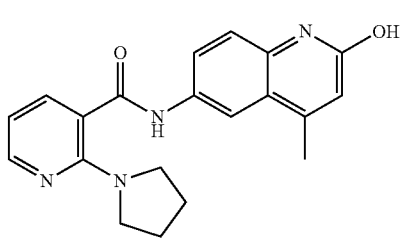

Preparation of 2-bromo-N-(2-hydroxy-4-methyl-6-quinolyl)pyridine-3-carboxamide: to a solution of 2-bromopyridine-3-carboxylic acid (125 mg, 0.62 mmol, 1 eq) in NMP (1 mL) were added 6-amino-4-methyl-quinolin-2-ol (113 mg, 0.93 mmol, 1.1 eq), HOAt (127 mg, 0.93 mmol, 1.5 eq), EDC (179 mg, 0.93 mmol, 1.5 eq), DMAP (15 mg, 0.12 mmol, 0.2 eq) and DIPEA (323 μL, 1.86 mmol, 3 eq). The mixture was stirred at room temperature for 4 days. Water was added and the reaction mixture was extracted with EtOAc, dried over $Na_2SO_4$, filtered and evaporated to dryness. The crude product was purified by flash chromatography yielding 2-bromo-N-(2-hydroxy-4-methyl-6-quinolyl)pyridine-3-carboxamide (148 mg, 67%). LCMS: (M+H)=359, UV=95%.

$^1$H NMR (300 MHz, DMSO-$d_6$) δ 11.61 (s, 1H), 10.72 (s, 1H), 8.51 (dd, J=4.8, 2.0 Hz, 1H), 8.13 (d, J=2.3 Hz, 1H), 8.02 (dd, J=7.5, 2.0 Hz, 1H), 7.77 (dd, J=8.9, 2.3 Hz, 1H), 7.59 (dd, J=7.5, 4.8 Hz, 1H), 7.31 (d, J=8.9 Hz, 1H), 6.44 (d, J=1.4 Hz, 1H), 2.40 (d, J=1.2 Hz, 3H).

Preparation of N-(2-hydroxy-4-methyl-6-quinolyl)-2-pyrrolidin-1-yl-pyridine-3-carboxamide (Compound-96): a solution of 2-bromo-N-(2-hydroxy-4-methyl-6-quinolyl) pyridine-3-carboxamide (100 mg, 0.28 mmol, 1 eq) in NMP (1 mL) were added pyrrolidine (100 μL, 1.4 mmol, 5 eq) and DIPEA (146 μL, 0.84 mmol, 3 eq). The reaction mixture was heated at 150° C. in a microwave oven for 1 h and poured into water. The precipitated solid was filtered off and dried yielding N-(2-hydroxy-4-methyl-6-quinolyl)-2-pyrrolidin-1-yl-pyridine-3-carboxamide (Compound-96) (90 mg, 98%). LCMS: (M+H)=349, UV=100%.

$^1$H NMR (300 MHz, DMSO-$d_6$) δ 11.55 (s, 1H), 10.44 (s, 1H), 8.18 (dd, J=4.8, 1.9 Hz, 1H), 8.12 (d, J=2.2 Hz, 1H), 7.80 (dd, J=8.8, 2.2 Hz, 1H), 7.64 (dd, J=7.4, 1.9 Hz, 1H), 7.28 (d, J=8.8 Hz, 1H), 6.66 (dd, J=7.4, 4.8 Hz, 1H), 6.42 (d, J=1.4 Hz, 1H), 3.47-3.37 (m, 4H), 2.39 (s, 3H), 1.88-1.79 (m, 4H).

Synthesis of and Compound-97

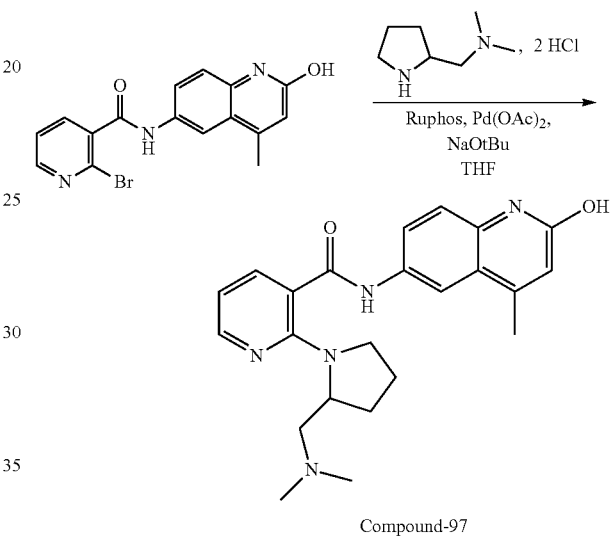

Compound-97

Preparation of 2-[2-(dimethylaminomethyl)pyrrolidin-1-yl]-N-(2-hydroxy-4-methyl-6-quinolyl)pyridine-3-carboxamide (Compound-97): a mixture of 2-bromo-N-(2-hydroxy-4-methyl-6-quinolyl)pyridine-3-carboxamide (36 mg, 0.1 mmol, 1 eq), N,N-dimethyl-1-pyrrolidin-2-yl-methanamine di hydrochloride (24 mg, 0.12 mmol, 1.2 eq) and NaOtBu (35 mg, 0.36 mmol, 3.6 eq) in THF (1 mL) was evacuated and filled with $N_2$. Ruphos (4 mg, 0.01 mmol, 0.1 eq) and Pd(OAc)$_2$ (2 mg, 0.01 mmol, 0.1 eq) were added and the reaction mixture was heated at reflux overnight under $N_2$. Water was added and the reaction mixture extracted with EtOAc, dried over $Na_2SO_4$, filtered and evaporated to dryness. Purified by flash chromatography (DCM+(MeOH/NH3-aq 10/1)) yielding 2-[2-(dimethylaminomethyl)pyrrolidin-1-yl]-N-(2-hydroxy-4-methyl-6-quinolyl)pyridine-3-carboxamide (Compound-97) (20 mg, 49%) as an off-white solid. LCMS: (M+H)=406, UV=96%.

$^1$H NMR (300 MHz, Chloroform-d) δ 12.42 (s, 1H), 10.62 (s, 1H), 8.33 (d, J=2.2 Hz, 1H), 8.21 (dd, J=4.7, 2.0 Hz, 1H), 8.03 (dd, J=7.5, 2.0 Hz, 1H), 7.50 (dd, J=8.8, 2.2 Hz, 1H), 7.37 (d, J=8.7 Hz, 1H), 6.85 (dd, J=7.6, 4.7 Hz, 1H), 6.53 (d, J=1.3 Hz, 1H), 5.00-4.84 (m, 1H), 3.59-3.38 (m, 1H), 3.30 (s, 3H), 3.19-2.97 (m, 1H), 2.48 (s, 2H), 2.23 (s, 6H), 2.13-2.01 (m, 1H), 1.91-1.74 (m, 2H), 1.70-1.50 (m, 1H).

Synthesis of Compound-98

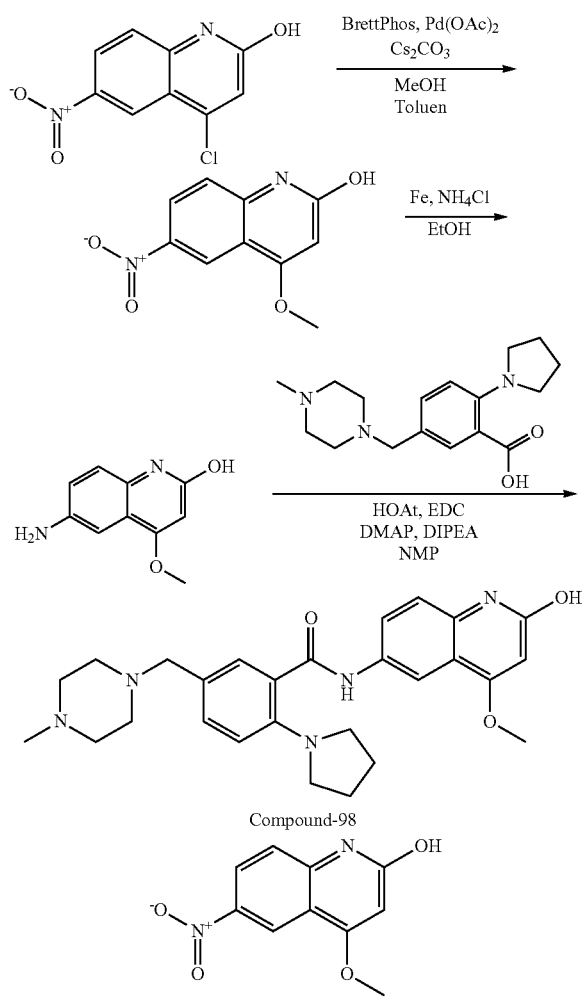

Preparation of 4-methoxy-6-nitro-quinolin-2-ol: a mixture of 4-chloro-6-nitro-quinolin-2-ol (200 mg, 0.59 mmol, 1 eq), methanol (1 mL), cesium carbonate (107 mg, 0.434 mmol, 1.5 eq) in Tolune (1 mL) was evacuated and the flask filled with $N_2$. $Pd(OAc)_2$ (8 mg, 0.04 mmol, 0.06 eq) and Brett Phos (25 mg, 0.05 mmol, 0.08 eq) were added and the mixture was stirred at 75° C. overnight under $N_2$. The reaction mixture was evaporated and purified by flash chromatography (DCM+(MeOH/NH3-aq 9/1)) yielding 4-methoxy-6-nitro-quinolin-2-ol (51 mg, 39%) as an off-white solid. LCMS: (M+H)=221, UV=95%.

$^1$H NMR (300 MHz, DMSO-$d_6$) δ 11.97 (s, 1H), 8.55 (d, J=2.5 Hz, 1H), 8.36 (dd, J=9.1, 2.6 Hz, 1H), 7.43 (d, J=9.1 Hz, 1H), 6.07 (s, 1H), 3.99 (s, 3H).

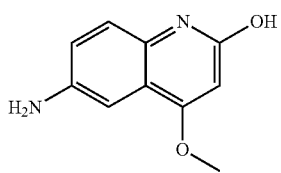

Preparation of 6-amino-4-methoxy-quinolin-2-ol: a mixture of 4-methoxy-6-nitro-quinolin-2-ol (51 mg, 0.23 mmol, 1 eq), ethanol (1.5 mL) and saturated ammonium chloride (1.5 mL) was heated at reflux. Iron powder (39 mg, 0.69 mmol, 3 eq) was added. After one hour the reaction mixture was cooled to room temperature, filtrated and evaporated. Water was added and the mixture extracted with EtOAc yielding 6-amino-4-methoxy-quinolin-2-ol (15 mg, 34%). Used without purification in the synthesis of Compound-98. LCMS: (M+H)=191.

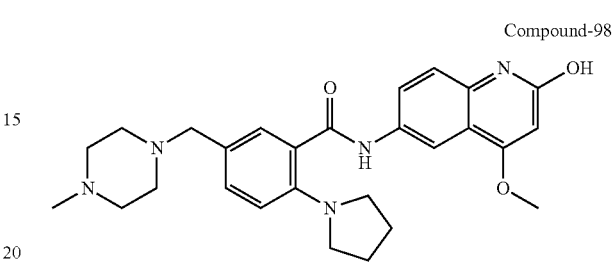

Preparation of N-(2-hydroxy-4-methoxy-6-quinolyl)-5-[(4-methylpiperazin-1-yl)methyl]-2-pyrrolidin-1-yl-benzamide (Compound-98): to a mixture of 5-[(4-methylpiperazin-1-yl)methyl]-2-pyrrolidin-1-yl-benzoic acid (24 mg, 0.079 mmol, 1 eq) and 6-amino-4-methoxy-quinolin-2-ol (15 mg, 0.079 mmol, 1 eq) in NMP (1 ML) were added HOAt (1 mg, 0.119 mmol, 1.5 eq), EDC (23 mg, 0.119 mmol, 1.5 eq), DMAP (2 mg, 0.016 mmol, 0.2 eq) and DIPEA (41 µL, 0.24 mmol, 3 eq). The reaction mixture was stirred overnight at 60° C. Water was added and the mixture extracted with EtOAc. The combined extracts were washed with water and brine, dried over $Na_2SO_4$, filtered and evaporated to dryness. The crude product was purified by flash chromatography (DCM+(MeOH/NH3-aq 9/1) yielding N-(2-hydroxy-4-methoxy-6-quinolyl)-5-[(4-methylpiperazin-1-yl)methyl]-2-pyrrolidin-1-yl-benzamide (Compound-98) (14 mg, 37%) as a brownish solid. LCMS: (M+H)=476, UV=90%.

$^1$H NMR (300 MHz, Chloroform-d) δ 11.78 (s, 1H), 11.01 (s, 1H), 8.27 (d, J=2.4 Hz, 1H), 7.91 (d, J=2.2 Hz, 1H), 7.63 (dd, J=8.8, 2.4 Hz, 1H), 7.34-7.25 (m, 2H), 7.03 (d, J=8.3 Hz, 1H), 5.95 (s, 1H), 3.92 (s, 3H), 3.51 (s, 2H), 3.23-3.11 (m, 4H), 2.58 (s, 9H), 2.35 (s, 3H), 1.96 (dd, J=6.8, 3.4 Hz, 5H).

Synthesis of Compound-99

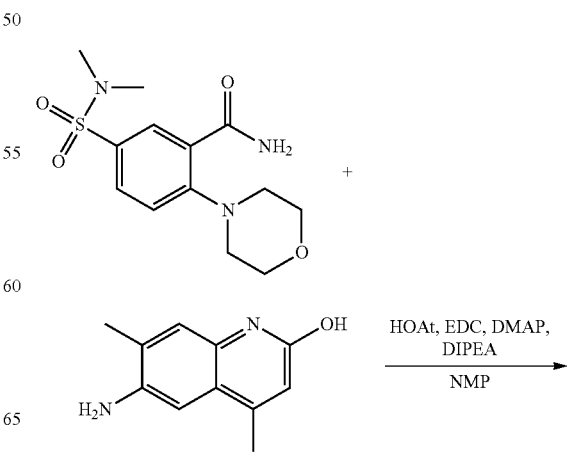

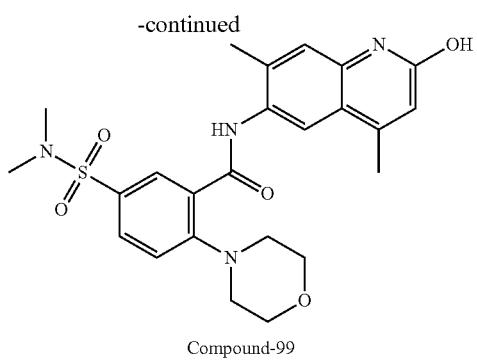

Compound-99

Preparation of 5-(dimethylsulfamoyl)-N-(2-hydroxy-4,7-dimethyl-6-quinolyl)-2-morpholino-benzamide (Compound-99): 5-(dimethylsulfamoyl)-2-morpholino-benzoic acid (100 mg, 0.32 mmol, 1 eq) and 6-amino-4,7-dimethyl-quinolin-2-ol (60 mg, 0.32 mmol, 1 eq) were suspended in NMP (1.5 ml). HOAt (65 mg, 0.48 mmol, 1.5 eq), EDC (92 mg, 0.48 mmol, 1.5 eq), DMAP (8 mg, 0.06 mmol, 0.2 eq) and DIPEA (166 µL, 0.96 mmol, 3 eq) were added and the reaction mixture heated at 80° C. for 90 min. Water (50 mL) was added and the reaction mixture stirred for 30 min at room temperature. The precipitated compound was filtered off, washed with water and EtOAc and dried on the filter yielding (5-(dimethylsulfamoyl)-N-(2-hydroxy-4,7-dimethyl-6-quinolyl)-2-morpholino-benzamide (Compound-99) (113 mg, 73%) as an off-white solid.

LCMS (DMSO): (M+H)=485, UV=100% pure.

$^1$H NMR (300 MHz, DMSO-$d_6$) δ 11.57 (s, 1H), 10.17 (s, 1H), 7.90-7.83 (m, 2H), 7.78 (dd, J=8.6, 2.4 Hz, 1H), 7.36 (d, J=8.6 Hz, 1H), 7.19 (s, 1H), 6.38 (s, 1H), 3.83-3.68 (m, 4H), 3.24-3.15 (m, 4H), 2.64 (s, 6H), 2.40 (s, 3H), 2.36 (s, 3H).

Synthesis of Compound-100

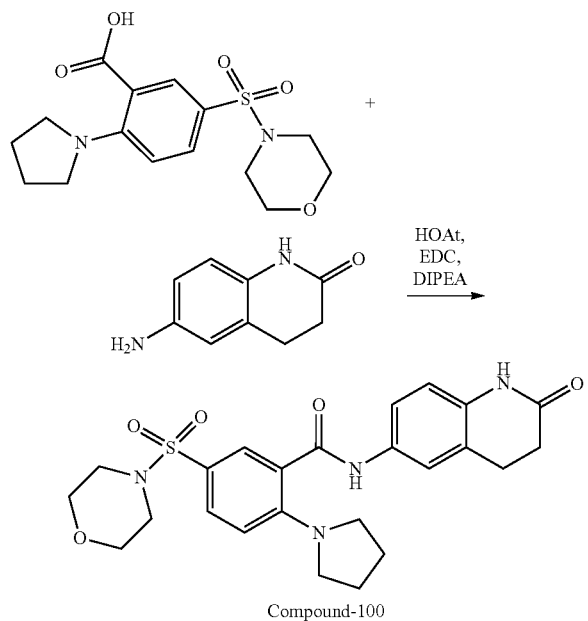

Compound-100

Preparation of 5-morpholinosulfonyl-N-(2-oxo-3,4-dihydro-1H-quinolin-6-yl)-2-pyrrolidin-1-yl-benzamide (Compound-100): to a solution of 5-morpholino sulfonyl-2-pyrrolidin-1-yl-benzoic acid (54 mg 0.16 mmol, 1 eq) in DMF (3 mL), HOAt (22 mg, 0.16 mmol, 1 eq), EDC×HCl (25 mg, 0.16 mmol, 1 eq) and DIPEA (56 µL, 0.32 mmol, 2 eq) were added, followed by addition of 6-amino-3,4-dihydro-1H-quinolin-2-one (26 mg, 0.16 mmol, 1 eq) and the reaction stirred in DMF at room temperature for 16 h. Reaction mixture was diluted with 20 mL EtOAC and 20 mL water and extracted. The organic layer was washed with water and evaporated to give 66 mg of crude product. LC-MS indicated that it mostly consisted of adduct with HOAt. Another equivalent of HOAt (22 mg, 0.16 mmol), EDC×HCl (25 mg, 0.16 mmol), DIPEA (56 µL, 0.32 mmol) and 6-amino-3,4-dihydro-1H-quinolin-2-one (26 mg, 0.16 mmol) were added and the reaction stirred at 50° C. overnight. Reaction mixture was poured into water and extracted with EtOAc (2×20 mL). Organic layer was washed with brine, dried over MgSO$_4$ and concentrated under reduced pressure. The obtained mixture was purified by flash chromatography on a silicagel column in the solvent system DCM:MeOH, 1-10% MeOH. Purest fractions were combined and solvent evaporated in vacuo to give 15 mg of pure 5-morpholinosulfonyl-N-(2-oxo-3,4-dihydro-1H-quinolin-6-yl)-2-pyrrolidin-1-yl-benzamide (Compound-100). MS: m/z (M+H)$^+$ 485; UV 96% pure.

$^1$H NMR (300 MHz, Chloroform-d) δ 7.95 (1H, s), 7.83 (1H, d, J=2.3 Hz), 7.78 (1H, s), 7.69-7.57 (2H, m), 7.36 (1H, dd, J=8.4, 2.3 Hz), 6.87 (1H, d, J=9.0 Hz), 6.77 (1H, d, J=8.4 Hz), 3.75 (4H, m), 3.52-3.38 (4H, m), 3.10-2.89 (m, 6H), 2.67 (m, 2H), 2.10-1.96 (m, 4H)

Synthesis of Compound-101

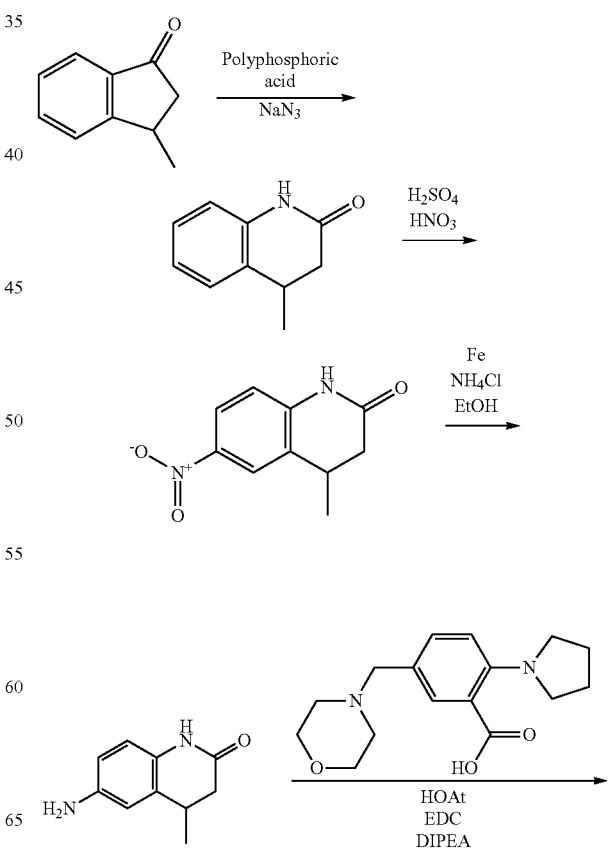

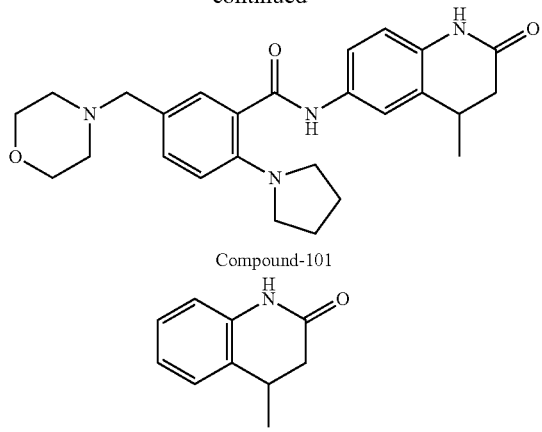

Compound-101

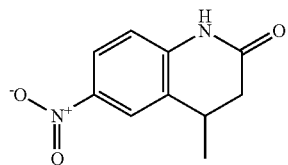

Preparation of 4-methyl-3,4-dihydro-1H-quinolin-2-one: to 2 mL of polyphosphoric acid was added 3-methylindan-1-one (500 mg, 3.42 mmol, 1 eq) and stirred with mechanical stirrer for 10 minutes. Sodium azide (234 mg, 3.59 mmol, 1.05 eq) was added in portions while stirring for 20 minutes. The mixture was heated at 50° C. while stirring overnight. Small portion of ice-cold water was added to the reaction mixture and stirred until all polyphosphoric acid dissolved. Mixture was then poured onto 20 mL of water/ice and pH made basic with 2N NaOH. Extracted with 2×20 mL EtOAC. Organic layer was washed with water and concentrated in vacuo. Crude product was purified by flash chromatography in the solvent system EtOAc-heptane, 0-35% EtOAc. Purest fractions were combined and solvent evaporated to give 313 mg of 4-methyl-3,4-dihydro-1H-quinolin-2-one as white solid (yield 57%). MS: m/z (M+H)$^+$ 162

$^1$H NMR (300 MHz, DMSO-d$_6$) δ 10.07 (s, 1H), 7.25-7.07 (m, 2H),) 6.93 (td, J=7.5, 1.3 Hz, 1H), 6.85 (dd, J=7.8, 1.2 Hz, 1H), 3.11-2.97 (m, 1H), 2.57 (dd, J=16.0, 5.9 Hz, 1H), 2.22 (dd, J=15.9, 7.1 Hz, 1H), 1.17 (d, J=6.9 Hz, 3H).

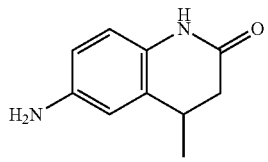

Preparation of 4-methyl-6-nitro-3,4-dihydro-1H-quinolin-2-one: 4-methyl-3,4-dihydro-1H-quinolin-2-one (310 mg, 1.92 mmol, 1 eq) was dissolved in conc. sulfuric acid (5 mL). Water (1.5 mL) was slowly added while cooling on ice. The mixture was stirred on ice for 10 min, then fuming nitric acid (160 µL, 3.84 mmol, 1.05 eq) was added and the reaction stirred on ice for 1 h. TLC (EtOAc:heptane 1:1) indicated complete conversion of starting material. Reaction mixture was diluted with water/ice (50 mL) and extracted with EtOAc (50 mL). Organic extract was washed with water and concentrated under reduced pressure to give 370 mg of 4-methyl-6-nitro-3,4-dihydro-1H-quinolin-2-one as yellow solid (yield 94%).

$^1$H NMR (300 MHz, DMSO-d$_6$) δ 10.73 (s, 1H), 8.10 (m, 2H), 7.03 (dt, J=9.1, 1.3 Hz, 1H), 3.24 (h, J=6.8 Hz, 1H), 2.69 (dd, J=16.2, 6.0 Hz, 1H), 2.34 (dd, J=16.2, 7.0 Hz, 1H), 1.23 (d, J=6.9 Hz, 3H).

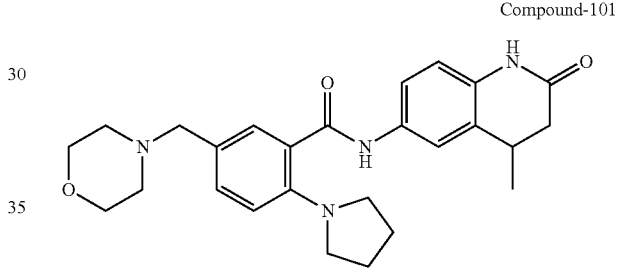

Preparation of 6-amino-4-methyl-3,4-dihydro-1H-quinolin-2-one: 4-methyl-6-nitro-3,4-dihydro-1H-quinolin-2-one (368 mg, 1.78 mmol, 1 eq) was suspended in 5 mL EtOH and 5 mL saturated NH4Cl and heated to reflux. After 30 min, iron powder (299 mg, 5.35 mmol, 3 eq) was added in portions over 10 min. After refluxing for another 2 h, reaction mixture was cooled, filtered and washed with water and DCM. The filtrate layers were separated and the organic extract washed with brine and concentrated under reduced pressure to afford 265 mg of 6-amino-4-methyl-3,4-dihydro-1H-quinolin-2-one, yield 85%.

$^1$H NMR (300 MHz, DMSO-d$_6$) δ 9.67 (s, 1H), 6.54 (d, J=8.3 Hz, 1H), 6.43 (d, J=2.4 Hz, 1H), 6.35 (dd, J=8.3, 2.4 Hz, 1H), 4.72 (s, 2H), 2.94-2.80 (m, 1H), 2.48-2.39 (m, 1H), 2.12 (dd, J=15.8, 7.2 Hz, 1H), 1.12 (d, J=6.9 Hz, 3H).

Compound-101

Preparation of N-(4-methyl-2-oxo-3,4-dihydro-1H-quinolin-6-yl)-5-(morpholinomethyl)-2-pyrrolidin-1-yl-benzamide (Compound-101): to a solution of 5-(morpholinomethyl)-2-pyrrolidin-1-yl-benzoic acid (46 mg 0.16 mmol, 1 eq) in DMF (3 mL), HOAt (22 mg, 0.16 mmol, 1 eq), EDCxHCl (25 mg, 0.16 mmol, 1 eq) and DIPEA (56 µL, 0.32 mmol, 2 eq) were added, followed by addition of 6-amino-4-methyl-3,4-dihydro-1H-quinolin-2-one (28 mg, 0.16 mmol, 1 eq) and the reaction stirred in DMF at 70° C. for 20 h. Reaction mixture was diluted with 20 mL EtOAc and 20 mL water and extracted. Organic layer was washed with water (20 mL) and concentrated under reduced pressure. Crude product was purified by flash chromatography in the solvent system DCM-MeOH, 0-10% MeOH. Purest fractions were combined and solvent evaporated under reduced pressure to give 17 mg of N-(4-methyl-2-oxo-3,4-dihydro-1H-quinolin-6-yl)-5-(morpholinomethyl)-2-pyrrolidin-1-yl-benzamide. MS: m/z (M+H)$^+$=449; 98% purity.

$^1$H NMR (300 MHz, DMSO-d$_6$) δ 10.24 (s, 1H), 10.03 (s, 1H), 7.58 (d, J=2.2 Hz, 1H), 7.48 (dd, J=8.5, 2.3 Hz, 1H), 7.24-7.14 (m, 2H), 6.80 (d, J=8.5 Hz, 1H), 6.77-6.71 (m, 1H), 3.61-3.50 (m, 4H), 3.36 (s, 2H), 3.26-3.15 (m, 4H), 3.03 (q, J=6.5 Hz, 1H), 2.57 (dd, J=15.9, 5.7 Hz, 1H), 2.41-2.29 (m, 4H), 2.22 (dd, J=15.9, 7.3 Hz, 1H), 1.92-1.76 (m, 4H), 1.18 (d, J=6.9 Hz, 3H).

Synthesis of Compound-102

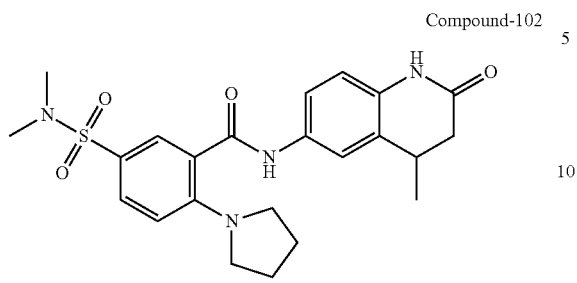
Compound-102

Preparation of 5-(dimethylsulfamoyl)-N-(4-methyl-2-oxo-3,4-dihydro-1H-quinolin-6-yl)-2-pyrrolidin-1-yl-benzamide (Compound-102): compound was prepared following the same procedure as for Compound-101 from 5-(dimethylsulfamoyl)-2-pyrrolidin-1-yl-benzoic acid (48 mg 0.16 mmol, 1 eq) and 6-amino-4-methyl-3,4-dihydro-1H-quinolin-2-one (28 mg, 0.16 mmol, 1 eq). 28 mg of 5-(dimethylsulfamoyl)-N-(4-methyl-2-oxo-3,4-dihydro-1H-quinolin-6-yl)-2-pyrrolidin-1-yl-benzamide (Compound-102) was obtained. MS: m/z (M+H)$^+$=457, 97% purity.

$^1$H NMR (300 MHz, DMSO-d$_6$) δ 10.36 (s, 1H), 10.05 (s, 1H), 7.60-7.53 (m, 2H), 7.53-7.44 (m, 2H), 6.90-6.79 (m, 2H), 3.39-3.32 (m, 4H), 3.04 (q, J=6.7 Hz, 1H), 2.58 (s, 6H), 2.57-2.52 (m, 1H), 2.22 (dd, J=15.9, 7.1 Hz, 1H), 1.96-1.83 (m, 4H), 1.18 (d, J=7.0, 3H).

Synthesis of Compound-103

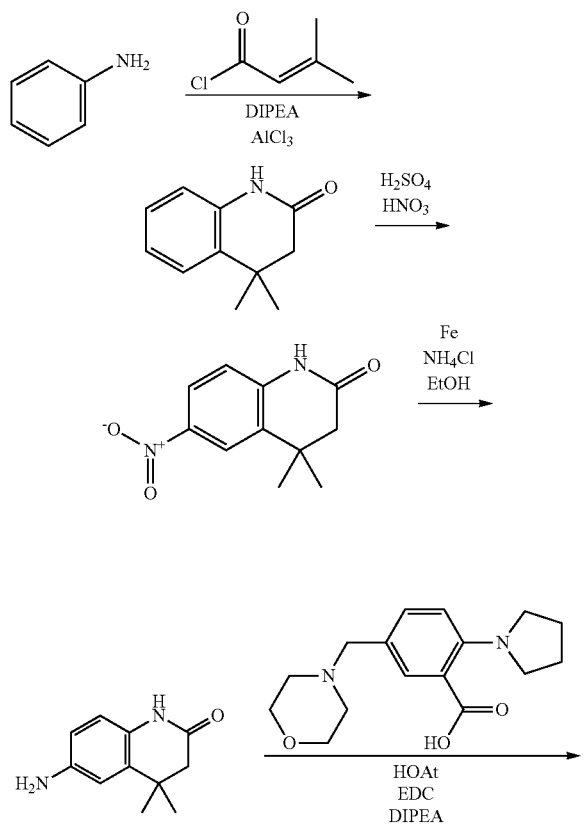

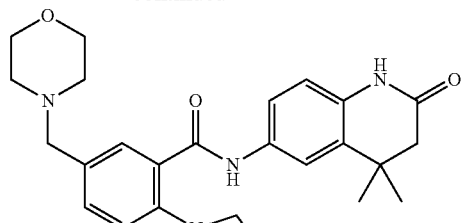
Compound-103

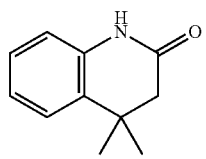

Preparation of 4,4-dimethyl-1,3-dihydroquinolin-2-one: to 3-methylbut-2-enoyl chloride (590 mg, 5.00 mmol, 1 eq) in DCM (50 mL), aniline (0.456 mL, 5.0 mmol, 1 eq) and DIPEA (1.741 mL, 10.0 mmol, 2 eq) were added and the mixture stirred for 2 h at r.t. Saturated NaHCO$_3$ was added to quench the reaction. The organic layer was separated and washed with sat. NaHCO3 (50 mL) and water (50 mL×2). The resulting solution was dried over MgSO4 and the filtrate evaporated to afford crude product as a brown solid. Product was dissolved in DCM (50 mL) and AlCl3 (1.333 g, 10.0 mmol, 2 eq) was added. Reaction mixture was stirred at 50° C. for 5 h then quenched with water/ice. Layers were separated and the organic extract additionally washed with 50 mL water. DCM was evaporated under reduced pressure to give 977 mg of 4,4-dimethyl-1,3-dihydroquinolin-2-one.

$^1$H NMR (300 MHz, DMSO-d$_6$) δ 10.11 (s, 1H), 7.28 (dd, J=7.7, 1.4 Hz, 1H), 7.13 (td, J=7.6, 1.4 Hz, 1H), 6.96 (td, J=7.5, 1.3 Hz, 1H), 6.86 (dd, J=7.8, 1.3 Hz, 1H), 2.34 (s, 2H), 1.22 (s, 6H).

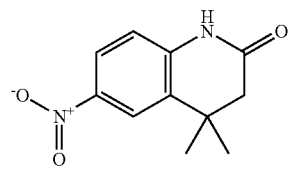

Preparation of 4,4-dimethyl-6-nitro-1,3-dihydroquinolin-2-one: 4,4-dimethyl-1,3-dihydroquinolin-2-one (976 mg, 5.57 mmol, 1 eq) was dissolved in conc. sulphuric acid (5 mL). Water (1.5 mL) was slowly added while cooling on ice. The mixture was stirred on ice for 10 min, then fuming nitric acid (465 μL, 11.14 mmol, 2 eq) was added and the reaction stirred on ice for 1 h, turning dark brown. Reaction mixture was diluted with water/ice (50 mL) and extracted with EtOAc (2×50 mL). Organic layer was washed with water and evaporated under reduced pressure to give 370 mg of 4,4-dimethyl-6-nitro-1,3-dihydroquinolin-2-one as yellow solid.

$^1$H NMR (300 MHz, DMSO-d$_6$) δ 10.79 (s, 1H), 8.16-8.05 (m, 2H), 7.06 (d, J=9.4 Hz, 1H), 2.47 (s, 2H), 1.29 (s, 6H).

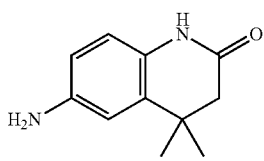

Preparation of 6-amino-4,4-dimethyl-1,3-dihydroquinolin-2-one: 4,4-dimethyl-6-nitro-1,3-dihydroquinolin-2-one (1200 mg, 5.45 mmol, 1 eq) was suspended in 15 mL EtOH and 15 mL saturated NH4Cl and heated to reflux. After 30 min, iron powder (913 mg, 16.35 mmol, 3 eq) was added. After refluxing for another 45 min, reaction mixture was cooled, filtered and the filtrate extracted two times with DCM. Organic extracts were combined, washed with brine and evaporated under reduced pressure to afford 583 mg of 6-amino-4,4-dimethyl-1,3-dihydroquinolin-2-one. MS: m/z (M+H)+ 191.

$^1$H NMR (300 MHz, DMSO-d$_6$) δ 9.71 (s, 1H), 6.60-6.50 (m, 2H), 6.35 (dd, J=8.2, 2.4 Hz, 1H), 4.74 (s, 2H), 2.23 (s, 2H), 1.15 (s, 6H).

Compound-103

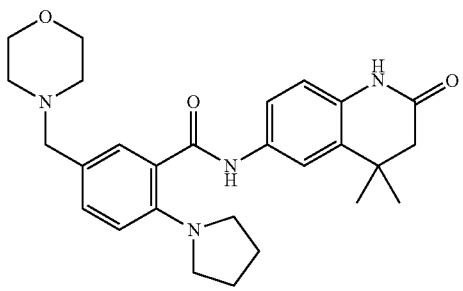

Preparation of N-(4,4-dimethyl-2-oxo-1,3-dihydroquinolin-6-yl)-5-(morpholinomethyl)-2-pyrrolidin-1-yl-benzamide (Compound-103): to a solution of 5-(morpholinomethyl)-2-pyrrolidin-1-yl-benzoic acid (52 mg 0.16 mmol, 1 eq) in DMF (3 mL), HOAt (22 mg, 0.16 mmol, 1 eq), EDC×HCl (25 mg, 0.16 mmol, 1 eq) and DIPEA (56 μL, 0.32 mmol, 2 eq) were added, followed by addition of 6-amino-4,4-dimethyl-1,3-dihydroquinolin-2-one (31 mg, 0.16 mmol, 1 eq) and the reaction stirred in DMF at 70° C. for 20 h. Reaction mixture was diluted with 20 mL EtOAC and 20 mL water and extracted. The organic layer was washed with water (20 mL) and concentrated under reduced pressure. The obtained crude product was purified by flash chromatography in the solvent system DCM-MeOH, 0-10% MeOH. Purest fractions were combined and solvent evaporated to give 22 mg of N-(4,4-dimethyl-2-oxo-1,3-dihydroquinolin-6-yl)-5-(morpholinomethyl)-2-pyrrolidin-1-yl-benzamide. MS: m/z (M+H)+ 463; 97% purity.

$^1$H NMR (300 MHz, DMSO-d$_6$) δ 10.25 (s, 1H), 10.07 (s, 1H), 7.64 (d, J=2.2 Hz, 1H), 7.55 (dd, J=8.6, 2.2 Hz, 1H), 7.23-7.14 (m, 2H), 6.81 (d, J=8.5 Hz, 1H), 6.74 (d, J=9.1 Hz, 1H), 3.61-3.50 (m, 4H), 3.36 (s, 2H), 3.27-3.15 (m, 4H), 2.40-2.28 (m, 6H), 1.92-1.78 (m, 4H), 1.21 (s, 6H).

Synthesis of Compound-104

Compound-104

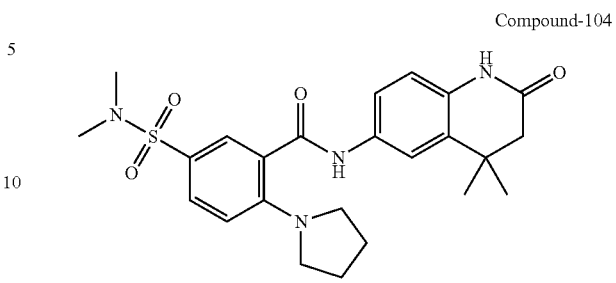

N-(4,4-dimethyl-2-oxo-1,3-dihydroquinolin-6-yl)-5-(dimethylsulfamoyl)-2-pyrrolidin-1-yl-benzamide (Compound-104): compound was prepared following the same procedure as for Compound-103 from 5-(dimethylsulfamoyl)-2-pyrrolidin-1-yl-benzoic acid (60 mg 0.16 mmol, 1 eq) and 6-amino-4,4-dimethyl-1,3-dihydroquinolin-2-one (38 mg, 0.16 mmol, 1 eq). 35 mg of N-(4,4-dimethyl-2-oxo-1,3-dihydroquinolin-6-yl)-5-(dimethylsulfamoyl)-2-pyrrolidin-1-yl-benzamide (Compound-104) was obtained. MS: m/z (M+H)+=471; 97% purity.

$^1$H NMR (300 MHz, DMSO-d$_6$) δ 10.37 (s, 1H), 10.10 (s, 1H), 7.62 (d, J=2.2 Hz, 1H), 7.61-7.47 (m, 3H), 6.94-6.76 (m, 2H), 3.37-3.33 (m, 4H), 2.58 (s, 6H), 2.34 (s, 2H), 1.98-1.82 (m, 4H), 1.22 (s, 6H).

Synthesis of Compound-105

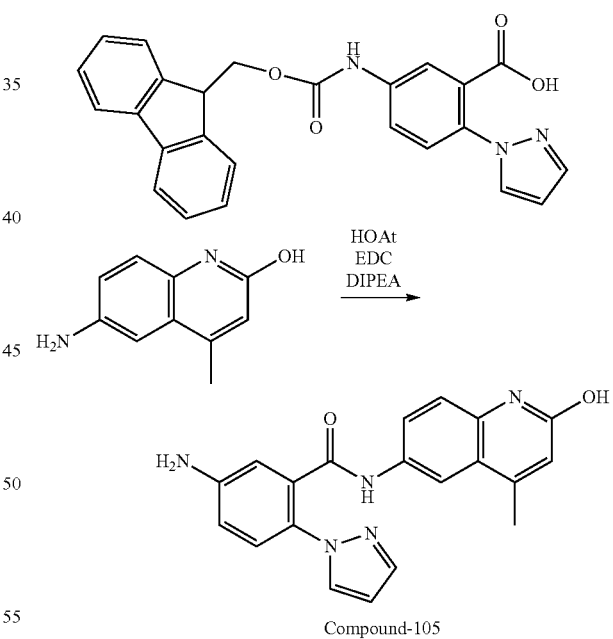

Compound-105

Preparation of 5-amino-N-(2-hydroxy-4-methyl-6-quinolyl)-2-pyrazol-1-yl-benzamide (Compound-105): to a solution of 5-(9H-fluoren-9-ylmethoxycarbonylamino)-2-pyrazol-1-yl-benzoic acid (100 mg 0.23 mmol, 1 eq) in DMF (5 mL), HOAt (31 mg, 0.23 mmol, 1 eq), EDC×HCl (44 mg, 0.23 mmol, 1 eq) and DIPEA (80 μL, 0.46 mmol, 2 eq) were added, followed by addition of 6-amino-4-methyl-quinolin-2-ol (40 mg, 0.23 mmol, 1 eq) and the reaction stirred in DMF at 70° C. for 16 h. Reaction mixture was diluted with 20 mL EtOAC and 20 mL water and extracted.

The organic layer was washed with water (20 mL) and concentrated under reduced pressure. LC-MS and TLC (DCM:MeOH 10:1) indicated that product was Fmoc-deprotected. Crude mixture was purified by flash chromatography in the solvent system DCM-MeOH, 0-10% MeOH. Purest fractions were combined and solvent evaporated to give 10 mg of 5-amino-N-(2-hydroxy-4-methyl-6-quinolyl)-2-pyrazol-yl-benzamide (Compound-105) as white solid. MS: m/z (M+H)+ 360; 94.5% purity.

$^1$H NMR (300 MHz, DMSO-$d_6$) δ 11.51 (s, 1H), 9.92 (s, 1H), 8.00-7.86 (m, 2H), 7.66-7.53 (m, 2H), 7.35 (d, J=8.3 Hz, 1H), 7.20 (d, J=8.8 Hz, 1H), 6.71 (d, J=2.1 Hz, 1H), 6.63 (dd, J=8.3, 2.2 Hz, 1H), 6.47-6.35 (m, 2H), 5.81 (s, 2H), 2.34 (s, 3H).

Synthesis of Compound-106

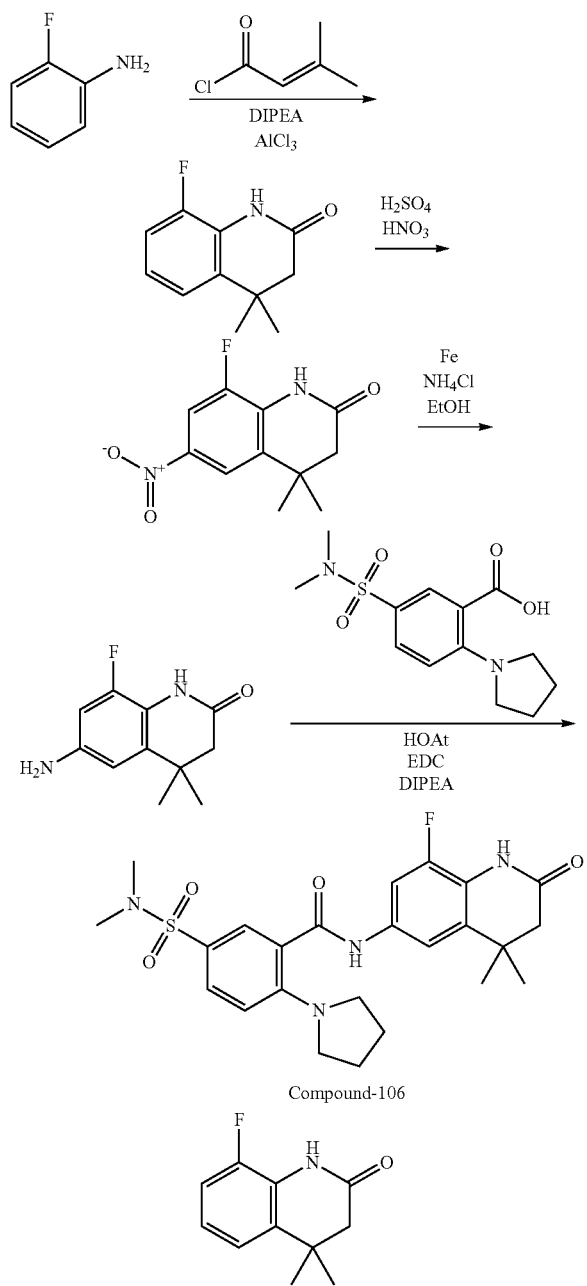

Compound-106

Preparation of 8-fluoro-4,4-dimethyl-1,3-dihydroquinolin-2-one: to crotonoyl chloride (590 mg, 5.00 mmol, 1 eq) in DCM (50 mL), 2-fluoroaniline (483 μL, 5.0 mml, 1 eq) and DIPEA (1.741 mL, 10.0 mmol, 2 eq) were added and the mixture stirred for 2 h at r.t. and saturated NaHCO3 was added to quench the reaction. The organic layer was separated and washed with sat. NaHCO3 (50 mL) and water (50 mL×2). The resulting solution was dried over MgSO4 and the filtrate evaporated to afford N-(2-fluorophenyl)-3-methyl-but-2-enamide as a yellow-brown solid. Product was dissolved in DCM (50 mL) and AlCl3 (1.333 g, 10.0 mmol, 2 eq) was added. Reaction mixture was stirred at 50° C. for 3 h. After cooling to room temperature, reaction was extracted from DCM/water. Organic extracts were combined, washed with brine and concentrated under reduced pressure to give 949 mg of 8-fluoro-4,4-dimethyl-1,3-dihydroquinolin-2-one as brown solid.

$^1$H NMR (300 MHz, DMSO-$d_6$) δ 10.11 (s, 1H), 7.18-6.93 (m, 3H), 2.39 (s, 2H), 1.23 (s, 6H).

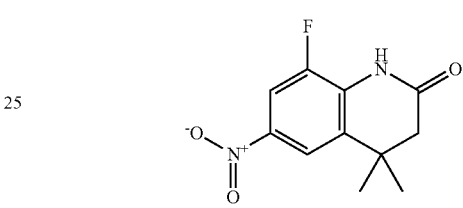

Preparation of 8-fluoro-4,4-dimethyl-6-nitro-1,3-dihydroquinolin-2-one: 8-fluoro-4,4-dimethyl-1,3-dihydroquinolin-2-one (945 mg, 4.89 mmol, 1 eq) was dissolved in conc. sulphuric acid (5 mL). Water (1.5 mL) was slowly added while cooling on ice. The mixture was stirred on ice for 10 min, then fuming nitric acid (408 μL, 9.79 mmol) was added and the reaction stirred on ice for 2 h. Reaction mixture was diluted with water/ice (50 mL) and extracted with EtOAc (2×50 mL). Organic extracts were combined, washed with water, dried over anhydrous Mg2SO4 and evaporated under reduced pressure to give 951 mg of 8-fluoro-4,4-dimethyl-6-nitro-1,3-dihydroquinolin-2-one as brown solid.

$^1$H NMR (300 MHz, DMSO-$d_6$) δ 10.82 (s, 1H), 8.07 (dd, J=10.3, 2.4 Hz, 1H), 8.04-7.95 (m, 1H), 2.52 (s, 2H), 1.30 (s, 6H).

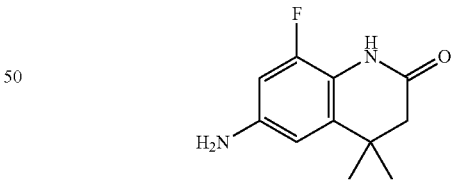

Preparation of 6-amino-8-fluoro-4,4-dimethyl-1,3-dihydroquinolin-2-one: 8-fluoro-4,4-dimethyl-6-nitro-1,3-dihydroquinolin-2-one (950 mg, 3.99 mmol, 1 eq) was suspended in 15 mL EtOH and 15 mL saturated NH4Cl and heated to reflux for 30 min. Iron powder (668 mg, 11.97 mmol, 3 eq) was added in portions. After refluxing for another 45 min, reaction mixture was cooled, filtered and the filtrate extracted three times with DCM. Organic extracts were combined, washed with brine and concentrated under reduced pressure to afford 533 mg of 6-amino-8-fluoro-4,4-dimethyl-1,3-dihydroquinolin-2-one. MS: m/z (M+H)+ 209.

¹H NMR (300 MHz, DMSO-d₆) δ 9.63 (s, 1H), 6.40-6.32 (m, 1H), 6.25 (dd, J=12.7, 2.2 Hz, 1H), 5.07 (s, 2H), 2.27 (s, 2H), 1.17 (s, 6H).

Compound-106

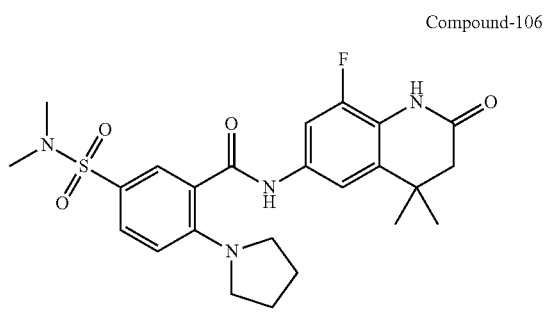 [SMILES: CN(C)S(=O)(=O)c1ccc(N2CCCC2)c(C(=O)Nc2cc(F)c3c(c2)C(C)(C)CC(=O)N3)c1]

Preparation of 5-(dimethylsulfamoyl)-N-(8-fluoro-4,4-dimethyl-2-oxo-1,3-dihydroquinolin-6-yl)-2-pyrrolidin-1-yl-benzamide (Compound-106): to a solution of 5-(dimethylsulfamoyl)-2-pyrrolidin-1-yl-benzoic acid (60 mg 0.20 mmol, 1 eq) in DMF (3 mL), HOAt (27 mg, 0.20 mmol, 1 eq), EDC×HCl (38 mg, 0.20 mmol, 1 eq) and DIPEA (70 µL, 0.40 mmol, 1 eq) were added, followed by addition of 6-amino-8-fluoro-4,4-dimethyl-1,3-dihydroquinolin-2-one (41 mg, 0.20 mmol, 1 eq) and the reaction stirred in DMF at 70° C. for 20 h. Reaction mixture was diluted with 20 mL EtOAC and 20 mL water and extracted. The organic layer was washed with water (20 mL) and concentrated under reduced pressure. The obtained crude product was purified by flash chromatography in the solvent system DCM-MeOH, 0-10% MeOH. Purest fractions were combined and solvent evaporated to give 5 mg of 5-(dimethylsulfamoyl)-N-(8-fluoro-4,4-dimethyl-2-oxo-1,3-dihydroquinolin-6-yl)-2-pyrrolidin-1-yl-benzamide as white solid. MS: m/z (M+H)⁺ 489; 99% purity.

¹H NMR (300 MHz, DMSO-d₆) δ 10.56 (s, 1H), 10.12 (s, 1H), 7.67 (dd, J=12.7, 2.1 Hz, 1H), 7.57 (dd, J=8.9, 2.3 Hz, 1H), 7.53 (d, J=2.3 Hz, 1H), 7.37 (s, 1H), 6.88 (d, J=8.9 Hz, 1H), 3.30-3.35 (m, 4H), 2.58 (s, 6H), 2.39 (s, 2H), 1.95-1.84 (m, 4H), 1.23 (s, 6H).

Synthesis of Compound-107

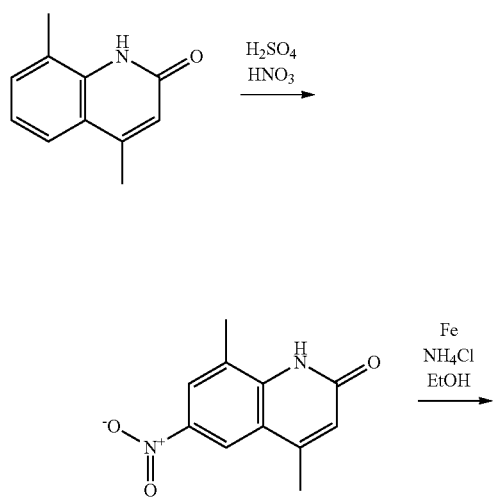

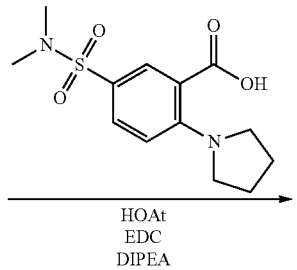

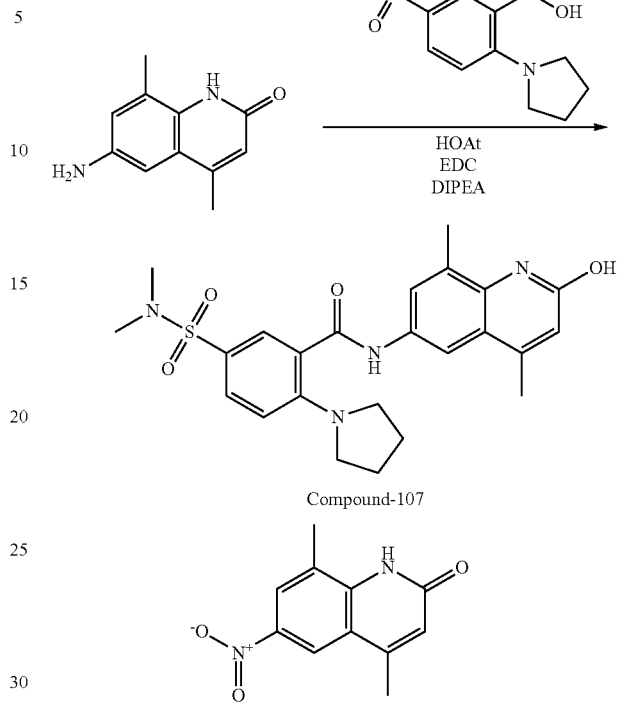

Compound-107

Preparation of 4,8-dimethyl-6-nitro-quinolin-2-one: 4,8-dimethyl-1H-quinolin-2-one (300 mg, 1.73 mmol, 1 eq) was dissolved in acetanhydride (5 mL). The mixture was stirred on ice for 10 min, then nitric acid (145 µL, 3.46 mmol, 2 eq) was added and the reaction stirred on ice for 2 h. Reaction mixture was diluted with water/ice (50 mL) and extracted with EtOAc (2×50 mL). Organic layer was washed with water and evaporated under reduced pressure to give 261 mg of 4,8-dimethyl-6-nitro-quinolin-2-one as brown solid.

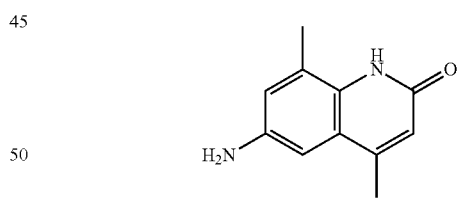

Preparation of 6 6-amino-4,8-dimethyl-quinolin-2-one: 4,8-dimethyl-6-nitro-1H-quinolin-2-one (260 mg, 1.19 mmol, 1 eq) was suspended in 15 mL EtOH and 15 mL saturated NH4Cl and heated to reflux. After 30 min, iron powder (200 mg, 3.58 mmol, 3 eq) was added. After refluxing for another 45 min, reaction mixture was cooled, filtered and washed with water and DCM. Leyers were separated and the organic extracts washed with brine and concentrated under reduced pressure to afford 152 mg of 6-amino-4,8-dimethyl-quinolin-2-one. MS: m/z (M+H)⁺ 189.

¹H NMR (300 MHz, DMSO-d₆) δ 10.35 (s, 1H), 6.75-6.63 (m, 2H), 6.31 (s, 1H), 4.93 (s, 2H), 2.36-2.28 (m, 6H).

Compound-107

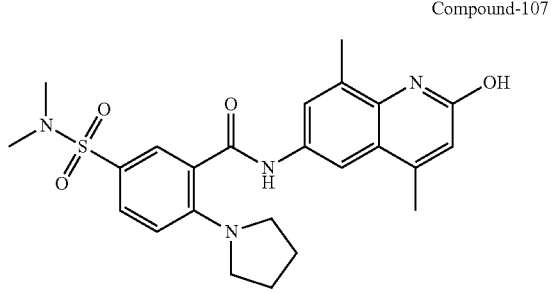 [SMILES: Cc1cc(O)nc2c(C)cc(NC(=O)c3cc(S(=O)(=O)N(C)C)ccc3N3CCCC3)cc12]

Preparation of 5-(dimethylsulfamoyl)-N-(2-hydroxy-4,8-dimethyl-6-quinolyl)-2-pyrrolidin-1-yl-benzamide (Compound-107): to a solution of 5-(dimethylsulfamoyl)-2-pyrrolidin-1-yl-benzoic acid (100 mg 0.33 mmol, 1 eq) in DMF (3 mL), HOAt (45 mg, 0.33 mmol, 1 eq), EDC×HCl (63 mg, 0.33 mmol, 1 eq) and DIPEA (115 µL, 0.66 mmol, 2 eq) was added, followed by addition of 6-amino-4,8-dimethyl-quinolin-2-one (62 mg, 0.33 mmol, 1 eq) and the reaction stirred in DMF at 70° C. for 20 h. Reaction mixture was diluted with 20 mL EtOAC and 20 mL water and extracted. The organic layer was washed with water (20 mL) and concentrated under reduced pressure. The obtained crude product was purified by flash chromatography in the solvent system DCM-MeOH, 0-10% MeOH. Purest fractions were combined and solvent evaporated to give 15 mg of 5-(dimethylsulfamoyl)-N-(2-hydroxy-4,8-dimethyl-6-quinolyl)-2-pyrrolidin-1-yl-benzamide as white solid. MS: m/z (M+H)$^+$ 496; 94% purity.

$^1$H NMR (300 MHz, DMSO-d$_6$) δ 10.73 (s, 1H), 10.51 (s, 1H), 7.98 (d, J=2.2 Hz, 1H), 7.69 (d, J=2.3 Hz, 1H), 7.65-7.47 (m, 2H), 6.89 (d, J=8.9 Hz, 1H), 6.45 (s, 1H), 3.38-3.33 (m, 4H), 2.59 (s, 6H), 2.43 (s, 3H), 2.40 (s, 3H), 1.99-1.79 (m, 4H).

Synthesis of Compound-108

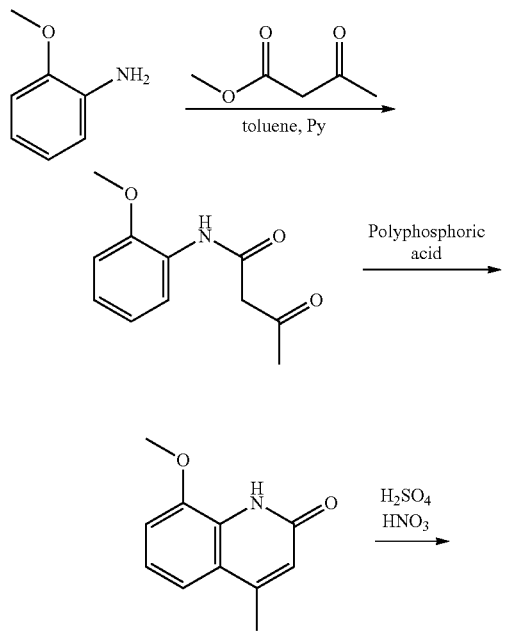

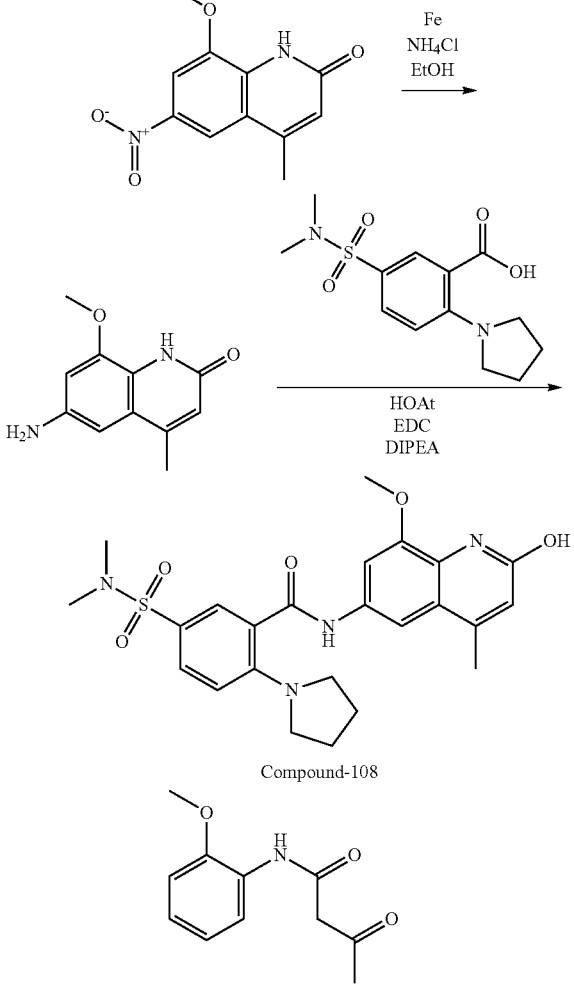

Compound-108

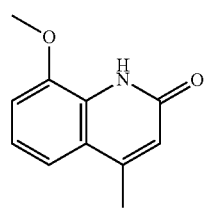

Preparation of N-(2-methoxyphenyl)-3-oxo-butanamide: a solution of methyl 3-oxobutanoate (870 mg, 7.5 mmol, 1.5 eq) in toluene/pyridine (5 mL/1 mL) was heated to gentle reflux for 30 min. 2-methoxyaniline (615 mg, 5.0 mmol, 1 eq) was then added dropwise into the reaction mixture and it was refluxed for 16 h. The solution was allowed to cool to 25° C. and was extracted with 2M NaOH. The aqueous layer was separated and made weakly acidic with conc HCl. It was then extracted with EtOAc (2×30 mL). Organic extract was concentrated under reduced pressure to give 1.251 g of crude N-(2-methoxyphenyl)-3-oxo-butanamide. Product was used as such without further purification.

Preparation of 8-methoxy-4-methyl-1H-quinolin-2-one: to 5 mL of polyphosphoric acid was added N-(2-methoxyphenyl)-3-oxo-butanamide (1.035 mg, 5.0 mmol) and the mixture stirred at 100° C. for 20 h. After cooling to room temperature, small portion of ice-cold water was added to the reaction mixture and stirred until all polyphosphoric acid dissolved. Mixture was then poured onto 20 mL of water/ice and pH made basic with 2N NaOH. It was extracted with 2×20 mL EtOAC. Organic layer was washed with water and concentrated in vacuo to give 650 mg of 8-methoxy-4-methyl-1H-quinolin-2-one.

$^1$H NMR (300 MHz, DMSO-d$_6$) δ 10.56 (s, 1H), 7.34-7.25 (m, 1H), 7.20-7.11 (m, 2H), 6.42 (q, J=1.2 Hz, 1H), 3.89 (s, 3H), 2.41 (d, J=1.2 Hz, 3H).

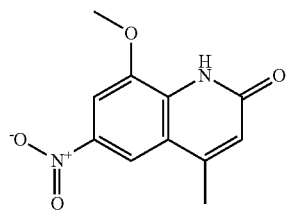

Preparation of 8-methoxy-4-methyl-6-nitro-1H-quinolin-2-one: 8-methoxy-4-methyl-1H-quinolin-2-one (647 mg, 3.42 mmo, 1 eq) was dissolved in acetanhydride (5 mL). The mixture was stirred on ice for 10 min, then nitric acid (285 µL, 6.84 mmol, 2 eq) was added and the reaction stirred on ice for 2 h. Reaction mixture was diluted with water/ice (50 mL) and the resulting precipitate was washed with water and dried to give 412 mg of 8-methoxy-4-methyl-6-nitro-1H-quinolin-2-one as yellow solid.

$^1$H NMR (300 MHz, DMSO-d$_6$) δ 11.38 (s, 1H), 8.17 (d, J=2.2 Hz, 1H), 7.84 (d, J=2.2 Hz, 1H), 6.59 (d, J=1.4 Hz, 1H), 4.01 (s, 3H), 2.49 (d, J=1.2 Hz, 3H).

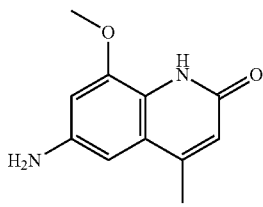

Preparation of 6-amino-8-methoxy-4-methyl-1H-quinolin-2-one: 8-methoxy-4-methyl-6-nitro-1H-quinolin-2-one (410 mg, 1.75 mmol, 1 eq) was suspended in 15 mL EtOH and 15 mL saturated NH4Cl and heated to reflux. After 30 min, iron powder (293 mg, 5.25 mmol, 3 eq) was added. After refluxing for another 2 h, reaction mixture was cooled, filtered and washed with water and DCM. The filtrate layers were separated and the organic extract washed with brine and concentrated under reduced pressure to afford 152 mg of 6-amino-4,8-dimethyl-quinolin-2-one. MS: m/z (M+H)$^+$ 205.

$^1$H NMR (300 MHz, DMSO-d$_6$) δ 10.09 (s, 1H), 6.53 (d, J=2.0 Hz, 1H), 6.40 (d, J=2.0 Hz, 1H), 6.31 (d, J=1.3 Hz, 1H), 5.03 (s, 2H), 3.81 (s, 3H), 2.29 (d, J=1.2 Hz, 3H).

Compound-108

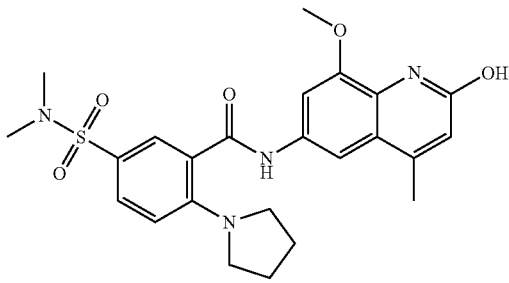

Preparation of 5-(dimethylsulfamoyl)-N-(2-hydroxy-8-methoxy-4-methyl-6-quinolyl)-2-pyrrolidin-1-yl-benzamide (Compound-108): to a solution of 5-(dimethylsulfamoyl)-2-pyrrolidin-1-yl-benzoic acid (60 mg 0.20 mmol, 1 eq) in DMF (3 mL), HOAt (27 mg, 0.20 mmol, 1 eq), EDC×HC (38 mg, 0.20 mmol, 1 eq) and DIPEA (70 µL, 0.40 mmol, 2 eq) was added, followed by addition of 6-amino-8-methoxy-4-methyl-1H-quinolin-2-one (41 mg, 0.20 mmol, 2 eq) and the reaction stirred in DMF at 70° C. for 20 h. Reaction mixture was diluted with 20 mL EtOAC and 20 mL water and extracted. The organic layer was washed with water and concentrated under reduced pressure. The obtained crude product was purified by flash chromatography in the solvent system DCM-MeOH, 0-10% MeOH. Purest fractions were combined and solvent evaporated to give 36 mg of 5-(dimethylsulfamoyl)-N-(2-hydroxy-8-methoxy-4-methyl-6-quinolyl)-2-pyrrolidin-1-yl-benzamide (Compound-108) as a white solid. MS: m/z (M+H)$^+$ 485; 96% purity.

$^1$H NMR (300 MHz, DMSO-d$_6$) δ 10.62 (s, 1H), 10.56 (s, 1H), 7.74 (d, J=1.9 Hz, 1H), 7.61-7.53 (m, 3H), 6.90 (d, J=8.8 Hz, 1H), 6.45 (s, 1H), 3.89 (s, 3H), 3.41-3.34 (m, 4H), 2.59 (s, 6H), 2.38 (d, J=1.2 Hz, 3H), 2.01-1.80 (m, 4H).

Synthesis of Compound-109

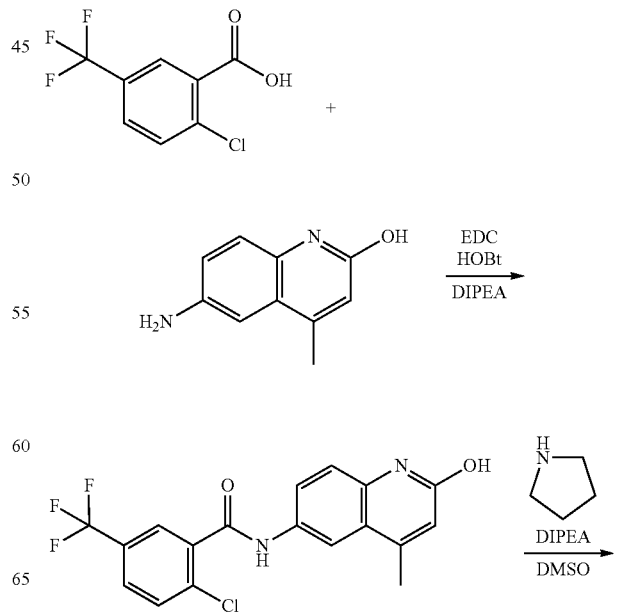

-continued

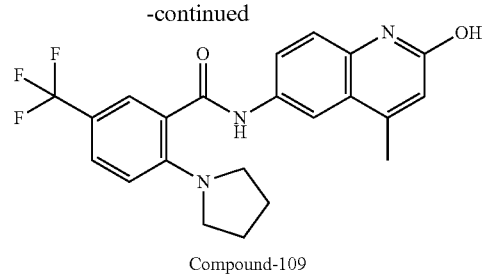

Compound-109

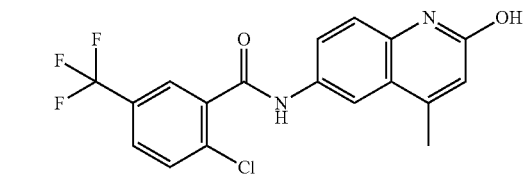

Preparation of 2-chloro-N-(2-hydroxy-4-methyl-6-quinolyl)-5-(trifluoromethyl)benzamide: to a solution of 2-chloro-5-(trifluoromethyl)benzoic acid (150 mg 0.67 mmol, 1 eq) in DMF (5 mL), HOAt (109 mg, 0.67 mmol, 1 eq), EDC×HCl (128 mg, 0.67 mmol, 1 eq) and DIPEA (233 µL, 1.34 mmol, 2 eq) was added, followed by addition of 6-amino-4-methyl-1H-quinolin-2-ol (117 mg, 0.67 mmol, 1 eq) and the reaction stirred in DMF at 70° C. for 20 h. Reaction mixture was diluted with 20 mL EtOAC and 20 mL water and extracted. Product partly precipitated in EtOAC. It was filtered off, washed with water/EtOAc and dried to give 43 mg of pure 2-chloro-N-(2-hydroxy-4-methyl-6-quinolyl)-5-(trifluoromethyl)benzamide. The filtrate layers were separated, the organic extract washed with water and concentrated under reduced pressure to give another 147 mg of title product.

$^1$H NMR (300 MHz, DMSO-d$_6$) δ 11.62 (s, 1H), 10.74 (s, 1H), 8.13 (d, J=2.2 Hz, 1H), 8.04 (d, J=2.1 Hz, 1H), 7.94-7.72 (m, 3H), 7.31 (d, J=8.8 Hz, 1H), 6.44 (s, 1H), 2.40 (d, J=1.2 Hz, 3H).

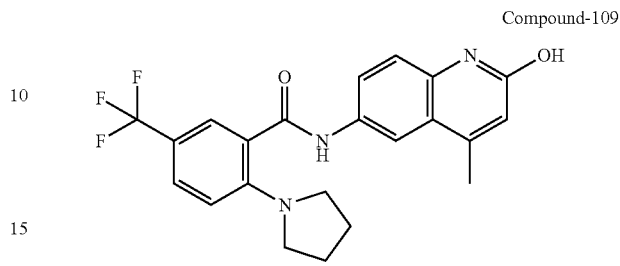

Compound-109

Preparation of N-(2-hydroxy-4-methyl-6-quinolyl)-2-pyrrolidin-1-yl-5-(trifluoromethyl)benzamide (Compound-109): to a solution of 2-chloro-N-(2-hydroxy-4-methyl-6-quinolyl)-5-(trifluoromethyl)benzamide (77 mg 0.20 mmol, 1 eq) in DMSO (2 mL), DIPEA (105 µL, 0.60 mmol, 3 eq) and pyrrolidine (28 mg, 0.40 mmol, 2 eq) were added and the reaction stirred at 100° C. for three days. Reaction mixture was diluted with 20 mL EtOAC and 20 mL water and extracted. The organic layer was washed with water (20 mL) and concentrated in vacuo. Crude product was purified by flash chromatography in the solvent system DCM-MeOH, 0-10% MeOH. Purest fractions were combined and solvent evaporated to give 16 mg of pure N-(2-hydroxy-4-methyl-6-quinolyl)-2-pyrrolidin-1-yl-5-(trifluoromethyl) benzamide (Compound-109). MS: m/z (M+H)$^+$ 416, purity 93.4%.

$^1$H NMR (300 MHz, DMSO-d$_6$) δ 11.57 (s, 1H), 10.53 (s, 1H), 8.11 (d, J=2.2 Hz, 1H), 7.81 (dd, J=8.8, 2.2 Hz, 1H), 7.61-7.49 (m, 2H), 7.29 (d, J=8.8 Hz, 1H), 6.87 (d, J=9.4 Hz, 1H), 6.42 (s, 1H), 3.31-3.16 (m, 4H), 2.39 (d, J=1.1 Hz, 3H), 1.98-1.79 (m, 4H).

Synthesis of Compound-110 and Compound-111

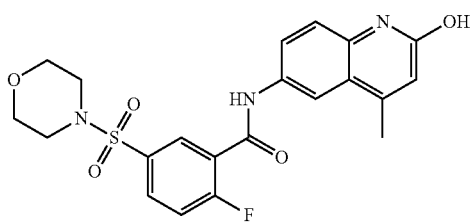

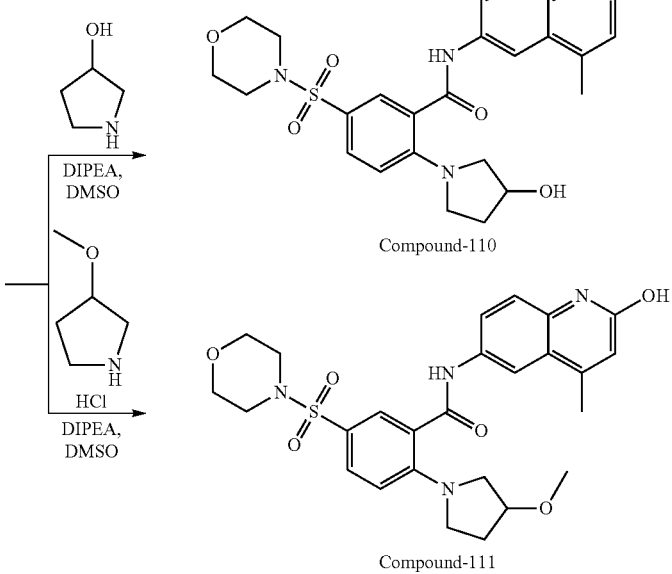

Compound-110

Compound-111

Preparation of N-(2-hydroxy-4-methyl-6-quinolyl)-2-(3-hydroxypyrrolidin-1-yl)-5-morpholino-sulfonyl-benzamide (Compound-110)

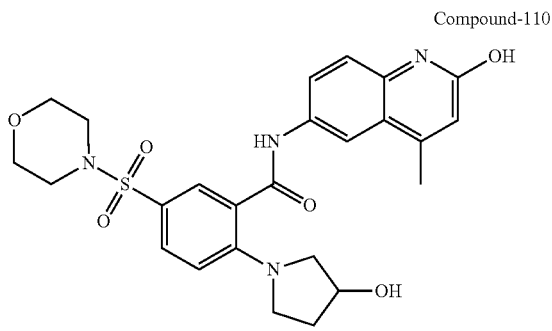 [SMILES: Cc1cc(O)nc2ccc(NC(=O)c3cc(S(=O)(=O)N4CCOCC4)ccc3N3CCC(O)C3)cc12]

Compound-110

2-fluoro-N-(2-hydroxy-4-methyl-6-quinolyl)-5-morpholinosulfonyl-benzamide (0.0502 g, 0.112 mmol, 1 eq) is dissolved in 1 mL DMSO. Pyrrolidin-3-ol (0.0113 g, 0.123 mmol, 1.1 eg) and DIPEA (44 μL, 0.336 mmol, 3 eq) are added to the solution. The reaction is heated for 3 h at 40° C. under stirring. Solvent is removed by air-flow overnight. Crude is washed 2 times with Methanol and 2 times with Ether. Compound is dried overnight on oil pump. Yield of N-(2-hydroxy-4-methyl-6-quinolyl)-2-(3-hydroxy-pyrrolidin-1-yl)-5-morpholinosulfonyl-benzamide (Compound-110) (38.5 mg, 0.075 mmol). LCMS: 98% pure.

$^1$H NMR (300 MHz, DMSO-d$_6$) δ 11.60 (s, 1H), 10.63 (s, 1H), 8.13 (d, J=2.2 Hz, 1H), 7.80 (dd, J=8.9, 2.2 Hz, 1H), 7.63-7.48 (m, 2H), 7.29 (d, J=8.8 Hz, 1H), 6.89 (d, J=8.9 Hz, 1H), 6.43 (s, 1H), 5.00 (d, J=3.2 Hz, 1H), 4.33 (s, 1H), 3.64 (t, J=4.6 Hz, 4H), 3.59-3.45 (m, 2H), 3.45-3.36 (m, 1H), 3.12 (d, J=10.9 Hz, 1H), 2.85 (q, J=3.9 Hz, 4H), 2.40 (d, J=1.2 Hz, 3H), 2.07-1.78 (m, 2H).

Preparation of N-(2-hydroxy-4-methyl-6-quinolyl)-2-(3-methoxypyrrolidin-1-yl)-5-morpholino-sulfonyl-benzamide (Compound-111)

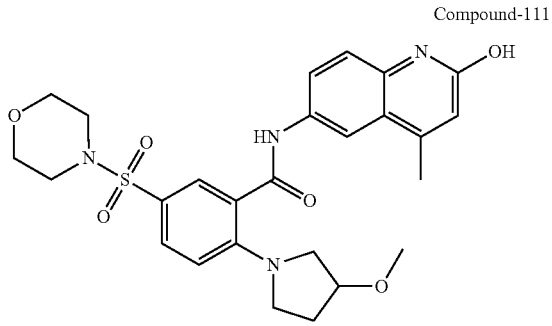 [SMILES: COC1CCN(c2ccc(S(=O)(=O)N3CCOCC3)cc2C(=O)Nc2ccc3nc(O)cc(C)c3c2)C1]

Compound-111

2-fluoro-N-(2-hydroxy-4-methyl-6-quinolyl)-5-morpholinosulfonyl-benzamide (0.0511 g, 0.112 mmol, 1 eq) is dissolved in 1 mL DMSO. 3-Methoxy-pyrrolidine (0.0171 g, 0.123 mmol, 1.1 eg) and DIPEA (73 μL, 0.56 mmol, 5 eq) is added to the solution. The reaction is heated for 3 h at 40° C. under stirring. Extra 3-Methoxy-pyrrolidine (0.0154 g, 0.112 mmol, 1.0 eg) and DIPEA (50 μL, 0.29 mmol, 2.6 eq) was added. The reaction is heated for additional 2 h at 40° C. under stirring. Solvent is removed by air-flow overnight. Crude is purified by prep-LCMS. Relevant fractions are collected and solvent is removed by rotavap. Compound is dried overnight on oil pump. Yield of N-(2-hydroxy-4-methyl-6-quinolyl)-2-(3-methoxypyrrolidin-1-yl)-5-morpholino-sulfonyl-benzamide (Compound-111) (32.4 mg, 0.0615 mmol). LCMS: 100% pure.

$^1$H NMR (300 MHz, DMSO-d$_6$) δ 11.60 (s, 1H), 10.65 (s, 1H), 8.12 (d, J=2.2 Hz, 1H), 7.79 (dd, J=8.9, 2.2 Hz, 1H), 7.60-7.50 (m, 2H), 7.30 (d, J=8.8 Hz, 1H), 6.90 (d, J=8.8 Hz, 1H), 6.43 (s, 1H), 4.03 (tt, J=4.3, 1.9 Hz, 1H), 3.64 (t, J=4.6 Hz, 4H), 3.56 (dd, J=11.4, 4.5 Hz, 1H), 3.51-3.36 (m, 2H), 3.20 (s, 3H), 2.85 (q, J=4.2 Hz, 4H), 2.40 (d, J=1.1 Hz, 3H), 2.15-1.84 (m, 2H).

Synthesis Compound-112

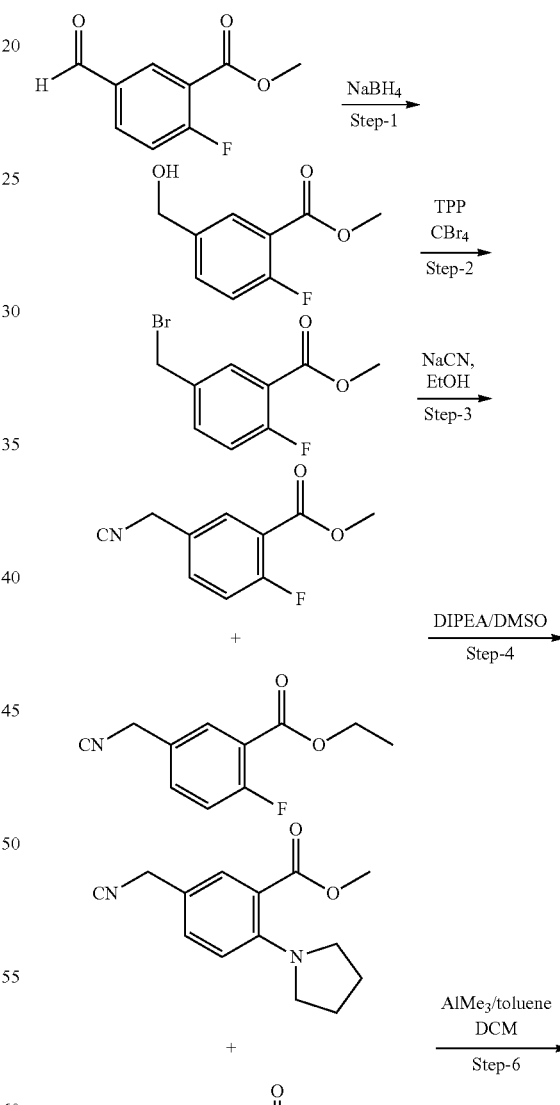

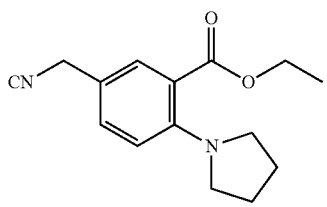

-continued

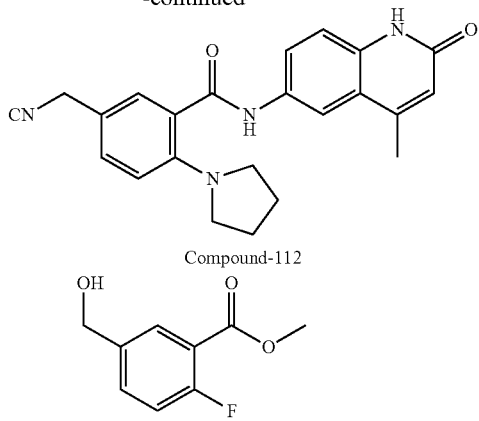

Compound-112

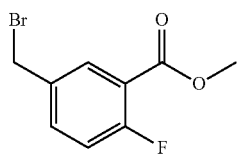

Preparation of methyl 2-fluoro-5-formylbenzoate: o a solution of methyl 2-fluoro-5-formylbenzoate (7 g, 38.46 mmol, 1 eq) in EtOH (5 mL) was added NaBH₄ (2.84 g, 76.92 mmol, 2.0 eq) and stirred at RT for 1 h. After completion, the solvent was evaporated, the residue was taken in water and extracted with EtOAc (100 mL). The combined extracts were washed with water (100 mL), brine (100 mL), dried over anhydrous Na₂SO₄, filtered and evaporated to afford methyl 2-fluoro-5-(hydroxymethyl)benzoate (5 g) as a pale yellow liquid.

Preparation of methyl 5-(bromomethyl)-2-fluorobenzoate: to a solution of methyl 2-fluoro-5-(hydroxymethyl) benzoate (5 g, 27.17 mmol, 1 eq) in Dry DCM (50 mL) was added PBr₃ (2.19 g, 8.12 mmol, 0.3 eq) and stirred at RT for 3 h. After completion, the reaction mixture was quenched with saturated NaHCO₃ solution and extracted with DCM (3×100 mL). The combined extracts were washed with water (100 mL), brine (100 mL), dried over anhydrous Na₂SO₄, filtered and evaporated to afford methyl 5-(bromomethyl)-2-fluorobenzoate (4.8 g) as an off white solid.

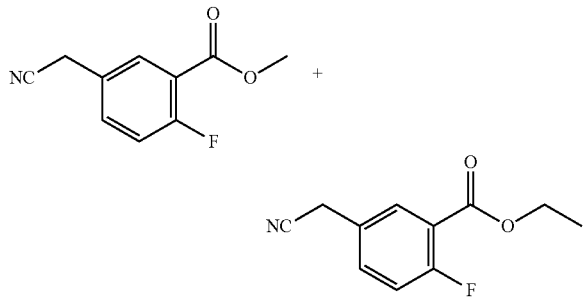

Preparation of methyl 5-(cyanomethyl)-2-fluorobenzoate and ethyl 5-(cyanomethyl)-2-fluorobenzoate: to a solution of methyl 5-(bromomethyl)-2-fluorobenzoate (Compound-3) (4.8 g, 19.51 mmol, 1 eq) in dry EtOH (25 mL) and H₂O (25 mL) was added NaCN (1.91 g, 39.02 mmol, 2 eq) and stirred at RT for 16 h. After completion, the reaction mixture was poured into ice water and extracted with EtOAc (3×50 mL). The combined extracts were washed with water (50 mL), brine (50 mL), dried over anhydrous Na₂SO₄, filtered and evaporated. The crude compound was purified by column chromatography (SiO₂) using EtOAc:Pet ether (15:85) to afford methyl 5-(cyanomethyl)-2-fluorobenzoate and ethyl 5-(cyanomethyl)-2-fluorobenzoate (Compound-4&4A) (2.3 g) as an off white solid.

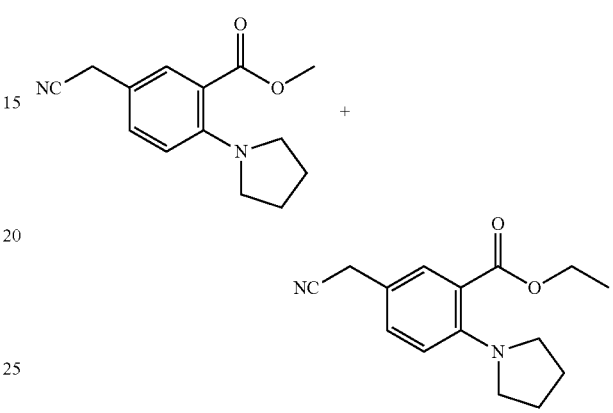

Preparation of methyl 5-(cyanomethyl)-2-(pyrrolidin-1-yl) benzoate and ethyl 5-(cyanomethyl)-2-(pyrrolidin-1-yl) benzoate: to a solution of methyl 5-(cyanomethyl)-2-fluorobenzoate and ethyl 5-(cyanomethyl)-2-fluorobenzoate (Compound-4&4A) (2.3 g, 11.917 mmol, 1 eq) in dry DMSO (23 mL) at RT was added pyrrolidine (0.847 g, 11.917 mmol, 1 eq), DIPEA (4.61 g mg, 35.751 mmol, 3 eq) and stirred at RT for 48 h. After completion, the reaction mixture poured into ice water and extracted with EtOAc (3×30 mL). The combined extracts were washed with water (40 mL), brine (40 mL), dried over anhydrous Na₂SO₄, filtered and evaporated. The crude compound was purified by column chromatography (SiO₂) using EtOAc:Pet ether (15:85) to afford methyl 5-(cyanomethyl)-2-(pyrrolidin-1-yl) benzoate and ethyl 5-(cyanomethyl)-2-(pyrrolidin-1-yl) benzoate (Compound-5&5A) (2.1 g) as an off white solid.

Compound-112

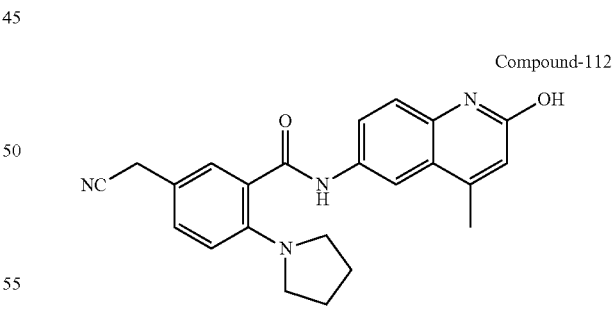

Preparation of 5-(cyanomethyl)-N-(4-methyl-2-oxo-1,2-dihydroquinolin-6-yl)-2-(pyrrolidin-1-yl)benzamide (Compound-112): to a solution of methyl 5-(cyanomethyl)-2-fluorobenzoate and ethyl 5-(cyanomethyl)-2-fluorobenzoate (Compound-5&5A) (50 mg, 0.204 mmol, 1 eq) in Dry DCM (2 mL) at RT was added Compound-6 (35.49 mg, 0.204 mmol, 1 eq), Tri methyl aluminum 2M solution in toluene (29.4 mg, 0.408 mmol, 2 eq) and stirred at RT for 48 h. After completion, the reaction mixture was poured into ice water and extracted with MeOH: CHCl₃ (1:9) (3×30 mL). The combined extracts were washed with water (40 mL), brine (40 mL), dried over anhydrous Na₂SO₄, filtered and evaporated. The crude compound was purified by column chromatography (SiO₂) by using MeOH: CHCl₃ (5:95) to afford N-(2-hydroxy-4-methylquinolin-6-yl)-5-(morpholine-4-carbonyl)-2-morpholinobenzamide (Compound-112) (25 mg) as an off white solid.

¹H NMR (300 MHz, DMSO-d₆) δ 11.56 (s, 1H), 10.47 (s, 1H), 8.13 (d, J=2.3 Hz, 1H), 7.81 (dd, J=8.9, 2.3 Hz, 1H), 7.47-7.08 (m, 3H), 6.80 (d, J=8.5 Hz, 1H), 6.42 (s, 1H), 3.91 (s, 2H), 3.28-3.19 (m, 4H), 2.39 (s, 3H), 1.90-1.82 (m, 4H).

Synthesis Compound-113

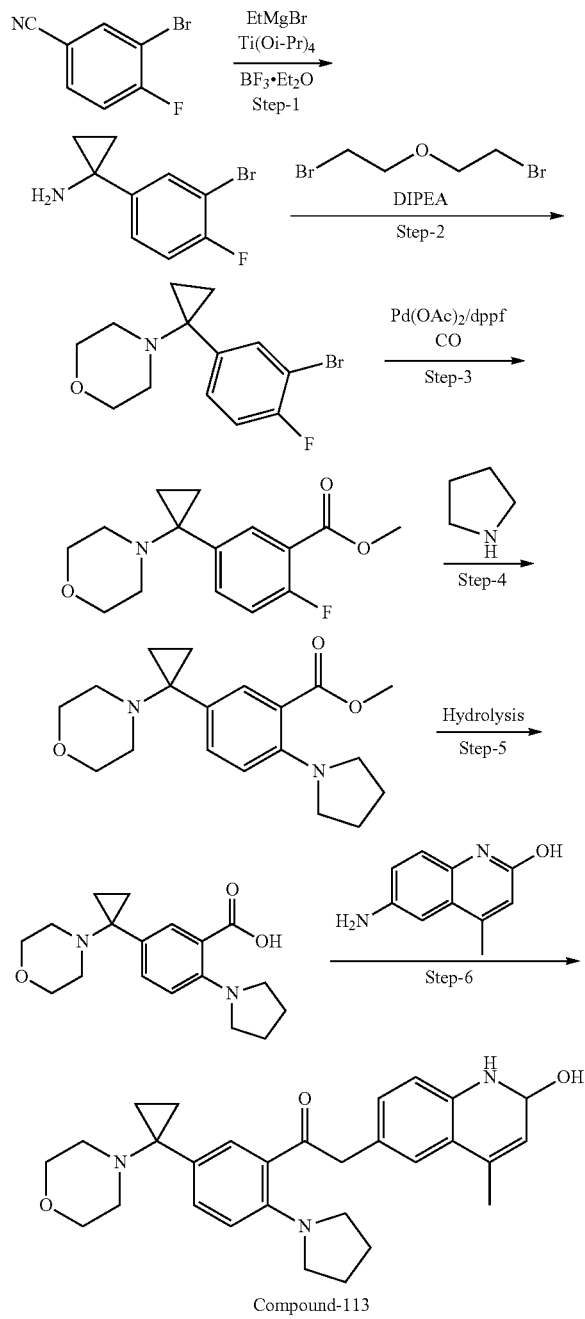

Compound-113

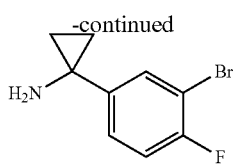

Preparation of 1-(3-bromo-4-fluorophenyl) cyclopropanamine: to a solution of 3-bromo-4-fluorobenzonitrile (10 g, 50 mmol, 1 eq) in dry ether (400 mL) at −78° C. was added titanium isopropoxide (15.63 mL, 55 mmol, 1.1 eq), EtMgBr (36.6 mL, 110 mmol, 2.2 eq) as drop wise, the resulting yellow suspension was warmed to RT over 1 h. After stirring for additional 30 min, BF₃.Et₂O (12.34 mL, 100 mmol, 2 eq) was added to reaction mixture at RT and the mixture was further stirred for 1 h. After completion, the reaction mixture was quenched with 1N HCl (200 mL) and then basified with 5N NaOH. The aqueous layer was extracted with diethyl ether (2×200 mL). The combined extracts were washed with water (100 mL), brine (100 mL), dried over anhydrous Na₂SO₄, filtered and evaporated. The crude residue was purified by combiflash to get 1-(3-bromo-4-fluorophenyl) cyclopropanamine (8 g) as a brown liquid.

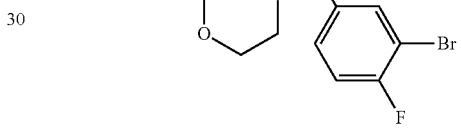

Preparation of 4-(1-(3-bromo-4-fluorophenyl) cyclopropyl) morpholine: to a solution of 1-(3-bromo-4-fluorophenyl) cyclopropanamine (8 g, 34.78 mmol, 1 eq) in DMF (50 mL) was added K₂CO₃ (24 g, 173.9 mmol, 5 eq) and 1-bromo-2-(2-bromoethoxy) ethane (9.67 g, 41.73 mmol, 1.2 eq), stirred for 5 h at 80° C. After completion, the reaction mixture was poured into water (100 mL) and extracted with EtOAc (2×200 mL). The combined extracts were washed with water (100 mL), brine (100 mL), dried over anhydrous Na₂SO₄, filtered and evaporated. The crude product was purified by column chromatography (100-200 mesh silica EtOAc:Hexane (1:9)) to get 4-(1-(3-bromo-4-fluorophenyl) cyclopropyl) morpholine (5.1 g) as a pale yellow liquid.

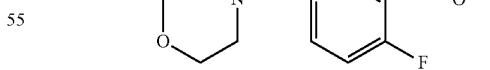

Preparation of methyl 2-fluoro-5-(1-morpholinocyclopropyl) benzoate: to a solution of 4-(1-(3-bromo-4-fluorophenyl) cyclopropyl) morpholine (3.0 g, 10 mmol, 1 eq) in MeOH: DMF (DMF (2.5 vols) & MeOH (4 vols)) was added TEA (2 g, 20 mmol, 2 eq), dppf (0.55 g, 1.0 mmol, 1 eq) and degassed for 15 min then added Pd(OAc)₂ (336 mg, 5 mmol, 0.05 eq). The reaction mixture was stirred at 80° C. for 24 h under CO pressure (100 psi). After completion, the solvent was evaporated; the crude was taken in water (100 mL) and extracted with EtOAc (2×200 mL). The combined extracts were washed with water (100 mL), brine solution (100 mL), dried over anhydrous $Na_2SO_4$, filtered and evaporated, The crude residue was purified by column chromatography (100-200 mesh silica, EtOAc:Hexane (15:85)) to get methyl 2-fluoro-5-(1-morpholinocyclopropyl)benzoate (Compound-4) (2.0 gm) as an off white solid.

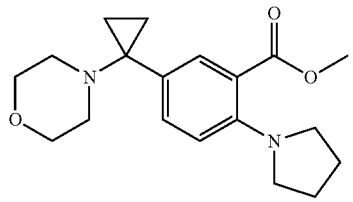 [SMILES: COC(=O)c1cc(C2(N3CCOCC3)CC2)ccc1N1CCCC1]

Preparation of methyl 5-(1-morpholinocyclopropyl)-2-(pyrrolidin-1-yl) benzoate: to a solution of methyl 2-fluoro-5-(1-morpholinocyclopropyl)benzoate (1.0 g, 3.58 mmol, 1 eq) in Dry DMSO (10 mL) was added pyrrolidine (0.508 gm, 7.16 mmol, 2 eq), $K_2CO_3$ (2.4 gm, 17.9 mmol, 5 eq) and stirred at 50° C. for 16 h. After completion the reaction mixture was poured into ice water and extracted with EtOAc (3×20 mL). The combined extracts were washed with water (20 mL), brine (20 mL), dried over anhydrous $Na_2SO_4$, filtered and evaporated. The crude compound was purified by column chromatography using (100-200 mesh silica, EtOAc:Hexane (1:9)) to afford methyl 5-(1-morpholinocyclopropyl)-2-(pyrrolidin-1-yl) benzoate (1.1 g) as an off white solid.

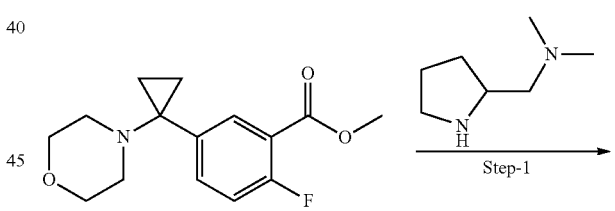

Preparation of 5-(1-morpholinocyclopropyl)-2-(pyrrolidin-1-yl) benzoic acid: to a solution of methyl 5-(1-morpholinocyclopropyl)-2-(pyrrolidin-1-yl) benzoate (1.1 g, 3.33 mmol, 1 eq) in MeOH:$H_2O$ (20 mL) at RT was added LiOH (419 mg, 9.99 mmol, 3 eq) and stirred at 80° C. for 16 h. After completion, the solvent was evaporated and the residue was taken in water and neutralized with 1N HCl. The solid formed was filtered and washed with ether to afford 5-(1-morpholinocyclopropyl)-2-(pyrrolidin-1-yl) benzoic acid (0.7 g) as an off white solid.

$^1$H NMR (300 MHz, DMSO-$d_6$) δ 13.38 (s, 1H), 7.42 (d, J=2.1 Hz, 1H), 7.23 (dd, J=8.5, 2.2 Hz, 1H), 6.89 (d, J=8.5 Hz, 1H), 3.47 (t, J=4.4 Hz, 4H), 3.25-3.10 (m, 4H), 2.39 (t, J=4.4 Hz, 4H), 1.90 (q, J=4.6, 3.3 Hz, 4H), 0.84 (q, J=3.8, 3.3 Hz, 2H), 0.68 (q, J=3.9 Hz, 2H).

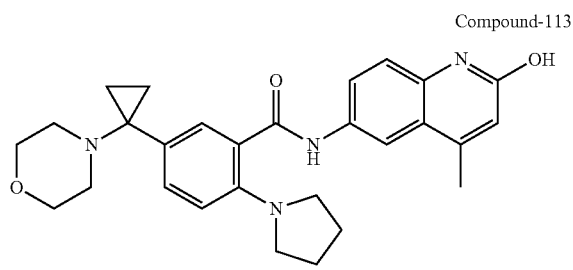 [SMILES: Cc1cc(O)nc2ccc(NC(=O)c3cc(C4(N5CCOCC5)CC4)ccc3N3CCCC3)cc12]

Compound-113

Preparation of N-(4-methyl-2-oxo-1,2-dihydroquinolin-6-yl)-5-(1-morpholinocyclopropyl)-2-(pyrrolidin-1-yl)benzamide (Compound-113): to a solution of 5-(1-morpholinocyclopropyl)-2-(pyrrolidin-1-yl)benzoic acid (200 mg, 0.632 mmol, 1 eq), in Dry DMF (5 mL) added EDC.HCl (241 mg, 1.26 mmol, 2 eq), HOAT (171 mg, 1.26 mmol, 2 eq) and DIPEA (3 eq) allowed to stir at RT for 15 min's next added 6-amino-4-methylquinlin-2-ol (Compound-7) (132 mg, 0.75 mmol, 1.2 eq), and stirred at RT for 16 h. After completion, the reaction mixture was poured into water and precipitated solid was filtered. The crude compound was purified by column chromatography (100-200 mesh silica, MeOH:DCM (4:96)) to afford N-(4-methyl-2-oxo-1, 2-dihydroquinolin-6-yl)-5-(1-morpholino cyclopropyl)-2-(pyrrolidin-1-yl) benzamide (Compound-113) (210 mg) as a pale yellow solid.

$^1$H NMR (300 MHz, DMSO-$d_6$) δ 11.55 (s, 1H), 10.41 (s, 1H), 8.18 (d, J=2.3 Hz, 1H), 7.80 (dd, J=8.8, 2.3 Hz, 1H), 7.32-7.13 (m, 3H), 6.76 (d, J=8.3 Hz, 1H), 6.42 (s, 1H), 3.48 (t, J=4.4 Hz, 4H), 3.28-3.18 (m, 4H), 2.53-2.37 (m, 7H), 1.93-1.65 (m, 4H), 0.86-0.82 (m, 2H), 0.70 (m, 2H).

Synthesis of Compound-114

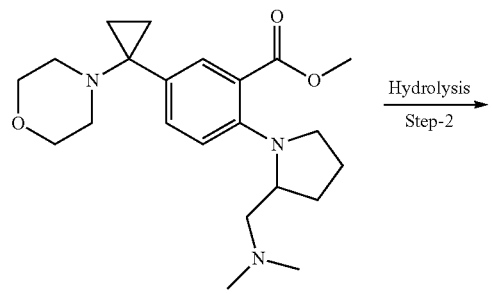

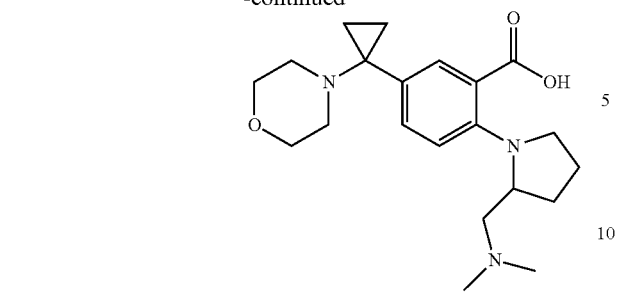
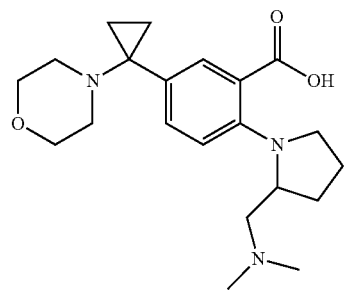 [SMILES: CN(C)CC1CCCN1c1ccc(C2(N3CCOCC3)CC2)cc1C(=O)O]

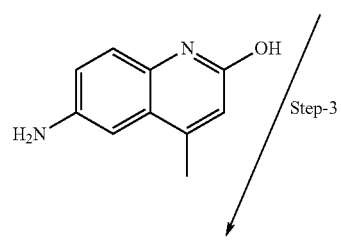

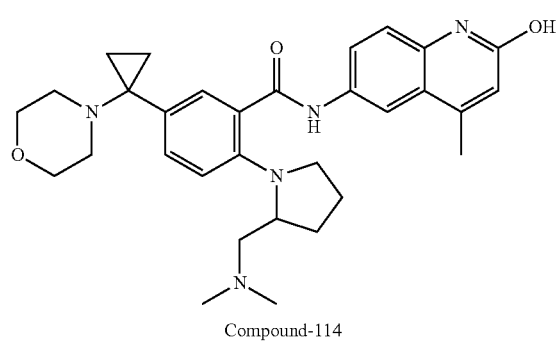

Compound-114

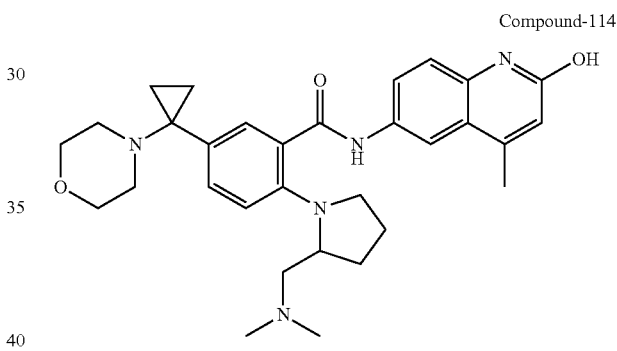

Preparation of 2-(2-((dimethylamino) methyl) pyrrolidin-1-yl)-5-(1-morpholinocyclopropyl) benzoic acid: to a solution of methyl 2-(2-((dimethylamino) methyl) pyrrolidin-1-yl)-5-(1-morpholinocyclopropyl) benzoate (100 mg, 0.258 mmol, 1 eq) in MeOH:H$_2$O (4 mL) at RT was added LiOH (32.47 mg, 0.774 mmol, 3 eq) and stirred at 80° C. for 16 h. After completion, the solvent was evaporated to afford 2-(2-((dimethylamino) methyl) pyrrolidin-1-yl)-5-(1-morpholinocyclopropyl) benzoic acid as Li salt (Compound-3) (100 mg crude) as an off white solid. The crude was carried to next step without purification.

Compound-114

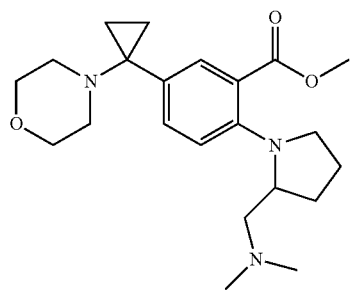

Preparation of methyl 2-(2-((dimethylamino) methyl) pyrrolidin-1-yl)-5-(1-morpholinocyclopropyl) benzoate: to a solution of methyl 2-fluoro-5-(1-morpholinocyclopropyl) benzoate (500 mg, 1.792 mmol, 1 eq) in dry DMSO (5 mL) at RT was added N,N-dimethyl-1-pyrrolidin-2-yl-methanamine (360.4 mg, 1.792 mmol, 1 eq), K$_2$CO$_3$ (741.8 mg, 5.376 mmol, 3 eq) and stirred at RT for 48 h. After completion, the reaction mixture poured into ice water, extracted with EtOAc (3×20 mL). The combined extracts were washed with water (20 mL), brine (20 mL), dried over anhydrous Na$_2$SO$_4$, filtered and evaporated. The crude compound was purified by column chromatography (SiO$_2$) by using MeOH:DCM (3:97) to afford methyl 2-(2-((dimethylamino) methyl) pyrrolidin-1-yl)-5-(1-morpholinocyclopropyl) benzoate (100 mg) as a brown liquid.

Preparation of 2-(2-((dimethylamino) methyl) pyrrolidin-1-yl)-N-(2-hydroxy-4-methylquinolin-6-yl)-5-(1-morpholinocyclopropyl) benzamide (Compound-114): to a solution of 2-(2-((dimethylamino)methyl)pyrrolidin-1-yl)-5-(1-morpholinocyclopropyl) benzoic acid Li salt (100 mg, 0.268 mmol, 1 eq) in Dry DMF (2 mL) at RT was added 6-amino-4-methyl-quinolin-2-ol (46.63 mg, 0.268 mmol, 1 eq), HOAt (72.8 mg, 0.536 mmol, 2 eq), EDC (102.7 mg, 0.536 mmol, 2 eq), DIPEA (207.4 mg, 0.1.608 mmol, 6 eq) and stirred for 48 h. After completion, the reaction mixture was poured into ice water and extracted with MeOH: CHCl$_3$ (1:9) (3×20 mL). The combined extracts were washed with water (30 mL), brine (30 mL), dried over anhydrous Na$_2$SO$_4$, filtered and evaporated. The crude compound was purified by column chromatography (SiO$_2$) by using MeOH: CHCl$_3$ (5:95) to afford 2-(2-((dimethylamino) methyl) pyrrolidin-1-yl)-N-(2-hydroxy-4-methylquinolin-6-yl)-5-(1-morpholino cyclopropyl) benzamide (Compound-114) (25 mg) as an off white solid.

$^1$H NMR (400 MHz, CD$_3$COOD) δ 8.43 (s, 1H), 8.08-7.78 (m, 2H), 7.78-7.56 (m, 1H), 7.47 (d, J=8.8 Hz, 1H), 7.29 (d, J=8.7 Hz, 1H), 6.82 (s, 1H), 4.46 (s, 1H), 4.06-3.89 (m, 4H), 3.72-3.62 (m, 2H), 3.48-3.20 (m, 7H), 2.98 (s, 6H), 2.59 (s, 3H), 1.99-1.84 (m, 4H), 1.24 (dd, J=27.0, 17.0 Hz, 3H).

Synthesis Compound-115:

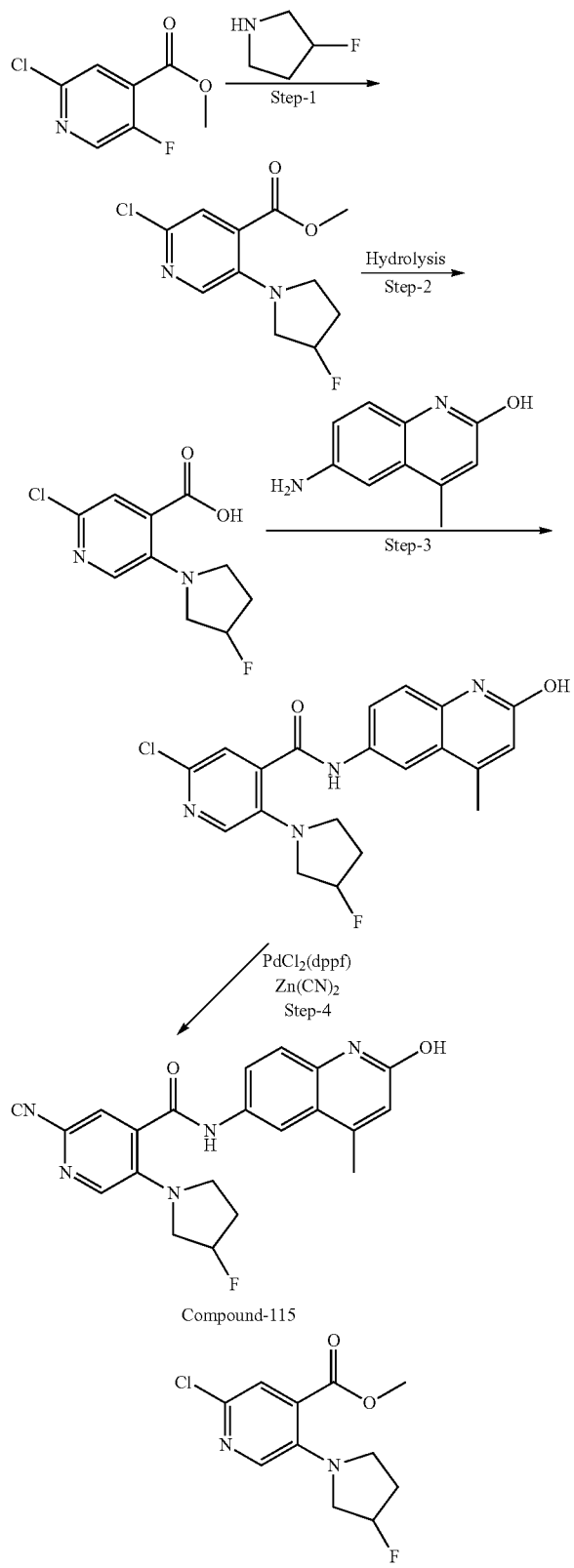

Compound-115

Preparation of methyl 2-chloro-5-(3-fluoropyrrolidin-1-yl) isonicotinate: to a solution of methyl-2-chloro-5-fluoroisonicotinate (1 g, 5.29 mmol, 1 eq) in DMSO was added 3-fluoropyrrolidine (0.73 g, 5.29 mmol, 1 eq), DIPEA (3 eq) and stirred at RT for 16 h. After completion, the reaction mixture was poured into water (50 mL) and extracted with EtOAc (3×50 mL). The combined extracts were washed with water (20 mL), brine (20 mL), dried over anhydrous $Na_2SO_4$, filtered and evaporated. The crude residue was purified by column chromatography (100-200 mesh silica, EtOAc:Hexane (15:85)) to afford methyl 2-chloro-5-(3-fluoropyrrolidin-1-yl) isonicotinate (800 mg) as a white solid.

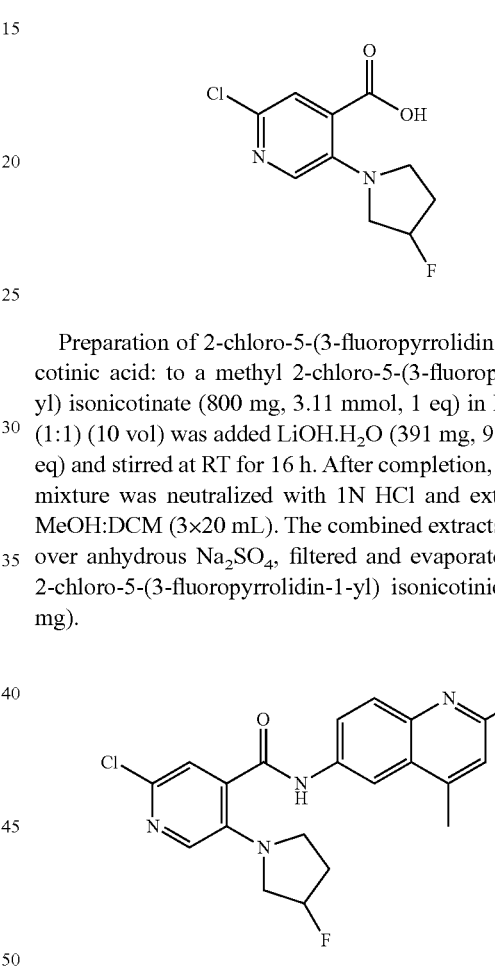

Preparation of 2-chloro-5-(3-fluoropyrrolidin-1-yl) isonicotinic acid: to a methyl 2-chloro-5-(3-fluoropyrrolidin-1-yl) isonicotinate (800 mg, 3.11 mmol, 1 eq) in MeOH:$H_2O$ (1:1) (10 vol) was added LiOH.$H_2O$ (391 mg, 9.33 mmol, 3 eq) and stirred at RT for 16 h. After completion, the reaction mixture was neutralized with 1N HCl and extracted with MeOH:DCM (3×20 mL). The combined extracts were dried over anhydrous $Na_2SO_4$, filtered and evaporated to afford 2-chloro-5-(3-fluoropyrrolidin-1-yl) isonicotinic acid (700 mg).

Preparation of 2-chloro-5-(3-fluoropyrrolidin-1-yl)-N-(2-hydroxy-4-methylquinolin-6-yl) isonicotinamide: to a solution of 2-chloro-5-(3-fluoropyrrolidin-1-yl) isonicotinic acid (700 mg, 2.73 mmol, 1 eq) in DMF was added EDC.HCl (1.04 g, 5.46 mmol, 2 eq), HOAT (742 mg, 5.46 mmol, 2 eq), DIEA (3 eq) followed by 6-amino-4-methylquinlin-2-ol (570 mg, 3.27 mmol, 1 eq) and stirred at RT for 16 h. After completion, the reaction mixture was poured into water and precipitated solid was filtered. The crude compound was purified by column chromatography (100-200 mesh silica, MeOH:DCM (5:95)) to afford 2-chloro-5-(3-fluoropyrrolidin-1-yl)-N-(2-hydroxy-4-methylquinlin-6-yl) isonicotinamide (550 mg).

Compound-115

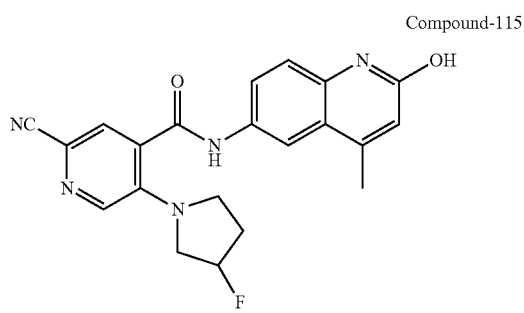 [SMILES: Cc1cc(O)nc2ccc(NC(=O)c3cc(C#N)ncc3N3CCC(F)C3)cc12]

Preparation of 2-cyano-5-(3-fluoropyrrolidin-1-yl)-N-(2-hydroxy-4-methylquinolin-6-yl) isonicotinamide (Compound-115): to a solution 2-chloro-5-(3-fluoropyrrolidin-1-yl)-N-(2-hydroxy-4-methylquinolin-6-yl) isonicotinamide (50 mg, 0.125 mmol, 1 eq) in DMF was added Zn(CN)$_2$ (17.5 mg, 0.15 mmol, 1.2 eq) and degassed with N$_2$ for 15 min, then added PdCl$_2$.dppf (10.20 mg, 0.0125 mmol, 0.3 eq). The reaction mixture heated at 150° C. for 1 h under microwave irradiation. After completion, the reaction mixture was poured into water and extracted with MeOH:DCM (1:9) (3×20 mL). The combined extracts were washed with ice water (20 mL), brine (20 mL), dried over anhydrous Na$_2$SO$_4$, filtered and evaporated. The crude compound was purified by column chromatography (100-200 mesh silica, MeOH:DCM (6:94)), to afford 2-cyano-5-(3-fluoro pyrrolidin-1-yl)-N-(2-hydroxy-4-methyl quinolin-6-yl) isonicotinamide (Compound-115) (20 mg).

$^1$H NMR (300 MHz, DMSO-d$_6$) δ 11.61 (s, 1H), 10.75 (s, 1H), 8.30 (s, 1H), 8.09 (d, J=2.3 Hz, 1H), 7.94 (s, 1H), 7.78 (d, J=9.0 Hz, 1H), 7.31 (d, J=8.9 Hz, 1H), 6.44 (s, 1H), 5.43 (m, 1H), 3.92-3.45 (m, 4H), 2.40 (s, 2H), 1.24 (s, 2H).

Synthesis of Compound-116

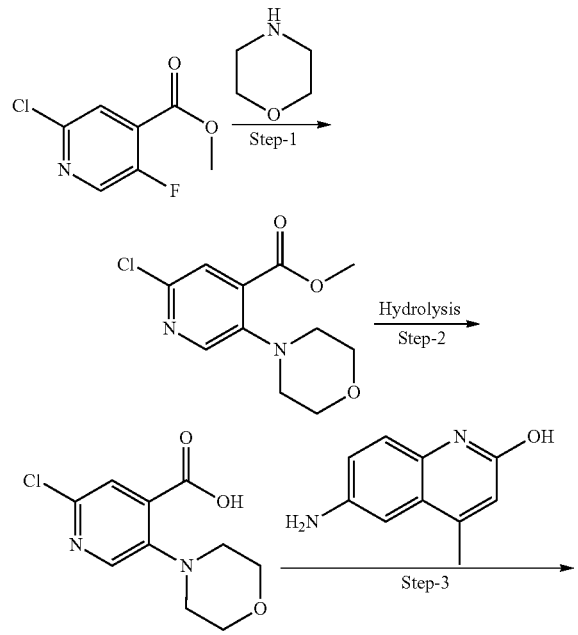

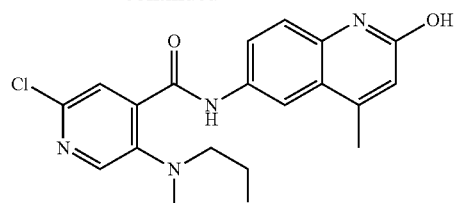

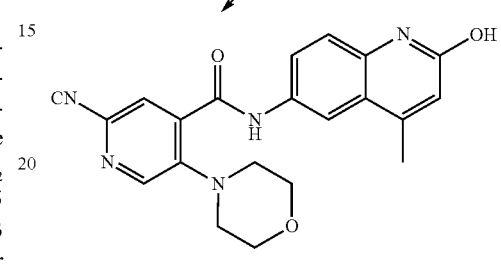

Compound-116

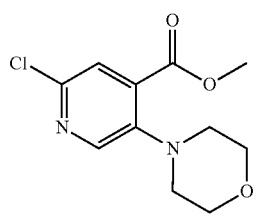

Preparation of methyl 2-chloro-5-morpholinoisonicotinate: to a solution of methyl 2-chloro-5-fluoroisonicotinate (2 g, 10.58 mmol, 1 eq) in DMSO added morpholine (1.1 g, 12.69 mmol, 1.2 eq), DIPEA (3 eq) and stirred at RT for 16 h. After completion, the reaction mixture was poured into water (50 mL) and extracted with EtOAc (3×20 mL). The combined extracts were washed with water (30 mL), brine (30 mL), dried over anhydrous Na$_2$SO$_4$, filtered and evaporated. The crude residue was purified by column chromatography (100-200 mesh silica EtOAc:Hexane (15:85)), to afford methyl 2-chloro-5-morpholinoisonicotinate (2 g).

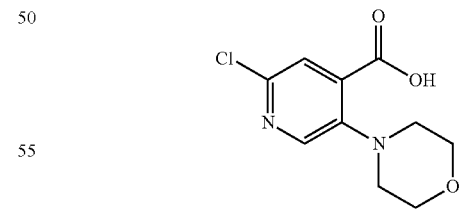

Preparation of 2-chloro-5-morpholinoisonicotinic acid: to a solution of methyl 2-chloro-5-morpholinoisonicotinate (1.5 g, 5.85 mmol, 1 eq) in MeOH:H$_2$O (1:1) (10 vol) added LiOH.H$_2$O (0.737 g, 17.55 mmol, 3 eq) and stirred at RT for 16 h. After completion reaction mixture was diluted with water and acidified with 1N HCl. The solid precipitated was filtered and dried to afford 2-chloro-5-morpholinoisonicotinic acid (1 g) as a white solid.

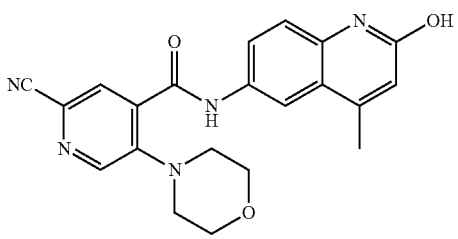 [SMILES: Cc1cc(O)nc2ccc(NC(=O)c3cc(C#N)ncc3N3CCOCC3)cc12]

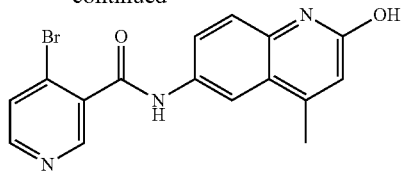

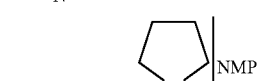

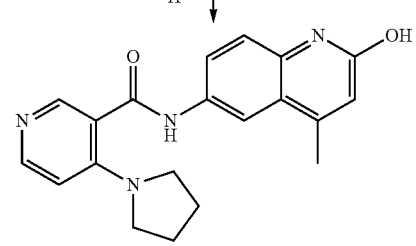

Compound-117

Preparation of 2-chloro-N-(2-hydroxy-4-methylquinolin-6-yl)-5-morpholinoisonicotinamide: to a solution of 2-chloro-5-morpholinoisonicotinic acid (1 g, 4.13 mmol, 1 eq) in DMF was added EDC.HCl (1.57 g, 8.26 mmol, 2 eq), HOAt (1.12 mg, 8.26 mmol, 2 eq) and DIPEA (3 eq) followed by 6-amino-4-methylquinlin-2-ol (0.862 mg, 4.95 mmol, 1 eq), and stirred at RT for 16 h. After completion, the reaction mixture was poured into water and precipitated solid was filtered and washed with diethyl ether to afford 2-chloro-N-(2-hydroxy-4-methylquinolin-6-yl)-5-morpholinoisonicotinamide (650 mg) as a pale yellow solid.

Compound-116

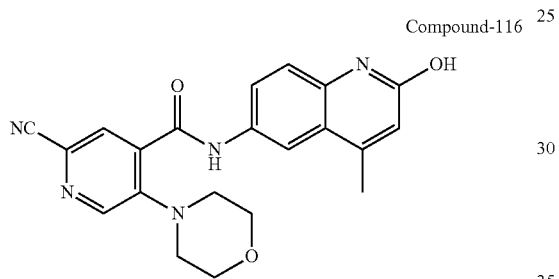

Preparation of 2-cyano-N-(2-hydroxy-4-methylquinolin-6-yl)-5-morpholinoisonicotinamide (Compound-116): to a solution of 2-chloro-N-(2-hydroxy-4-methylquinolin-6-yl)-5-morpholinoisonicotinamide (650 mg, 1.625 mmol, 1 eq) in DMF was added $Zn(CN)_2$ (380 mg, 3.25 mmol, 2 eq) and degassed with $N_2$ for 15 min, then added $PdCl_2.dppf$ (132 mg, 0.1625 mmol, 0.1 eq). The reaction mixture heated at 150° C. for 1 h under microwave irradiation. After completion, the reaction mixture was poured into water and extracted with MeOH:DCM (3×20 mL). The combined extracts were washed with ice water (50 mL), brine (50 mL), dried over anhydrous $Na_2SO_4$, filtered and evaporated. The crude compound was purified by column chromatography (100-200 mesh silica, MeOH:DCM (6:94)), to afford 2-cyano-N-(2-hydroxy-4-methylquinolin-6-yl)-5-morpholinoisonicotinamide (Compound-116) (160 mg) as an off white solid.

$^1$H NMR (300 MHz, DMSO-$d_6$) δ 11.62 (s, 1H), 10.70 (s, 1H), 8.55 (s, 1H), 8.11 (d, J=2.3 Hz, 1H), 8.00 (s, 1H), 7.76 (dd, J=8.8, 2.3 Hz, 1H), 7.32 (d, J=8.8 Hz, 1H), 6.44 (s, 1H), 3.66 (t, J=4.5 Hz, 4H), 3.32 (s, 4H), 2.40 (s, 3H).

Synthesis of Compound-117

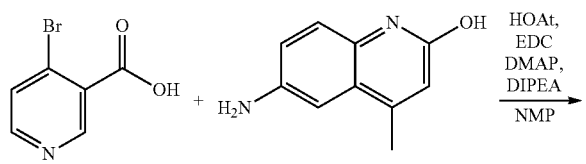

Preparation of 4-bromo-N-(2-hydroxy-4-methyl-6-quinolyl)pyridine-3-carboxamide: to a solution of 4-bromopyridine-3-carboxylic acid (125 mg, 0.62 mmo, 1 eq) in NMP (2 mL) were added 6-amino-4-methyl-quinolin-2-ol (118 mg, 0.68 mmol, 1.1 eq), HOAt, (126 mg, 0.93 mmol, 1.5 eq), EDC (180 mg, 0.93 mmol, 1.5 eq), DMAP (15 mg, 0.12 mmol, 0.2 eq) and DIPEA (323 µl, 1.86 mmol, 3 eq). The mixture was stirred at room temperature for 2 h. Water was added to the reaction mixture resulting in precipitation which was filtered of and dried to yield 4-bromo-N-(2-hydroxy-4-methyl-6-quinolyl)pyridine-3-carboxamide (100 mg, 45%) as a purple solid.

The crude product was used without purification in the synthesis of N-(2-hydroxy-4-methyl-6-quinolyl)-4-pyrrolidin-1-yl-pyridine-3-carboxamide.

LCMS: (M+H)=358, UV=57%

Compound-117

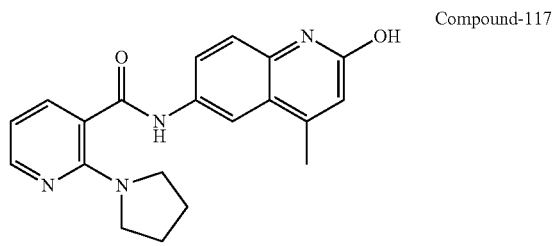 [SMILES: Cc1cc(O)nc2ccc(NC(=O)c3cccnc3N3CCCC3)cc12]

Preparation of N-(2-hydroxy-4-methyl-6-quinolyl)-4-pyrrolidin-1-yl-pyridine-3-carboxamide (Compound-117): 4-bromo-N-(2-hydroxy-4-methyl-6-quinolyl)pyridine-3-carboxamide (30 mg, 0.084 mmol, 1 eq) was dissolved in NMP (0.5 mL). Pyrrolidine (59 µL, 0.84 mmol, 10 eq) was added and the reaction mixture heated at 120° C. for 1 hour. Water was added (25 ml). The precipitated compound was spun down in a centrifuge, washed with water and EtOAC and dried to yield N-(2-hydroxy-4-methyl-6-quinolyl)-4-pyrrolidin-1-yl-pyridine-3-carboxamide (14 mg, 48%) as a light brown solid. LCMS: (M+H)=349, UV=94%.

$^1$H NMR (300 MHz, DMSO-$d_6$) δ 11.56 (s, 1H), 10.53 (s, 1H), 8.22 (s, 1H), 8.20-8.08 (m, 2H), 7.81 (dd, J=8.8, 2.2 Hz, 1H), 7.28 (d, J=8.8 Hz, 1H), 6.64 (d, J=6.1 Hz, 1H), 6.42 (s, 1H), 3.33-3.22 (m, 4H), 2.39 (d, J=1.2 Hz, 3H), 1.97-1.79 (m, 4H).

Synthesis of Compound-118

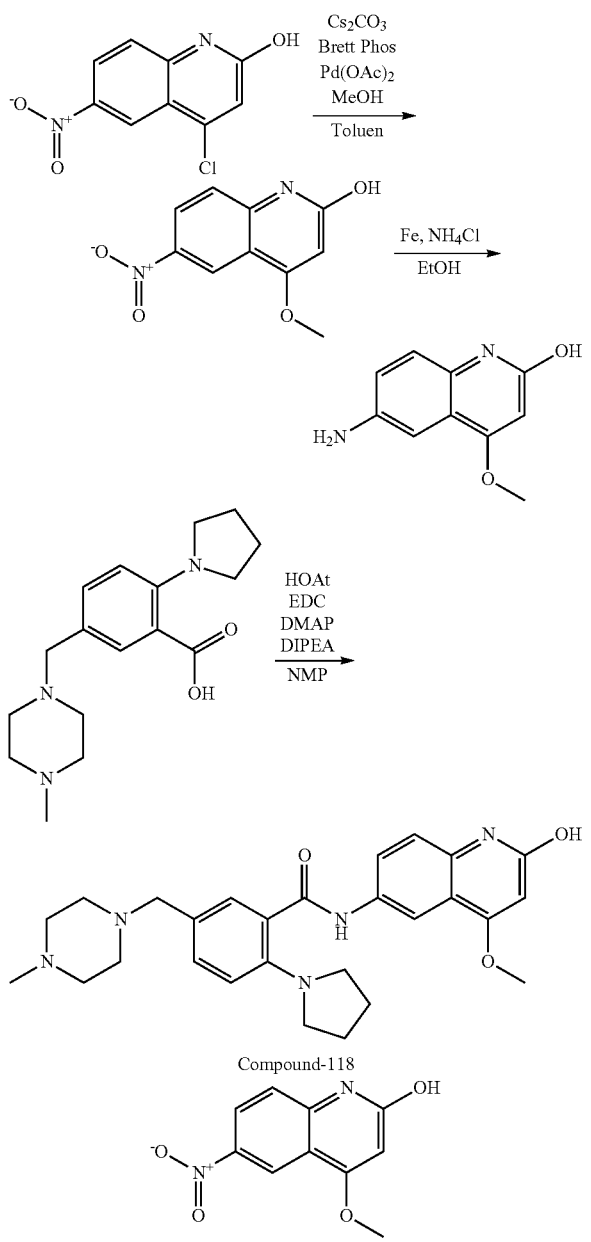

Preparation of 4-methoxy-6-nitro-quinolin-2-ol: a mixture of 4-chloro-6-nitro-quinolin-2-ol (200 mg, 0.59 mmol, 1 eq) and Cs$_2$CO$_3$ (107 mg, 0.43 mmol, 1.5 eq) in MeOH (1 mL) was evacuated and filled with N$_2$. Pd(OAc)$_2$ (8 mg, 0.04 mmol, 0.08 eq) and Brett Phos (25 mg, 0.05 mmol, 0.06 eq) were added and the mixture stirred at 75° C. overnight. Evaporated on celite and purified by flash chromatography yielding (DCM/MeOH) 4-methoxy-6-nitro-quinolin-2-ol (51 mg, 39%) as an off-white solid. LCMS: (M+H)=221, UV=92%.

$^1$H NMR (300 MHz, DMSO-$d_6$) δ 11.98 (s, 1H), 8.55 (t, J=2.0 Hz, 1H), 8.36 (ddd, J=9.0, 2.8, 1.3 Hz, 1H), 7.43 (dd, J=9.1, 1.3 Hz, 1H), 6.07 (s, 1H), 3.99 (s, 3H).

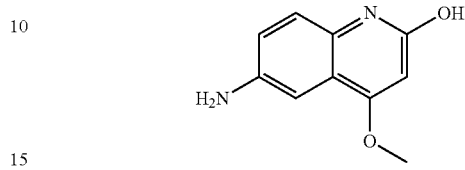

Preparation of 6-amino-4-methoxy-quinolin-2-ol

A suspension of 4-methoxy-6-nitro-quinolin-2-ol (168 mg, 0.78 mmol, 1 eq) and saturated NH$_4$Cl (4 mL) in EtOH (4 mL) was heated at reflux. Iron powder (39 mg, 0.69 mmol, 3 eq) was added. After 45 minutes at reflux the mixture was cooled and poured into water and extracted with EtOAc. Dried over Na$_2$SO$_4$ filtered and evaporated to yield 6-amino-4-methoxy-quinolin-2-ol (74 mg, 51%) as a beige coloured solid. LCMS: (M+H)=191, UV=95%.

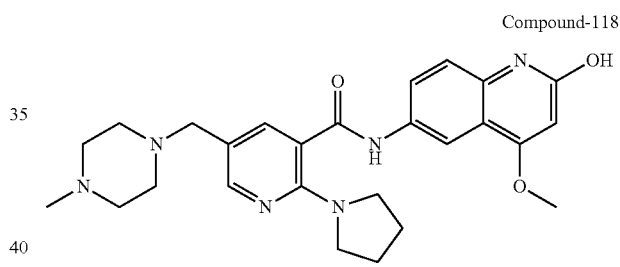

Compound-118

Preparation of N-(2-hydroxy-4-methoxy-6-quinolyl)-5-[(4-methylpiperazin-1-yl)methyl]-2-pyrrolidin-1-yl-benzamide (compound-118): to a suspension of 4-methoxy-6-nitro-quinolin-2-ol (15 mg, 0.079, 1 eq) in NMP (1 mL) were added 5-[(4-methylpiperazin-1-yl)methyl]-2-pyrrolidin-1-yl-benzoic acid (24 mg, 0.079 mmol, 1 eq), HOAt (16 mg, 0.12 mmol, 1.5 eq), EDC (23 mg, 0.12 mmol, 1.5 eq) DMAP (2 mg, 0.016 mmol, 0.2 eq) and DIPEA (41 μL, 0.24 mmol, 3 eq) and the reaction mixture was stirred overnight at 60° C. Water was added and the mixture extracted with EtOAc, dried over Na$_2$SO$_4$, filtered and evaporated to dryness. The crude product was purified by flash chromatography (DCM/MeOH/NH$_3$-aq) yielding N-(2-hydroxy-4-methoxy-6-quinolyl)-5-[(4-methylpiperazin-1-yl)methyl]-2-pyrrolidin-1-yl-benzamide (compound 118) (14 mg, 37%) as a light brown solid. LCMS (M+H)=476, UV=90% pure.

$^1$H NMR (300 MHz, Chloroform-d) δ 11.78 (s, 1H), 11.01 (s, 1H), 8.27 (d, J=2.4 Hz, 1H), 7.91 (d, J=2.2 Hz, 1H), 7.63 (dd, J=8.8, 2.4 Hz, 1H), 7.34-7.25 (m, 2H), 7.03 (d, J=8.3 Hz, 1H), 5.95 (s, 1H), 3.92 (s, 3H), 3.51 (s, 2H), 3.23-3.11 (m, 4H), 2.58 (s, 9H), 2.35 (s, 3H), 1.96 (dd, J=6.8, 3.4 Hz, 5H).

Synthesis of Compound-119, Compound-120 and Compound-121

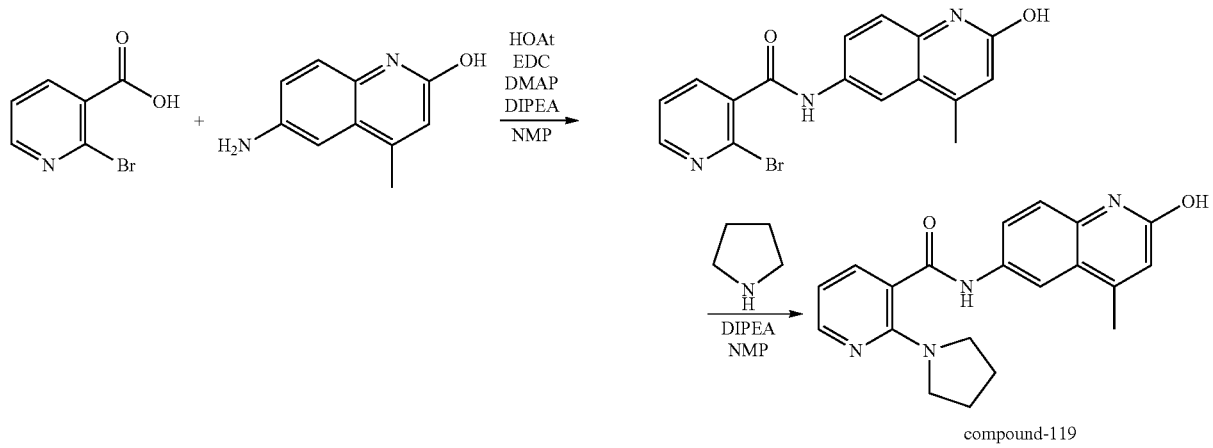

compound-119

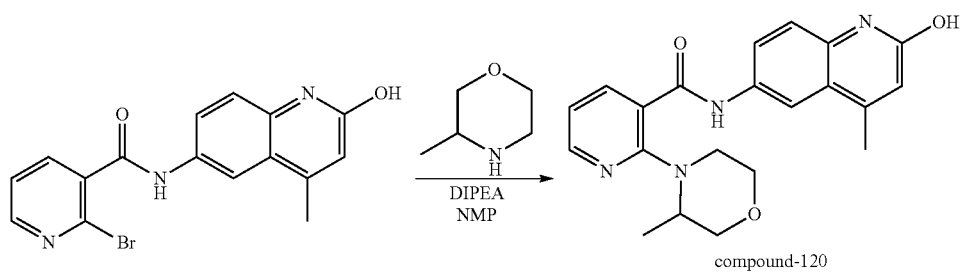

compound-120

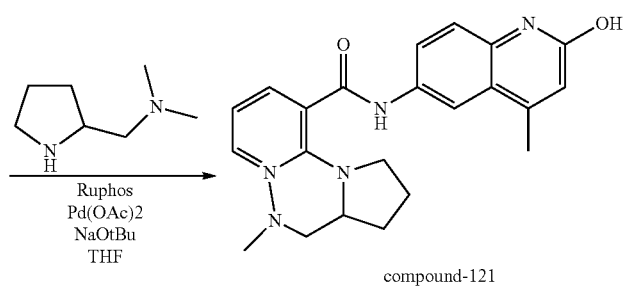

compound-121

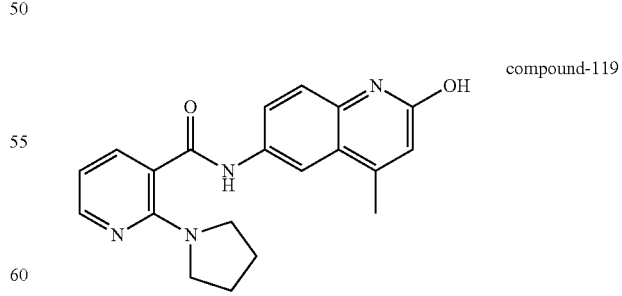

compound-119

Preparation of 2-bromo-N-(2-hydroxy-4-methyl-6-quinolyl)pyridine-3-carboxamide: to a solution of 2-bromopyridine-3-carboxylic acid (125 mg, 0.62 mmol, 1 eq) in NMP (1 mL) were added 6-amino-4-methyl-quinolin-2-ol (107 mg, 10.62 mmol, 1 eq), HOAT (127 mg, 0.93 mmol, 1.5 eq), EDC (179 mg, 0.93 mmol, 1.5 eq), DMAP (15 mg, 0.12 mmol, 0.2 eq) and DIPEA (323 µL, 1.86 mmol, 3 eq). The mixture was stirred at room temperature for 4 days. Water was added and the mixture extracted with EtOAc, dried over $Na_2SO_4$, filtered and evaporated to dryness. The crude product was purified by flash chromatography (DCM/MeOH/$NH_3$-aq) yielding 2-bromo-N-(2-hydroxy-4-methyl-6-quinolyl)pyridine-3-carboxamide (148 mg, 67%) as a reddish solid. LCMS: (M+H)=358, UV=100%.

$^1$H NMR (300 MHz, DMSO-$d_6$) δ 11.61 (s, 1H), 10.72 (s, 1H), 8.51 (dd, J=4.8, 2.0 Hz, 1H), 8.13 (d, J=2.3 Hz, 1H), 8.02 (dd, J=7.5, 2.0 Hz, 1H), 7.77 (dd, J=8.9, 2.3 Hz, 1H), 7.59 (dd, J=7.5, 4.8 Hz, 1H), 7.31 (d, J=8.9 Hz, 1H), 6.44 (d, J=1.4 Hz, 1H), 2.40 (d, J=1.2 Hz, 3H).

Preparation of N-(2-hydroxy-4-methyl-6-quinolyl)-2-pyrrolidin-1-yl-pyridine-3-carboxamide (compound-119): to a solution of 2-bromo-N-(2-hydroxy-4-methyl-6-quinolyl)pyridine-3-carboxamide (100 mg, 0.28 mmol, 1 eq) in NMP (1 mL) were added pyrrolidine (100 µl, 1.4 mmol, 5 eq) and DIPEA (146 μl, 0.84 mmol, 3 eq). The reaction mixture was heated at 150° C. for 30 min in a micro wave oven. The reaction mixture was poured into water. Precipitated compound was filtered of and dried yielding N-(2-hydroxy-4-methyl-6-quinolyl)-2-pyrrolidin-1-yl-pyridine-3-carboxamide (compound 119) (90 mg, 98%) as a white solid. LCMS: (M+H)=349, UV=100%.

$^1$H NMR (300 MHz, DMSO-$d_6$) δ 11.55 (s, 1H), 10.44 (s, 1H), 8.18 (dd, J=4.8, 1.9 Hz, 1H), 8.12 (d, J=2.2 Hz, 1H), 7.80 (dd, J=8.8, 2.2 Hz, 1H), 7.64 (dd, J=7.4, 1.9 Hz, 1H), 7.28 (d, J=8.8 Hz, 1H), 6.66 (dd, J=7.4, 4.8 Hz, 1H), 6.42 (d, J=1.4 Hz, 1H), 3.47-3.37 (m, 4H), 2.39 (s, 3H), 1.88-1.79 (m, 4H).

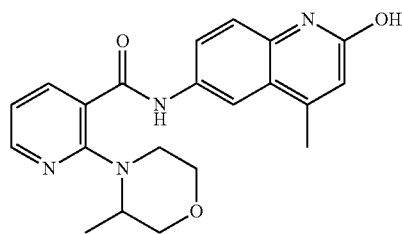

compound-120

Preparation of N-(2-hydroxy-4-methyl-6-quinolyl)-2-(3-methylmorpholin-4-yl)pyridine-3-carboxamide (compound-120): synthesized according to the procedure used in the synthesis of N-(2-hydroxy-4-methyl-6-quinolyl)-2-pyrrolidin-1-yl-pyridine-3-carboxamide (compound-119). Yield: 28 mg, 53%. LCMS (M+H)=379, UV=100% pure.

$^1$H NMR (300 MHz, DMSO-$d_6$) δ 11.61 (s, 1H), 11.07 (s, 1H), 8.40 (dd, J=4.8, 1.9 Hz, 1H), 8.20 (d, J=2.2 Hz, 1H), 7.97 (dd, J=7.5, 1.9 Hz, 1H), 7.79 (dd, J=8.8, 2.2 Hz, 1H), 7.32 (d, J=8.8 Hz, 1H), 7.08 (dd, J=7.5, 4.8 Hz, 1H), 6.44 (s, 1H), 3.80 (ddt, J=14.6, 7.3, 3.8 Hz, 2H), 3.64 (td, J=11.3, 3.8 Hz, 2H), 3.52 (dd, J=11.2, 3.8 Hz, 1H), 3.27 (dt, J=7.8, 3.7 Hz, 2H), 3.17 (d, J=5.1 Hz, 1H), 2.40 (d, J=1.2 Hz, 3H), 1.02 (d, J=6.6 Hz, 3H).

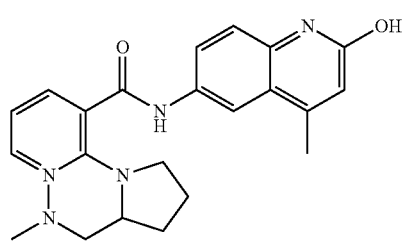

compound-121

Preparation of 2-[2-(dimethylaminomethyl)pyrrolidin-1-yl]-N-(2-hydroxy-4-methyl-6-quinolyl)pyridine-3-carboxamide (compound-121): a mixture of 2-bromo-N-(2-hydroxy-4-methyl-6-quinolyl)pyridine-3-carboxamide (36 mg, 0.1 mmol, 1 eq), N,N-dimethyl-1-pyrrolidin-2-yl-methanamine hydro chloric acid (24 mg, 0.12 mmol, 1.2 eq) and Potassium tertbutoxide (35 mg, 0.36 mmol, 3.6 eq) in THF (1 mL) was evaporated and filled with $N_2$ three times. Ruphos and Palladium(II) acetate were added. The mixture was heated overnight at 75° C. Water was added and the mixture extracted with EtOAc, dried over $Na_2SO_4$, filtered and evaporated to dryness. The crude product was purified by flash chromatography (DCM/MeOH/$NH_3$-aq) to yield 2-[2-(dimethylaminomethyl)pyrrolidin-1-yl]-N-(2-hydroxy-4-methyl-6-quinolyl)pyridine-3-carboxamide (compound 121) (20 mg, 49%) as an off-white solid. LCMS (M+H)=406, UV=96% pure $^1$H NMR (300 MHz, Chloroform-d) δ 12.42 (s, 1H), 10.62 (s, 1H), 8.33 (d, J=2.2 Hz, 1H), 8.21 (dd, J=4.7, 2.0 Hz, 1H), 8.03 (dd, J=7.5, 2.0 Hz, 1H), 7.50 (dd, J=8.8, 2.2 Hz, 1H), 7.37 (d, J=8.7 Hz, 1H), 6.85 (dd, J=7.6, 4.7 Hz, 1H), 6.53 (d, J=1.3 Hz, 1H), 5.00-4.84 (m, 1H), 3.59-3.38 (m, 1H), 3.30 (s, 3H), 3.19-2.97 (m, 1H), 2.48 (s, 2H), 2.23 (s, 6H), 2.13-2.01 (m, 1H), 1.91-1.74 (m, 2H), 1.70-1.50 (m, 1H).

Synthesis of Compound-122

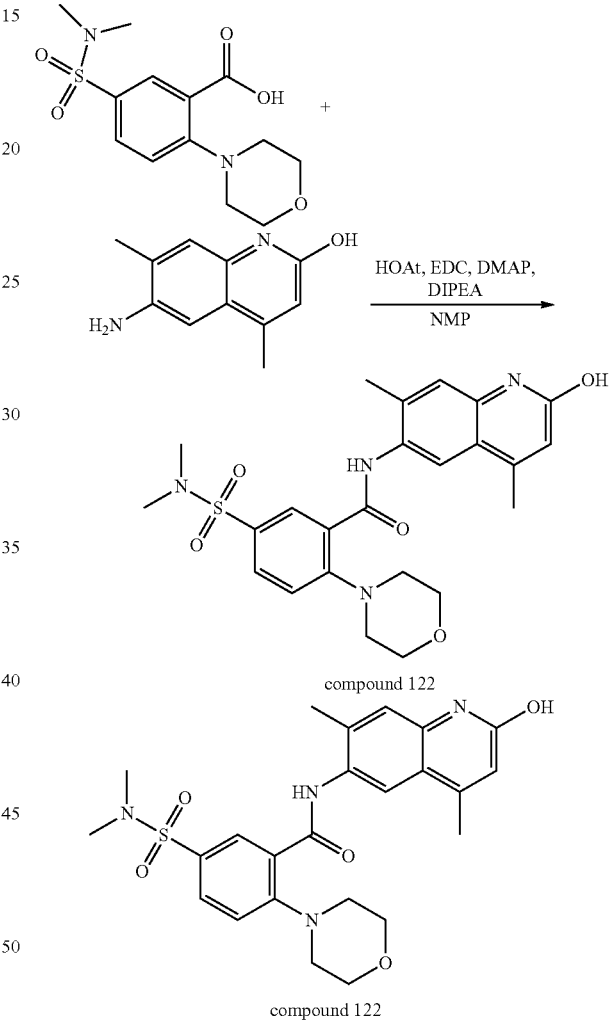

compound 122

Preparation of 5-(dimethylsulfamoyl)-N-(2-hydroxy-4,7-dimethyl-6-quinolyl)-2-morpholino-benzamide (compound-122): to a suspension of (5-(dimethylsulfamoyl)-2-morpholino-benzoic acid) (100 mg, 0.32 mmol, 1 eq) and (6-amino-4,7-dimethyl-quinolin-2-ol) (60 mg, 0.32 mmol, 1 eq) in NMP (1.5 ml) were added HOAt (65 mg, 0.48 mmol, 1.5 eq), EDC (92 mg, 0.48 mmol, 1.5 eq), DMAP (8 mg, 0.06 mmol, 0.2 eq) and DIPEA (166 μl, 0.96 mmol, 3 eq). The reaction mixture was heated at 80° C. for 90 min.

Water (50 ml) was added and the reaction mixture stirred for 30 min at room temperature. The precipitated compound was filtered off, washed with water and EtOAc. The crude product was dried on the filter yielding (5-(dimethylsulfamoyl)-N-(2-hydroxy-4,7-dimethyl-6-quinolyl)-2-morpholino-benzamide)(compound-122) (113 mg, 73%). LCMS: (M+H)=485, UV=100% pure.

¹H NMR (300 MHz, DMSO-d₆) δ 11.57 (s, 1H), 10.17 (s, 1H), 7.90-7.83 (m, 2H), 7.78 (dd, J=8.6, 2.4 Hz, 1H), 7.36 (d, J=8.6 Hz, 1H), 7.19 (s, 1H), 6.38 (s, 1H), 3.83-3.68 (m, 4H), 3.24-3.15 (m, 4H), 2.64 (s, 6H), 2.40 (s, 3H), 2.36 (s, 3H).

Synthesis of Compound-123 and Compound-124

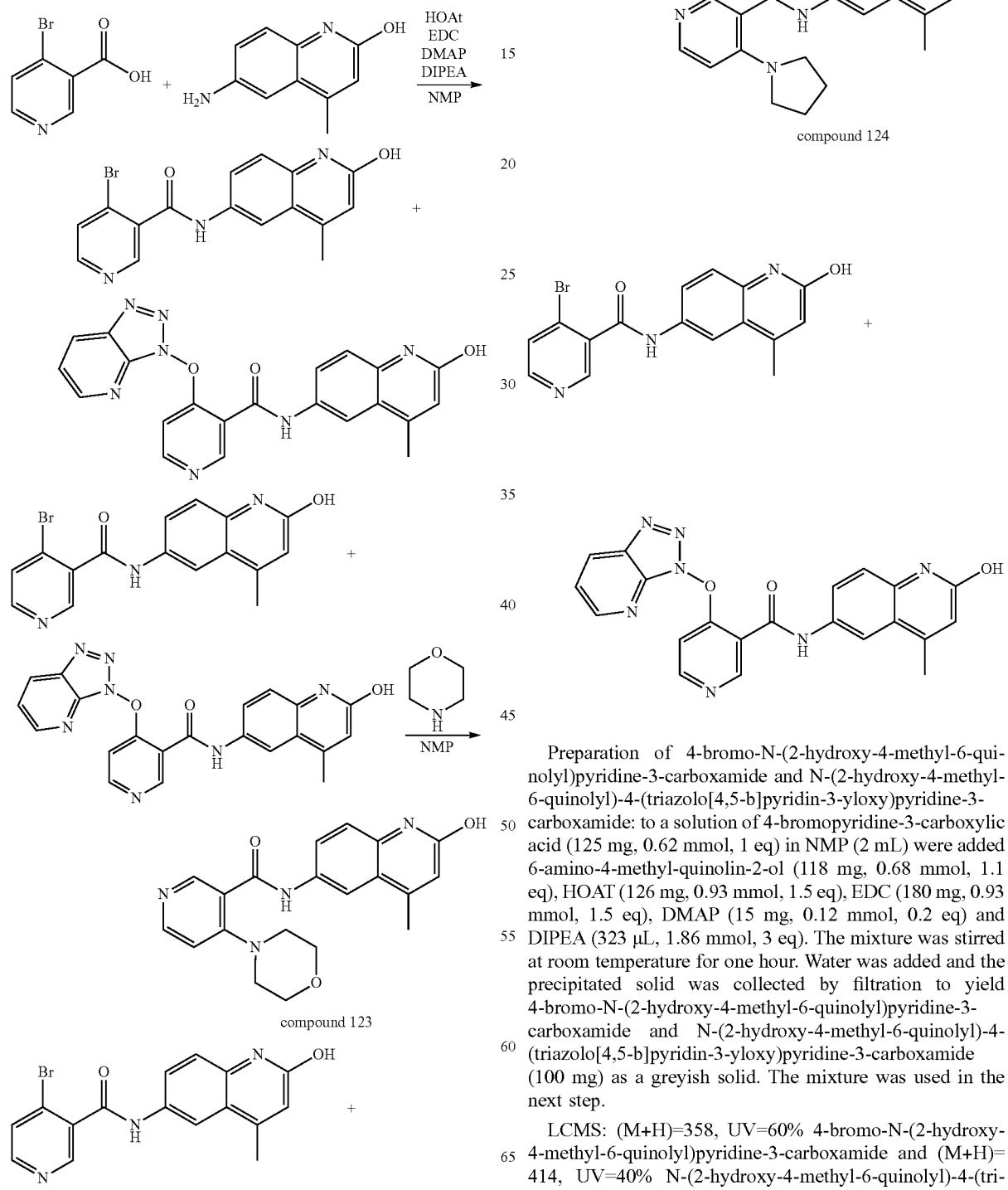

compound 123

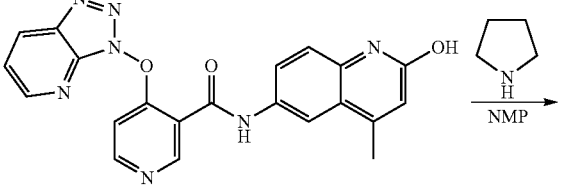

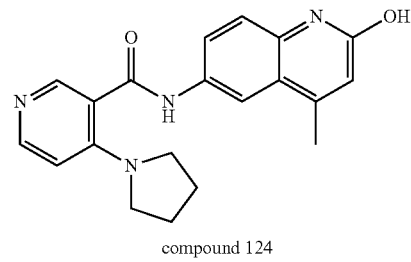

compound 124

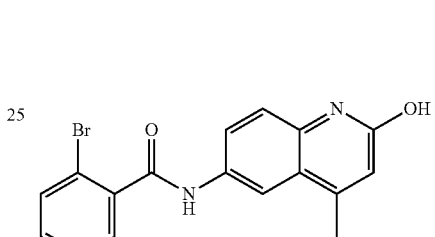

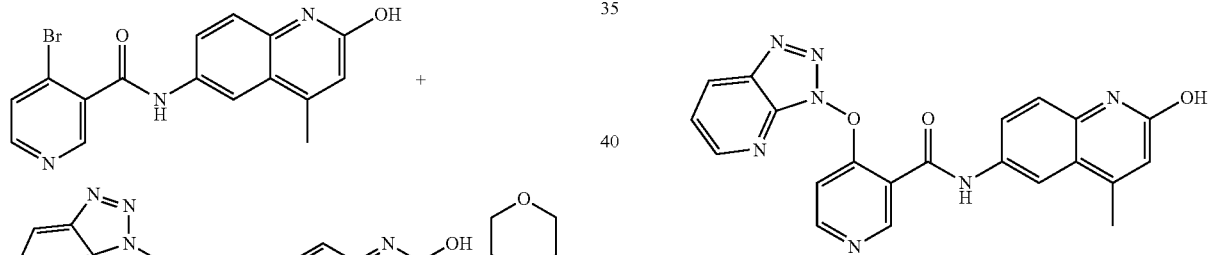

Preparation of 4-bromo-N-(2-hydroxy-4-methyl-6-quinolyl)pyridine-3-carboxamide and N-(2-hydroxy-4-methyl-6-quinolyl)-4-(triazolo[4,5-b]pyridin-3-yloxy)pyridine-3-carboxamide: to a solution of 4-bromopyridine-3-carboxylic acid (125 mg, 0.62 mmol, 1 eq) in NMP (2 mL) were added 6-amino-4-methyl-quinolin-2-ol (118 mg, 0.68 mmol, 1.1 eq), HOAT (126 mg, 0.93 mmol, 1.5 eq), EDC (180 mg, 0.93 mmol, 1.5 eq), DMAP (15 mg, 0.12 mmol, 0.2 eq) and DIPEA (323 μL, 1.86 mmol, 3 eq). The mixture was stirred at room temperature for one hour. Water was added and the precipitated solid was collected by filtration to yield 4-bromo-N-(2-hydroxy-4-methyl-6-quinolyl)pyridine-3-carboxamide and N-(2-hydroxy-4-methyl-6-quinolyl)-4-(triazolo[4,5-b]pyridin-3-yloxy)pyridine-3-carboxamide (100 mg) as a greyish solid. The mixture was used in the next step.

LCMS: (M+H)=358, UV=60% 4-bromo-N-(2-hydroxy-4-methyl-6-quinolyl)pyridine-3-carboxamide and (M+H)=414, UV=40% N-(2-hydroxy-4-methyl-6-quinolyl)-4-(triazolo[4,5-b]pyridin-3-yloxy)pyridine-3-carboxamide

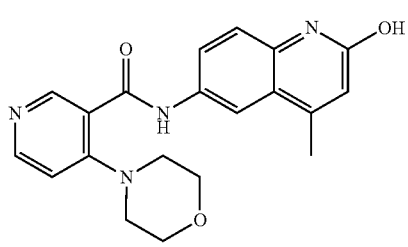
compound 123

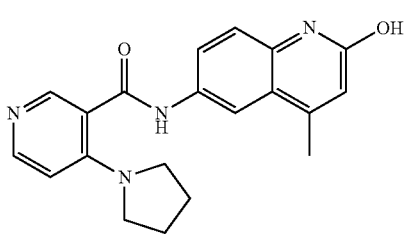
compound 124

Preparation of N-(2-hydroxy-4-methyl-6-quinolyl)-4-morpholino-pyridine-3-carboxamide (compound-123): to a solution of the mixture of 4-bromo-N-(2-hydroxy-4-methyl-6-quinolyl)pyridine-3-carboxamide and N-(2-hydroxy-4-methyl-6-quinolyl)-4-(triazolo[4,5-b]pyridin-3-yloxy)pyridine-3-carboxamide (50 mg, 0.12 mmol, 1 eq) in NMP (0.5 mL) was added morpholine (0.3 mL, 3.4 mmol, 30 eq). The reaction mixture was heated at 120° C. for 30 min. Water was added and the mixture was extracted with EtOAc, dried over Na$_2$SO$_4$, filtered and evaporated to dryness. The crude product was purified by flash chromatography (DCM/MeOH/NH$_3$-aq) yielding N-(2-hydroxy-4-methyl-6-quinolyl)-4-morpholino-pyridine-3-carboxamide (compound-123) (6 mg, 14%) as a solid. LCMS: (M+H)=365, UV=93%.

$^1$H NMR (300 MHz, Methanol-d$_4$) δ 8.51 (s, 1H), 8.39 (d, J=5.9 Hz, 1H), 8.28 (d, J=2.2 Hz, 1H), 7.92-7.79 (m, 1H), 7.41 (dd, J=8.9, 1.2 Hz, 1H), 7.08 (d, J=6.0 Hz, 1H), 6.57 (d, J=1.4 Hz, 1H), 3.86-3.72 (m, 4H), 3.32-3.20 (m, 4H), 2.55 (d, J=1.4 Hz, 3H).

Preparation of N-(2-hydroxy-4-methyl-6-quinolyl)-4-pyrrolidin-1-yl-pyridine-3-carboxamide (compound-124): to a solution of 4-bromo-N-(2-hydroxy-4-methyl-6-quinolyl)pyridine-3-carboxamide and N-(2-hydroxy-4-methyl-6-quinolyl)-4-(triazolo[4,5-b]pyridin-3-yloxy)pyridine-3-carboxamide (30 mg, 0.08 mmol, 1 eq) in NMP (1 mL) was added pyrrolidine (59 μL, 0.84 mmol, 10 eq). The reaction mixture was heated at 120° C. for 1 hour. Water was added and the precipitated solid isolated yielding N-(2-hydroxy-4-methyl-6-quinolyl)-4-pyrrolidin-1-yl-pyridine-3-carboxamide (compound-124) (14 mg, 48%) as a solid. LCMS: (M+H)=349, UV=94%.

$^1$H NMR (300 MHz, DMSO-d$_6$) δ 11.56 (s, 1H), 10.53 (s, 1H), 8.22 (s, 1H), 8.20-8.08 (m, 2H), 7.81 (dd, J=8.8, 2.2 Hz, 1H), 7.28 (d, J=8.8 Hz, 1H), 6.64 (d, J=6.1 Hz, 1H), 6.42 (s, 1H), 3.33-3.22 (m, 4H), 2.39 (d, J=1.2 Hz, 3H), 1.97-1.79 (m, 4H).

Synthesis of Compound-125, Compound-126 and Compound-127

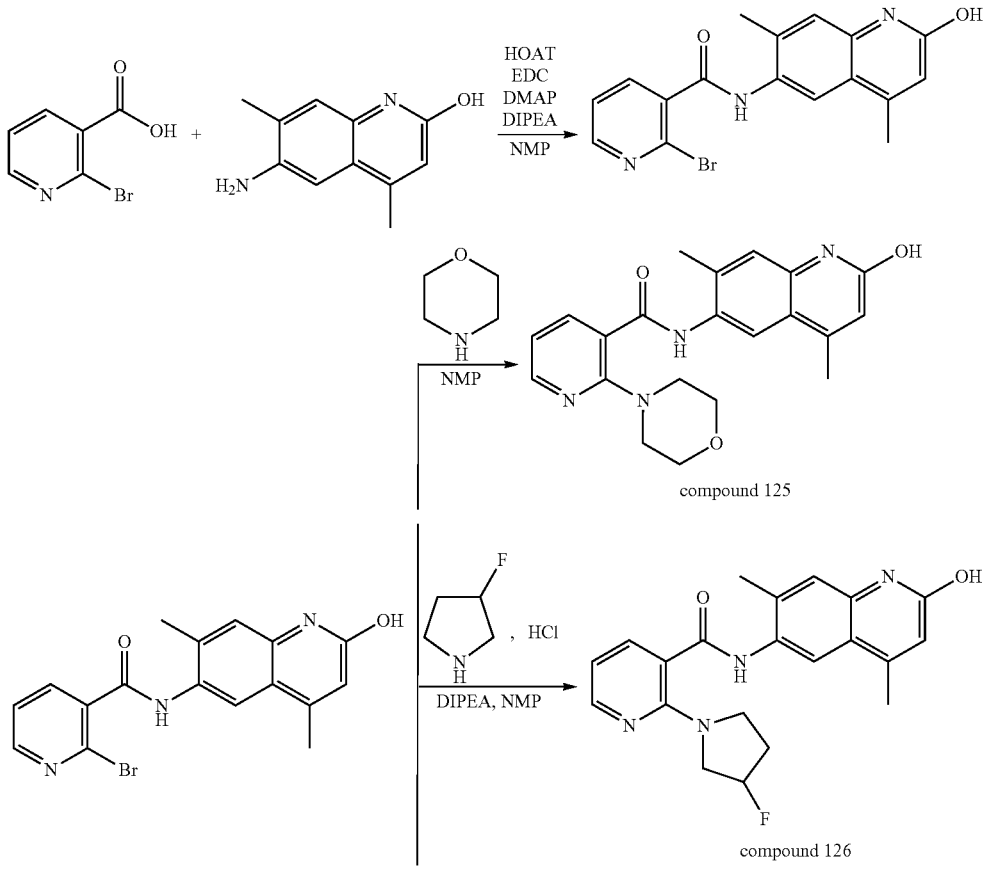

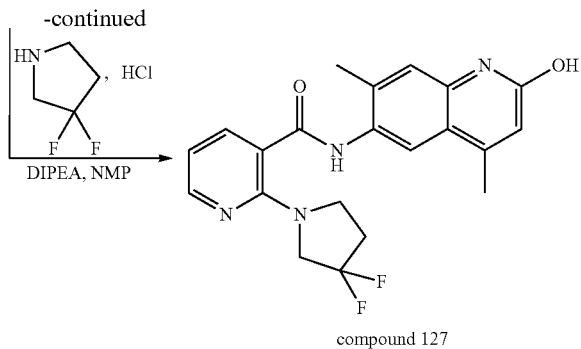

compound 127

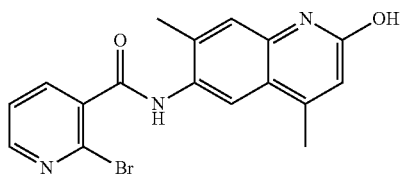

Preparation of 2-bromo-N-(2-hydroxy-4,7-dimethyl-6-quinolyl)pyridine-3-carboxamide: to a solution of 2-bromopyridine-3-carboxylic acid (125 mg. 0.62 mmol, 1 eq) in NMP (1.5 mL) were added 6-amino-4,7-dimethyl-quinolin-2-ol (116 mg, 0.62 mmol, 1 eq), HOAT (126 mg, 0.93 mmol, 1.5 eq), EDC (180 mg, 0.93 mmol, 1.5 eq), DMAP (15 mg, 0.12 mmol, 0.2 eq) and DIPEA (323 µL, 1.86 mmol, 3 eq). The mixture was stirred at 50° C. for one hour. Water was added and the precipitated solid was collected by filtration. The crude compound was stirred in 3 mL MeOH, filtered and dried yielding 2-bromo-N-(2-hydroxy-4,7-dimethyl-6-quinolyl)pyridine-3-carboxamide (105 mg, 46%) as a brown solid. LCMS: (M+H)=373, UV 86%

$^1$H NMR (300 MHz, DMSO-d$_6$) δ 11.60 (s, 1H), 10.17 (s, 1H), 8.50 (d, J=4.8 Hz, 1H), 8.22-7.99 (m, 1H), 7.76 (s, 1H), 7.72-7.47 (m, 1H), 7.17 (s, 1H), 6.38 (s, 1H), 2.39 (s, 3H), 2.37 (s, 3H).

compound 125

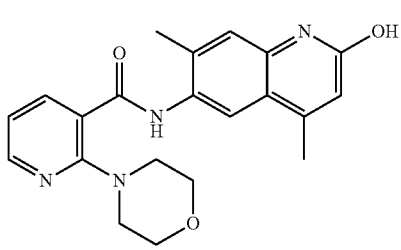

Preparation of N-(2-hydroxy-4,7-dimethyl-6-quinolyl)-2-morpholino-pyridine-3-carboxamide (compound-125): to a solution of 2-bromo-N-(2-hydroxy-4,7-dimethyl-6-quinolyl)pyridine-3-carboxamide (50 mg, 0.134 mmol, 1 eq) in NMP (0.5 mL) was added morpholine (117 µL, 1.34 mmol, 10 eq). The reaction mixture was stirred at 100° C. overnight. The reaction mixture was poured into water and the precipitated solid was filtered off, washed with water and dried yielding N-(2-hydroxy-4,7-dimethyl-6-quinolyl)-2-morpholino-pyridine-3-carboxamide (compound-125)(32 mg, 73%) as an off-white solid. LCMS: (M+H)=379, UV=98%.

$^1$H NMR (300 MHz, DMSO-d$_6$) δ 11.56 (s, 1H), 10.07 (s, 1H), 8.33 (dd, J=4.8, 1.9 Hz, 1H), 7.92 (dd, J=7.4, 1.9 Hz, 1H), 7.84 (s, 1H), 7.17 (s, 1H), 7.02 (dd, J=7.4, 4.8 Hz, 1H), 6.37 (s, 1H), 3.71 (t, J=4.6 Hz, 4H), 3.39-3.27 (m, 4H), 2.39 (s, 3H), 2.35 (s, 3H).

compound 126

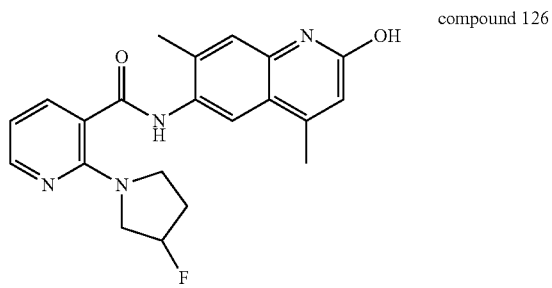 [SMILES: Cc1cc2nc(O)cc(C)c2cc1NC(=O)c1cccnc1N1CCC(F)C1]

Preparation of 2-(3-fluoropyrrolidin-1-yl)-N-(2-hydroxy-4,7-dimethyl-6-quinolyl)pyridine-3-carboxamide (compound-126): to a solution of 2-bromo-N-(2-hydroxy-4,7-dimethyl-6-quinolyl)pyridine-3-carboxamide (50 mg, 0.14 mmol, 1 eq) in NMP (0.5 mL) were added 3-fluoropyrrolidine hydrochloride (70 mg, 0.56 mmol, 4 eq) and DIPEA (97 µL, 0.56 mmol, 4 eq). The reaction mixture was stirred at 100° C. overnight. The mixture was poured into water and extracted with Ethyl acetate, dried over Na$_2$SO$_4$, filtered and evaporated. The crude compound was purified by flash chromatography (DCM/MeOH/NH$_3$-aq) yielding 2-(3-fluoropyrrolidin-1-yl)-N-(2-hydroxy-4,7-dimethyl-6-quinolyl)pyridine-3-carboxamide (compound-126)(9.2 mg, 17%) as a light brown solid. LCMS: (M+H)=381, UV=94%.

$^1$H NMR (300 MHz, DMSO-d$_6$) δ 11.55 (s, 1H), 9.95 (s, 1H), 8.31-8.14 (m, 1H), 7.85-7.74 (m, 2H), 7.17 (s, 1H), 6.83-6.68 (m, 1H), 6.37 (s, 1H), 5.42 (d, J=53.6 Hz, 1H), 3.92-3.45 (m, 4H), 2.46-2.37 (m, 3H), 2.34 (s, 3H), 2.31-1.94 (m, 2H).

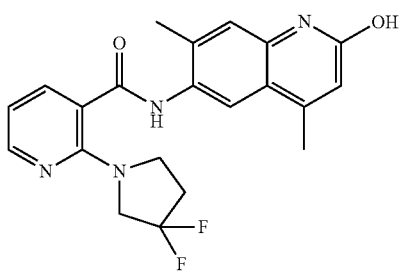

compound 127

Preparation of 2-(3,3-difluoropyrrolidin-1-yl)-N-(2-hydroxy-4,7-dimethyl-6-quinolyl)pyridine-3-carboxamide by flash chromatography (DCM/MeOH) yielding 2-(3,3-difluoropyrrolidin-1-yl)-N-(2-hydroxy-4,7-dimethyl-6-quinolyl)pyridine-3-carboxamide (compound-127) (5 mg, 10%). LCMS: (M+H)=399, UV=96%.

$^1$H NMR (300 MHz, DMSO-$d_6$) δ 11.56 (s, 1H), 10.02 (s, 1H), 8.36-8.10 (m, 1H), 7.87 (dt, J=7.4, 2.0 Hz, 1H), 7.76 (d, J=2.0 Hz, 1H), 7.17 (s, 1H), 6.93-6.75 (m, 1H), 6.37 (s, 1H), 3.84 (t, J=13.1 Hz, 2H), 3.70 (t, J=7.2 Hz, 2H), 2.38 (s, 3H), 2.34 (s, 3H).

Synthesis of Compound-128, Compound-129, Compound-130, and Compound-131

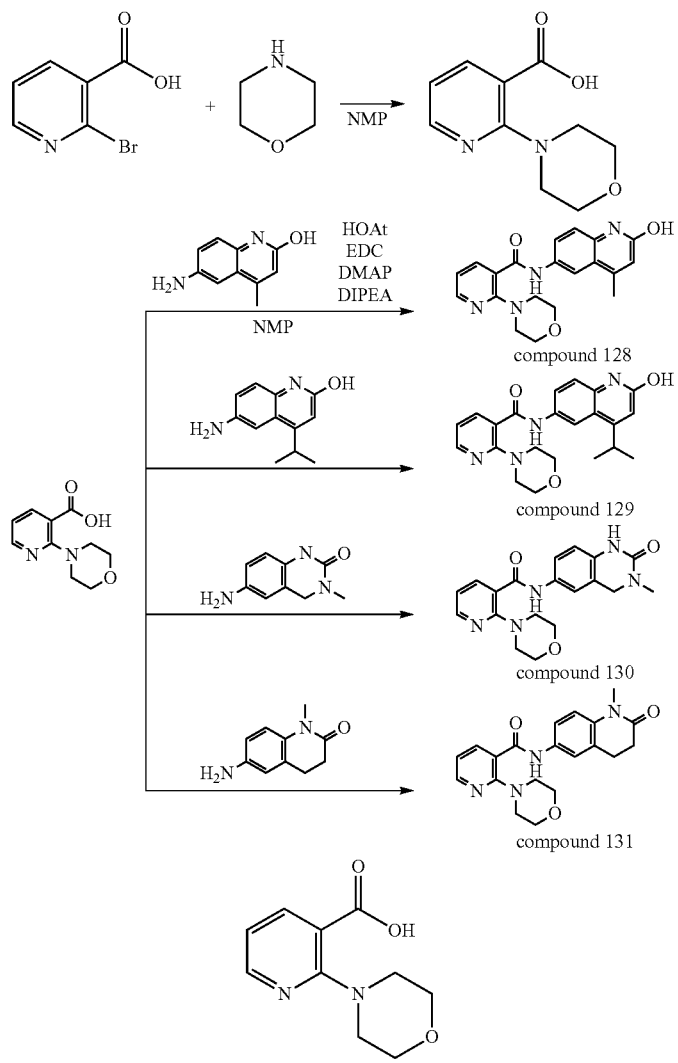

(compound-127): to a solution of 2-bromo-N-(2-hydroxy-4,7-dimethyl-6-quinolyl)pyridine-3-carboxamide (50 mg 0.14 mmol, 1 eq) in NMP (0.5 mL) were added 3,3-difluoropyrrolidine hydrochloride (96 mg, 0.67 mmol, 5 eq) and DIPEA (233 µL, 1.4 mmol, 10 eq). The reaction mixture was stirred at 100° C. overnight. The mixture was poured into water and extracted with Ethyl acetate, dried over Na$_2$SO$_4$, filtered and evaporated. The crude compound was purified Preparation of 2-morpholinopyridine-3-carboxylic acid: To a solution of 2-bromopyridine-3-carboxylic acid in NMP (0.5 mL) was added morpholine (3.2 mL, 15 mmol, 6 eq). The mixture was heated at 70° C. for 2 h and then water was added. The mixture was extracted with EtOAc. The organic phase was dried over Na$_2$SO$_4$, filtered and evaporated yielding 2-morpholinopyridine-3-carboxylic acid (290 mg, 50%) as an off-white solid. LCMS: (M+H)=209, UV=100%.

$^1$H NMR (300 MHz, DMSO-d$_6$) δ 13.11 (s, 1H), 8.28 (dd, J=4.7, 2.0 Hz, 1H), 7.96 (dd, J=7.5, 2.0 Hz, 1H), 6.87 (dd, J=7.6, 4.8 Hz, 1H), 3.72-3.62 (m, 4H), 3.33-3.26 (m, 4H).

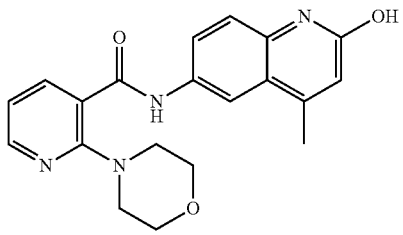

compound 128

Preparation of N-(2-hydroxy-4-methyl-6-quinolyl)-2-morpholino-pyridine-3-carboxamide (compound-128): to a solution of 2-morpholinopyridine-3-carboxylic acid (75 mg, 0.36 mg, 1 eq) in NMP (1 mL) were added 6-amino-4-methyl-quinolin-2-ol (63 mg, 0.36 mmol, 1 eq), HOAT (73 mg, 0.54 mmol, 1.5 eq), EDC (106 mg, 0.54 mmol, 1.5 eq), DMAP (9 mg, 0.07 mmol, 0.2 eq) and DIPEA (375 mL, 2.2 mmol, 6 eq). The reaction mixture was stirred at room temperature overnight. Water was added and the precipitated solid was collected by filtration and purified by flash chromatography (DCM/MeOH) N-(2-hydroxy-4-methyl-6-quinolyl)-2-morpholino-pyridine-3-carboxamide (compound-128)(70 mg, 53%). LCMS: (M+H)=365, UV=100%.

$^1$H NMR (300 MHz, DMSO-d$_6$) δ 11.60 (s, 1H), 10.58 (s, 1H), 8.32 (dd, J=4.8, 1.9 Hz, 1H), 8.19 (d, J=2.2 Hz, 1H), 7.85 (dd, J=7.5, 1.9 Hz, 1H), 7.79 (dd, J=8.8, 2.2 Hz, 1H), 7.30 (d, J=8.8 Hz, 1H), 7.00 (dd, J=7.4, 4.8 Hz, 1H), 6.43 (s, 1H), 3.71-3.57 (m, 4H), 3.31-3.23 (m, 4H), 2.40 (d, J=1.2 Hz, 3H).

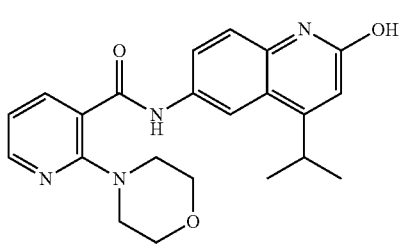

compound 129

Preparation of N-(2-hydroxy-4-sec-butyl-6-quinolyl)-2-morpholino-pyridine-3-carboxamide (compound-129): to a solution of 2-morpholinopyridine-3-carboxylic acid (36 mg, 0.17 mmol, 1 eq) in NMP (0.5 mL) were added 6-amino-4-isopropyl-quinolin-2-ol (35 mg, 0.17 mmol, 1 eq), HOAT (35 mg, 0.26 mmol, 1.5 eq), EDC (50 mg, 0.26 mmol, 1.5 eq), DMAP (4 mg, 0.034 mmol, 0.2 eq) and DIPEA (177 µL, 1.04 mmol, 6 eq). The reaction mixture was stirred at room temperature overnight. Water was added and the precipitated solid was collected by filtration, washed with water and dried yielding N-(2-hydroxy-4-sec-butyl-6-quinolyl)-2-morpholino-pyridine-3-carboxamide (Compound-129) (29 mg, 43%) as a light brown solid. LCMS: (M+H)=393, UV=95%.

$^1$H NMR (300 MHz, DMSO-d$_6$) δ 11.61 (s, 1H), 10.57 (s, 1H), 8.33 (dd, J=4.8, 1.9 Hz, 1H), 8.29 (d, J=2.1 Hz, 1H), 7.85 (td, J=8.5, 7.9, 2.0 Hz, 2H), 7.32 (d, J=8.8 Hz, 1H), 7.00 (dd, J=7.5, 4.8 Hz, 1H), 6.38 (s, 1H), 3.74-3.55 (m, 4H), 3.31-3.19 (m, 5H), 1.29 (d, J=6.7 Hz, 6H).

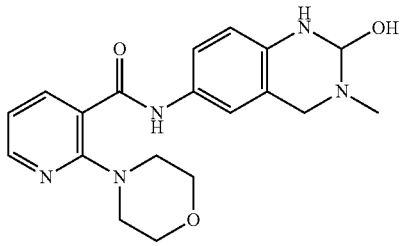

compound 130

Preparation of N-(3-methyl-2-oxo-1,4-dihydroquinazolin-6-yl)-2-morpholino-pyridine-3-carboxamide (Compound-130): to a solution of 2-morpholinopyridine-3-carboxylic acid (50 mg, 0.24 mmol, 1 eq) in NMP (1.0 mL) were added 6-amino-3-methyl-1,4-dihydroquinazolin-2-one (42 mg, 0.24 mmol, 1 eq), HOAT (50 mg, 0.36 mmol, 1.5 eq), EDC (69 mg, 0.36 mmol, 1.5 eq), DMAP (4 mg, 0.05 mmol, 0.2 eq) and DIPEA (250 µL, 1.44 mmol, 6 eq). The reaction mixture was stirred at room temperature overnight. Water was added and the precipitated solid was collected by filtration, washed with water and dried yielding N-(3-methyl-2-oxo-1,4-dihydroquinazolin-6-yl)-2-morpholino-pyridine-3-carboxamide (Compound-130) (56 mg, 64%) as a light brown solid. LCMS: (M+H)=368, UV=100%.

$^1$H NMR (300 MHz, DMSO-d$_6$) δ 10.36 (s, 1H), 9.16 (s, 1H), 8.30 (dd, J=4.8, 1.9 Hz, 1H), 7.79 (dd, J=7.4, 1.9 Hz, 1H), 7.53 (d, J=2.2 Hz, 1H), 7.41 (dd, J=8.5, 2.3 Hz, 1H), 6.98 (dd, J=7.4, 4.8 Hz, 1H), 6.74 (d, J=8.5 Hz, 1H), 4.40 (s, 2H), 3.69-3.58 (m, 4H), 3.28-3.21 (m, 4H), 2.86 (s, 3H).

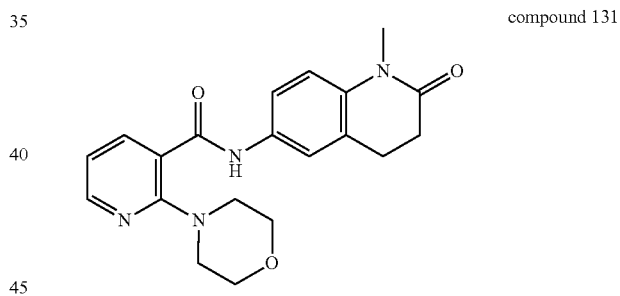

compound 131

Preparation of N-(1-methyl-2-oxo-3,4-dihydroquinolin-6-yl)-2-morpholino-pyridine-3-carboxamide (compound-131): to a solution of 2-morpholinopyridine-3-carboxylic acid (50 mg, 0.24 mmol, 1 eq) in NMP (1.0 mL) were added 6-amino-1-methyl-3,4-dihydroquinolin-2-one (42 mg, 0.24 mmol, 1 eq), HOAT (50 mg, 0.36 mmol, 1.5 eq), EDC (69 mg, 0.36 mmol, 1.5 eq), DMAP (4 mg, 0.05 mmol, 0.2 eq) and DIPEA (255 µL, 1.04 mmol, 6 eq). The reaction mixture was stirred at room temperature overnight. The mixture was poured into water and extracted with EtOAc, dried over Na$_2$SO$_4$, filtered and evaporated. The crude compound was purified by flash chromatography (DCM/MeOH). The purified compound was stirred in heptane, filtered and dried yielding N-(1-methyl-2-oxo-3,4-dihydroquinolin-6-yl)-2-morpholino-pyridine-3-carboxamide (compound-131) (11 mg, 13%) as a white solid. LCMS: (M+H)=367, UV=100%.

$^1$H NMR (300 MHz, DMSO-d$_6$) δ 10.43 (s, 1H), 8.31 (dd, J=4.8, 1.9 Hz, 1H), 7.81 (dd, J=7.5, 2.0 Hz, 1H), 7.65 (d, J=2.3 Hz, 1H), 7.08 (d, J=8.7 Hz, 1H), 6.99 (dd, J=7.4, 4.8 Hz, 1H), 3.71-3.59 (m, 4H), 3.31-3.25 (m, 4H), 3.25 (s, 3H), 2.86 (t, J=7.3 Hz, 2H), 2.52 (t, 2H).

Synthesis of Compound-132 and Compound-133

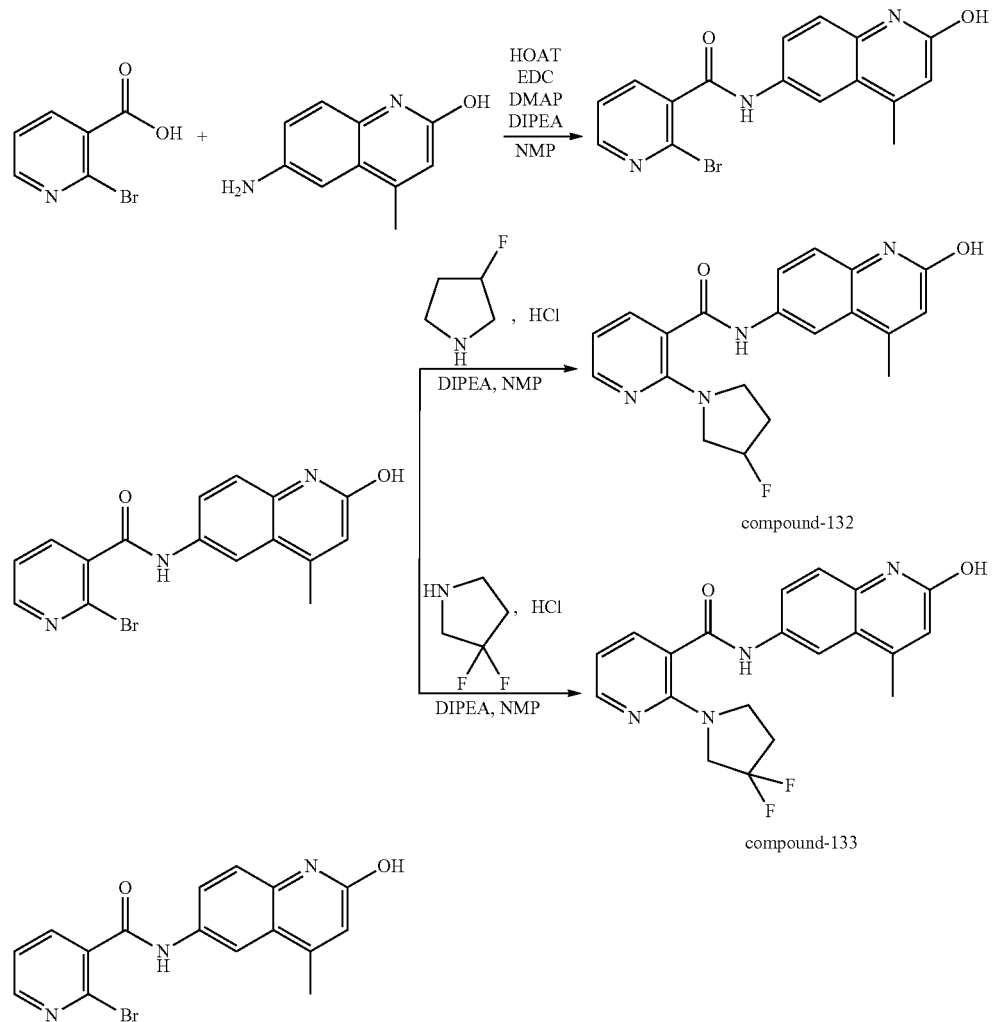

Preparation of 2-bromo-N-(2-hydroxy-4-methyl-6-quinolyl)pyridine-3-carboxamide: to a solution of 2-bromopyridine-3-carboxylic acid (125 mg, 0.62 mmol, 1 eq) in 1 mL (NMP) were added 6-amino-4-methyl-quinolin-2-ol (108 mg, 0.62 mmol, 1 eq), HOAT (127 mg, 0.93 mmol, 1.5 eq), EDC (197 mg, 0.93 mmol, 1.5 eq), DMAP (15 mg, 0.12 mmol, 0.2 eq) and DIPEA (323 µL, 1.86 mmol, 3 eq) The reaction mixture was stirred at 80° C. for 1 hour. Water was added and precipitated compound filtered of. The supernatant was extracted with Ethyl acetate, dried over $Na_2SO_4$, filtered and evaporated. The extracted compound and the compound collected by filtration were pooled and purified by flash chromatography, (DCM/MeOH) to yield 2-bromo-N-(2-hydroxy-4-methyl-6-quinolyl)pyridine-3-carboxamide (185 mg, 83%) as a purple solid. LCMS: (M+H)=358, UV=97%.

$^1$H NMR (300 MHz, DMSO-$d_6$) δ 11.62 (s, 1H), 10.73 (s, 1H), 8.51 (dd, J=4.8, 2.0 Hz, 1H), 8.14 (d, J=2.3 Hz, 1H), 8.02 (dd, J=7.5, 2.0 Hz, 1H), 7.76 (dd, J=8.8, 2.2 Hz, 1H), 7.59 (dd, J=7.5, 4.8 Hz, 1H), 7.31 (d, J=8.8 Hz, 1H), 6.44 (s, 1H), 2.40 (d, J=1.2 Hz, 3H).

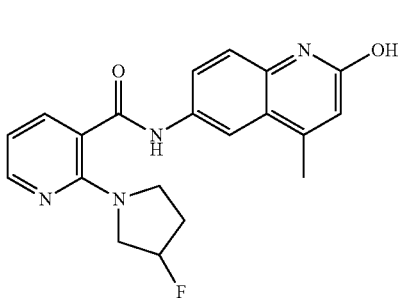

compound-132

Preparation of 2-(3-fluoropyrrolidin-1-yl)-N-(2-hydroxy-4-methyl-6-quinolyl)pyridine-3-carboxamide (compound-132): to a solution of 2-bromo-N-(2-hydroxy-4-methyl-6-quinolyl)pyridine-3-carboxamide 50 mg, 0.14 mmol, 1 eq) in NMP (0.5 mL) were added 3-fluoropyrrolidine hydrochloride 70 mg, 0.56 mmol, 4 eq) and DIPEA (97 µL, 0.56 mmol, 4 eq). The reaction mixture was stirred at 100° C. overnight, poured into water and extracted with Ethyl acetate, dried over $MgSO_4$, filtered and evaporated. The crude compound was purified by flash chromatography (DCM/MeOH) yielding 2-(3-fluoropyrrolidin-1-yl)-N-(2-hydroxy-4-methyl-6-quinolyl)pyridine-3-carboxamide (compound-132)(14 mg, 27%) as a light brown solid. LCMS: (M+H)=367, UV=97%.

$^1$H NMR (300 MHz, DMSO-d$_6$) δ 11.58 (s, 1H), 10.54 (s, 1H), 8.27-8.17 (m, 1H), 8.13 (d, J=2.1 Hz, 1H), 7.80 (dt, 1H), 7.69 (dt, J=7.4, 1.9 Hz, 1H), 7.29 (dd, J=8.9, 1.8 Hz, 1H), 6.82-6.65 (m, 1H), 6.42 (s, 1H), 5.36 (d, J=53.8 Hz, 1H), 3.98-3.45 (m, 4H), 2.39 (s, 3H), 2.29-1.89 (m, 2H).

Preparation of 2-(3,3-difluoropyrrolidin-1-yl)-N-(2-hydroxy-4-methyl-6-quinolyl)pyridine-3-carboxamide (compound-133): to a solution of 2-bromo-N-(2-hydroxy-4-methyl-6-quinolyl)pyridine-3-carboxamide 50 mg, 0.14 mmol, 1 eq) in NMP (0.5 mL) were added 3,3-difluoropyrrolidine hydrochloride (100 mg, 0.69 mmol, 5 eq) and DIPEA (122 µL, 0.69 mmol, 5 eq). The mixture was stirred at 100° C. overnight, poured into water and extracted with Ethyl acetate, dried over Na$_2$SO$_4$, filtered and evaporated. The crude compound was purified by flash chromatography (DCM/MeOH) and recrystallized in MeOH yielding 2-(3,3-difluoropyrrolidin-1-yl)-N-(2-hydroxy-4-methyl-6-quinolyl)pyridine-3-carboxamide (compound-133) (12 mg, 22%) as an off-white solid. LCMS: (M+H)=385, UV=95%.

$^1$H NMR (300 MHz, DMSO-d$_6$) δ 11.61 (s, 1H), 10.60 (s, 1H), 8.30-8.21 (m, 1H), 8.12 (s, 1H), 7.85-7.70 (m, 2H), 7.29 (d, J=8.9 Hz, 1H), 6.88-6.77 (m, 1H), 6.43 (s, 1H), 3.80 (t, J=13.3 Hz, 2H), 3.64 (t, J=7.2 Hz, 2H), 2.52-2.35 (m, 1H), 2.39 (s, 3H).

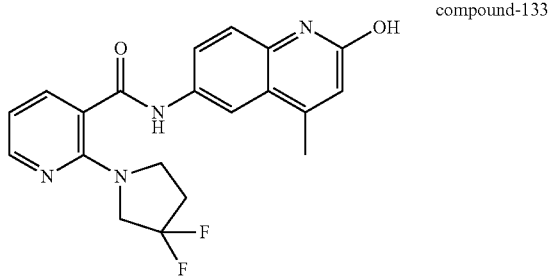 [SMILES: Cc1cc(O)nc2ccc(NC(=O)c3cccnc3N3CCC(F)(F)C3)cc12]

compound-133

Synthesis of Compound-134 and Compound-135

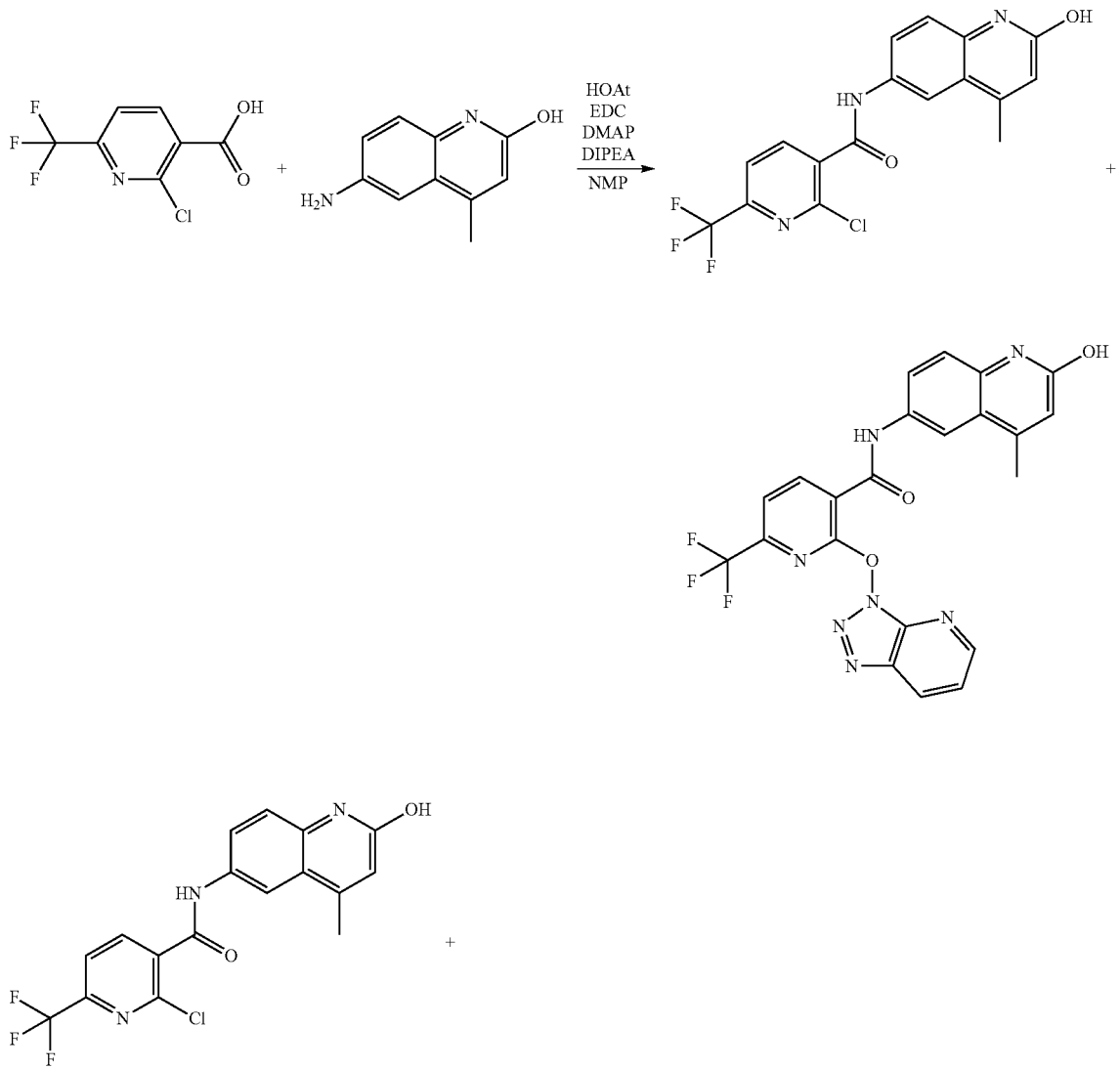

-continued

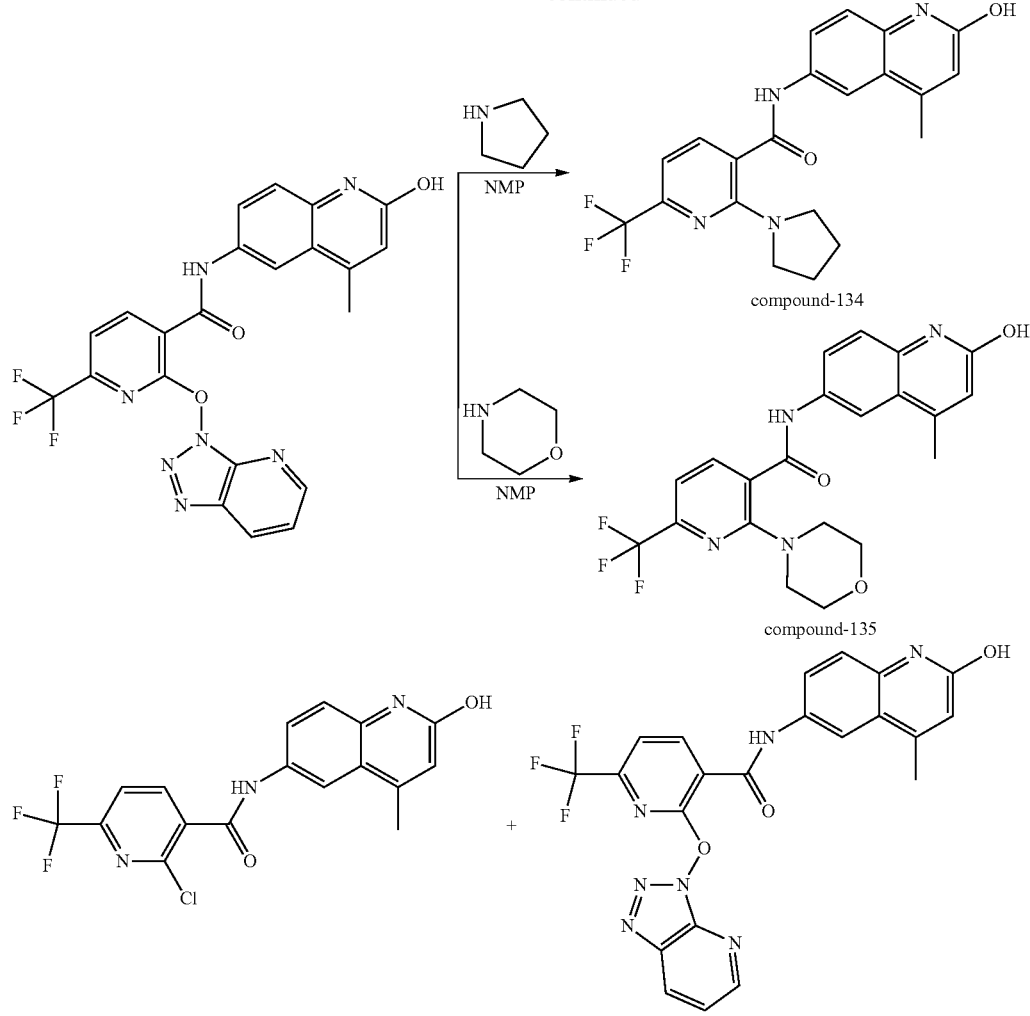

compound-134 compound-135

Preparation of 2-chloro-N-(2-hydroxy-4-methyl-6-quinolyl)-6-(trifluoromethyl)pyridine-3-carboxamide and N-(2-hydroxy-4-methyl-6-quinolyl)-2-(triazolo[4,5-b]pyridin-3-yloxy)-6-(trifluoromethyl)pyridine-3-carboxamide: to a solution of 2-chloro-6-(trifluoromethyl)pyridine-3-carboxylic acid (100 mg, 0.44 mmol, 1 eq) in NMP (1 mL) were added 6-amino-4-methyl-quinolin-2-ol (78 mg, 0.44 mmol, 1 eq), HOAT (127 mg, 93 mmol, 2.1 eq), EDC (179 mg, 0.93 mmol, 2.1 eq), DMAP (19 mg, 0.9 mmol, 0.2 eq) and DIPEA (229 µL, 1.3 mmol, 3 eq). Water was added and the precipitated solid was collected by filtration to give a mixture of 2-chloro-N-(2-hydroxy-4-methyl-6-quinolyl)-6-(trifluoromethyl)pyridine-3-carboxamide and N-(2-hydroxy-4-methyl-6-quinolyl)-2-(triazolo[4,5-b]pyridin-3-yloxy)-6-(trifluoromethyl)pyridine-3-carboxamide (150 mg). The mixture was used in the next step. LCMS (M+H) =382, UV=25% 2-chloro-N-(2-hydroxy-4-methyl-6-quinolyl)-6-(trifluoromethyl)pyridine-3-carboxamide and (M+H)=482, UV=75% N-(2-hydroxy-4-methyl-6-quinolyl)-2-(triazolo[4,5-b]pyridin-3-yloxy)-6-(trifluoromethyl)pyridine-3-carboxamide compound-134

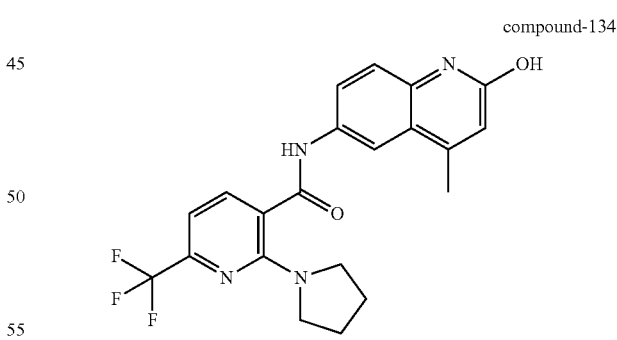

Preparation of N-(2-hydroxy-4-methyl-6-quinolyl)-2-pyrrolidin-1-yl-6-(trifluoromethyl)pyridine-3-carboxamide (compound-134): to a solution of a mixture of 2-chloro-N-(2-hydroxy-4-methyl-6-quinolyl)-6-(trifluoromethyl)pyridine-3-carboxamide and N-(2-hydroxy-4-methyl-6-quinolyl)-2-(triazolo[4,5-b]pyridin-3-yloxy)-6-(trifluoromethyl)pyridine-3-carboxamide (50 mg, 0.1 mmol, 1 eq) in NMP (0.5 mL) were added pyrrolidine (82 µL, 1.0 mmol, 10 eq). The mixture was heated at 100° C. for 90 min. The heat was turned off and the reaction mixture stirred overnight at room temperature and poured into water. The precipitated solid was collected by filtration and stirred in a mixture of DCM/MeOH, filtered and dried to yield N-(2-hydroxy-4-methyl-6-quinolyl)-2-pyrrolidin-1-yl-6-(trifluoromethyl)pyridine-3-carboxamide (compound-134) (26 mg, 63%) as an off-white solid. LCMS: (M+H)=417, UV=100%.

$^{1}$H NMR (300 MHz, DMSO-d$_{6}$) δ 11.59 (s, 1H), 10.63 (s, 1H), 8.11 (d, J=2.1 Hz, 1H), 7.86 (d, J=7.5 Hz, 1H), 7.79 (d, J=9.1 Hz, 1H), 7.29 (d, J=8.8 Hz, 1H), 7.07 (d, J=7.4 Hz, 1H), 6.43 (s, 1H), 3.60-3.40 (m, 4H), 2.39 (s, 3H), 1.98-1.74 (m, 4H).

compound-135

Preparation of N-(2-hydroxy-4-methyl-6-quinolyl)-2-morpholino-6-(trifluoromethyl)pyridine-3-carboxamide (compound-135): to a solution of a mixture of 2-chloro-N-(2-hydroxy-4-methyl-6-quinolyl)-6-(trifluoromethyl)pyridine-3-carboxamide and N-(2-hydroxy-4-methyl-6-quinolyl)-2-(triazolo[4,5-b]pyridin-3-yloxy)-6-(trifluoromethyl)pyridine-3-carboxamide (50 mg, 0.1 mmol, 1 eq) in NMP (0.5 mL) were added morpholine (87 µL, 1.0 mmol, 10 eq). The reaction mixture was stirred at 110° C. for 1 hour and poured into water. The precipitated compound was collected by filtration, washed with water and dried yielding N-(2-hydroxy-4-methyl-6-quinolyl)-2-morpholino-6-(trifluoromethyl)pyridine-3-carboxamide (compound-135) (20 mg, 47%) as an off-white solid. LCMS: (M+H)=433, UV=100%.

$^{1}$H NMR (300 MHz, DMSO-d$_{6}$) δ 11.70 (s, 1H), 10.75 (s, 1H), 8.20 (d, 1H), 8.07 (d, J=7.6 Hz, 1H), 7.84 (dd, J=8.7, 2.3 Hz, 1H), 7.49-7.31 (m, 2H), 6.51 (s, 1H), 3.87-3.65 (m, 4H), 2.69-2.54 (m, 4H), 2.47 (s, 3H).

Synthesis of Compound-136

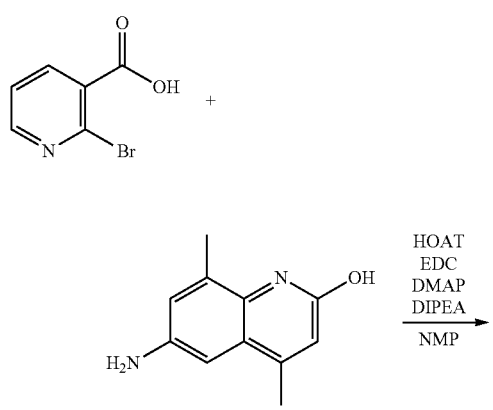

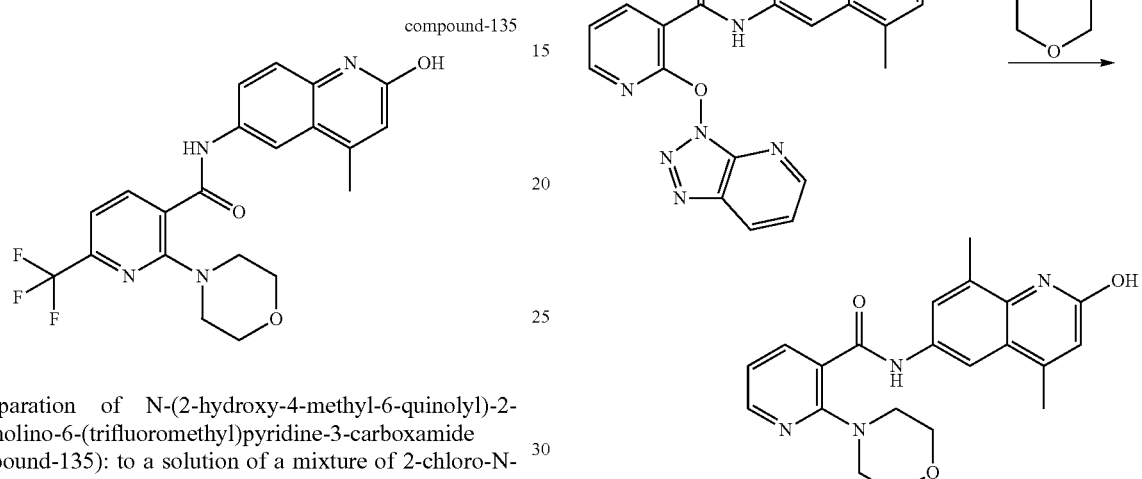

compound-136

Preparation of 2-bromo-N-(2-hydroxy-4,8-dimethyl-6-quinolyl)pyridine-3-carboxamide and N-(2-hydroxy-4,8-dimethyl-6-quinolyl)-2-(triazolo[4,5-b]pyridin-3-yloxy)pyridine-3-carboxamide: to a solution of 2-bromopyridine-3-carboxylic acid (55 mg, 0.27 mmol, 1 eq) in NMP (0.6 mL) were added 2-bromopyridine-3-carboxylic acid (50 mg, 0.27 mmol, 1 eq), HOAT (40 mg, 0.30 mmol, 1.1 eq), EDC (58 mg, 0.30 mmol, 1.1 eq, DMAP (7 mg, 0.05 mmol, 0.2 eq) and DIPEA (140 µL, 0.81 mmol, 3 eq). The mixture was heated at 60° C. overnight, poured into water and extracted with EtOAc. The crude compound was purified by flash chromatography (DCM/MeOH) yielding a mixture of

253

2-bromo-N-(2-hydroxy-4,8-dimethyl-6-quinolyl)pyridine-3-carboxamide and N-(2-hydroxy-4,8-dimethyl-6-quinolyl)-2-(triazolo[4,5-b]pyridin-3-yloxy)pyridine-3-carboxamide (66 mg). The mixture was used in the next sted. LCMS: (M+H)=372, UV=67% 2-bromo-N-(2-hydroxy-4,8-dimethyl-6-quinolyl)pyridine-3-carboxamide and (M+H)=428, UV=33% N-(2-hydroxy-4,8-dimethyl-6-quinolyl)-2-(triazolo[4,5-b]pyridin-3-yloxy)pyridine-3-carboxamide.

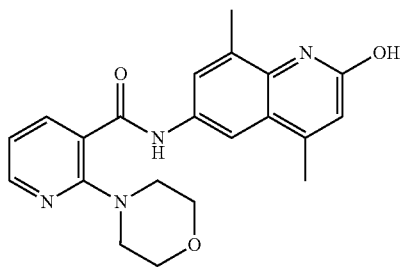

compound-136

Preparation of N-(2-hydroxy-4,8-dimethyl-6-quinolyl)-2-morpholino-pyridine-3-carboxamide (Compound-136): to a Solution of a mixture of 2-bromo-N-(2-hydroxy-4,8-dimethyl-6-quinolyl)pyridine-3-carboxamide (67%) and N-(2-hydroxy-4,8-dimethyl-6-quinolyl)-2-(triazolo[4,5-b]pyridin-3-yloxy)pyridine-3-carboxamide (33%) (66 mg, ~0.18 mmol) in NMP (0.5 mL) was added morpholine (154 µL, 1.8 mmol, 10 eq). The reaction mixture was heated at 100° C. overnight. Water was added and the precipitated solid collected by filtration. The crude compound was purified by flash chromatography (DCM/MeOH) yielding N-(2-hydroxy-4,8-dimethyl-6-quinolyl)-2-morpholino-pyridine-3-carboxamide (Compound-136)(9 mg, 13%) as an off-white solid. LCMS: (M+H)=379, UV=98%.

$^1$H NMR (300 MHz, DMSO-d$_6$) δ 10.74 (s, 1H), 10.51 (s, 1H), 8.48-8.24 (m, 1H), 8.04 (s, 1H), 7.96-7.78 (m, 1H), 7.68 (s, 1H), 7.17-6.84 (m, 1H), 6.45 (s, 1H), 3.87-3.54 (m, 5H), 3.31-3.22 (m, 5H), 2.43 (d, J=1.5 Hz, 3H), 2.40 (t, J=1.5 Hz, 3H).

Synthesis of Compound-137 and Compound-138

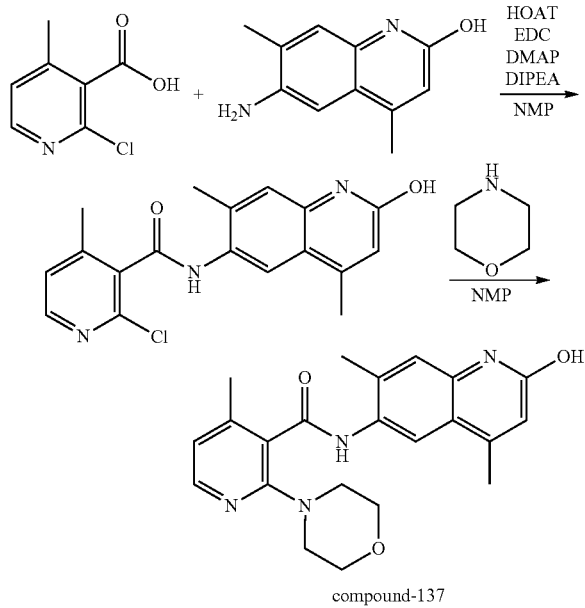

compound-137

254

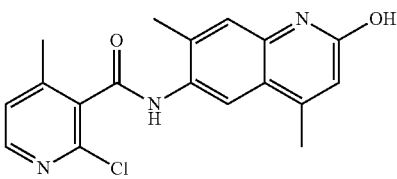

Preparation of 2-chloro-N-(2-hydroxy-4,7-dimethyl-6-quinolyl)-4-methyl-pyridine-3-carboxamide: to a solution of 2-chloro-4-methyl-pyridine-3-carboxylic acid (200 mg, 1.17 mmol, 1 eq) were added 6-amino-4,7-dimethyl-quinolin-2-ol (220 mg, 1.17 mmol, 1 eq), HOAT (190 mg, 1.4 mmol, 1.2 eq), EDC (270 mg, 1.4 mmol, 1.2 eq), DMAP (30 mg, 0.23 mmol, 0.2 eq) and DIPEA (610 µL, 3.5 mmol, 3 eq). The mixture was heated at 70° C. for 2 hours and poured into water. The precipitated solid was collected by filtration and purified by flash chromatography (DCM/MeOH) yielding 2-chloro-N-(2-hydroxy-4,7-dimethyl-6-quinolyl)-4-methyl-pyridine-3-carboxamide (100 mg, 25%) as a solid. LCMS: (M+H)=342, UV=100%.

$^1$H NMR (300 MHz, DMSO-d$_6$) δ 11.59 (s, 1H), 10.24 (s, 1H), 8.36 (dd, J=5.0, 1.8 Hz, 1H), 7.70 (d, J=1.7 Hz, 1H), 7.56-7.38 (m, 1H), 7.19 (s, 1H), 6.38 (s, 1H), 2.44 (d, J=1.7 Hz, 3H), 2.40 (s, 3H), 2.37 (d, J=1.7 Hz, 3H).

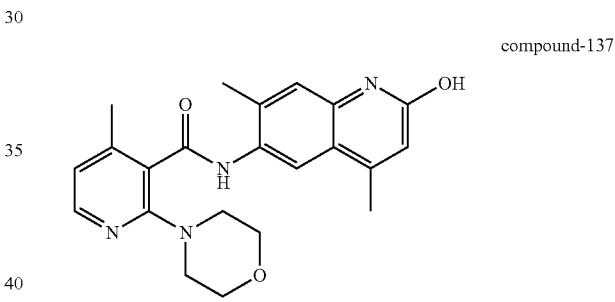

compound-137

Preparation of N-(2-hydroxy-4,7-dimethyl-6-quinolyl)-4-methyl-2-morpholino-pyridine-3-carboxamide (compound-137): to a solution of 2-chloro-N-(2-hydroxy-4,7-dimethyl-6-quinolyl)-4-methyl-pyridine-3-carboxamide (50 mg, 0.15 mmol, 1 eq) in NMP (0.3 mL) was added morpholine (640 µL, 7.5 mmol, 50 eq). The reaction mixture was heated at 100° C. for 3 days. Water was added and the precipitated compound collected by filtration yielding N-(2-hydroxy-4,7-dimethyl-6-quinolyl)-4-methyl-2-morpholino-pyridine-3-carboxamide (compound-137) (23 mg, 39%) as an off-white solid. LCMS: (M+H)=393, UV=100%.

$^1$H NMR (300 MHz, DMSO-d$_6$) δ 11.58 (s, 1H), 9.94 (s, 1H), 8.19 (d, J=5.0 Hz, 1H), 7.72 (s, 1H), 7.18 (s, 1H), 6.94 (d, J=5.1 Hz, 1H), 6.38 (s, 1H), 3.75-3.66 (m, 4H), 3.34-3.23 (m, 5H), 2.39 (d, J=1.2 Hz, 3H), 2.37 (s, 3H), 2.34 (s, 3H).

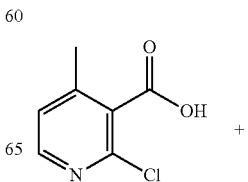

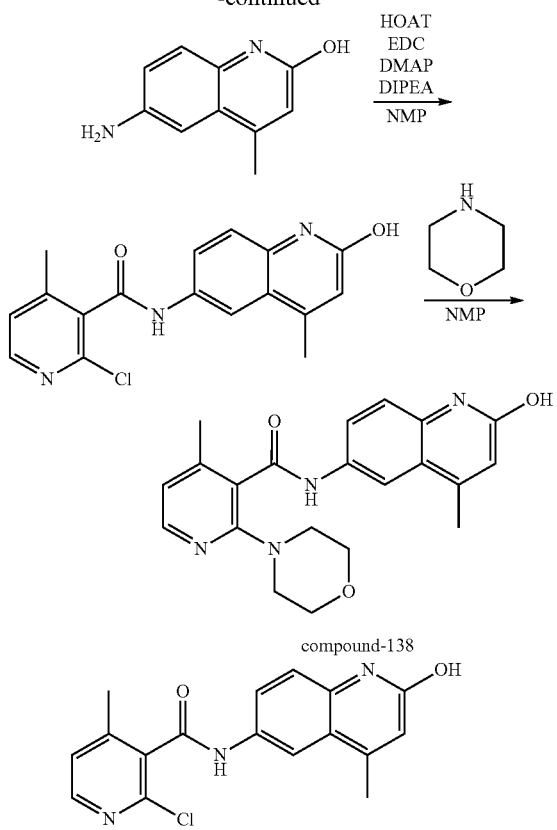

Preparation of 2-chloro-N-(2-hydroxy-4-methyl-6-quinolyl)-4-methyl-pyridine-3-carboxamide: the compound was made according to the procedure used in the synthesis of 2-chloro-N-(2-hydroxy-4,7-dimethyl-6-quinolyl)-4-methyl-pyridine-3-carboxamide. Yield: 249 mg, 65%. LCMS: (M+H)=327, UV=82%.

$^1$H NMR (300 MHz, DMSO-d$_6$) δ 11.63 (s, 1H), 10.80 (s, 1H), 8.37 (d, J=5.0 Hz, 1H), 8.13 (d, J=2.2 Hz, 1H), 7.76 (dd, J=8.8, 2.3 Hz, 1H), 7.48-7.39 (m, 1H), 7.31 (d, J=8.8 Hz, 1H), 6.44 (s, 1H), 2.40 (d, J=1.2 Hz, 3H), 2.36 (s, 3H).

compound-138

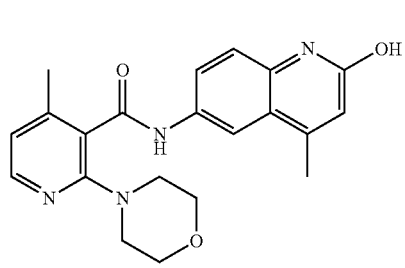

Preparation of N-(2-hydroxy-4-methyl-6-quinolyl)-4-methyl-2-morpholino-pyridine-3-carboxamide (compound-138): the compound was made according to the procedure used in the synthesis of N-(2-hydroxy-4,7-dimethyl-6-quinolyl)-4-methyl-2-morpholino-pyridine-3-carboxamide (compound-138). Yield: 38 mg, 67%. LCMS: (M+H)=379, UV=100%.

$^1$H NMR (300 MHz, DMSO-d$_6$) δ 11.60 (s, 1H), 10.50 (s, 1H), 8.34-7.97 (m, 2H), 7.78 (dd, J=8.9, 2.2 Hz, 1H), 7.30 (d, J=8.8 Hz, 1H), 6.87 (dd, J=5.0, 0.7 Hz, 1H), 6.49-6.33 (m, 1H), 3.63-3.49 (m, 4H), 3.30-3.20 (m, 4H), 2.39 (d, J=1.2 Hz, 3H), 2.27 (s, 3H).

Synthesis of Compound-139

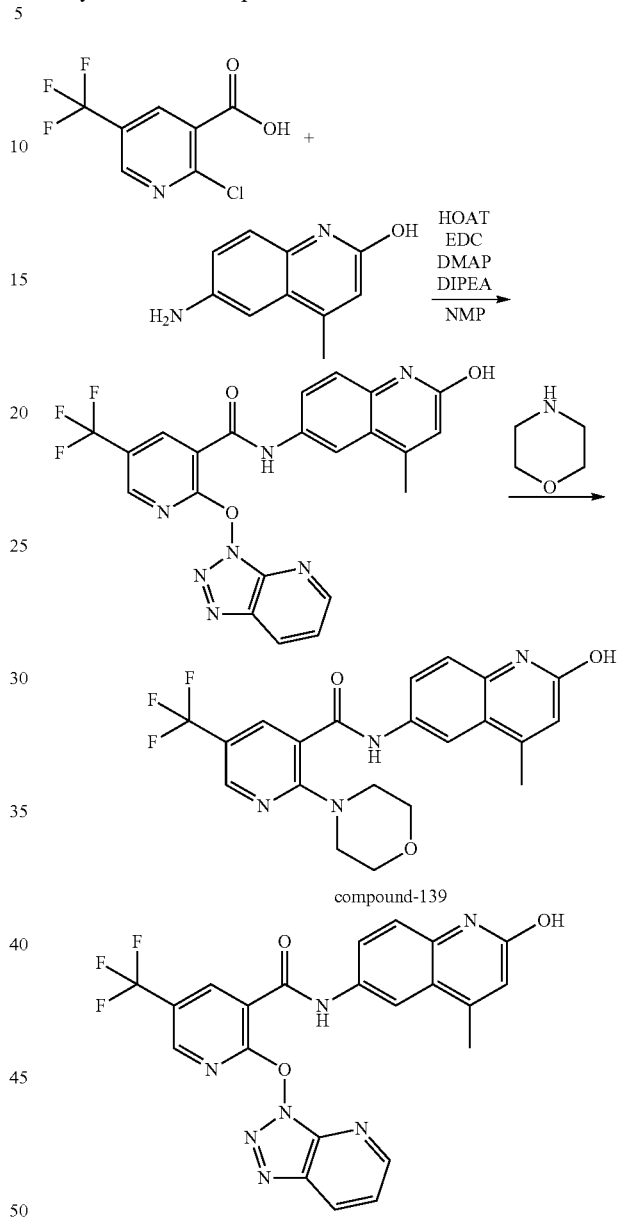

Preparation of N-(2-hydroxy-4-methyl-6-quinolyl)-2-(triazolo[4,5-b]pyridin-3-yloxy)-5-(trifluoromethyl)pyridine-3-carboxamide: to a solution of 2-chloro-5-(trifluoromethyl)pyridine-3-carboxylic acid (166 mg, 0.74, 1 eq) in NMP (1.5 mL) were added 6-amino-4-methyl-quinolin-2-ol (129 mg, 0.74 mmol, 1 eq), HOAt (120 mg, 0.89 mmol. 1.2 eq), EDC (170 mg, 0.89 mmol, 1.2 eq), DMAP (18 mg, 0.15 mmol, 0.2 eq) and DIPEA (385 μL, 2.22 mmol, 3 eq), The reaction mixture were heated overnight at 70° C. The mixture was poured into water and the precipitated solid collected by filtration and purified by flash chromatography (DCM/MeOH) yielding N-(2-hydroxy-4-methyl-6-quinolyl)-2-(triazolo[4,5-b]pyridin-3-yloxy)-5-(trifluoromethyl)pyridine-3-carboxamide (100 mg, 35%) as a brown solid. LCMS: (M+H)=482, UV=100%.

¹H NMR (300 MHz, DMSO-d₆) δ 11.68 (s, 1H), 11.13 (s, 1H), 8.86 (dd, J=2.3, 0.8 Hz, 1H), 8.82 (dd, J=4.5, 1.4 Hz, 1H), 8.76 (dd, J=8.4, 1.4 Hz, 1H), 8.69-8.63 (m, 1H), 8.21 (d, J=2.2 Hz, 1H), 7.85 (dd, J=8.8, 2.2 Hz, 1H), 7.67 (dd, J=8.4, 4.5 Hz, 1H), 7.35 (d, J=8.8 Hz, 1H), 6.46 (s, 1H), 2.46-2.36 (m, 3H).

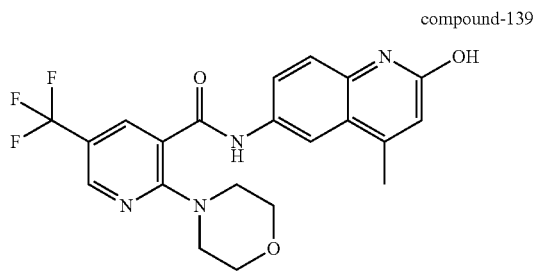 [SMILES: Cc1cc(O)nc2ccc(NC(=O)c3cc(C(F)(F)F)cnc3N3CCOCC3)cc12]

compound-139

Preparation of N-(2-hydroxy-4-methyl-6-quinolyl)-2-morpholino-5-(trifluoromethyl)pyridine-3-carboxamide (compound-139): to a solution of N-(2-hydroxy-4-methyl-6-quinolyl)-2-(triazolo[4,5-b]pyridin-3-yloxy)-5-(trifluoromethyl)pyridine-3-carboxamide (50 mg, 0.10 mmol, 1 eq) in NMP (0.5 mL) was added morpholine (200 μL, 2.3 mmol, 23 eq). The reaction mixture was stirred at room temperature over the weekend and poured into water. The precipitated solid was collected by filtration, washed with water and dried. The crude product was purified by flash chromathography (DCM/MeOH) yielding N-(2-hydroxy-4-methyl-6-quinolyl)-2-morpholino-5-(trifluoromethyl)pyridine-3-carboxamide (compound-139) (34 g, 79%) as a white solid. LCMS: (M+H)=433, UV=100%.

¹H NMR (300 MHz, DMSO-d₆) δ 11.60 (s, 1H), 10.65 (s, 1H), 8.72-8.36 (m, 1H), 8.10 (d, J=2.2 Hz, 1H), 8.03 (dd, J=2.5, 0.8 Hz, 1H), 7.78 (dd, J=8.9, 2.2 Hz, 1H), 7.31 (d, J=8.8 Hz, 1H), 6.43 (d, J=1.3 Hz, 1H), 3.72-3.58 (m, 4H), 3.58-3.45 (m, 4H), 2.40 (d, J=1.2 Hz, 3H).

Synthesis of Compound-140

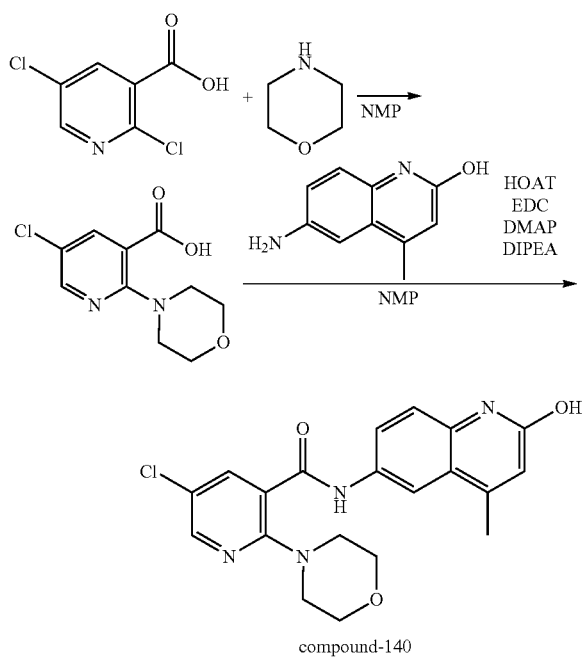

compound-140

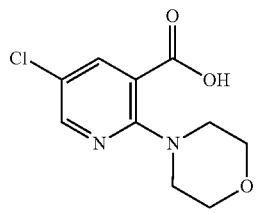

Preparation of 5-chloro-2-morpholino-pyridine-3-carboxylic acid: to a solution of 2,5-dichloropyridine-3-carboxylic acid (50 mg, 0.26 mmol, 1 eq) in NMP (300 μL) was added morpholine (250 μL, 2.6 mmol, 10 eq). The reaction mixture was stirred at 100° C. for 1 h. The mixture was poured into water and made acid with 1 M HCl, extracted with EtOAc to yield 5-chloro-2-morpholino-pyridine-3-carboxylic acid. The crude compound contained NMP and was used in the next step without purification. LCMS: (M+H)=243, UV=96% pure.

¹H NMR (300 MHz, DMSO-d₆) δ 8.30 (d, J=2.6 Hz, 1H), 7.95 (d, J=2.6 Hz, 1H), 3.66 (dd, J=5.5, 3.8 Hz, 4H), 3.41-3.35 (m, 4H).

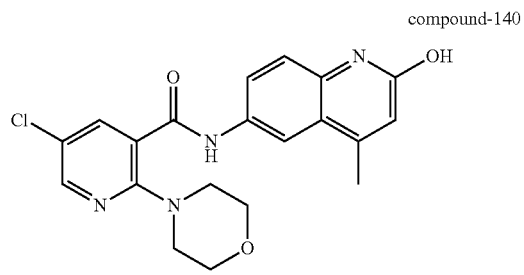 [SMILES: Cc1cc(O)nc2ccc(NC(=O)c3cc(Cl)cnc3N3CCOCC3)cc12]

compound-140

Preparation of 5-chloro-N-(2-hydroxy-4-methyl-6-quinolyl)-2-morpholino-pyridine-3-carboxamide (compound-140): to a solution of 5-chloro-2-morpholino-pyridine-3-carboxylic acid (0.26 mmol, 1 eq) in NMP (1 mL) were added 6-amino-4-methyl-quinolin-2-ol (45 mg, 0.26 mmol, 1 eq), HOAT (42 mg, 31 mmol, 1.5 eq), EDC (60 mg, 0.31 mmol, 1.5), DMAP (6 mg, 0.05 mmol, 0.2 eq) and DIPEA (136 μL, 0.78 mmol, 3 eq). The mixture was heated for 1 hour at 70° C. Water was added and the precipitated solid collected by filtration. The crude product was purified by flash chromatography (DCM/MeOH) yielding 5-chloro-N-(2-hydroxy-4-methyl-6-quinolyl)-2-morpholino-pyridine-3-carboxamide (compound-140) (41 mg, 39%) as a purple solid. LCMS: (M+H)=399, UV=100% pure.

¹H NMR (300 MHz, DMSO-d₆) δ 11.60 (s, 1H), 10.62 (s, 1H), 8.34 (d, J=2.6 Hz, 1H), 8.13 (d, J=2.2 Hz, 1H), 7.90 (d, J=2.6 Hz, 1H), 7.78 (dd, J=8.9, 2.3 Hz, 1H), 7.31 (d, J=8.8 Hz, 1H), 6.43 (s, 1H), 3.71-3.56 (m, 4H), 3.31-3.29 (m, 4H), 2.40 (d, J=1.2 Hz, 3H).-

Synthesis of Compound-141, Compound-142, Compound-143, Compound-144, Compound-145, Compound-146, Compound-147 and Compound-148
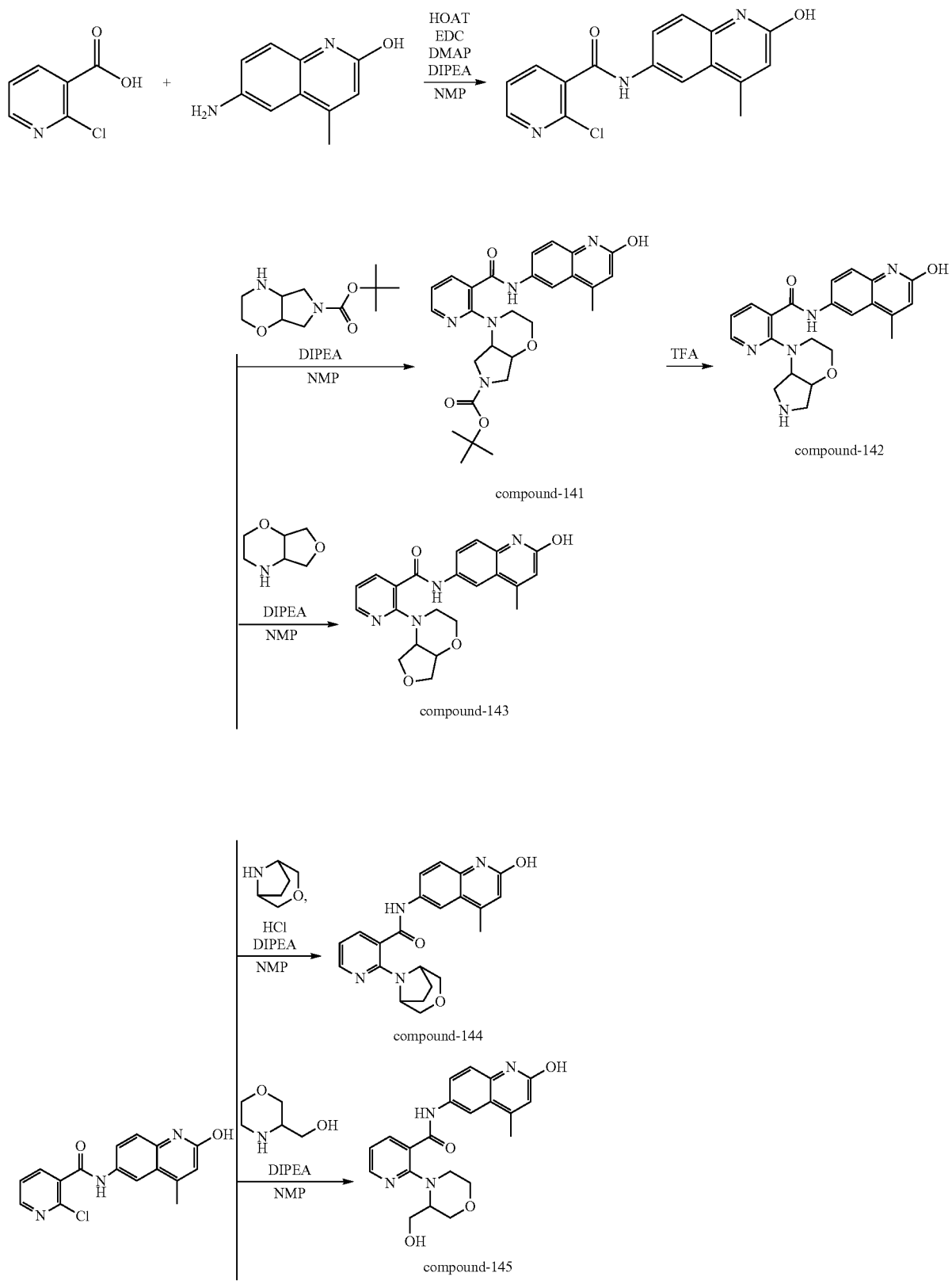

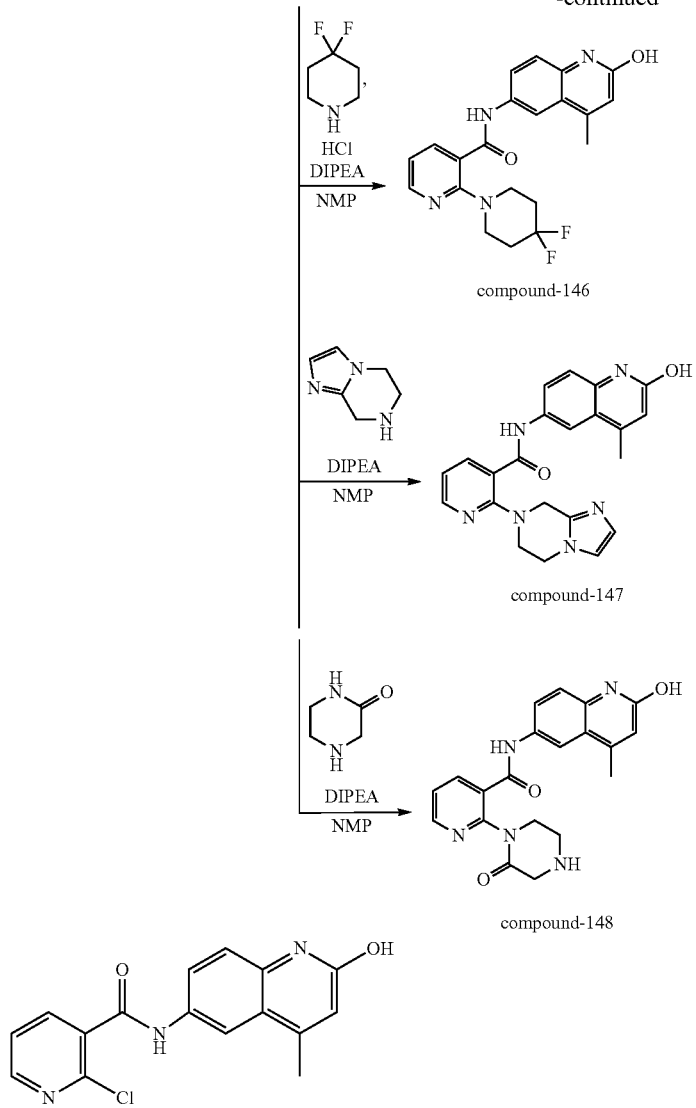

Preparation of 2-chloro-N-(2-hydroxy-4-methyl-6-quinolyl)pyridine-3-carboxamide: to a solution of 2-chloropyridine-3-carboxylic acid (400 mg, 2.54 mmol, 1 eq) in NMP (4 mL) were added 6-amino-4-methyl-quinolin-2-ol (440 mg, 2.54 mmol, 1 eq), HOAT (518 mg, 3.82 mmol, 1.5 eq), EDC (730 mg, 3.82 mmol, 1.5 eq), DMAP (62 mg, 0.50 mmol, 0.2 eq) and DIPEA (2.64 mL, 15.24 mmol, 3 eq). The reaction mixture was stirred at room temperature for 2 h. Water was added and the precipitated solid collected by filtration. The crude product was washed with water and dried yielding 2-chloro-N-(2-hydroxy-4-methyl-6-quinolyl)pyridine-3-carboxamide (437 mg, 62%) as an yellow solid. LCMS: (M+H)=314, UV=97%.

$^1$H NMR (300 MHz, DMSO-$d_6$) δ 11.63 (s, 1H), 10.75 (s, 1H), 8.54 (dd, J=4.8, 1.9 Hz, 1H), 8.14 (d, J=2.2 Hz, 1H), 8.09 (dd, J=7.5, 1.9 Hz, 1H), 7.76 (dd, J=8.8, 2.2 Hz, 1H), 7.57 (dd, J=7.6, 4.8 Hz, 1H), 7.31 (d, J=8.8 Hz, 1H), 6.44 (s, 1H), 2.45-2.33 (m, 3H).

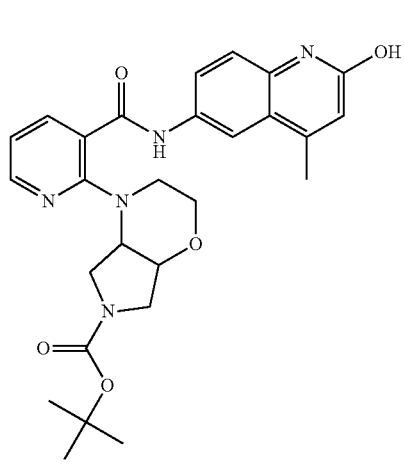

compound-141

Preparation of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141): to a solution of 2-chloro-N-(2-hydroxy-4-methyl-6-quinolyl)pyridine-3-carboxamide (80 mg, 0.26 mmol, 1 eq) in NMP (1 mL) were added tert-butyl 3,4,4a,5,7,7a-hexahydro-2H-pyrrolo[3,4-b][1,4]oxazine-6-carboxylate (236 mg, 1.04 mmol, 4 eq) and DIPEA (272 µL, 1.56 mmol, 6 eq). The reaction mixture was heated in a microwave oven at 150° C. for 4 hours. Water was added and the mixture extracted with EtOAc. The combined organic phases were dried over $Na_2SO_4$, filtered and evaporated. The crude product was purified by flash chromatography (DCM/MeOH) yielding tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141) (65 mg, 50%) as a brown oil. LCMS: (M+H)=506, UV=88% pure.

Preparation of 2-(2,3,4a,5,7,7a-hexahydrofuro[3,4-b][1,4]oxazin-4-yl)-N-(2-hydroxy-4-methyl-6-quinolyl)pyridine-3-carboxamide (compound-143): Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 30 mg, 23%. LCMS: (M+H)=407, UV=100% pure.

$^1$H NMR (300 MHz, DMSO-$d_6$) δ 11.60 (s, 1H), 10.54 (s, 1H), 8.28 (dd, J=4.8, 1.9 Hz, 1H), 8.13 (d, J=2.2 Hz, 1H), 7.78 (ddd, J=8.1, 5.2, 2.0 Hz, 2H), 7.30 (d, J=8.8 Hz, 1H), 6.93 (dd, J=7.4, 4.8 Hz, 1H), 6.43 (s, 1H), 4.55 (td, J=9.0, 4.0 Hz, 1H), 4.03 (t, J=3.8 Hz, 1H), 3.98-3.64 (m, 5H), 3.49 (td, J=11.2, 2.6 Hz, 1H), 3.43-3.37 (m, 1H), 3.30-3.21 (m, 1H), 2.39 (d, J=1.2 Hz, 3H).

compound-142

Preparation of 2-(3,4a,5,6,7,7a-hexahydro-2H-pyrrolo[3,4-b][1,4]oxazin-4-yl)-N-(2-hydroxy-4-methyl-6-quinolyl)pyridine-3-carboxamide (compound-142): Trifluoroacetic acid (250 µL) was added to a solution of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (65 mg, 0.16 mmol, 1 eq) in DCM (0.5 mL). Stirred at room temperature for 45 min. Evaporated and purified by flash chromatography (DCM/MeOH/NH$_3$-aq) yielding 2-(3,4a,5,6,7,7a-hexahydro-2H-pyrrolo[3,4-b][1,4]oxazin-4-yl)-N-(2-hydroxy-4-methyl-6-quinolyl)pyridine-3-carboxamide (compound-142) (15 mg, 23%) as a brown solid. LCMS: (M+H)=406, UV=100% pure.

$^1$H NMR (300 MHz, Methanol-$d_4$) δ 8.32 (dd, J=4.9, 1.9 Hz, 1H), 8.26 (d, J=2.3 Hz, 1H), 7.92 (dd, J=7.5, 1.9 Hz, 1H), 7.83 (dd, J=8.9, 2.3 Hz, 1H), 7.41 (d, J=8.8 Hz, 1H), 7.02 (dd, J=7.5, 4.8 Hz, 1H), 6.56 (s, 1H), 4.36 (td, J=8.8, 3.8 Hz, 1H), 4.02 (t, J=3.8 Hz, 1H), 3.88 (dt, J=11.2, 2.4 Hz, 1H), 3.69 (td, J=10.8, 3.6 Hz, 1H), 3.54-3.35 (m, 2H), 3.18-2.99 (m, 3H), 2.92 (d, J=12.7 Hz, 1H), 2.54 (s, 3H).

compound-144

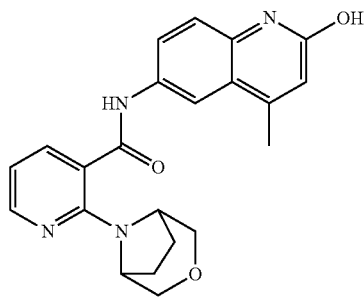

Preparation of N-(2-hydroxy-4-methyl-6-quinolyl)-2-(3-oxa-8-azabicyclo[3.2.1]octan-8-yl)pyridine-3-carboxamide (compound-144)

Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 16 mg, 26%. LCMS: (M+H)=391, UV=100% pure.

$^1$H NMR (300 MHz, DMSO-$d_6$) δ 11.59 (s, 1H), 10.52 (s, 1H), 8.31-8.14 (m, 2H), 7.76 (ddd, J=6.5, 5.3, 2.1 Hz, 2H), 7.29 (d, J=8.8 Hz, 1H), 6.90 (dd, J=7.4, 4.9 Hz, 1H), 6.42 (s, 1H), 4.21 (s, 2H), 3.66 (d, J=10.4 Hz, 2H), 3.49 (d, J=10.0 Hz, 2H), 2.39 (d, J=1.2 Hz, 3H), 1.93-1.62 (m, 4H).

compound-145

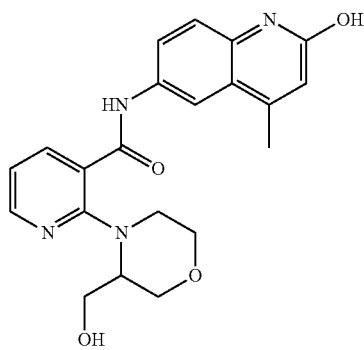

compound-143

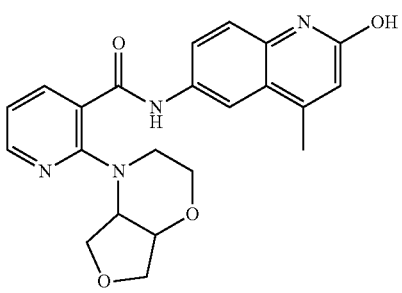

Preparation of 2-[3-(hydroxymethyl)morpholin-4-yl]-N-(2-hydroxy-4-methyl-6-quinolyl)pyridine-3-carboxamide (Compound-145)

Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 5 mg, 8% LCMS: (M+H)=395, UV=95% pure.

$^1$H NMR (300 MHz, Methanol-$d_4$) δ 8.42 (dd, J=4.8, 1.9 Hz, 1H), 8.36 (d, J=2.2 Hz, 1H), 8.15 (dd, J=7.6, 1.9 Hz, 1H), 7.90 (dd, J=8.9, 2.2 Hz, 1H), 7.41 (d, J=8.8 Hz, 1H), 7.15 (dd, J=7.6, 4.8 Hz, 1H), 6.57 (d, J=1.5 Hz, 1H), 4.19-4.04 (m, 1H), 3.93 (dd, J=4.1, 2.3 Hz, 2H), 3.84-3.62 (m, 4H), 3.50-3.33 (m, 4H), 3.26-3.11 (m, 1H), 2.56 (d, J=1.3 Hz, 3H).

Preparation of 2-(6,8-dihydro-5H-imidazo[1,2-a]pyrazin-7-yl)-N-(2-hydroxy-4-methyl-6-quinolyl)pyridine-3-carboxamide (compound-147)

Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 11 mg, 17%. LCMS: (M+H)=401, UV=100% pure.

$^1$H NMR (300 MHz, DMSO-$d_6$) δ 11.61 (s, 1H), 10.60 (s, 1H), 8.34 (dd, J=4.8, 1.9 Hz, 1H), 8.10 (d, J=2.2 Hz, 1H), 7.86 (dd, J=7.5, 1.9 Hz, 1H), 7.76 (dd, J=8.9, 2.2 Hz, 1H), 7.29 (d, J=8.8 Hz, 1H), 7.07 (d, J=1.2 Hz, 1H), 7.01 (dd, J=7.4, 4.8 Hz, 1H), 6.84 (d, J=1.2 Hz, 1H), 6.43 (s, 1H), 4.52 (s, 2H), 4.02 (t, J=5.2 Hz, 2H), 3.81 (t, 2H), 2.39 (d, J=1.2 Hz, 3H).

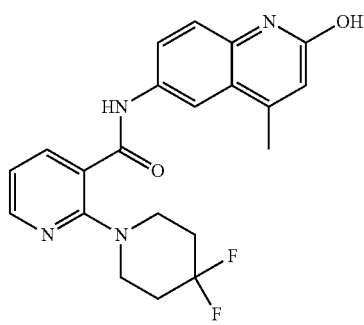

compound-146

Preparation of 2-(4,4-difluoro-1-piperidyl)-N-(2-hydroxy-4-methyl-6-quinolyl)pyridine-3-carboxamide (Compound-146)

Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 50 mg, 79%. LCMS: (M+H)=399, UV=100% pure.

$^1$H NMR (300 MHz, DMSO-$d_6$) δ 11.61 (s, 1H), 10.53 (s, 1H), 8.32 (dd, J=4.9, 1.9 Hz, 1H), 8.17 (d, J=2.2 Hz, 1H), 7.85 (dd, J=7.5, 1.9 Hz, 1H), 7.79 (dd, J=8.8, 2.2 Hz, 1H), 7.30 (d, J=8.8 Hz, 1H), 7.01 (dd, J=7.5, 4.8 Hz, 1H), 6.43 (s, 1H), 3.52-3.37 (m, 4H), 2.39 (d, J=1.2 Hz, 3H), 2.14-1.88 (m, 4H).

Preparation of N-(2-hydroxy-4-methyl-6-quinolyl)-2-(2-oxopiperazin-1-yl)pyridine-3-carboxamide (Compound-148)

Synthesized according to the procedure used in the synthesis of tert-butyl 4-[3-[(2-hydroxy-4-methyl-6-quinolyl)carbamoyl]-2-pyridyl]-2,3,4a,5,7,7a-hexahydropyrrolo[3,4-b][1,4]oxazine-6-carboxylate (compound-141). Yield: 49 mg, 81%. LCMS: (M+H)=378, UV=100% pure.

$^1$H NMR (300 MHz, DMSO-$d_6$) δ 11.60 (s, 1H), 10.55 (s, 1H), 8.30 (dd, J=4.8, 1.9 Hz, 1H), 8.13 (d, J=2.2 Hz, 1H), 7.97 (s, 1H), 7.80 (ddd, J=13.4, 8.1, 2.1 Hz, 2H), 7.29 (d, J=8.8 Hz, 1H), 6.97 (dd, J=7.4, 4.8 Hz, 1H), 6.43 (s, 1H), 3.86 (s, 2H), 3.61-3.49 (m, 2H), 3.25-3.13 (m, 2H), 2.39 (s, 3H).

Synthesis of Compound-149

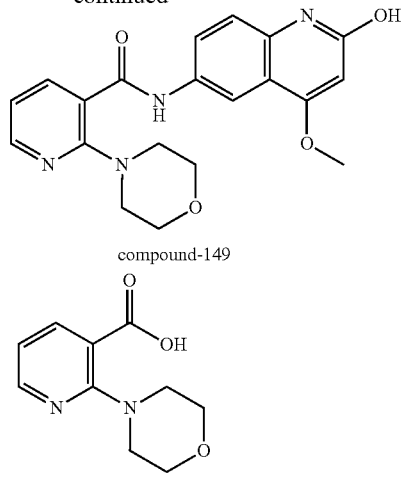

compound-149

Preparation of 2-morpholinopyridine-3-carboxylic acid 2-bromopyridine-3-carboxylic acid (700 mg, 3.47 mmol, 1 eq) was mixed with morpholine (2 mL, 22 mmol, 6 eq) and heated at 70° C. overnight. The mixture was evaporated, water was added and the mixture was made slightly acidic by drop wise adding 4 M HCl. The reaction mixture was then extracted 8 times with EtOAc. The combined organic phases were dried over $Na_2SO_4$, filtered and evaporated to dryness yielding 2-morpholinopyridine-3-carboxylic acid (649, 90%) as a beige coloured solid. LCMS: (M+H)=209, UV=100% pure.

$^1$H NMR (300 MHz, DMSO-$d_6$) δ 13.08 (s, 1H), 8.28 (dd, J=4.7, 1.9 Hz, 1H), 7.95 (dd, J=7.5, 2.0 Hz, 1H), 6.87 (dd, J=7.5, 4.7 Hz, 1H), 3.73-3.63 (m, 4H), 3.44-3.20 (m, 4H).

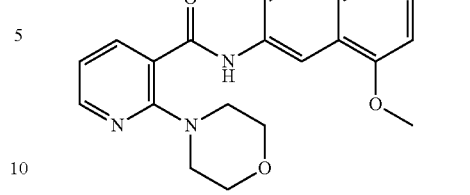

compound-149

Preparation of N-(2-hydroxy-4-methoxy-6-quinolyl)-2-morpholino-pyridine-3-carboxamide (Compound-149): to a solution of 2-morpholinopyridine-3-carboxylic acid (82 mg, 0.39 mmol 1 eq) in NMP (0.5 mL) were added 6-amino-4-methoxy-quinolin-2-ol (75 mg, 0.39 mmol, 1.5 eq), HOAT (80 mg, 0.59 mmol, 1.5 eq), EDC (112 mg, 0.59 mmol, 1.5 eq), DMAP (10 mg, 0.08 mmol, 0.2 eq) and DIPEA (407 μL, 2.34 mmol, 3 eq). The reaction mixture was stirred at room temperature for 30 min and poured into water. The precipitated solid was collected by filtration and purified by flash chromatography (DCM/MeOH/$NH_3$-aq) yielding N-(2-hydroxy-4-methoxy-6-quinolyl)-2-morpholino-pyridine-3-carboxamide (compound-149)(26 mg, 18%) as an off-white solid. LCMS: (M+H)=381, UV=95% pure.

$^1$H NMR (300 MHz, DMSO-$d_6$) δ 11.35 (s, 1H), 10.56 (s, 1H), 8.35 (d, J=2.4 Hz, 1H), 8.32 (dd, J=4.8, 1.9 Hz, 1H), 7.82 (dd, J=7.4, 1.9 Hz, 1H), 7.74 (dd, J=8.9, 2.4 Hz, 1H), 7.27 (d, J=8.8 Hz, 1H), 6.99 (dd, J=7.4, 4.8 Hz, 1H), 5.90 (s, 1H), 3.94 (s, 3H), 3.63 (t, J=4.7 Hz, 4H), 3.27 (t, J=4.7 Hz, 4H).

Synthesis of Compound-150, Compound-151, and Compound-152

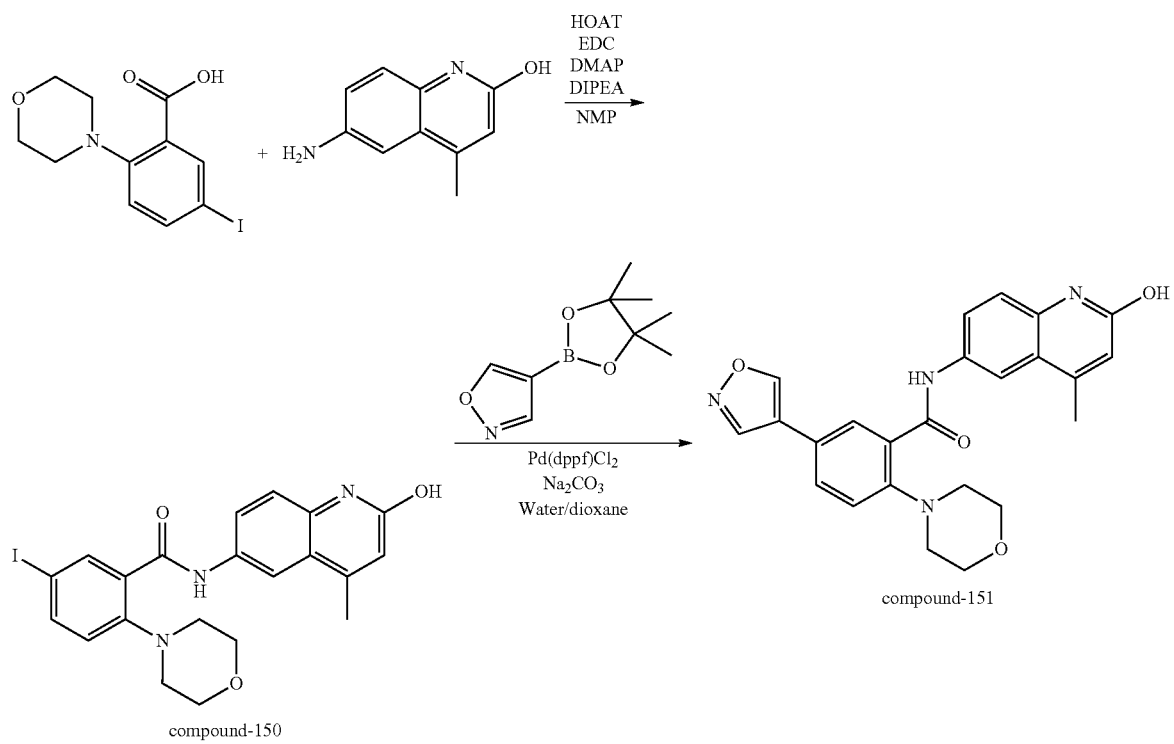

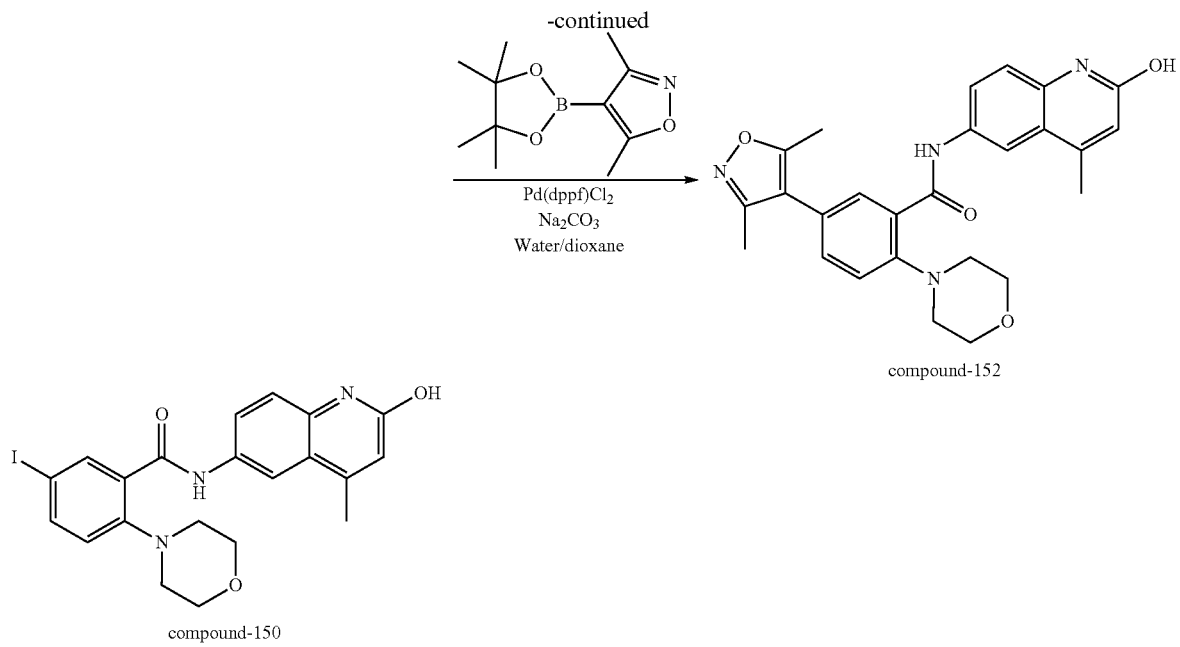

compound-152

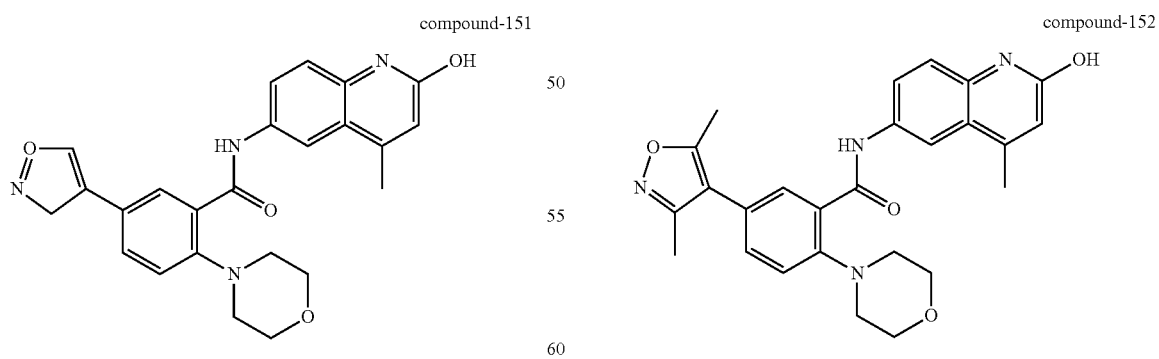

compound-150

Preparation of N-(2-hydroxy-4-methyl-6-quinolyl)-5-iodo-2-morpholino-benzamide (compound-150): to a solution of 5-iodo-2-morpholino-benzoic acid (600 mg, 1.8 mmol, 1 eq) in DMF (6 mL) were added 6-amino-4-methyl-quinolin-2-ol (314 mg, 1.8 mmol, 1 eq), HOAT (294 mg, 2.16 mmol, 1.2 eq), EDC (414 mg, 2.16 mmol, 1.2 eq), DMAP (44 mg, 0.36 mmol, 0.2 eq) and DIPEA (939 µL, 5.4 mmol, 3 eq). The reaction mixture was stirred at 70° C. for 1 h and poured into water. The precipitated solid was collected by filtration. The crude product was stirred in EtOAc, filtrated and dried to yield N-(2-hydroxy-4-methyl-6-quinolyl)-5-iodo-2-morpholino-benzamide (compound-150) (771 mg, 88%) as a beige coloured solid. LCMS: (M+H)=490, UV=98% pure.

$^1$H NMR (300 MHz, DMSO-$d_6$) δ 11.60 (s, 1H), 10.97 (s, 1H), 8.22 (d, J=2.3 Hz, 1H), 7.93 (d, J=2.2 Hz, 1H), 7.88-7.67 (m, 2H), 7.32 (d, J=8.8 Hz, 1H), 7.05 (d, J=8.5 Hz, 1H), 6.43 (s, 1H), 3.68 (t, J=4.6 Hz, 4H), 2.97 (t, J=4.6 Hz, 4H), 2.40 (s, 3H).

0.10 mmol, 1 eq) and 4-(4,4,5,5-tetramethyl-1,3,2-dioxaborolan-2-yl)isoxazole (compound 4)(39 mg, 0.20 mmol, 2 eq) in dioxane (2.5 mL) was added a solution of Na$_2$CO$_3$ (32 mg, 0.30 mmol, 3 eq) in water (0.5 mL). The reaction mixture was purged with argon and added [1,1'-Bis(diphenylphosphino)-ferrocene]dichloropalladium(II) (Pd(dppf)Cl$_2$) (15 mg, 0.2 mmol, 0.02 eq). The reaction mixture was heated at 70° C. for one hour. Water was added and the mixture extracted with EtOAc, dried over Na$_2$SO$_4$, filtered and evaporated. The crude product was purified by flash chromatography (DCM/MeOH) yielding N-(2-hydroxy-4-methyl-6-quinolyl)-5-isoxazol-4-yl-2-morpholino-benzamide (compound-151) (4 mg, 9%) as a solid. LCMS: (M+H)=431, UV=95% pure.

$^1$H NMR (300 MHz, Chloroform-d+Methanol-$d_4$) δ 8.73 (s, 1H), 8.58 (s, 1H), 8.47 (d, J=2.2 Hz, 1H), 8.35 (d, J=2.2 Hz, 1H), 7.69-7.49 (m, 2H), 7.40 (d, J=8.7 Hz, 1H), 7.33 (d, J=8.3 Hz, 1H), 6.59 (s, 1H), 4.06-3.83 (m, 6H), 3.23-2.97 (m, 6H), 2.52 (s, 4H).

Preparation of N-(2-hydroxy-4-methyl-6-quinolyl)-5-isoxazol-4-yl-2-morpholino-benzamide (Compound-151)

To a solution of N-(2-hydroxy-4-methyl-6-quinolyl)-5-iodo-2-morpholino-benzamide (compound-150) (50 mg, Preparation of 5-(3,5-dimethylisoxazol-4-yl)-N-(2-hydroxy-4-methyl-6-quinolyl)-2-morpholino-benzamide (Compound-152)

Synthesized according to the procedure used in the synthesis of N-(2-hydroxy-4-methyl-6-quinolyl)-5-isoxazol-4- yl-2-morpholino-benzamide (compound-151): Yield: 30 mg, 33% as a brown solid. LCMS: (M+H)=459, UV=95% pure.

¹H NMR (300 MHz, DMSO-d₆) δ 11.61 (s, 1H), 11.08 (s, 1H), 8.31 (d, J=2.2 Hz, 1H), 7.81 (dd, J=8.8, 2.3 Hz, 1H), 7.66 (d, J=2.2 Hz, 1H), 7.52 (dd, J=8.3, 2.3 Hz, 1H), 7.34 (dd, J=8.6, 6.4 Hz, 2H), 6.44 (s, 1H), 3.71 (dd, J=5.3, 3.5 Hz, 4H), 3.03 (t, J=4.5 Hz, 4H), 2.41 (d, J=1.1 Hz, 6H), 2.23 (s, 3H).

Synthesis of Compound-153, Compound-154, and Compound-155

Preparation of N-(2-hydroxy-4,7-dimethyl-6-quinolyl)-5-iodo-2-morpholino-benzamide (Compound-153)

Synthesized according to the procedure used in the synthesis of N-(2-hydroxy-4-methyl-6-quinolyl)-5-iodo-2-morpholino-benzamide (compound-150). Yield: 233 mg, 87%. LCMS: (M+H)=504, UV=95% pure.

¹H NMR (300 MHz, DMSO-d₆) δ 11.57 (s, 1H), 10.39 (s, 1H), 7.96 (d, J=2.2 Hz, 1H), 7.88 (s, 1H), 7.81 (dd, J=8.5, 2.3 Hz, 1H), 7.18 (d, J=0.9 Hz, 1H), 7.09 (d, J=8.6 Hz, 1H), 6.37 (s, 1H), 3.72 (dd, J=5.4, 3.6 Hz, 4H), 3.02 (t, J=4.6 Hz, 4H), 2.39 (d, J=1.2 Hz, 3H), 2.36 (s, 3H).

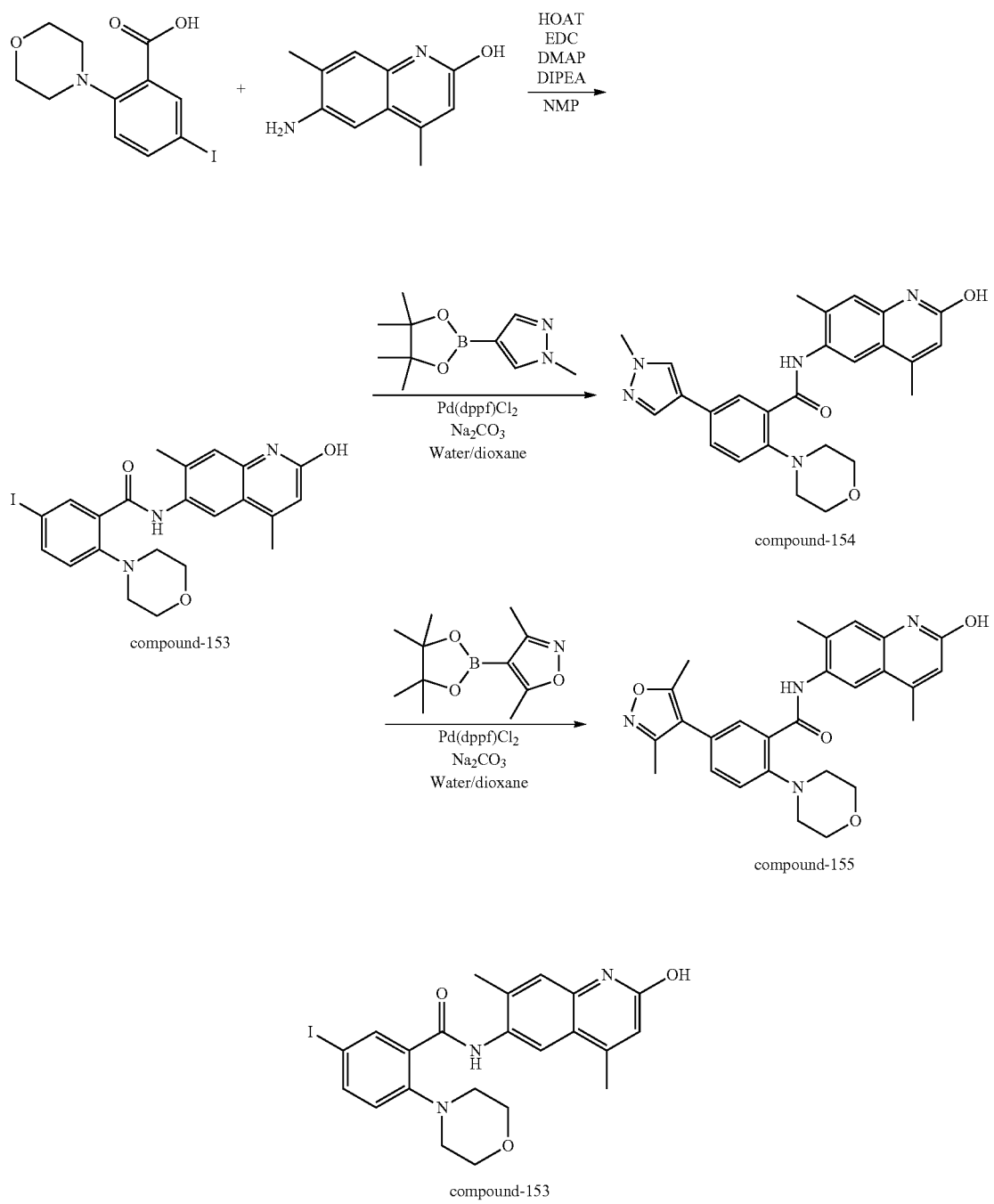

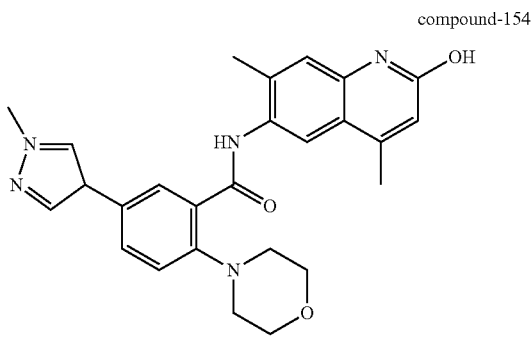

compound-154

Preparation of N-(2-hydroxy-4,7-dimethyl-6-quinolyl)-5-(1-methylpyrazol-4-yl)-2-morpholino-benzamide (compound-154): synthesized according to the procedure used in the synthesis of N-(2-hydroxy-4-methyl-6-quinolyl)-5-isoxazol-4-yl-2-morpholino-benzamide (compound-151) Yield: 15 mg (16%). LCMS: (M+H)=458, UV=97% pure.

$^1$H NMR (300 MHz, DMSO-$d_6$) δ 11.58 (s, 1H), 10.69 (s, 1H), 8.18 (d, J=0.8 Hz, 1H), 8.01 (s, 1H), 7.94 (d, J=2.3 Hz, 1H), 7.87 (d, J=0.8 Hz, 1H), 7.69 (dd, J=8.4, 2.3 Hz, 1H), 7.33 (d, J=8.4 Hz, 1H), 7.19 (s, 1H), 6.38 (s, 1H), 3.86 (s, 3H), 3.81-3.68 (m, 4H), 3.11-2.92 (m, 4H), 2.40 (s, 6H).

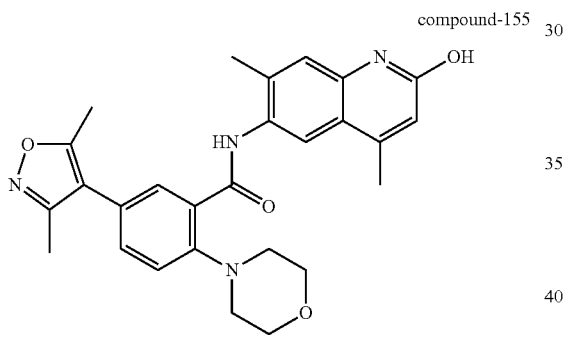

compound-155

Preparation of 5-(3,5-dimethylisoxazol-4-yl)-N-(2-hydroxy-4,7-dimethyl-6-quinolyl)-2-morpholino-benzamide (Compound-155)

Synthesized according to the procedure used in the synthesis of N-(2-hydroxy-4-methyl-6-quinolyl)-5-isoxazol-4-yl-2-morpholino-benzamide (compound-151). Yield: 34 mg, 60%. LCMS: (M+H)=473, UV=94% pure.

$^1$H NMR (300 MHz, DMSO-$d_6$) δ 11.57 (s, 1H), 10.52 (s, 1H), 8.00 (s, 1H), 7.70 (d, J=2.2 Hz, 1H), 7.53 (dd, J=8.4, 2.3 Hz, 1H), 7.39 (d, J=8.4 Hz, 1H), 7.19 (s, 1H), 6.37 (s, 1H), 3.88-3.54 (m, 4H), 3.21-2.82 (m, 4H), 2.43 (s, 3H), 2.40 (d, J=1.2 Hz, 6H), 2.25 (s, 3H).

Synthesis of Compound-156 and Compound-157

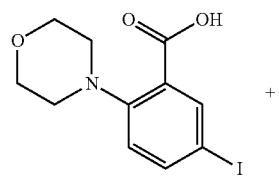

+

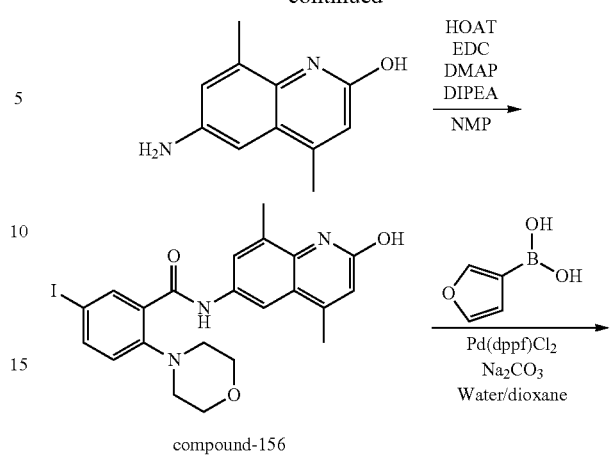

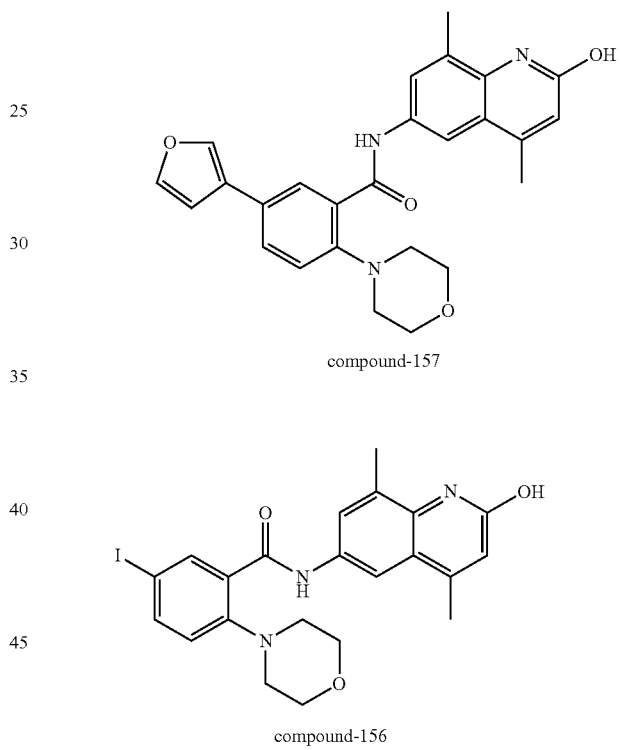

compound-156

Preparation of N-(2-hydroxy-4,8-dimethyl-6-quinolyl)-5-iodo-2-morpholino-benzamide (Compound-156)

Synthesized according to the procedure used in the synthesis of N-(2-hydroxy-4-methyl-6-quinolyl)-5-iodo-2-morpholino-benzamide (compound-150). Yield: 162 mg, 77%. LCMS: (M+H)=504, UV=98% pure.

$^1$H NMR (300 MHz, DMSO-$d_6$) δ 10.88 (s, 1H), 10.75 (s, 1H), 8.05 (d, J=2.3 Hz, 1H), 7.91 (d, J=2.2 Hz, 1H), 7.80 (dd, J=8.5, 2.3 Hz, 1H), 7.75-7.65 (m, 1H), 7.05 (d, J=8.6 Hz, 1H), 6.46 (d, J=2.0 Hz, 1H), 3.68 (dd, J=5.8, 3.2 Hz, 4H), 2.97 (dd, J=5.7, 3.5 Hz, 4H), 2.44 (s, 3H), 2.40 (d, J=1.1 Hz, 3H).

compound-157

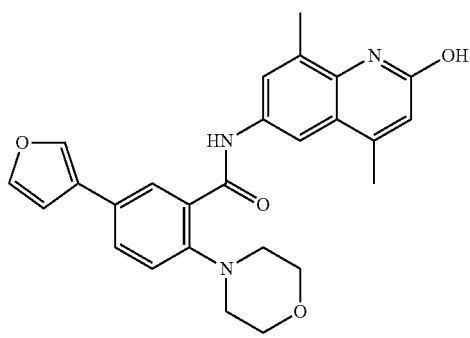

Preparation of 5-(3-furyl)-N-(2-hydroxy-4,8-dimethyl-6-quinolyl)-2-morpholino-benzamide (compound-157): Synthesized according to the procedure used in the synthesis of N-(2-hydroxy-4-methyl-6-quinolyl)-5-isoxazol-4-yl-2-morpholino-benzamide (compound-151). Yield: 49 mg, 55%. LCMS: (M+H)=444, UV=95% pure.

$^1$H NMR (300 MHz, DMSO-d$_6$) δ 11.06 (s, 1H), 10.76 (s, 1H), 8.26-8.13 (m, 2H), 7.93 (d, J=2.3 Hz, 1H), 7.78-7.67 (m, 3H), 7.28 (d, J=8.4 Hz, 1H), 6.99 (dd, J=1.9, 0.9 Hz, 1H), 6.46 (s, 1H), 5.76 (s, 2H), 3.72 (t, J=4.5 Hz, 4H), 3.31 (s, 2H), 3.00 (t, J=4.5 Hz, 4H), 2.45 (s, 3H), 2.42 (d, J=1.2 Hz, 3H).

Synthesis of Compound-158, Compound-159, Compound-160, and Compound-161

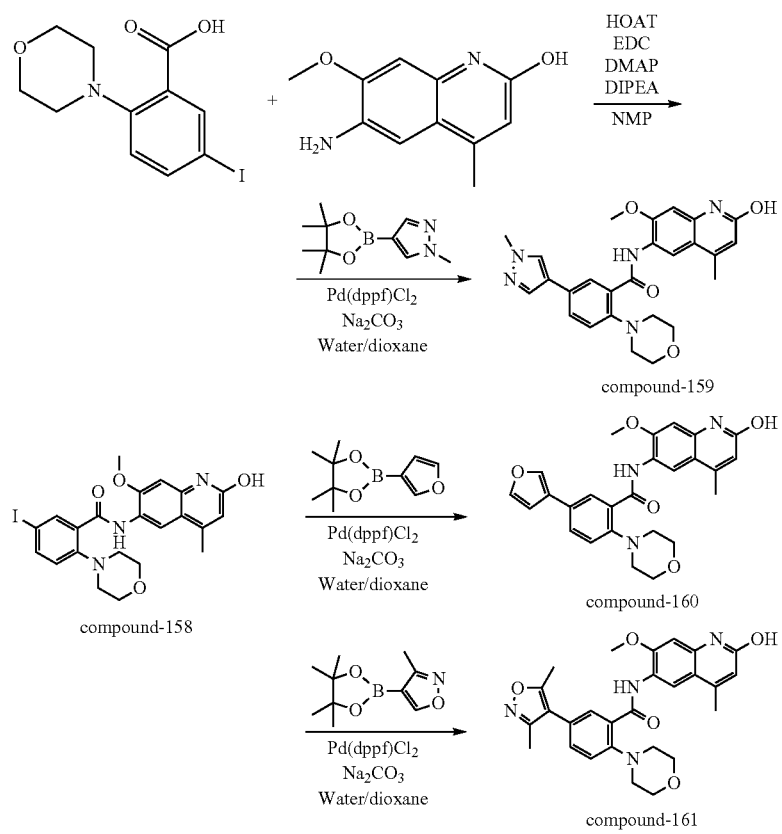

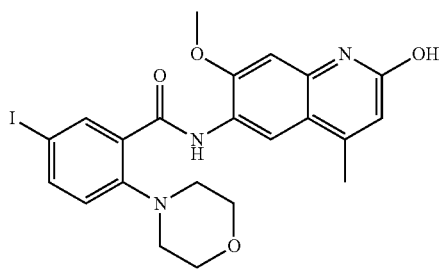

Preparation of N-(2-hydroxy-7-methoxy-4-methyl-6-quinolyl)-5-iodo-2-morpholino-benzamide (Compound-158)

Synthesized according to the procedure used in the synthesis of N-(2-hydroxy-4-methyl-6-quinolyl)-5-isoxazol-4-yl-2-morpholino-benzamide (compound-150). Yield: 164 mg, 32%. LCMS: (M+H)=520, UV=100% pure.

$^1$H NMR (300 MHz, DMSO-d$_6$) δ 11.53 (s, 1H), 11.40 (s, 1H), 8.84 (s, 1H), 8.25 (d, J=2.3 Hz, 1H), 7.89 (dd, J=8.5, 2.3 Hz, 1H), 7.20 (d, J=8.6 Hz, 1H), 6.99 (s, 1H), 6.29 (s, 1H), 5.76 (s, 1H), 3.97 (s, 3H), 3.77 (t, J=4.5 Hz, 4H), 2.98 (t, J=4.6 Hz, 4H), 2.38 (d, J=1.1 Hz, 3H).

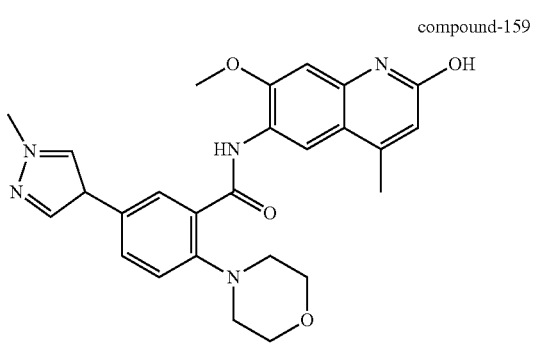

compound-159

Preparation of N-(2-hydroxy-7-methoxy-4-methyl-6-quinolyl)-5-(1-methylpyrazol-4-yl)-2-morpholino-benzamide (Compound-159)

Synthesized according to the procedure used in the synthesis of N-(2-hydroxy-4-methyl-6-quinolyl)-5-isoxazol-4-yl-2-morpholino-benzamide (compound-151). Yield: 40 mg, 56%. LCMS: (M+H)=474, UV=96% pure.

$^1$H NMR (300 MHz, DMSO-d$_6$) δ 11.66 (s, 1H), 11.52 (s, 1H), 8.96 (s, 1H), 8.21 (d, J=0.7 Hz, 1H), 8.18 (d, J=2.3 Hz, 1H), 7.88 (d, J=0.8 Hz, 1H), 7.75 (dd, J=8.4, 2.3 Hz, 1H), 7.40 (d, J=8.4 Hz, 1H), 7.00 (s, 1H), 6.30 (s, 1H), 3.99 (s, 3H), 3.87 (s, 3H), 3.84-3.71 (m, 4H), 3.04-2.92 (m, 4H), 2.40 (d, J=1.2 Hz, 3H).

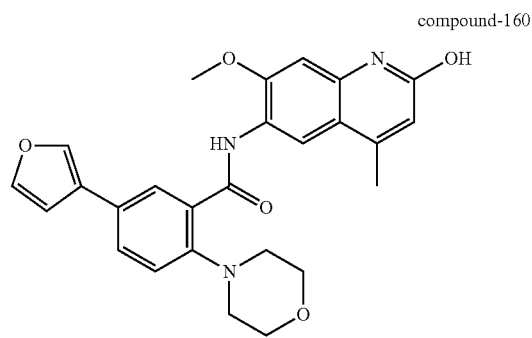 [SMILES: COc1cc2nc(O)cc(C)c2cc1NC(=O)c1cc(-c2ccoc2)ccc1N1CCOCC1]

compound-160

Preparation of 5-(3-furyl)-N-(2-hydroxy-7-methoxy-4-methyl-6-quinolyl)-2-morpholino-benzamide (Compound-160)

Synthesized according to the procedure used in the synthesis of N-(2-hydroxy-4-methyl-6-quinolyl)-5-isoxazol-4-yl-2-morpholino-benzamide (compound-151). Yield: 70 mg, 73%. LCMS: (M+H)=460, UV=95% pure.

$^1$H NMR (300 MHz, DMSO-d$_6$) δ 11.58 (s, 1H), 11.53 (s, 1H), 8.96 (s, 1H), 8.26 (dd, J=1.6, 0.9 Hz, 1H), 8.22 (d, J=2.2 Hz, 1H), 7.80 (dd, J=8.3, 2.3 Hz, 1H), 7.76 (t, J=1.7 Hz, 1H), 7.11-6.82 (m, 2H), 6.30 (s, 1H), 5.76 (s, 2H), 3.99 (s, 3H), 3.92-3.67 (m, 4H), 3.12-2.92 (m, 4H), 2.40 (d, J=1.1 Hz, 4H).

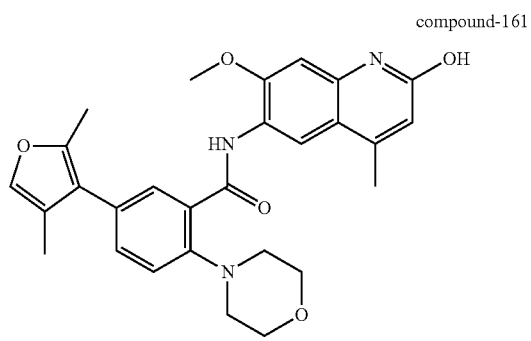 [SMILES: COc1cc2nc(O)cc(C)c2cc1NC(=O)c1cc(-c2c(C)coc2C)ccc1N1CCOCC1]

compound-161

Preparation of 5-(3,5-dimethylisoxazol-4-yl)-N-(2-hydroxy-7-methoxy-4-methyl-6-quinolyl)-2-morpholino-benzamide (Compound-161)

Synthesized according to the procedure used in the synthesis of N-(2-hydroxy-4-methyl-6-quinolyl)-5-isoxazol-4-yl-2-morpholino-benzamide (compound 36). Yield: 10 mg, 17%. LCMS: (M+H)=489, UV=94% pure.

Synthesis of Compound-162

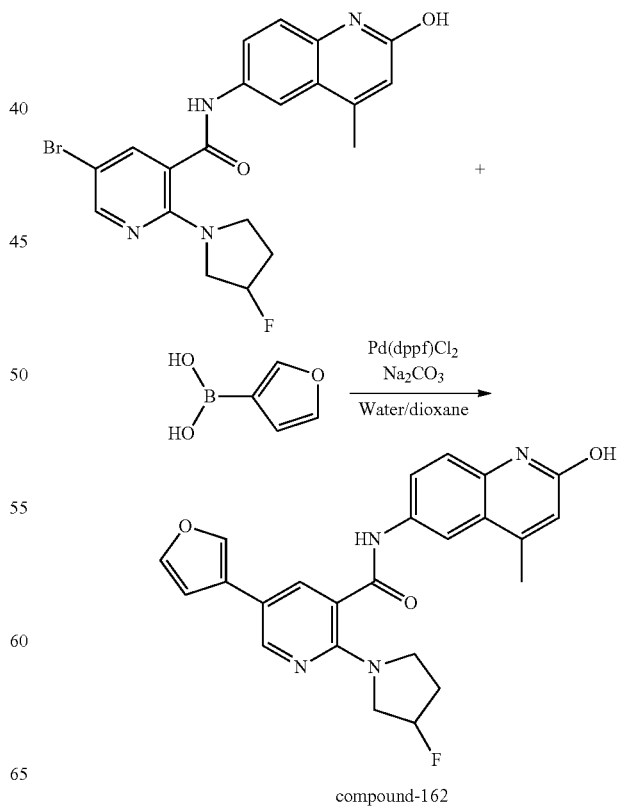

compound-162

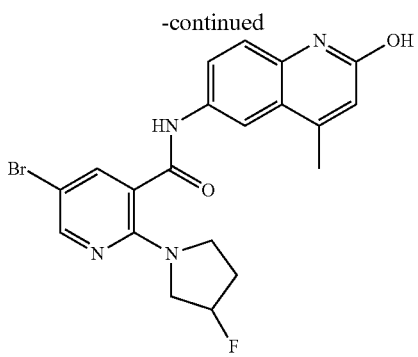

Preparation of 2-(3-fluoropyrrolidin-1-yl)-5-(3-furyl)-N-(2-hydroxy-4-methyl-8,8a-dihydroquinolin-6-yl)pyridine-3-carboxamide (Compound-162)

Synthesized according to the procedure used in the synthesis of N-(2-hydroxy-4-methyl-6-quinolyl)-5-isoxazol-4-yl-2-morpholino-benzamide (compound-151). Yield: 26 mg, 26%. LCMS: (M+H)=433, UV=94% pure.

$^1$H NMR (300 MHz, DMSO-d$_6$) δ 11.60 (s, 1H), 10.64 (s, 1H), 8.51 (d, J=2.3 Hz, 1H), 8.28-8.10 (m, 2H), 7.96 (d, J=2.4 Hz, 1H), 7.83 (dd, J=8.9, 2.2 Hz, 1H), 7.73 (t, J=1.7 Hz, 1H), 7.30 (d, J=8.8 Hz, 1H), 7.00 (dd, J=1.9, 0.9 Hz, 1H), 6.43 (s, 1H), 5.53-5.24 (m, 1H), 3.95-3.46 (m, 4H), 2.40 (d, J=1.2 Hz, 3H), 2.29-1.93 (m, 2H).

Synthesis of Compound-163

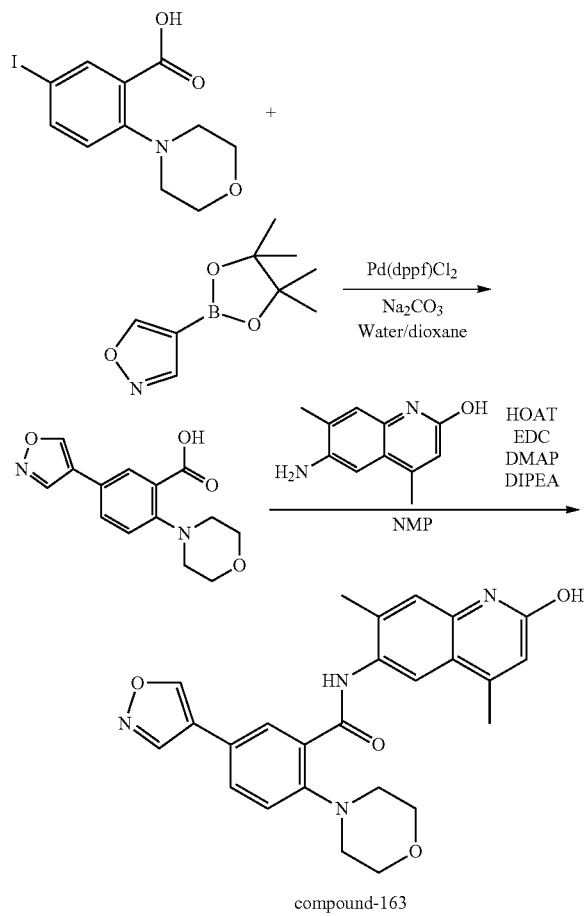

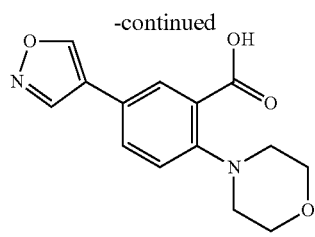

Preparation of 5-isoxazol-4-yl-2-morpholino-benzoic acid: to a solution of 5-iodo-2-morpholino-benzoic acid (200 mg, 0.60 mmol, 1 eq) and 4-(4,4,5,5-tetramethyl-1,3,2-dioxaborolan-2-yl)isoxazole (234 mg, 1.2 mmol, 2 eq) in dioxane (5 mL) was added a solution of Na$_2$CO$_3$ (254 mg, 2.4 mmol, 4 eq) in water (2 mL). The reaction mixture was purged with argon and added [1,1'-Bis(diphenylphosphino)ferrocene]dichloropalladium(II) (Pd(dppf)Cl$_2$) (44 mg, 0.06 mmol, 0.1 eq). The reaction mixture was heated at 60° C. for 20 min. Water was added and the mixture made acidic with 1 M HCl, extracted with EtOAc, dried over Na$_2$SO$_4$, filtered and evaporated. The crude product was purified by flash chromatography (DCM/MeOH) yielding 5-isoxazol-4-yl-2-morpholino-benzoic acid (82 mg, 50%) as a brown solid. LCMS: (M+H)=275, UV=100% pure.

$^1$H NMR (300 MHz, DMSO-d$_6$) δ 15.95 (s, 1H), 9.56 (s, 1H), 9.24 (s, 1H), 8.19 (d, J=2.3 Hz, 1H), 7.93 (dd, J=8.4, 2.3 Hz, 1H), 7.64 (d, J=8.4 Hz, 1H), 3.84-3.74 (m, 4H), 3.13-3.03 (m, 4H).

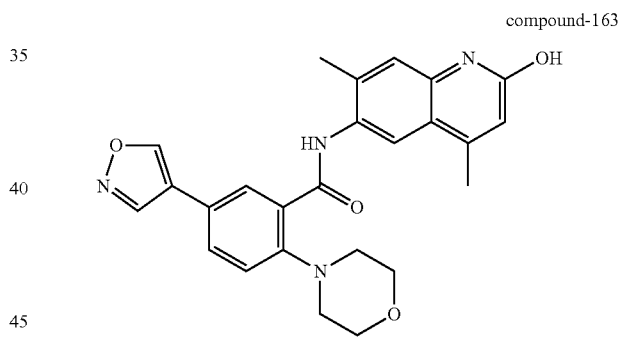

Preparation of N-(2-hydroxy-4,7-dimethyl-6-quinolyl)-5-isoxazol-4-yl-2-morpholino-benzamide (compound-163): to a solution of 5-isoxazol-4-yl-2-morpholino-benzoic acid (40 mg, 0.15 mmol, 1 eq) and 6-amino-4,7-dimethyl-quinolin-2-ol (34 mg, 0.18 mmol, 1.2 eq) were added HOAT (31 mg, 0.23 mmol, 1.5 eq), EDC (44 mg, 0.23 mmol, 1.5 eq), DMAP (4 mg, 0.03 mmol, 0.2 eq) and 78 μL, 0.45 mmol, 3 eq). The reaction mixture was stirred at room temperature for 4 hours and poured into water. The precipitated solid was collected by filtration and purified by flash chromatography (DCM/MeOH) yielding N-(2-hydroxy-4,7-dimethyl-6-quinolyl)-5-isoxazol-4-yl-2-morpholino-benzamide (compound-163) (13 mg, 20%) as a yellowish solid. LCMS: (M+H)=445, UV=94% pure.

$^1$H NMR (300 MHz, Methanol-d$_4$) δ 9.14 (d, J=1.4 Hz, 1H), 8.90 (d, J=1.4 Hz, 1H), 8.19 (t, J=1.8 Hz, 1H), 8.14 (d, J=1.3 Hz, 1H), 7.83 (dt, J=8.4, 1.8 Hz, 1H), 7.46 (dd, J=8.4, 1.3 Hz, 1H), 7.33 (s, 1H), 6.52 (s, 1H), 3.97-3.74 (m, 4H), 3.24-3.10 (m, 4H), 2.55 (s, 3H), 2.50 (s, 3H).

Synthesis of Compound-164

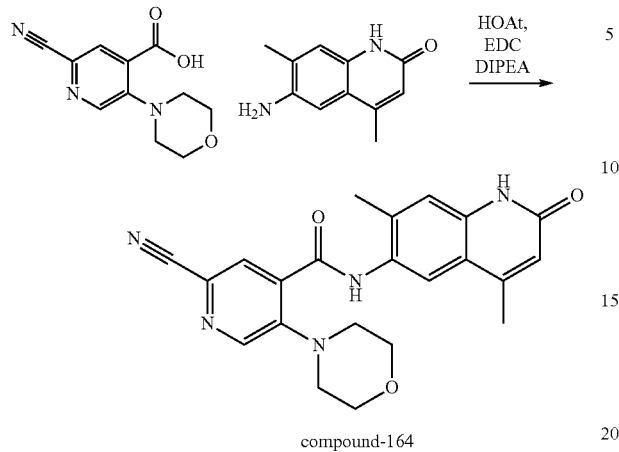

compound-164

To a solution of 2-cyano-5-morpholino-pyridine-4-carboxy acid (53 mg 0.23 mmol, 1 eq) in DMF (3 mL), HOAt (31 mg, 0.23 mmol), EDC×HCl (44 mg, 0.23 mmol) and DIPEA (80 µL, 0.46 mmol) were added, followed by addition of 6-amino-4,7-dimethyl-1H-quinolin-2-one (41 mg, 0.20 mmol) and the reaction mixture stirred at 70° C. for 20 h. Reaction mixture was diluted with 20 mL EtOAC and 20 mL water and extracted. The organic layer was washed with water (20 mL) and concentrated under reduced pressure. The obtained crude product was purified by flash chromatography in the solvent system DCM-MeOH, 0-10% MeOH. Purest fractions were combined and solvent evaporated to give 5 mg of 2-cyano-N-(4,7-dimethyl-2-oxo-1H-quinolin-6-yl)-5-morpholino-pyridine-4-carboxamide (compound-164) as white solid. MS: m/z (M+H)$^+$ 404; 99% purity.

$^1$H NMR (300 MHz, DMSO-d$_6$) δ 11.57 (s, 1H), 10.18 (s, 1H), 8.54 (s, 1H), 8.07 (s, 1H), 7.77 (s, 1H), 7.19 (s, 1H), 6.38 (s, 1H), 3.78-3.68 (m, 4H), 3.34-3.29 (m, 4H), 2.39 (d, J=1.2 Hz, 3H), 2.34 (s, 3H).

Synthesis of Compound-165

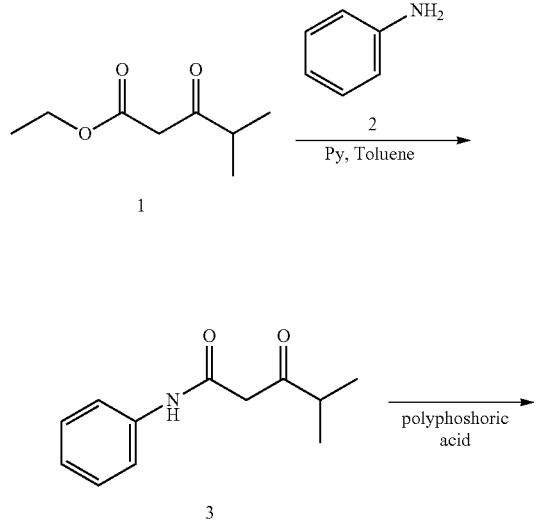

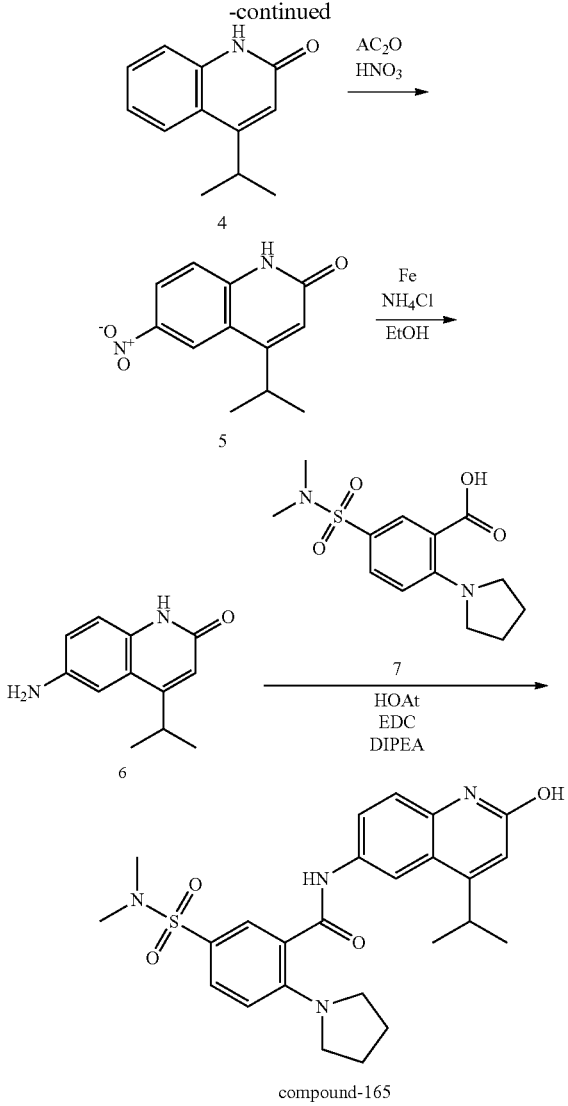

compound-165

Preparation of 4-methyl-3-oxo-N-phenyl-pentanamide (3)

A solution of ethyl 4-methyl-3-oxo-pentanoate (1086 mg, 7.5 mmol) in toluene/pyridine (5 mL/1 mL) was heated to gentle reflux for 30 min. Aniline (465 mg, 5.0 mmol) was then added dropwise into the above reaction mixture and it was refluxed for 16 h. The solution was allowed to cool to 25° C. and was extracted with 2M NaOH. The aqueous layer was separated and made weakly acidic with conc. HCl. It was then extracted with EtOAc (2×30 mL). Organic layer was concentrated under reduced pressure to give 1.048 g of crude 4-methyl-3-oxo-N-phenyl-pentanamide. Product was used as such without further purification.

Preparation of 4-isopropyl-1H-quinolin-2-one (4)

To 5 mL g of polyphosphoric acid was added 4-methyl-3-oxo-N-phenyl-pentanamide (1026 mg, 5.0 mmol) and the mixture stirred at 100° C. for 20 h.

After cooling to r.t., small portion of ice-cold water was added to the reaction mixture and stirred until all polyphosphoric acid dissolved. Mixture was then poured onto 20 mL of water/ice and pH made basic with 2N NaOH. Product precipitated and it was filtered off, washed with water and dried to afford 448 mg of 4-isopropyl-1H-quinolin-2-one. MS: m/z (M+H)$^+$ 188, purity 99%.

$^1$H NMR (300 MHz, DMSO-d$_6$) δ 11.60 (s, 1H), 7.89-7.77 (m, 1H), 7.49 (ddd, J=8.3, 7.1, 1.3 Hz, 1H), 7.33 (dd, J=8.3, 1.2 Hz, 1H), 7.20 (ddd, J=8.3, 7.1, 1.3 Hz, 1H), 6.36 (s, 1H), 3.50-3.43 (m, 1H), 1.25 (d, J=6.8 Hz, 6H).

Preparation of
4-isopropyl-6-nitro-1H-quinolin-2-one (5)

4-isopropyl-1H-quinolin-2-one (448 mg, 2.39 mmol) was dissolved in acetanhydride (5 mL). The mixture was stirred on ice for 10 min, then nitric acid (200 µL, 4.79 mmol) was added and the reaction stirred on ice for 2 h. Reaction mixture was diluted with water/ice (50 mL) and the resulting precipitate was washed with water and dried to give 235 mg of 4-isopropyl-6-nitro-1H-quinolin-2-one as yellow solid.

$^1$H NMR (300 MHz, DMSO-d$_6$) δ 12.22 (s, 1H), 8.62 (d, J=2.5 Hz, 1H), 8.35 (dd, J=9.1, 2.5 Hz, 1H), 7.48 (d, J=9.1 Hz, 1H), 6.53 (s, 1H), 3.31 (d, J=6.2 Hz, 1H), 1.28 (d, J=6.8 Hz, 6H).

Preparation of
6-amino-4-isopropyl-1H-quinolin-2-one (6)

4-isopropyl-6-nitro-1H-quinolin-2-one (232 mg, 1.0 mmol) was suspended in 15 mL EtOH and 15 mL saturated NH4Cl and heated to reflux. Iron powder (168 mg, 3.0 mmol) was added. After refluxing for another 45 min, reaction mixture was cooled, filtered and washed with water and DCM. Layers were separated and the organic extracts washed with brine and concentrated under reduced pressure to afford 161 mg of 6-amino-4-isopropyl-1H-quinolin-2-one. MS: m/z (M+H)$^+$ 203, purity 77.2%

$^1$H NMR (300 MHz, DMSO-d$_6$) δ 11.25 (s, 1H), 7.06 (d, J=8.6 Hz, 1H), 6.95 (d, J=2.4 Hz, 1H), 6.83 (dd, J=8.6, 2.3 Hz, 1H), 6.25 (s, 1H), 5.00 (s, 2H), 3.31 (s, 1H), 1.24 (d, J=6.8 Hz, 6H).

Preparation of 5-(dimethylsulfamoyl)-N-(2-hydroxy-4-isopropyl-6-quinolyl)-2-pyrrolidin-1-yl-benzamide (Compound-165)

To a solution of 5-(dimethylsulfamoyl)-2-pyrrolidin-1-yl-benzoic acid (95 mg 0.32 mmol, 1 eq) in DMF (5 mL), HOAt (44 mg, 0.32 mmol), EDC×HCl (61 mg, 0.32 mmol) and DIPEA (111 µL, 0.32 mmol) was added, followed by addition of 6-amino-4-ethyl-1H-quinolin-2-one (65 mg, 0.32 mmol) and the reaction stirred in DMF at 70° C. for 20 h. Reaction mixture was evaporated to dryness and purified by flash chromatography on a 12 g silicagel column in the solvent system DCM-MeOH, 0-10% MeOH. Purest fractions were combined and washed with water. Organic solvent was then evaporated under reduced pressure to give 73 mg of pure 5-(dimethylsulfamoyl)-N-(2-hydroxy-4-isopropyl-6-quinolyl)-2-pyrrolidin-1-yl-benzamide (compound-165). MS: m/z (M+H)$^+$ 483 purity 95%.

$^1$H NMR (300 MHz, DMSO-d$_6$) δ 11.61 (s, 1H), 10.55 (s, 1H), 8.24 (d, J=2.1 Hz, 1H), 7.79 (dd, J=8.9, 2.1 Hz, 1H), 7.65-7.53 (m, 2H), 7.31 (d, J=8.8 Hz, 1H), 6.89 (d, J=9.0 Hz, 1H), 6.38 (s, 1H), 3.47-3.29 (m, 5H), 2.59 (s, 6H), 1.99-1.79 (m, 4H), 1.28 (d, J=6.7 Hz, 6H).

Synthesis of Compound-166

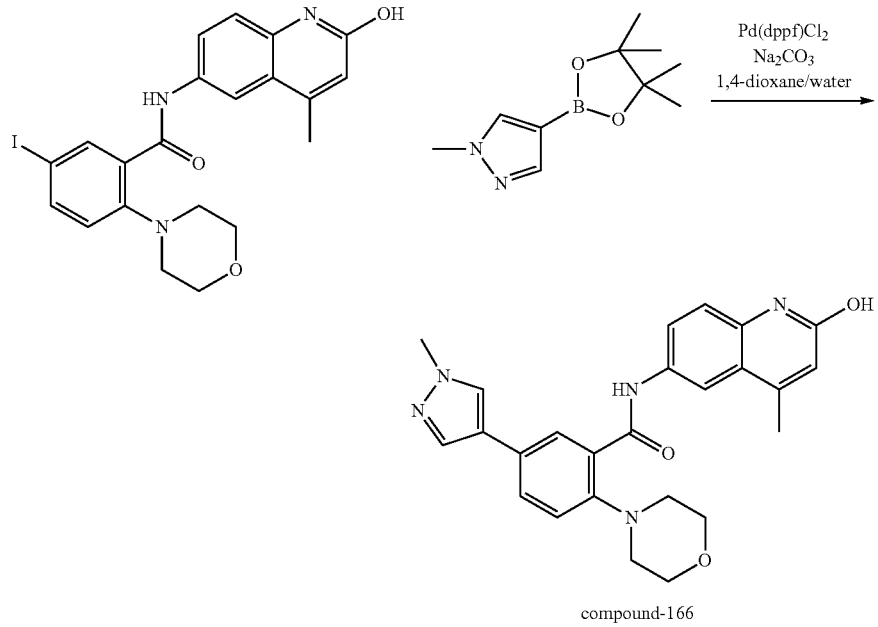

compound-166

Sodium carbonate (38 mg, 0.36 mmol) in water (1 mL) was added to a mixture of N-(2-hydroxy-4-methyl-6-quinolyl)-5-iodo-2-morpholino-benzamide (60 mg, 0.12 mmol) and 1-methyl-4-(4,4,5,5-tetramethyl-1,3,2-dioxaborolan-2-yl)pyrazole (50 mg, 0.24 mmol) in 1,4-dioxane (5 mL) in 10 mL microwave vial and purged with argon before Pd(dppf)Cl2 (9 mg, 0.012 mmol) was added. Reaction was then stirred in microwave reactor at 140° C. for 45 min. Mixture was poured into 30 mL water and 30 mL DCM and extracted. DCM layer was washed with water and concentrated under reduced pressure. Crude product was purified by flash chromatography on 4 g silica gel column in DCM: MeOH, gradient 0-10% MeOH, 20CV. After evaporation of the solvent, 8 mg of N-(2-hydroxy-4-methyl-6-quinolyl)-5-(1-methylpyrazol-4-yl)-2-morpholino-benzamide (compound-166) was isolated. MS: m/z (M+H)$^+$ 444, purity 99%.

$^1$H NMR (300 MHz, DMSO-d$_6$) δ 11.62 (s, 1H), 11.31 (s, 1H), 8.38-8.25 (m, 1H), 8.16 (s, 1H), 7.94-7.90 (m, 1H), 7.88-7.78 (m, 2H), 7.72-7.65 (m, 1H), 7.34 (dd, J=8.4, 1.1 Hz, 2H), 6.44 (s, 1H), 3.87-3.84 (m, 3H), 3.75-3.72 (m, 4H), 3.03-2.93 (m, 4H), 2.42 (t, J=1.4 Hz, 3H).

Synthesis of Compound-167 mmol) was added. Reaction was then stirred in microwave reactor at 140° C. for 45 min. Mixture was diluted with DCM and water and product precipitated. Water layer was decanted and organic layer filtered off. The obtained precipitate was washed with DCM and water and dried to give 43 mg of pure product 5-(3-furyl)-N-(2-hydroxy-4-methyl-6-quinolyl)-2-morpholino-benzamide (compound-167). MS: m/z (M+H)$^+$ 430.06, purity 99%

$^1$H NMR (300 MHz, DMSO-d$_6$) δ 11.60 (s, 1H), 11.16 (s, 1H), 8.33 (d, J=2.3 Hz, 1H), 8.28-8.17 (m, 1H), 7.95 (t, J=2.1 Hz, 1H), 7.82 (dd, J=9.0, 2.4 Hz, 1H), 7.77-7.69 (m, 2H), 7.40-7.25 (m, 2H), 6.99 (t, J=1.8 Hz, 1H), 6.44 (s, 1H), 3.82-3.61 (m, 4H), 3.09-2.92 (m, 4H), 2.46-2.35 (m, 3H).

Synthesis of Compound-168

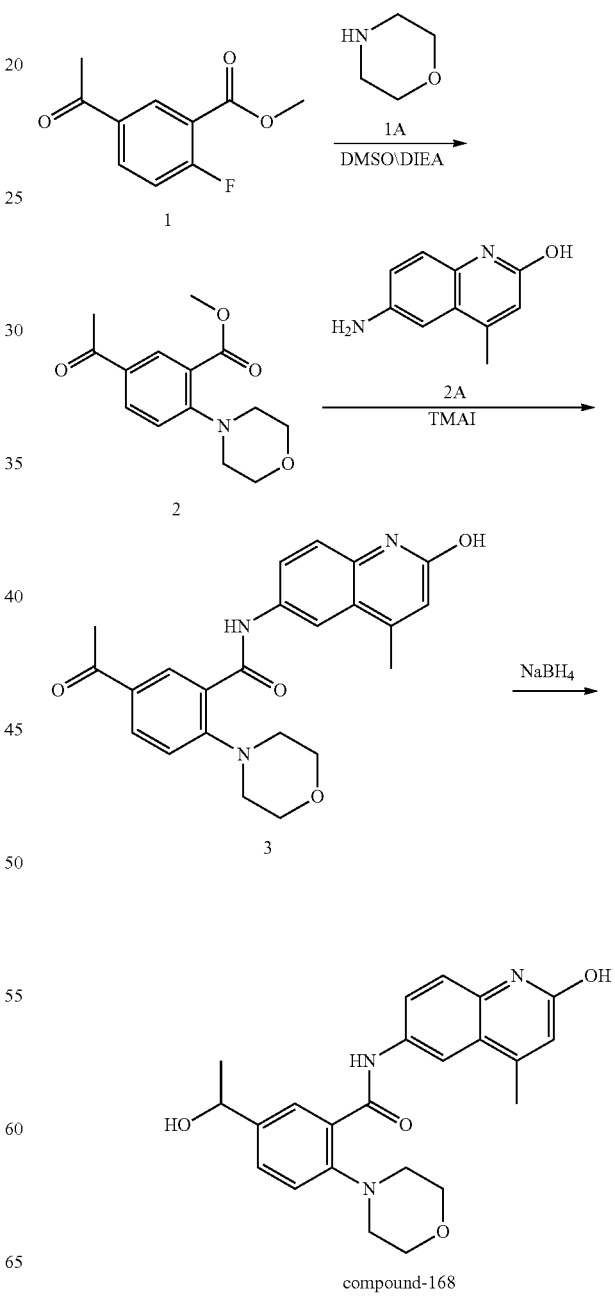

Sodium carbonate (38 mg, 0.36 mmol) in water (1 mL) was added to a mixture of N-(2-hydroxy-4-methyl-6-quinolyl)-5-iodo-2-morpholino-benzamide (60 mg, 0.12 mmol) and 2-(3-furyl)-4,4,5,5-tetramethyl-1,3,2-dioxaborolane (50 mg, 0.24 mmol) in 1,4-dioxane (5 mL) in 10 mL microwave vial and purged with argon before Pd(dppf)Cl2 (9 mg, 0.012

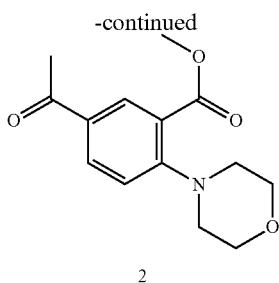

2

Preparation of methyl 5-acetyl-2-morpholinobenzoate (2): to a solution of methyl 5-acetyl-2-fluorobenzoate (1) (2 g, 10.2 mmol, 1 eq) in Dry DMF (20 mL) at RT was added morpholine (1.06 g, 12.24 mmol, 1.2 eq), DIPEA (3.95 g, 30.6 mmol, 3 eq) and stirred at RT for 3 h. After completion, the reaction mixture poured into water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography using (SiO$_2$) by eluting EtOAc:Pet ether (50:50) to afford methyl 5-acetyl-2-morpholinobenzoate (2) (2.2 g, 82%) as yellow solid.

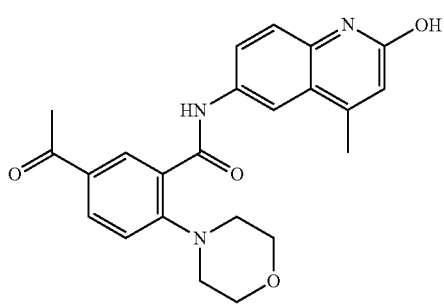

3

Preparation of 5-acetyl-N-(2-hydroxy-4-methylquinolin-6-yl)-2-morpholinobenzamide (3): to a solution of methyl 5-acetyl-2-morpholinobenzoate (2) (2 g, 7.6 mmol, 1 eq) in Dry toluene (20 mL) at RT added 6-amino-4-methylquinolin-2-ol (2.64 g, 15.20 mmol, 2 eq), trimethylaluminium (1.64 g, 22.8 mmol, 3 eq) and stirred at 100° C. for 3 h. After completion, the reaction mixture was quenched with ammonium chloride solution and filtered the solid obtained. The solid was washed with water and purified the compound by reverse phase method (0.05% formic acid in water: 0.05% formic acid in acetonitrile) to afford 5-acetyl-N-(2-hydroxy-4-methylquinolin-6-yl)-2-morpholinobenzamide (3) (450 mg, 15%) as yellow solid.

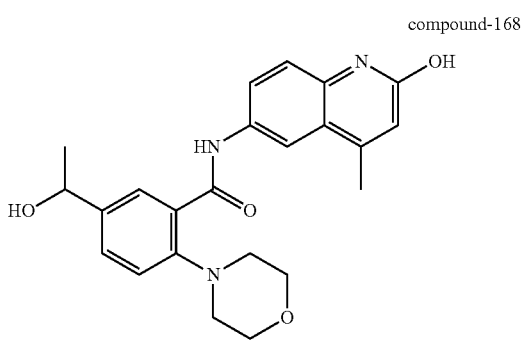 [SMILES: Cc1cc(O)nc2ccc(NC(=O)c3cc(C(C)O)ccc3N3CCOCC3)cc12]

compound-168

Preparation of N-(2-hydroxy-4-methylquinolin-6-yl)-5-(1-hydroxyethyl)-2-morpholinobenzamide (compound-168): to a solution of 5-acetyl-N-(2-hydroxy-4-methylquinolin-6-yl)-2-morpholinobenzamide (3) (450 mg, 1.11 mmol, 1 eq) in methanol (10 mL) was added sodium borohydride at 0° C. and stirred at RT for 1 h. After completion, the reaction mixture was quenched with ice water, filtered the solid, washed with water and dried to afford N-(2-hydroxy-4-methylquinolin-6-yl)-5-(1-hydroxyethyl)-2-morpholinobenzamide (compound-168) (430 mg, 98%) as yellow solid.

$^1$H NMR (300 MHz, DMSO-d$_6$): δ 11.59 (s, 1H), 11.40 (s, 1H), 8.29 (d, J=2.3 Hz, 1H), 7.82 (d, J=10.5 Hz, 2H), 7.48 (d, J=8.5 Hz, 1H), 7.30 (dd, J=17.5, 8.6 Hz, 2H), 6.43 (s, 1H), 5.19 (s, 1H), 4.74 (s, 1H), 3.74 (m, 4H), 2.97 (m, 4H), 2.42 (d, J=1.2 Hz, 2H), 1.33 (d, J=6.4 Hz, 3H).

Synthesis of Compound-169, Compound-170, and Compound-171:

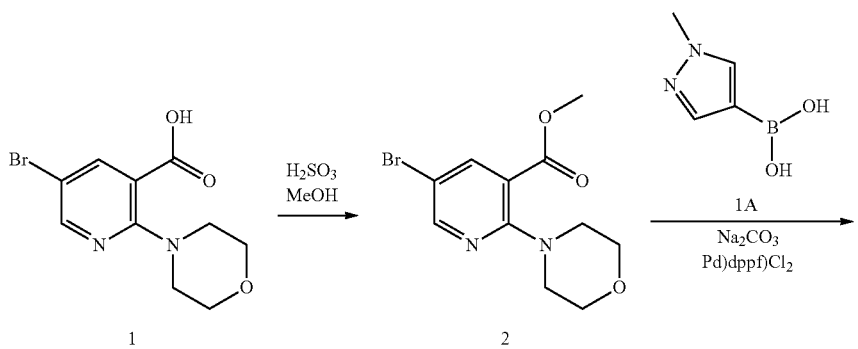

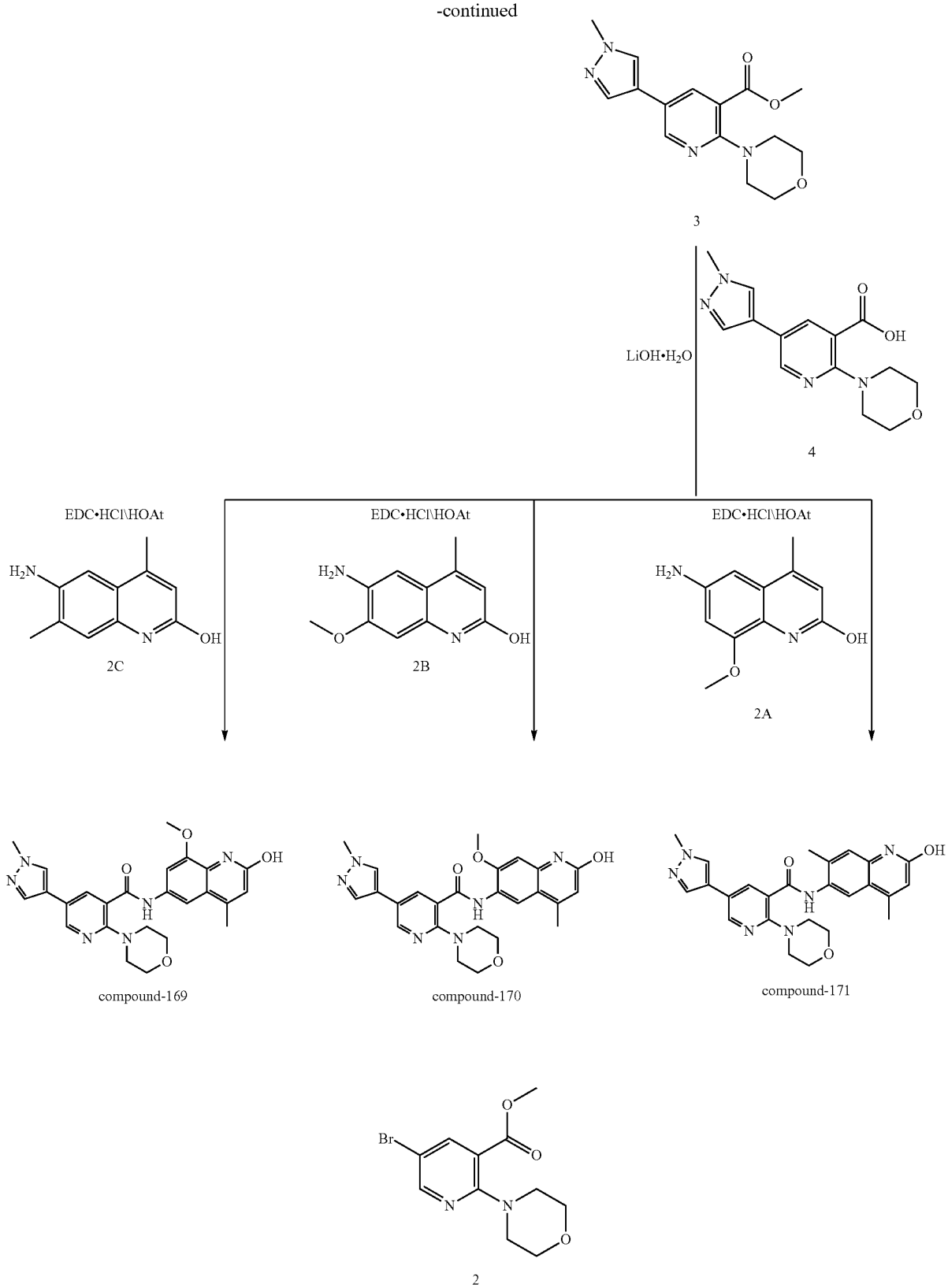
Preparation of methyl 5-bromo-2-morpholinonicotinate (2): to a solution of 5-bromo-2-morpholinonicotinic acid (1) (3 g, 10.452 mmol, 1 eq) in MeOH (30 mL), added Conc.H$_2$SO$_4$ (0.6 mL), and stirred at 70° C. for 18 h. After completion of the reaction, the reaction mixture was quenched with solid NaHCO$_3$ and added water and extracted with EtOAc (2×50 mL). The combined extracts were washed with water (40 mL), brine (40 mL), dried over anhydrous Na$_2$SO$_4$, filtered and evaporated to afford methyl 5-bromo-2-morpholinonicotinate (2) (2.3 g, 73%) as off white solid.

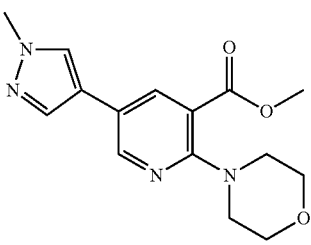

Preparation of methyl 5-(1-methyl-1H-pyrazol-4-yl)-2-morpholinonicotinate (3): to a solution of methyl 5-bromo-2-morpholinonicotinate (2) (1.2 g, 4 mmol, 1 eq) in Dioxane: H$_2$O (2:1) (10 vol) was added 2A (1 g, 8 mmol, 2 eq) and Na$_2$CO$_3$ (1.27 g, 12 mmol, 3 eq) and stirred at 100° C. for 16 h. After completion of the reaction, the solvent was evaporated and The crude compound was purified by column chromatography using (SiO$_2$) by eluting MeOH:DCM (5:95) to afford methyl 5-(1-methyl-1H-pyrazol-4-yl)-2-morpholinonicotinate (3) (700 mg, 58%) as off white solid.

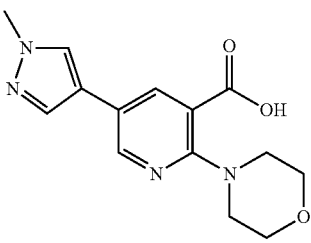

Preparation of 5-(1-methyl-1H-pyrazol-4-yl)-2-morpholinonicotinic acid (4): to a solution of methyl 5-(1-methyl-1H-pyrazol-4-yl)-2-morpholinonicotinate (3) (700 mg, 2.317 mmol, 1 eq) in Methanol: H$_2$O (5:1) (10 vol) was added LiOH (291.6 mg, 6.951 mmol, 3 eq) and stirred at RT for 16 h. After completion of the reaction, the solvent was evaporated, diluted with water (20 mL), acidified by using 5% citric acid solution and extracted with EtOAc (2×30 mL). The combined extracts were washed with water (20 mL), brine (20 mL), dried over anhydrous Na$_2$SO$_4$, filtered and evaporated to afford 5-(1-methyl-1H-pyrazol-4-yl)-2-morpholinonicotinic acid (4) (360 mg, 54%) as off white solid.

compound-169

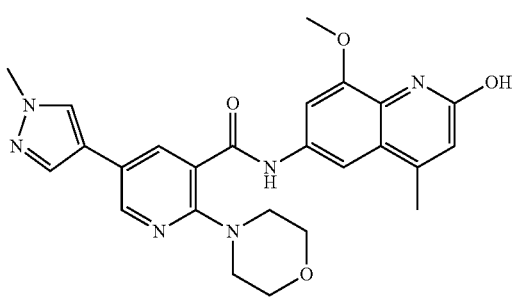

Preparation of N-(2-hydroxy-8-methoxy-4-methylquinolin-6-yl)-5-(1-methyl-1H-pyrazol-4-yl)-2-morpholinonicotinamide (Compound-169): to a solution of 5-(1-methyl-1H-pyrazol-4-yl)-2-morpholinonicotinic acid (4) (100 mg, 0.34 mmol, 1 eq) in Dry DMF (2 mL), added HOAt (94.38 mg, 0.69 mmol, 2 eq), EDC (133 mg, 0.69 mmol, 2 eq), DIPEA (179.05 mg, 1.38 mmol, 4 eq), 6-amino-8-methoxy-4-methylquinolin-2-ol (70.7 mg, 0.34 mmol, 1.0 eq) and stirred at RT for 16 h. After completion, the reaction mixture was poured into ice water. Filtered the solid, washed with diethyl ether and dried to afford N-(2-hydroxy-8-methoxy-4-methylquinolin-6-yl)-5-(1-methyl-1H-pyrazol-4-yl)-2-morpholinonicotinamide (Compound-169) (112 mg, 68%) as an off white solid.

$^1$H NMR (400 MHz, DMSO-d6): δ 10.65 (d, J=3.9 Hz, 2H), 8.58 (d, J=2.4 Hz, 1H), 8.20 (s, 1H), 8.03 (d, J=2.4 Hz, 1H), 7.92 (s, 1H), 7.78 (d, J=2.0 Hz, 1H), 7.59 (d, J=2.0 Hz, 1H), 6.46 (s, 1H), 3.90 (s, 3H), 3.86 (s, 3H), 3.70-3.63 (m, 4H), 3.30-3.23 (m, 4H), 2.39 (s, 3H).

compound-170

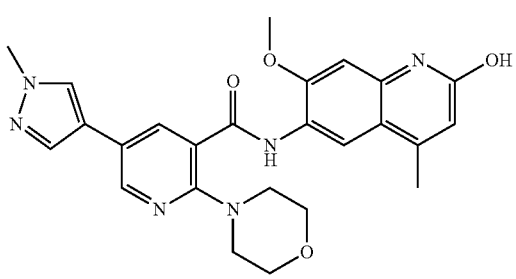

Preparation of N-(2-hydroxy-7-methoxy-4-methylquinolin-6-yl)-5-(1-methyl-1H-pyrazol-4-yl)-2-morpholinonicotinamide (compound-170): to a solution of 5-(1-methyl-1H-pyrazol-4-yl)-2-morpholinonicotinic acid (4) (100 mg, 0.34 mmol, 1 eq) in Dry DMF (2 mL) was added HOAt (94.38 mg, 0.69 mmol, 2 eq), EDC (133 mg, 0.69 mmol, 2 eq), DIPEA (179.05 mg, 1.38 mmol, 4 eq) and 6-amino-7-methoxy-4-methylquinolin-2-ol (70.7 mg, 0.34 mmol, 1.0 eq) and stirred at RT for 16 h. After completion, the reaction mixture was poured into ice water. Filtered the solid, washed with Diethyl ether and dried. The crude compound was purified by column chromatography using (SiO$_2$) by eluting with MeOH:DCM (4:96) to afford N-(2-hydroxy-7-methoxy-4-methylquinolin-6-yl)-5-(1-methyl-1H-pyrazol-4-yl)-2-morpholinonicotinamide (compound-170) (36 mg, 21%) as an off white solid.

$^1$H NMR (300 MHz, DMSO-d6): δ 11.52 (s, 1H), 10.95 (s, 1H), 8.81 (s, 1H), 8.71 (s, 1H), 8.37 (s, 1H), 8.28 (s, 1H), 7.97 (s, 1H), 7.00 (s, 1H), 6.30 (s, 1H), 3.98 (s, 3H), 3.88 (s, 3H), 3.78 (m, 4H), 3.19 (m, 4H), 2.39 (s, 3H).

compound-171

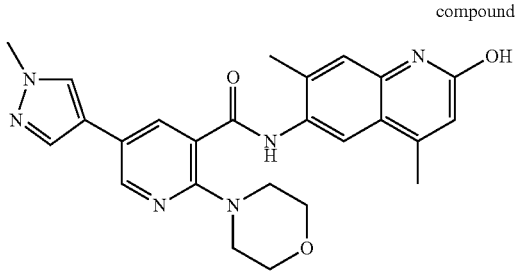

Preparation of N-(2-hydroxy-4,7-dimethylquinolin-6-yl)-5-(1-methyl-1H-pyrazol-4-yl)-2-morpholinonicotinamide (compound-171): to a solution of 5-(1-methyl-1H-pyrazol-4-yl)-2-morpholinonicotinic acid (Compound-4) (100 mg, 0.34 mmol, 1 eq) in Dry DMF (2 mL) was added HOAt (94.38 mg, 0.69 mmol, 2 eq), EDC (133 mg, 0.69 mmol, 2 eq), DIPEA (179.05 mg, 1.38 mmol, 4 eq) and 6-amino-4,7-dimethylquinolin-2-ol (65.2 mg, 0.34 mmol, 1.0 eq) and stirred at RT for 16 h. After completion, the reaction mixture was poured into ice water. Filtered the solid, washed with Diethyl ether and dried. The crude compound was purified by column chromatography using (SiO$_2$) by eluting with MeOH:DCM (4:96) to afford N-(2-hydroxy-4,7-dimethylquinolin-6-yl)-5-(1-methyl-1H-pyrazol-4-yl)-2-morpholinonicotinamide (compound-171) (45 mg, 28%) as an off white solid.

$^1$H NMR (400 MHz, DMSO-d6): δ 11.56 (s, 1H), 10.14 (s, 1H), 8.59 (d, J=2.4 Hz, 1H), 8.21 (s, 1H), 8.08 (d, J=2.4 Hz, 1H), 7.92 (d, J=6.4 Hz, 2H), 7.18 (s, 1H), 6.38 (s, 1H), 3.87 (s, 3H), 3.77-3.67 (m, 4H), 3.34 (m, 4H), 2.39 (d, J=7.8 Hz, 6H).

Synthesis of Compound-172 and Compound-173:

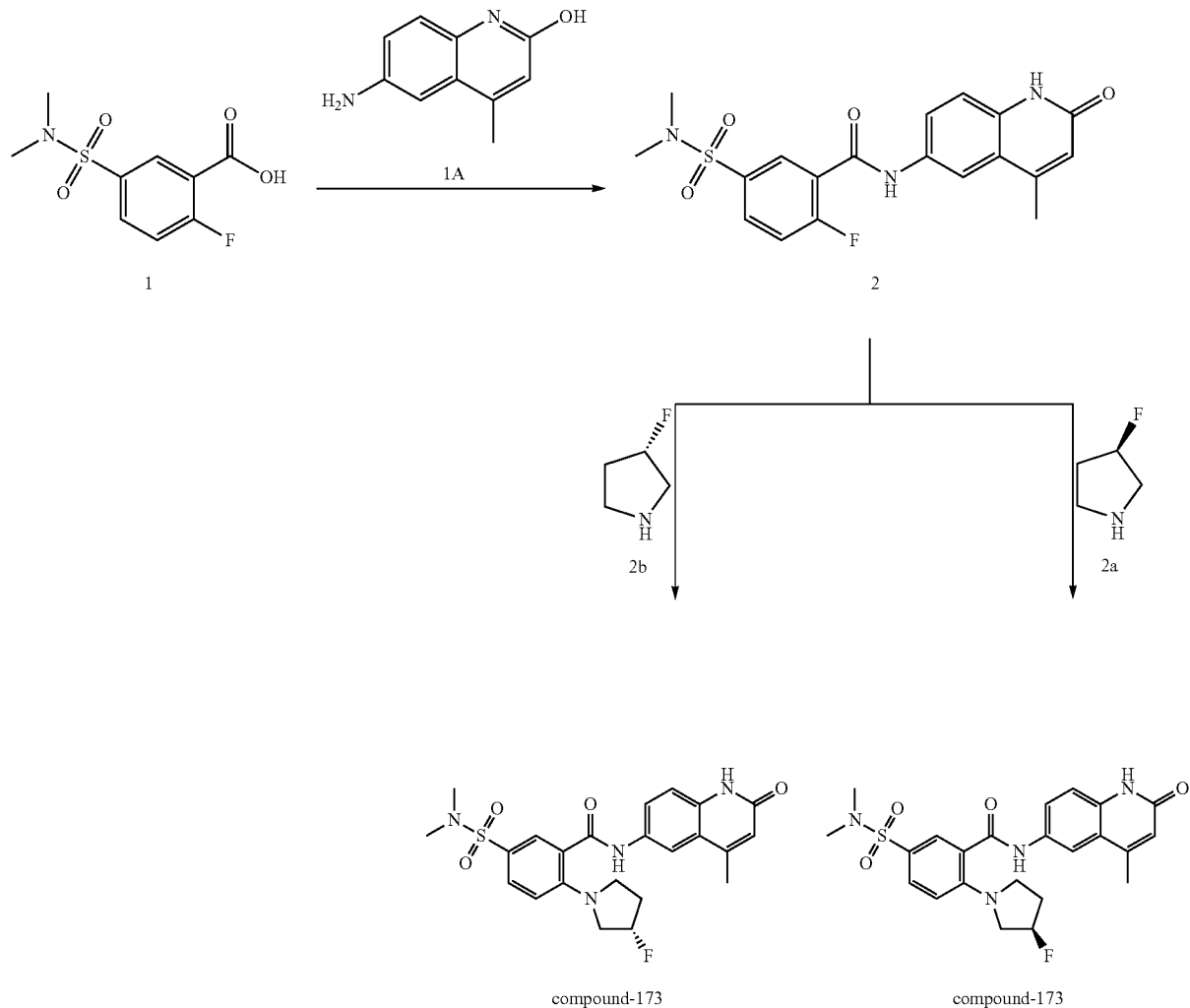

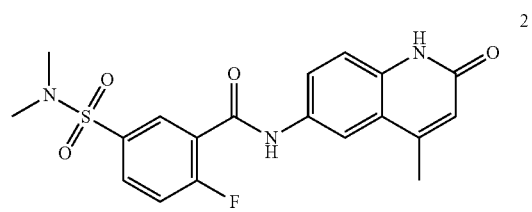 [SMILES: Cc1cc(=O)[nH]c2ccc(NC(=O)c3cc(S(=O)(=O)N(C)C)ccc3F)cc12]

Preparation of 5-(N,N-dimethylsulfamoyl)-2-fluoro-N-(4-methyl-2-oxo-1,2-dihydroquinolin-6-yl)benzamide (2): to a solution of 5-(N,N-dimethylsulfamoyl)-2-fluorobenzoic acid (1) (200 mg, 0.808 mmol, 1 eq) in Dry DMF (5 mL) at RT was added 1A (140.7 mg, 0.808 mmol, 1 eq), HOAt (220 mg, 1.617 mmol, 2 eq), EDC.HCl (310.14 mg, 1.617 mmol, 1 eq) and DIPEA (0.59 mL, 417.4 mmol, 4 eq) and stirred at RT for 16 h. After completion, the reaction mixture was poured into water and the resulting solid was filtered and dried to afford 5-(N, N-dimethylsulfamoyl)-2-fluoro-N-(4-methyl-2-oxo-1,2-dihydroquinolin-6-yl)benzamide (2) (190 mg, 58.2%) as pale yellow solid.

$^1$H NMR (300 MHz, DMSO-d6) δ 11.59 (s, 1H), 10.66 (s, 1H), 8.12 (d, J=2.2 Hz, 1H), 7.81 (dd, J=8.8, 2.3 Hz, 1H), 7.69-7.51 (m, 2H), 7.30 (d, J=8.8 Hz, 1H), 6.95 (d, J=8.8 Hz, 1H), 6.43 (s, 1H), 5.64-5.12 (m, 1H), 3.82-3.36 (m, 4H), 2.60 (s, 6H), 2.40 (s, 3H), 2.33-1.96 (m, 2H).

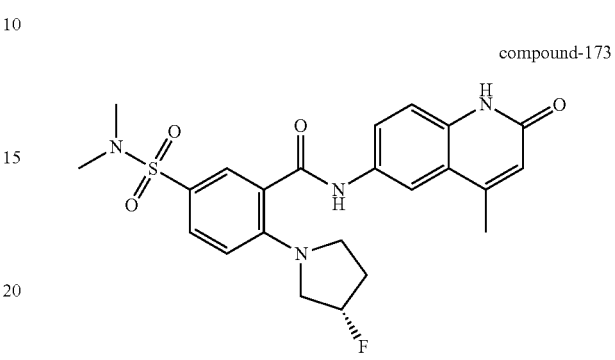

compound-173

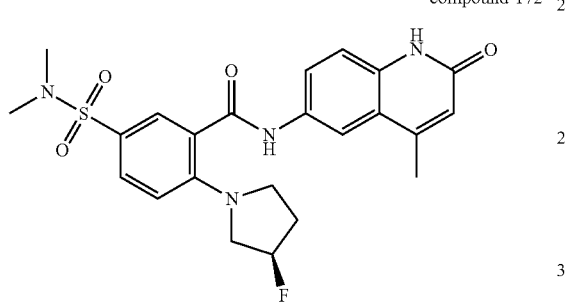

compound-172

Preparation of (R)-5-(N,N-dimethylsulfamoyl)-2-(3-fluoropyrrolidin-1-yl)-N-(4-methyl-2-oxo-1,2-dihydroquinolin-6-yl)benzamide (compound-172): to a solution of 5-(N,N-dimethylsulfamoyl)-2-fluoro-N-(4-methyl-2-oxo-1,2-dihydroquinolin-6-yl)benzamide (2) (70 mg, 0.173 mmol, 1 eq) and (R)-3-fluoropyrrolidine hydrochloride (2a) (21.8 mg, 0.173 mmol, 1 eq) in DMSO was added DIPEA (0.1 mL, 89.6 mg, 0.694 mmol, 4 eq) and stirred at RT for 16 h. After completion, the reaction mixture was poured into water and the resulting solid was filtered. The crude was triturated with DCM and n-Pentane to afford (R)-5-(N,N-dimethylsulfamoyl)-2-(3-fluoropyrrolidin-1-yl)-N-(4-methyl-2-oxo-1,2-dihydroquinolin-6-yl)benzamide (compound-172) (42 mg, 51.2%) as pale yellow solid.

Preparation of (S)-5-(N,N-dimethylsulfamoyl)-2-(3-fluoropyrrolidin-1-yl)-N-(4-methyl-2-oxo-1,2-dihydroquinolin-6-yl)benzamide (compound-173): to a solution of 5-(N,N-dimethylsulfamoyl)-2-fluoro-N-(4-methyl-2-oxo-1,2-dihydroquinolin-6-yl)benzamide (2) (70 mg, 0.173 mmol, 1 eq) and (S)-3-fluoropyrrolidine hydrochloride (2b) (21.8 mg, 0.173 mmol, 1 eq) in DMSO (10 vol) was added DIPEA (0.1 mL, 89.6 mg, 0.694 mmol, 4 eq) and stirred at RT for 16 h. After completion, the reaction mixture was poured into water, the resulting solid was filtered and dried. The crude was triturated with DCM-n-Pentane to afford (S)-5-(N,N-dimethylsulfamoyl)-2-(3-fluoropyrrolidin-1-yl)-N-(4-methyl-2-oxo-1,2-dihydroquinolin-6-yl)benzamide (compound-173) (39 mg, 47.6%) as pale yellow solid.

$^1$H NMR (300 MHz, DMSO-d$_6$): δ 11.59 (s, 1H), 10.66 (s, 1H), 8.12 (d, J=2.2 Hz, 1H), 7.80 (dd, J=8.8, 2.3 Hz, 1H), 7.67-7.57 (m, 2H), 7.30 (d, J=8.8 Hz, 1H), 6.95 (d, J=8.8 Hz, 1H), 6.43 (s, 1H), 5.53-5.26 (m, 1H), 3.85-3.61 (m, 1H), 3.62-3.36 (m, 3H), 2.60 (s, 6H), 2.40 (s, 3H), 2.32-2.15 (m, 2H).

Synthesis of Compound-174, Compound-175, Compound-176, and Compound-177:

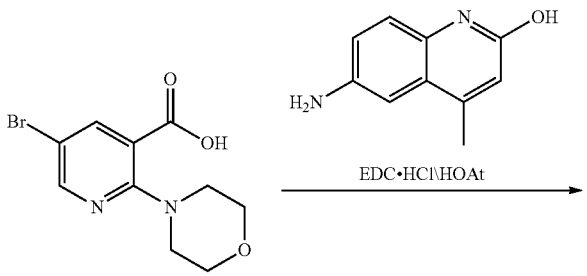

-continued

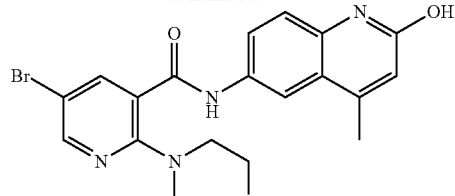

2

PdCl₂(dppf), Na₂CO₃ | 1,4-dioxane

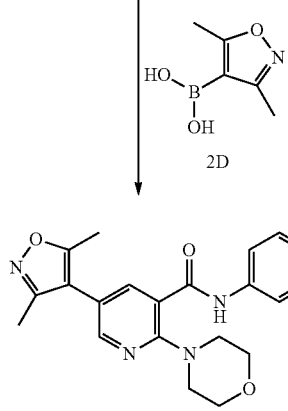

2D

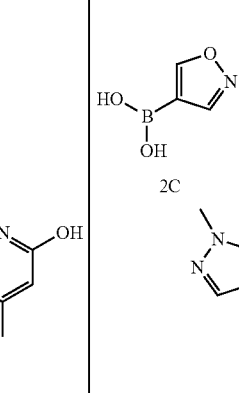

2C

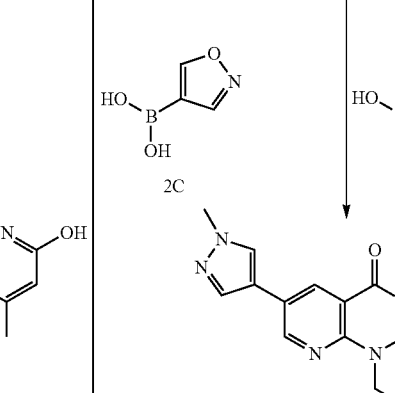

2B

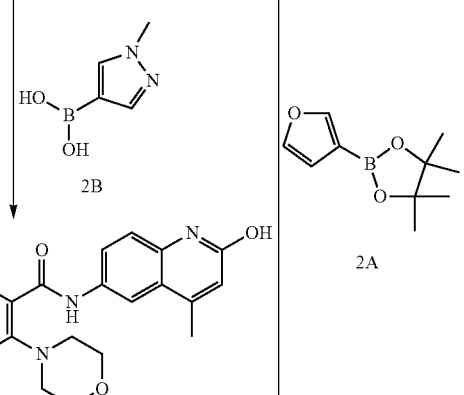

2A

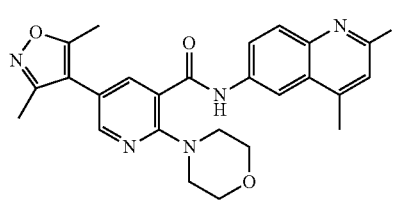

compound-177

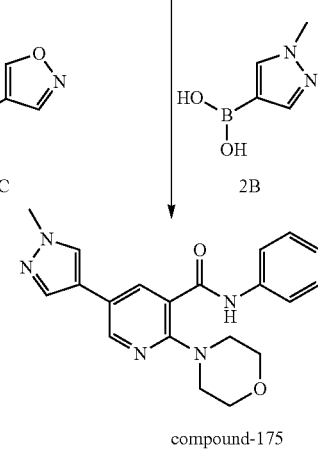

compound-175

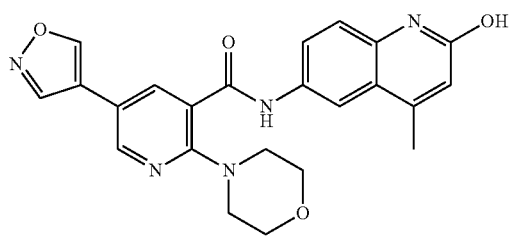

compound-176

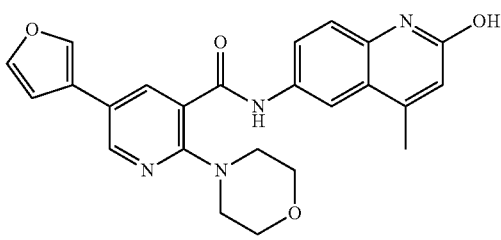

compound-174

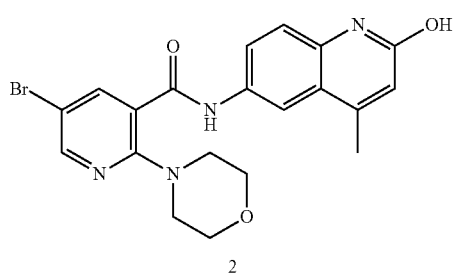 [SMILES: Cc1cc(O)nc2ccc(NC(=O)c3cc(Br)cnc3N3CCOCC3)cc12]

2

Preparation of 5-bromo-N-(2-hydroxy-4-methylquinolin-6-yl)-2-morpholinonicotinamide (2): to a solution of 5-bromo-2-morpholinonicotinic acid (1) (500 mg, 1.742 mmol, 1 eq) in Dry DMF (1 mL) at RT was added 6-amino-4-methylquinolin-2-ol (303 mg, 1.742 mmol, 1.0 eq), HOAt (473 mg, 3.484 mmol, 2 eq), EDC (665 mg, 3.484 mmol, 2 eq), DIPEA (898 mg, 6.968 mmol, 4 eq) and stirred at RT for 3 h. After completion, the reaction mixture was poured into ice water and then filtered the solid obtained. The solid was washed with water and dried to afford 5-bromo-N-(2-hydroxy-4-methylquinolin-6-yl)-2-morpholinonicotinamide (2) (550 mg, 71%) as yellow solid.

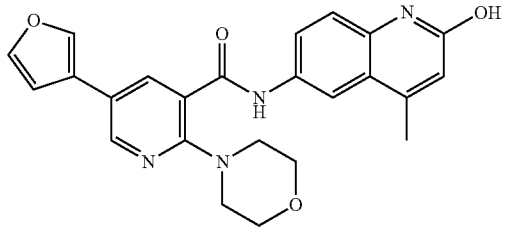

compound-174

Preparation of 5-(furan-3-yl)-N-(2-hydroxy-4-methylquinolin-6-yl)-2-morpholinonicotinamide (compound-174): a suspension of 5-bromo-N-(2-hydroxy-4-methylquinolin-6-yl)-2-morpholinonicotinamide (2) (200 mg, 0.452 mmol, 1 eq), Furan-4-boronic acid (175 mg, 0.904 mmol, 2 eq), Na$_2$CO$_3$ (144 mg, 1.357 mmol, 3 eq) in Dioxane (5 mL) was degassed for 15 min. Then added Pd(PPh$_3$)$_4$(53 mg, 0.045 mmol, 0.1 eq) and stirred at 100° C. for 16 h. After completion, the reaction mixture poured into ice water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) by using MeOH:DCM (10:90) to afford 5-(furan-3-yl)-N-(2-hydroxy-4-methylquinolin-6-yl)-2-morpholinonicotinamide (compound-174) (10 mg, 4%) as pale yellow solid.

$^1$H NMR (300 MHz, DMSO-d6): δ 11.60 (s, 1H), 10.63 (s, 1H), 8.61 (d, J=2.2 Hz, 1H), 8.23 (d, J=12.8 Hz, 2H), 8.08 (d, J=2.6 Hz, 1H), 7.84-7.74 (m, 2H), 7.31 (d, J=8.8 Hz, 1H), 7.04 (s, 1H), 6.44 (s, 1H), 3.65 (m, 4H), 3.24 (m, 4H), 2.40 (s, 3H).

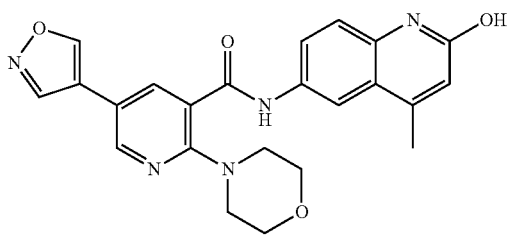

compound-176

Preparation of N-(2-hydroxy-4-methylquinolin-6-yl)-5-(isoxazol-4-yl)-2-morpholinonicotinamide (compound-176): a suspension of 5-bromo-N-(2-hydroxy-4-methylquinolin-6-yl)-2-morpholinonicotinamide (2) (300 mg, 0.678 mmol, 1 eq), isoxazole-4-boronic acid (154 mg, 1.357 mmol, 2 eq), Na$_2$CO$_3$ (215 mg, 2.034 mmol, 3 eq) in Dioxane (5 mL) was degassed for 15 min. Then added PdCl$_2$(PPh$_3$)$_2$(48 mg, 0.067 mmol, 0.1 eq) and stirred at 100° C. for 16 h. After completion, the reaction mixture poured into ice water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) by using MeOH:DCM (10:90) to afford N-(2-hydroxy-4-methylquinolin-6-yl)-5-(isoxazol-4-yl)-2-morpholinonicotinamide (compound-176) (6 mg, 2%) as pale yellow solid.

$^1$H NMR (300 MHz, DMSO-d6): δ 11.57 (s, 1H), 10.95 (s, 1H), 8.68 (s, 1H), 8.41-8.27 (m, 2H), 8.26-8.17 (m, 1H), 7.87-7.72 (m, 2H), 7.37-7.24 (m, 2H), 6.42 (s, 1H), 3.67 (m, 6H), 3.25 (m, 2H), 3.16 (m, 4H), 2.41 (s, 5H).

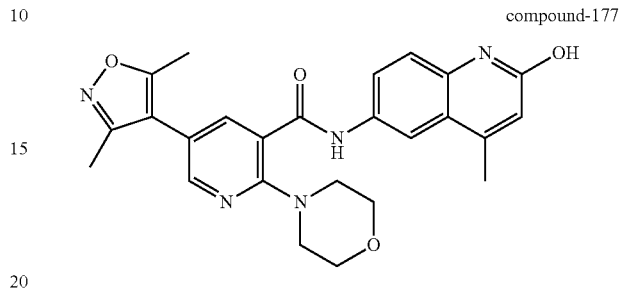

compound-177

Preparation of 5-(3, 5-dimethylisoxazol-4-yl)-N-(2-hydroxy-4-methylquinolin-6-yl)-2-morpholino nicotinamide (compound-177): a suspension of 5-bromo-N-(2-hydroxy-4-methylquinolin-6-yl)-2-morpholinonicotinamide (2) (200 mg, 0.440 mmol, 1 eq), 3,5 dimethyl isoxazole-4-boronic acid (115 mg, 0.881 mmol, 2 eq), Cs$_2$CO$_3$ (430 mg, 1.32 mmol, 3 eq) in Dioxane (5 mL) was degassed for 15 min. Then added PdCl$_2$(dppf) (36 mg, 0.044 mmol, 0.1 eq) and stirred at 100° C. for 15 min in microwave. After completion, the reaction mixture was poured into ice water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) by using MeOH:DCM (10:90) to afford 5-(3,5-dimethyl-isoxazol-4-yl)-N-(2-hydroxy-4-methylquinolin-6-yl)-2-morpholinonicotinamide (compound-177) (90 mg, 45%) as yellow solid.

$^1$H NMR (400 MHz, CDCl$_3$): δ 11.11 (s, 1H), 10.60 (br s, 1H), 8.40 (dt, J=2.2, 10.4 Hz, 3H), 7.63 (dd, J=2.4, 8.8 Hz, 1H), 7.33 (d, J=8.8 Hz, 1H), 6.62 (s, 1H), 4.03-3.84 (m, 4H), 3.42-3.25 (m, 4H), 2.56 (s, 3H), 2.46 (s, 3H), 2.32 (s, 3H).

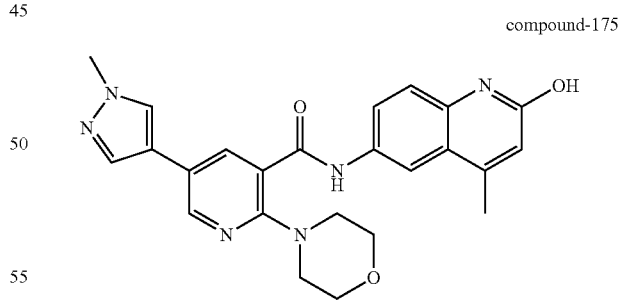

compound-175

Preparation of N-(2-hydroxy-4-methylquinolin-6-yl)-5-(1-methyl-1H-pyrazol-4-yl)-2-morpholinonicotinamide (compound-175): a suspension of 5-bromo-N-(2-hydroxy-4-methylquinolin-6-yl)-2-morpholinonicotinamide (2) (100 mg, 0.226 mmol, 1 eq) 1-methyl-1H-pyrazol-4-ylboronic acid (43 mg, 0.339 mmol, 1.5 eq), Na$_2$CO$_3$ (72 mg, 0.678 mmol, 3 eq) in Dioxane (5 mL) was degassed for 15 min. Then added PdCl$_2$(dppf) (20 mg, 0.022 mmol, 0.1 eq) and stirred at 100° C. for 15 h. After completion, the reaction mixture poured into ice water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) by using MeOH:DCM (10:90) to afford N-(2-hydroxy-4-methylquinolin-6-yl)-5-(1-methyl-1H-pyrazol-4-yl)-2-morpholinonicotinamide (compound-175) (30 mg, 31%) as yellow solid.

$^1$H NMR (400 MHz, DMSO-d6): δ 11.59 (br s, 1H), 10.66 (s, 1H), 8.58 (d, J=2.4 Hz, 1H), 8.21 (d, J=2.0 Hz, 1H), 8.20 (s, 1H), 8.03 (d, J=2.4 Hz, 1H), 7.92 (s, 1H), 7.80 (dd, J=2.4, 8.8 Hz, 1H), 7.31 (d, J=8.8 Hz, 1H), 6.44 (s, 1H), 3.86 (s, 3H), 3.68-3.63 (m, 4H), 3.30-3.25 (m, 4H), 2.41 (s, 3H).

Synthesis of Compound-178

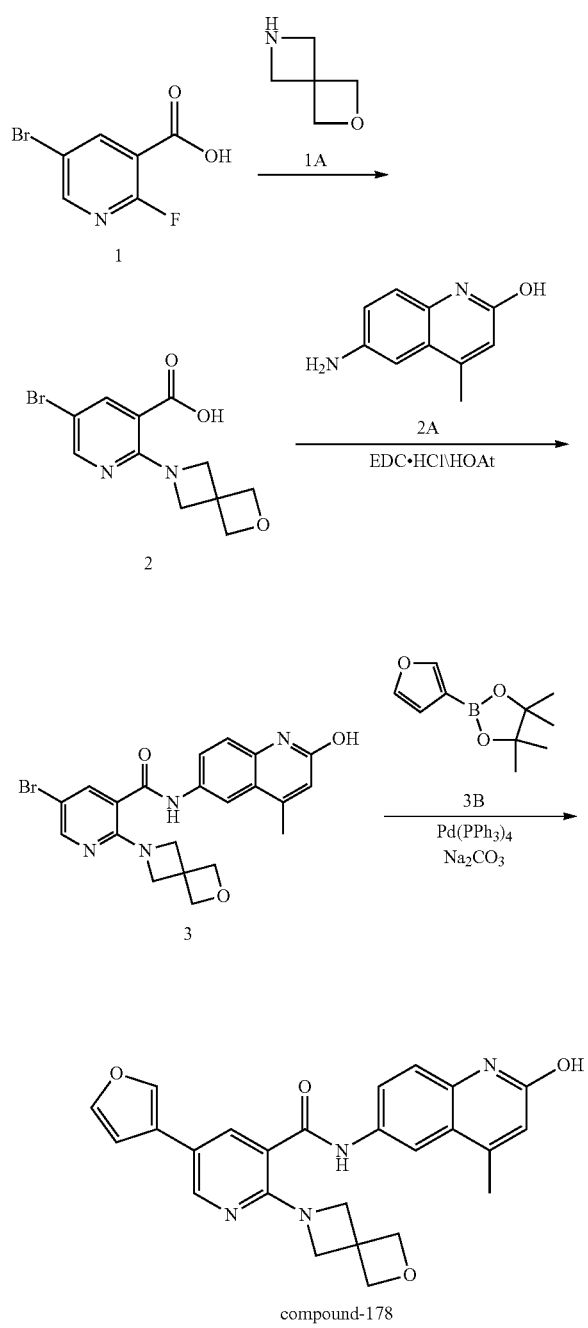

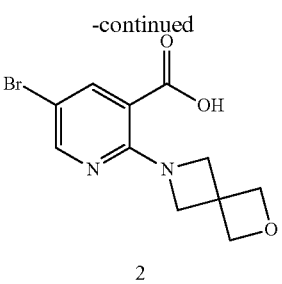

Preparation of 5-bromo-2-(2-oxa-6-azaspiro[3.3]heptan-6-yl)nicotinic acid (2): to a solution of 5-bromo-2-fluoronicotinic acid (1) (500 mg, 2.27 mmol, 1 eq) in dry DMSO (5 mL) was added 2-oxa-6-azaspiro[3.3]heptane (1A) (326 mg, 2.27 mmol, 1 eq), DIPEA (878 mg, 6.81 mmol, 3 eq) and stirred at RT for 3 h. After completion, the reaction mixture was poured in ice water and acidified with 1N HCl and filtered the solid to afford 5-bromo-2-(2-oxa-6-azaspiro[3.3]heptan-6-yl)nicotinic acid (2) (400 mg, 82%) as yellow solid.

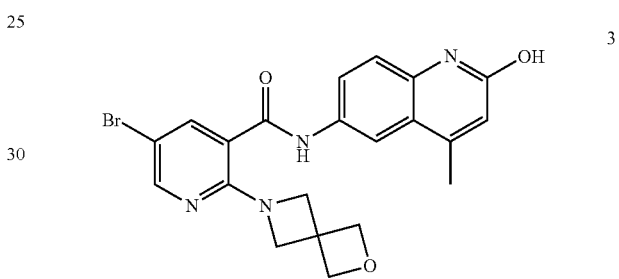

Preparation of 5-bromo-N-(2-hydroxy-4-methylquinolin-6-yl)-2-(2-oxa-6-azaspiro[3.3]heptan-6-yl)nicotinamide (3): to a solution of 5-bromo-2-(2-oxa-6-azaspiro[3.3]heptan-6-yl)nicotinic acid (2) (400 mg, 1.34 mmol, 1 eq) in dry DMF (1 mL) was added 6-amino-4-methylquinolin-2-ol (2A) (233 mg, 1.34 mmol, 1.0 eq), HOAt (365 mg, 2.68 mmol, 2 eq), EDC (512 mg, 2.68 mmol, 2 eq), DIPEA (692 mg, 5.36 mmol, 4 eq) and stirred at RT for 3 h. After completion, the reaction mixture was poured into ice water. The solid obtained was filtered, washed with water and dried to afford 5-bromo-N-(2-hydroxy-4-methylquinolin-6-yl)-2-(2-oxa-6-azaspiro[3.3]heptan-6-yl)nicotinamide (3) (350 mg, 35%) as yellow solid.

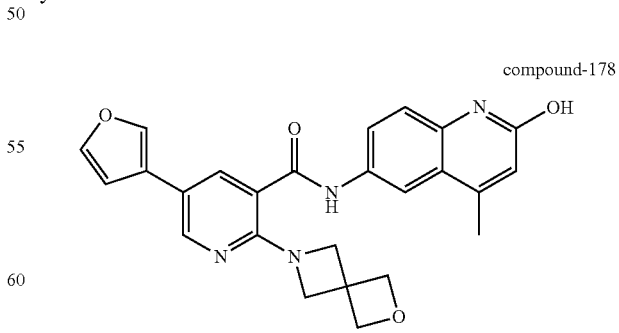

Preparation of 5-(furan-3-yl)-N-(2-hydroxy-4-methylquinolin-6-yl)-2-(2-oxa-6-azaspiro[3.3]heptan-6-yl)nicotinamide (compound-178): a suspension of 5-bromo-N-(2-hydroxy-4-methylquinolin-6-yl)-2-(2-oxa-6-azaspiro[3.3]

heptan-6-yl)nicotinamide (3) (200 mg, 0.440 mmol, 1 eq), Furan-4-boronic acid (171 mg, 0.881 mmol, 2 eq), Na₂CO₃ (187 mg, 1.76 mmol, 3 eq) in Dioxane (3 mL) was degassed for 15 min. Then added Pd(PPh₃)₄(51 mg, 0.044 mmol, 0.1 eq) and stirred at 100° C. for 16 h. After completion, the reaction mixture was poured into ice water and extracted with EtOAc (2×30 mL). The combined extracts were washed with water (2×40 mL), brine (40 mL), dried over anhydrous Na₂SO₄, filtered and evaporated. The crude compound was purified by column chromatography (SiO₂) by using MeOH:DCM (10:90) to afford 5-(furan-3-yl)-N-(2-hydroxy-4-methylquinolin-6-yl)-2-(2-oxa-6-azaspiro[3.3]heptan-6-yl)nicotinamide (compound-178) (69 mg, 35%) as yellow solid.

¹H NMR (400 MHz, DMSO-d6): δ 11.59 (s, 1H), 10.49 (s, 1H), 8.50 (d, J=2.4 Hz, 1H), 8.19-8.10 (m, 2H), 7.94 (d, J=2.4 Hz, 1H), 7.85 (dd, J=2.0, 8.8 Hz, 1H), 7.73 (s, 1H), 7.31 (d, J=8.8 Hz, 1H), 6.99 (s, 1H), 6.44 (s, 1H), 4.68 (s, 4H), 4.14 (s, 4H), 2.41 (s, 3H).

Synthesis of Compound-179:

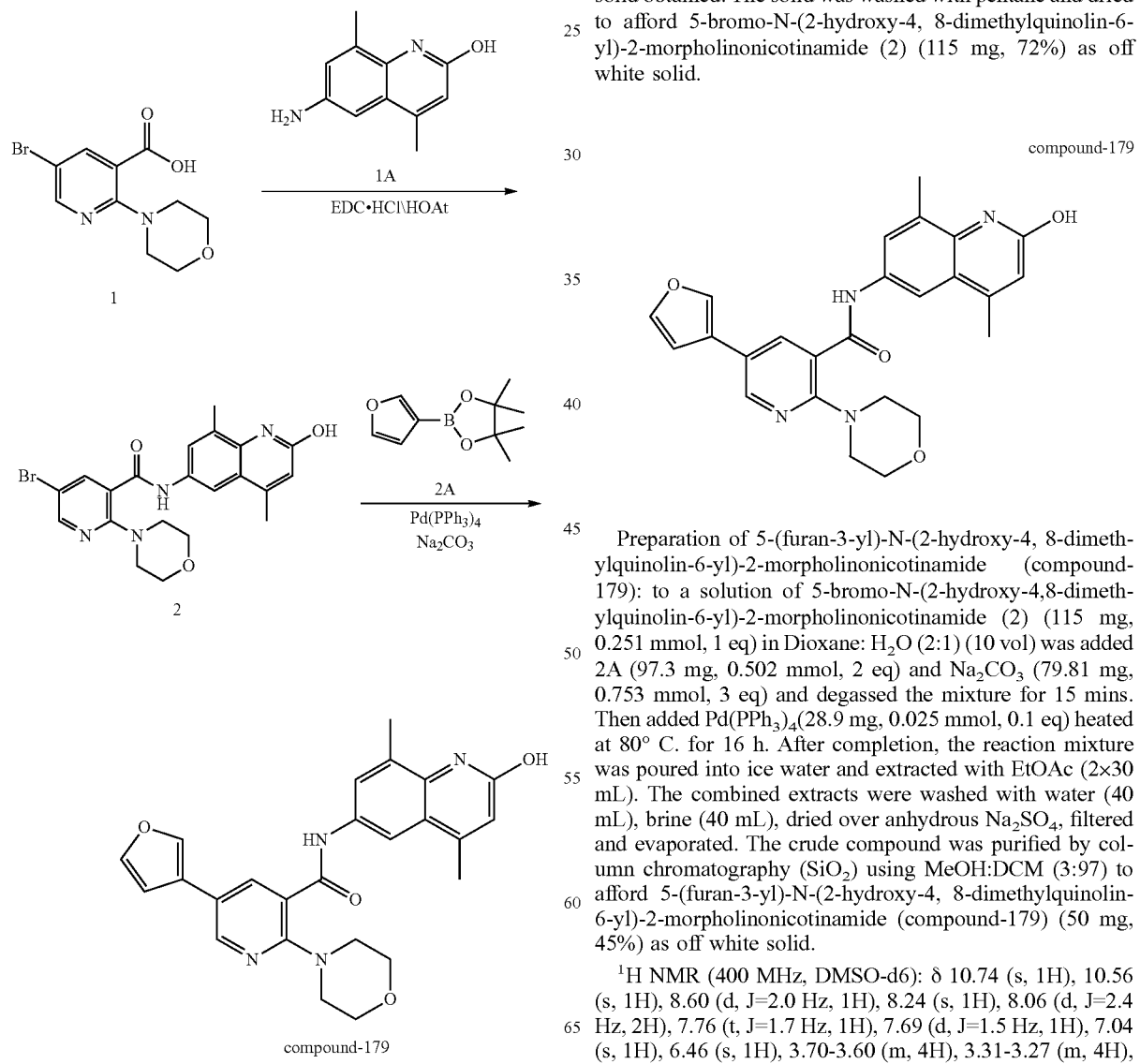

Preparation of 5-bromo-N-(2-hydroxy-4,8-dimethylquinolin-6-yl)-2-morpholinonicotinamide (2): to a solution of 5-bromo-2-morpholinonicotinic acid (1) (100 mg, 0.34 mmol, 1 eq) in DMF (2 mL) was added 1A (63.9 mg, 0.34 mmol, 1 eq), HOAt (92.4 mg, 0.68 mmol, 2 eq), EDC.HCl (130.3 mg, 0.68 mmol, 2 eq), DIPEA (175.4 mg, 1.36 mmol, 4 eq) and stirred at RT for 18 h. After completion, the reaction mixture was poured into ice water and filtered the solid obtained. The solid was washed with pentane and dried to afford 5-bromo-N-(2-hydroxy-4, 8-dimethylquinolin-6-yl)-2-morpholinonicotinamide (2) (115 mg, 72%) as off white solid.

Preparation of 5-(furan-3-yl)-N-(2-hydroxy-4, 8-dimethylquinolin-6-yl)-2-morpholinonicotinamide (compound-179): to a solution of 5-bromo-N-(2-hydroxy-4,8-dimethylquinolin-6-yl)-2-morpholinonicotinamide (2) (115 mg, 0.251 mmol, 1 eq) in Dioxane: H₂O (2:1) (10 vol) was added 2A (97.3 mg, 0.502 mmol, 2 eq) and Na₂CO₃ (79.81 mg, 0.753 mmol, 3 eq) and degassed the mixture for 15 mins. Then added Pd(PPh₃)₄(28.9 mg, 0.025 mmol, 0.1 eq) heated at 80° C. for 16 h. After completion, the reaction mixture was poured into ice water and extracted with EtOAc (2×30 mL). The combined extracts were washed with water (40 mL), brine (40 mL), dried over anhydrous Na₂SO₄, filtered and evaporated. The crude compound was purified by column chromatography (SiO₂) using MeOH:DCM (3:97) to afford 5-(furan-3-yl)-N-(2-hydroxy-4, 8-dimethylquinolin-6-yl)-2-morpholinonicotinamide (compound-179) (50 mg, 45%) as off white solid.

¹H NMR (400 MHz, DMSO-d6): δ 10.74 (s, 1H), 10.56 (s, 1H), 8.60 (d, J=2.0 Hz, 1H), 8.24 (s, 1H), 8.06 (d, J=2.4 Hz, 2H), 7.76 (t, J=1.7 Hz, 1H), 7.69 (d, J=1.5 Hz, 1H), 7.04 (s, 1H), 6.46 (s, 1H), 3.70-3.60 (m, 4H), 3.31-3.27 (m, 4H), 2.44 (s, 3H), 2.41 (s, 3H).

Synthesis of Compound-180

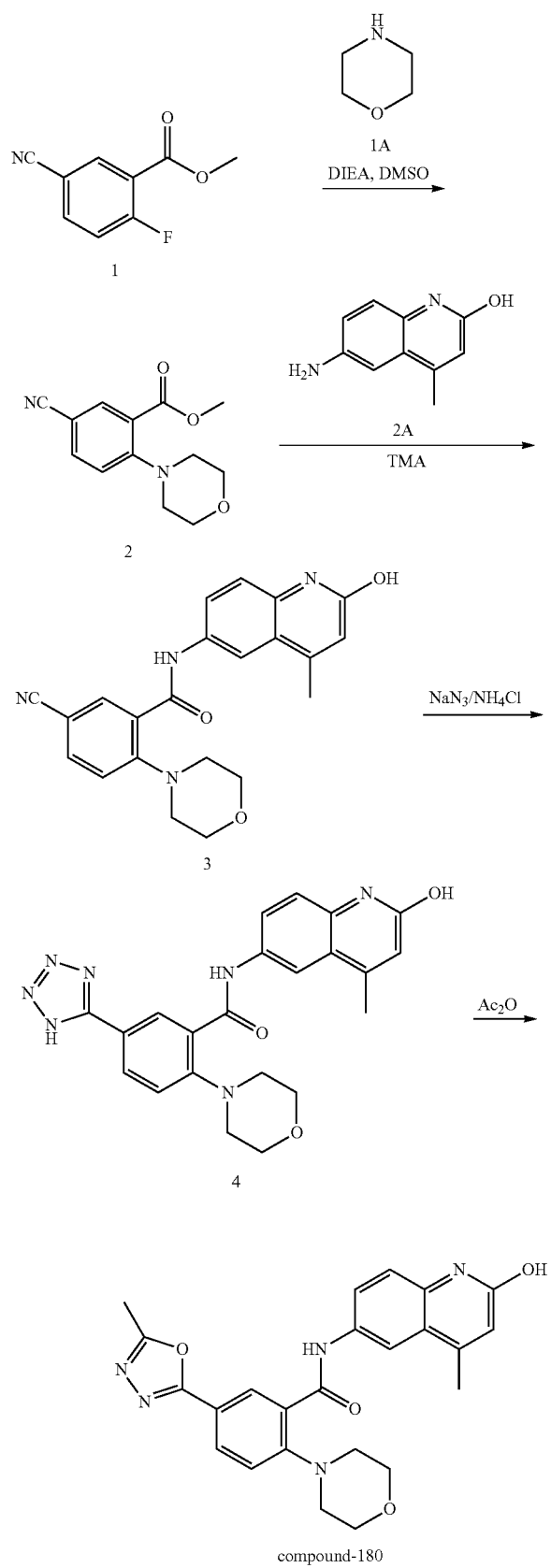

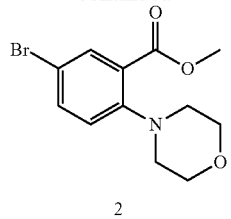 [SMILES: COC(=O)c1cc(Br)ccc1N1CCOCC1]

Preparation of methyl 5-cyano-2-morpholinobenzoate (2)

To a solution of methyl 5-cyano-2-fluorobenzoate (1) (450 mg, 2.51 mmol, 1 eq) in Dry DMSO (5 mL) was added morpholine (262 mg, 3.01 mmol, 1.2 eq), DIPEA (972 mg, 7.53 mmol, 3 eq) and stirred at RT for 3 h. After completion, the reaction mixture was poured into ice water and then filtered the compound to afford methyl 5-cyano-2-morpholinobenzoate (2) (700 mg, 99%) as an off white solid.

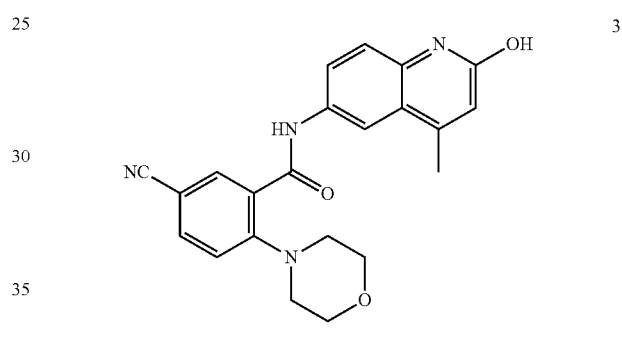

Preparation of 5-cyano-N-(2-hydroxy-4-methylquinolin-6-yl)-2-morpholinobenzamide (3): to a solution of methyl 5-cyano-2-morpholinobenzoate (2) (600 mg, 2.436 mmol, 1 eq) in Dry toluene (10 mL) was added 6-amino-4-methylquinolin-2-ol (2A) (423 mg, 2.436 mmol, 1 eq), trimethyl aluminium solution (526 mg, 7.308 mmol, 3 eq) and stirred at 100° C. for 16 h. After completion, the reaction mixture was poured into ice water and filtered crude solid. The crude product was purified by reverse phase chromatography (0.1% ammonium acetate in water: aceto nitrile) to afford 5-cyano-N-(2-hydroxy-4-methylquinolin-6-yl)-2-morpholinobenzamide (3) (200 mg, 21%) as yellow solid.

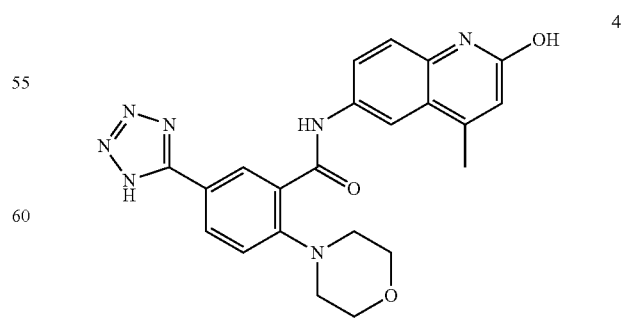

Preparation of N-(2-hydroxy-4-methylquinolin-6-yl)-2-morpholino-5-(1H-tetrazol-5-yl)benzamide (4): to a solution of 5-cyano-N-(2-hydroxy-4-methylquinolin-6-yl)-2-morpholinobenzamide (3) (100 mg, 0.257 mmol, 1 eq) in IPA (5 mL) was added sodium azide (50 mg, 0.771 mmol, 3 eq), ZnBr$_2$ (86 mg, 0.385 mmol, 1.5 eq) and stirred at 100° C. for 16 h. After completion, evaporated the solvent, the residue was taken in water and extracted with ethyl acetate (4×20 mL). The combined extracts were washed with water (20 mL), brine (20 mL), dried over anhydrous Na$_2$SO$_4$, filtered and evaporated to afford N-(2-hydroxy-4-methylqinolin-6-yl)-2-morpholino-5-(1H-tetrazol-5-yl) benzamide (4) (30 mg, 27%) as yellow solid.

Preparation of N-(2-hydroxy-4-methylquinolin-6-yl)-5-(5-methyl-1,3,4-oxadiazol-2-yl)-2-morpholinobenzamide (compound-180): a solution of N-(2-hydroxy-4-methylqinolin-6-yl)-2-morpholino-5-(1H-tetrazol-5-yl) benzamide (4) (30 mg, 0.069 mmol, 1 eq) in acetic anhydride (2 mL) was stirred at 140° C. for 16 h. After completion, evaporated the solvent, the residue was taken in water and extracted with ethyl acetate (4×20 mL). The combined extracts were washed with water (20 mL), brine (20 mL), dried over anhydrous Na$_2$SO$_4$, filtered and evaporated. The residue was purified by column chromatography (SiO$_2$) using EtOAc:pet ether (7:3) to afford N-(2-hydroxy-4-methylquinolin-6-yl)-5-(5-methyl-1,3,4-oxadiazol-2-yl)-2-morpholinobenzamide (compound-180) (5 mg, 6%) as yellow solid.

$^1$H NMR (400 MHz, DMSO-d$_6$): δ 11.59 (s, 1H), 10.77 (s, 1H), 8.29-8.21 (m, 1H), 8.12 (s, 1H), 8.06-7.97 (m, 1H), 7.83 (d, J=6.8 Hz, 1H), 7.41-7.24 (m, 2H), 6.44 (s, 1H), 3.69 (m, 4H), 3.11 (m, 4H), 2.58 (s, 3H), 2.41 (s, 3H).

Synthesis of Compound-181 and Compound-182:

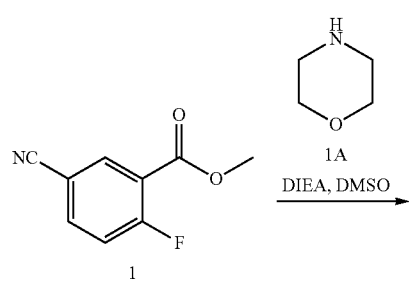

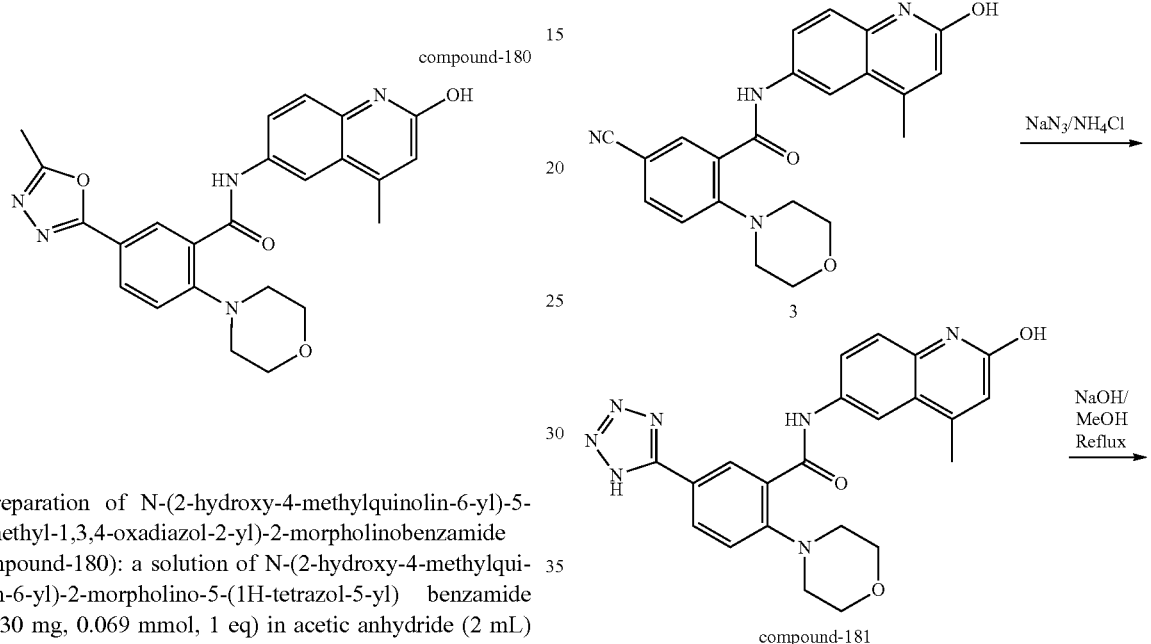

Preparation of methyl-5-cyano-2-morpholinobenzoate (2): to a solution of methyl 5-cyano-2-fluorobenzoate (1) (450 mg, 2.51 mmol, 1 eq) in Dry DMSO (5 mL) was added morpholine (262 mg, 3.01 mmol, 1.2 eq), DIPEA (972 mg, 7.53 mmol, 3 eq) and stirred at RT for 3 h. After completion, the reaction mixture was poured into ice water and then filtered the compound to afford methyl 5-cyano-2-morpholinobenzoate (2) (700 mg, 99%) as an off white solid.

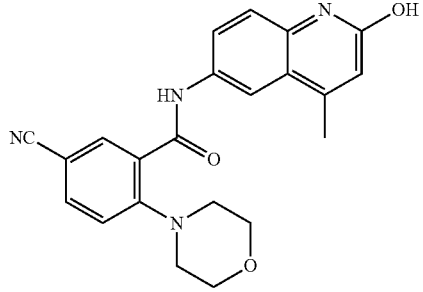

Preparation of 5-cyano-N-(2-hydroxy-4-methylquinolin-6-yl)-2-morpholinobenzamide (3): to a solution of methyl 5-cyano-2-morpholinobenzoate (2) (600 mg, 2.436 mmol, 1 eq) in Dry toluene (10 mL) was added 6-amino-4-methylquinolin-2-ol (2A) (423 mg, 2.436 mmol, 1 eq), trimethyl aluminium solution (526 mg, 7.308 mmol, 3 eq) and stirred at 100° C. for 16 h. After completion, the reaction mixture was poured into ice water and filtered crude solid. The crude product was purified by reverse phase chromatography (0.1% ammonium acetate in water: aceto nitrile) to afford 5-cyano-N-(2-hydroxy-4-methylquinolin-6-yl)-2-morpholinobenzamide (3) (200 mg, 21%) as yellow solid.

compound-182

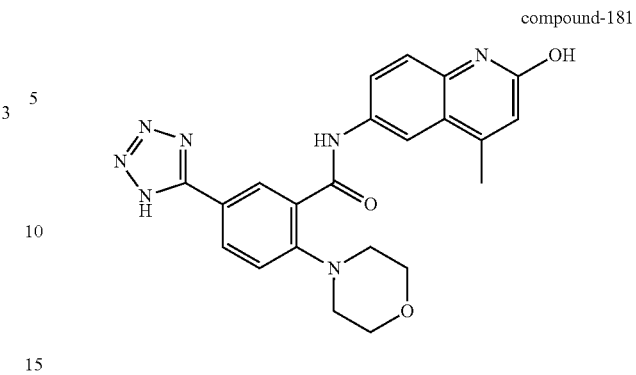

compound-181

Preparation of N-(2-hydroxy-4-methylquinolin-6-yl)-2-morpholino-5-(1H-tetrazol-5-yl)benzamide (compound-181): to a solution of 5-cyano-N-(2-hydroxy-4-methylquinolin-6-yl)-2-morpholinobenzamide (3) (100 mg, 0.257 mmol, 1 eq) in IPA (5 mL) was added sodium azide (50 mg, 0.771 mmol, 3 eq), ZnBr$_2$ (86 mg, 0.385 mmol, 1.5 eq) and stirred at 100° C. for 16 h. After completion, evaporated the solvent, the residue was taken in water and extracted with ethyl acetate (4×20 mL). The combined extracts were washed with water (20 mL), brine (20 mL), dried over anhydrous Na$_2$SO$_4$, filtered and evaporated to afford N-(2-hydroxy-4-methylquinolin-6-yl)-2-morpholino-5-(1H-tetrazol-5-yl) benzamide (compound-181) (30 mg, 27%) as yellow solid.

$^1$H NMR (300 MHz, DMSO-d6): δ 11.58 (s, 1H), 11.25 (s, 1H), 8.37 (s, 1H), 8.27 (s, 1H), 8.08 (d, J=8.1 Hz, 1H), 7.86 (d, J=8.1 Hz, 1H), 7.32 (t, J=8.8 Hz, 2H), 6.43 (s, 1H), 3.73 (s, 4H), 3.02 (s, 4H), 2.43 (s, 3H).

Synthesis of Compound-183

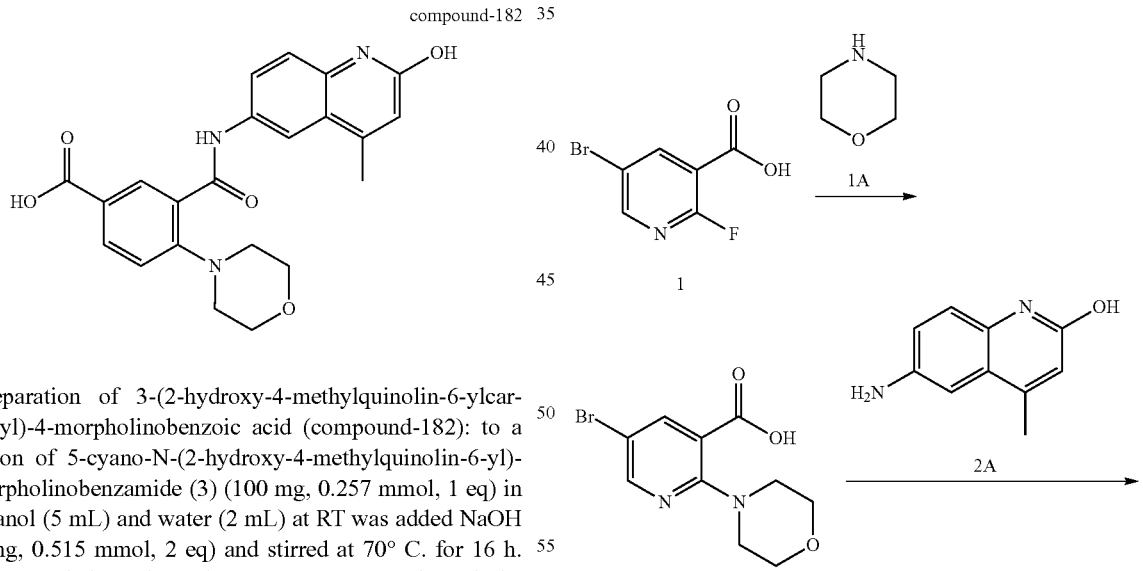

Preparation of 3-(2-hydroxy-4-methylquinolin-6-ylcarbamoyl)-4-morpholinobenzoic acid (compound-182): to a solution of 5-cyano-N-(2-hydroxy-4-methylquinolin-6-yl)-2-morpholinobenzamide (3) (100 mg, 0.257 mmol, 1 eq) in methanol (5 mL) and water (2 mL) at RT was added NaOH (20 mg, 0.515 mmol, 2 eq) and stirred at 70° C. for 16 h. After completion, the solvent was evaporated, and the residue was taken in water and acidified using 1N HCl. The solid was filtered and dried to afford 3-(2-hydroxy-4-methylquinolin-6-ylcarbamoyl)-4-morpholinobenzoic acid (compound-182) (65 mg, 62%) as yellow solid.

$^1$H NMR (300 MHz, DMSO-d6): δ 12.91-12.74 (m, 1H), 11.59 (s, 1H), 10.67 (s, 1H), 8.22 (s, 1H), 8.10 (d, J=2.2 Hz, 1H), 7.99 (d, J=8.4 Hz, 1H), 7.82 (d, J=9.2 Hz, 1H), 7.32 (d, J=8.8 Hz, 1H), 7.22 (d, J=8.8 Hz, 1H), 6.43 (s, 1H), 3.68 (s, 4H), 3.09 (s, 4H), 2.41 (s, 3H).

-continued

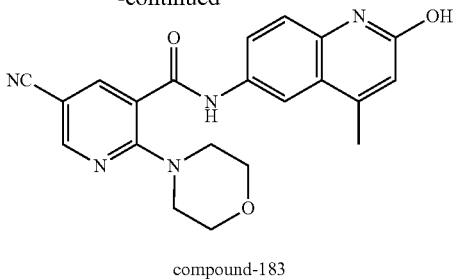

compound-183

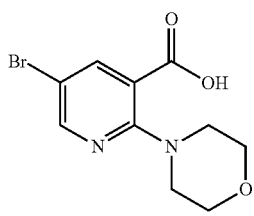

Preparation of 5-bromo-2-morpholinonicotinic acid (2): to a solution of 5-bromo-2-fluoronicotinic acid (1) (1 g, 4.56 mmol, 1 eq) and morpholine (1A) (397.8 mg, 4.56 mmol, 1 eq) in DMSO (10 mL) at RT was added $K_2CO_3$ (1.8 g, 13.69 mmol, 3 eq) and stirred at RT for 2 h. After completion reaction mixture was acidified with 1 N HCl and the resulting solid was filtered to afford 5-bromo-2-morpholinonicotinic acid (2) (600 mg, 45.8%) as off white solid.

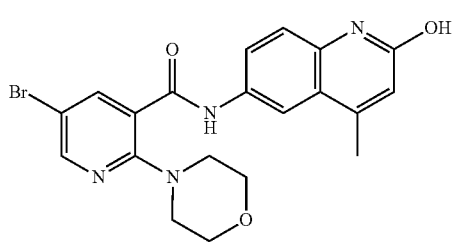

Preparation of 5-bromo-N-(2-hydroxy-4-methylquinolin-6-yl)-2-morpholinonicotinamide (3): to a solution 5-bromo-2-morpholinonicotinic acid (2) (700 mg, 2.439 mmol, 1 eq) in Dry DMF (10 vol) at RT was added 2A (424.3 mg, 2.439 mmol, 1 eq), HOAt (663.4 mg, 4.878 mmol, 2 eq), EDC (935.1 mg, 4.878 mmol, 2 eq), DIPEA (1.258 g, 9.756 mmol, 4 eq) and stirred at RT for 48 h. After completion, the reaction mixture was taken in water and the resulting solid was filtered to afford 5-bromo-N-(2-hydroxy-4-methylquinolin-6-yl)-2-morpholinonicotinamide (3) (700 mg, 64%) as pale yellow solid.

compound-183

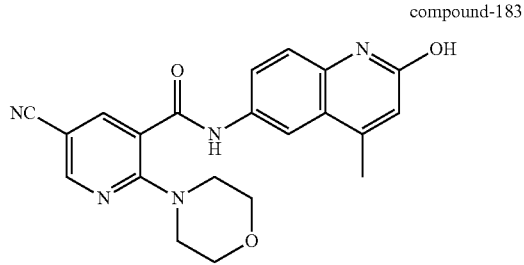 [SMILES: Cc1cc(O)nc2ccc(NC(=O)c3cc(C#N)cnc3N3CCOCC3)cc12]

Preparation of 5-cyano-N-(2-hydroxy-4-methylquinolin-6-yl)-2-morpholinonicotinamide (Compound-183): to a degassed solution 5-bromo-N-(2-hydroxy-4-methylquinolin-6-yl)-2-morpholinonicotinamide (3) (200 mg, 0.45 mmol, 1 eq) $K_4[Fe(CN)_6].3H_2O$ (57 mg, 0.13 mmol, 0.3 eq) and $Na_2CO_3$ (37 mg, 0.45 mmol, 1 eq) in DMA (10 vol) was added Pd(OAc)$_2$ (4.56 mg, 0.006 mmol, 0.015 eq) and stirred at 120° C. for 48 h in a sealed tube. After completion, the reaction mixture was taken in water and extracted with EtOAc (3×15 mL). The combined extracts were washed with cold water (7 mL) brine solution (7 mL), dried over anhydrous $Na_2SO_4$ and concentrated. The crude compound was purified by column chromatography ($SiO_2$) using EtOAc:Pet Ether (20:80) to afford 5-cyano-N-(2-hydroxy-4-methylquinolin-6-yl)-2-morpholinonicotinamide (Compound-183) (40 mg, 22.8%) as pale yellow solid.

$^1$H NMR (300 MHz, DMSO-d$_6$): δ 11.60 (s, 1H), 10.64 (s, 1H), 8.63 (d, J=2.2 Hz, 1H), 8.16 (d, J=2.2 Hz, 1H), 8.08 (d, J=2.2 Hz, 1H), 7.83-7.69 (m, 1H), 7.30 (d, J=8.8 Hz, 1H), 6.43 (s, 1H), 3.64-3.62 (m, 4H), 3.56 (d, J=5.0 Hz, 4H), 2.40 (d, J=1.3 Hz, 3H).

Synthesis of compound-184

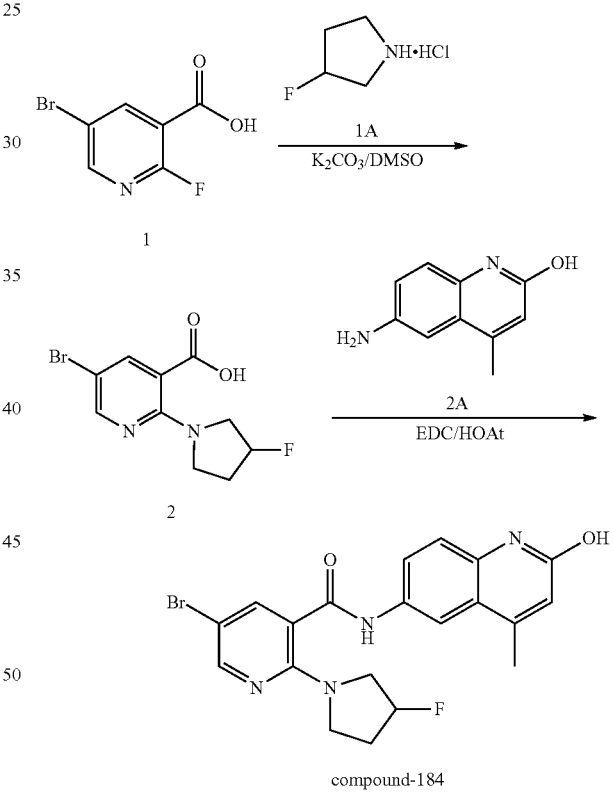

compound-184

Preparation of 5-bromo-2-(3-fluoropyrrolidin-1-yl) nicotinic acid (2): to a solution of 5-bromo-2-fluoronicotinic acid (1) (4 g, 18.26 mmol, 1 eq) and 3-fluoropyrrolidine hydrochloride (1A) (2.3 g, 18.26 mmol, 1 eq) in DMSO (40 mL)

at RT was added K$_2$CO$_3$ (10.08 g, 73.06 mmol, 4 eq) and stirred at 60° C. for 48 h. After completion, the reaction mixture was acidified with 1 N HCl and the resulting solid was filtered. The crude compound was purified by silica gel column chromatography (SiO$_2$) using MeOH:DCM (5:95) to afford 5-bromo-2-(3-fluoropyrrolidin-1-yl) nicotinic acid (2) (3.5 g, 92%) as off white solid.

Preparation of 5-bromo-2-(3-fluoropyrrolidin-1-yl)-N-(2-hydroxy-4-methylquinolin-6-yl) nicotinamide (Compound-184): to a solution of 5-bromo-2-(3-fluoropyrrolidin-1-yl) nicotinic acid (2) (2.1 g, 7.266 mmol, 1 eq) in Dry DMF (21 mL) at RT was added 2A (1.26 g, 7.26 mmol, 1 eq), HOAt (1.98 g, 14.53 mmol, 2 eq), EDC.HCl (2.785 g, 14.53 mmol, 2 eq), DIPEA (3.749 g, 29.065 mmol, 4 eq) and stirred at RT for 16 h. After completion, the reaction mixture was poured into water and the resulting solid was filtered. The crude compound was purified by silica gel column chromatography (SiO$_2$) using MeOH:DCM (4:96) to afford 5-bromo-2-(3-fluoropyrrolidin-1-yl)-N-(2-hydroxy-4-methylquinolin-6-yl) nicotinamide (Compound-184) (2.2 g, 68%) as pale yellow solid.

$^1$H NMR (400 MHz, DMSO-d$_6$): δ 11.59 (s, 1H), 10.63 (s, 1H), 8.30 (d, J=2.4 Hz, 1H), 8.10 (d, J=2.4 Hz, 1H), 7.90 (d, J=2.4 Hz, 1H), 7.80 (dd, J=8.8, 2.2 Hz, 1H), 7.30 (d, J=8.8 Hz, 1H), 6.43 (s, 1H), 5.44-5.30 (m, 1H), 3.77 (d, J=13.3 Hz, 1H), 3.65-3.51 (m, 3H), 2.55 (s, 1H), 2.40 (d, J=1.2 Hz, 3H), 2.16 (m, 1H).

Synthesis of Compound-185, Compound-186, and Compound-187 compound-184

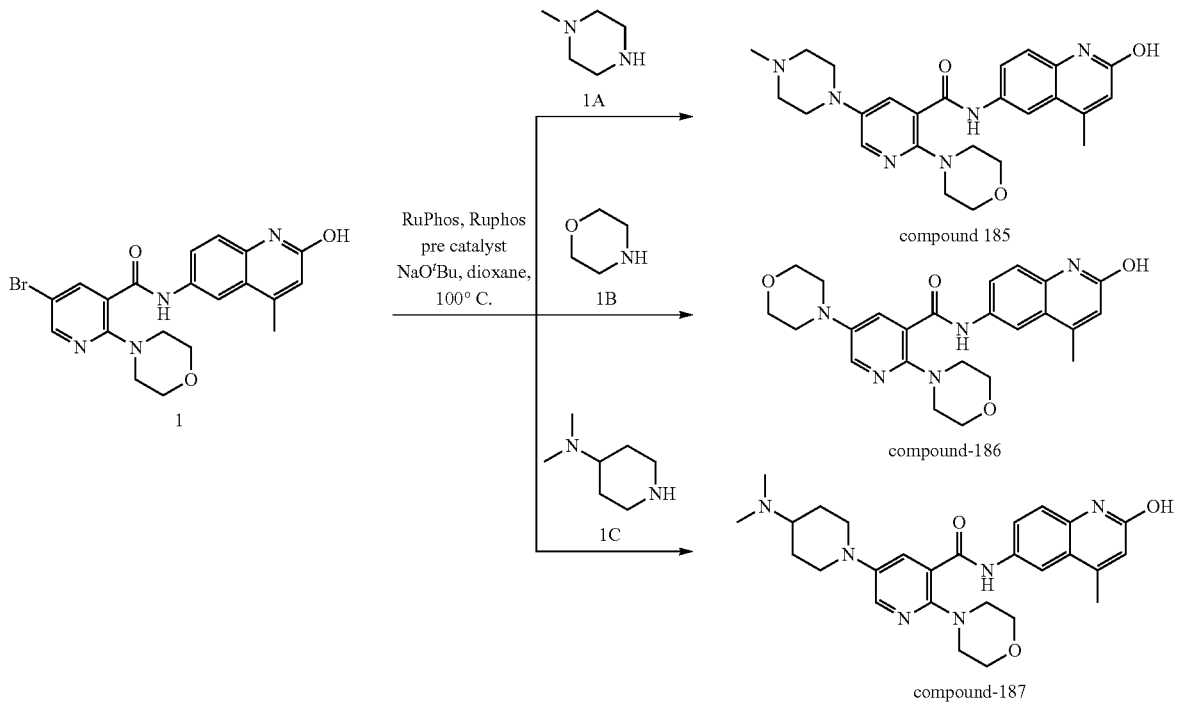

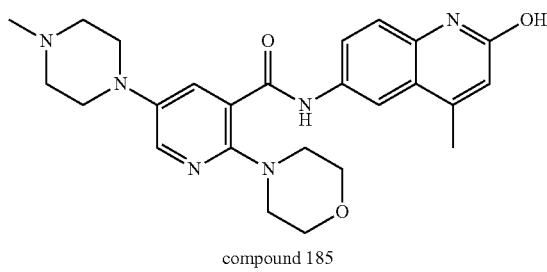

compound 185

Preparation of N-(2-hydroxy-4-methylquinolin-6-yl)-5-(4-methylpiperazin-1-yl)-2-morpholinonicotinamide (compound-185): a suspension of 5-bromo-N-(2-hydroxy-4-methylquinolin-6-yl)-2-morpholinonicotinamide (1) (200 mg, 0.452 mmol, 1 eq), N-Methyl piperazine (45 mg, 0.452 mmol, 1 eq) Na$^t$OBu (130 mg, 1.356 mmol, 3 eq) in 1,4 Dioxane (10 Vol) was degassed for 10 min. Then added Ruphos (20 mg, 0.0452 mmol, 0.1 eq), Ruphos precatalyst (32 mg, 0.0452 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by column chromatography (SiO$_2$) by using MeOH:DCM (6:94) to afford N-(2-hydroxy-4-methylquinolin-6-yl)-5-(4-methylpiperazin-1-yl)-2-morpholinonicotinamide (compound-185) (82 mg, 40%) as an off white solid.

$^1$H NMR (300 MHz, DMSO-d6): δ 11.59 (s, 1H), 11.21 (s, 1H), 8.26 (d, J=2.2 Hz, 1H), 8.16 (d, J=2.9 Hz, 1H), 7.79 (dd, J=2.2, 8.8 Hz, 1H), 7.66 (d, J=2.9 Hz, 1H), 7.32 (d, J=9.1 Hz, 1H), 6.44 (s, 1H), 3.78-3.66 (m, 4H), 3.16 (br d, J=4.8 Hz, 4H), 3.12-3.03 (m, 4H), 2.49-2.43 (m, 4H), 2.41 (s, 3H), 2.23 (s, 3H).

compound-186

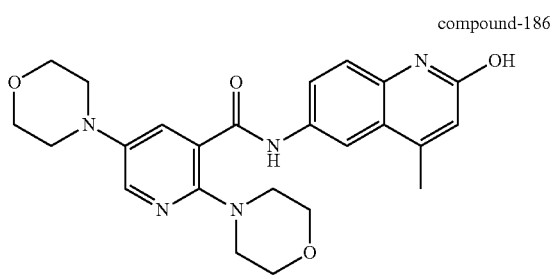 [SMILES: Cc1cc(O)nc2ccc(NC(=O)c3cc(N4CCOCC4)cnc3N3CCOCC3)cc12]

Preparation of N-(2-hydroxy-4-methylquinolin-6-yl)-2,5-dimorpholinonicotinamide (compound-186): a suspension of 5-bromo-N-(2-hydroxy-4-methylquinolin-6-yl)-2-morpholinonicotinamide (1) (200 mg, 0.452 mmol, 1 eq), Morpholine (39 mg, 0.452 mmol, 1 eq) Na$^t$OBu (130 mg, 1.356 mmol, 3 eq) in 1,4 Dioxane (10 Vol) was degassed for 10 min. Then added Ruphos (20 mg, 0.0452 mmol, 0.1 eq), Ruphos precatalyst (32 mg, 0.0452 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by column chromatography (SiO$_2$) by using MeOH:DCM (6:94) to afford N-(2-hydroxy-4-methylquinolin-6-yl)-2,5-dimorpholinonicotinamide (compound-186) (55 mg, 27%) as an off white solid.

$^1$H NMR (400 MHz, DMSO-d6): δ 11.59 (s, 1H), 11.17 (s, 1H), 8.26 (d, J=2.0 Hz, 1H), 8.17 (d, J=2.9 Hz, 1H), 7.79 (dd, J=2.0, 8.8 Hz, 1H), 7.66 (d, J=2.9 Hz, 1H), 7.33 (d, J=8.8 Hz, 1H), 6.44 (s, 1H), 3.73 (td, J=4.2, 18.0 Hz, 8H), 3.12 (td, J=4.4, 17.1 Hz, 8H), 2.41 (s, 3H).

compound-187

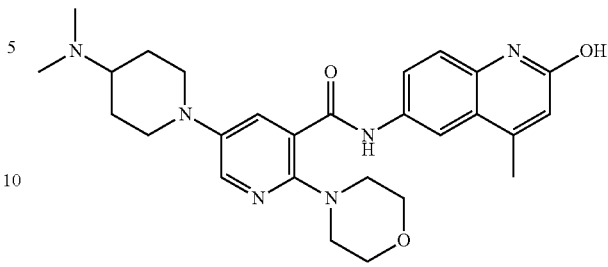

Preparation of 5-(4-(dimethylamino) piperidin-1-yl)-N-(2-hydroxy-4-methylquinolin-6-yl)-2-morpholinonicotinamide (compound-187): a suspension of 5-bromo-N-(2-hydroxy-4-methylquinolin-6-yl)-2-morpholinonicotinamide (1) (100 mg, 0.226 mmol, 1 eq), 4-Dimethylamino piperidine (29 mg, 0.226 mmol, 1 eq) Na$^t$OBu (63 mg, 0.66 mmol, 3 eq) in 1,4 Dioxane (10 Vol) was degassed for 10 min. Then added Ruphos (10 mg, 0.0226 mmol, 0.1 eq), Ruphos precatalyst (16 mg, 0.0226 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by column chromatography (SiO$_2$) by using MeOH:DCM (6:94) to afford 5-(4-(dimethylamino) piperidin-1-yl)-N-(2-hydroxy-4-methylquinolin-6-yl)-2-morpholinonicotinamide (compound-187) (10 mg, 9%) as an off white solid.

$^1$H NMR (400 MHz, DMSO-d6): δ 11.60 (s, 1H), 11.24 (s, 1H), 8.26 (s, 1H), 8.17 (s, 1H), 7.79 (d, J=7.8 Hz, 1H), 7.66 (s, 1H), 7.33 (d, J=8.8 Hz, 1H), 6.44 (s, 1H), 3.71 (m, 6H), 3.08 (m, 4H), 2.80-2.62 (m, 2H), 2.41 (m, 4H), 2.21 (m, 6H), 1.84 (m, 2H), 1.49 (m, 2H).

Synthesis of Compound-188

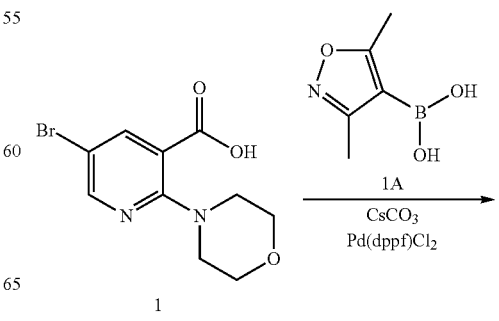

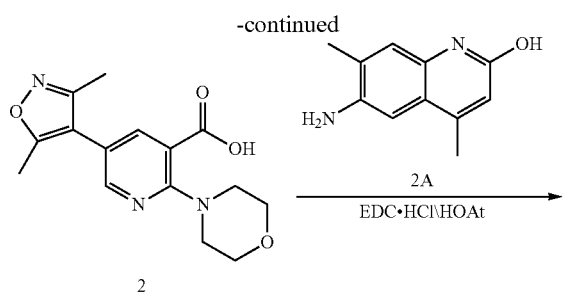

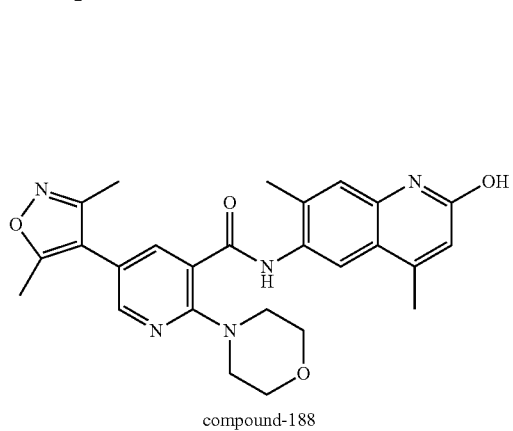

compound-188

Preparation of 5-(3, 5-dimethylisoxazol-4-yl)-2-morpholinonicotinic acid (2): a suspension of 5-bromo-2-morpholinonicotinic acid (1) (1 g, 3.484 mmol, 1 eq), 3,5-dimethylisoxazol-4-ylboronic acid (975.5 mg, 6.968 mmol, 2 eq) and Cs₂CO₃ (3.39 g, 10.452 mmol, 3 eq) in Dioxane: H₂O (2:1) (10 vol) was degassed for 15 mins. Then added Pd(PPh₃)₄(283.9 mg, 0.348 mmol, 0.1 eq) and stirred at 80° C. for 16 h. After completion, the reaction mixture was poured into ice water and extracted with EtOAc (2×30 mL). The combined extracts were washed with water (40 mL), brine (40 mL), dried over anhydrous Na₂SO₄, filtered and evaporated. The crude compound was purified by column chromatography (SiO₂) by using MeOH:DCM (3:97) to afford 5-(3, 5-dimethylisoxazol-4-yl)-2-morpholinonicotinic acid (1) (300 mg, 28%) as off white solid.

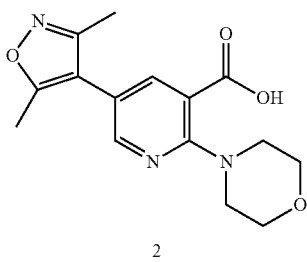

compound-188

Preparation of 5-(3,5-dimethylisoxazol-4-yl)-N-(2-hydroxy-4,7-dimethylquinolin-6-yl)-2-morpholino nicotinamide (compound-188): to a solution of 5-(3,5-dimethylisoxazol-4-yl)-2-morpholinonicotinic acid (Compound-2) (150 mg, 0.49 mmol, 1 eq) in Dry DMF (2 mL) at RT was added 2A (93 mg, 0.36 mmol, 1 eq), HOAt (135 mg, 0.99 mmol, 2 eq), EDC (190 mg, 0.99 mmol, 2 eq) and DIPEA (255 mg, 1.98 mmol, 4 eq) and stirred at RT for 16 h. After completion, the reaction mixture poured into ice water and extracted with EtOAc (2×30 mL). The combined extracts were washed with water (2×40 mL), brine (40 mL), dried over anhydrous Na₂SO₄, filtered and evaporated. The crude compound was purified by column chromatography (SiO₂) by using MeOH:DCM (10:90) to afford 5-(3,5-dimethylisoxazol-4-yl)-N-(2-hydroxy-4,7-dimethylquinolin-6-yl)-2-morpholinonicotinamide (compound-188) (80 mg, 34%) as an off white solid.

¹H NMR (400 MHz, DMSO-d6): δ 11.55 (s, 1H), 10.07 (s, 1H), 8.35 (d, J=2.4 Hz, 1H), 7.93 (s, 2H), 7.17 (s, 1H), 6.37 (s, 1H), 3.80-3.65 (m, 4H), 3.52-3.36 (m, 4H), 2.44 (s, 3H), 2.38 (d, J=12.7 Hz, 6H), 2.26 (s, 3H).

Synthesis of Compound-189, Compound-190 & Compound-191

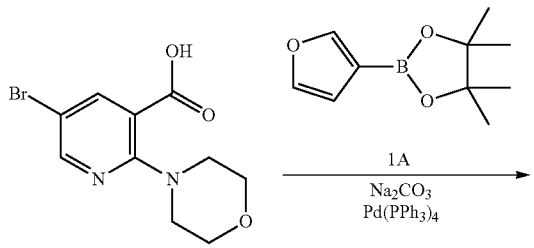

-continued
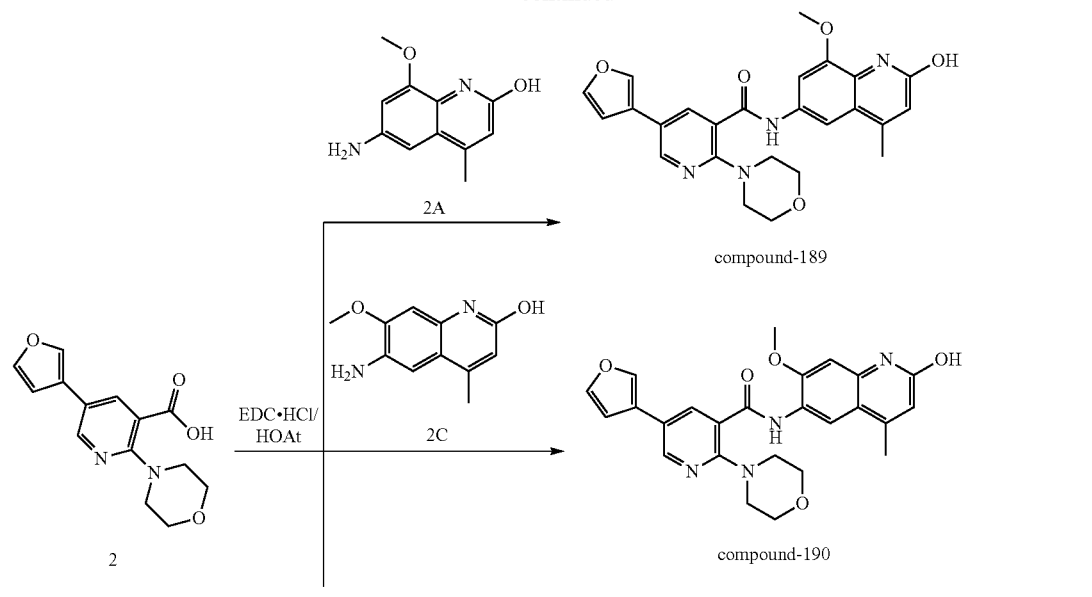
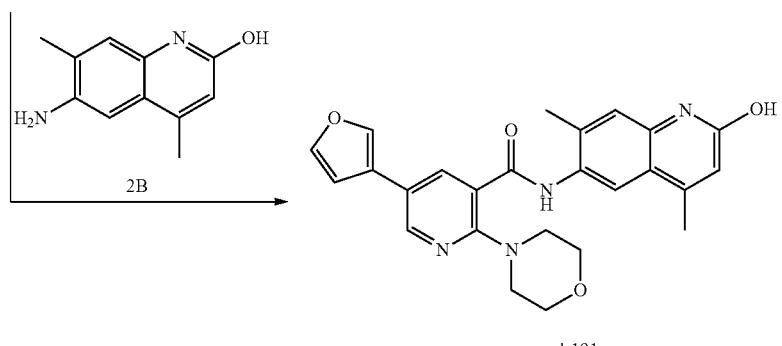
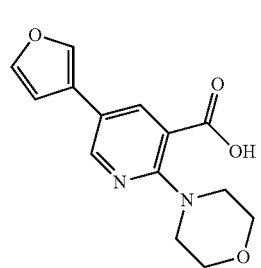

Preparation of 5-(furan-3-yl)-2-morpholinonicotinic acid (2): a suspension of 5-bromo-2-morpholinonicotinic acid (1) (1.0 g, 3.49 mmol, 1 eq), 2-(furan-3-yl)-4,4,5,5-tetramethyl-1,3,2-dioxaborolane (1A) (1.36 g, 6.99 mmol, 2 eq), $Na_2CO_3$ (1.48 g, 13.98 mmol, 4 eq) in Dioxane (20 mL) was degassed for 10 min. Then added $Pd(PPh_3)_4$ (404 mg, 0.34 mmol, 0.1 eq) and stirred at 100° C. for 16 h. After completion, the solvent was evaporated, the residue was taken in water and extracted with EtOAc (3×30 mL). The combined extracts were washed with water (60 mL), brine (60 mL), dried over anhydrous $Na_2SO_4$, filtered and evaporated. The crude compound was purified by column chromatography ($SiO_2$) by using MeOH:DCM (10:90) to afford 5-(furan-3-yl)-2-morpholinonicotinic acid (2) (500 mg, 51%) as yellow solid.

compound-189

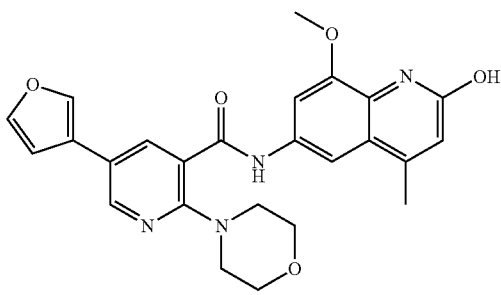

Preparation of 5-(furan-3-yl)-N-(2-hydroxy-8-methoxy-4-methylquinolin-6-yl)-2-morpholinonicotinamide (compound-189): to a solution of 5-(furan-3-yl)-2-morpholinonicotinic acid (2) (100 mg, 0.36 mmol, 1 eq) in Dry DMF (2 mL) at RT was added 6-amino-8-methoxy-4-methylquinolin-2-ol (2A) (75 mg, 0.36 mmol, 1 eq), HOAt (100 mg, 0.72 mmol, 2 eq), EDC (140 mg, 0.72 mmol, 2 eq), DIPEA (188 mg, 0.25 mmol, 4 eq) and stirred at RT for 16 h. After completion, the reaction mixture poured into ice water and extracted with EtOAc (2×20 mL). The combined extracts were washed with water (2×30 mL), brine (30 mL), dried over anhydrous $Na_2SO_4$, filtered and evaporated. The crude compound was purified by column chromatography using ($SiO_2$) by eluting MeOH:DCM (10:90) to afford 5-(furan-3-yl)-N-(2-hydroxy-8-methoxy-4-methylquinolin-6-yl)-2-morpholinonicotinamide (compound-189) (75 mg, 45%) as an off white solid.

$^1$H NMR (400 MHz, DMSO-d6): δ 10.63 (br d, J=10.8 Hz, 2H), 8.61 (d, J=2.4 Hz, 1H), 8.25 (s, 1H), 8.08 (d, J=2.4 Hz, 1H), 7.83-7.71 (m, 2H), 7.59 (d, J=2.0 Hz, 1H), 7.04 (d, J=1.5 Hz, 1H), 6.46 (s, 1H), 3.90 (s, 3H), 3.73-3.60 (m, 4H), 3.33 (m, 4H), 2.39 (s, 3H).

compound-191

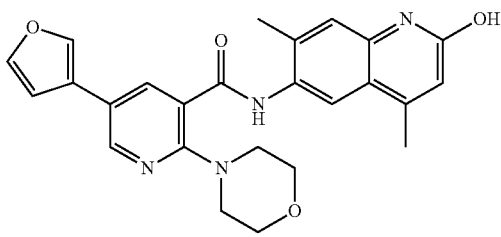

Preparation of 5-(furan-3-yl)-N-(2-hydroxy-4,7-dimethylquinolin-6-yl)-2-morpholinonicotinamide (compound-191): to a solution of 5-(furan-3-yl)-2-morpholinonicotinic acid (2) (100 mg, 0.36 mmol, 1 eq) in Dry DMF (2 mL) at RT was added 6-amino-4,7-dimethylquinolin-2-ol (2B) (69 mg, 0.36 mmol, 1 eq), HOAt (100 mg, 0.72 mmol, 2 eq), EDC (140 mg, 0.72 mmol, 2 eq), DIPEA (188 mg, 0.25 mmol, 4 eq) and stirred at RT for 16 h. After completion, the reaction mixture was poured into ice water and extracted with EtOAc (2×20 mL). The combined extracts were washed with water (2×30 mL), brine (30 mL), dried over anhydrous $Na_2SO_4$, filtered and evaporated. The crude compound was purified by column chromatography ($SiO_2$) by using MeOH:DCM (10:90) to afford 5-(furan-3-yl)-N-(2-hydroxy-4,7-dimethylquinolin-6-yl)-2-morpholinonicotinamide (compound-191) (46 mg, 27%) as a pale yellow solid.

$^1$H NMR (400 MHz, DMSO-d6): δ 11.55 (s, 1H), 10.09 (s, 1H), 8.62 (d, J=2.0 Hz, 1H), 8.25 (s, 1H), 8.12 (d, J=2.0 Hz, 1H), 7.90 (s, 1H), 7.77 (s, 1H), 7.18 (s, 1H), 7.04 (s, 1H), 6.38 (s, 1H), 3.77-3.63 (m, 4H), 3.41-3.33 (m, 4H), 2.39 (d, J=7.8 Hz, 6H).

compound-190

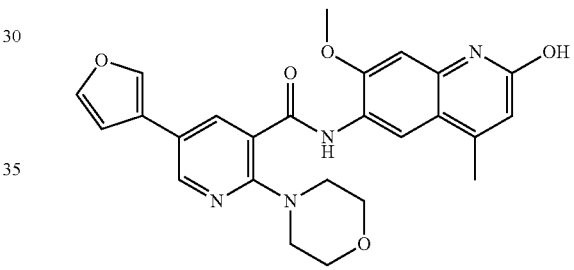

Preparation of 5-(furan-3-yl)-N-(2-hydroxy-7-methoxy-4-methylquinolin-6-yl)-2-morpholinonicotinamide (compound-190): to a solution of 5-(furan-3-yl)-2-morpholinonicotinic acid (2) (100 mg, 0.36 mmol, 1 eq) in Dry DMF (2 mL) at RT was added 6-amino-7-methoxy-4-methylquinolin-2-ol (2C) (75 mg, 0.36 mmol, 1 eq), HOAt (100 mg, 0.72 mmol, 2 eq), EDC (140 mg, 0.72 mmol, 2 eq), DIPEA (188 mg, 0.25 mmol, 4 eq) and stirred at RT for 16 h. After completion, the reaction mixture poured into ice water and extracted with EtOAc (2×20 mL). The combined extracts were washed with water (2×30 mL), brine (30 mL), dried over anhydrous $Na_2SO_4$, filtered and evaporated. The crude compound was purified by column chromatography ($SiO_2$) by using MeOH:DCM (10:90) to afford 5-(furan-3-yl)-N-(2-hydroxy-7-methoxy-4-methylquinolin-6-yl)-2-morpholinonicotinamide (compound-190) (45 mg, 29%) as an off white solid.

$^1$H NMR (300 MHz, DMSO-d6): δ 11.52 (s, 1H), 10.81 (s, 1H), 8.78 (s, 1H), 8.74 (d, J=2.6 Hz, 1H), 8.40 (d, J=2.6 Hz, 1H), 8.33 (s, 1H), 7.79 (t, J=1.7 Hz, 1H), 7.08 (d, J=1.1 Hz, 1H), 7.00 (s, 1H), 6.30 (s, 1H), 3.98 (s, 3H), 3.76 (m, 4H), 3.27-3.14 (m, 4H), 2.39 (s, 3H).

Synthesis of Compound-192, Compound-193 & Compound-194

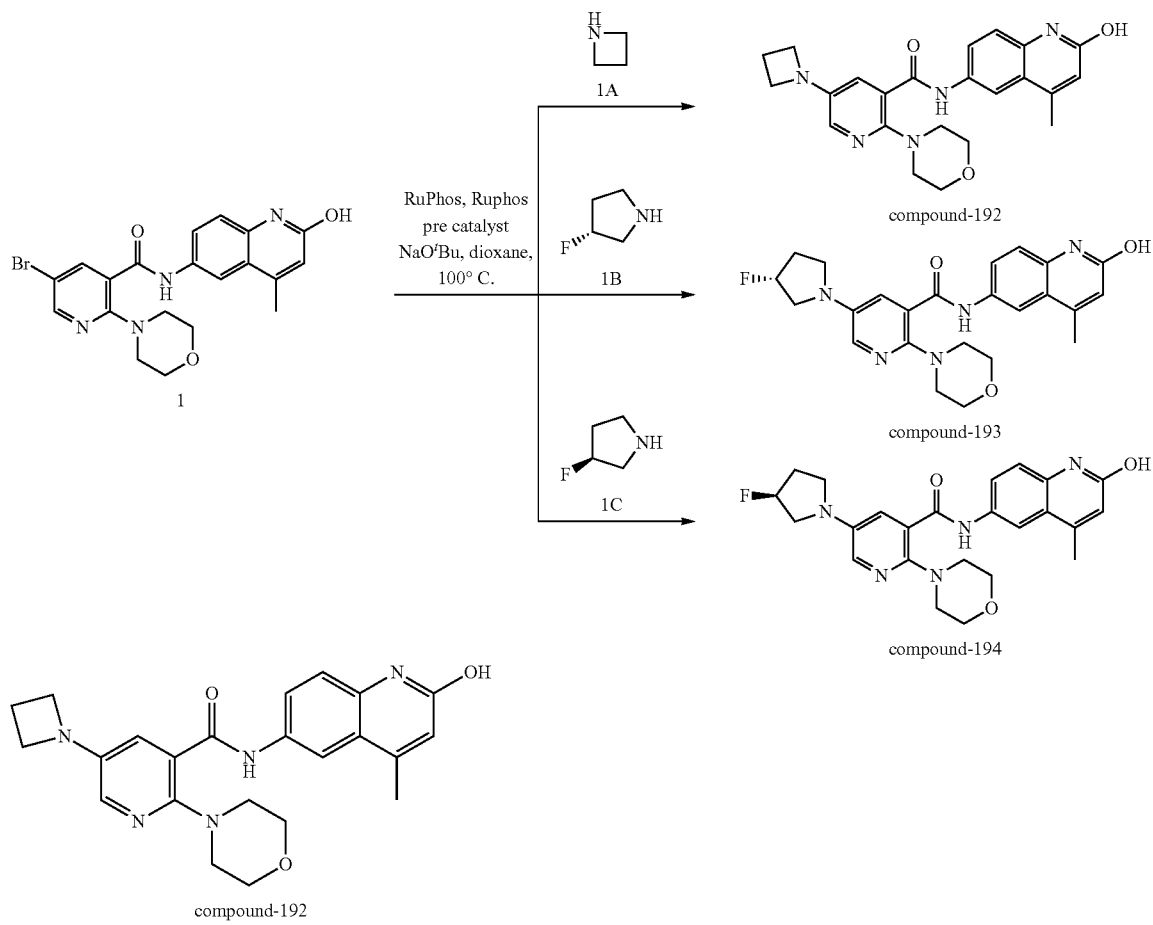

Preparation of 5-(azetidin-1-yl)-N-(2-hydroxy-4-methylquinolin-6-yl)-2 morpholinonicotinamide (compound-192): a suspension of 5-bromo-N-(2-hydroxy-4-methylquinolin-6-yl)-2-morpholinonicotinamide (1) (200 mg, 0.452 mmol, 1 eq), azetidine (26 mg, 0.452 mmol, 1 eq) Na$^t$OBu (130 mg, 1.356 mmol, 3 eq) in 1,4 Dioxane (10 Vol) was degassed for 10 min. Then added Ruphos (20 mg, 0.0452 mmol, 0.1 eq), Ruphos precatalyst (32 mg, 0.0452 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by preparative HPLC to afford 5-(azetidin-1-yl)-N-(2-hydroxy-4-methylquinolin-6-yl)-2 morpholinonicotinamide (compound-192) (2 mg) as an off white solid.

$^1$H NMR (400 MHz, DMSO-d6): δ 11.60 (s, 1H), 11.50 (s, 1H), 8.28 (s, 1H), 7.78 (d, J=8.8 Hz, 1H), 7.72 (d, J=2.9 Hz, 1H), 7.33 (d, J=8.8 Hz, 1H), 7.25 (d, J=2.9 Hz, 1H), 6.44 (s, 1H), 3.87 (t, J=7.3 Hz, 4H), 3.73 (m, 4H), 3.05 (d, J=4.4 Hz, 4H), 2.41 (s, 3H), 2.39-2.30 (m, 2H).

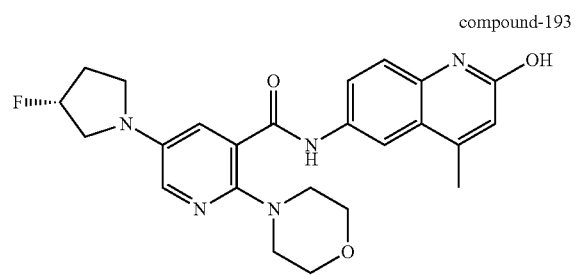 [SMILES: Cc1cc(O)nc2ccc(NC(=O)c3cc(N4CC[C@@H](F)C4)cnc3N3CCOCC3)cc12]

Preparation of (R)-5-(3-fluoropyrrolidin-1-yl)-N-(2-hydroxy-4-methylquinolin-6-yl)-2-morpholinonicotinamide (compound-193): a suspension of 5-bromo-N-(2-hydroxy-4-methylquinolin-6-yl)-2-morpholinonicotinamide (1) (200 mg, 0.452 mmol, 1 eq), (R)-3-fluoropyrrolidine (57 mg, 0.452 mmol, 1 eq) Na$^t$OBu (130 mg, 1.356 mmol, 3 eq) in 1,4-Dioxane (10 Vol) was degassed for 10 min. Then added Ruphos (20 mg, 0.0452 mmol, 0.1 eq), Ruphos precatalyst (32 mg, 0.0452 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by preparative HPLC to afford (R)-5-(3-fluoropyrrolidin-1-yl)-N-(2-hydroxy-4-methylquinolin-6-yl)-2-morpholinonicotinamide (compound-193) (3 mg) as an off white solid.

$^1$H NMR (300 MHz, DMSO-d6): δ 11.73 (s, 1H), 11.61 (s, 1H), 8.31 (s, 1H), 7.90 (d, J=2.9 Hz, 1H), 7.80 (d, J=6.9 Hz, 1H), 7.43 (d, J=2.6 Hz, 1H), 7.34 (d, J=8.8 Hz, 1H), 6.44 (s, 1H), 5.63-5.33 (m, 1H), 3.76 (m, 3H), 3.67-3.56 (m, 1H), 3.53-3.36 (m, 3H), 3.05 (s, 4H), 2.42 (s, 3H), 2.35-2.18 (m, 2H).

compound-194

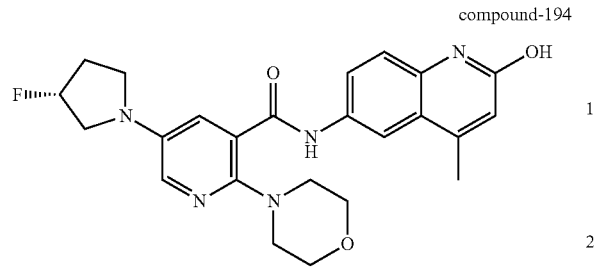

Preparation of (S)-5-(3-fluoropyrrolidin-1-yl)-N-(2-hydroxy-4-methylquinolin-6-yl)-2-morpholinonicotinamide (compound-194): a suspension of 5-bromo-N-(2-hydroxy-4-methylquinolin-6-yl)-2-morpholinonicotinamide (1) (200 mg, 0.452 mmol, 1 eq), (S)-3-fluoropyrrolidine (57 mg, 0.452 mmol, 1 eq) Na$^t$OBu (130 mg, 1.356 mmol, 3 eq) in 1,4 Dioxane (10 Vol) was degassed for 10 min. Then added Ruphos (20 mg, 0.0452 mmol, 0.1 eq), Ruphos precatalyst (32 mg, 0.0452 mmol, 0.1 eq) and stirred at 90° C. for 16 h in a sealed tube. After completion, the reaction mixture was poured into water and extracted with MeOH:DCM (1:9) (3×20 mL). The combined extracts were washed with water (40 mL), brine (40 mL), dried over anhydrous Na$_2$SO$_4$, filtered and evaporated. The crude compound was purified by preparative HPLC to afford (S)-5-(3-fluoropyrrolidin-1-yl)-N-(2-hydroxy-4-methylquinolin-6-yl)-2-morpholinonicotinamide (compound-194) (17 mg) as an off white solid.

$^1$H NMR (300 MHz, DMSO-d6): δ 11.73 (s, 1H), 11.61 (s, 1H), 8.31 (d, J=2.2 Hz, 1H), 7.90 (d, J=2.9 Hz, 1H), 7.80 (dd, J=1.8, 8.8 Hz, 1H), 7.43 (d, J=2.9 Hz, 1H), 7.34 (d, J=8.8 Hz, 1H), 6.44 (s, 1H), 5.61-5.34 (m, 1H), 3.82-3.70 (m, 4H), 3.67-3.37 (m, 4H), 3.10-2.97 (m, 4H), 2.42 (s, 3H), 2.29 (m, 2H).

Synthesis of Compound-195 & Compound-196

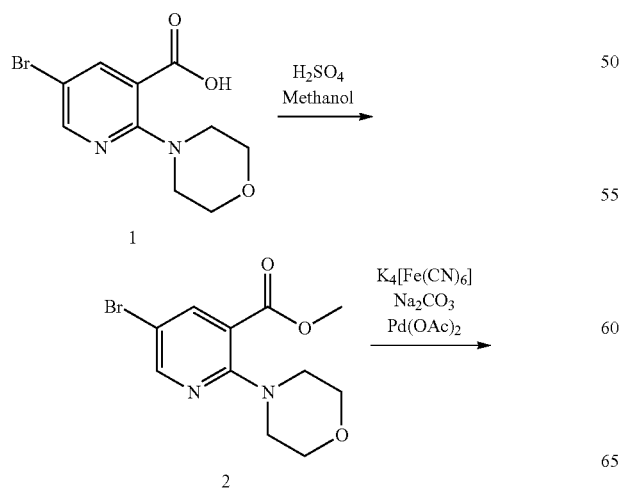

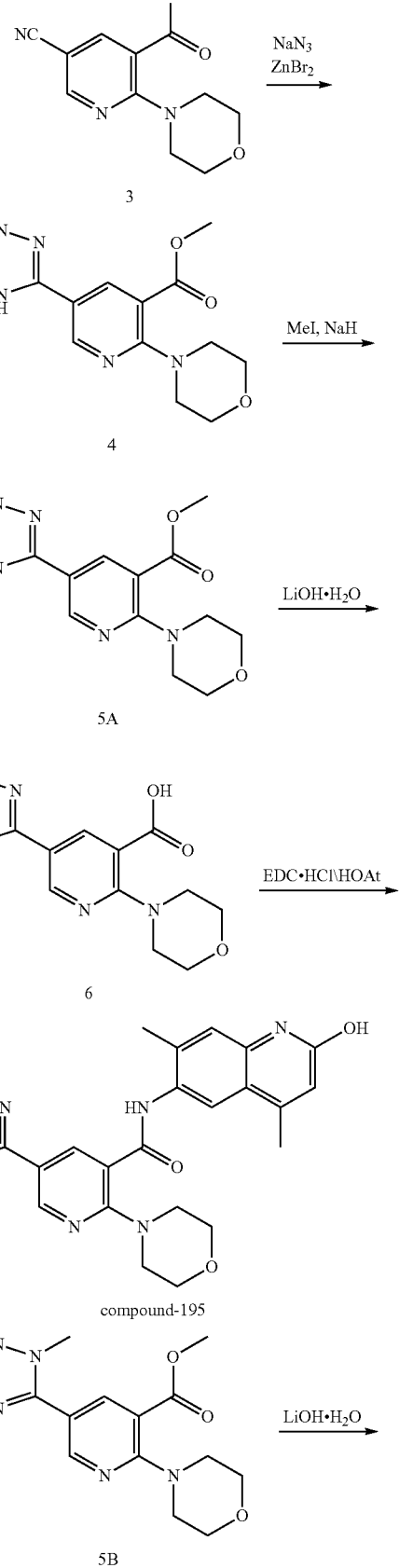

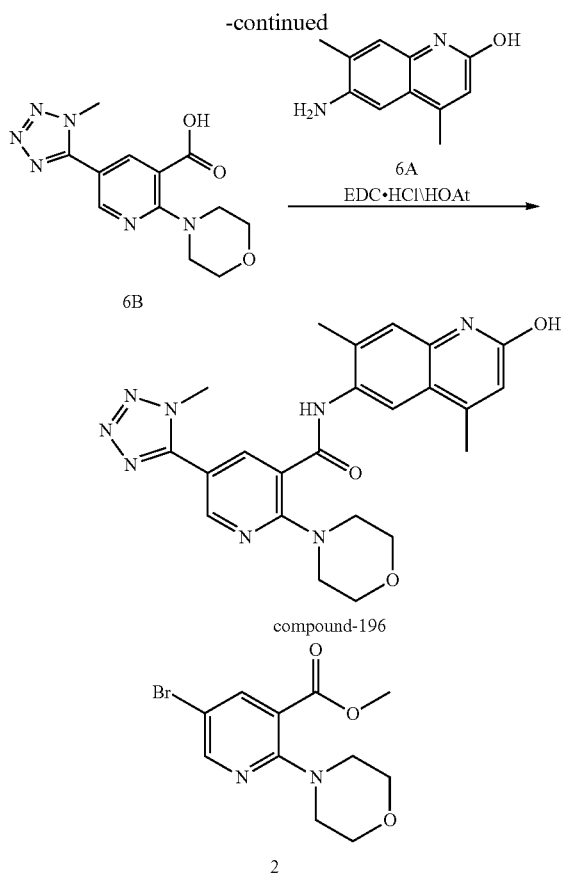

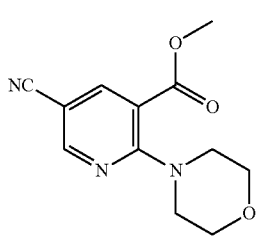

Preparation of methyl 5-bromo-2-morpholinonicotinate (2): to a solution of 5-bromo-2-morpholinonicotinic acid (1) (1 g, 3.496 mmol, 1 eq) in methanol (10 vol) was added sulfuric acid (0.1 ml, catalytic) at RT and stirred at 80° C. for 16 h. After completion, the solvent was evaporated, the residue was taken in sodium bicarbonate solution and extracted with EtOAc (2×30 mL). The combined extracts were washed with water (40 mL), brine (40 mL), dried over anhydrous Na₂SO₄, filtered and evaporated. The crude compound was purified by column chromatography (SiO₂) by using MeOH:DCM (3:97) to afford methyl 5-bromo-2-morpholinonicotinate (2) (1 g, 96%) as an off white solid.

Preparation of methyl 5-cyano-2-morpholinonicotinate (3): a suspension of methyl 5-bromo-2-morpholinonicotinate (2) (900 mg, 3.0 mmol, 1 eq), K₄[Fe(CN)₆].3H₂O (380 mg, 0.9 mmol, 0.3 eq), Na₂CO₃ (318 mg, 3.0 mmol, 1 eq) in Dry DMA (10 mL) was degassed for 15 min. Then added palladium acetate (30 mg, 0.045 mmol, 0.015 eq), and stirred at 100° C. for 16 h. After completion, the reaction mixture poured into ice water and extracted with EtOAc (3×40 mL). The combined extracts were washed with water (2×50 mL), brine (50 mL), dried over anhydrous Na₂SO₄, filtered and evaporated. The crude compound was purified by column chromatography (SiO₂) by using MeOH:DCM (10:90) to afford methyl 5-cyano-2-morpholinonicotinate (3) (700 mg, 88%) as yellow solid.

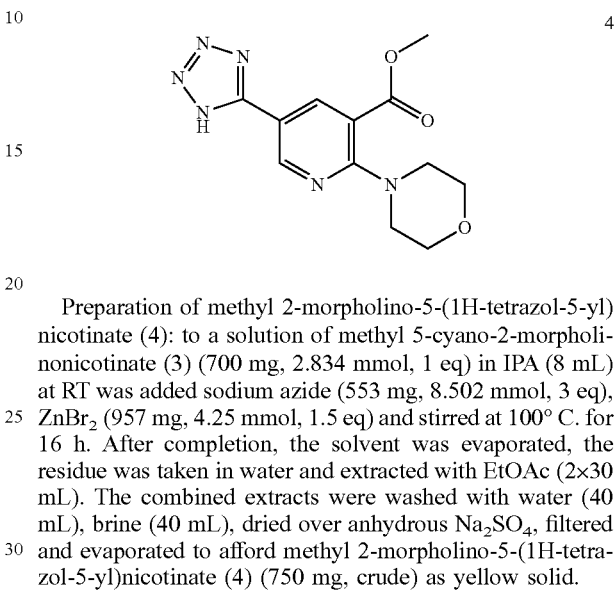

Preparation of methyl 2-morpholino-5-(1H-tetrazol-5-yl)nicotinate (4): to a solution of methyl 5-cyano-2-morpholinonicotinate (3) (700 mg, 2.834 mmol, 1 eq) in IPA (8 mL) at RT was added sodium azide (553 mg, 8.502 mmol, 3 eq), ZnBr₂ (957 mg, 4.25 mmol, 1.5 eq) and stirred at 100° C. for 16 h. After completion, the solvent was evaporated, the residue was taken in water and extracted with EtOAc (2×30 mL). The combined extracts were washed with water (40 mL), brine (40 mL), dried over anhydrous Na₂SO₄, filtered and evaporated to afford methyl 2-morpholino-5-(1H-tetrazol-5-yl)nicotinate (4) (750 mg, crude) as yellow solid.

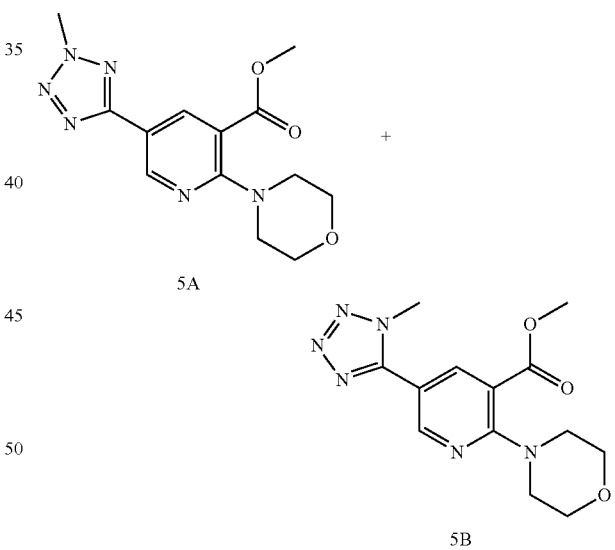

Preparation of methyl 5-(2-methyl-2H-tetrazol-5-yl)-2-morpholinonicotinate (5A) & methyl 5-(1-methyl-1H-tetrazol-5-yl)-2-morpholinonicotinate (5B): to a solution of methyl 2-morpholino-5-(1H-tetrazol-5-yl)nicotinate (4) (350 mg, 1.206 mmol, 1 eq) in Dry DMF (5 mL) at 0° C. was added sodium hydride (84 mg, 3.620 mmol, 3 eq) and stirred for 30 mins. Then added methyl iodide (255 mg, 1.809 mmol, 1.5 eq) and stirred at RT for 16 h. After completion, the reaction mixture poured into ice water extracted with EtOAc (2×30 mL). The combined extracts were washed with water (2×40 mL), brine (40 mL), dried over anhydrous Na₂SO₄, filtered and evaporated. The crude compound was purified by column chromatography using (SiO$_2$) by eluting EtOAC: Pet ether (50:50) to afford methyl 5-(2-methyl-2H-tetrazol-5-yl)-2-morpholinonicotinate (5A) (70 mg, 19%) as yellow solid and methyl 5-(1-methyl-1H-tetrazol-5-yl)-2-morpholinonicotinate (5B) (40 mg, 10%) as yellow solid $^1$H NMR (300 MHz, DMSO-d6): δ 11.57 (s, 1H), 10.18 (s, 1H), 8.90 (s, 1H), 8.38 (s, 1H), 7.78 (s, 1H), 7.19 (s, 1H), 6.37 (s, 1H), 4.43 (s, 3H), 3.72 (s, 4H), 3.54 (m, 4H), 2.40 (s, 3H), 2.35 (s, 3H).

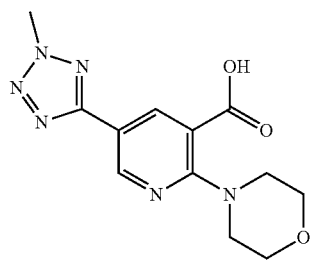

6

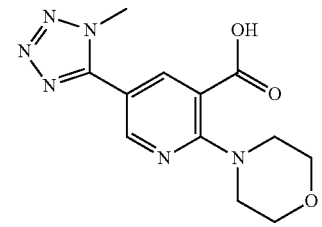

6B

Preparation of 5-(2-methyl-2H-tetrazol-5-yl)-2-morpholinonicotinic acid (6): to a solution of methyl 5-(2-methyl-2H-tetrazol-5-yl)-2-morpholinonicotinate (5A) (70 mg, 0.23 mmol, 1 eq) in methanol (5 mL) at RT added LiOH (20 mg, 0.46 mmol, 2 eq) solution and stirred at RT for 3 h. After completion, the solvent was evaporated. The crude was acidified with 1N HCl and filtered the solid to afford 5-(2-methyl-2H-tetrazol-5-yl)-2-morpholinonicotinic acid (6) (30 mg, 45%) as yellow solid.

Preparation of 5-(1-methyl-1H-tetrazol-5-yl)-2-morpholinonicotinic acid (6B): to a solution of methyl 5-(1-methyl-1H-tetrazol-5-yl)-2-morpholinonicotinate (5B) (40 mg, 0.13 mmol, 1 eq) in methanol (1 mL) at RT added LiOH (12 mg, 0.24 mmol, 2 eq) solution and stirred at RT for 3 h. After completion, the solvent was evaporated. The crude was acidified with 1N HCl and filtered the solid to afford 5-(1-methyl-1H-tetrazol-5-yl)-2-morpholinonicotinic acid (6B) (30 mg, 53%) as yellow solid.

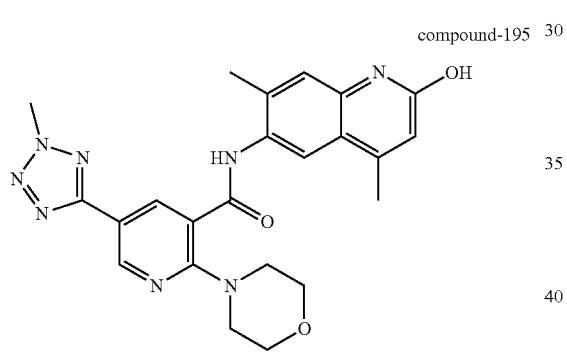

compound-195

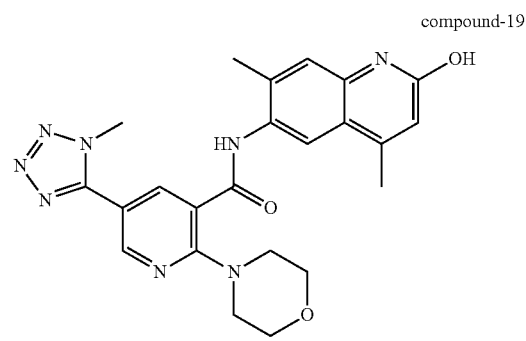

compound-196

Preparation of N-(2-hydroxy-4,7-dimethylquinolin-6-yl)-5-(2-methyl-2H-tetrazol-5-yl)-2-morpholinonicotinamide (compound-195): to a solution of 5-(2-methyl-2H-tetrazol-5-yl)-2-morpholinonicotinic acid (6) (30 mg, 0.098 mmol, 1 eq) in dry DMF (1 mL) at RT was added 6-amino-4,7-dimethylquinolin-2-ol (6A) (18 mg, 0.098 mmol, 1 eq), HOAt (27 mg, 0.197 mmol, 2 eq), EDC (38 mg, 0.19 mmol, 2 eq), DIPEA (50 mg, 0.39 mmol, 4 eq) and stirred at RT for 16 h. After completion, the reaction mixture was poured into ice water, filtered the solid, washed with pentane and dried to afford N-(2-hydroxy-4,7-dimethylquinolin-6-yl)-5-(2-methyl-2H-tetrazol-5-yl)-2-morpholinonicotinamide (compound-195) (7 mg, 14%) as an off white solid.

Preparation of N-(2-hydroxy-4,7-dimethylquinolin-6-yl)-5-(1-methyl-1H-tetrazol-5-yl)-2-morpholinonicotinamide (compound-196): to a solution of 5-(1-methyl-1H-tetrazol-5-yl)-2-morpholinonicotinic acid (6B) (30 mg, 0.098 mmol, 1 eq) in dry DMF (1 mL) at RT was added 6-amino-4,7-dimethylquinolin-2-ol (6A) (18 mg, 0.098 mmol, 1 eq), HOAt (27 mg, 0.197 mmol, 2 eq), EDC (38 mg, 0.19 mmol, 2 eq), DIPEA (50 mg, 0.39 mmol, 4 eq) and stirred at RT for 16 h. After completion, the reaction mixture was poured into ice water, filtered the solid, washed with pentane and dried to afford N-(2-hydroxy-4,7-dimethylquinolin-6-yl)-5-(1-methyl-1H-tetrazol-5-yl)-2-morpholinonicotinamide (compound-196) (3 mg, 8%) as yellow solid.

Synthesis of Compound-197

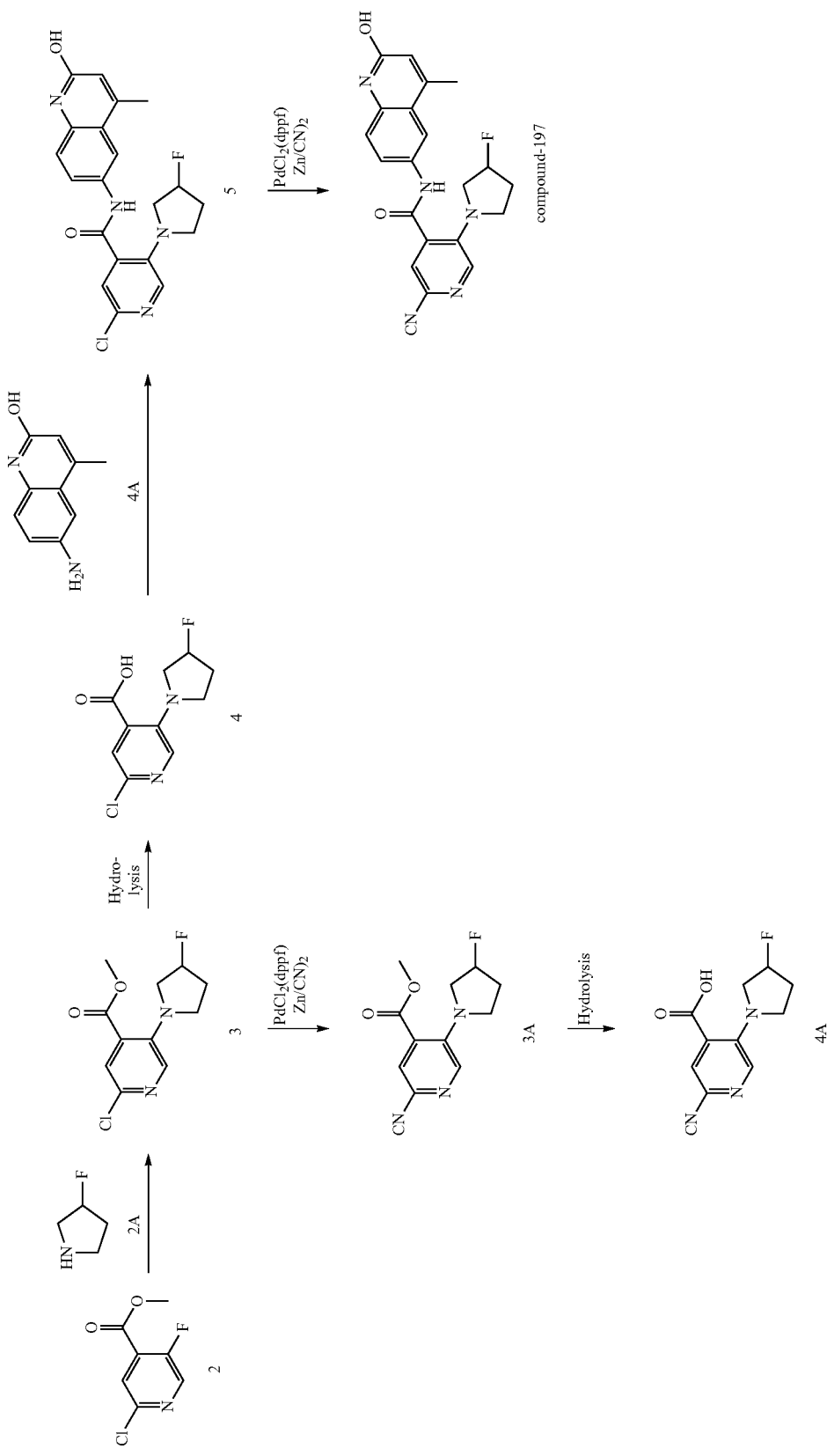

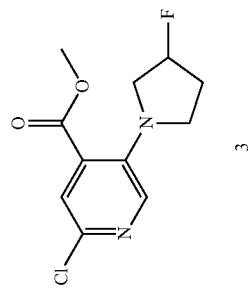

Preparation of methyl 2-chloro-5-(3-fluoropyrrolidin-1-yl) isonicotinate (3): to a solution of methyl-2-chloro-5-fluroisonicotinate (2) (1 g, 5.29 mmol, 1 eq) in DMSO was added 2A (0.73 g, 5.29 mmol, 1 eq), DIPEA (3 eq) and stirred at RT for 16 h. After completion, the reaction mixture was poured into water (50 mL) and extracted with EtOAc (3×50 mL). The combined extracts were washed with water (20 mL), brine (20 mL), dried over anhydrous $Na_2SO_4$, filtered and evaporated. The crude residue was purified by column chromatography (100-200 mesh silica, EtOAc: Hexane (15:85)) to afford methyl 2-chloro-5-(3-fluoropyrrolidin-1-yl) isonicotinate (3) (800 mg, 70%) as a white solid

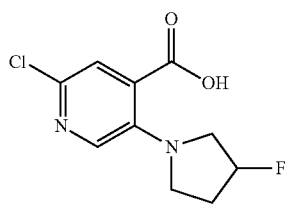

4

Preparation of 2-chloro-5-(3-fluoropyrrolidin-1-yl) isonicotinic acid (4): to a methyl 2-chloro-5-(3-fluoropyrrolidin-1-yl) isonicotinate (3) (800 mg, 3.11 mmol, 1 eq) in MeOH: $H_2O$ (1:1) (10 vol) was added $LiOH.H_2O$ (391 mg, 9.33 mmol, 3 eq) and stirred at RT for 16 h. After completion, the reaction mixture was neutralized with 1N HCl and extracted with MeOH:DCM (3×20 mL). The combined extracts were dried over anhydrous $Na_2SO_4$, filtered and evaporated to afford 2-chloro-5-(3-fluoropyrrolidin-1-yl) isonicotinic acid (4) (700 mg, 92%).

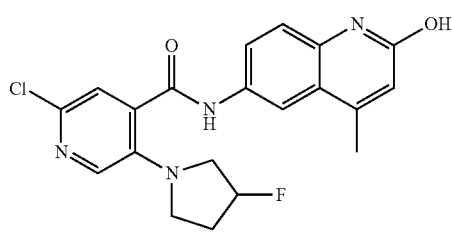

5

Preparation of 2-chloro-5-(3-fluoropyrrolidin-1-yl)-N-(2-hydroxy-4-methylquinolin-6-yl) isonicotinamide (5): to a solution of 2-chloro-5-(3-fluoropyrrolidin-1-yl) isonicotinic acid (4) (700 mg, 2.73 mmol, 1 eq) in DMF was added EDC.HCl (1.04 g, 5.46 mmol, 2 eq), HOAT (742 mg, 5.46 mmol, 2 eq), DIPEA (3 eq) followed by 6-amino-4-methylquinlin-2-ol (4A) (570 mg, 3.27 mmol, 1 eq) and stirred at RT for 16 h. After completion, the reaction mixture was poured into water and precipitated solid was filtered. The crude compound was purified by column chromatography (100-200 mesh silica, MeOH:DCM (5:95)) to afford 2-chloro-5-(3-fluoropyrrolidin-1-yl)-N-(2-hydroxy-4-methylquinolin-6-yl) isonicotinamide (5) (550 mg, 55%).

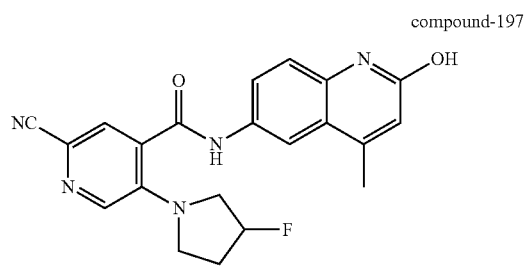 [SMILES: Cc1cc(O)nc2ccc(NC(=O)c3cc(C#N)ncc3N3CCC(F)C3)cc12]

compound-197

Preparation of 2-cyano-5-(3-fluoropyrrolidin-1-yl)-N-(2-hydroxy-4-methylquinolin-6-yl) isonicotinamide (compound-197): to a solution 2-chloro-5-(3-fluoropyrrolidin-1-yl)-N-(2-hydroxy-4-methylquinolin-6-yl) isonicotinamide (5) (50 mg, 0.125 mmol, 1 eq) in DMF was added $Zn(CN)_2$ (17.5 mg, 0.15 mmol, 1.2 eq) and degassed with $N_2$ for 15 min, then added $PdCl_2.dppf$ (10.20 mg, 0.0125 mmol, 0.3 eq). The reaction mixture heated at 150° C. for 1 h under microwave irradiation. After completion, the reaction mixture was poured into water and extracted with MeOH:DCM (1:9) (3×20 mL). The combined extracts were washed with ice water (20 mL), brine (20 mL), dried over anhydrous $Na_2SO_4$, filtered and evaporated. The crude compound was purified by column chromatography (100-200 mesh silica, MeOH:DCM (6:94)), to afford 2-cyano-5-(3-fluoro pyrrolidin-1-yl)-N-(2-hydroxy-4-methyl quinolin-6-yl) isonicotinamide (compound-197) (20 mg, 41.6%).

$^1$H NMR (300 MHz, DMSO-$d_6$) δ 11.61 (s, 1H), 10.75 (s, 1H), 8.30 (s, 1H), 8.09 (d, J=2.3 Hz, 1H), 7.94 (s, 1H), 7.78 (d, J=9.0 Hz, 1H), 7.31 (d, J=8.9 Hz, 1H), 6.44 (s, 1H), 5.43 (m, 1H), 3.92-3.45 (m, 4H), 2.40 (s, 2H), 1.24 (s, 2H).

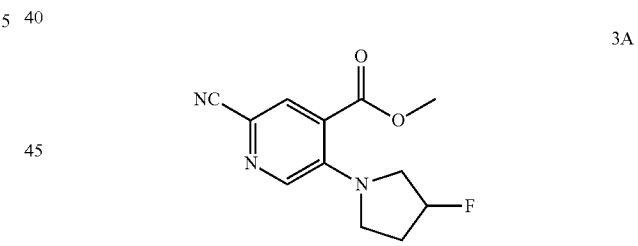

3A

Preparation of methyl 2-cyano-5-(3-fluoropyrrolidin-1-yl) isonicotinate (3A): to a solution of methyl 2-chloro-5-(3-fluoropyrrolidin-1-yl) isonicotinate (3) (600 mg, 2.32 mmol, 1 eq) in DMF was added $Zn(CN)_2$ (326 mg, 2.79 mmol, 1.2 eq) and degassed with $N_2$ for 15 min, then added $PdCl_2.dpf$ (189.4 mg, 0.232 mmol, 0.3 eq). The reaction mixture heated at 150° C. for 1 h under microwave irradiation. After completion, the reaction mixture was poured into water and extracted with MeOH:DCM (1:9) (3×30 mL). The combined extracts were washed with ice cold water (50 mL), brine (50 mL), dried over anhydrous $Na_2SO_4$, filtered and evaporated. The crude compound was purified by column chromatography (100-200 mesh silica, MeOH:DCM (6:94)), to afford methyl 2-cyano-5-(3-fluoropyrrolidin-1-yl) isonicotinate (3A) (270 mg, 46.7%).

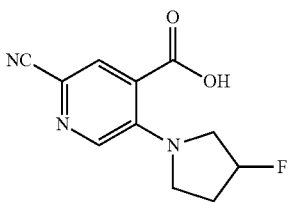

Preparation of 2-cyano-5-(3-fluoropyrrolidin-1-yl) isonicotinic acid (4A): to a solution of methyl 2-cyano-5-(3-fluoropyrrolidin-1-yl) isonicotinate (Compound-3A) (270 mg, 1.08 mmol, 1 eq) in THF:H$_2$O (1:1) (10 mL) at RT was added LiOH (0.91 mg, 2.1 mmol, 3 eq) and stirred at RT for 16 h. After completion, the reaction mixture was neutralized with 1N HCl and extracted with MeOH:DCM (1:9) (3×50 mL). The combined extracts were dried over anhydrous Na$_2$SO$_4$, filtered and evaporated. The crude product was triturated with Diethyl ether to afford 2-cyano-5-(3-fluoropyrrolidin-1-yl) isonicotinic acid (4A) (85 mg, 33.5%) as a white solid.

$^1$H NMR (300 MHz, DMSO-d$_6$) δ 13.70 (s, 1H), 8.33 (s, 1H), 7.92 (s, 1H), 5.56 (d, J=3.5 Hz, 1H), 3.77-3.58 (m, 2H), 3.51-3.28 (m, 2H), 2.32-2.19 (m, 2H).

Synthesis of Compound-198

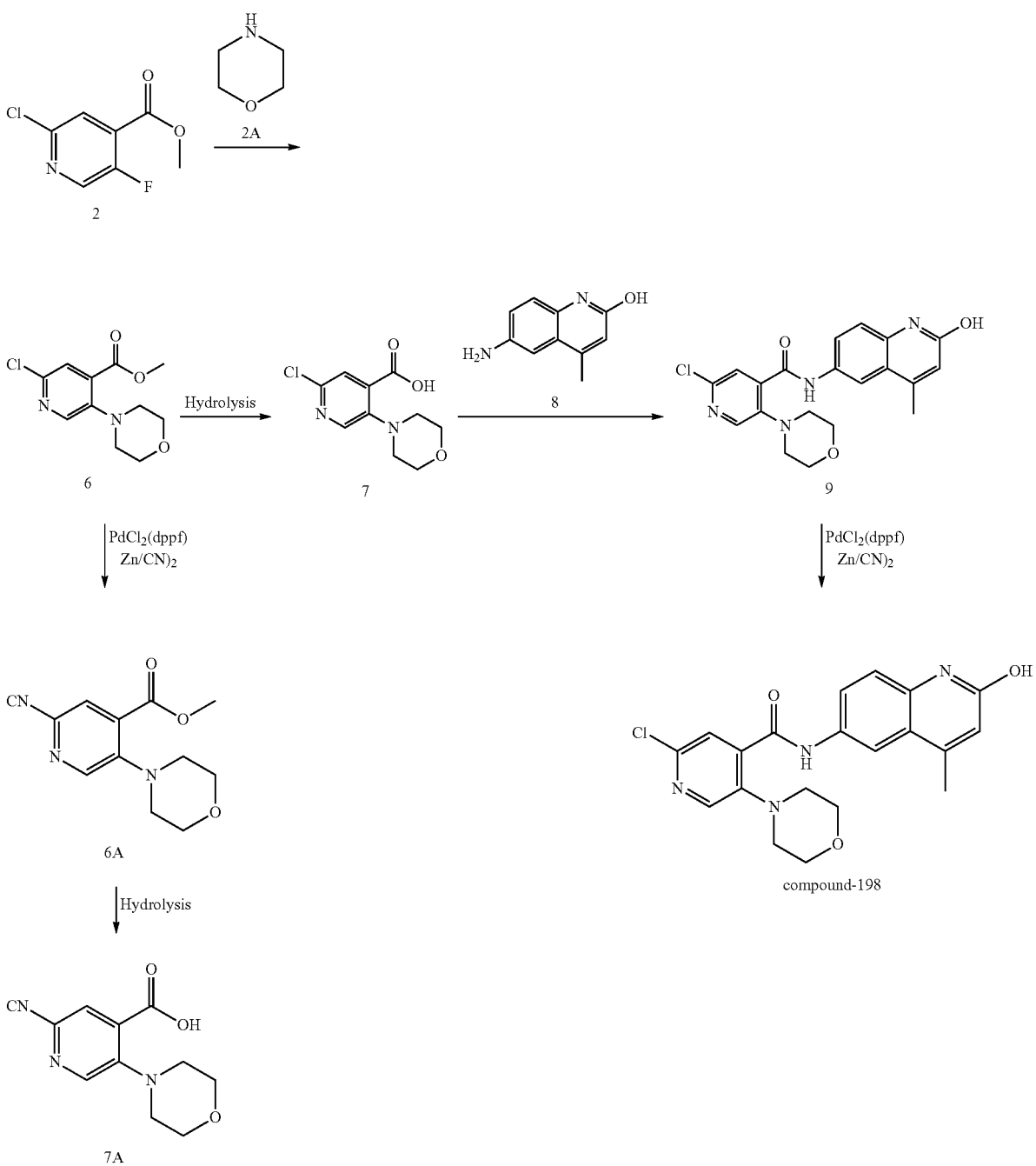

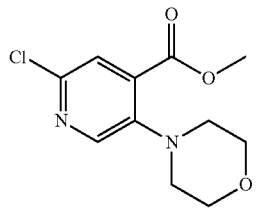

6

Preparation of methyl 2-chloro-5-morpholinoisonicotinate (6): to a solution of methyl 2-chloro-5-fluoroisonicotinate (2) (2 g, 10.58 mmol, 1 eq) in DMSO added (2A) (1.1 g, 12.69 mmol, 1.2 eq), DIPEA (3 eq) and stirred at RT for 16 h. After completion, the reaction mixture was poured into water (50 mL) and extracted with EtOAc (3×20 mL). The combined extracts were washed with water (30 mL), brine (30 mL), dried over anhydrous $Na_2SO_4$, filtered and evaporated. The crude residue was purified by column chromatography (100-200 mesh silica EtOAc:Hexane (15:85)), to afford methyl 2-chloro-5-morpholinoisonicotinate (6) (2 g, 74%).

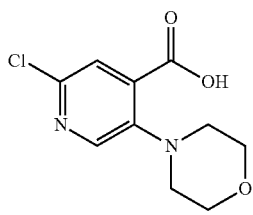

7

Preparation of 2-chloro-5-morpholinoisonicotinic acid (7): to a solution of methyl 2-chloro-5-morpholinoisonicotinate (6) (1.5 g, 5.85 mmol, 1 eq) in MeOH:$H_2O$ (1:1) (10 vol) added LiOH.$H_2O$ (0.737 g, 17.55 mmol, 3 eq) and stirred at RT for 16 h. After completion reaction mixture was diluted with water and acidified with 1N HCl. The solid precipitated was filtered and dried to afford 2-chloro-5-morpholinoisonicotinic acid (7) (1 g, 71%) as a white solid.

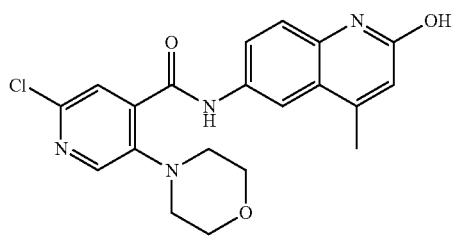

9

Preparation of 2-chloro-N-(2-hydroxy-4-methylquinolin-6-yl)-5-morpholinoisonicotinamide (9): to a solution of 2-chloro-5-morpholinoisonicotinic acid (7) (1 g, 4.13 mmol, 1 eq) in DMF was added EDC.HCl (1.57 g, 8.26 mmol, 2 eq), HOAT (1.12 mg, 8.26 mmol, 2 eq) and DIPEA (3 eq) followed by 6-amino-4-methylquinlin-2-ol (8) (0.862 mg, 4.95 mmol, 1 eq), and stirred at RT for 16 h. After completion, the reaction mixture was poured into water and precipitated solid was filtered and washed with diethyl ether to afford 2-chloro-N-(2-hydroxy-4-methylquinolin-6-yl)-5-morpholinoisonicotinamide (9) (650 mg, 40.6%) as a pale yellow solid.

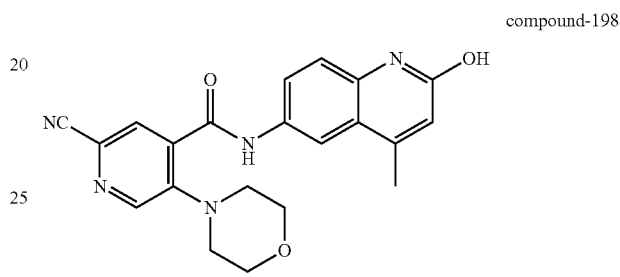

compound-198

Preparation of 2-cyano-N-(2-hydroxy-4-methylquinolin-6-yl)-5-morpholinoisonicotinamide (compound-198): to a solution of 2-chloro-N-(2-hydroxy-4-methylquinolin-6-yl)-5-morpholinoisonicotinamide (9) (650 mg, 1.625 mmol, 1 eq) in DMF was added Zn(CN)$_2$ (380 mg, 3.25 mmol, 2 eq) and degassed with $N_2$ for 15 min, then added PdCl$_2$.dppf (132 mg, 0.1625 mmol, 0.1 eq). The reaction mixture heated at 150° C. for 1 h under microwave irradiation. After completion, the reaction mixture was poured into water and extracted with MeOH:DCM (3×20 mL). The combined extracts were washed with ice water (50 mL), brine (50 mL), dried over anhydrous $Na_2SO_4$, filtered and evaporated. The crude compound was purified by column chromatography (100-200 mesh silica, MeOH:DCM (6:94)), to afford 2-cyano-N-(2-hydroxy-4-methylquinolin-6-yl)-5-morpholinoisonicotinamide (compound-198) (160 mg, 25.3%) as an off white solid.

$^1$H NMR (300 MHz, DMSO-d$_6$) δ 11.62 (s, 1H), 10.70 (s, 1H), 8.55 (s, 1H), 8.11 (d, J=2.3 Hz, 1H), 8.00 (s, 1H), 7.76 (dd, J=8.8, 2.3 Hz, 1H), 7.32 (d, J=8.8 Hz, 1H), 6.44 (s, 1H), 3.66 (t, J=4.5 Hz, 4H), 3.32 (s, 4H), 2.40 (s, 3H).

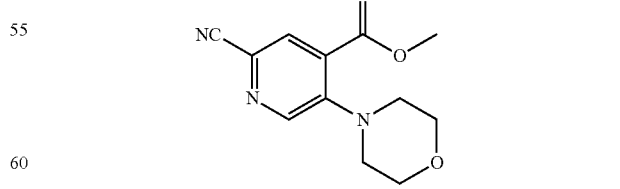

6A

Preparation of methyl 2-cyano-5-morpholinoisonicotinate (6A): to a solution of methyl 2-chloro-5-morpholinoisonicotinate (6) (400 mg, 1.56 mmol, 1 eq) in DMF was added Zn (CN)$_2$ (365 mg, 3.12 mmol, 2 eq) and degassed with $N_2$ for 15 min, then added PdCl$_2$.dppf (127.3 mg, 0.156 mmol, 0.1 eq). The reaction mixture heated at 150° C. for 1 h under microwave irradiation. After completion, the reaction mixture was poured into water and extracted with MeOH:DCM (3×100 mL). The combined extracts were washed with ice water (50 mL), brine (50 mL), dried over anhydrous Na₂SO₄, filtered and evaporated. The crude compound was purified by column chromatography (100-200 mesh silica, MeOH:DCM (4:96)), to afford methyl 2-cyano-5-morpholinoisonicotinate (6A) (200 mg, 51.9%) as a white solid.

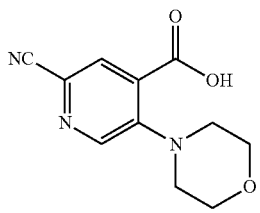

Preparation of 2-cyano-5-morpholinoisonicotinic acid (7A)

To a solution of methyl 2-cyano-5-morpholinoisonicotinate (6A)) (180 mg, 0.72 mmol, 1 eq) in THF:H₂O (1:1) (10 mL) at RT was added LiOH (0.61.2 mg, 1.45 mmol, 2 eq) and stirred at RT for 16 h. After completion, the reaction mixture was acidified neutralized with 1N HCl and extracted with MeOH:DCM (3×50 mL). The combined extracts were dried over anhydrous Na₂SO₄, filtered and evaporated. The crude compound was purified by triturating with diethyl ether to afford 2-cyano-5-morpholinoisonicotinic acid (7A) (110 mg, 65.47%) as a white solid.

¹H NMR (400 MHz, DMSO-d₆) δ 13.79 (s, 1H), 8.52 (s, 1H), 7.97 (s, 1H), 3.70 (t, J=4.6 Hz, 4H), 3.35-3.25 (m, 4H).

Synthesis of Compound-199:

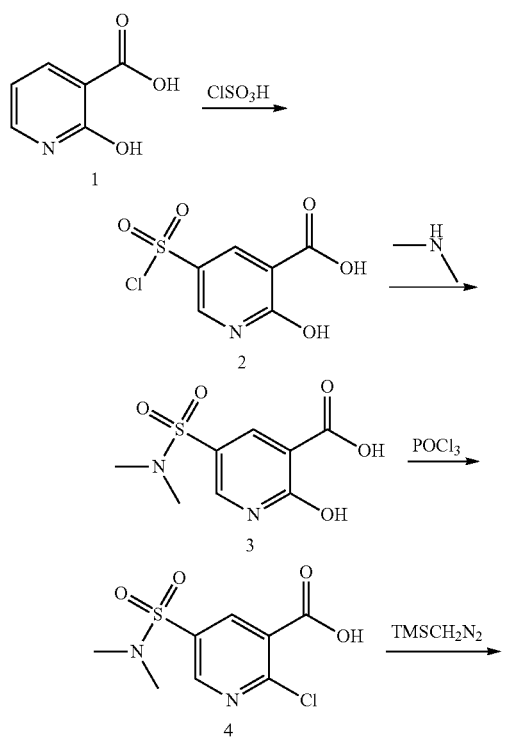

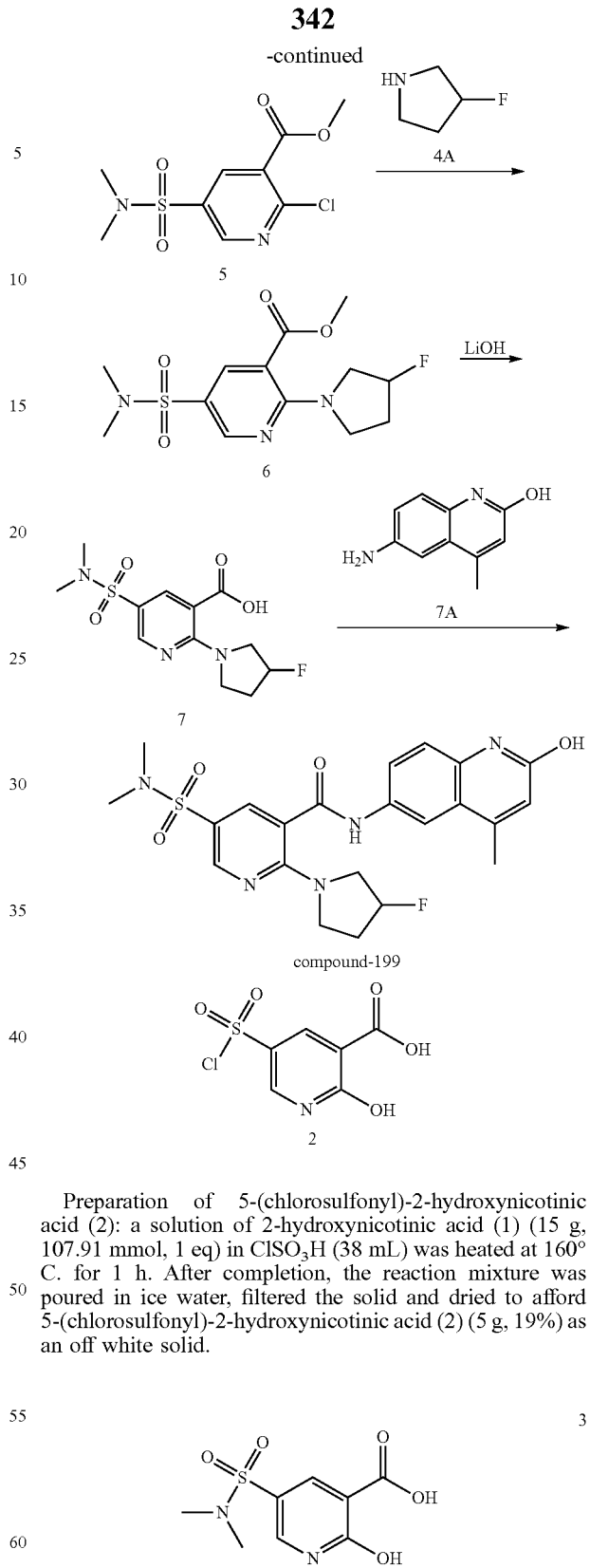

Preparation of 5-(chlorosulfonyl)-2-hydroxynicotinic acid (2): a solution of 2-hydroxynicotinic acid (1) (15 g, 107.91 mmol, 1 eq) in ClSO₃H (38 mL) was heated at 160° C. for 1 h. After completion, the reaction mixture was poured in ice water, filtered the solid and dried to afford 5-(chlorosulfonyl)-2-hydroxynicotinic acid (2) (5 g, 19%) as an off white solid.

Preparation of 5-(N,N-dimethylsulfamoyl)-2-hydroxynicotinic acid (3): to a solution of 5-(chlorosulfonyl)-2-hydroxynicotinic acid (2) (2.8 g, 11.81 mmol, 1 eq) in dry THF (20 mL) at 0° C. was added Dimethyl amine (800 mg, 17.72 mmol, 1.5 eq) and stirred at 10° C. for 6 h. After completion, the solvent was evaporated, the residue was taken in water and acidified with 1N HCl. The solid obtained was filtered and dried to afford 5-(N,N-dimethylsulfamoyl)-2-hydroxynicotinic acid (3) (2 g, 60%) as an off white solid.

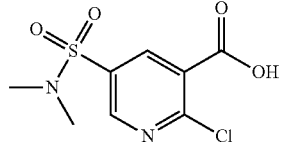

4

Preparation of 2-chloro-5-(N,N-dimethylsulfamoyl)nicotinic acid (4): a solution of 5-(N,N-dimethylsulfamoyl)-2-hydroxynicotinic acid (3) (2 g, 8.13 mmol, 1 eq) in POCl$_3$ (20 mL) was heated at 130° C. for 1 h. After completion, the reaction mixture was poured in ice water, filtered the solid and dried to afford 2-chloro-5-(N,N-dimethylsulfamoyl)nicotinic acid (4) (700 mg, 33%) as an off white solid.

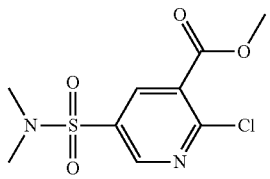

5

Preparation of methyl 2-chloro-5-(N,N-dimethylsulfamoyl)nicotinate (5): to a solution of 2-chloro-5-(N,N-dimethylsulfamoyl)nicotinic acid (4) (700 mg, 2.651 mmol, 1 eq) in methanol (1 mL) was added TMS-CHN$_2$ (1.5 eq) at 0° C. and stirred for 6 h. After completion, The solvent was evaporated. The crude compound was purified by column chromatography (SiO$_2$) using EtOAc:Pet ether (70:30) to afford methyl 2-chloro-5-(N,N-dimethylsulfamoyl)nicotinate (5) (600 mg, 81%) as an off white solid.

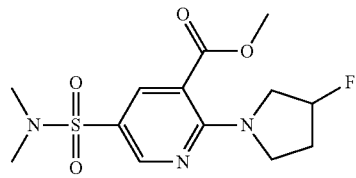

6

Preparation of methyl 5-(N,N-dimethylsulfamoyl)-2-(3-fluoropyrrolidin-1-yl)nicotinate (6): to a solution of methyl 2-chloro-5-(N,N-dimethylsulfamoyl)nicotinate (5) (250 mg, 0.899 mmol, 1 eq) in dry DMSO (5 mL) at RT was added 3-fluoropyrrolidine (170 mg, 1.348 mmol, 1.5 eq), DIPEA (348 mg, 2.697 mmol, 3 eq) and stirred at RT for 3 h. After completion, the reaction mixture was poured in ice water, filtered the solid and dried to afford methyl 5-(N,N-dimethylsulfamoyl)-2-(3-fluoropyrrolidin-1-yl)nicotinate (6) (250 mg, 88%) as an off white solid.

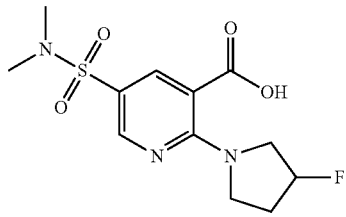

7

Preparation of 5-(N,N-dimethylsulfamoyl)-2-(3-fluoropyrrolidin-1-yl)nicotinic acid (7): to a solution of methyl 5-(N,N-dimethylsulfamoyl)-2-(3-fluoropyrrolidin-1-yl)nicotinate (6) (300 mg, 0.9063 mmol, 1 eq) in methanol (5 mL) was added LiOH (76 mg, 1.8126 mmol, 2 eq) in water (1 mL) and stirred at RT for 3 h. After completion, the solvent was evaporated. The residue was taken in water and acidified with 1N HCl. The solid obtained was filtered and dried to afford 5-(N,N-dimethylsulfamoyl)-2-(3-fluoropyrrolidin-1-yl)nicotinic acid (7) (300 mg, 99%) as an off white solid.

compound-199

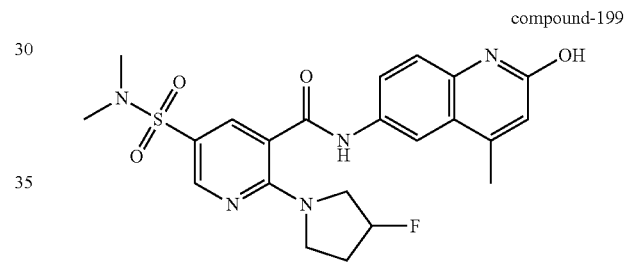

Preparation of 5-(N,N-dimethylsulfamoyl)-2-(3-fluoropyrrolidin-1-yl)-N-(2-hydroxy-4-methylquinolin-6-yl)nicotinamide (compound-199): to a solution of 5-(N,N-dimethylsulfamoyl)-2-(3-fluoropyrrolidin-1-yl)nicotinic acid (7) (200 mg, 0.630 mmol, 1 eq) in Dry DMF (1 mL) at RT was added 6-amino-4-methylquinolin-2-ol (132 mg, 0.7570 mmol, 1.2 eq), HOAt (129 mg, 0.946 mmol, 2 eq), EDC (180 mg, 0.946 mmol, 2 eq), DIPEA (244 mg, 1.892 mmol, 4 eq) and stirred at RT for 3 h. After completion, the reaction mixture was poured into ice water, filtered the solid and washed with water. The crude compound was purified by reverse phase chromatography (0.05% formic acid in water: 0.05% formic acid in aceto nitrile) to afford 5-(N,N-dimethylsulfamoyl)-2-(3-fluoropyrrolidin-1-yl)-N-(2-hydroxy-4-methylquinolin-6-yl)nicotinamide (compound-199) (50 mg, 17%) as an off white solid.

$^1$H NMR (300 MHz, DMSO-d6) δ 11.60 (s, 1H), 10.74 (s, 1H), 8.51 (d, J=2.4 Hz, 1H), 8.09 (d, J=2.2 Hz, 1H), 7.90 (d, J=2.4 Hz, 1H), 7.79 (dd, J=8.8, 2.2 Hz, 1H), 7.31 (d, J=8.8 Hz, 1H), 6.44 (s, 1H), 5.41 (m, 1H), 3.93-3.57 (m, 4H), 2.65 (s, 6H), 2.50 (s, 3H), 2.41 (m, 2H).

Synthesis of Compound-200

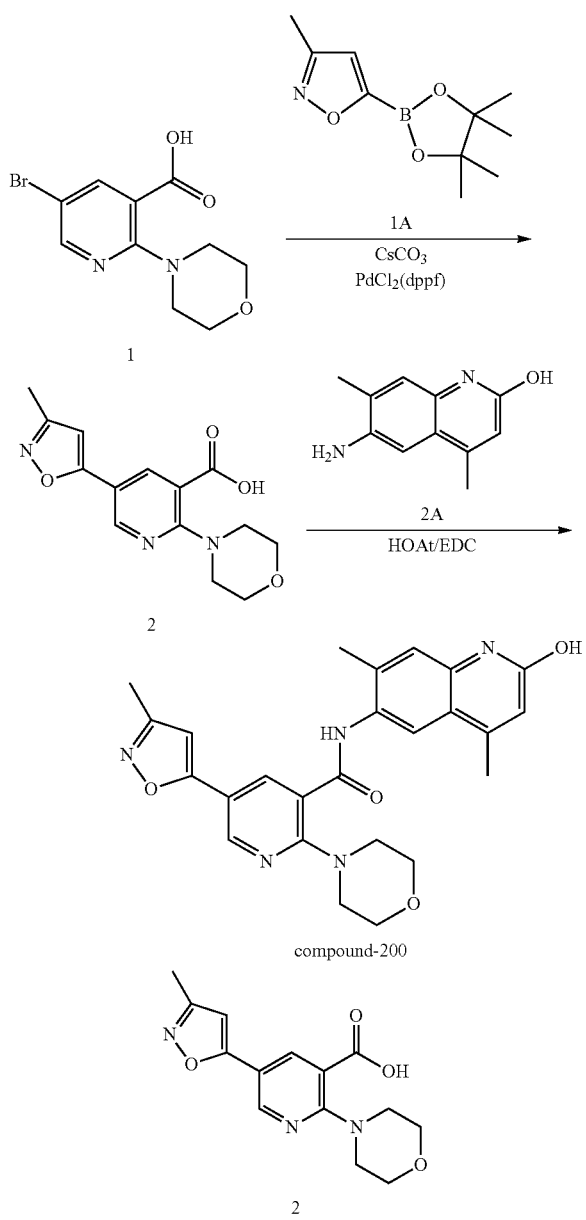

Preparation of 5-(3-methylisoxazol-5-yl)-2-morpholinonicotinic acid (2): a suspension of 5-bromo-2-morpholinonicotinic acid (1) (200 mg, 0.699 mmol, 1 eq), 3-methyl-5-(4,4,5,5-tetramethyl-1,3,2-dioxaborolan-2-yl)isoxazole (292.18 mg, 1.398 mmol, 2 eq) and $Cs_2CO_3$ (680.5 mg, 2.094 mmol, 3 eq) in Dioxane:$H_2O$ (2:1) (10 vol) was degassed for 15 mins. Then added Pd(dppf)$Cl_2$ (57.08 mg, 0.069 mmol, 0.1 eq) and stirred at 80° C. for 16 h in Microwave. After completion, the reaction mixture was filtered on celite pad and extracted with ethyl acetate (2×20 mL). The combined extracts were washed with water (20 mL), brine (20 mL), dried over anhydrous $Na_2SO_4$, filtered and evaporated. The crude compound was purified by column chromatography ($SiO_2$) by using MeOH:DCM (5:95) to afford 5-(3-methylisoxazol-5-yl)-2-morpholinonicotinic acid (2) (80 mg, 39%) as a brown solid.

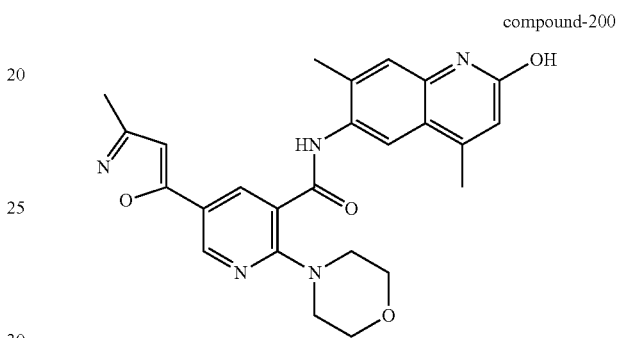

Preparation of N-(2-hydroxy-4, 7-dimethylquinolin-6-yl)-5-(3-methylisoxazol-5-yl)-2-morpholino nicotinamide (compound-200): to a solution of 5-(3-methylisoxazol-5-yl)-2-morpholinonicotinic acid (Compound-2) (70 mg, 0.24 mmol, 1 eq) in DMF (2 mL) was added Compound-2A (45 mg, 0.24 mmol, 1 eq), HOAt (65.8 mg, 0.48 mmol, 2 eq), EDC.HCl (92.7 mg, 0.48 mmol, 2 eq), DIPEA (124.8 mg, 0.96 mmol, 4 eq) and stirred at RT for 18 h. After completion, the reaction mixture was poured into ice water and filtered solid obtained. The crude compound was purified by column chromatography ($SiO_2$) by using MeOH:DCM (4:96) to afford N-(2-hydroxy-4, 7-dimethylquinolin-6-yl)-5-(3-methylisoxazol-5-yl)-2-morpholinonicotinamide (compound-200) (20 mg, 15%) as an off white solid.

$^1$H NMR (300 MHz, DMSO-d6): δ 11.59 (s, 1H), 10.13 (s, 1H), 8.73 (d, J=2.2 Hz, 1H), 8.21 (d, J=2.2 Hz, 1H), 7.81 (s, 1H), 7.18 (s, 1H), 6.87 (s, 1H), 6.38 (s, 1H), 3.76-3.64 (m, 4H), 3.54 (d, J=4.4 Hz, 4H), 2.40 (s, 3H), 2.36 (s, 3H), 2.29 (s, 3H).

Synthesis of Compound-201

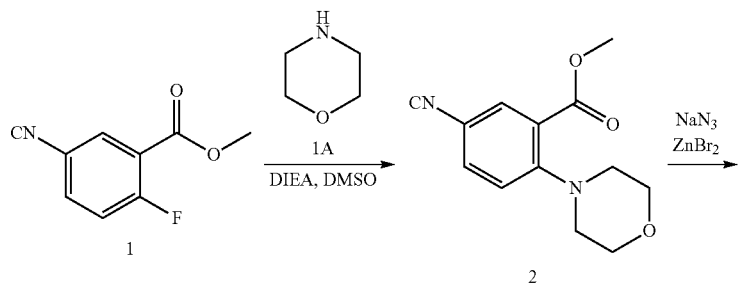

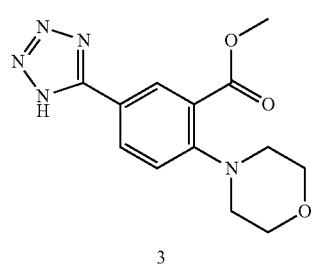 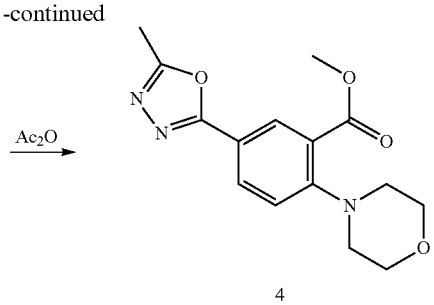

-continued

| LiOH·H₂O

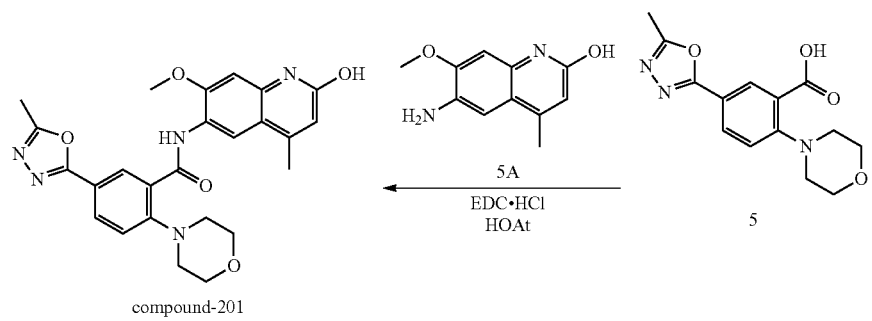

Preparation of methyl 5-cyano-2-morpholinobenzoate (2): to a solution of methyl 5-cyano-2-fluorobenzoate (2) (450 mg, 2.51 mmol, 1 eq) in Dry DMSO (5 mL) at RT was added morpholine (262 mg, 3.01 mmol, 1.2 eq), DIPEA (972 mg, 7.53 mmol, 3 eq) and stirred at RT for 3 h. After completion, the reaction mixture was poured in ice water and then filtered the compound to afford methyl 5-cyano-2-morpholinobenzoate (2) (700 mg, 99%) as an off white solid.

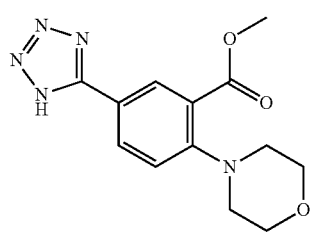

Preparation of methyl 2-morpholino-5-(1H-tetrazol-5-yl) benzoate (3): to a solution of methyl 5-cyano-2-morpholinobenzoate (2) (250 mg, 1.016 mmol, 1 eq) in IPA (5 mL) at RT was added sodium azide (200 mg, 3.048 mmol, 3 eq), ZnBr₂ (343 mg, 1.524 mmol, 1.5 eq) and stirred at 100° C. for 16 h. After completion, evaporated the solvent, the residue was taken in water and extracted with ethyl acetate (4×20 mL). The combined extracts were washed with water (20 mL), brine (20 mL), dried over anhydrous Na₂SO₄, filtered and evaporated to afford methyl 2-morpholino-5-(1H-tetrazol-5-yl)benzoate (3) (150 mg, 62%) as yellow solid.

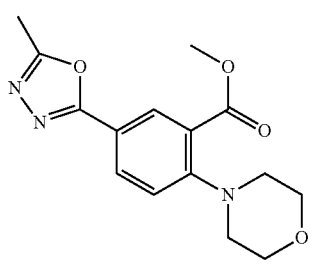

Preparation of methyl 5-(5-methyl-1,3,4-oxadiazol-2-yl)-2-morpholinobenzoate (4): a solution of methyl 2-morpholino-5-(1H-tetrazol-5-yl)benzoate (3) (150 mg, 0.52 mmol, 1 eq) in acetic anhydride (5 mL) was stirred at 140° C. for 16 h. After completion, evaporated the solvent, the residue was taken in water and extracted with ethyl acetate (4×20 mL). The combined extracts were washed with water (20 mL), brine (20 mL), dried over anhydrous Na₂SO₄, filtered and evaporated. The crude product was purified by column chromatography (SiO₂) using EtOAc:pet ether (70:30) to afford methyl 5-(5-methyl-1,3,4-oxadiazol-2-yl)-2-morpholinobenzoate (4) (80 mg, 49%) as brown sticky solid.

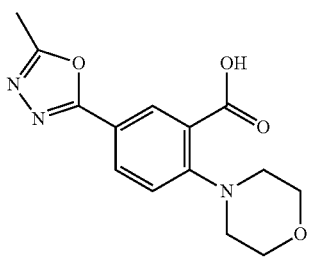

Preparation of 5-(5-methyl-1,3,4-oxadiazol-2-yl)-2-morpholinobenzoic acid (5): to a solution of methyl 5-(5-methyl-1,3,4-oxadiazol-2-yl)-2-morpholinobenzoate (4) (80 mg, 0.198 mmol, 1 eq) in methanol (5 mL) at RT was added LiOH (17 mg, 0.396 mmol, 2 eq) in water (1 mL) and stirred at RT for 3 h. After completion, the solvent was evaporated, the residue was taken in water and acidified with 1N HCl. The solid formed was filtered and dried to afford 5-(5-methyl-1,3,4-oxadiazol-2-yl)-2-morpholinobenzoic acid (5) (70 mg, 92%) as pale yellow solid.

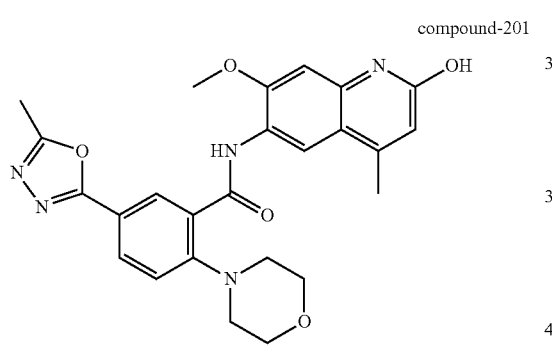

compound-201

Preparation of N-(2-hydroxy-7-methoxy-4-methylquinolin-6-yl)-5-(5-methyl-1,3,4-oxadiazol-2-yl)-2-morpholinobenzamide (COMPOUND-201): to a solution of 5-(5-methyl-1,3,4-oxadiazol-2-yl)-2-morpholinobenzoic acid (Compound-5) (70 mg, 0.242 mmol, 1 eq) in Dry DMF (1 mL) at RT was added 6-amino-7-methoxy-4-methylquinolin-2-ol (44 mg, 0.217 mmol, 0.9 eq), HOAt (66 mg, 0.484 mmol, 2 eq), EDC (93 mg, 0.484 mmol, 2 eq), DIPEA (124 mg, 0.968 mmol, 4 eq) and stirred at RT for 3 h. After completion, the reaction mixture poured into ice water and filtered the solid, washed with water and dried to afford N-(2-hydroxy-7-methoxy-4-methylquinolin-6-yl)-5-(5-methyl-1,3,4-oxadiazol-2-yl)-2-morpholinobenzamide (compound-201) (40 mg, 34%) as an Off white solid.

$^1$H NMR (400 MHz, DMSO-d6): δ 11.52 (s, 1H), 11.07 (s, 1H), 8.84 (s, 1H), 8.48 (d, J=2.0 Hz, 1H), 8.11 (dd, J=2.2, 8.6 Hz, 1H), 7.53 (d, J=8.3 Hz, 1H), 7.01 (s, 1H), 6.30 (s, 1H), 3.98 (s, 3H), 3.79 (s, 4H), 3.10 (m, 4H), 2.59 (s, 3H), 2.41 (s, 3H).

Synthesis of Compound-202 and Compound-203

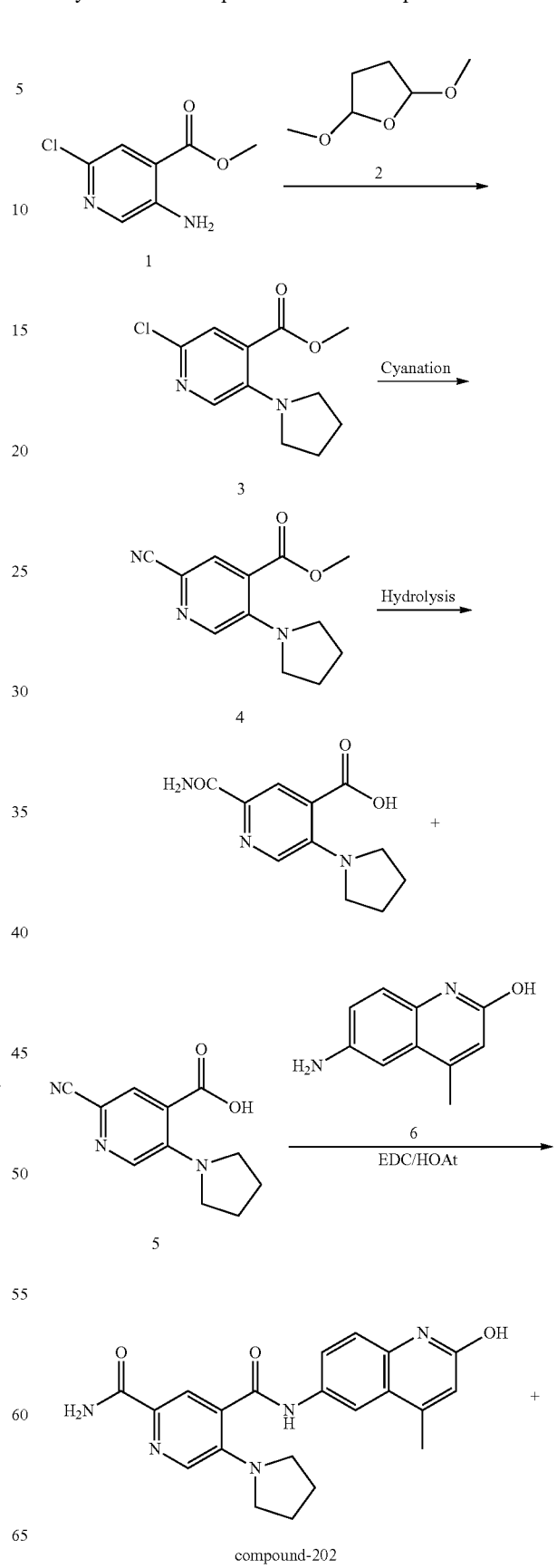

compound-202

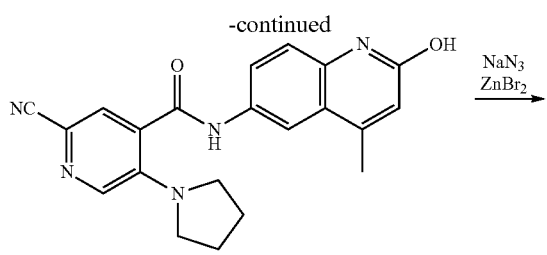

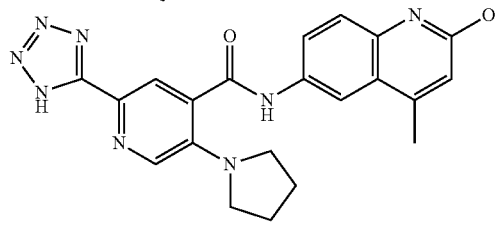

compound-203

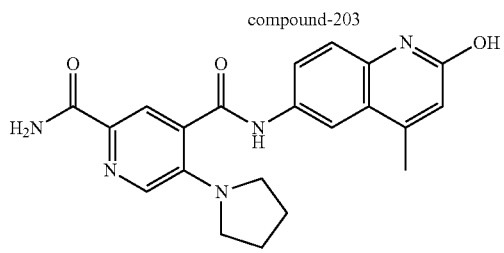

compound-202

Preparation of N4-(2-hydroxy-4-methylquinolin-6-yl)-5-(pyrrolidin-1-yl)pyridine-2,4-dicarboxamide (compound-202): to a solution of 2-carbomyl-5-(pyrrolidin-1-yl)isonicotinicacid (Compound-5A) (100 mg, 0.425 mmol, 1 eq) in DMF (2 mL) was added EDC.HCl (162 mg, 0.85 mmol, 2 eq), HOAT (115 mg, 0.85 mmol, 2 eq), DIEA (3 eq), followed by 6-amino-4-methylquinlin-2-ol (6) (88 mg, 0.51 mmol, 1.2 eq) and stirred at RT for 16 h. After completion, the reaction mixture was poured into water and precipitated solid was filtered. The crude residue was purified by column chromatography (100-200 mesh silica, MeOH:DCM (4:96)) to afford $N^4$-(2-hydroxy-4-methylquinolin-6-yl)-5-(pyrrolidin-1-yl) pyridine-2,4-dicarboxamide (compound-202) (24 mg) as pale yellow solid.

$^1$H NMR (300 MHz, DMSO-$d_6$) δ 11.59 (s, 1H), 10.68 (s, 1H), 8.13-8.07 (m, 2H), 7.87-7.74 (m, 2H), 7.30 (d, J=9.2 Hz, 2H), 6.43 (s, 1H), 3.49-3.34 (m, 4H), 2.40 (s, 3H), 1.98-1.86 (m, 4H).

compound-203

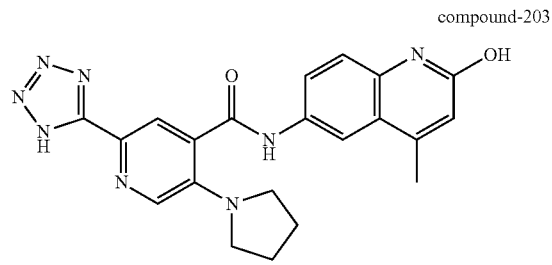 [SMILES: Cc1cc(O)nc2ccc(NC(=O)c3cc(-c4nnn[nH]4)ncc3N3CCCC3)cc12]

Preparation of N-(2-hydroxy-4-methylquinolin-6-yl)-5-(pyrrolidin-1-yl)-2-(1H-tetrazol-5-yl) isonicotinamide (compound-203): to a solution of 2-Cyano-N-(2-hydroxy-4-methylquinolin-6-yl)-5-(pyrrolidin-1-yl) isonicotinamide (60 mg, 0.16 mmol, 1 eq) in IPA: H$_2$O (10 vol) was added NaN$_3$ (3 eq), ZnBr$_2$ (1 eq) and stirred at 100° C. for 20 h. After completion, the reaction mixture was poured into water and precipitated solid was filtered. The crude residue was triturated with diethyl ether and pentane to afford to N-(2-hydroxy-4-methylquinolin-6-yl)-3-(pyrrolidin-1-yl)-6-(1H-tetrazol-5-yl) picolinamide (compound-203) (22 mg) as Pale yellow solid.

$^1$H NMR (400 MHz, DMSO-$d_6$) δ 11.60 (s, 1H), 10.74 (m, 1H), 8.08 (s, 1H), 7.92 (s, 1H), 7.80 (d, J=8.9 Hz, 1H), 7.56-7.40 (m, 1H), 7.31 (d, J=8.8 Hz, 1H), 6.43 (s, 1H), 3.26-3.15 (m, 4H), 2.40 (s, 3H), 1.96-1.85 (m, 4H).

Synthesis of Compound-204

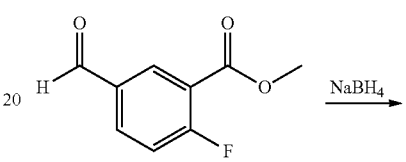

1

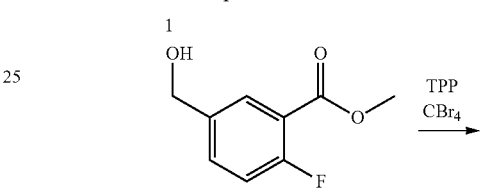

2

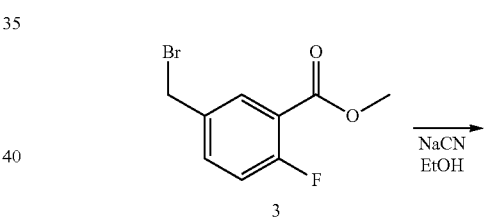

3

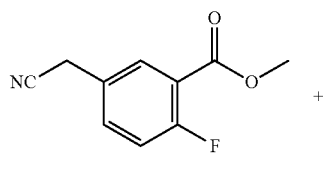

4

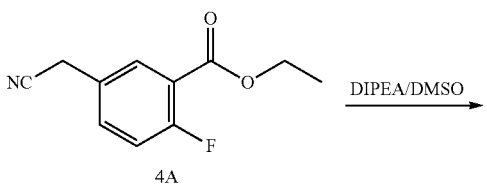

4A

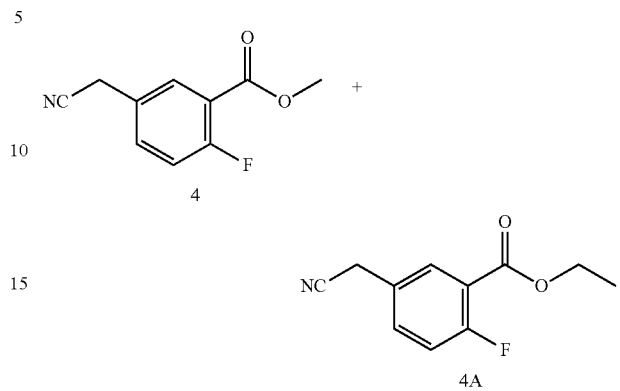

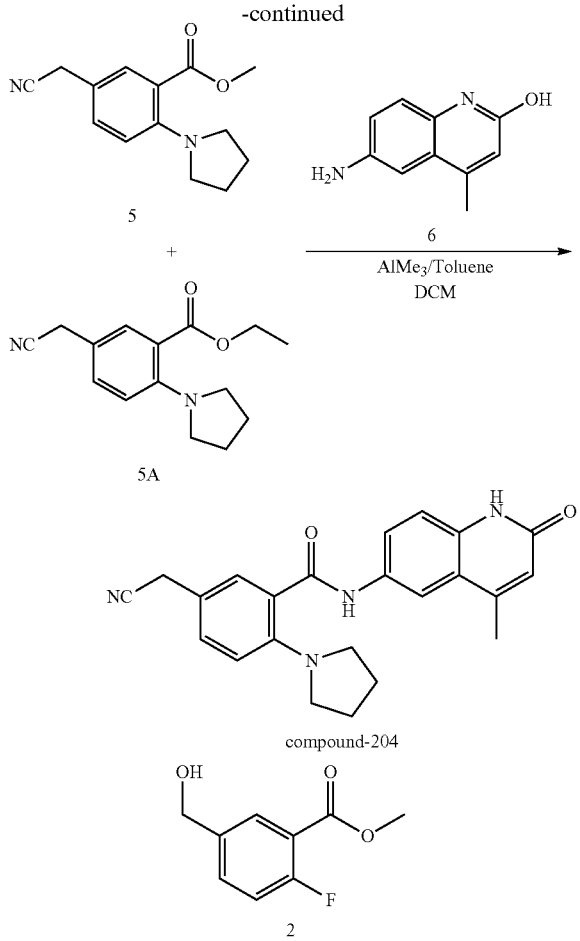

Preparation of methyl 2-fluoro-5-formylbenzoate (2)

To a solution of methyl 2-fluoro-5-formylbenzoate (1) (7 g, 38.46 mmol, 1 eq) in EtOH (5 mL) was added NaBH$_4$ (2.84 g 76.92 mmol, 2.0 eq) and stirred at RT for 1 h. After completion, the solvent was evaporated, residue was taken in water and extracted with EtOAc (3×50 mL). The combined extracts were washed with water (100 mL), brine (100 mL), dried over anhydrous Na$_2$SO$_4$, filtered and evaporated to afford methyl 2-fluoro-5-(hydroxymethyl)benzoate (2) (5 g, 70%) as a pale yellow liquid.

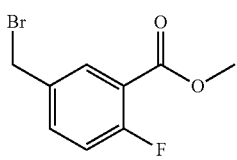

Preparation of methyl 5-(bromomethyl)-2-fluorobenzoate (3): to a solution of methyl 2-fluoro-5-(hydroxymethyl) benzoate (2) (5 g, 27.17 mmol, 1 eq) in Dry DCM (50 mL) was added PBr$_3$ (2.19 g, 8.12 mmol, 0.3 eq) and stirred at RT for 3 h. After completion, the reaction mixture was quenched with saturated NaHCO$_3$ solution and extracted with DCM (3×100 mL). The combined extracts were washed with water (3×30 mL), brine (1×30 mL), dried over anhydrous Na$_2$SO$_4$, filtered and evaporated to afford methyl 5-(bromomethyl)-2-fluorobenzoate (3) (4.8 g, 71%) as an off white solid.

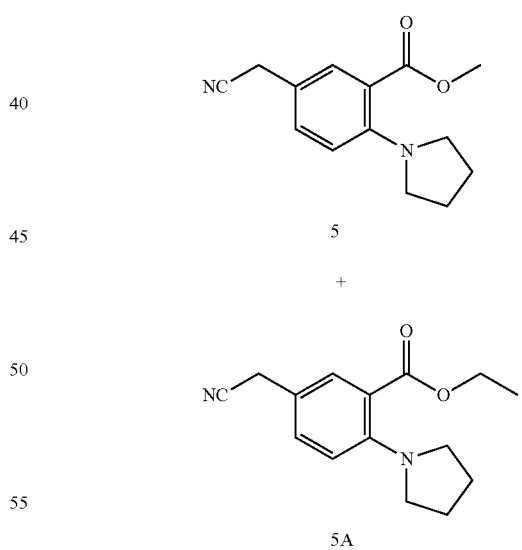

Preparation of methyl 5-(cyanomethyl)-2-fluorobenzoate and ethyl 5-(cyanomethyl)-2-fluorobenzoate (4&4A): to a solution of methyl 5-(bromomethyl)-2-fluorobenzoate (3) (4.8 g, 19.51 mmol, 1 eq) in EtOH (25 mL) and H$_2$O (25 mL) was added NaCN (1.91 g, 39.02 mmol, 2 eq) and stirred at RT for 16 h. After completion, the reaction mixture was poured into ice water and extracted with EtOAc (3×30 mL). The combined extracts were washed with water (40 mL), brine (40 mL), dried over anhydrous Na$_2$SO$_4$, filtered and evaporated. The crude compound was purified by column chromatography (SiO$_2$) using EtOAc:Pet ether (15:85) to afford methyl 5-(cyanomethyl)-2-fluorobenzoate and ethyl 5-(cyanomethyl)-2-fluorobenzoate (4&4A) (2.3 g, 61%) as an off white solid.

Preparation of methyl 5-(cyanomethyl)-2-(pyrrolidin-1-yl) benzoate and ethyl 5-(cyanomethyl)-2-(pyrrolidin-1-yl) benzoate (5&5A): to a solution of methyl 5-(cyanomethyl)-2-fluorobenzoate and ethyl 5-(cyanomethyl)-2-fluorobenzoate (4&4A) (2.3 g, 11.917 mmol, 1 eq) in Dry DMSO (23 mL) at RT was added pyrrolidine (0.847 g, 11.917 mmol, 1 eq), DIPEA (4.61 g, 35.75 mmol, 3 eq) and stirred at RT for 48 h. After completion, the reaction mixture poured into ice water, extracted with EtOAc (3×30 mL). The combined extracts were washed with water (40 mL), brine (40 mL), dried over anhydrous Na₂SO₄, filtered and evaporated. The crude compound was purified by column chromatography (SiO₂) using EtOAc:Pet ether (15:85) to afford methyl 5-(cyanomethyl)-2-(pyrrolidin-1-yl) benzoate and ethyl 5-(cyanomethyl)-2-(pyrrolidin-1-yl) benzoate (5&5A) (2.1 g, 72%) as an off white solid.

compound-204

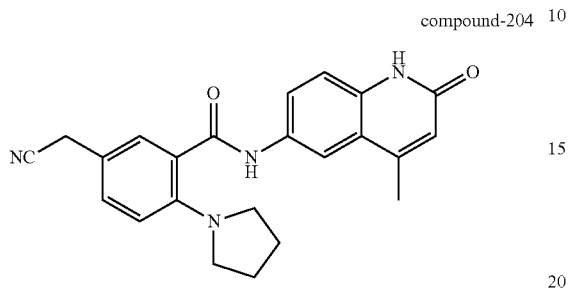

Preparation of 5-(cyanomethyl)-N-(4-methyl-2-oxo-1,2-dihydroquinolin-6-yl)-2-(pyrrolidin-1-yl)benzamide (compound-204): to a solution of methyl 5-(cyanomethyl)-2-fluorobenzoate and ethyl 5-(cyanomethyl)-2-fluorobenzoate (5&5A) (50 mg, 0.204 mmol, 1 eq) in dry DCM (2 mL) at RT was added 6 (35.49 mg, 0.204 mmol, 1 eq), Tri methyl aluminum 2M solution in toluene (29.4 mg, 0.408 mmol, 2 eq), and stirred at RT for 48 h. After completion, the reaction mixture poured into ice water and extracted with 10% MeOH: CHCl₃ (3×30 mL). The combined extracts were washed with water (40 mL), brine (40 mL), dried over anhydrous Na₂SO₄, filtered and evaporated. The crude compound was purified by column chromatography using (SiO₂) by eluting MeOH:CHCl₃ (5:95) to afford N-(2-hydroxy-4-methylquinolin-6-yl)-5-(morpholine-4-carbonyl)-2-morpholinobenzamide (compound-204) (25 mg, 30%) as Off white solid.

¹H NMR (300 MHz, DMSO-d₆) δ 11.56 (s, 1H), 10.47 (s, 1H), 8.13 (d, J=2.3 Hz, 1H), 7.81 (dd, J=8.9, 2.3 Hz, 1H), 7.47-7.08 (m, 3H), 6.80 (d, J=8.5 Hz, 1H), 6.42 (s, 1H), 3.91 (s, 2H), 3.28-3.19 (m, 4H), 2.39 (s, 3H), 1.90-1.82 (m, 4H).

Synthesis of Compound-205

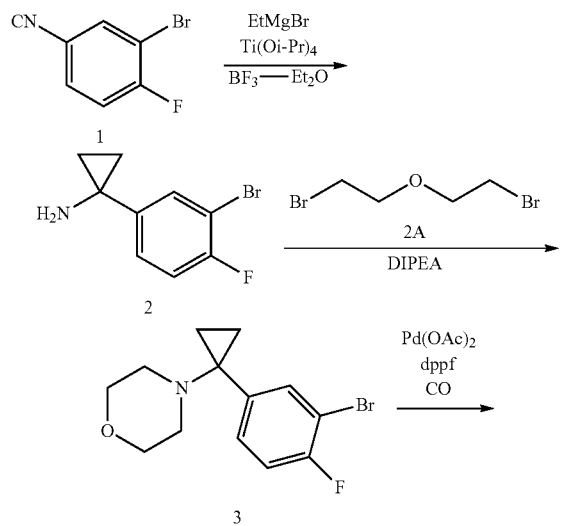

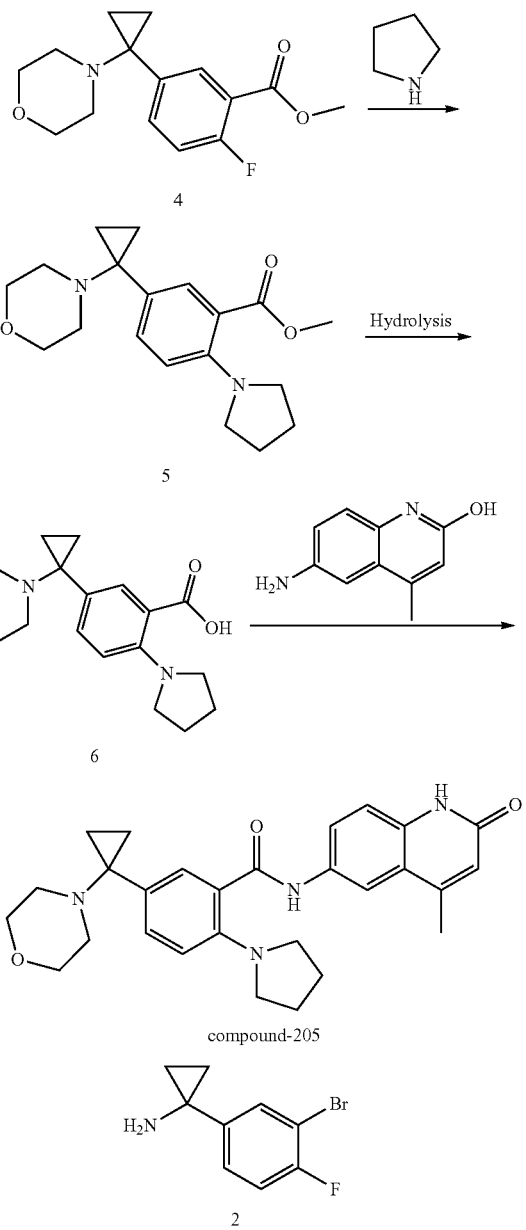

Preparation of 1-(3-bromo-4-fluorophenyl) cyclopropanamine: to a solution of 3-bromo-4-fluorobenzonitrile (1) (10 g, 50 mmol, 1 eq) in dry ether (400 mL) at −78° C. was added Titanium isopropoxide (15.63 mL, 55 mmol, 1.1 eq), EtMgBr (36.6 mL, 110 mmol, 2.2 eq) as drop wise, the resulting yellow suspension was warmed to RT over 1 h. After stirring for additional 30 min, BF₃.Et₂O (12.34 mL, 100 mmol, 2 eq) was added to reaction mixture at RT and the mixture was further stirred for 1 h. After completion, the reaction mixture was quenched with 1N HCl (200 mL) and then basified with 5N NaOH. The aqueous layer was extracted with diethyl ether (2×200 mL). The combined extracts were washed with water (100 mL), brine (100 mL), dried over anhydrous Na₂SO₄, filtered and evaporated. The crude residue was purified by combiflash to get 1-(3-bromo-4-fluorophenyl) cyclopropanamine (2) (8 g, 72%) as a brown liquid.

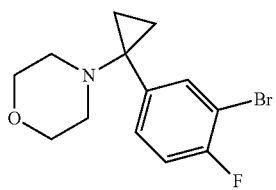

Preparation of 4-(1-(3-bromo-4-fluorophenyl) cyclopropyl) morpholine (3): to a solution of 1-(3-bromo-4-fluorophenyl) cyclopropanamine (2) (8 g, 34.78 mmol, 1 eq) in DMF (50 mL) was added K₂CO₃ (24 g, 173.9 mmol, 5 eq) and 1-bromo-2-(2-bromoethoxy) ethane (9.67 g, 41.73 mmol, 1.2 eq), stirred for 5 h at 80° C. After completion, the reaction mixture was poured into water (100 mL) and extracted with EtOAc (2×200 mL). The combined extracts were washed with water (100 mL), brine (100 mL), dried over anhydrous Na₂SO₄, filtered and evaporated. The crude product was purified by column chromatography (100-200 mesh silica EtOAc:Hexane (1:9)) to get 4-(1-(3-bromo-4-fluorophenyl) cyclopropyl) morpholine (3) (5.1 g, 53%) as a pale yellow liquid.

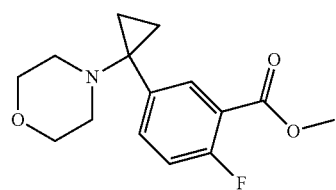

Preparation of methyl 2-fluoro-5-(1-morpholinocyclopropyl) benzoate (4): to a solution of 4-(1-(3-bromo-4-fluorophenyl) cyclopropyl) morpholine (3) (3.0 g, 10 mmol, 1 eq) in MeOH: DMF (DMF (2.5 vols) & MeOH (4 vols)) was added TEA (2 g, 20 mmol, 2 eq), dppf (0.55 g, 1.0 mmol, 1 eq) and degassed for 15 min then added Pd(OAc)₂ (336 mg, 5 mmol, 0.05 eq). The reaction mixture was stirred at 80° C. for 24 h under CO pressure (100 psi). After completion, the solvent was evaporated; the crude was taken in water (100 mL) and extracted with EtOAc (2×200 mL). The combined extracts were washed with water (100 mL), brine solution (100 mL), dried over anhydrous Na₂SO₄, filtered and evaporated, The crude residue was purified by column chromatography (100-200 mesh silica, EtOAc:Hexane (15:85)) to get methyl 2-fluoro-5-(1-morpholinocyclopropyl)benzoate (4) (2.0 g, 98.7%) as an off white solid.

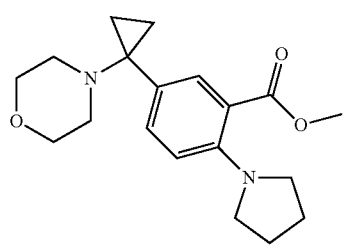

Preparation of methyl 5-(1-morpholinocyclopropyl)-2-(pyrrolidin-1-yl) benzoate (5): to a solution of methyl 2-fluoro-5-(1-morpholinocyclopropyl)benzoate (4) (1.0 g, 3.58 mmol, 1 eq) in Dry DMSO (10 mL) was added pyrrolidine (0.508 gm, 7.16 mmol, 2 eq), K₂CO₃ (2.4 gm, 17.9 mmol, 5 eq) and stirred at 50° C. for 16 h. After completion the reaction mixture was poured into ice water and extracted with EtOAc (3×20 mL). The combined extracts were washed with water (20 mL), brine (20 mL), dried over anhydrous Na₂SO₄, filtered and evaporated. The crude compound was purified by column chromatography using (100-200 mesh silica, EtOAc:Hexane (1:9)) to afford methyl 5-(1-morpholinocyclopropyl)-2-(pyrrolidin-1-yl) benzoate (5) (1.1 g, 90%) as an off white solid.

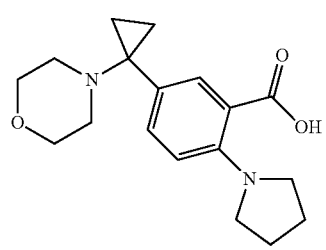

Preparation of 5-(1-morpholinocyclopropyl)-2-(pyrrolidin-1-yl) benzoic acid (6): to a solution of methyl 5-(1-morpholinocyclopropyl)-2-(pyrrolidin-1-yl) benzoate (5) (1.1 g, 3.33 mmol, 1 eq) in MeOH:H₂O (20 mL) at RT was added LiOH (419 mg, 9.99 mmol, 3 eq) and stirred at 80° C. for 16 h. After completion, the solvent was evaporated, the residue was taken in water and neutralized with 1N HCl. The solid formed was filtered and washed with ether to afford 5-(1-morpholinocyclopropyl)-2-(pyrrolidin-1-yl) benzoic acid (6) (0.7 g, 70%) as an off white solid.

¹H NMR (300 MHz, DMSO-d₆) δ 13.38 (s, 1H), 7.42 (d, J=2.1 Hz, 1H), 7.23 (dd, J=8.5, 2.2 Hz, 1H), 6.89 (d, J=8.5 Hz, 1H), 3.47 (t, J=4.4 Hz, 4H), 3.25-3.10 (m, 4H), 2.39 (t, J=4.4 Hz, 4H), 1.90 (q, J=4.6, 3.3 Hz, 4H), 0.84 (q, J=3.8, 3.3 Hz, 2H), 0.68 (q, J=3.9 Hz, 2H).

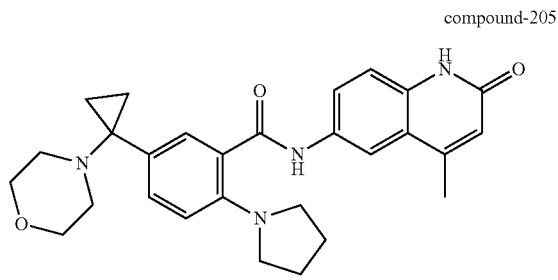 [SMILES: Cc1cc(=O)[nH]c2ccc(NC(=O)c3cc(C4(N5CCOCC5)CC4)ccc3N3CCCC3)cc12]

compound-205

Preparation of N-(4-methyl-2-oxo-1,2-dihydroquinolin-6-yl)-5-(1-morpholinocyclopropyl)-2-(pyrrolidin-1-yl)benzamide (compound-205): to a solution of 5-(1-morpholinocyclopropyl)-2-(pyrrolidin-1-yl)benzoic acid (6) (200 mg, 0.632 mmol, 1 eq), in Dry DMF (5 mL) added EDC.HCl (241 mg, 1.26 mmol, 2 eq), HOAT (171 mg, 1.26 mmol, 2 eq) and DIEA (3 eq) allowed to stir at RT for 15 min's next added 6-amino-4-methylquinlin-2-ol (Compound-7) (132 mg, 0.75 mmol, 1.2 eq), and stirred at RT for 16 h. After completion, the reaction mixture was poured into water and precipitated solid was filtered. The crude compound was purified by column chromatography (100-200 mesh silica, MeOH:DCM (4:96)) to afford N-(4-methyl-2-oxo-1, 2-dihydroquinolin-6-yl)-5-(1-morpholino cyclopropyl)-2-(pyrrolidin-1-yl) benzamide (compound-205) (210 mg, 70%) as Pale yellow solid.

$^1$H NMR (300 MHz, DMSO-d$_6$) δ 11.55 (s, 1H), 10.41 (s, 1H), 8.18 (d, J=2.3 Hz, 1H), 7.80 (dd, J=8.8, 2.3 Hz, 1H), 7.32-7.13 (m, 3H), 6.76 (d, J=8.3 Hz, 1H), 6.42 (s, 1H), 3.48 (t, J=4.4 Hz, 4H), 3.28-3.18 (m, 4H), 2.53-2.37 (m, 7H), 1.93-1.65 (m, 4H), 0.86-0.82 (m, 2H), 0.70 (m, 2H).

Synthesis of Compound-206

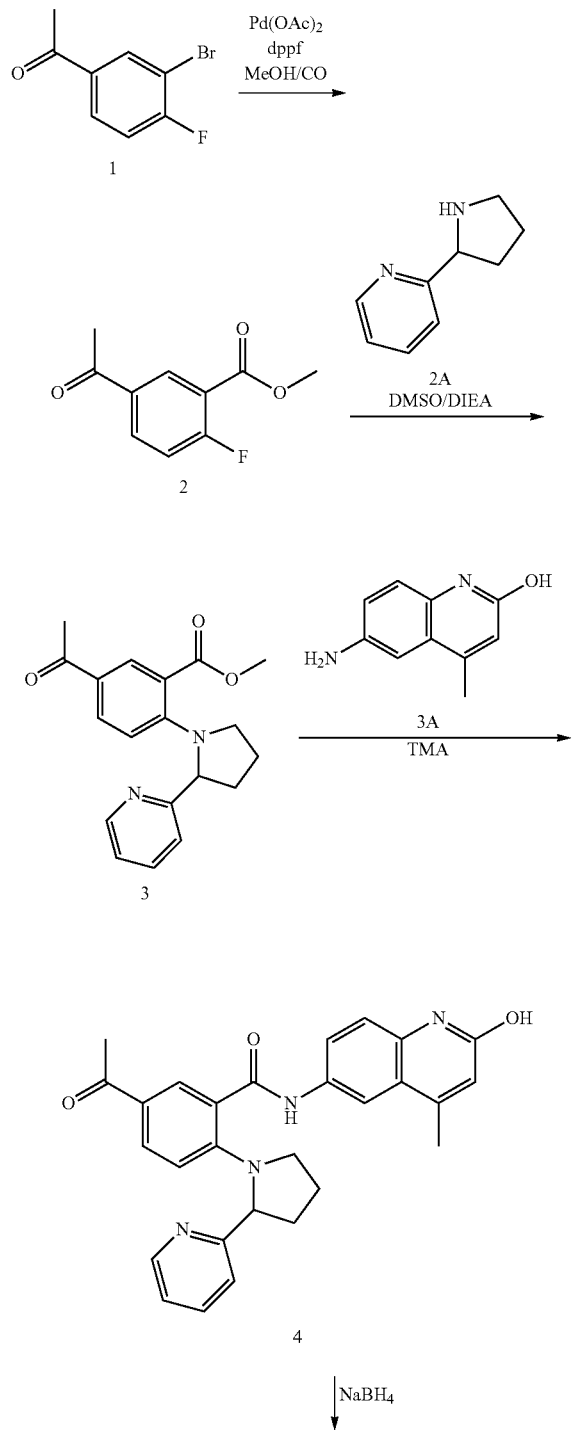

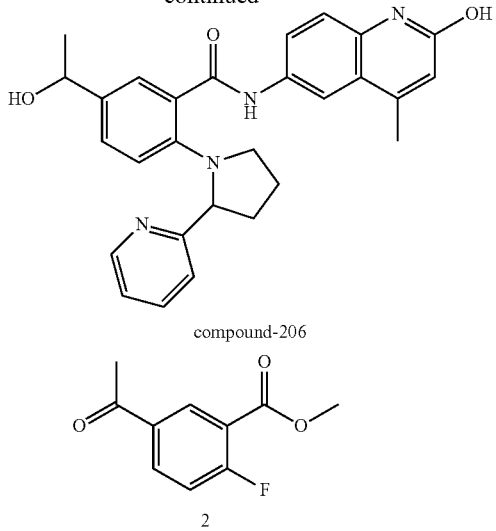

compound-206

Preparation of methyl 5-acetyl-2-fluorobenzoate (2): to a solution of 1-(3-bromo-4-fluorophenyl)ethanone (1) (2 g, 9.24 mmol, 1 eq) in dry MeOH (25 mL) and Dry DMF (45 mL) in autoclave was added dppf (256 mg, 0.462 mmol, 0.05 eq), Palladium acetate (58 mg, 0.258 mmol, 0.028 eq) and Triethyl amine (1.86 g, 18.48 mmol, 2.0 eq) and stirred at 80 Psi of CO gas and 80° C. for 24 h. After completion, the solvent was evaporated. The reaction mixture was poured into water and extracted with EtOAc (3×50 mL). The combined extracts were washed with water (100 mL), brine (100 mL), dried over anhydrous Na$_2$SO$_4$, filtered and evaporated. The crude compound was purified by column chromatography using (SiO$_2$) by eluting EtOAc:Pet ether (6:94) to afford 5-acetyl-2-fluorobenzoate (2) (1.2 g, 66%) as an off white solid.

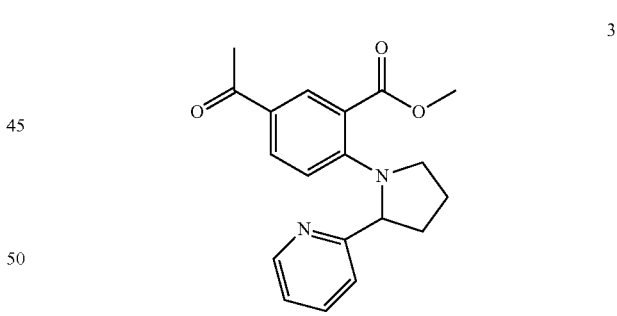

Preparation of methyl 5-acetyl-2-(2-(pyridin-2-yl)pyrrolidin-1-yl)benzoate (3): to a solution of methyl 5-acetyl-2-fluorobenzoate (2) (1 g, 2.55 mmol, 1 eq) in Dry DMF (20 mL) at RT was added 2-(pyrrolidin-2-yl)pyridine (452 mg, 3.06 mmol, 1.2 eq), DIPEA (986 mg, 7.65 mmol, 3 eq) and stirred at RT for 3 h. After completion, the reaction mixture was poured into water and extracted with EtOAc (2×30 mL). The combined extracts were washed with water (2×40 mL), brine (40 mL), dried over anhydrous Na$_2$SO$_4$, filtered and evaporated. The crude compound was purified by column chromatography (SiO$_2$) by using EtOAc:Pet ether (50:50) to afford methyl 5-acetyl-2-(2-(pyridin-2-yl)pyrrolidin-1-yl) benzoate (3) (300 mg, 36%) as an off white solid.

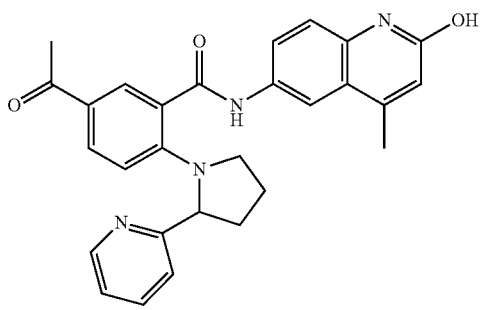

Preparation of 5-acetyl-N-(2-hydroxy-4-methylquinolin-6-yl)-2-(2-(pyridin-2-yl)pyrrolidin-1-yl)benzamide (4): to a solution of methyl 5-acetyl-2-(2-(pyridin-2-yl)pyrrolidin-1-yl)benzoate (3) (300 mg, 0.925 mmol, 1 eq) in dry Toluene (20 mL) at RT was added 6-amino-4-methylquinolin-2-ol (323 mg, 1.851 mmol, 2 eq), trimethylaluminium (200 mg, 2.77 mmol, 3 eq) and stirred at 100° C. for 3 h. After completion, the reaction mixture poured into ammonium chloride solution and filtered the solid. The crude compound was purified column chromatography (SiO$_2$) using DCM: MeOH (90:10) to afford 5-acetyl-N-(2-hydroxy-4-methylquinolin-6-yl)-2-(2-(pyridin-2-yl)pyrrolidin-1-yl)benzamide (4) (100 mg, 23%) as an off white solid.

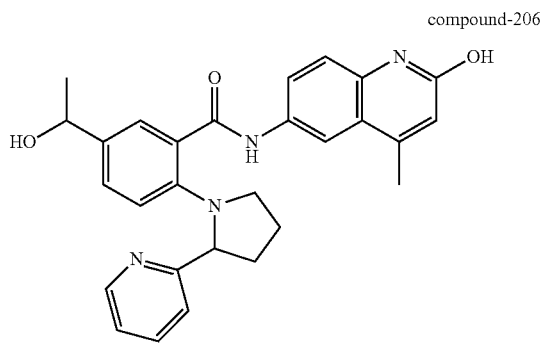 [SMILES: Cc1cc(O)nc2ccc(NC(=O)c3cc(C(C)O)ccc3N3CCCC3c3ccccn3)cc12]

Preparation of N-(2-hydroxy-4-methylquinolin-6-yl)-5-(1-hydroxyethyl)-2-(2-(pyridin-2-yl)pyrrolidin-1-yl)benzamide (compound-206): to a solution of 5-acetyl-N-(2-hydroxy-4-methylquinolin-6-yl)-2-(2-(pyridin-2-yl) pyrrolidin-1-yl)benzamide (4) (100 mg, 0.214 mmol, 1 eq) in methanol (10 mL) was added sodium borohydride (16 mg, 0.428 mmol, 2 eq) at 0° C. and stirred at RT for 1 h. After completion, the reaction mixture was quenched with ice water and then filtered the solid. The solid was washed with water, pentane and dried to afford N-(2-hydroxy-4-methylquinolin-6-yl)-5-(1-hydroxyethyl)-2-(2-(pyridin-2-yl)pyrrolidin-1-yl)benzamide (compound-206) (60 mg, 60%) as yellow solid.

$^1$H NMR (300 MHz, DMSO-d$_6$): δ 11.58 (s, 1H), 11.30 (s, 1H), 8.50 (d, J=4.7 Hz, 1H), 8.27 (s, 1H), 7.95 (d, J=8.9 Hz, 1H), 7.77-7.66 (m, 1H), 7.49 (dd, J=4.9, 2.2 Hz, 1H), 7.42 (d, J=7.8 Hz, 1H), 7.32 (d, J=8.8 Hz, 1H), 7.27-7.12 (m, 2H), 6.91 (dd, J=8.5, 4.2 Hz, 1H), 6.43 (s, 1H), 5.00 (d, J=4.2 Hz, 2H), 4.70-4.51 (m, 1H), 3.76-3.63 (m, 1H), 3.23-3.07 (m, 1H), 2.41 (s, 3H), 2.07-1.77 (m, 4H), 1.27 (d, J=6.4 Hz, 3H).

Synthesis of Compound-207 & Compound-208

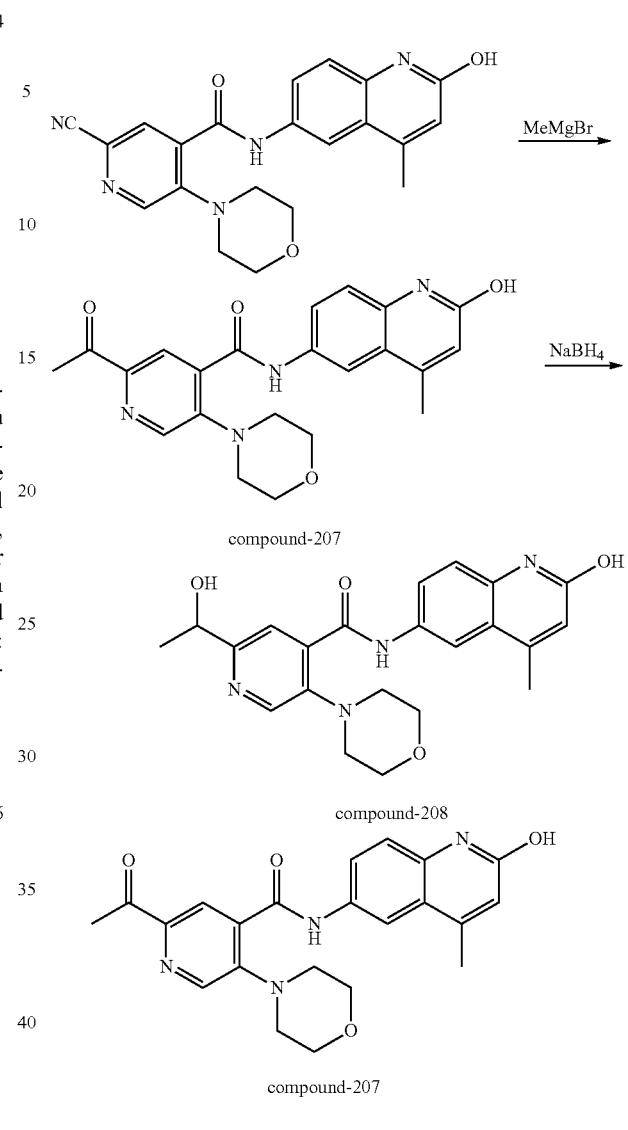

Preparation of 2-acetyl-N-(2-hydroxy-4-methylquinolin-6-yl)-5-morpholinoisonicotinamide (compound-207): to a solution of 2-cyano-N-(2-hydroxy-4-methylquinolin-6-yl)-5-morpholinoisonicotinamide (100 mg, 0.257 mmol, 1 eq) in dry THF was added MeMgBr (3M in THF) (0.25 ml, 0.771 mmol, 3 eq), and stirred at RT for 16 h. After completion, the reaction mixture was poured into water (50 mL) and extracted with EtOAc (3×50 mL). The combined extracts were washed with water (20 mL), brine (20 mL), dried over anhydrous Na$_2$SO$_4$, filtered and evaporated>the crude compound was purified by column chromatography (SiO$_2$) using EtOAc:Hexane (15:85) to afford 2-acetyl-N-(2-hydroxy-4-methylquinolin-6-yl)-5-morpholinoisonicotinamide (compound-207) (30 mg, 30%).

$^1$H NMR (400 MHz, DMSO-d$_6$): δ 11.60 (s, 1H), 10.70 (s, 1H), 8.52 (s, 1H), 8.13 (d, J=2.3 Hz, 1H), 7.93 (s, 1H), 7.79 (dd, J=8.8, 2.3 Hz, 1H), 7.32 (d, J=8.8 Hz, 1H), 6.44 (s, 1H), 3.68 (t, J=4.6 Hz, 4H), 3.27 (t, J=4.6 Hz, 4H), 2.60 (s, 3H), 2.40 (s, 3H).

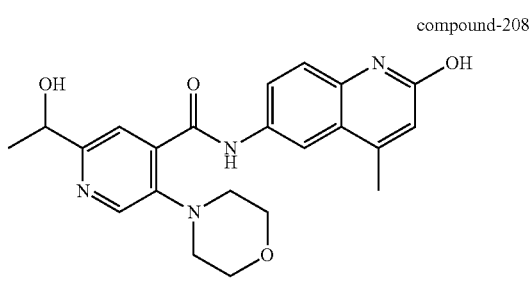 [SMILES: Cc1cc(O)nc2ccc(NC(=O)c3cc(C(C)O)ncc3N3CCOCC3)cc12]

compound-208

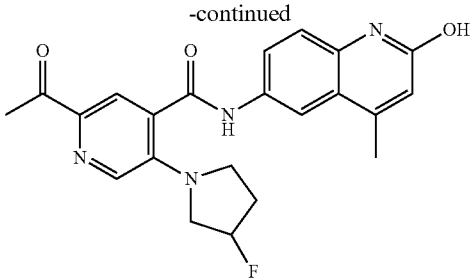

compound-209

Preparation of N-(2-hydroxy-4-methylquinolin-6-yl)-2-(1-hydroxyethyl)-5-morpholinoisonicotinamide (compound-208): to a 2-acetyl-N-(2-hydroxy-4-methylquinolin-6-yl)-5-morpholinoisonicotinamide (compound-207) (200 mg, 0.492 mmol, 1 eq) in MeOH (10 vol) was added NaBH$_4$ (37.4 mg, 0.985 mmol, 2 eq) and stirred at RT for 2 h. After completion, the solvent was evaporated, the residue was taken in water and extracted with EtOAc (3×20 mL). The combined extracts were dried over anhydrous Na$_2$SO$_4$, filtered and evaporated to afford N-(2-hydroxy-4-methylquinolin-6-yl)-2-(1-hydroxyethyl)-5-morpholino isonicotinamide (compound-208) (90 mg 45%).

$^1$H NMR (300 MHz, DMSO-d$_6$): δ 11.59 (s, 1H), 10.99 (s, 1H), 8.42 (s, 1H), 8.19 (d, J=2.3 Hz, 1H), 7.78 (dd, J=8.9, 2.3 Hz, 1H), 7.67 (s, 1H), 7.31 (d, J=8.8 Hz, 1H), 6.42 (d, J=2.0 Hz, 1H), 5.38 (d, J=4.8 Hz, 1H), 4.82-4.65 (m, 1H), 3.68 (t, J=4.5 Hz, 4H), 3.09-2.94 (m, 4H), 2.39 (d, J=1.2 Hz, 3H), 1.36 (d, J=6.5 Hz, 3H).

Synthesis of Compound-209 and Compound-210:

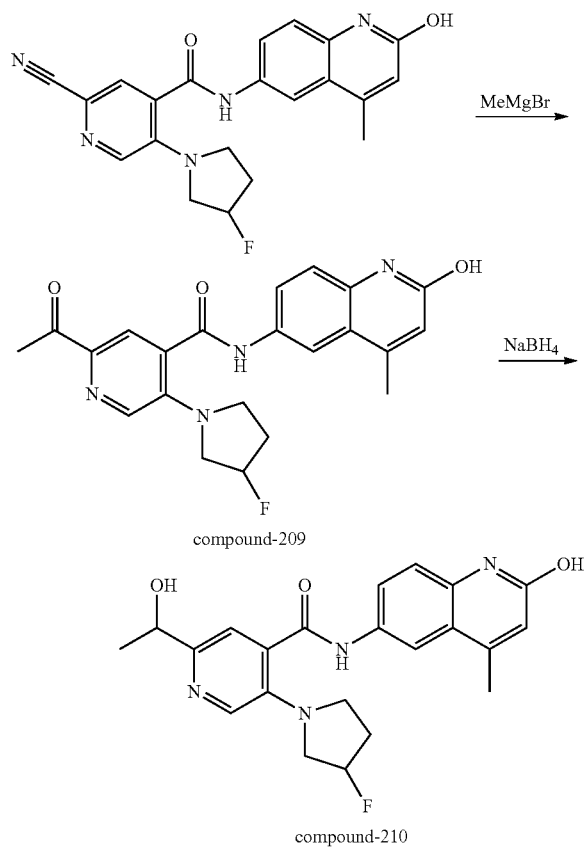

Preparation of 2-acetyl-5-(3-fluoropyrrolidin-1-yl)-N-(2-hydroxy-4-methylquinolin-6-yl isonicotinamide (compound-209): to a solution of 2-cyano-5-(3-fluoropyrrolidin-1-yl)-N-(2-hydroxy-4-methylquinolin-6-yl) isonicotinamide (300 mg, 0.769 mmol, 1 eq) in dry THF was added MeMgBr (3 M) (0.769 ml, 2.307 mmol, 3 eq) and stirred at RT for 16 h. After completion, the solvent was poured into water (50 mL) and extracted with EtOAc (3×50 mL). The combined extracts were washed with water (20 mL), brine (20 mL), dried over anhydrous Na$_2$SO$_4$, filtered and evaporated. The crude compound was purified by column chromatography (SiO$_2$) MeOH:DCM (5:95) to afford 2-acetyl-5-(3-fluoropyrrolidin-1-yl)-N-(2-hydroxy-4-methylquinolin-6-yl isonicotinamide (compound-209) (200 mg, 63.89%) as an off white solid.

$^1$H NMR (300 MHz, DMSO-d6) δ 11.58 (s, 1H), 10.74 (s, 1H), 8.24 (s, 1H), 8.07 (d, J=2.3 Hz, 1H), 7.84 (d, J=1.1 Hz, 1H), 7.78 (dd, J=8.9, 2.2 Hz, 1H), 7.28 (d, J=8.8 Hz, 1H), 6.41 (s, 1H), 5.67-5.15 (m, 1H), 3.89-3.40 (m, 4H), 2.54 (d, J=1.2 Hz, 3H), 2.48 (s, 3H), 2.38 (m, 2H).

Preparation of 5-(3-fluoropyrrolidin-1-yl)-N-(2-hydroxy-4-methylquinolin-6-yl)-2-(1-hydroxyethyl) isonicotinamide (compound-210): to a solution of 2-acetyl-5-(3-fluoropyrrolidin-1-yl)-N-(2-hydroxy-4-methylquinolin-6-yl isonicotinamide (compound-209) (160 mg, 0.392 mmol, 1 eq) in MeOH (10 vol) at 0° C. was added NaBH$_4$ (29.8 mg, 0.784 mmol, 2 eq) and stirred at RT for 2 h. After completion, the solvent was evaporated, residue was taken in water and extracted with EtOAc (3×20 mL). The combined extracts were dried over anhydrous Na$_2$SO$_4$, filtered and evaporated to afford 5-(3-fluoropyrrolidin-1-yl)-N-(2-hydroxy-4-methylquinolin-6-yl)-2-(1-hydroxyethyl) isonicotinamide (compound-210) (30 mg, 18.75%) as an off white solid.

$^1$H NMR (300 MHz, DMSO-d6) δ 11.58 (s, 1H), 10.67 (s, 1H), 8.11 (d, J=5.2 Hz, 2H), 7.85-7.75 (m, 1H), 7.38-7.25 (m, 2H), 6.43 (s, 1H), 5.47 (s, 1H), 5.32-5.17 (m, 1H), 4.70 (m, 1H), 3.80-3.66 (m, 1H), 3.66-3.55 (m, 1H), 3.55-3.37 (m, 3H), 2.39 (s, 3H), 2.32-2.10 (m, 2H), 1.41-1.34 (m, 3H).

Synthesis of Compound-211, Compound-212, and Compound-213

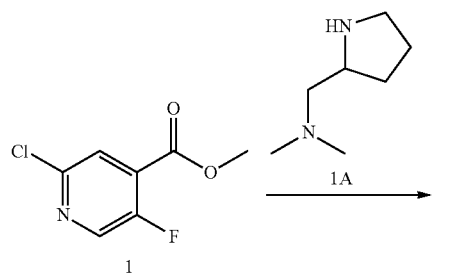

1

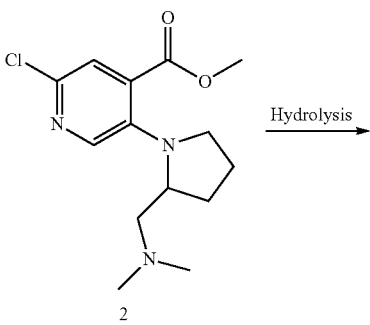

2

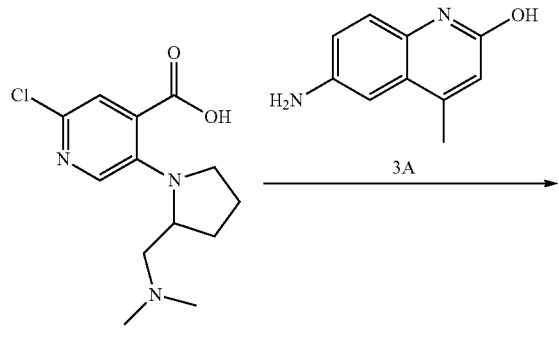

3

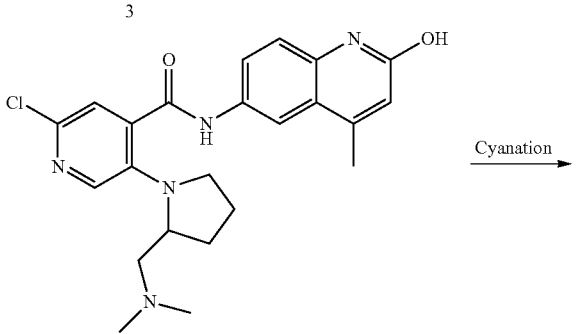

4

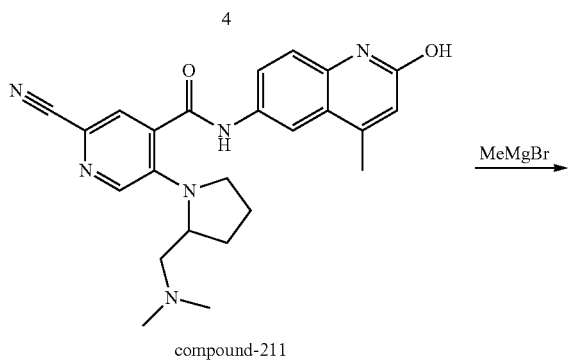

compound-211

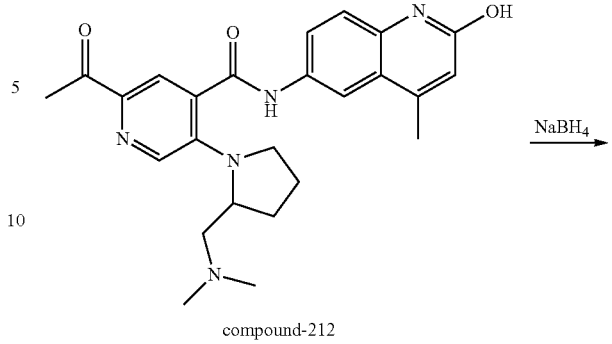

compound-212

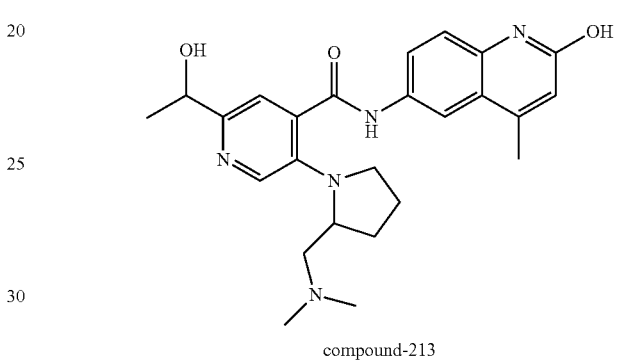

compound-213

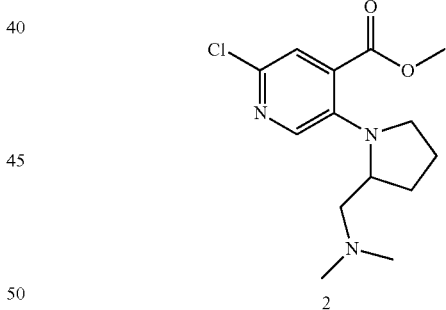

2

Preparation of methyl-2-chloro-5-(2-((dimethylamino) methylpyrrolidin-1-yl) isonicotinate (2): to a solution of methyl-2-chloro-5-fluroisonicotinate (1) (2 g, 10.58 mmol, 1 eq) in DMSO was added 1A (2.12 g, 10.58 mmol, 1 eq), DIEA (5.51 mL, 31.74 mmol, 3 eq) and stirred at RT for 16 h. After completion, the reaction mixture was poured into water (50 mL) and extracted with EtOAc (3×20 mL). The combined extracts were washed with water (20 mL), brine (20 mL), dried over anhydrous $Na_2SO_4$, filtered and evaporated. The crude compound was purified by column chromatography ($SiO_2$) using EtOAc:Hexane (15:85) to afford methyl-2-chloro-5-(2-((dimethylamino) methylpyrrolidin-1-yl) isonicotinate (2) (1.5 g, 47.61%) as a pale yellow liquid.

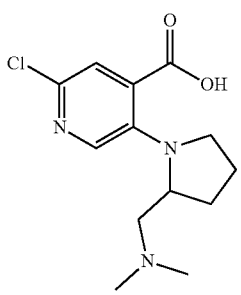

3

Preparation of 2-chloro-5-(2-((dimethylamino)methyl-pyrrolidin-1-yl)isonicotinic acid (3): to a solution of methyl-2-chloro-5-(2-((dimethylamino)methylpyrrolidin-1-yl) isonicotinate (Compound-2) (1.1 g, 3.70 mmol, 1 eq) in MeOH:H$_2$O (1:1) (10 vol) was added LiOH.H$_2$O (380 mg, 10.10 mmol, 3 eq) and stirred at RT for 16 h. After completion, the solvent was evaporated to afford 2-chloro-5-(2-((dimethylamino)methylpyrrolidin-1-yl)isonicotinic acid (3) as Li salt (1 g) as pale yellow solid.

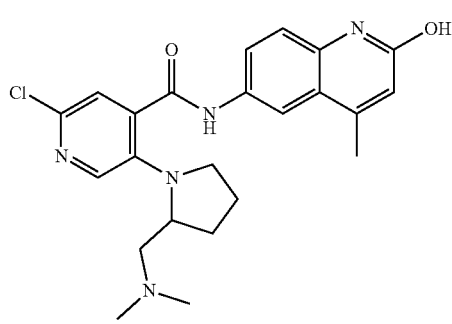

4

Preparation of 2-chloro-5-(2-((dimethylamino)methyl-pyrrolidin-1-yl)-N-(2-hydroxy-4-methylquinolin-6-yl)isoni-cotinamide (4): to a solution of 2-chloro-5-(2-((dimethyl-amino)methylpyrrolidin-1-yl)isonicotinic acid (3) as Li salt (1 g, 3.53 mmol, 1 eq) in DMF was added EDC.HCl (1.3 g, 7.06 mmol, 2 eq), HOAT (961 mg, 7.03 mmol, 2 eq) and DIEA (1.89 mL, 10.59 mmol, 3 eq) and 6-amino-4-meth-ylquinlin-2-ol (3A) (610 mg, 3.53 mmol, 1 eq) and stirred at RT for 16 h. After completion, the reaction mixture was poured into water and extracted with MeOH:DCM (1:9) (3×20 mL). The combined extracts were washed with ice water (20 mL), brine (20 mL), dried over anhydrous Na$_2$SO$_4$, filtered and evaporated. The crude compound was purified by column chromatography (SiO$_2$) using MeOH: DCM (5:95) to afford 2-chloro-5-(2-((dimethylamino)meth-ylpyrrolidin-1-yl)-N-(2-hydroxy-4-methylquinolin-6-yl) isonicotinamide (4) (350 mg, 23.3%) as pale yellow solid.

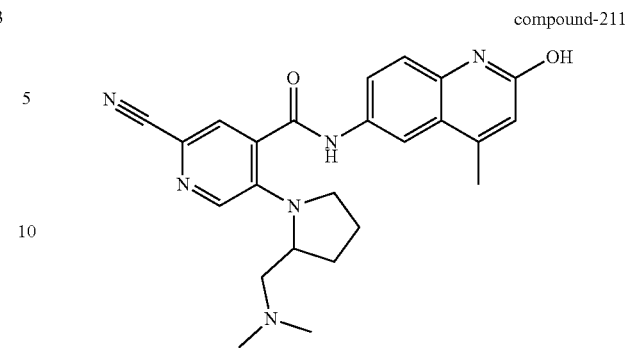

compound-211

Preparation of 2-cyano-5-(2-((dimethylamino)methylpyr-rolidin-1-yl)-N-(2-hydroxy-4-methylquinolin-6-yl)isonico-tinamide (compound-211): a suspension of 2-chloro-5-(2-((dimethylamino)methylpyrrolidin-1-yl)-N-(2-hydroxy-4-methylquinolin-6-yl)isonicotinamide (4) (350 mg, 0.79 mmol, 1 eq), Zn(CN)$_2$ (111.9 mg, 0.95 mmol, 1.2 eq) in DMF (10 vols) was degassed for 10 min. Then added PdCl$_2$.dppf (195 mg, 0.23 mmol, 0.3 eq) stirred at 150° C. for 1 h in a microwave. After completion, The reaction mixture was poured into water and extracted with MeOH: DCM (1:9) (3×20 mL). The combined extracts were washed with ice water (20 mL), brine (20 mL), dried over anhydrous Na$_2$SO$_4$, filtered and evaporated. The crude compound was purified by column chromatography (SiO$_2$) using MeOH: DCM (8:92) to afford 2-cyano-5-(2-((dimethylamino)meth-ylpyrrolidin-1-yl)-N-(2-hydroxy-4-methylquinolin-6-yl) isonicotinamide (compound-211) (230 mg, 67%) as an off white solid.

$^1$H NMR (300 MHz, DMSO-d6) δ 11.61 (s, 1H), 10.70 (s, 1H), 8.31 (s, 1H), 8.10 (d, J=2.2 Hz, 1H), 7.89 (s, 1H), 7.77 (dd, J=8.8, 2.3 Hz, 1H), 7.30 (d, J=8.8 Hz, 1H), 6.43 (s, 1H), 4.49-4.11 (m, 1H), 3.58-3.46 (m, 1H), 3.29-3.18 (m, 1H), 2.39 (d, J=1.3 Hz, 3H), 2.39-2.16 (m, 2H), 2.17 (s, 6H), 2.07-1.75 (m, 4H).

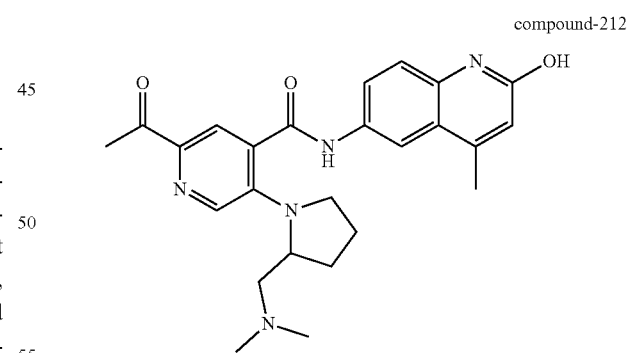

compound-212

Preparation of 2-acetyl-5-(2-((dimethylamino)methyl) pyrrolidin-1-yl)-N-(2-hydroxy-4-methylquinolin-6-yl)isoni-cotinamide (compound-212): to a solution of 2-cyano-5-(2-((dimethylamino)methylpyrrolidin-1-yl)-N-(2-hydroxy-4-methylquinolin-6-yl)isonicotinamide (compound-211) (225 mg, 0.511 mmol, 1 eq) in dry THF (10 vol) at 0° C. was added MeMgBr (0.85 mL, 2.55 mmol, 5 eq) and stirred at RT for 16 h. After completion, the reaction mixture was quenched with ice water and extracted with EtOAc (3×10 mL). The combined extracts were washed with water (20 mL), brine (20 mL), dried over anhydrous Na$_2$SO$_4$, filtered and evaporated. The crude compound was purified by combiflash using MeOH:DCM (8:92) to afford 2-acetyl-5-(2-((dimethylamino)methyl)pyrrolidin-1-yl)-N-(2-hydroxy-4-methylquinolin-6-yl)isonicotinamide (compound-212) (140 mg, 53.2%) as an pale yellow solid.

¹H NMR (400 MHz, DMSO-d6) δ 11.59 (s, 1H), 10.72 (s, 1H), 8.29 (s, 1H), 8.11 (d, J=2.3 Hz, 1H), 7.83 (s, 1H), 7.78 (dd, J=8.9, 2.2 Hz, 2H), 7.29 (d, J=8.8 Hz, 1H), 6.43 (s, 1H), 3.60-3.47 (m, 1H), 3.45-3.34 (m, 1H), 3.28-3.25 (m, 2H), 2.55 (s, 3H), 2.39 (d, J=1.3 Hz, 3H), 2.19 (s, 6H), 2.04-1.80 (m, 4H).

compound-213

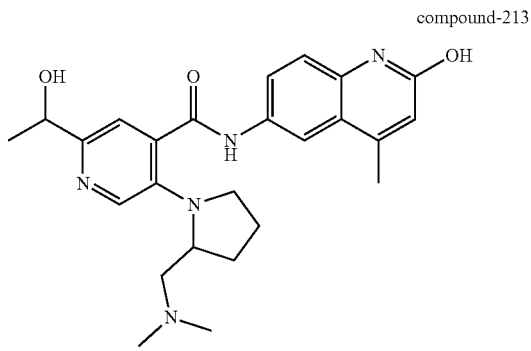 [SMILES: Cc1cc(O)nc2ccc(NC(=O)c3cc(C(C)O)ncc3N3CCCC3CN(C)C)cc12]

Preparation of 5-(2-((dimethylamino)methyl)pyrrolidin-1-yl)-N-(2-hydroxy-4-methylquinolin-6-yl)-2-(1-hydroxyethyl)isonicotinamide (compound-213): to a solution of 2-acetyl-5-(2-((dimethylamino)methyl)pyrrolidin-1-yl)-N-(2-hydroxy-4-methylquinolin-6-yl)isonicotinamide (compound-212) (100 mg, 0.223 mmol, 1 eq) in MeOH (10 vol) at 0° C. was added NaBH₄ (26.17 mg, 0.671 mmol, 3 eq) and stirred at RT for 16 h. After completion reaction was quenched with NH₄Cl solution and extracted with ethylactate (3×20 mL). The combined extracts were washed with water (20 mL), brine (20 mL), dried over anhydrous Na₂SO₄, filtered and evaporated. The crude compound was purified by combiflash using MeOH:DCM (8:92) to afford N-(2-hydroxy4-methylquinolin-6-yl)-6-(1-hydroxymethyl)-3-(pyrrolidin-1-yl)picolinamide (compound-213) (40 mg, 40%) as an off white solid.

¹H NMR (300 MHz, DMSO-d6) δ 11.59 (s, 1H), 10.87 (d, J=11.8 Hz, 1H), 8.21 (s, 1H), 8.13 (s, 1H), 7.77 (d, J=8.6 Hz, 1H), 7.42 (d, J=3.0 Hz, 1H), 7.36-7.19 (m, 1H), 6.43 (s, 1H), 5.23 (dd, J=9.5, 4.8 Hz, 1H), 4.69 (q, J=6.1 Hz, 1H), 4.02 (s, 1H), 3.57-3.37 (m, 2H), 3.11 (s, 1H), 2.46-2.25 (m, 4H), 2.12 (s, 7H), 1.84 (m, 3H), 1.47-1.31 (m, 4H).

Additional compounds are prepared according to the general procedures described below.

General Procedure 1 (Acylation):

1.2 μmol of acid building block (BB1) and 1.2 μmol of amine building block (BB2) were dissolved in 6 μl 200 mM HOAt in dry DMF in an Eppendorf Twin.Tec plate. Add 6 μL of a solution which is 200 mM EDC and 400 mM DIPEA in dry DMF was added and the mixture was shaken at RT overnight. The mixture was transferred to a filter plate for purification. 100 μL of dry THF was added to the well, washed down and transferred to a filter plate. Evaporated and analyzed by CLND.

General Procedure 2 (Nucleophilic Aromatic Substitution):

2.4 μmol of electrophile NAS building block (BB1) and 2.4 μmol of amine (BB2) were dissolved in 48 μL dry DMSO in an Eppendorf Twin.Tec plate. 9.6 μmol Cs2CO3 were added and the mixture shaken at 80° C. and then at 100° C. for 4 hrs, cool and spun down. 100 μL of dry THF was added to the well and spun down and collect supernatant. The precipitate was washed with 100 μL of THF, spun down and the supernatant collected. The combined supernatants were concentrated and analyzed by CLND.

General Procedure 3 (Reductive Amination):

2.4 μmol of amine (BB2) was dissolved in an Eppendorf Twin.Tec plate in 24 μL of a 300 mM solution of the aldehyde (BB1) in dry THF. 6.0 μmol SiliaBond Cyanoborohydride was placed in a filterplate and the solution above was added. The Twin.Tec plate was washed with 12 μL of 300 mM acetic acid in dry THF and the solution transferred to the filter plate. Shake at RT overnight, then add 100 μL THF to the well. Drain and collect the reaction mixture and wash with 100 μL acetonitrile and evaporate the combined solvents.

The following table discloses the additional compounds, their starting materials, their MS as well as the general procedure that were used for their preparation. The numbers: 1, 2, and 3, in the last column in the table relates to general procedures 1, 2 or 3 respectively.

| # | BB1 | BB2 | Structure and IUPAC Name | Prod. m/z |
|---|---|---|---|---|
| S1 | 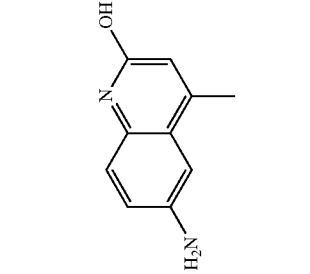 | 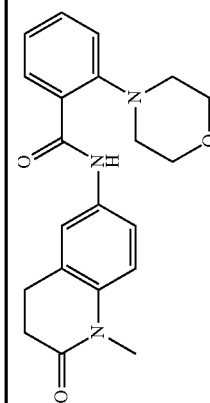 | 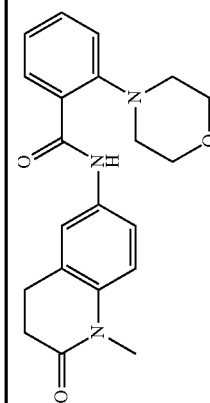<br>N-(1-methyl-2-oxo-3,4-dihydroquinolin-6-yl)-2-morpholino-benzamide | 365.4 |
| S2 | 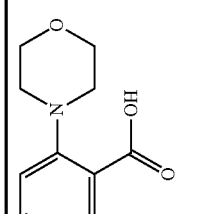 | 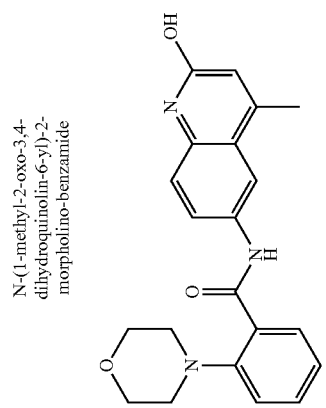 | 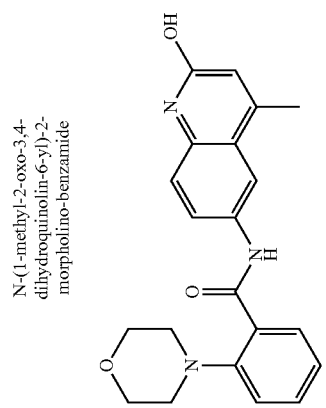<br>N-(2-hydroxy-4-methyl-6-quinolyl)-2-morpholino-benzamide | 363.4 |
| S3 | 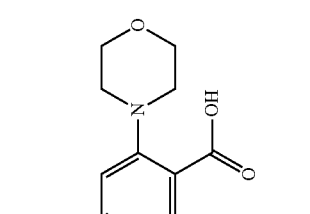 | 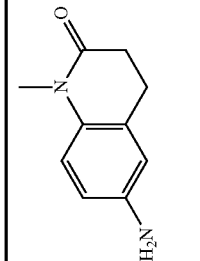 | 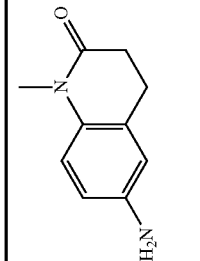<br>3-(cyclopentylsulfamoyl)-4-methyl-N-(1-methyl-2-oxo-3,4-dihydroquinolin-6-yl)benzamide | 441.5 |

| | | | | |
|---|---|---|---|---|
| S4 | 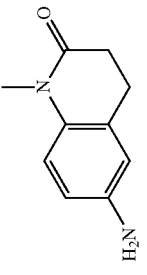 | 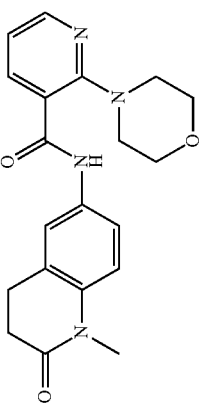 | 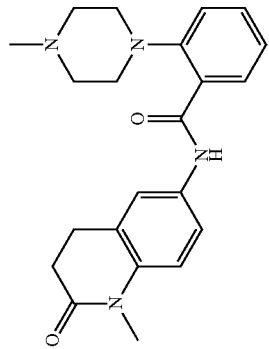<br>N-(1-methyl-2-oxo-3,4-dihydroquinolin-6-yl)-2-morpholino-pyridine-3-carboxamide | 366.4 | 1 |
| S5 | 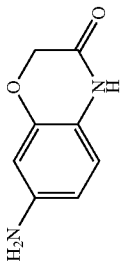 | 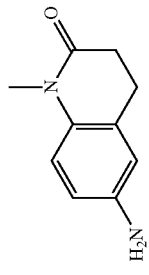 | 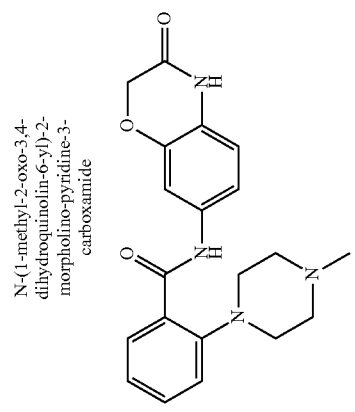<br>2-(4-methylpiperazin-1-yl)-N-(3-oxo-4H-1,4-benzoxazin-7-yl)benzamide | 366.4 | 1 |
| S6 | 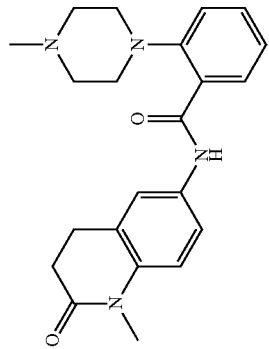 | 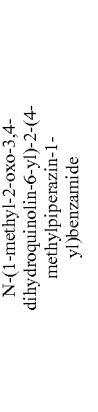 | <br>N-(1-methyl-2-oxo-3,4-dihydroquinolin-6-yl)-2-(4-methylpiperazin-1-yl)benzamide | 378.4 | 1 |

| | | | | |
|---|---|---|---|---|
| S7 | 2-(4-methylpiperazin-1-yl)benzoic acid | 7-amino-4-methyl-2H-benzo[b][1,4]oxazin-3(4H)-one | N-(4-methyl-3-oxo-1,4-benzoxazin-7-yl)-2-(4-methylpiperazin-1-yl)benzamide | 380.4 1 |
| S8 | 2-(4-(pyrazin-2-yl)piperazin-1-yl)benzoic acid | 6-amino-1-methyl-3,4-dihydroquinolin-2(1H)-one | N-(1-methyl-2-oxo-3,4-dihydroquinolin-6-yl)-2-(4-pyrazin-2-ylpiperazin-1-yl)benzamide | 442.5 1 |

| S9 | 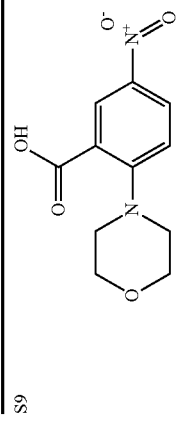 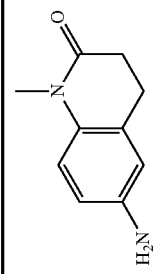 N-(1-methyl-2-oxo-3,4-dihydroquinolin-6-yl)-2-morpholino-5-nitrobenzamide 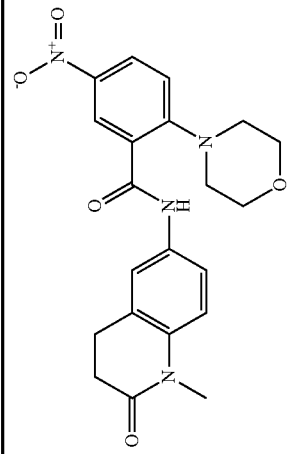 | 410.4 | 1 |
| S10 | 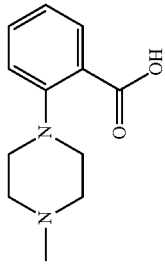 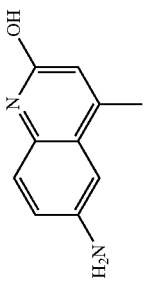 N-(2-hydroxy-4-methyl-6-quinolyl)-2-(4-methylpiperazin-1-yl)benzamide 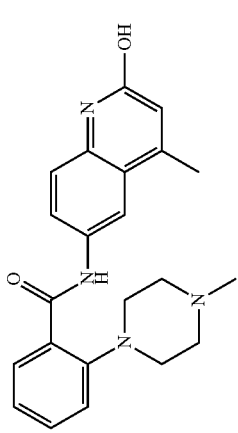 | 376.4 | 1 |
| S11 | 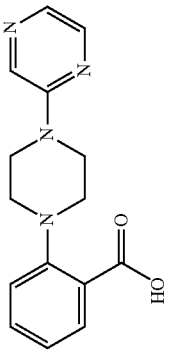 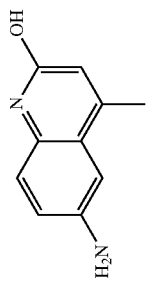 N-(2-hydroxy-4-methyl-6-quinolyl)-2-(4-methylpiperazin-1-yl)benzamide 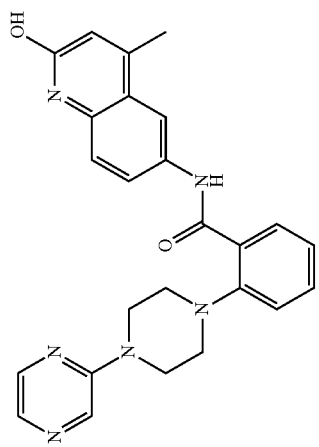 | 440.4 | 1 |

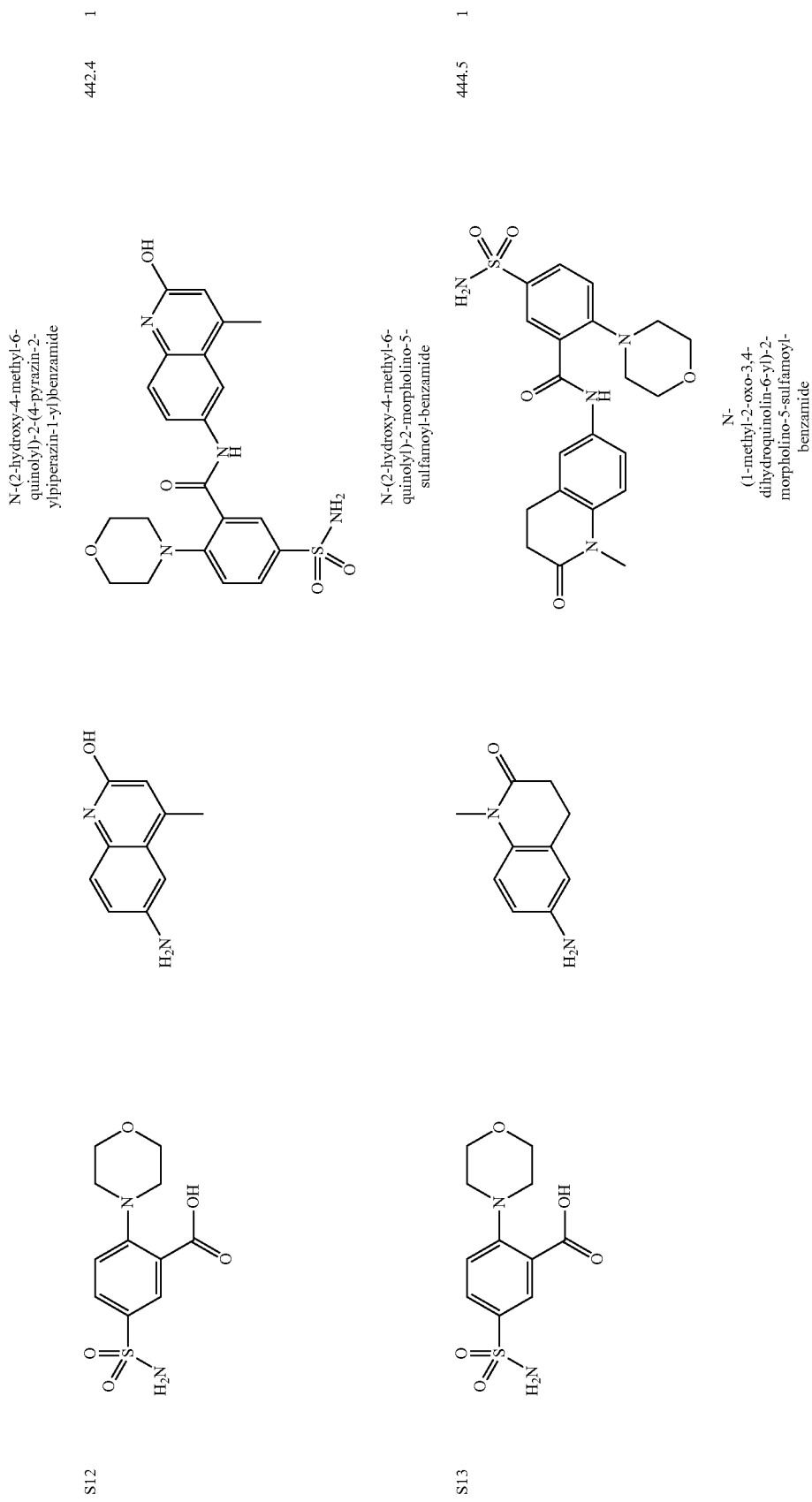

-continued
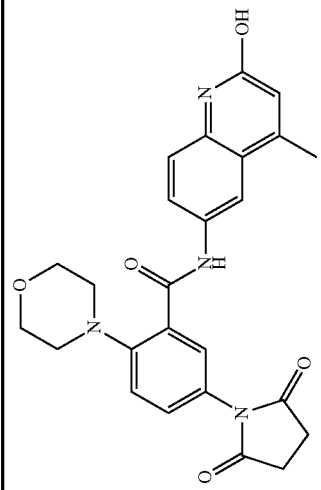
5-(2,5-dioxopyrrolidin-1-yl)-N-(2-hydroxy-4-methyl-6-quinolyl)-2-morpholino-benzamide
460.4  1
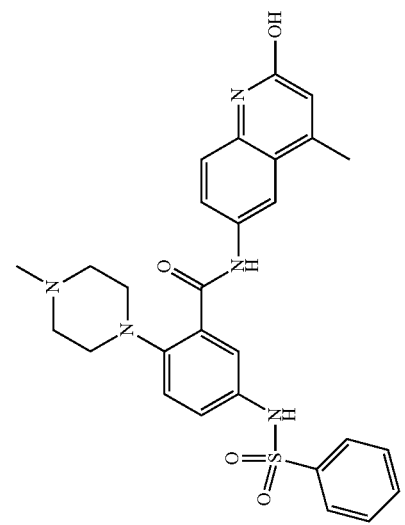
5-(benzenesulfonamido)-N-(2-hydroxy-4-methyl-6-quinolyl)-2-(4-methylpiperazin-1-yl)benzamide
531.6  1
S14
S15

-continued
| | | | |
|---|---|---|---|
| | 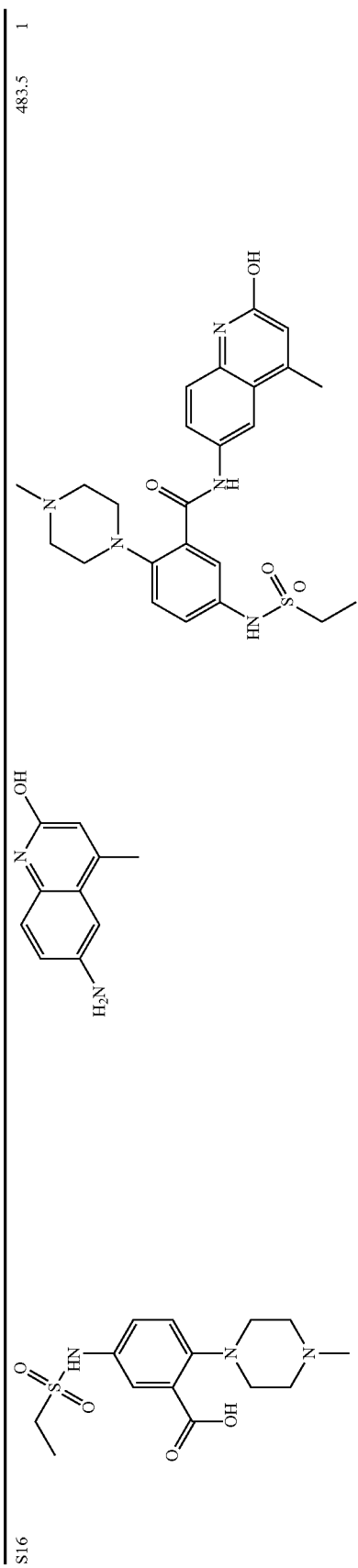 | 483.5 | 1 |
| | 5-(ethylsulfonyl)amino)-N-(2-hydroxy-4-methyl-6-quinolyl)-2-(4-methylpiperazin-1-yl)benzamide | | |
| S16 | | | |
| | 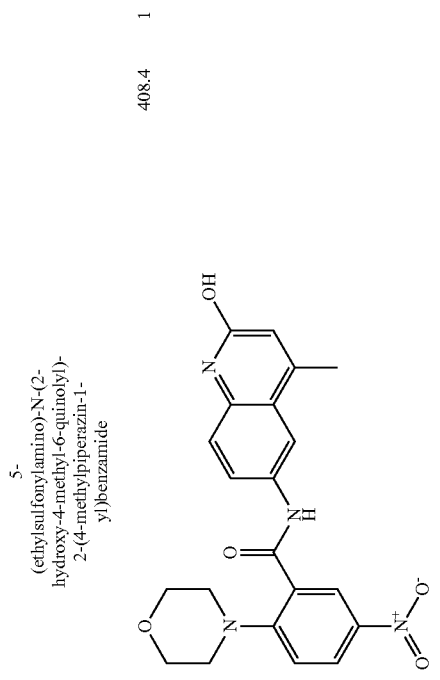 | 408.4 | 1 |
| | N-(2-hydroxy-4-methyl-6-quinolyl)-2-morpholino-5-nitro-benzamide | | |
| | 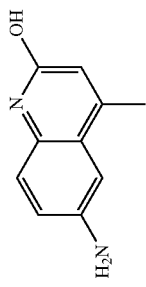 | | |
| S17 | 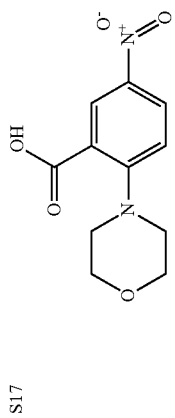 | | |

-continued
| S18 | 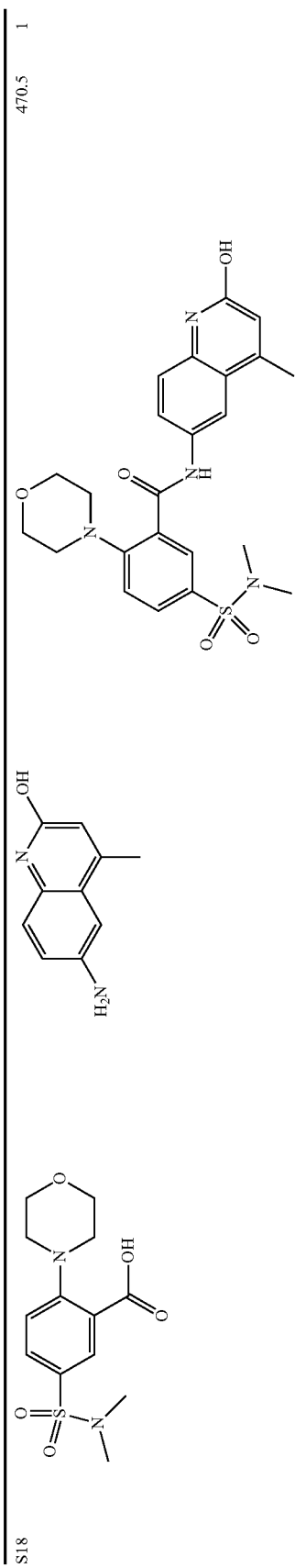 | | 5-(dimethylsulfamoyl)-N-(2-hydroxy-4-methyl-6-quinolyl)-2-morpholino-benzamide | 470.5 | 1 |
| S19 | 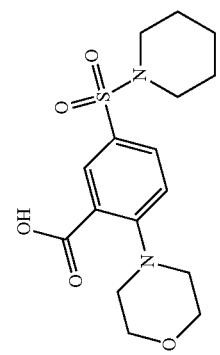 | 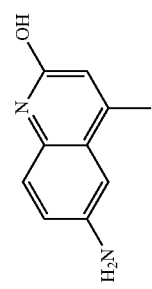 | 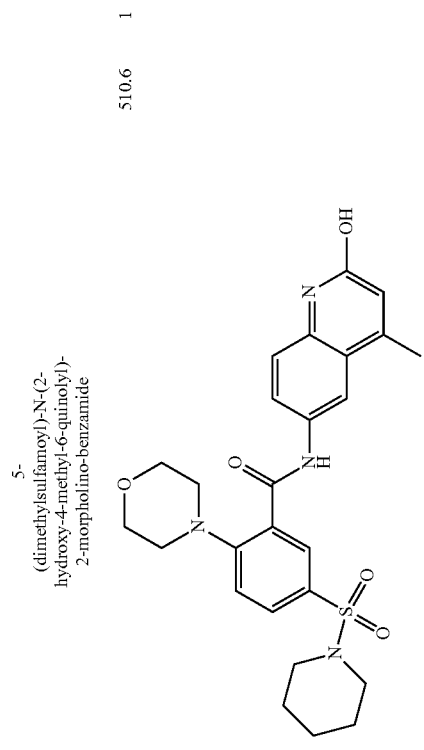 N-(2-hydroxy-4-methyl-6-quinolyl)-2-morpholino-5-(1-piperidylsulfonyl)benzamide | 510.6 | 1 |

| | | | |
|---|---|---|---|
| S20 | morpholine-sulfonyl benzoic acid with morpholine + 6-amino-2-hydroxy-4-methylquinoline | N-(2-hydroxy-4-methyl-6-quinolyl)-2-morpholino-5-morpholinosulfonyl-benzamide | 512.5  1 |
| S21 | Boc-piperazinylmethyl benzoic acid + 6-amino-2-hydroxy-4-methylquinoline | N-(2-hydroxy-4-methyl-6-quinolyl)-3-(piperazin-1-ylmethyl)benzamide | 376.4  1 |
| S22 | 2-(dimethylamino)-5-nitrobenzoic acid + 6-amino-2-hydroxy-4-methylquinoline | 2-(dimethylamino)-N-(2-hydroxy-4-methyl-6-quinolyl)-5-nitro-benzamide | 366.3  1 |

| | | | |
|---|---|---|---|
| S23 | (structure: 3-carboxy-N-methylbenzenesulfonamide) | (structure: N-(2-hydroxy-4-methyl-6-quinolyl)-3-(methylsulfamoyl)benzamide) N-(2-hydroxy-4-methyl-6-quinolyl)-3-(methylsulfamoyl)benzamide | 371.4 | 1 |
| S24* | (structure: 3-((2-oxopyrrolidin-1-yl)methyl)benzoic acid) | (structure: N-(2-hydroxy-4-methyl-6-quinolyl)-3-[(2-oxopyrrolidin-1-yl)methyl]benzamide) N-(2-hydroxy-4-methyl-6-quinolyl)-3-[(2-oxopyrrolidin-1-yl)methyl]benzamide | 375.4 | 1 |
| S25 | (structure: 5-nitro-2-(pyrrolidin-1-yl)benzoic acid) | (structure: N-(2-hydroxy-4-methyl-6-quinolyl)-5-nitro-2-pyrrolidin-1-yl-benzamide) N-(2-hydroxy-4-methyl-6-quinolyl)-5-nitro-2-pyrrolidin-1-yl-benzamide | 392.4 | 1 |

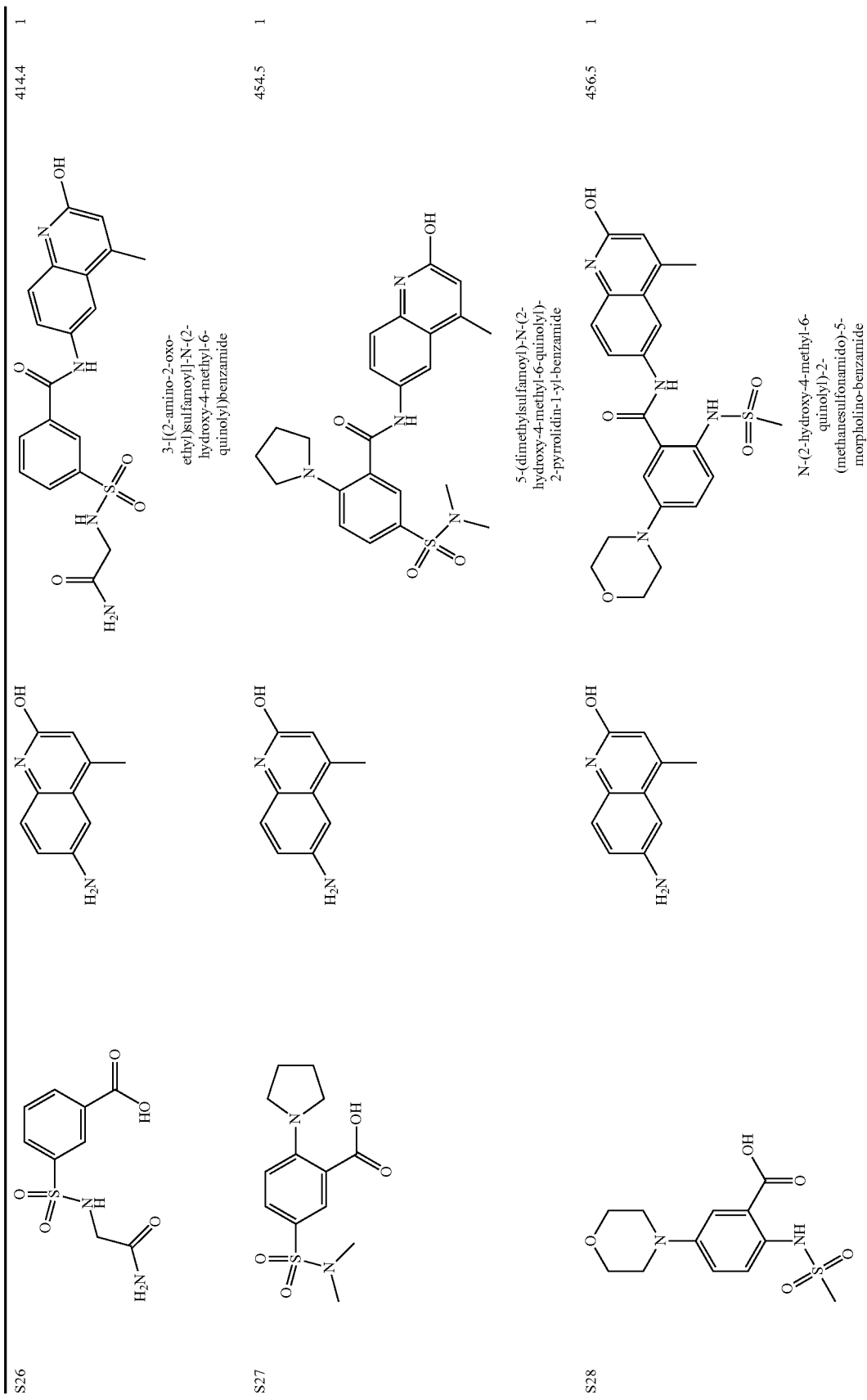

-continued

| | | | | |
|---|---|---|---|---|
| S29* | (3-pyrrolidin-1-yl-benzoic acid) | (6-amino-4-methyl-quinolin-2-ol) | N-(2-hydroxy-4-methyl-6-quinolyl)-3-pyrrolidin-1-yl-benzamide | 347.4 | 1 |
| S30* | (4-amino-3-nitro-benzoic acid) | (6-amino-4-methyl-quinolin-2-ol) | 4-amino-N-(2-hydroxy-4-methyl-6-quinolyl)-3-nitro-benzamide | 338.3 | 1 |
| S32 | (2-morpholino-5-sulfamoyl-benzoic acid) | (6-amino-4-trifluoromethyl-1H-quinolin-2-one) | 2-morpholino-N-[2-oxo-4-(trifluoromethyl)-1H-quinolin-6-yl]-5-sulfamoyl-benzamide | 496.4 | 1 |

| | | | | |
|---|---|---|---|---|
| S33 | ![structure] | ![structure] | 5-(dimethylsulfamoyl)-2-fluoro-N-(2-hydroxy-4-methyl-6-quinolyl)benzamide | 403.4 | 1 |
| S34 | ![structure] | ![structure] | 2-bromo-N-(2-hydroxy-4-methyl-6-quinolyl)-5-morpholinosulfonyl-benzamide | 506.3 | 1 |
| S35 | ![structure] | ![structure] | N-(4-hydroxy-2-oxo-1H-quinolin-6-yl)-2-morpholino-5-morpholinosulfonyl-benzamide | 514.5 | 1 |

| | | | | |
|---|---|---|---|---|
| S36 | (3-carboxyphenyl sulfonyl-4-methylpiperazine) | (6-amino-2-hydroxy-4-methylquinoline) | N-(2-hydroxy-4-methyl-6-quinolyl)-3-(4-methylpiperazin-1-yl)sulfonyl-benzamide | 440.5 | 1 |
| S37 | (2-morpholino-5-dimethylsulfamoyl benzoic acid) | (6-amino-quinazoline-2,4-dione) | N-(2,4-dioxo-1H-quinazolin-6-yl)sulfonyl-methylpiperazin-1-yl-benzamide | 473.5 | 1 |
| S38 | (2-pyrrolidino-5-dimethylsulfamoyl benzoic acid) | (6-amino-quinazoline-2,4-dione) | 5-(dimethylsulfamoyl)-N-(2,4-dioxo-1H-quinazolin-6-yl)-2-morpholino-benzamide | 457.5 | 1 |

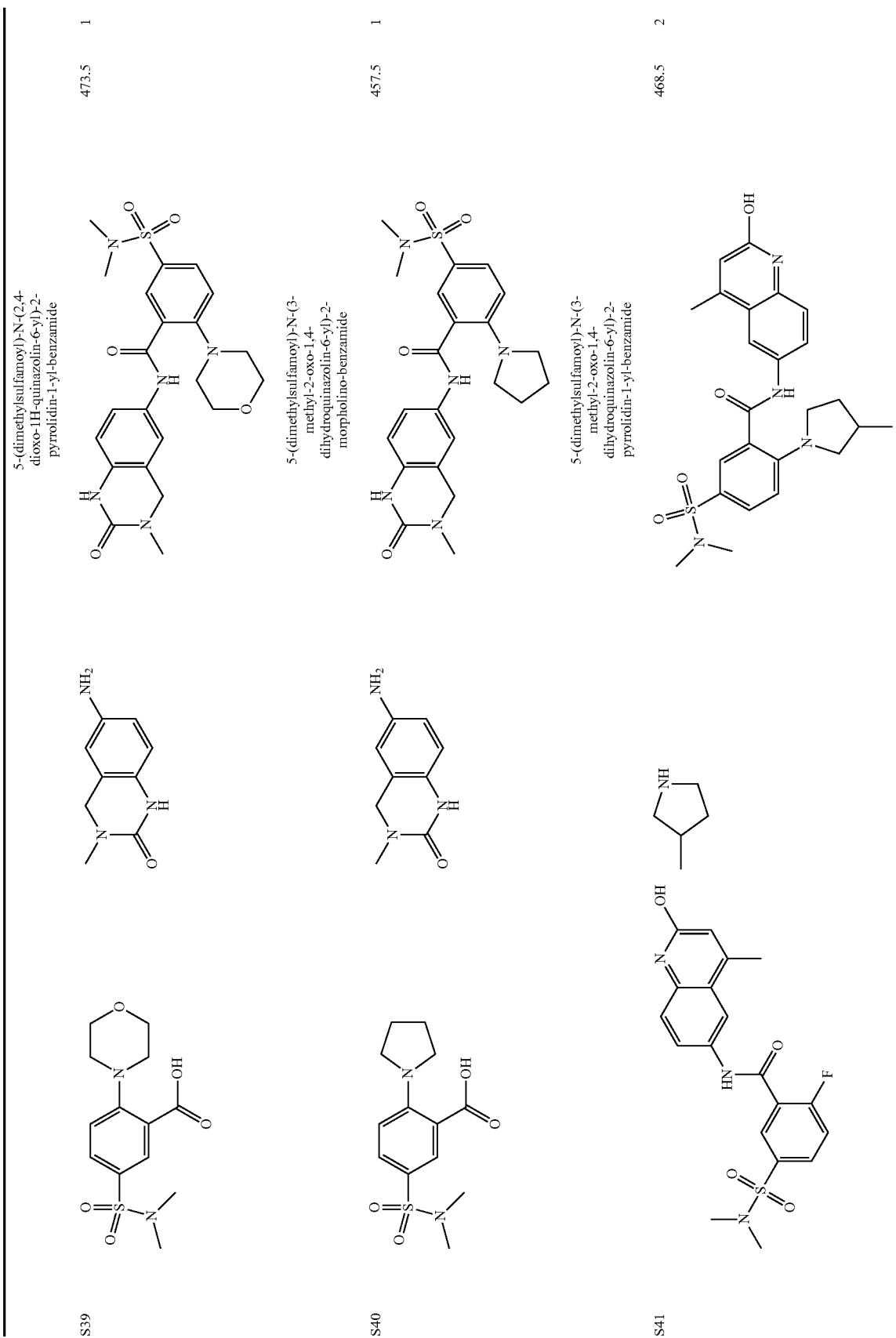

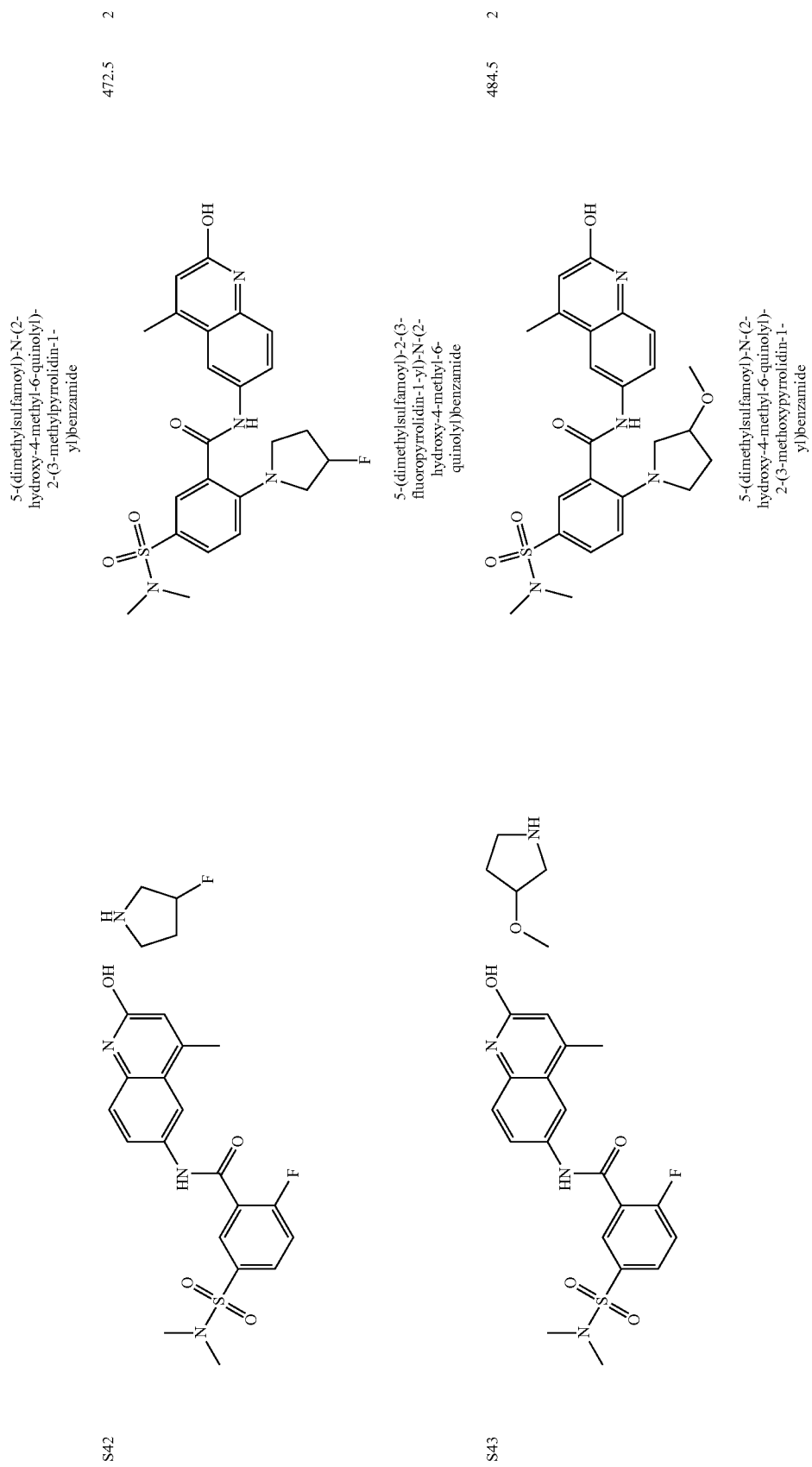

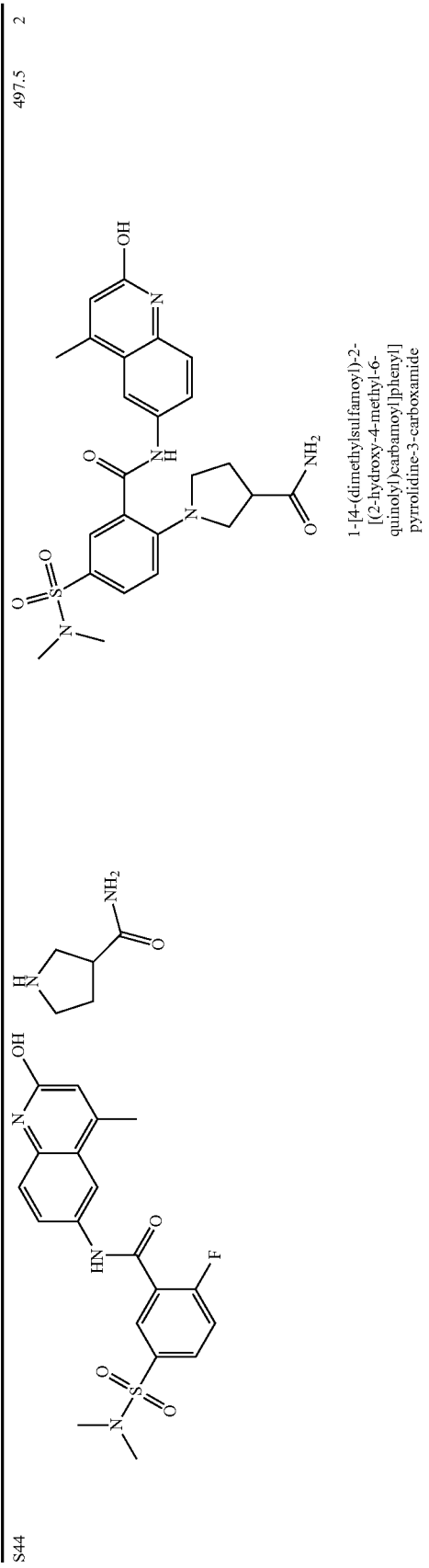
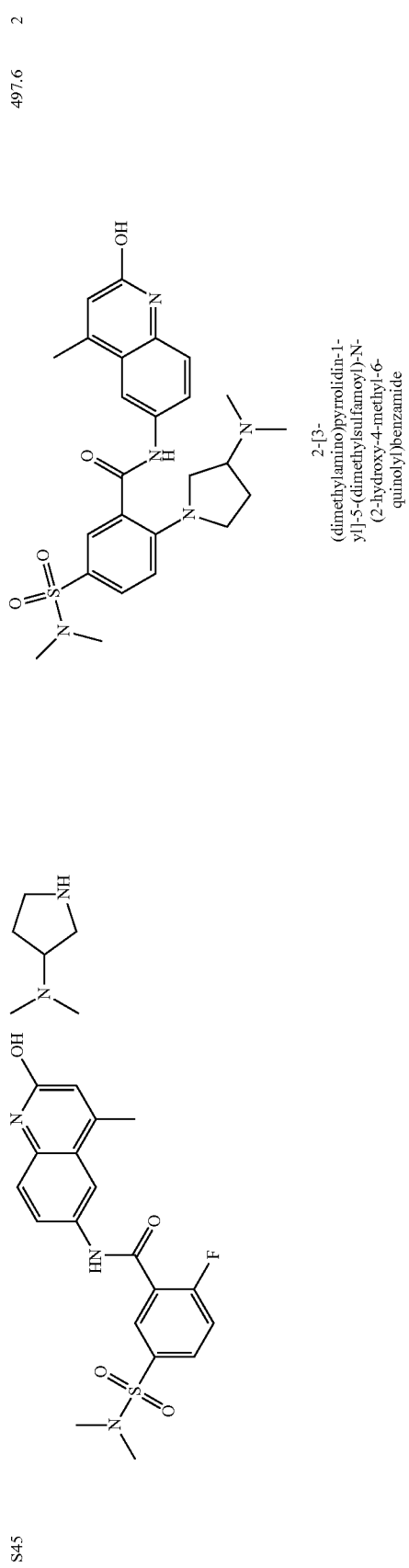
| | | |
|---|---|---|
| S44 | 1-[4-(dimethylsulfamoyl)-2-[(2-hydroxy-4-methyl-6-quinolyl)carbamoyl]phenyl]pyrrolidine-3-carboxamide | 497.5  2 |
| S45 | 2-[3-(dimethylamino)pyrrolidin-1-yl]-5-(dimethylsulfamoyl)-N-(2-hydroxy-4-methyl-6-quinolyl)benzamide | 497.6  2 |

| | | | |
|---|---|---|---|
| S46 | 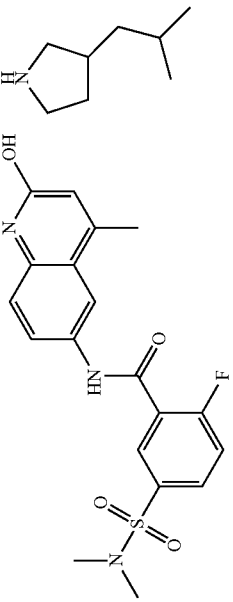 | 5-(dimethylsulfamoyl)-N-(2-hydroxy-4-methyl-6-quinolyl)-2-(3-isobutylpyrrolidin-1-yl)benzamide | 510.6 2 |
| S47 | 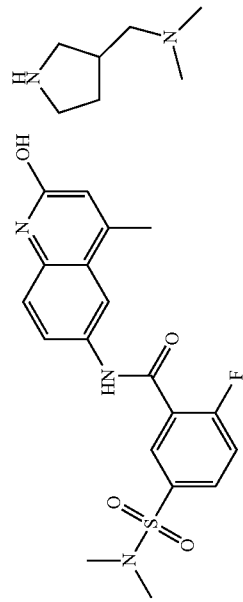 | 2-[3-(dimethylaminomethyl)pyrrolidin-1-yl]-5-(dimethylsulfamoyl)-N-(2-hydroxy-4-methyl-6-quinolyl)benzamide | 511.6 2 |

| | | | |
|---|---|---|---|
| S48 | 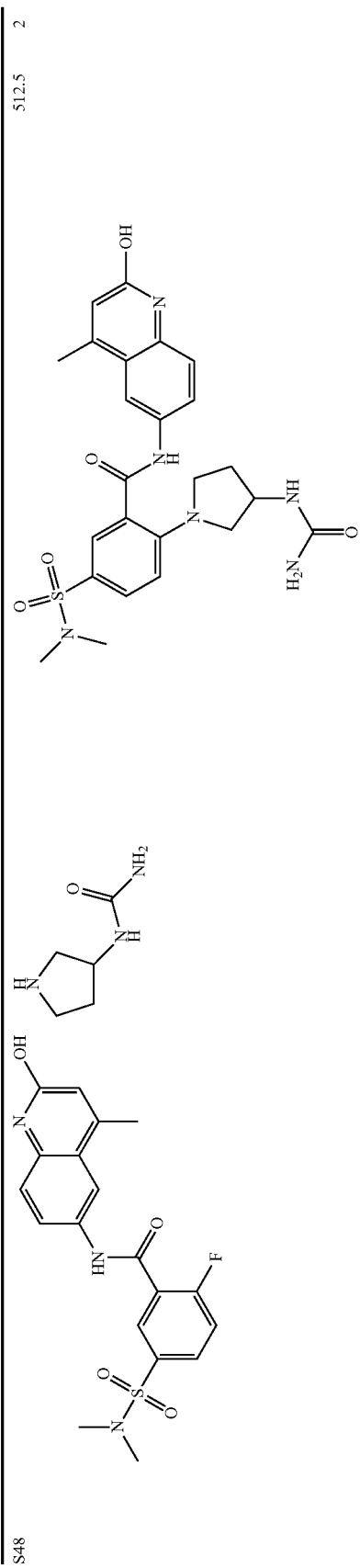 | 5-(dimethylsulfamoyl)-N-(2-hydroxy-4-methyl-6-quinolyl)-2-(3-ureidopyrrolidin-1-yl)benzamide | 512.5 | 2 |
| S49 | 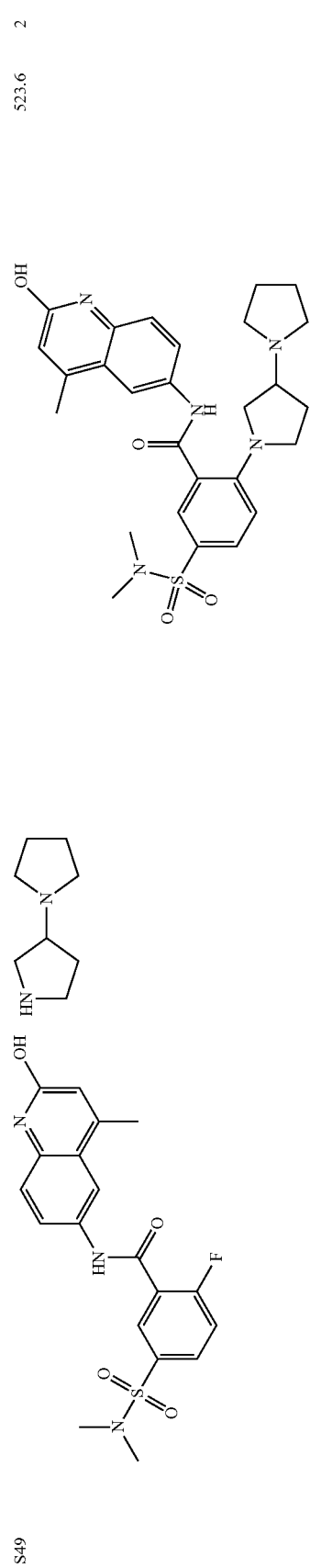 | 5-(dimethylsulfamoyl)-N-(2-hydroxy-4-methyl-6-quinolyl)-2-(3-pyrrolidin-1-ylpyrrolidin-1-yl)benzamide | 523.6 | 2 |

-continued
| | | |
|---|---|---|
| S50 | 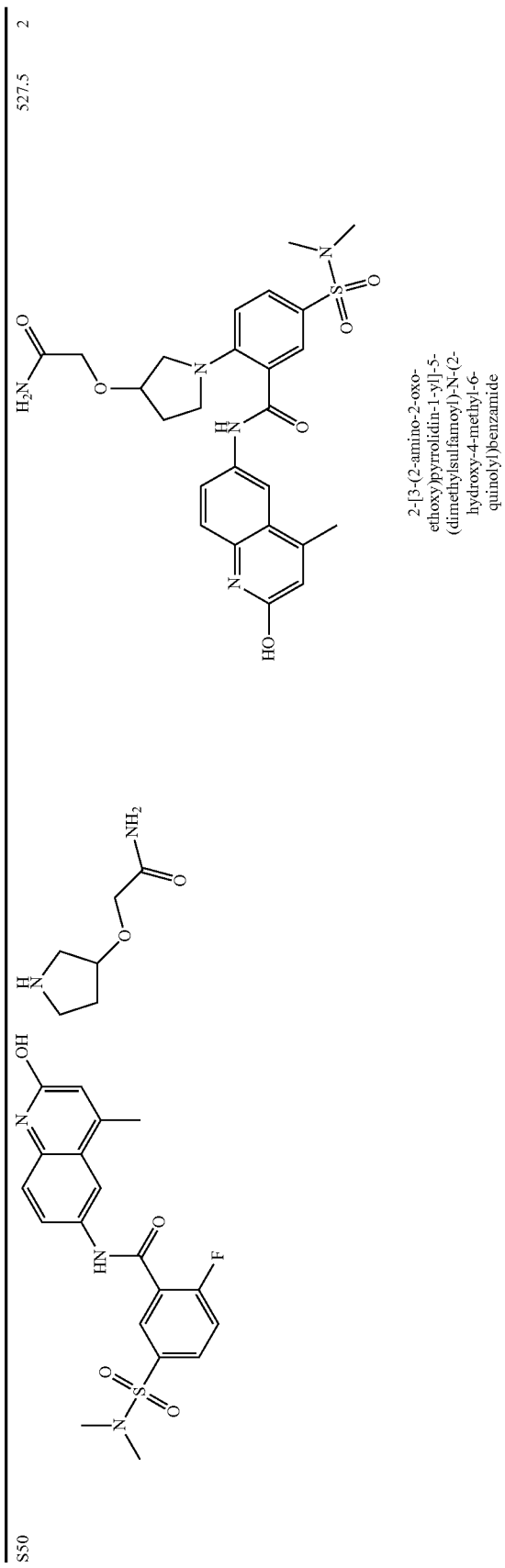 2-[3-(2-amino-2-oxo-ethoxy)pyrrolidin-1-yl]-5-(dimethylsulfamoyl)-N-(2-hydroxy-4-methyl-6-quinolyl)benzamide | 527.5 2 |
| S51 | 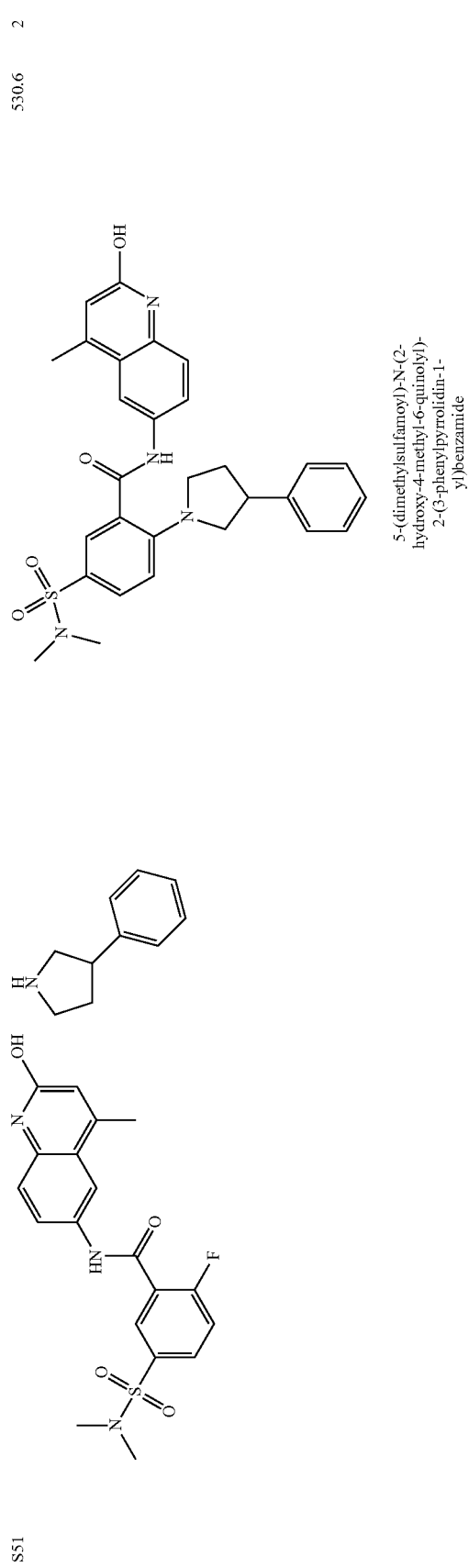 5-(dimethylsulfamoyl)-N-(2-hydroxy-4-methyl-6-quinolyl)-2-(3-phenylpyrrolidin-1-yl)benzamide | 530.6 2 |

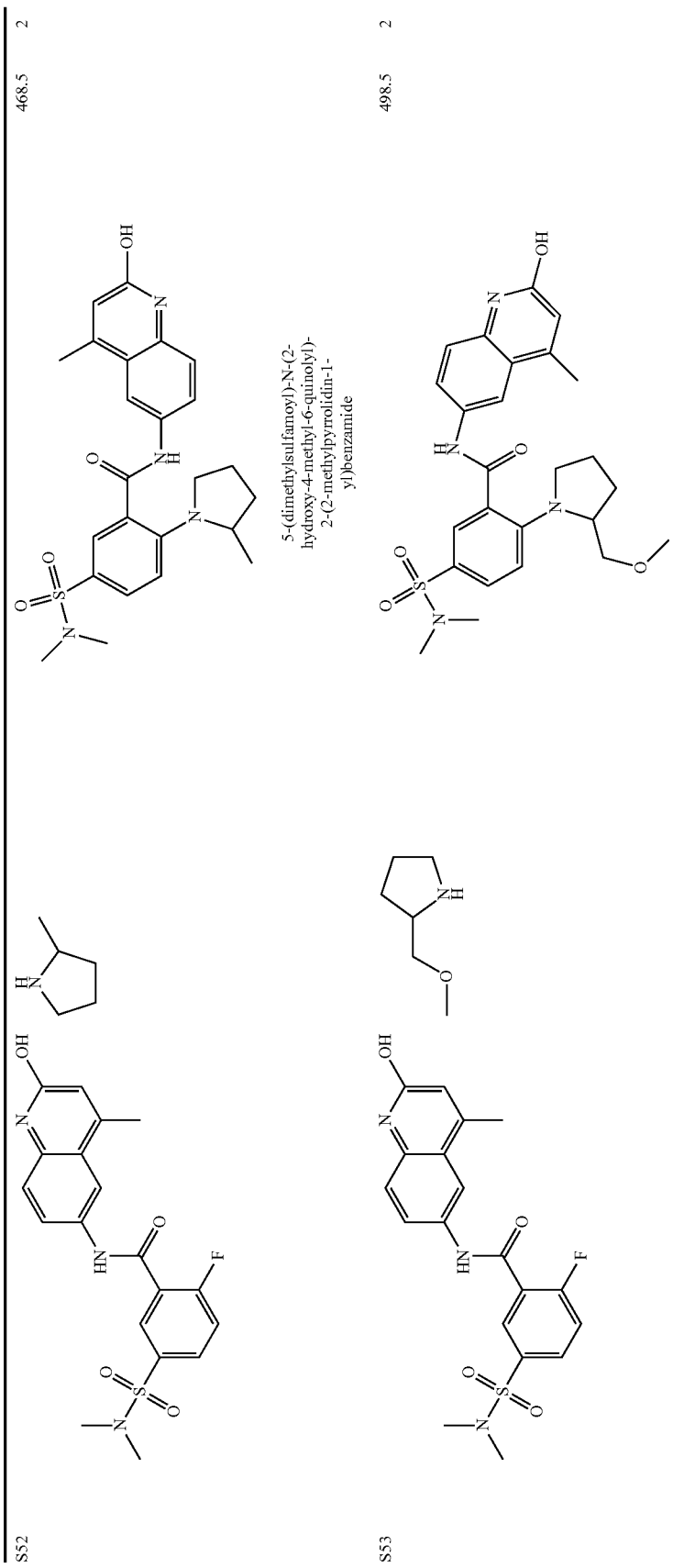

| | | | |
|---|---|---|---|
| S54 | 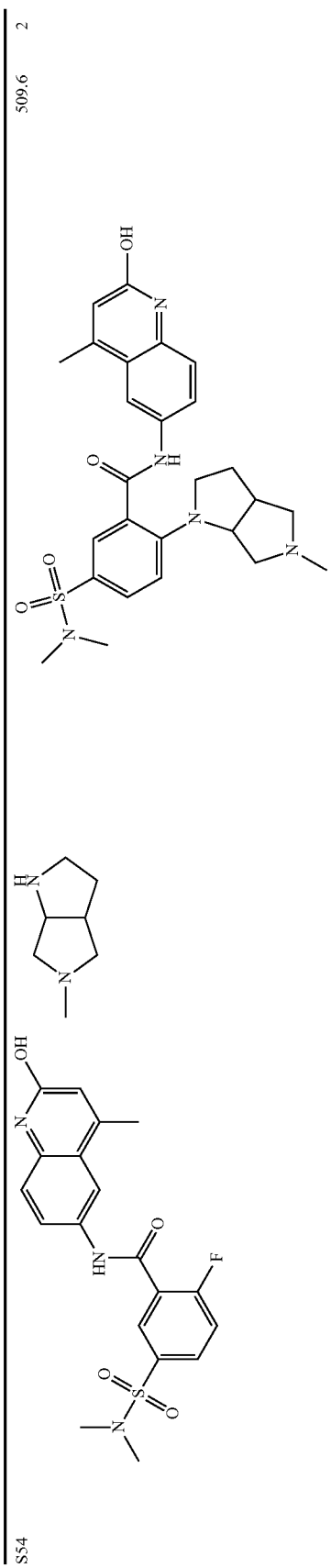 | 5-(dimethylsulfamoyl)-N-(2-hydroxy-4-methyl-6-quinolyl)-2-(5-methyl-2,3,3a,4,6,6a-hexahydropyrrolo[3,4-b]pyrrol-1-yl)benzamide | 509.6  2 |
| S55 | 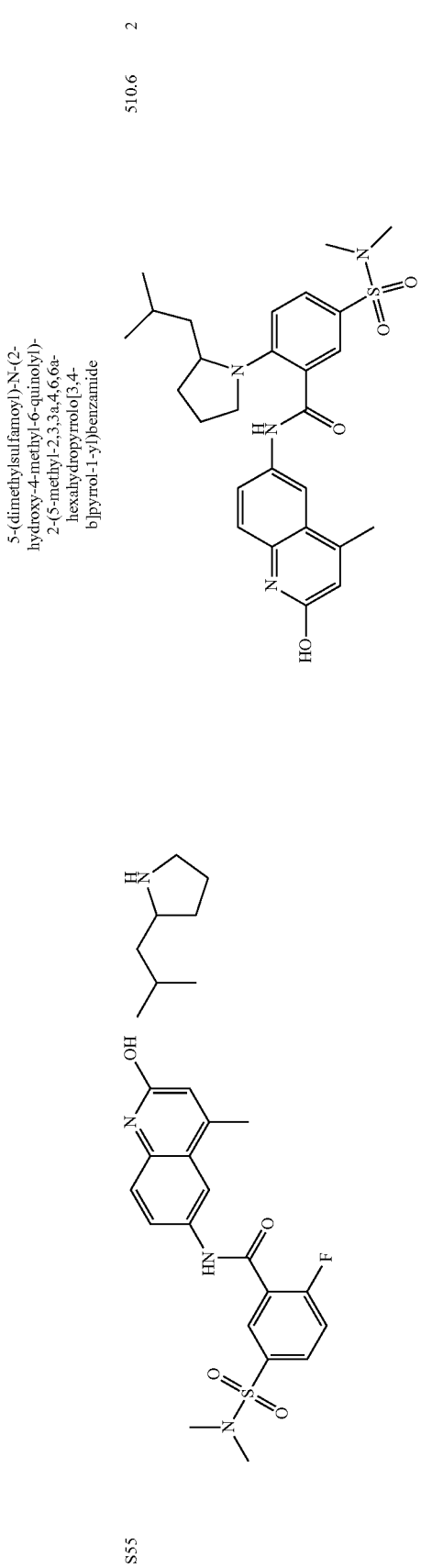 | 5-(dimethylsulfamoyl)-N-(2-hydroxy-4-methyl-6-quinolyl)-2-(2-isobutylpyrrolidin-1-yl)benzamide | 510.6  2 |

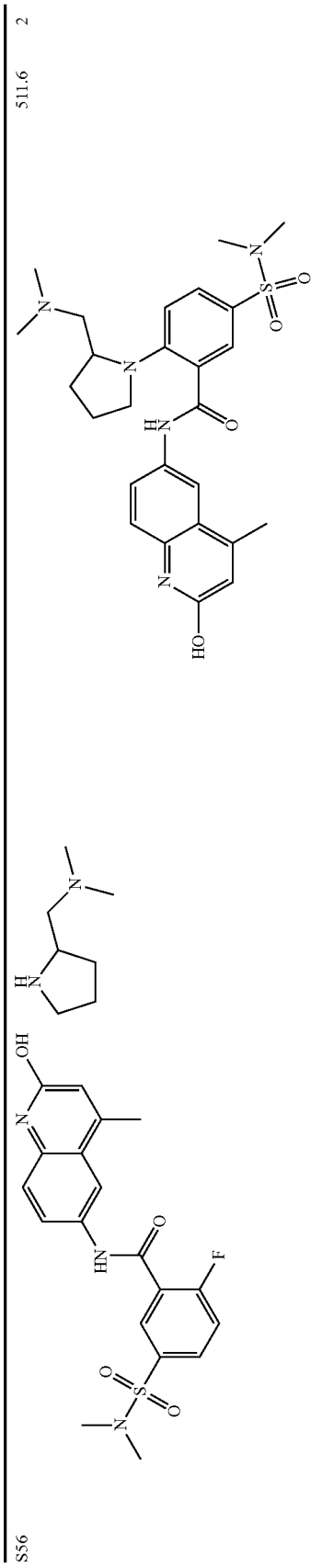
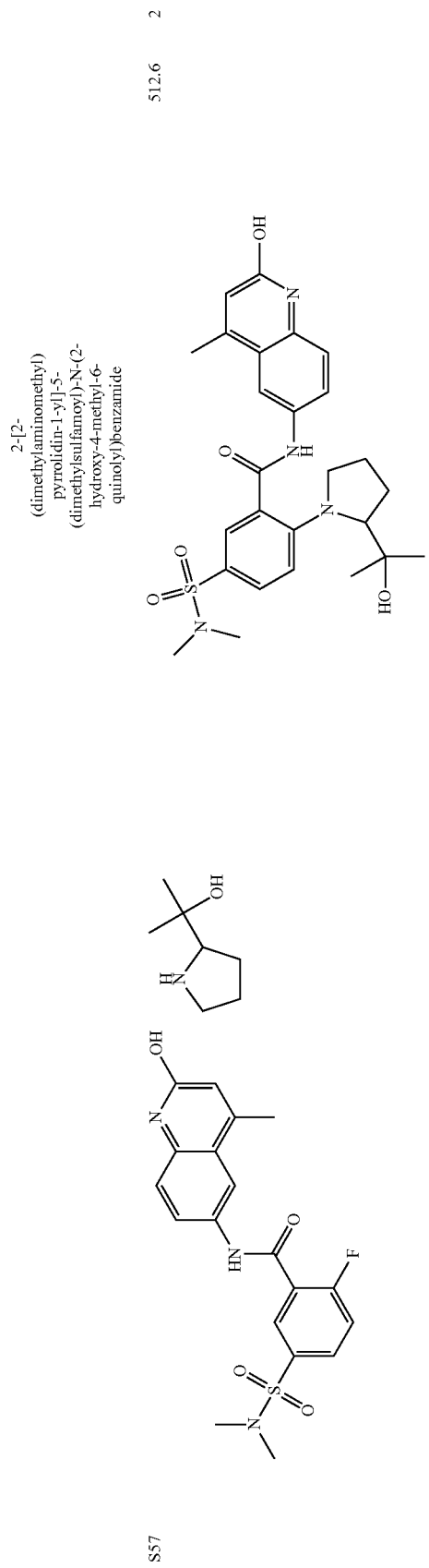

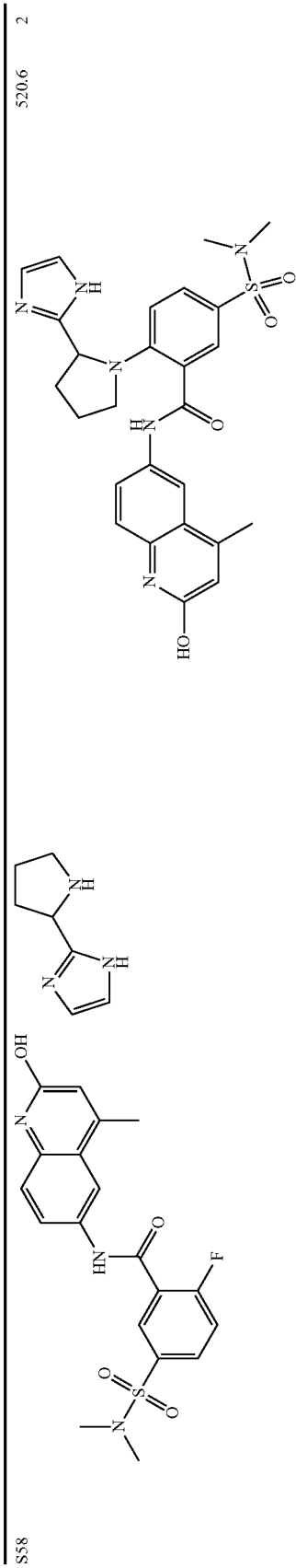
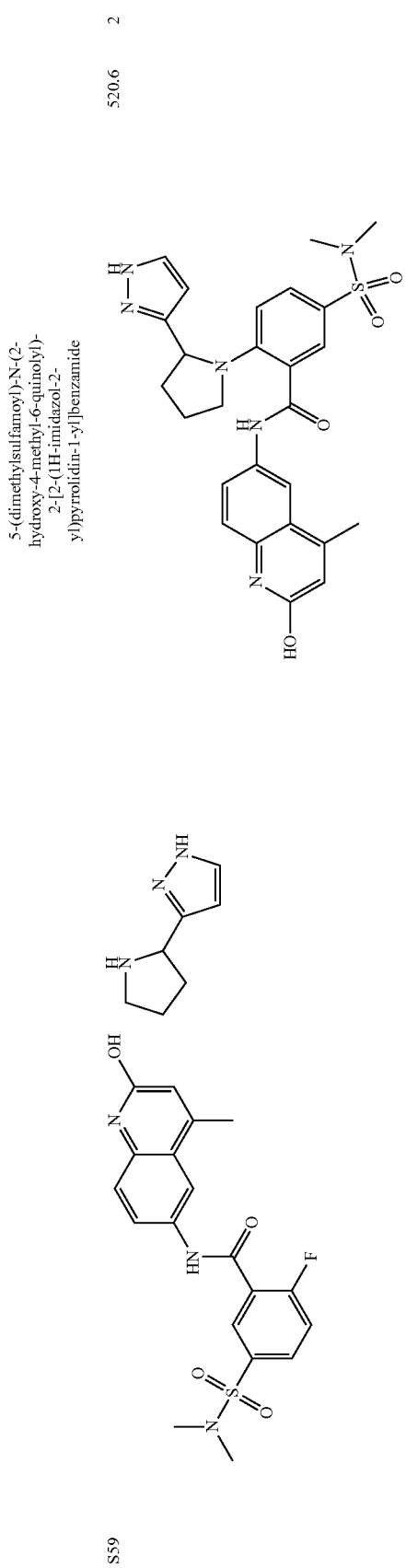

| | | | |
|---|---|---|---|
| S60 | 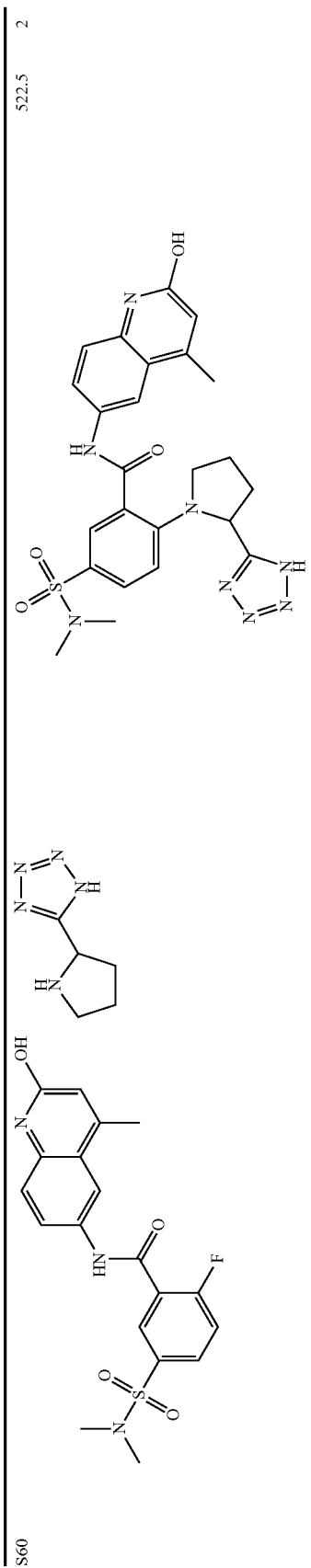 | 5-(dimethylsulfamoyl)-N-(2-hydroxy-4-methyl-6-quinolyl)-2-[2-(1H-tetrazol-5-yl)pyrrolidin-1-yl]benzamide | 522.5 2 |
| S61 | 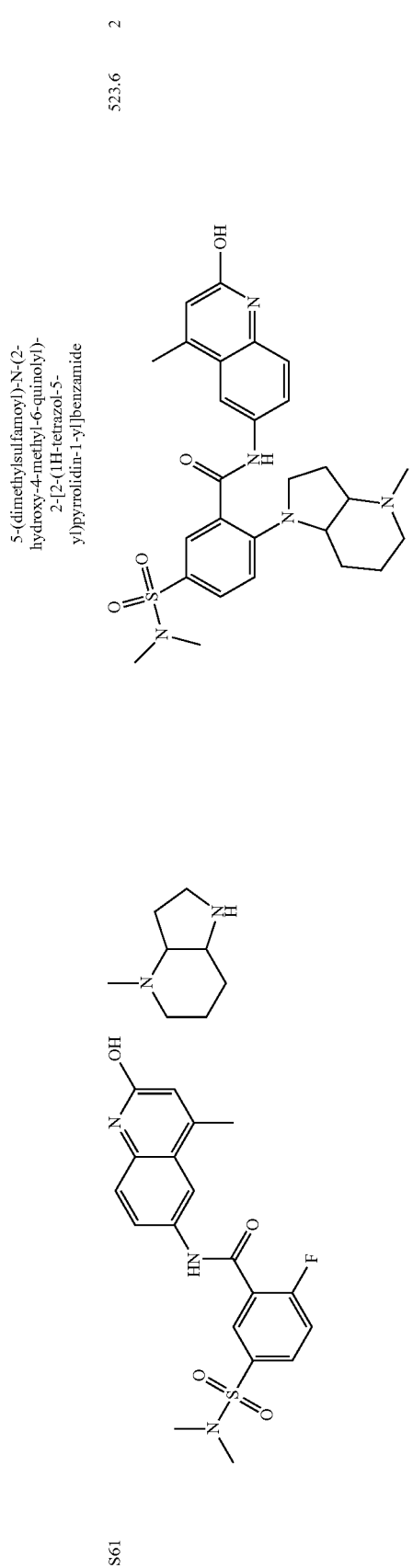 | 5-(dimethylsulfamoyl)-N-(2-hydroxy-4-methyl-6-quinolyl)-2-(4-methyl-3,3a,5,6,7,7a-hexahydro-2H-pyrrolo[3,2-b]pyridin-1-yl)benzamide | 523.6 2 |

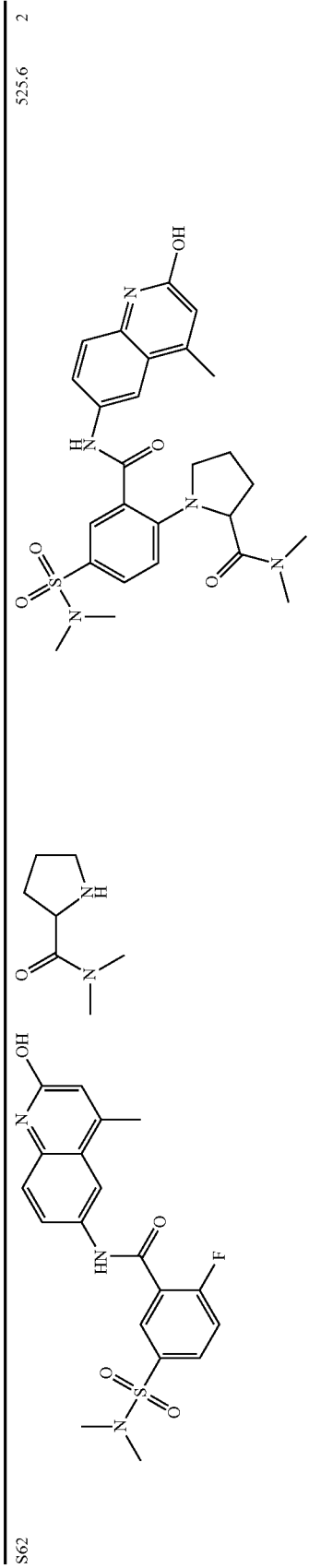
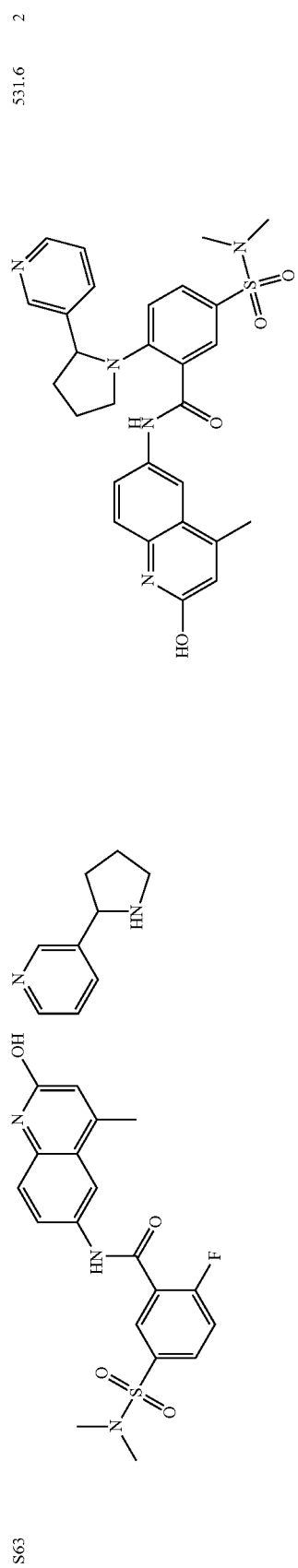
| | | | |
|---|---|---|---|
| S62 | | 525.6 | 2 |
| | 1-[4-(dimethylsulfamoyl)-2-[(2-hydroxy-4-methyl-6-quinolyl)carbamoyl]phenyl]-N,N-dimethyl-pyrrolidine-2-carboxamide | | |
| S63 | 5-(dimethylsulfamoyl)-N-(2-hydroxy-4-methyl-6-quinolyl)-2-[2-(3-pyridyl)pyrrolidin-1-yl]benzamide | 531.6 | 2 |

| | | | |
|---|---|---|---|
| S64 | 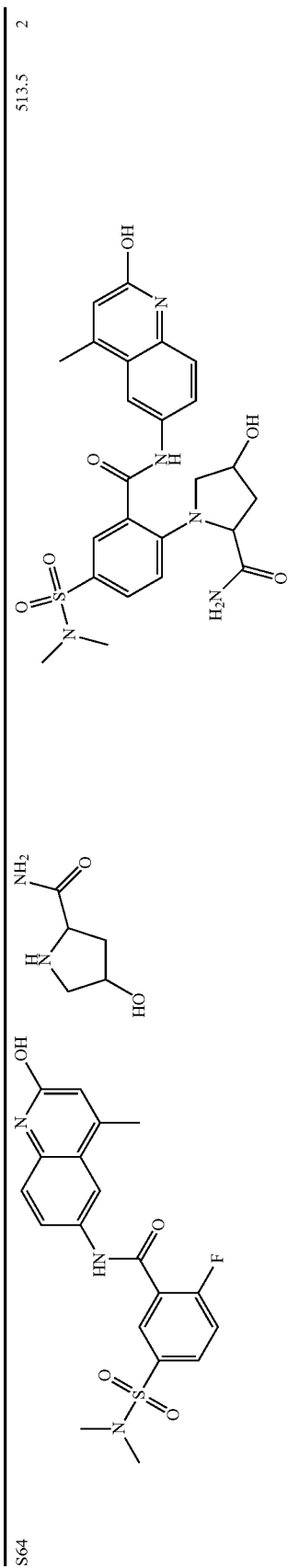 | 1-[4-(dimethylsulfamoyl)-2-[(2-hydroxy-4-methyl-6-quinolyl)carbamoyl]phenyl]-4-hydroxy-pyrrolidine-2-carboxamide | 513.5 | 2 |
| S65 | 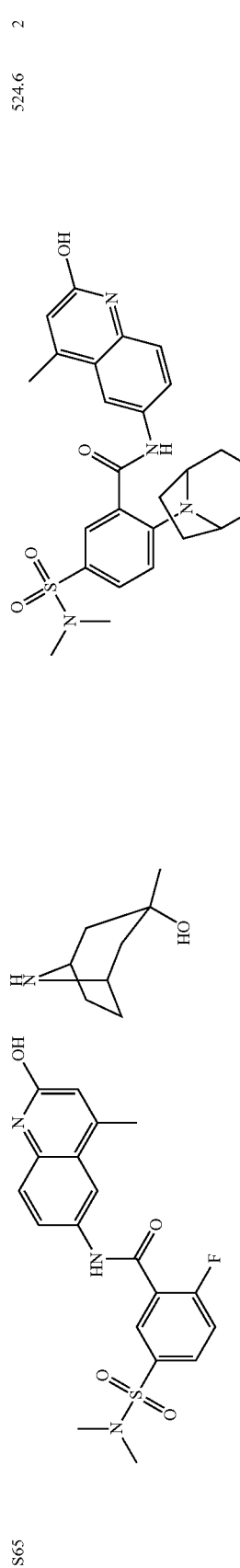 | 5-(dimethylsulfamoyl)-2-(3-hydroxy-3-methyl-8-azabicyclo[3.2.1]octan-8-yl)-N-(2-hydroxy-4-methyl-6-quinolyl)benzamide | 524.6 | 2 |

-continued
| | | | |
|---|---|---|---|
| S66 | 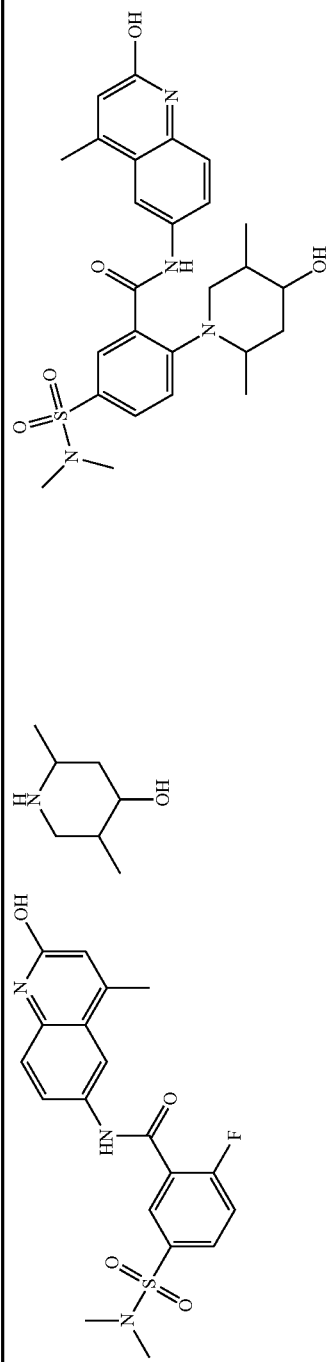 | 5-(dimethylsulfamoyl)-2-(4-hydroxy-2,5-dimethyl-1-piperidyl)-N-(2-hydroxy-4-methyl-6-quinolyl)benzamide | 512.6 2 |
| S67 | 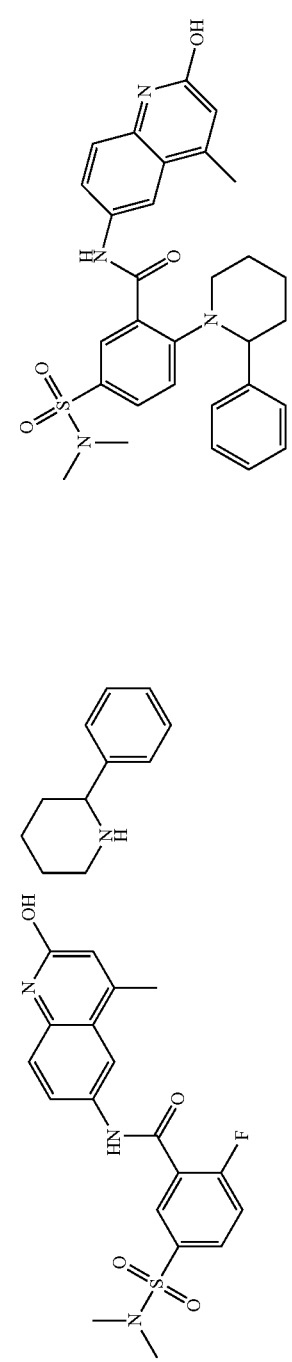 | 5-(dimethylsulfamoyl)-N-(2-hydroxy-4-methyl-6-quinolyl)-2-(2-phenyl-1-piperidyl)benzamide | 544.6 2 |

-continued
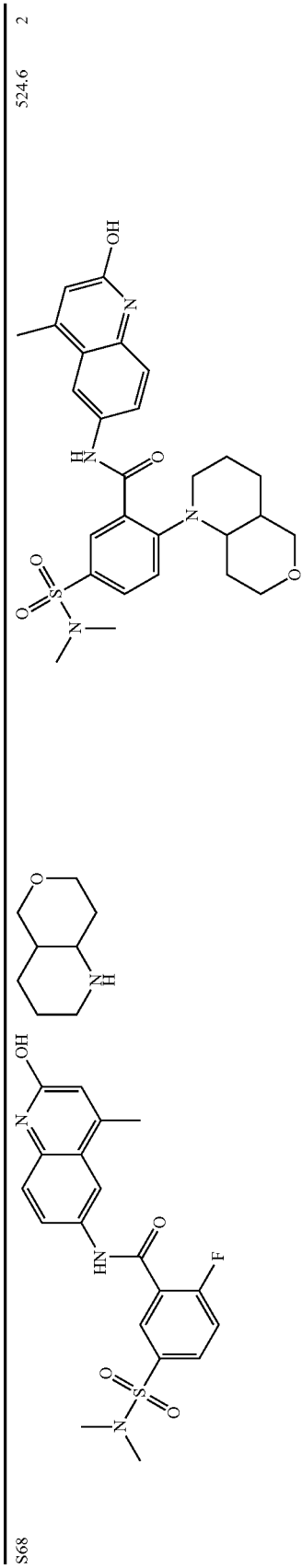
S68 2-(2,3,4,4a,5,7,8,8a-octahydropyrano[4,3-b]pyridin-1-yl)-5-(dimethylsulfamoyl)-N-(2-hydroxy-4-methyl-6-quinolyl)benzamide 524.6 2
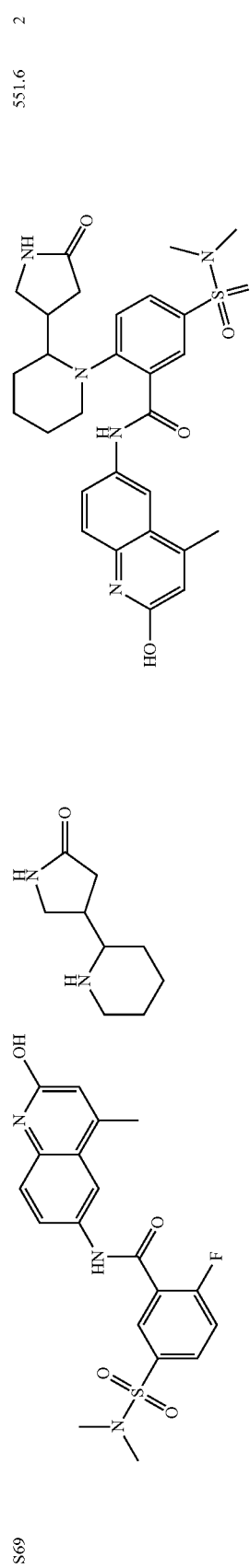
S69 5-(dimethylsulfamoyl)-N-(2-hydroxy-4-methyl-6-quinolyl)-2-[2-(5-oxopyrrolidin-3-yl)-1-piperidyl]benzamide 551.6 2

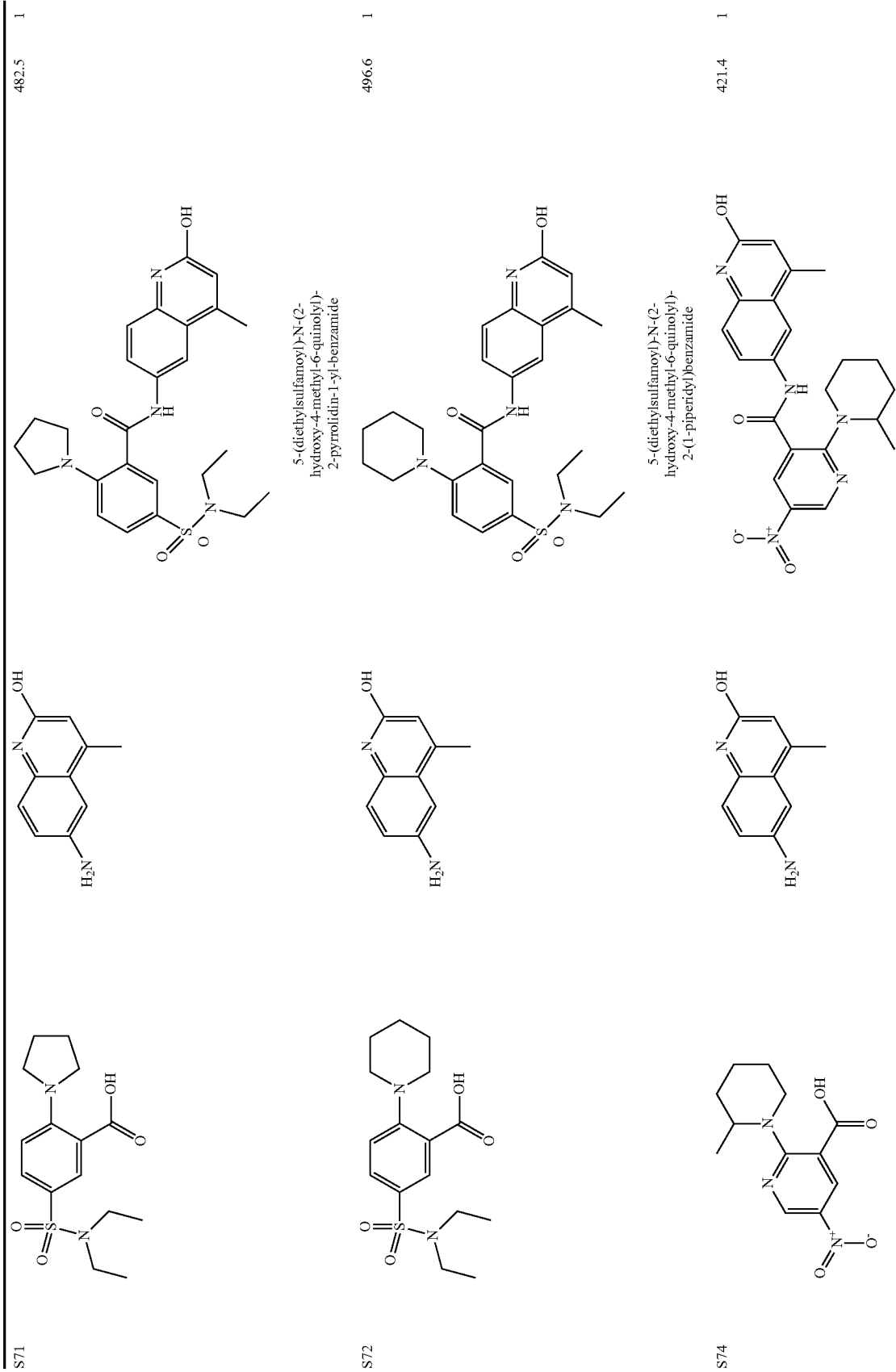

| | | | | |
|---|---|---|---|---|
| | N-(2-hydroxy-4-methyl-6-quinolyl)-2-(2-methyl-1-piperidyl)-5-nitro-pyridine-3-carboxamide | | 380.3 | 1 |
| S76 | 5-nitro-N-(2-oxo-3,4-dihydro-1H-quinolin-6-yl)-2-pyrrolidin-1-yl-benzamide | 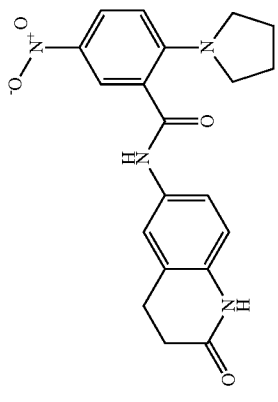 | 396.3 | 1 |
| S77 | N-(4-methyl-3-oxo-1,4-benzoxazin-7-yl)-5-nitro-2-pyrrolidin-1-yl-benzamide | 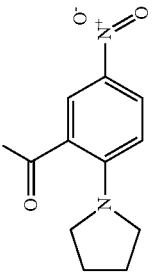 | | |

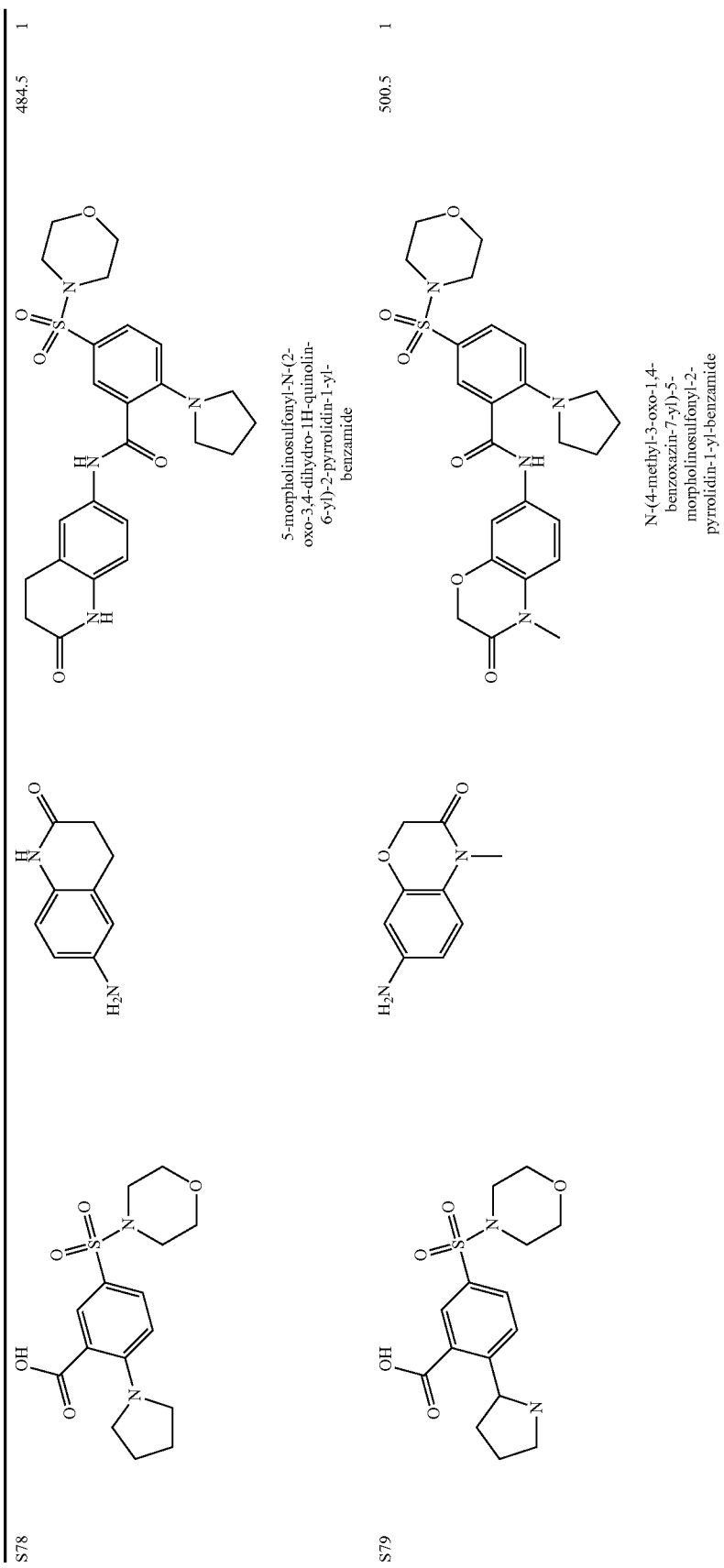

-continued
| S82 | 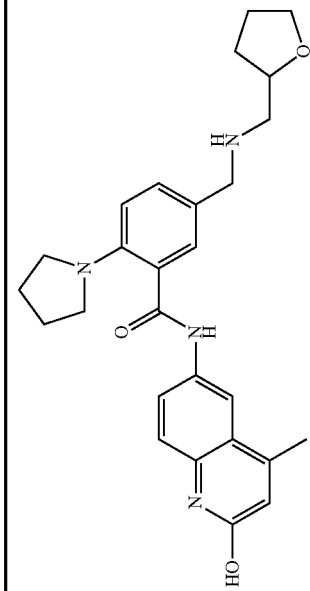 | 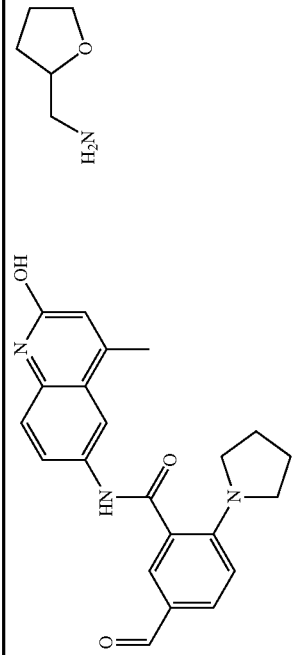 | 460.5 | 3 |
N-(2-hydroxy-4-methyl-6-quinolyl)-2-pyrrolidin-1-yl-5-[(tetrahydrofuran-2-ylmethylamino)methyl]benzamide
| S83 | 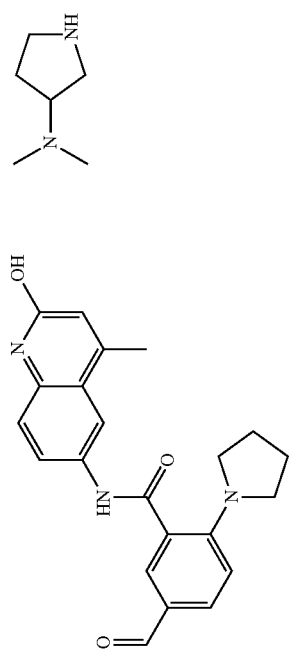 | | 473.6 | 3 |
5-[[3-(dimethylamino)pyrrolidin-1-yl]methyl]-N-(2-hydroxy-4-methyl-6-quinolyl)-2-pyrrolidin-1-yl-benzamide

| S84 | 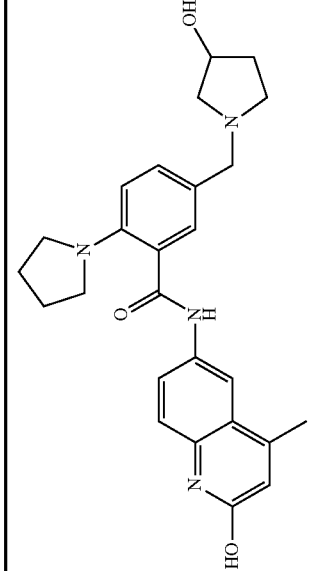 | 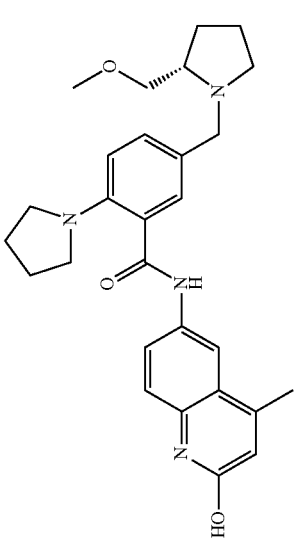 | 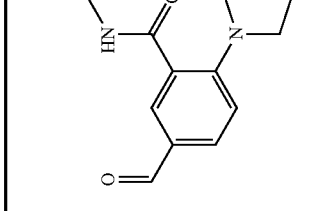 | N-(2-hydroxy-4-methyl-6-quinolyl)-5-[(3-hydroxypyrrolidin-1-yl)methyl]-2-pyrrolidin-1-yl-benzamide | 446.5 | 3 |
| S85 | 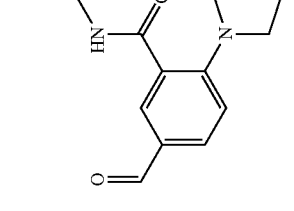 | | | N-(2-hydroxy-4-methyl-6-quinolyl)-5-[[(2S)-2-(methoxymethyl)pyrrolidin-1-yl]methyl]-2-pyrrolidin-1-yl-benzamide | 474.5 | 3 |

| | | | |
|---|---|---|---|
| S86 | 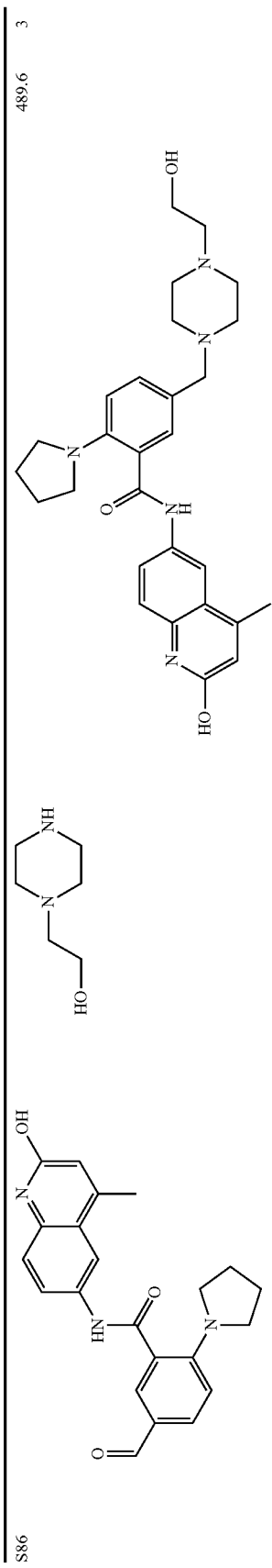 | 5-[[4-(2-hydroxyethyl)piperazin-1-yl]methyl]-N-(2-hydroxy-4-methyl-6-quinolyl)-2-pyrrolidin-1-yl-benzamide | 489.6 | 3 |
| S87 | 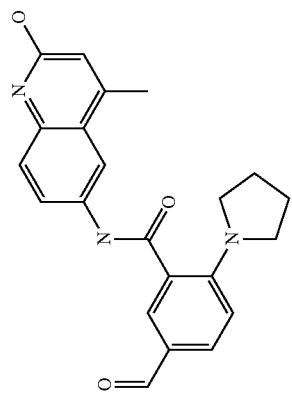 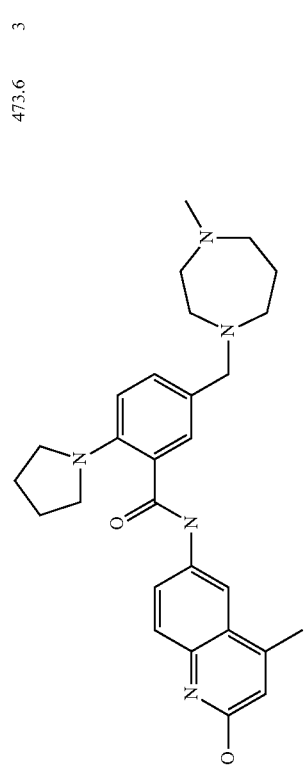 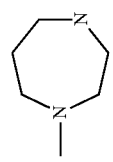 | N-(2-hydroxy-4-methyl-6-quinolyl)-5-[(4-methyl-1,4-diazepan-1-yl)methyl]-2-pyrrolidin-1-yl-benzamide | 473.6 | 3 |

-continued
| | | | |
|---|---|---|---|
| S88 | 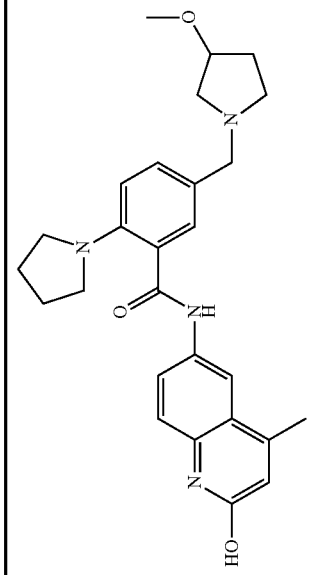 | 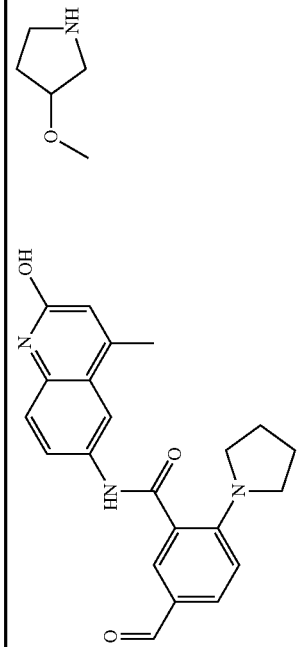 N-(2-hydroxy-4-methyl-6-quinolyl)-5-[(3-methoxypyrrolidin-1-yl)methyl]-2-pyrrolidin-1-yl-benzamide | 460.5  3 |
| S89 | 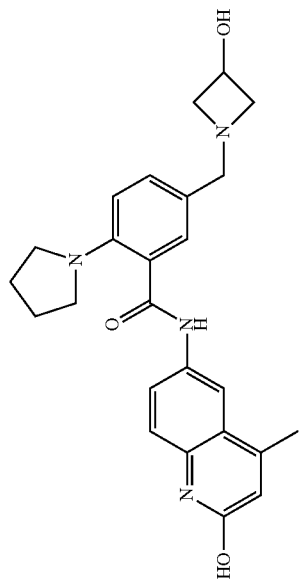 | 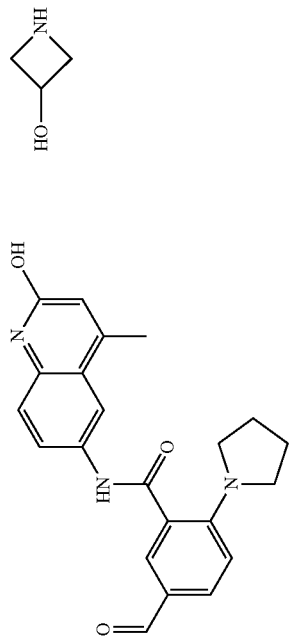 5-[(3-hydroxyazetidin-1-yl)methyl]-N-(2-hydroxy-4-methyl-6-quinolyl)-2-pyrrolidin-1-yl-benzamide | 432.5  3 |

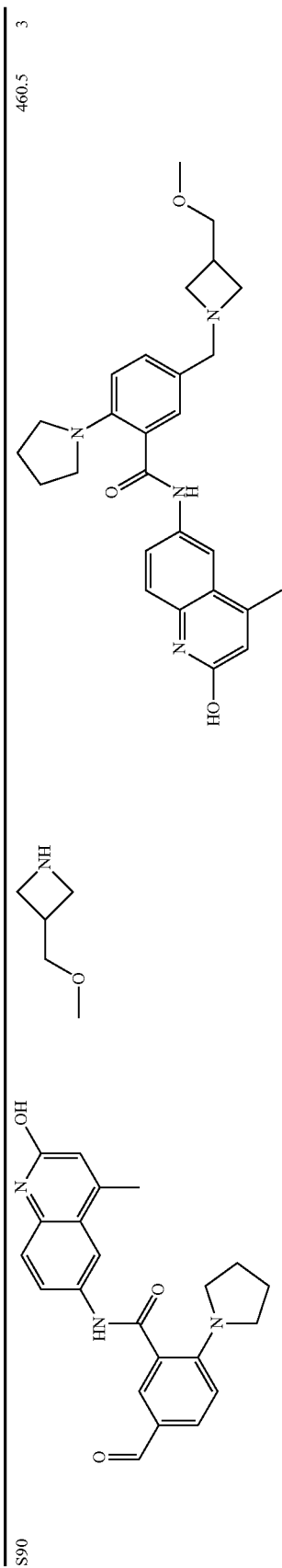
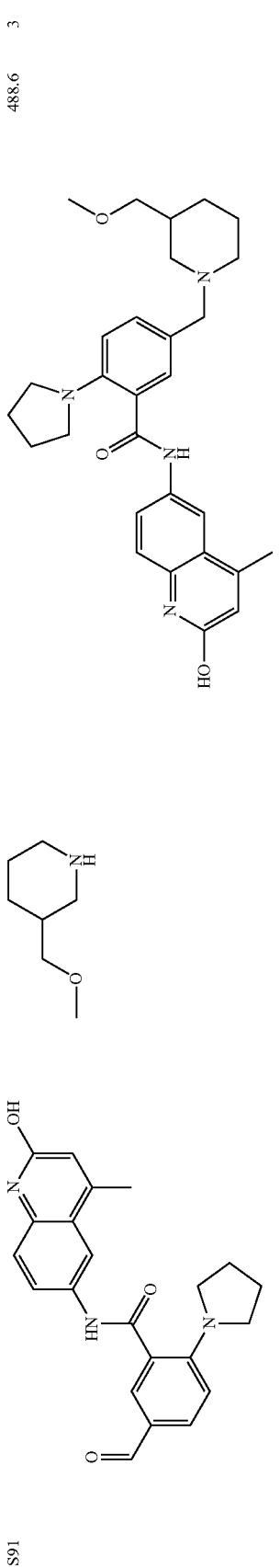
| | | |
|---|---|---|
| S90 | N-(2-hydroxy-4-methyl-6-quinolyl)-5-[[3-(methoxymethyl)azetidin-1-yl]methyl]-2-pyrrolidin-1-yl-benzamide | 460.5 3 |
| S91 | N-(2-hydroxy-4-methyl-6-quinolyl)-5-[[3-(methoxymethyl)-1-piperidyl]methyl]-2-pyrrolidin-1-yl-benzamide | 488.6 3 |

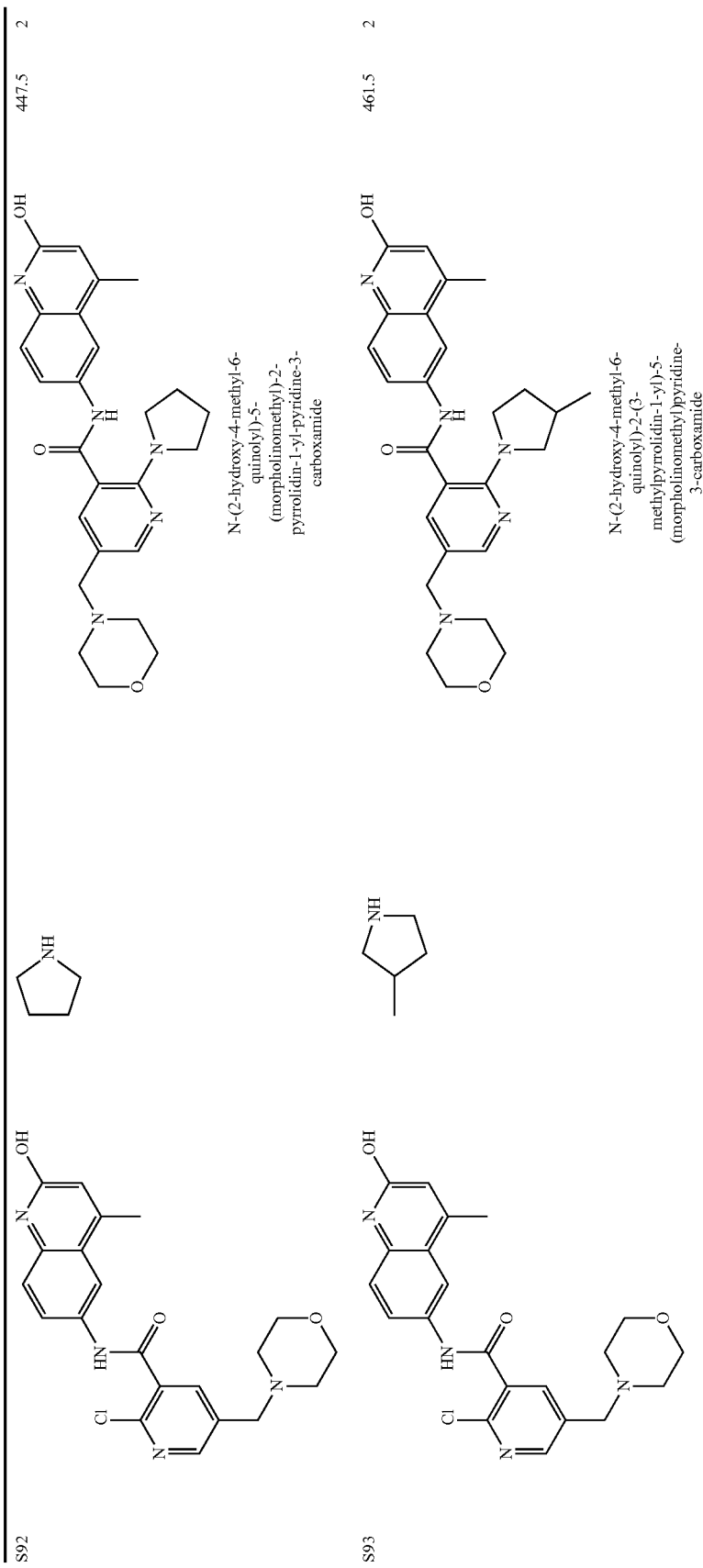

| | | | |
|---|---|---|---|
| S94 | 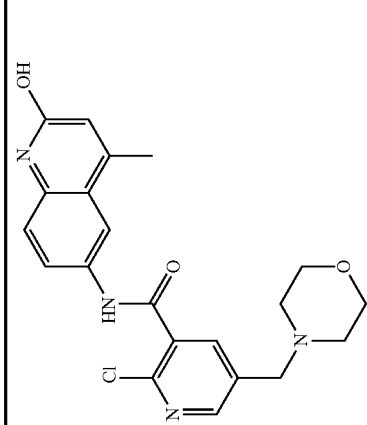 | 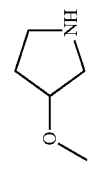 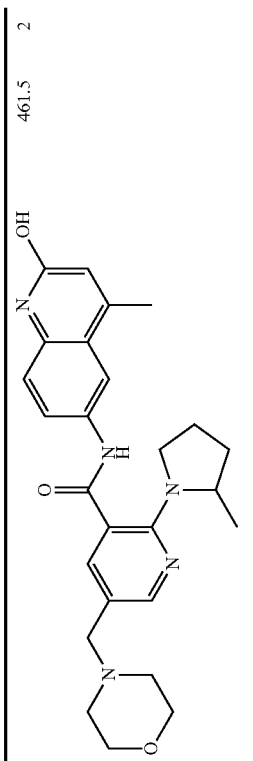 N-(2-hydroxy-4-methyl-6-quinolyl)-2-(2-methylpyrrolidin-1-yl)-5-(morpholinomethyl)pyridine-3-carboxamide | 461.5 2 |
| S96 | | 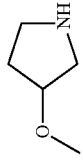 N-(2-hydroxy-4-methyl-6-quinolyl)-2-(3-methoxypyrrolidin-1-yl)-5-(morpholinomethyl)pyridine-3-carboxamide | 477.5 2 |

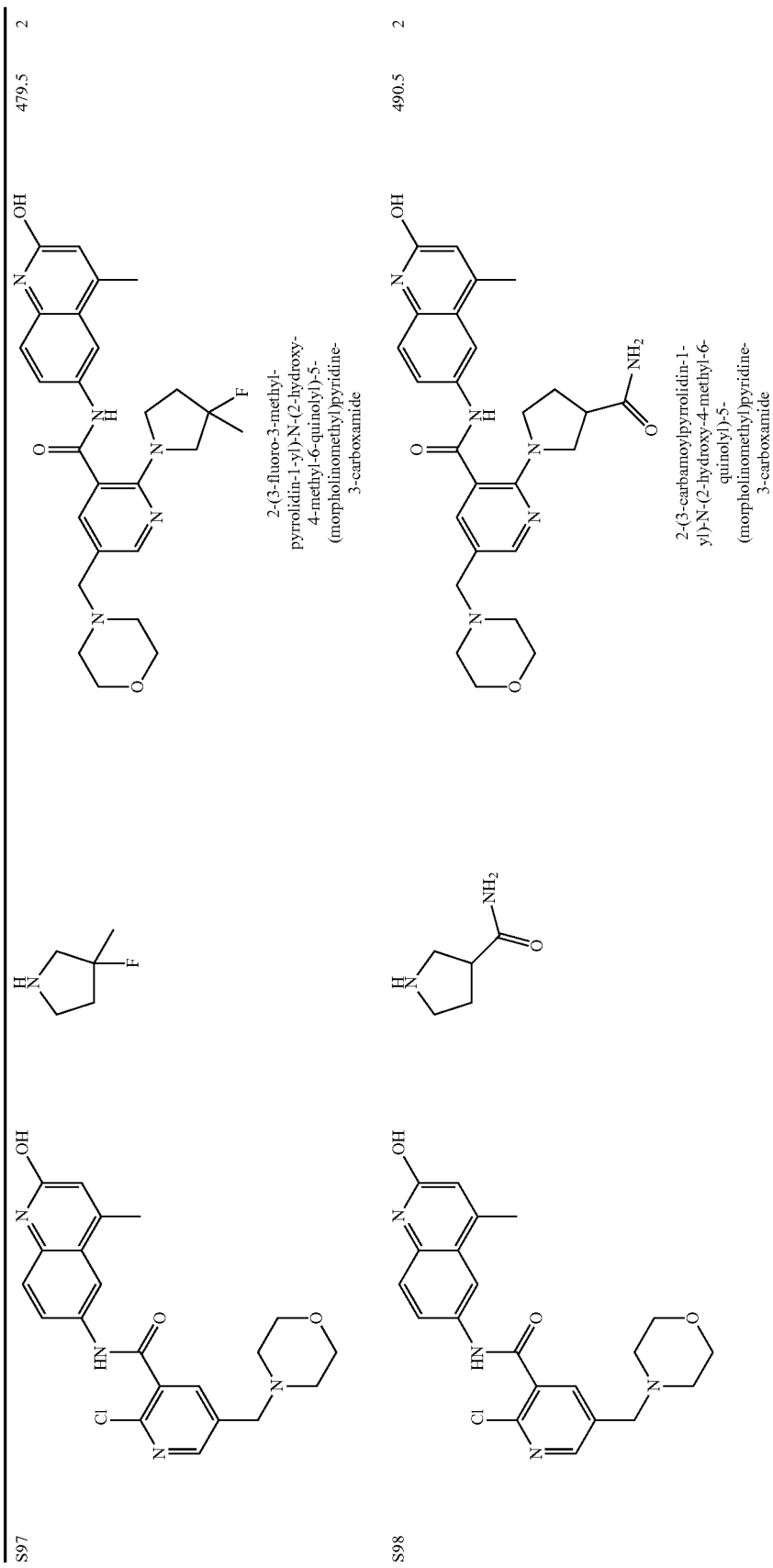

| | | | | |
|---|---|---|---|---|
| S99 | 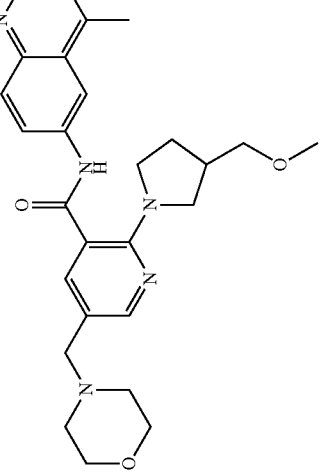 | 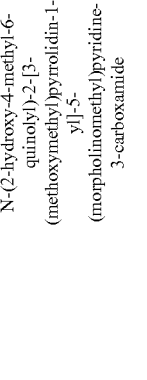 | N-(2-hydroxy-4-methyl-6-quinolyl)-2-[3-(methoxymethyl)pyrrolidin-1-yl]-5-(morpholinomethyl)pyridine-3-carboxamide | 491.5  2 |
| S100 | 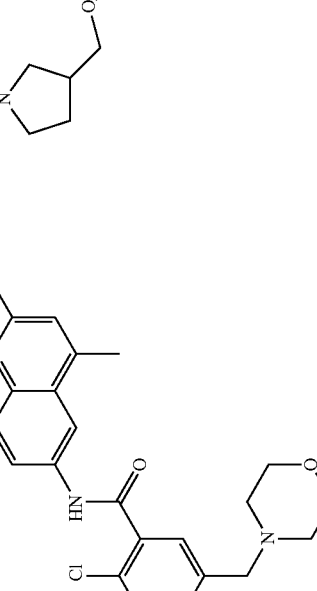 |  | N-(2-hydroxy-4-methyl-6-quinolyl)-2-(2-isobutylpyrrolidin-1-yl)-5-(morpholinomethyl)pyridine-3-carboxamide | 503.6  2 |

| | | | |
|---|---|---|---|
| S101 | 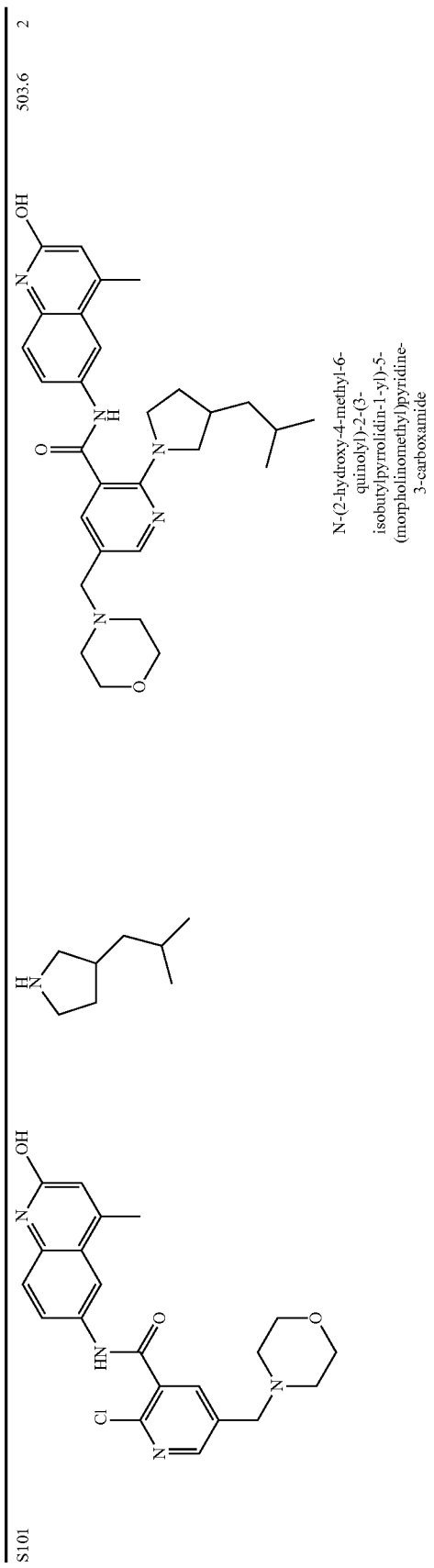 | N-(2-hydroxy-4-methyl-6-quinolyl)-2-(3-isobutylpyrrolidin-1-yl)-5-(morpholinomethyl)pyridine-3-carboxamide | 503.6 2 |
| S102 | 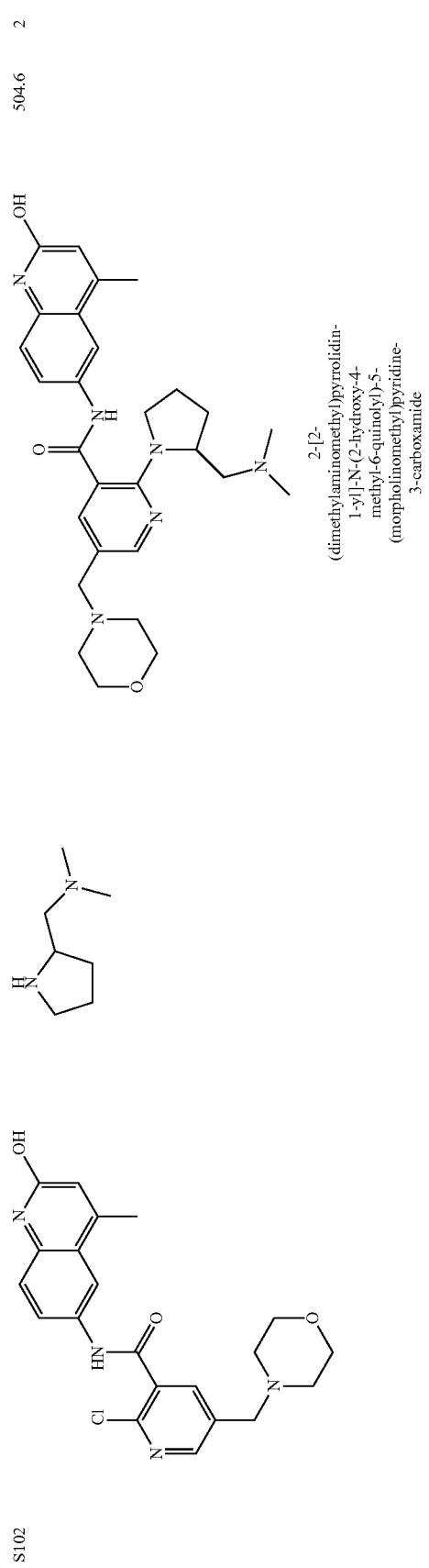 | 2-[2-(dimethylaminomethyl)pyrrolidin-1-yl]-N-(2-hydroxy-4-methyl-6-quinolyl)-5-(morpholinomethyl)pyridine-3-carboxamide | 504.6 2 |

| | | | | |
|---|---|---|---|---|
| S103 | 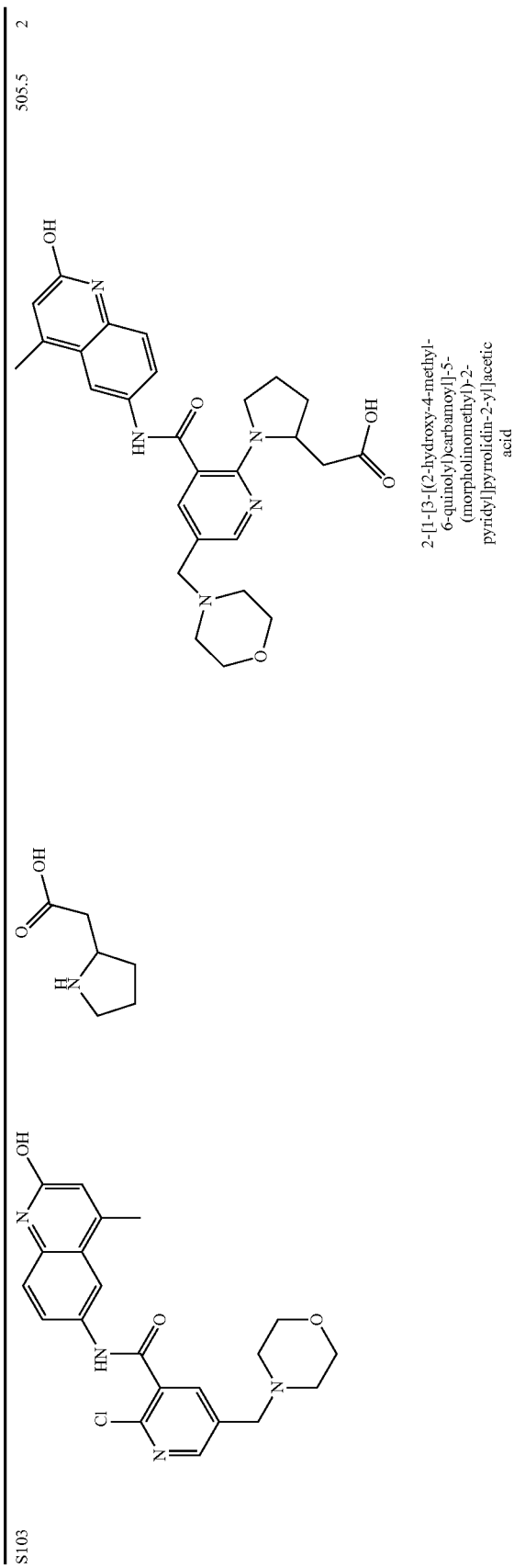 | | | 505.5 2<br>2-[1-[3-[(2-hydroxy-4-methyl-6-quinolyl)carbamoyl]-5-(morpholinomethyl)-2-pyridyl]pyrrolidin-2-yl]acetic acid |
| S104 | | 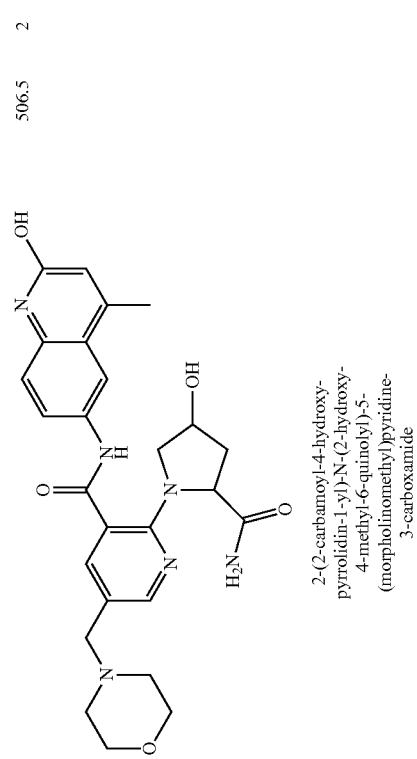 | 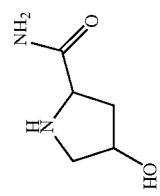<br>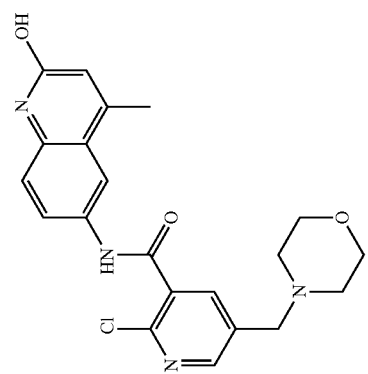 | 506.5 2<br>2-(2-carbamoyl-4-hydroxy-pyrrolidin-1-yl)-N-(2-hydroxy-4-methyl-6-quinolyl)-5-(morpholinomethyl)pyridine-3-carboxamide |

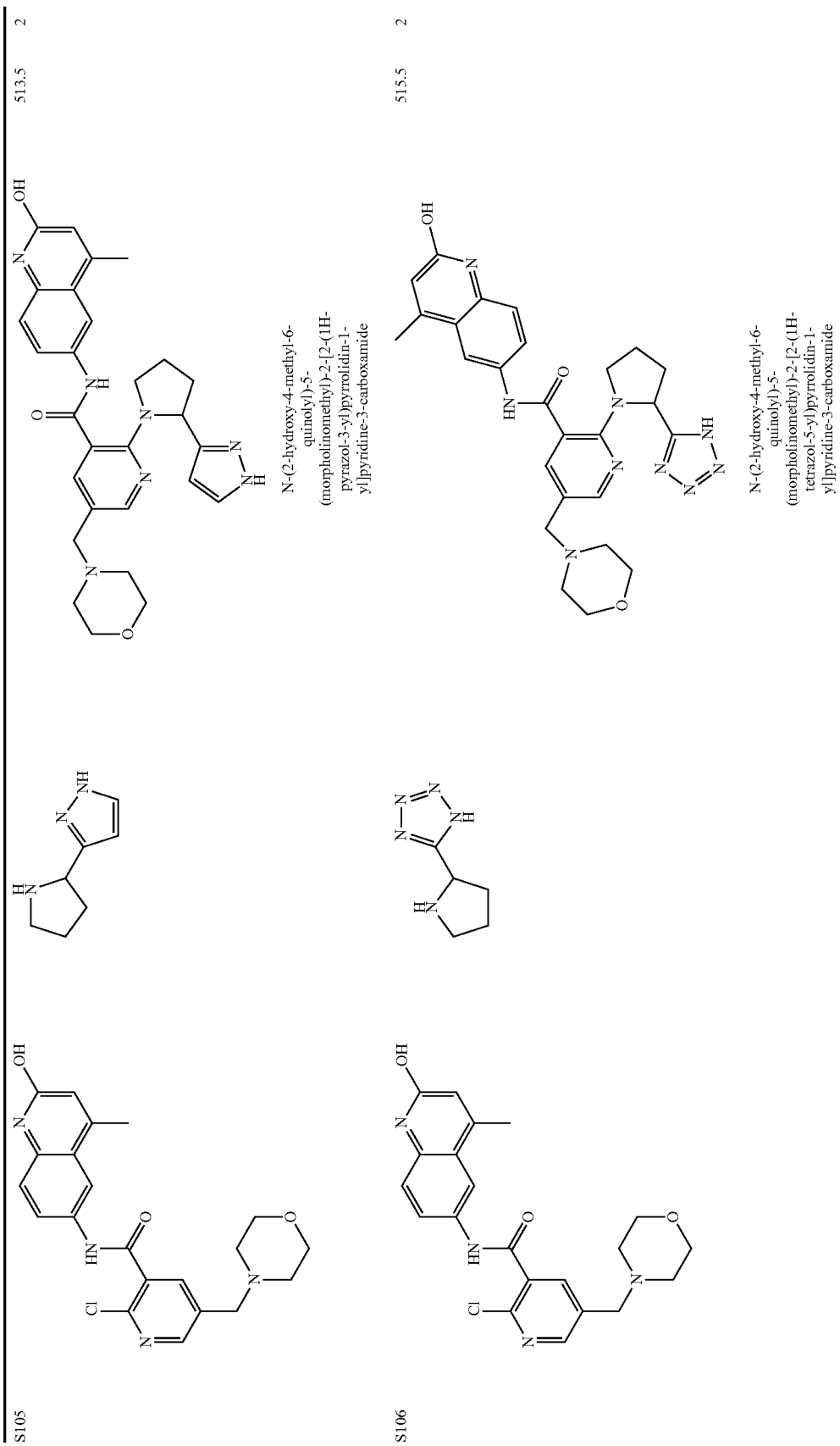

-continued
| S107 | 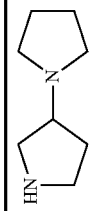 | 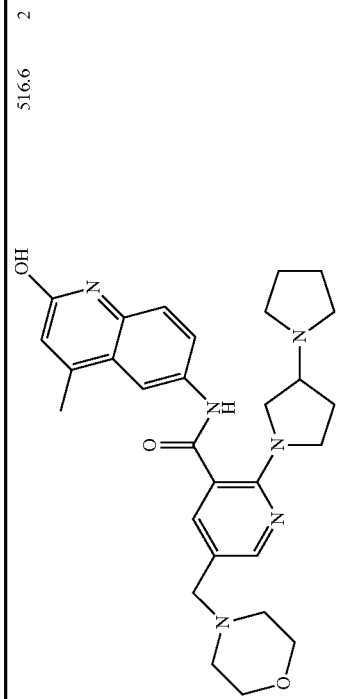 N-(2-hydroxy-4-methyl-6-quinolyl)-2-(3-pyrrolidin-1-ylpyrrolidin-1-yl)pyridine-3-carboxamide | 516.6 | 2 |
| S108 | 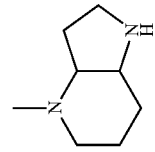 | 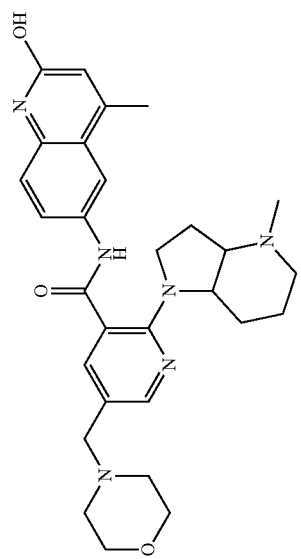 N-(2-hydroxy-4-methyl-6-quinolyl)-2-(4-methyl-3,3a,5,6,7,7a-hexahydro-2H-pyrrolo[3,2-b]pyridin-1-yl)-5-(morpholinomethyl)pyridine-3-carboxamide | 516.6 | 2 |
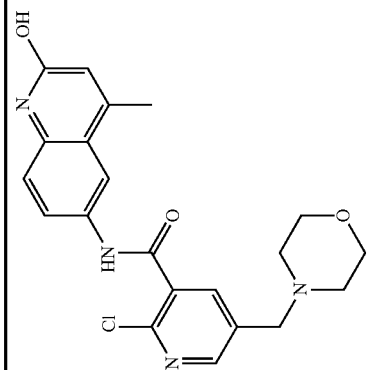
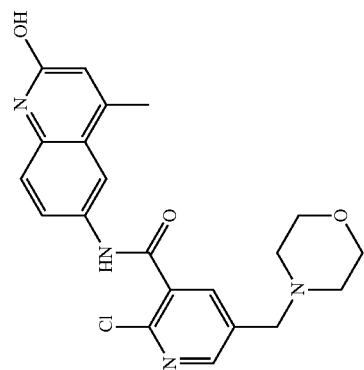

| | | | |
|---|---|---|---|
| S109 | 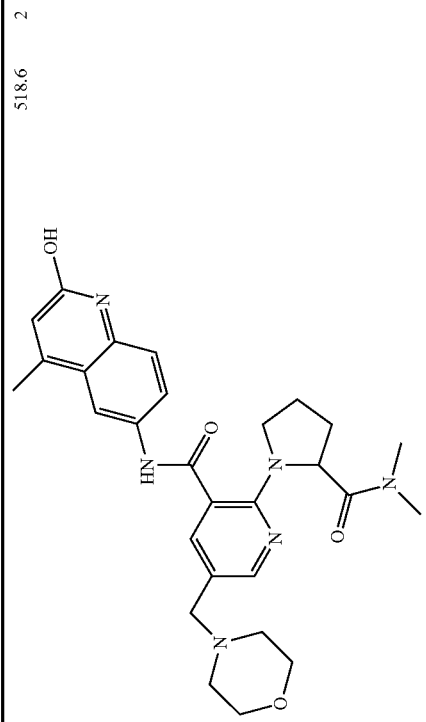<br>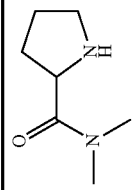 | 2-[2-(dimethylcarbamoyl)pyrrolidin-1-yl]-N-(2-hydroxy-4-methyl-6-quinolyl)-5-(morpholinomethyl)pyridine-3-carboxamide | 518.6  2 |
| S110 | 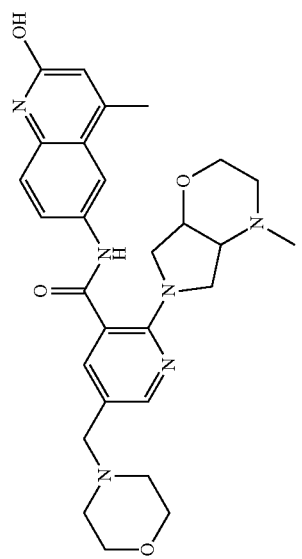<br>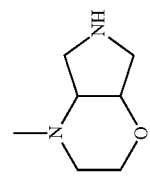 | N-(2-hydroxy-4-methyl-6-quinolyl)-2-(4-methyl-2,3,4a,5,7,7a-hexahydropyrrolo[3,4-b][1,4]oxazin-6-yl)-5-(morpholinomethyl)pyridine-3-carboxamide | 518.6  2 |
| S109 | 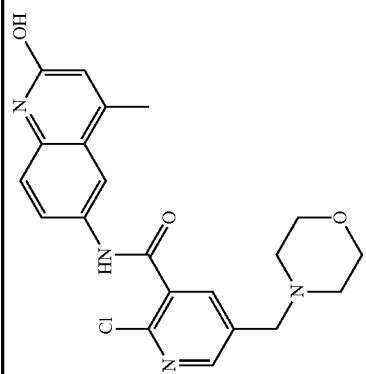 | | |
| S110 | 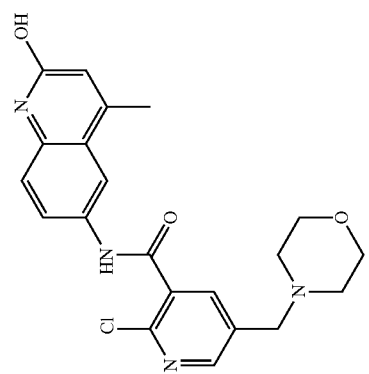 | | |

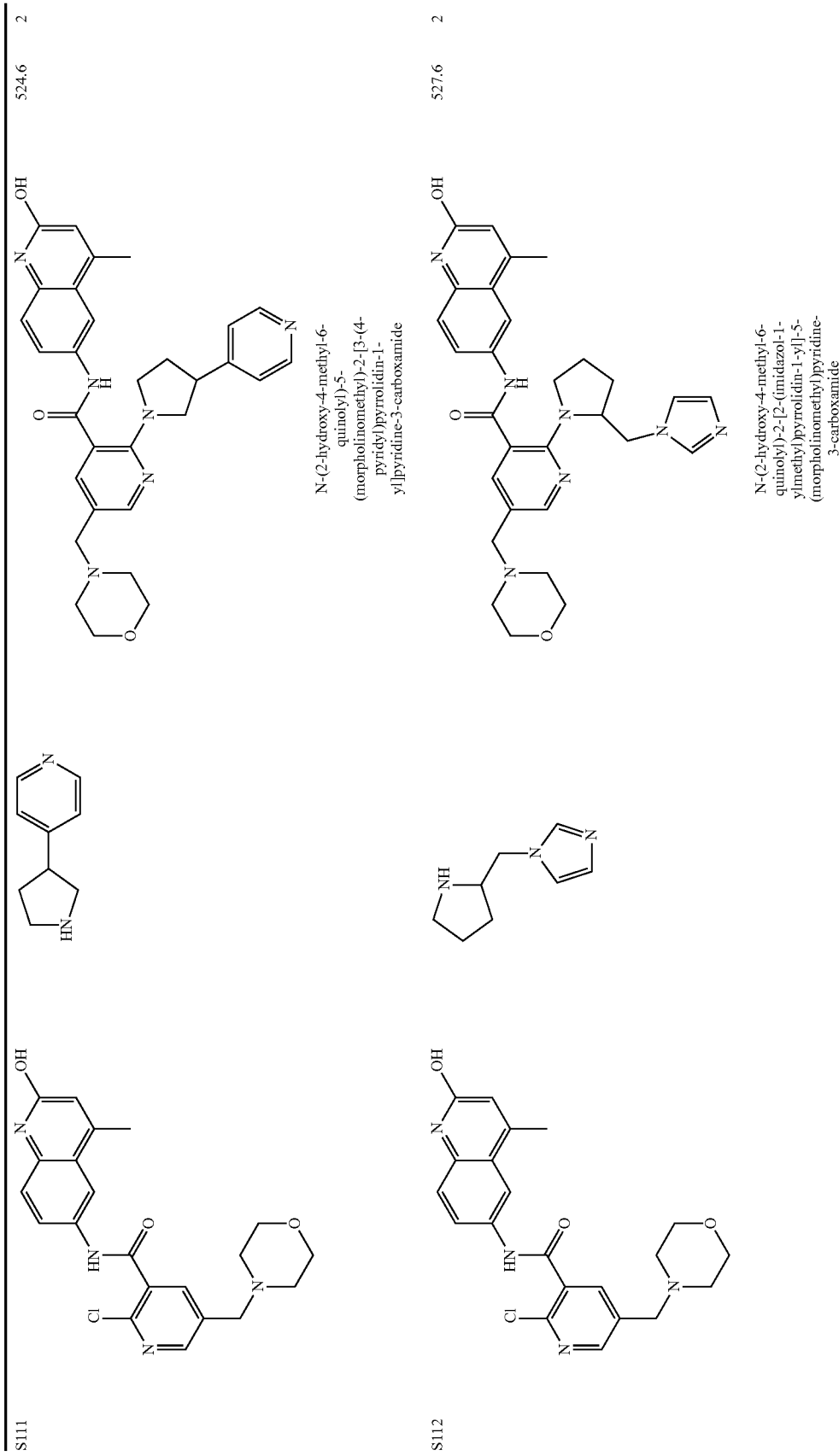

| S113 | 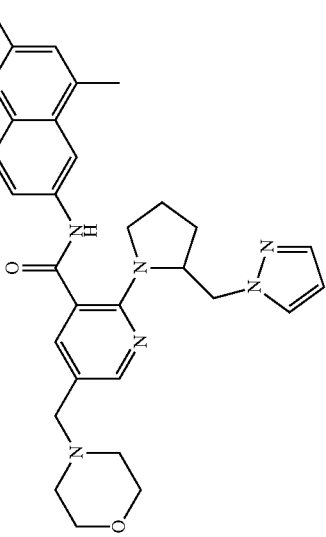 |  | N-(2-hydroxy-4-methyl-6-quinolyl)-5-(morpholinomethyl)-2-[2-(pyrazol-1-ylmethyl)pyrrolidin-1-yl]pyridine-3-carboxamide | 527.6 | 2 |
| S114 |  | 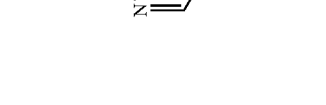 | 2-[2-(hydroxymethyl)morpholin-4-yl]-N-(2-hydroxy-4-methyl-6-quinolyl)-5-(morpholinomethyl)pyridine-3-carboxamide | 493.5 | 2 |

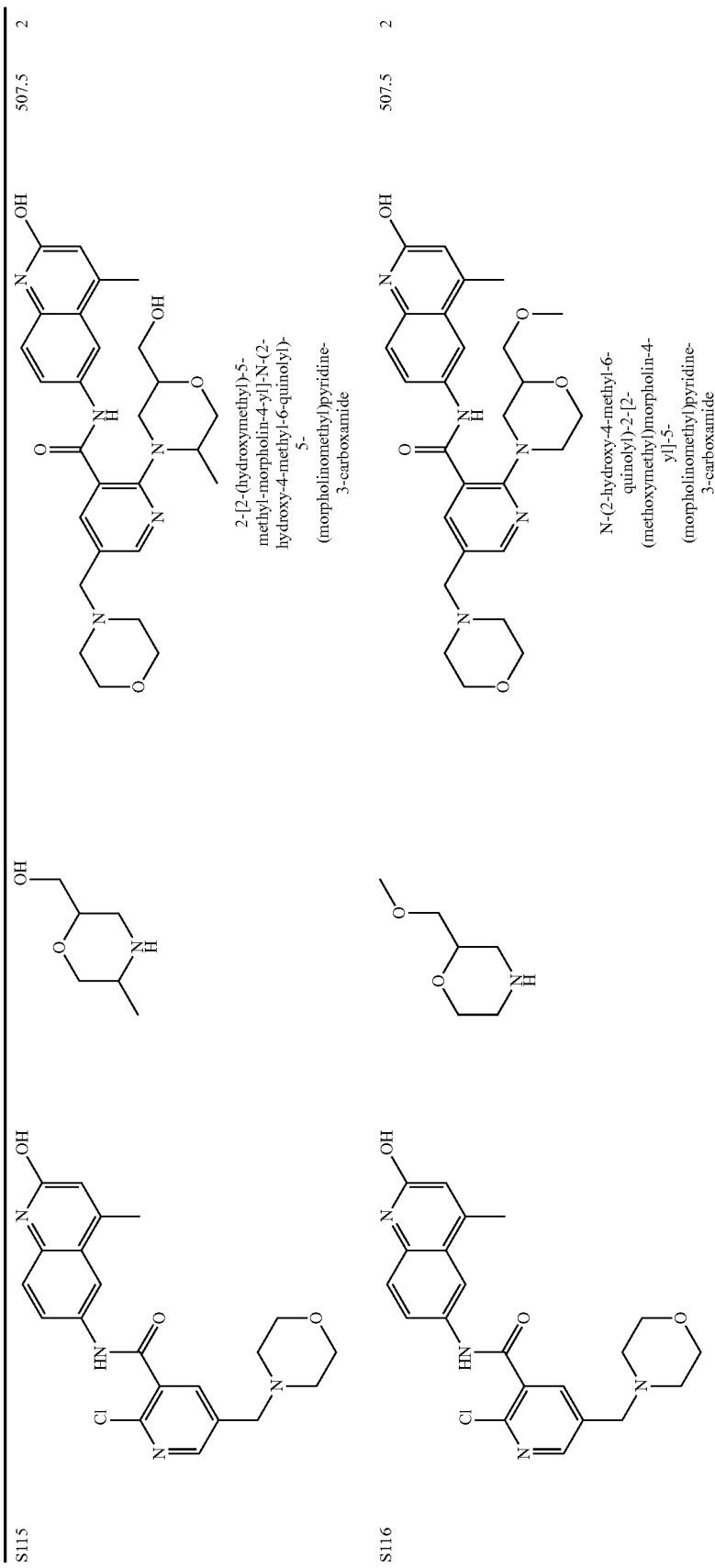

| ID | Structure | Name | MW | n |
|---|---|---|---|---|
| S117 | | 2-[2-(dimethylaminomethyl)morpholin-4-yl]-N-(2-hydroxy-4-methyl-6-quinolyl)-5-(morpholinomethyl)pyridine-3-carboxamide | 520.6 | 2 |
| S118 | | 2-[3-(hydroxymethyl)pyrrolidin-1-yl]-N-(2-hydroxy-4-methyl-6-quinolyl)-5-(morpholinomethyl)pyridine-3-carboxamide | 477.5 | 2 |

| Additional examples | | | Additional examples |
|---|---|---|---|
| S119 | 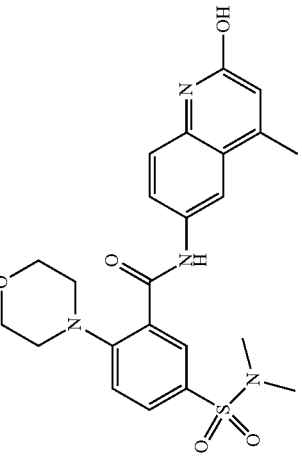 | 470.5 | 1 5-(dimethylsulfamoyl)-N-(2-hydroxy-4-methyl-6-quinolyl)-2-morpholino-benzamide |
| S120 | 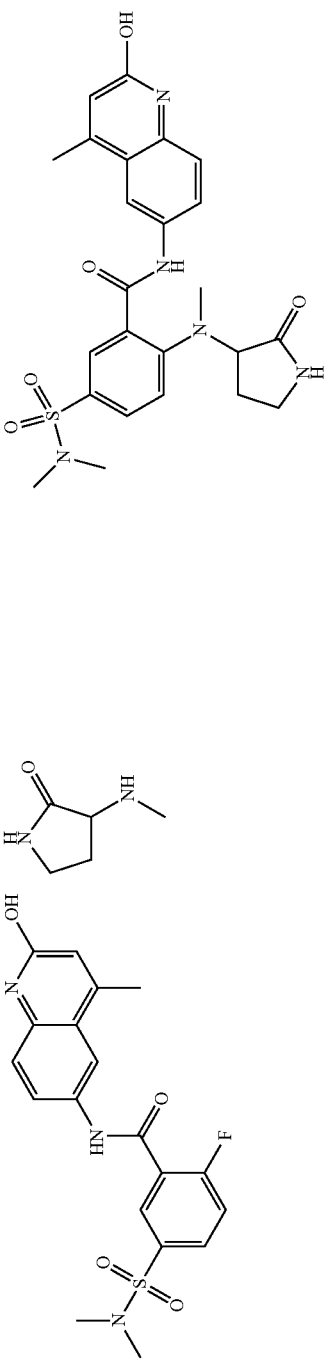 | 497.5 | 2 5-(dimethylsulfamoyl)-N-(2-hydroxy-4-methyl-6-quinolyl)-2-[methyl-(2-oxopyrrolidin-3-yl)amino]benzamide |

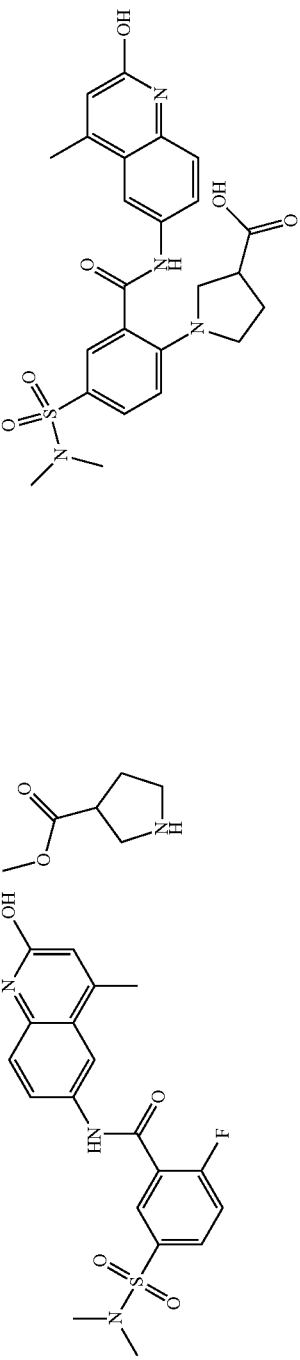
| | | |
|---|---|---|
| S121 | | 498.5 | 2 |
1-[4-(dimethylsulfamoyl)-2-[[(2-hydroxy-4-methyl-6-quinolyl)carbamoyl]phenyl]pyrrolidine-3-carboxylic acid
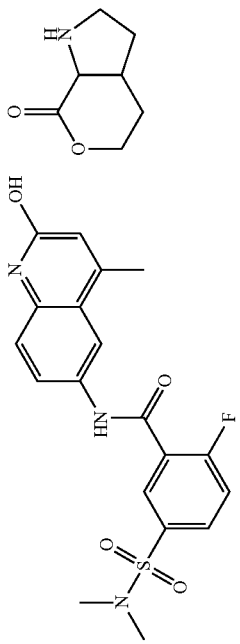
| S122 | | 524.5 | 2 |
5-(dimethylsulfamoyl)-N-(2-hydroxy-4-methyl-6-quinolyl)-2-(7-oxo-2,3,3a,4,5,7a-hexahydropyrano[3,4-b]pyrrol-1-yl)benzamide

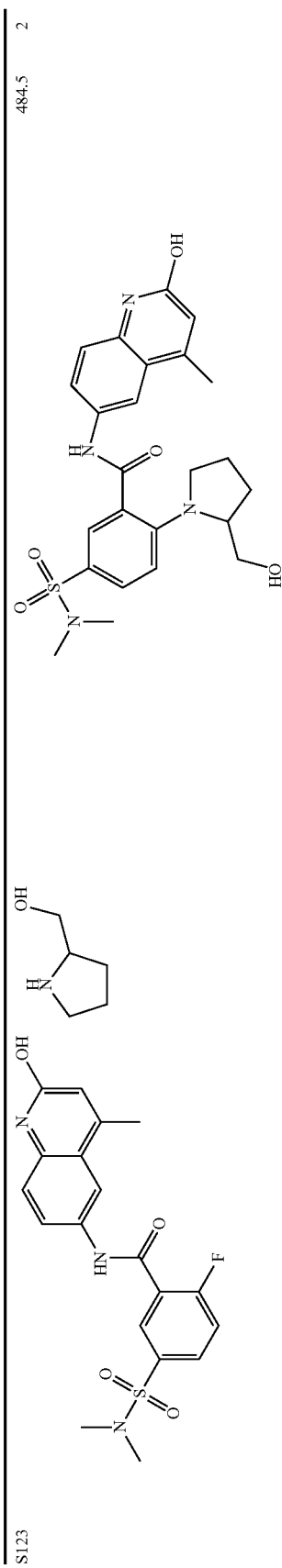
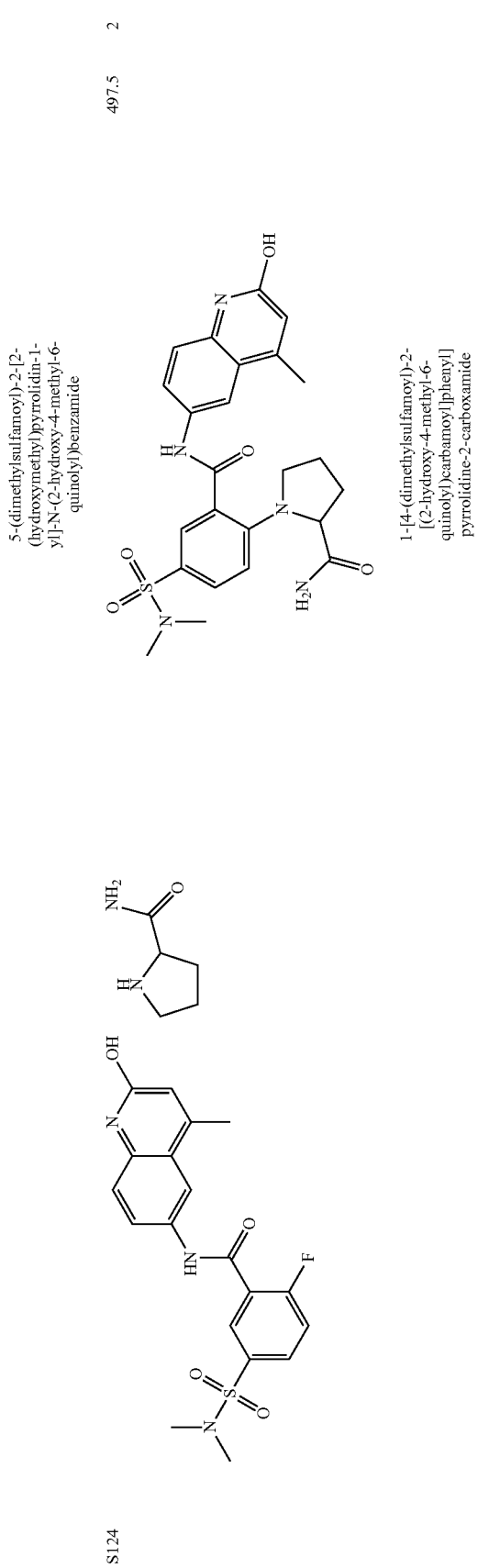

-continued
| | | |
|---|---|---|
| S125 | 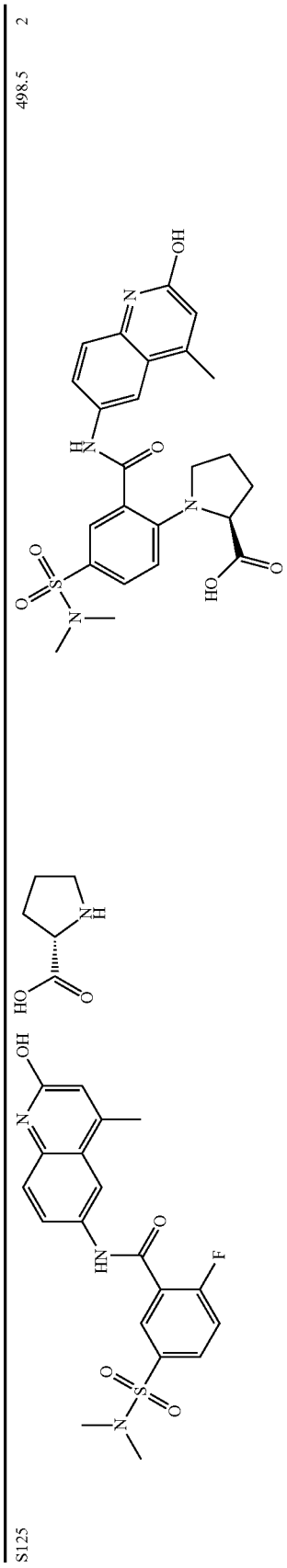 (2S)-1-[4-(dimethylsulfamoyl)-2-[(2-hydroxy-4-methyl-6-quinolyl)carbamoyl]phenyl]pyrrolidine-2-carboxylic acid | 498.5 2 |
| S126 | 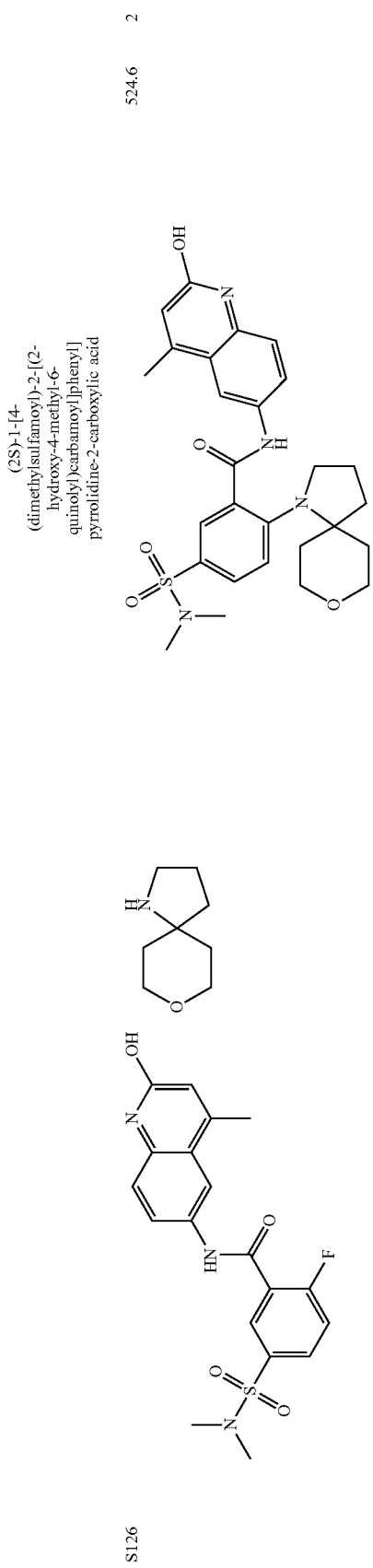 5-(dimethylsulfamoyl)-N-(2-hydroxy-4-methyl-6-quinolyl)-2-(8-oxa-4-azaspiro[4.5]decan-4-yl)benzamide | 524.6 2 |

| | | | |
|---|---|---|---|
| S127 | [structure] | 2-(2,5-dimethyl-4-oxo-1-piperidyl)-5-(dimethylsulfamoyl)-N-(2-hydroxy-4-methyl-6-quinolyl)benzamide | 510.6 | 2 |
| S128 | [structure] | 5-(dimethylsulfamoyl)-N-(2-hydroxy-4-methyl-6-quinolyl)-2-[2-(2H-tetrazol-5-yl)-1-piperidyl]benzamide | 536.6 | 2 |

| | | | |
|---|---|---|---|
| S129 | 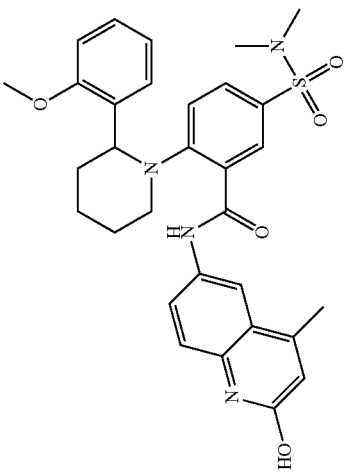 | 5-(dimethylsulfamoyl)-N-(2-hydroxy-4-methyl-6-quinolyl)-2-[2-(2-methoxyphenyl)-1-piperidyl]benzamide | 574.6 | 2 |
| S130 | 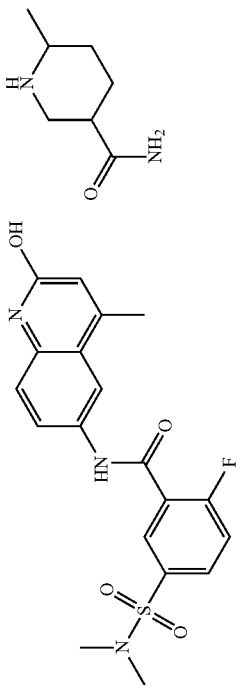 | 1-[4-(dimethylsulfamoyl)-2-[(2-hydroxy-4-methyl-6-quinolyl)carbamoyl]phenyl]-6-methyl-piperidine-3-carboxamide | 525.6 | 2 |

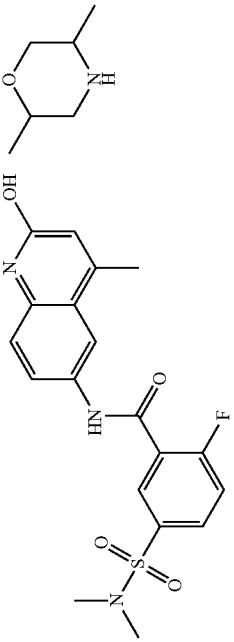
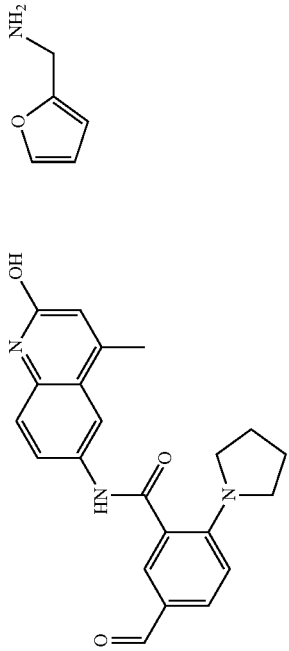
| | | |
|---|---|---|
| S131 | 2-(2,5-dimethylmorpholin-4-yl)-5-(dimethylsulfamoyl)-N-(2-hydroxy-4-methyl-6-quinolyl)benzamide | 498.5 2 |
| S132 | 5-[(2-furylmethylamino)methyl]-N-(2-hydroxy-4-methyl-6-quinolyl)-2-pyrrolidin-1-yl-benzamide | 456.5 3 |

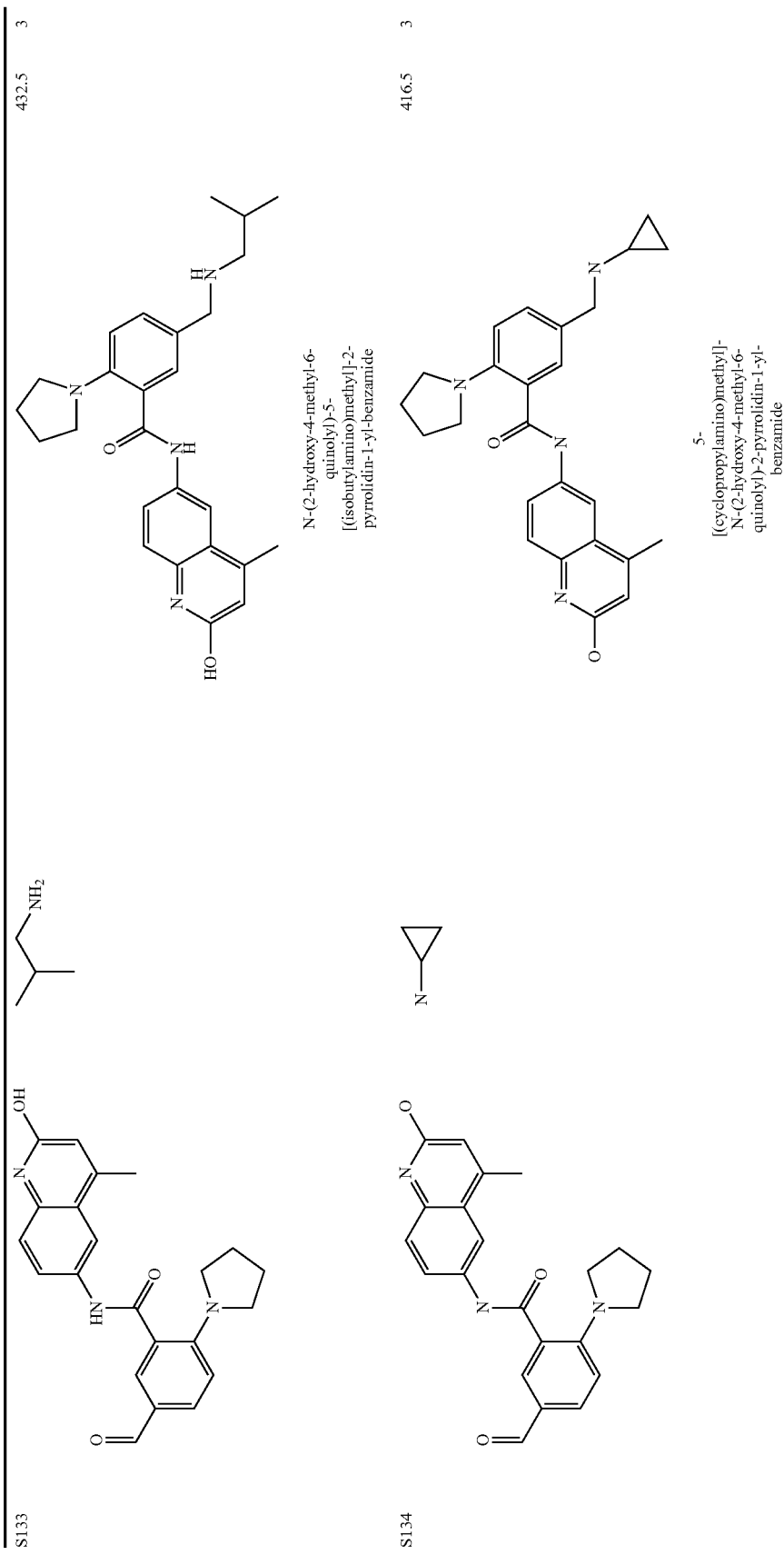

-continued
| | | | |
|---|---|---|---|
| S135 | 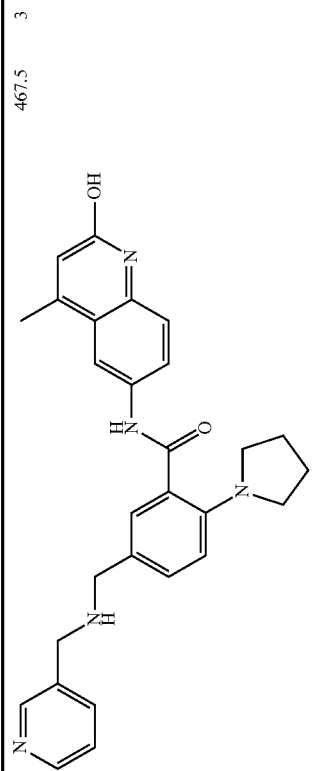 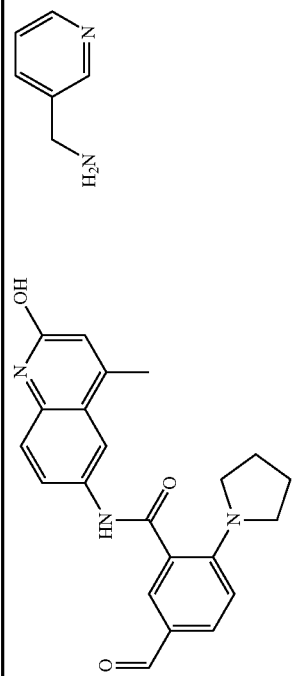 | 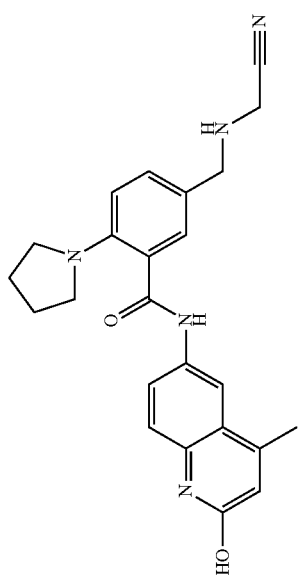 N-(2-hydroxy-4-methyl-6-quinolyl)-5-[(3-pyridylmethylamino)methyl]-2-pyrrolidin-1-yl-benzamide | 467.5  3 |
| S136 | 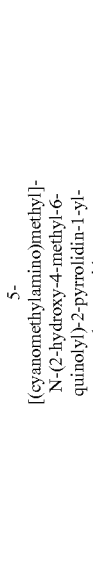 | 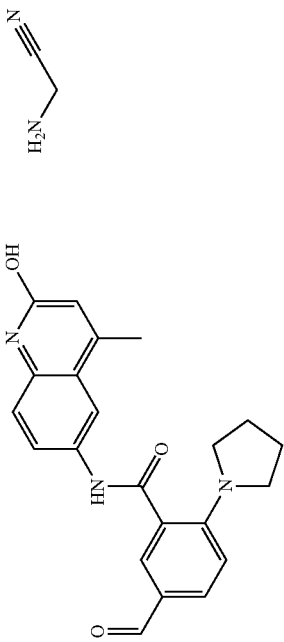 5-[(cyanomethylamino)methyl]-N-(2-hydroxy-4-methyl-6-quinolyl)-2-pyrrolidin-1-yl-benzamide | 415.4  3 |

| | | | | |
|---|---|---|---|---|
| S137 | 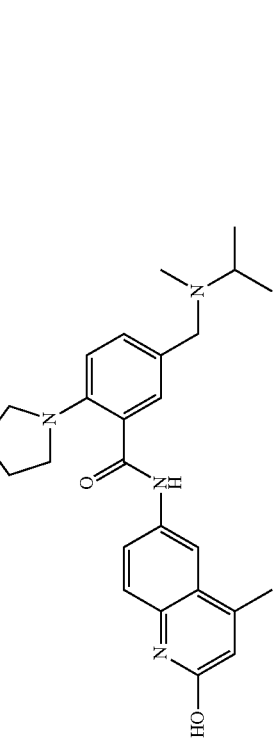 | 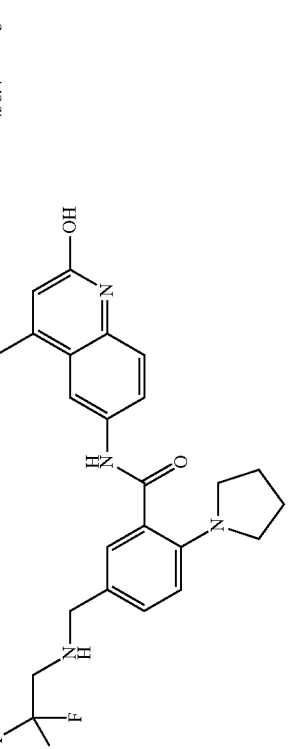 | N-(2-hydroxy-4-methyl-6-quinolyl)-5-[[isopropyl(methyl)amino]methyl]-2-pyrrolidin-1-yl-benzamide | 432.5 | 3 |
| S138 | | | N-(2-hydroxy-4-methyl-6-quinolyl)-2-pyrrolidin-1-yl-5-[(2,2,2-trifluoroethylamino)methyl]benzamide | 458.4 | 3 |

| | | | |
|---|---|---|---|
| S139 | 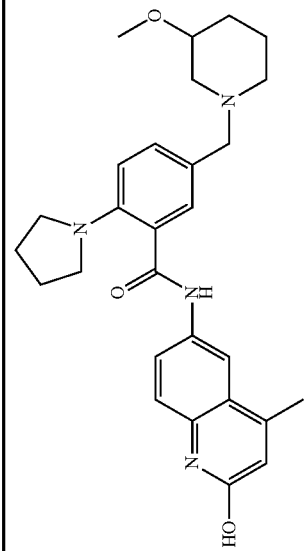 |  | N-(2-hydroxy-4-methyl-6-quinolyl)-5-[(3-methoxy-1-piperidyl)methyl]-2-pyrrolidin-1-yl-benzamide | 474.5 | 3 |
| S140 | 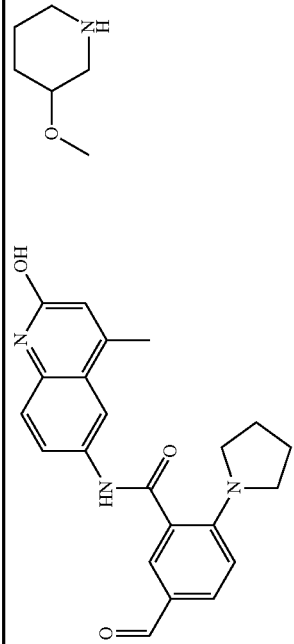 |  | 5-[[3-(dimethylamino)azetidin-1-yl]methyl]-N-(2-hydroxy-4-methyl-6-quinolyl)-2-pyrrolidin-1-yl-benzamide | 459.5 | 3 |

| | | | | |
|---|---|---|---|---|
| S141 | 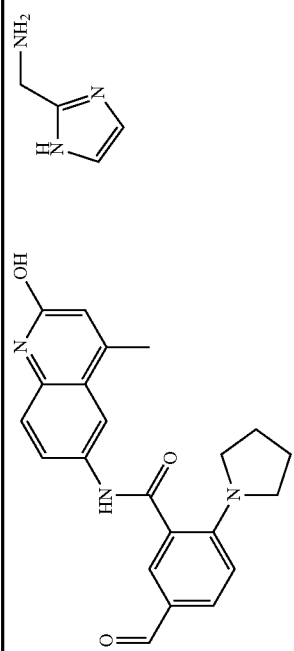 |  | N-(2-hydroxy-4-methyl-6-quinolyl)-5-[((1H-imidazol-2-yl)methylamino)methyl]-2-pyrrolidin-1-yl-benzamide | 456.5 3 |
| S142 | 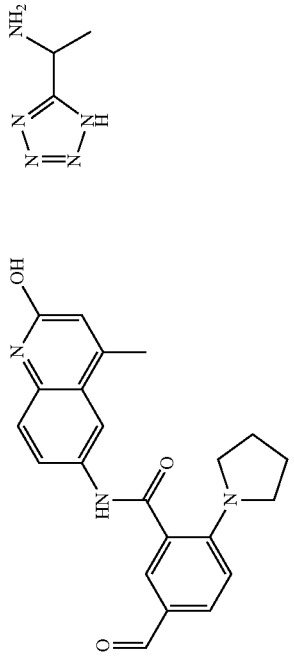 | 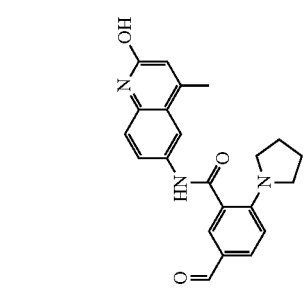 | N-(2-hydroxy-4-methyl-6-quinolyl)-2-pyrrolidin-1-yl-5-[[1-(1H-tetrazol-5-yl)ethylamino]methyl]benzamide | 472.5 3 |
| S143 | 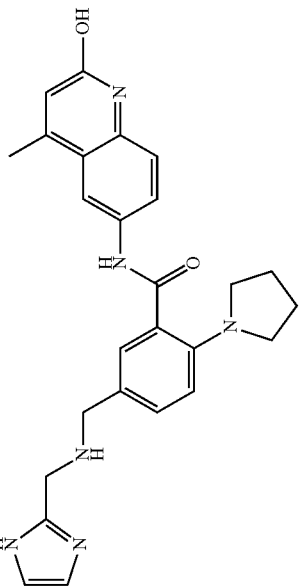 | 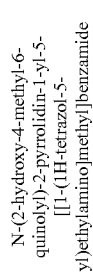 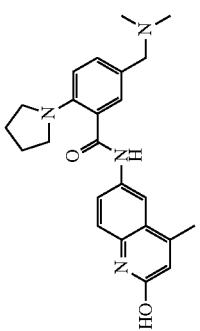 | 5-(dimethylaminomethyl)-N-(2-hydroxy-4-methyl-6- | 404.5 3 |

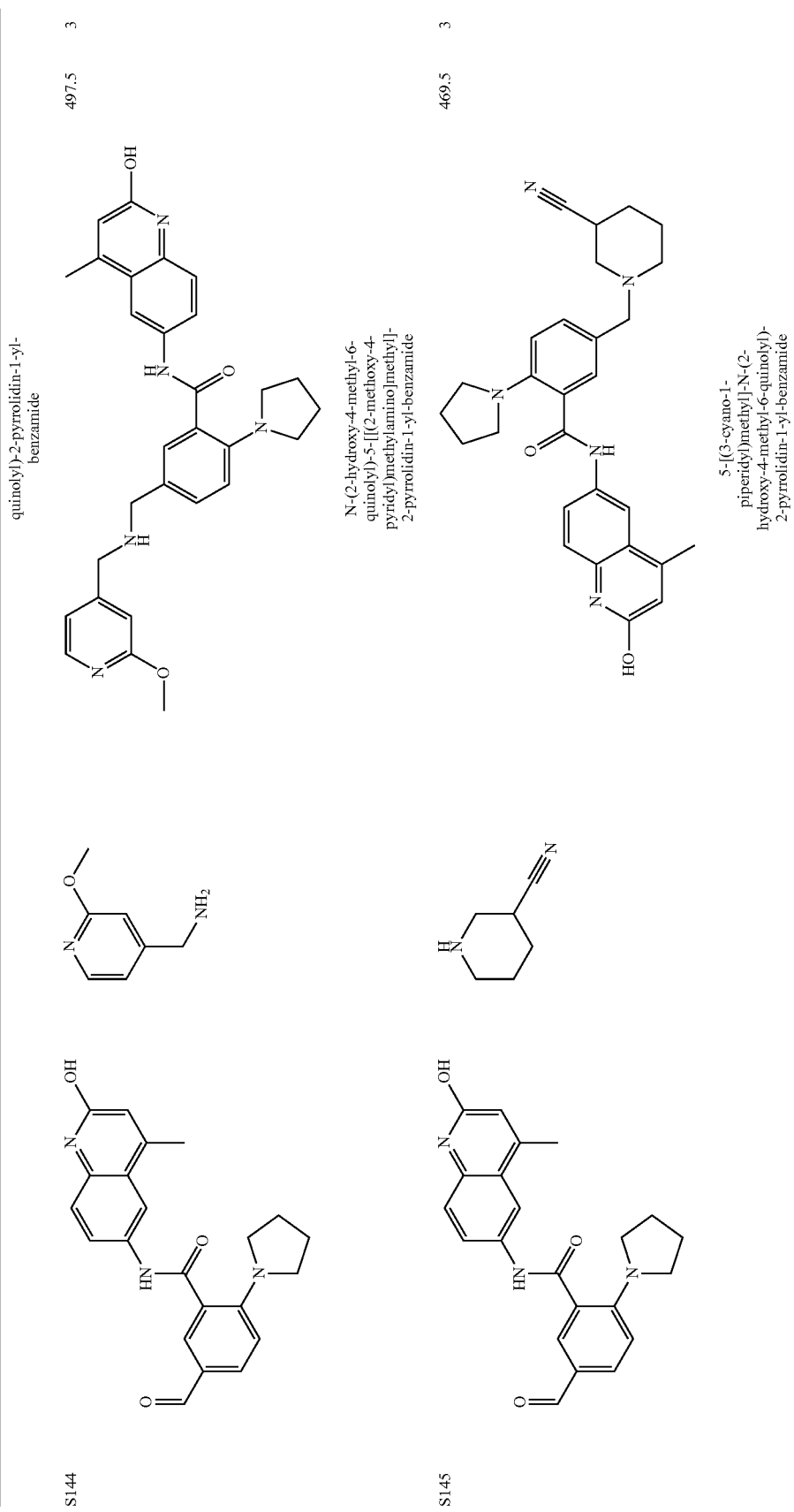

| | | | |
|---|---|---|---|
| S146 | 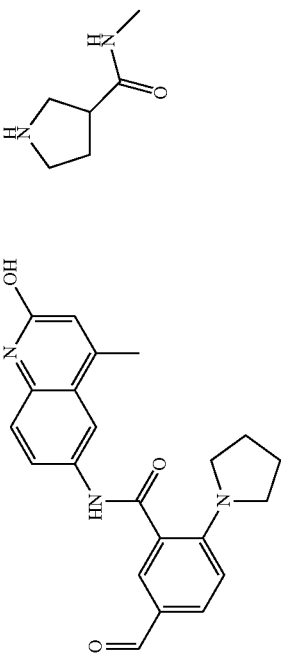 | 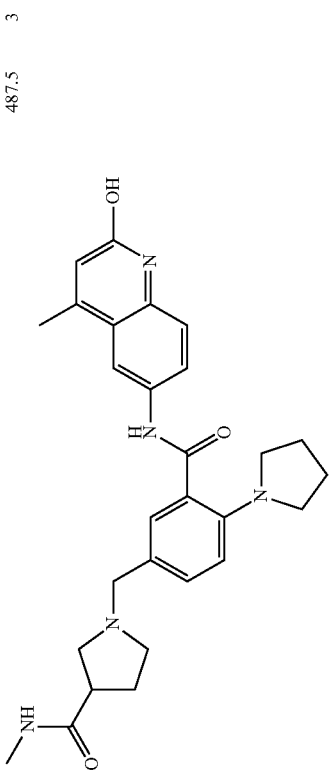 | 1-[[3-[(2-hydroxy-4-methyl-6-quinolyl)carbamoyl]-4-pyrrolidin-1-yl-phenyl]methyl]-N-methyl-pyrrolidine-3-carboxamide | 487.5 | 3 |
| S147 | 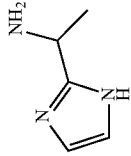 | 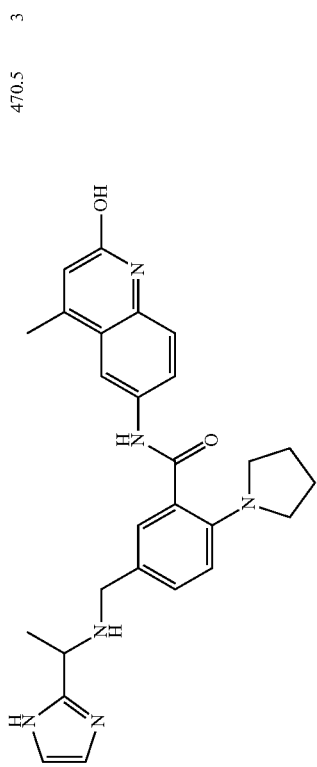 | N-(2-hydroxy-4-methyl-6-quinolyl)-5-[[[1-(1H-imidazol-2-yl)ethylamino]methyl]-2-pyrrolidin-1-yl-benzamide | 470.5 | 3 |

| | | | |
|---|---|---|---|
| S148 | 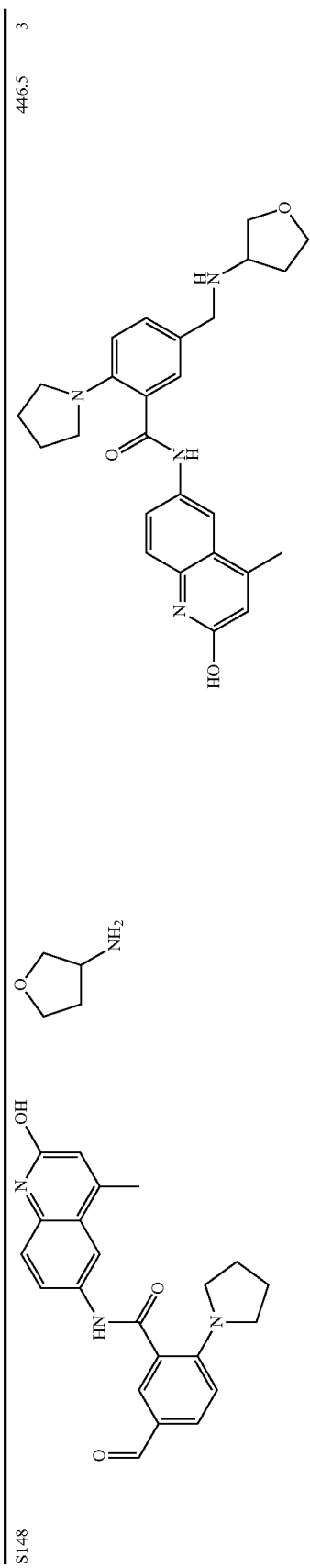 | N-(2-hydroxy-4-methyl-6-quinolyl)-2-pyrrolidin-1-yl-5-[(tetrahydrofuran-3-ylamino)methyl]benzamide | 446.5 3 |
| S149 | 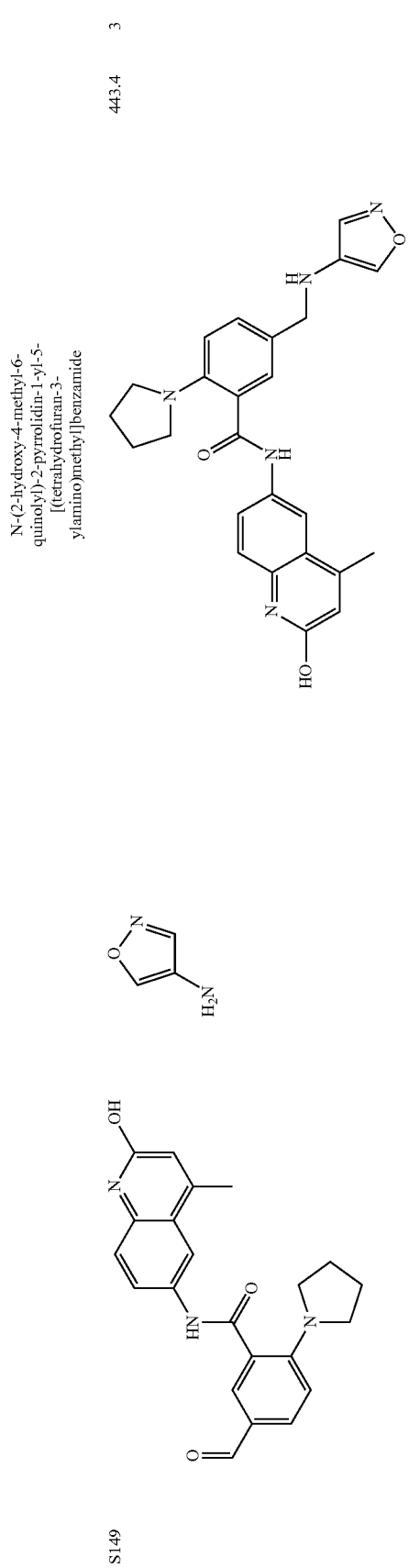 | N-(2-hydroxy-4-methyl-6-quinolyl)-5-[(isoxazol-4-ylamino)methyl]-2-pyrrolidin-1-yl-benzamide | 443.4 3 |

| | | | |
|---|---|---|---|
| S150 | 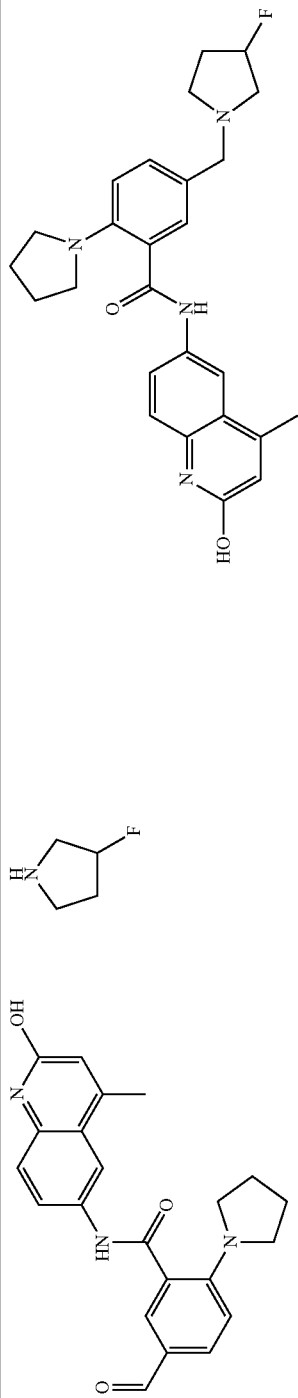 | 5-[(3-fluoropyrrolidin-1-yl)methyl]-N-(2-hydroxy-4-methyl-6-quinolyl)-2-pyrrolidin-1-yl-benzamide | 448.5 3 |
| S151 | 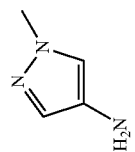 | N-(2-hydroxy-4-methyl-6-quinolyl)-5-[[(1-methylpyrazol-4-yl)amino]methyl]-2-pyrrolidin-1-yl-benzamide | 456.5 3 |

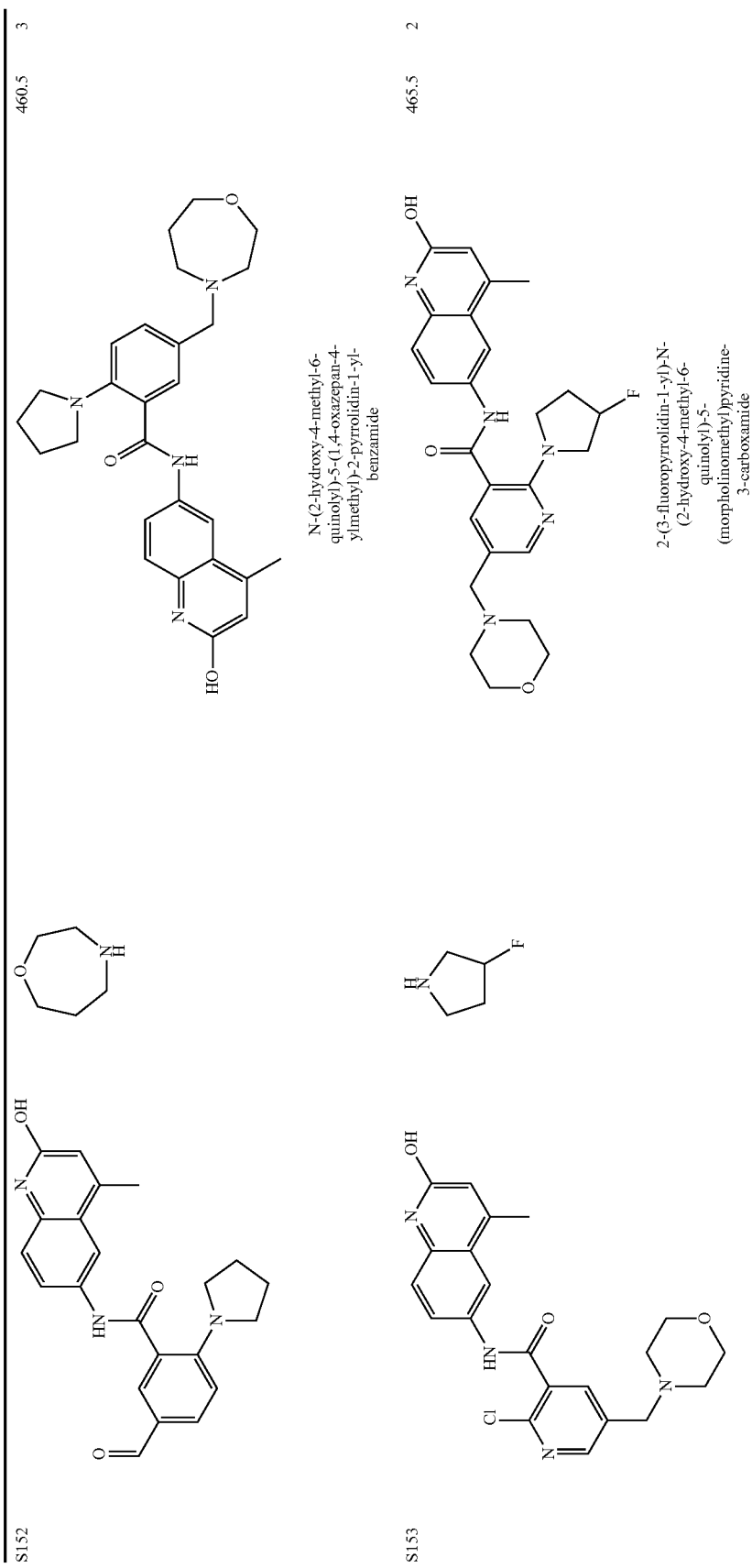

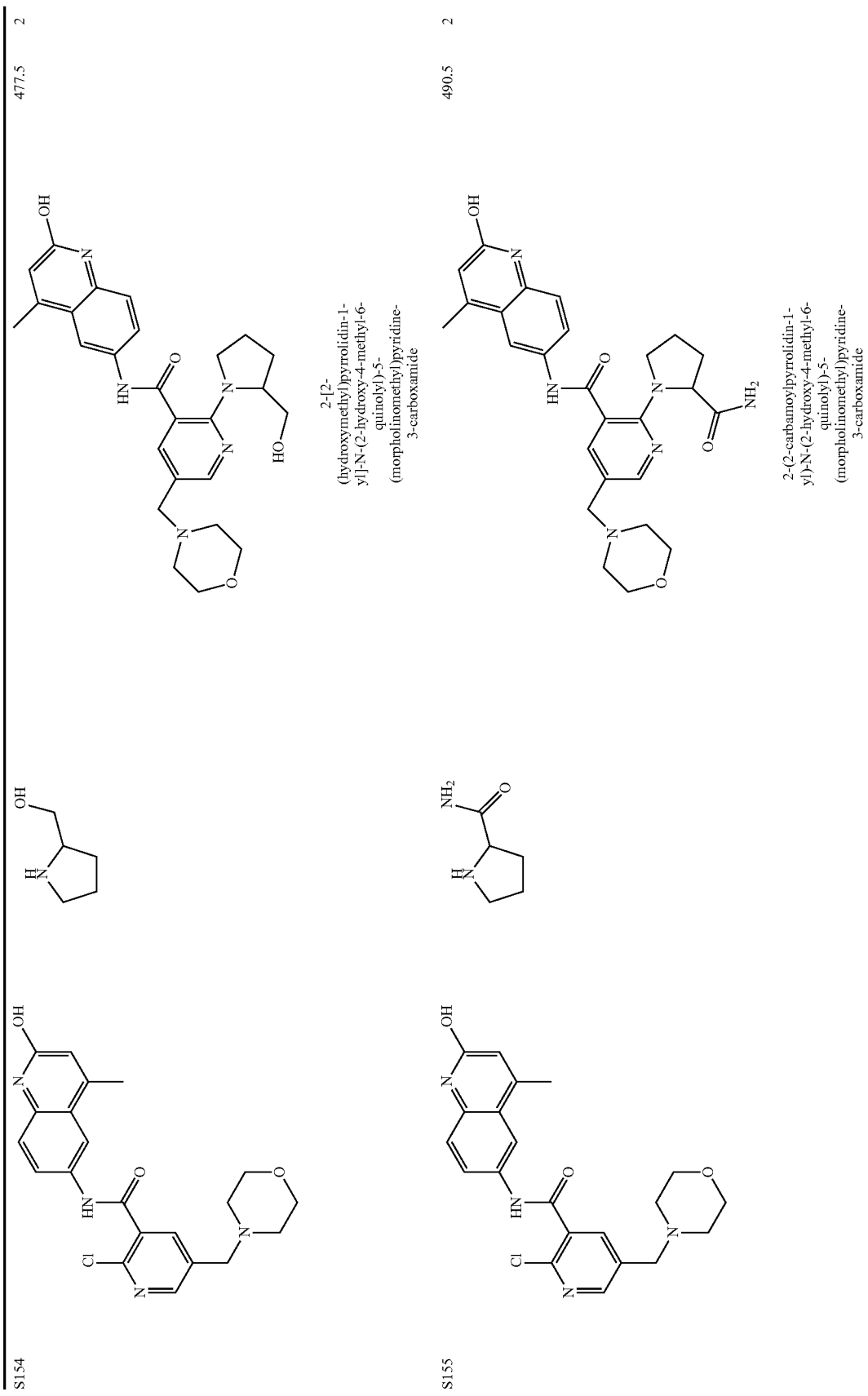

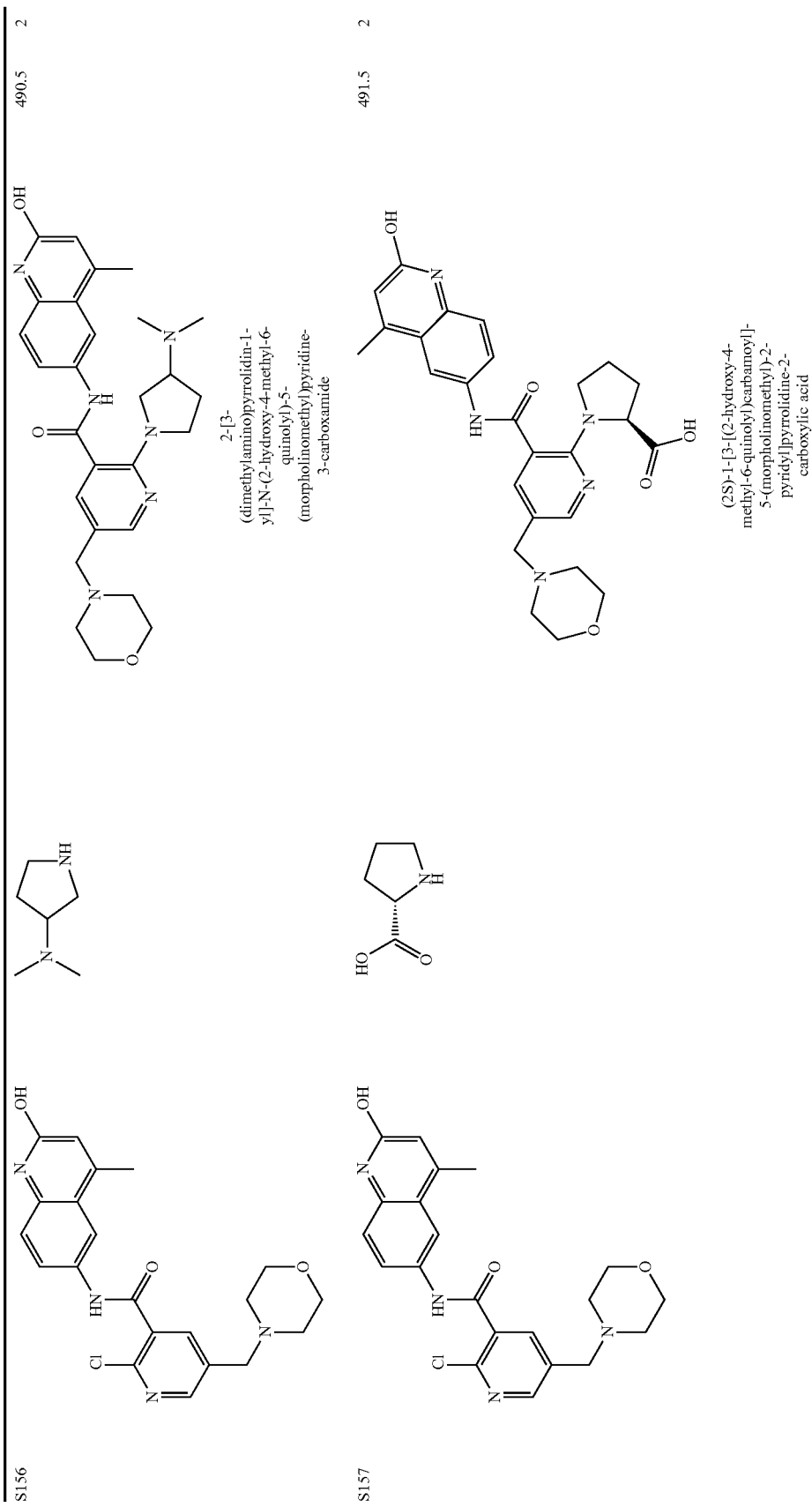

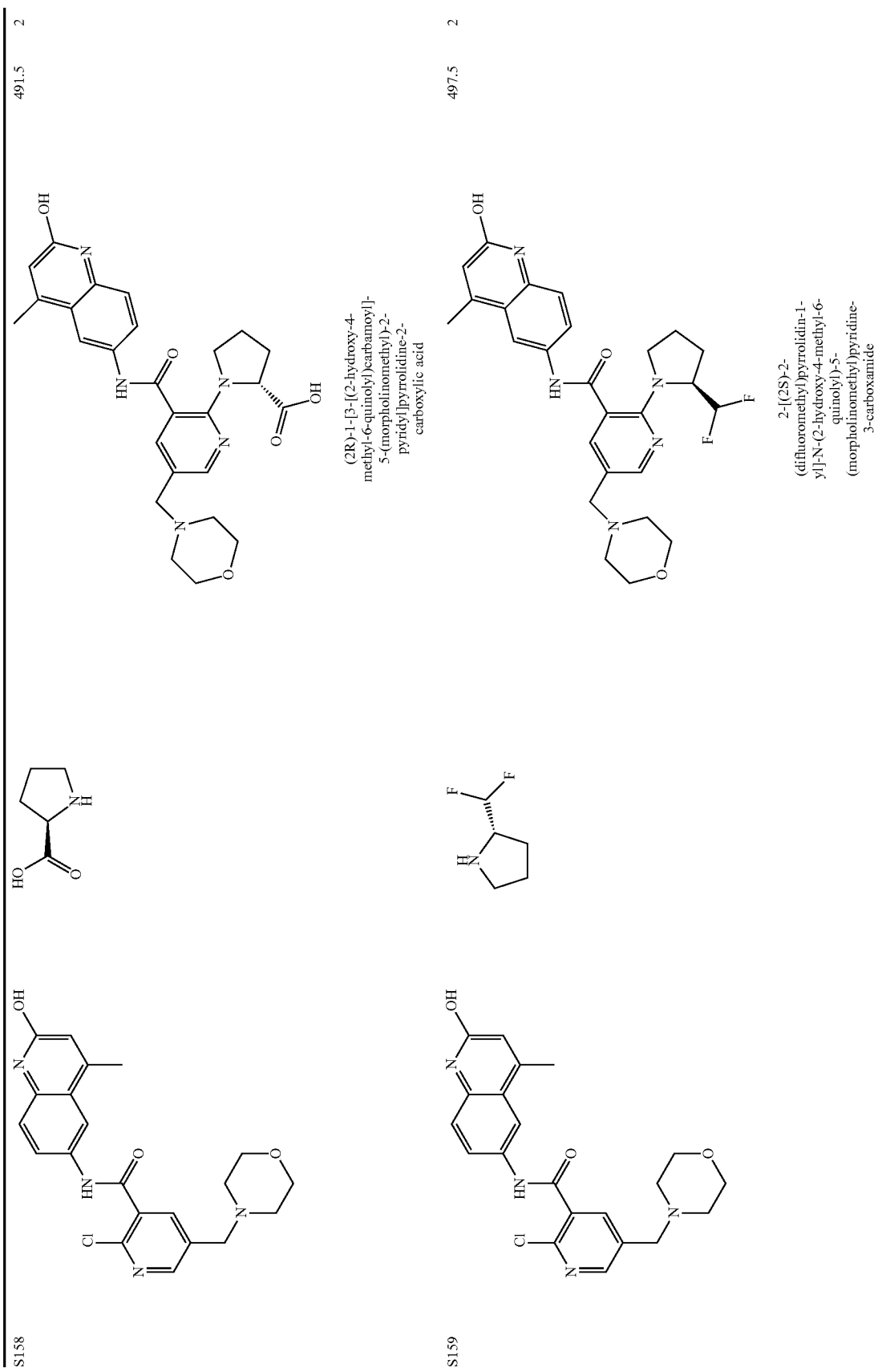

| | | | | |
|---|---|---|---|---|
| S160 | (structure) | (structure) | 1-[3-[(2-hydroxy-4-methyl-6-quinolyl)carbamoyl]-5-(morpholinomethyl)-2-pyridyl]pyrrolidine-3-carboxylic acid | 491.5 | 2 |
| S161 | (structure) | (structure) | N-(2-hydroxy-4-methyl-6-quinolyl)-2-[2-(1H-imidazol-2-yl)pyrrolidin-1-yl]-5-(morpholinomethyl)pyridine-3-carboxamide | 513.5 | 2 |

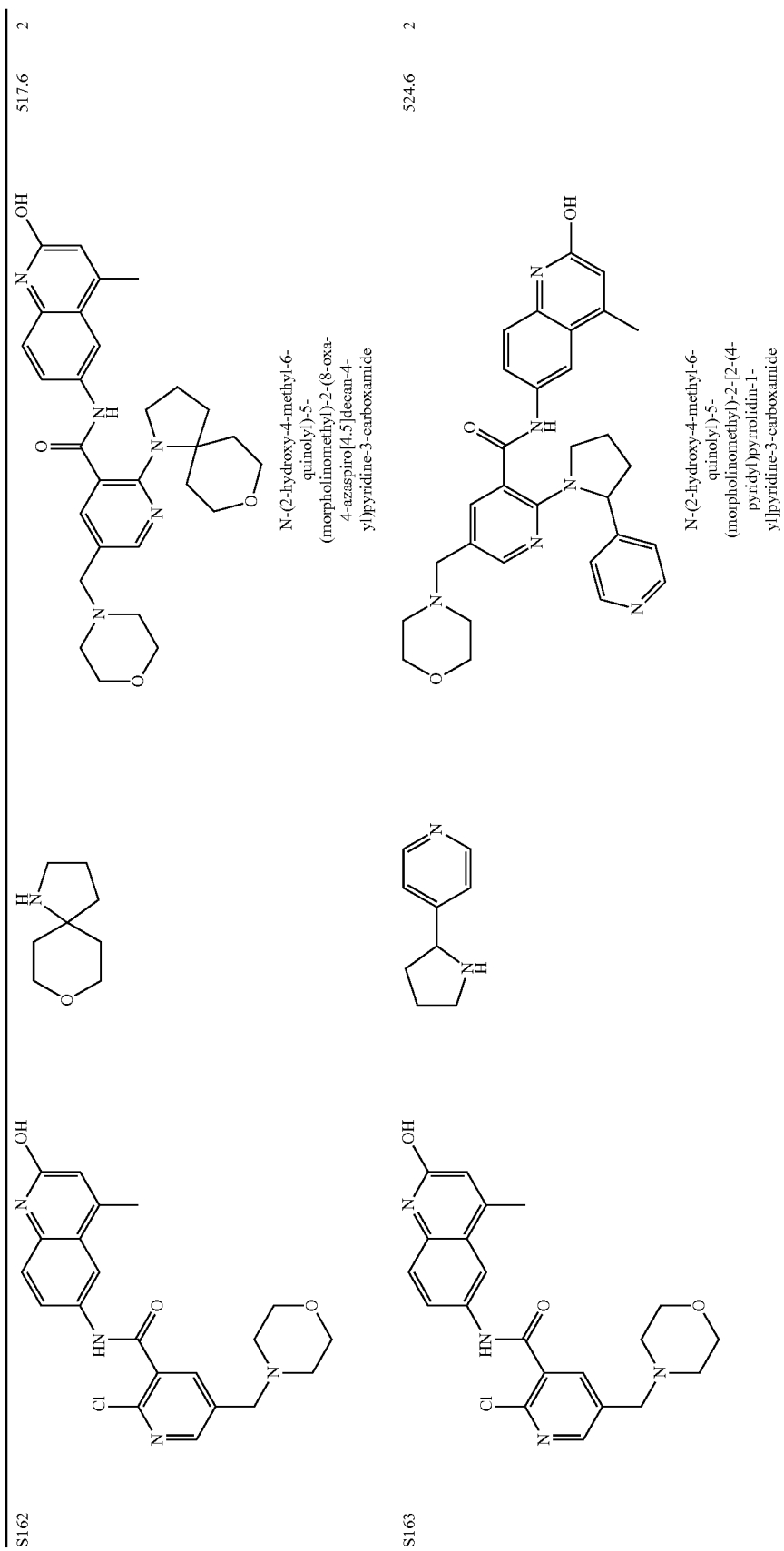

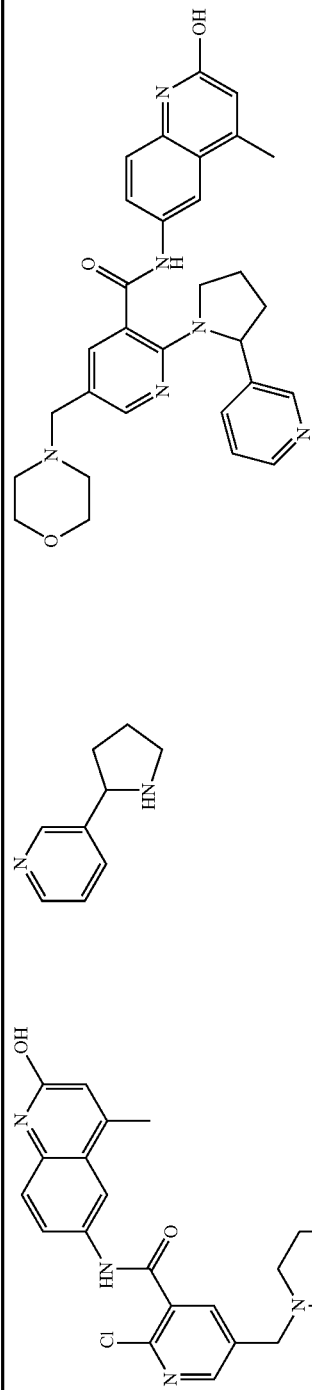
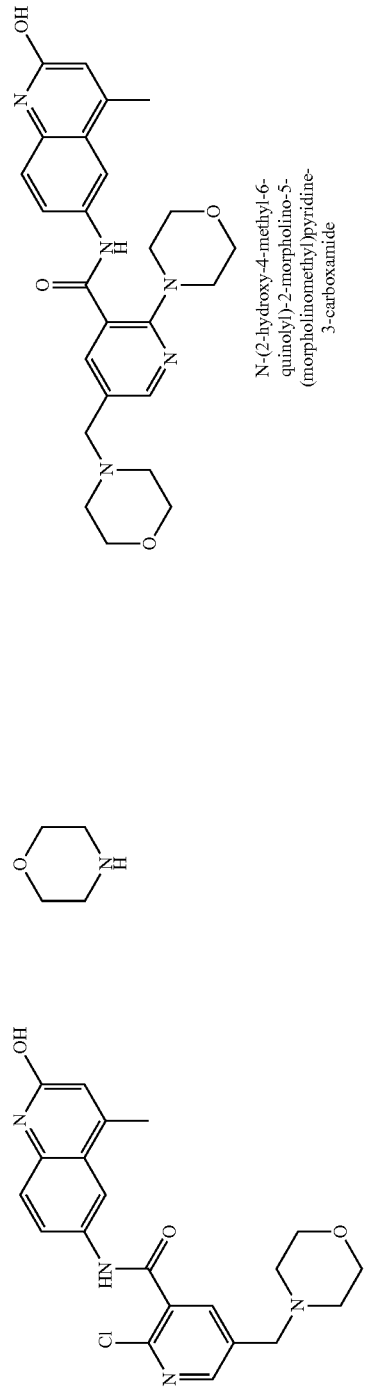

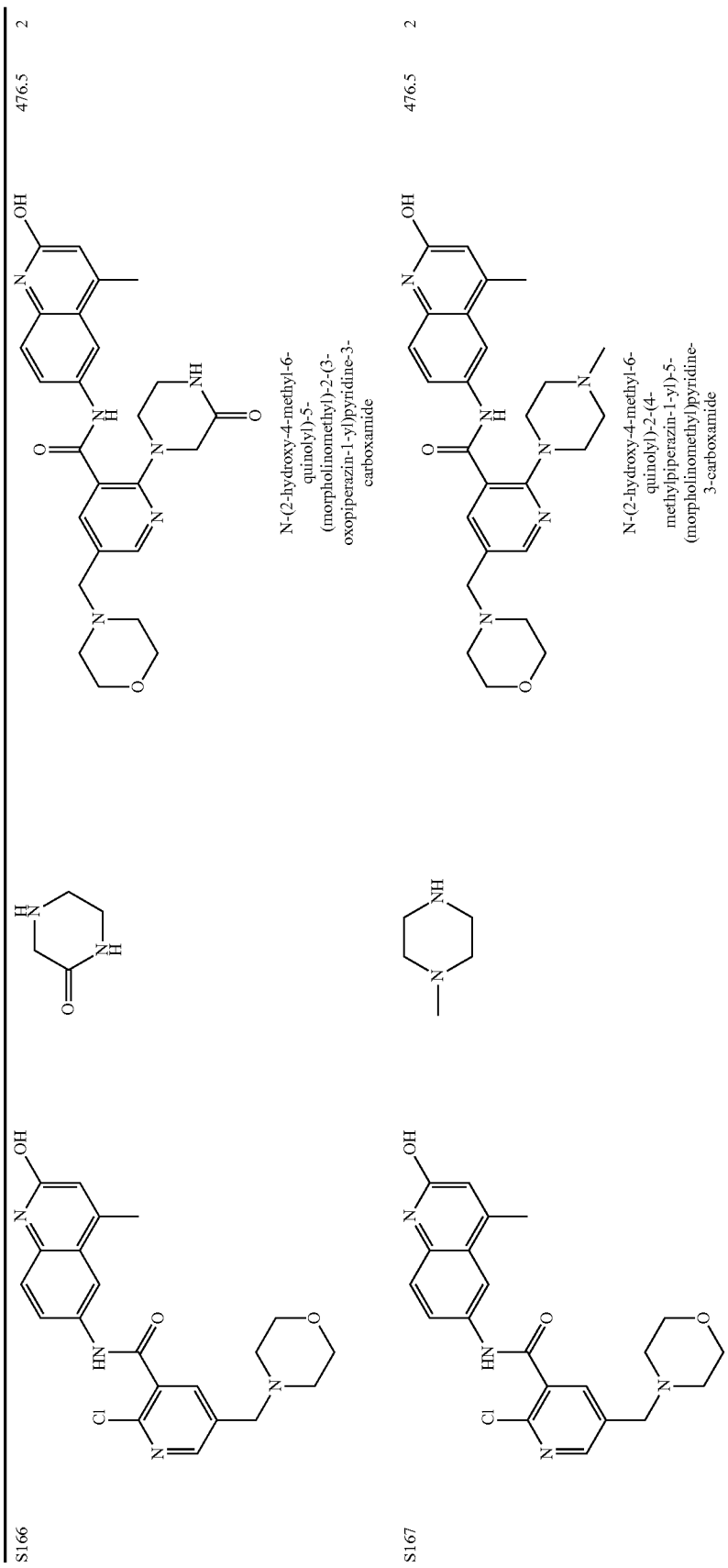

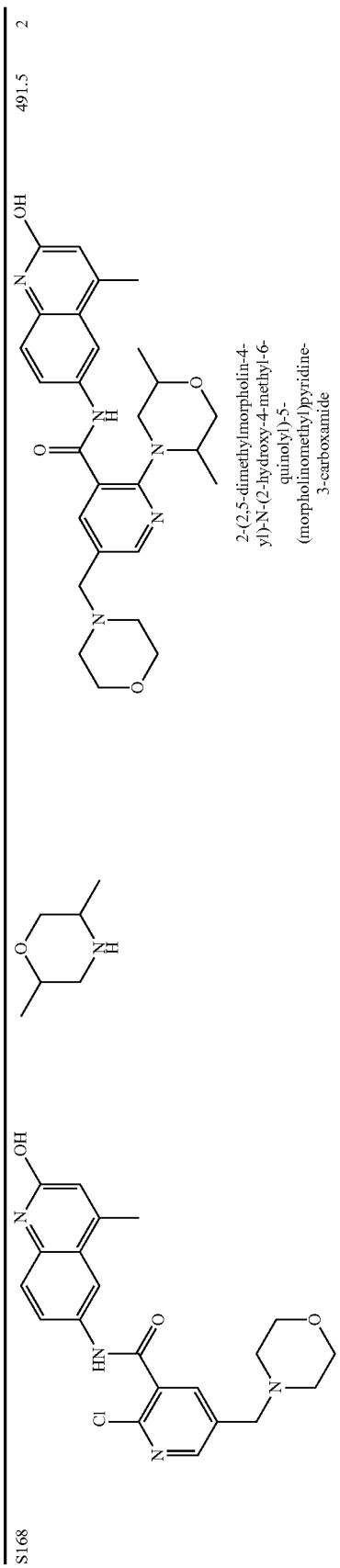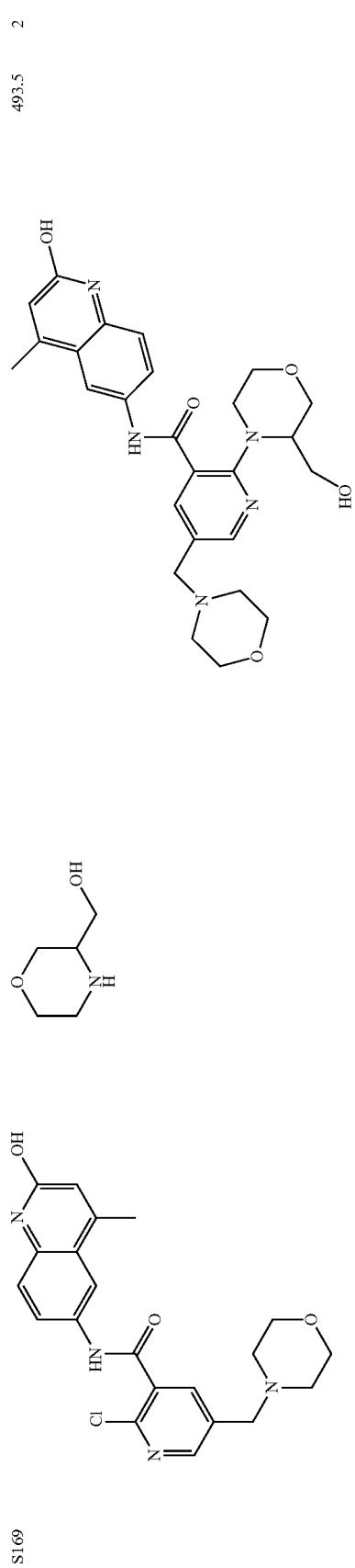

-continued
| | | | | |
|---|---|---|---|---|
| S170 | 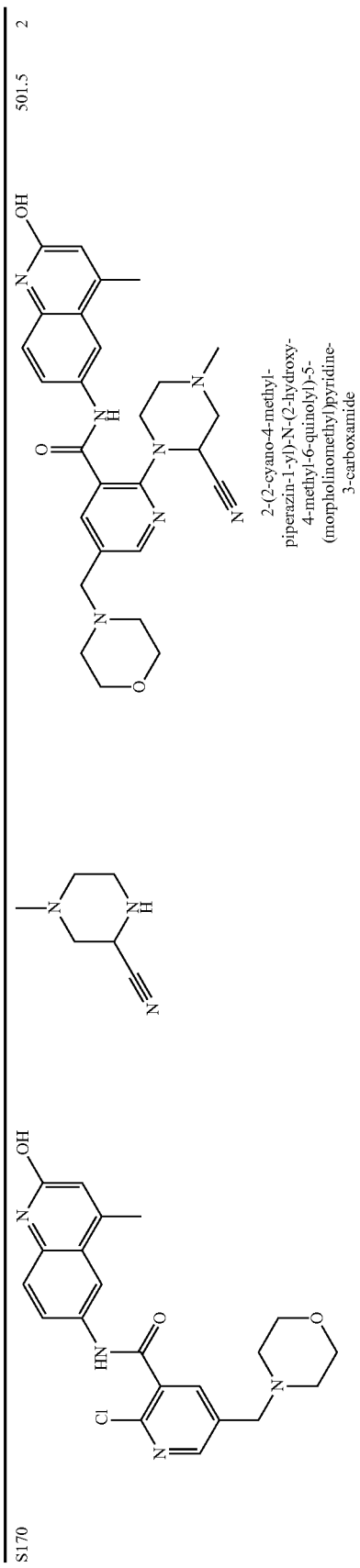 | | | 501.5 | 2 |
2-(2-cyano-4-methyl-piperazin-1-yl)-N-(2-hydroxy-4-methyl-6-quinolyl)-5-(morpholinomethyl)pyridine-3-carboxamide
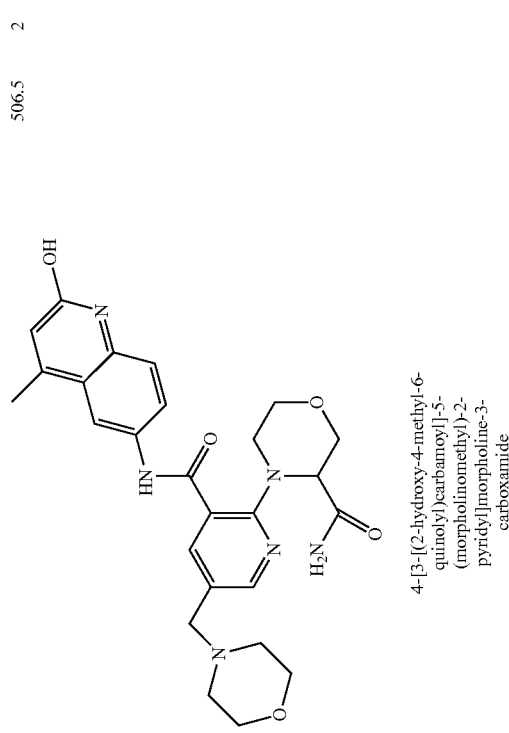
| S171 | | | 506.5 | 2 |
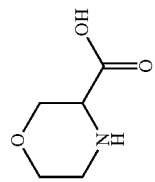
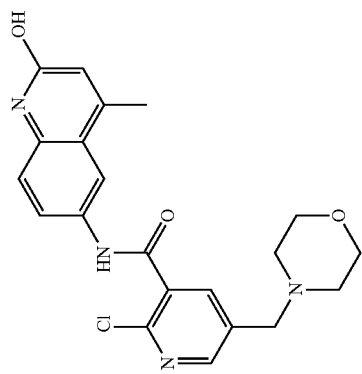
4-[3-[(2-hydroxy-4-methyl-6-quinolyl)carbamoyl]-5-(morpholinomethyl)-2-pyridyl]morpholine-3-carboxamide

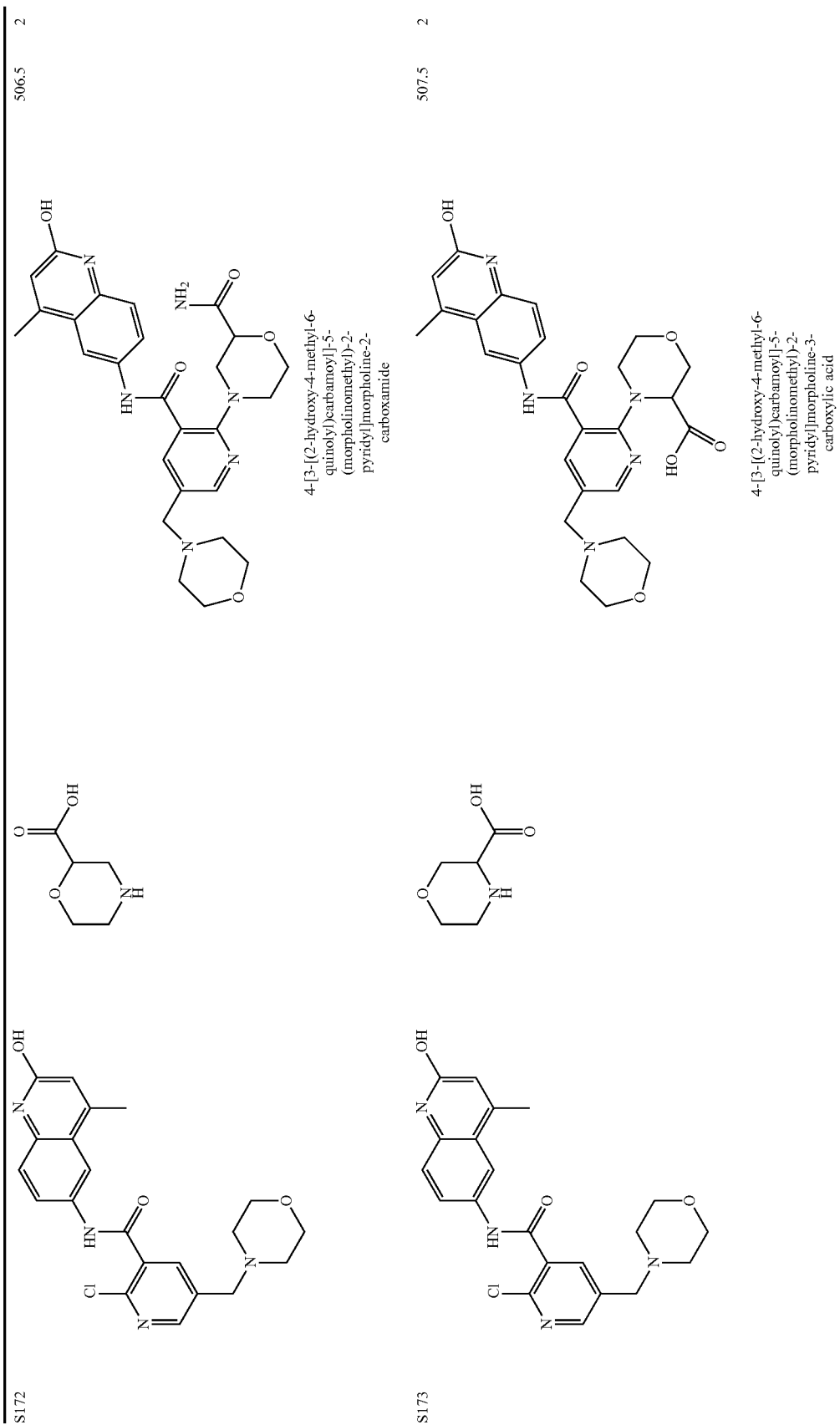

| | | | |
|---|---|---|---|
| S174 | 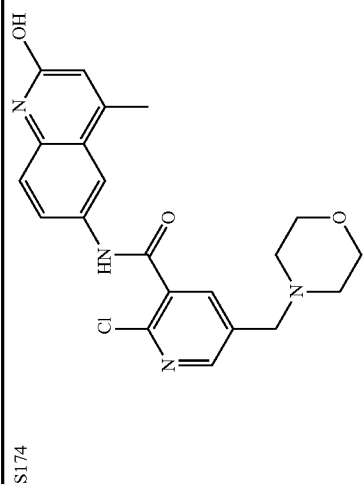 | 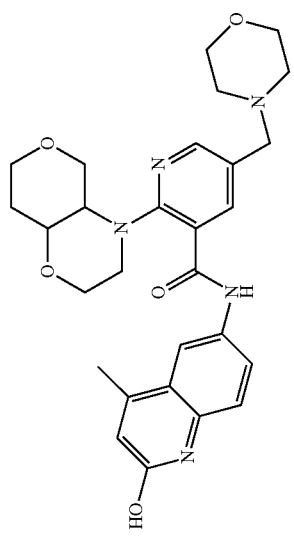 | 2-(3,4a,5,7,8,8a-hexahydro-2H-pyrano[4,3-b][1,4]oxazin-4-yl)-N-(2-hydroxy-4-methyl-6-quinolyl)-5-(morpholinomethyl)pyridine-3-carboxamide | 519.5 | 2 |
| S175 | | 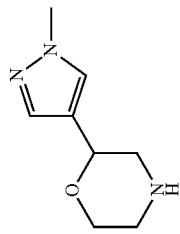 | N-(2-hydroxy-4-methyl-6-quinolyl)-2-[2-(1-methylpyrazol-4-yl)morpholin-4-yl]-5-(morpholinomethyl)pyridine-3-carboxamide | 543.6 | 2 |

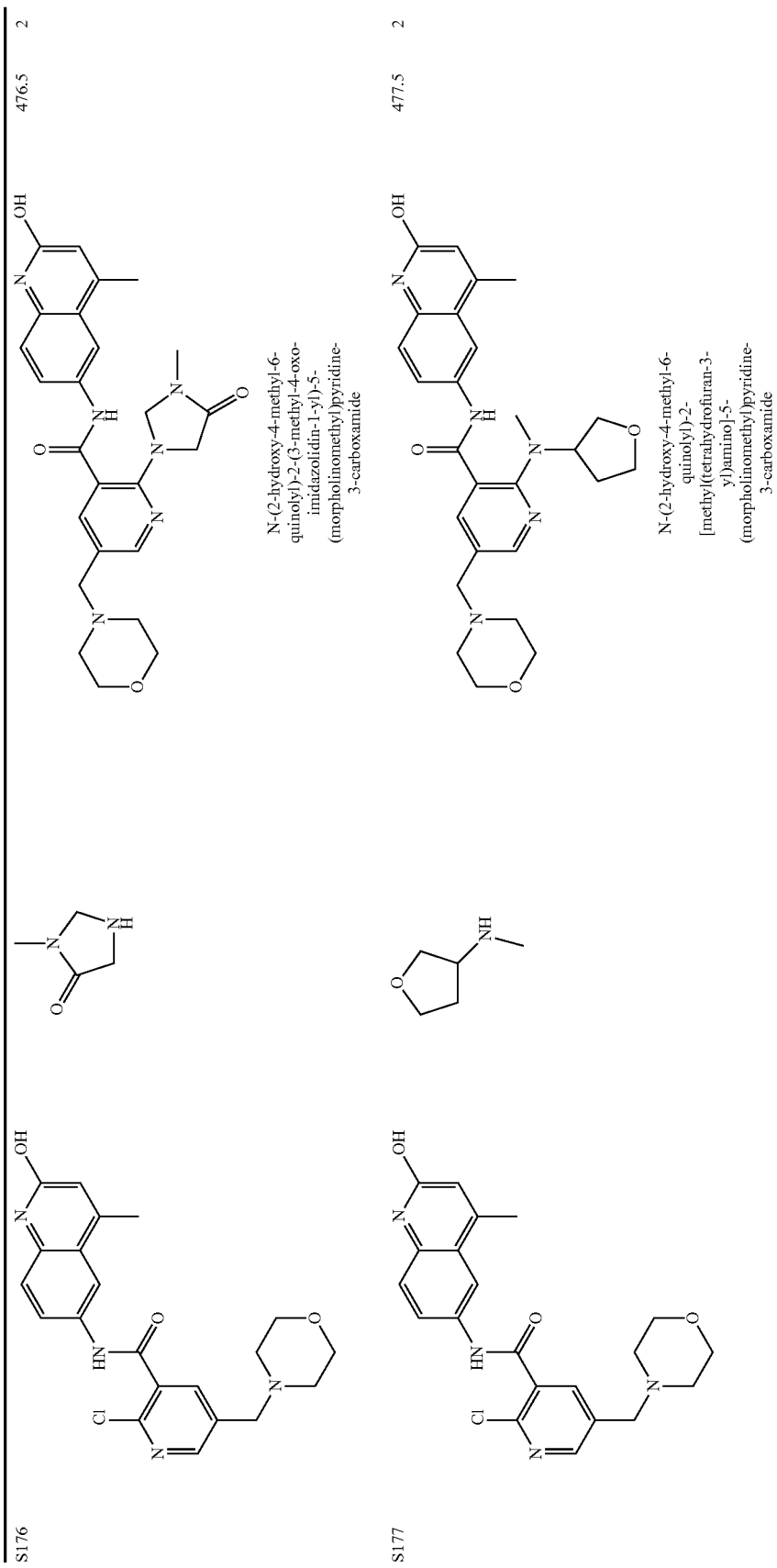

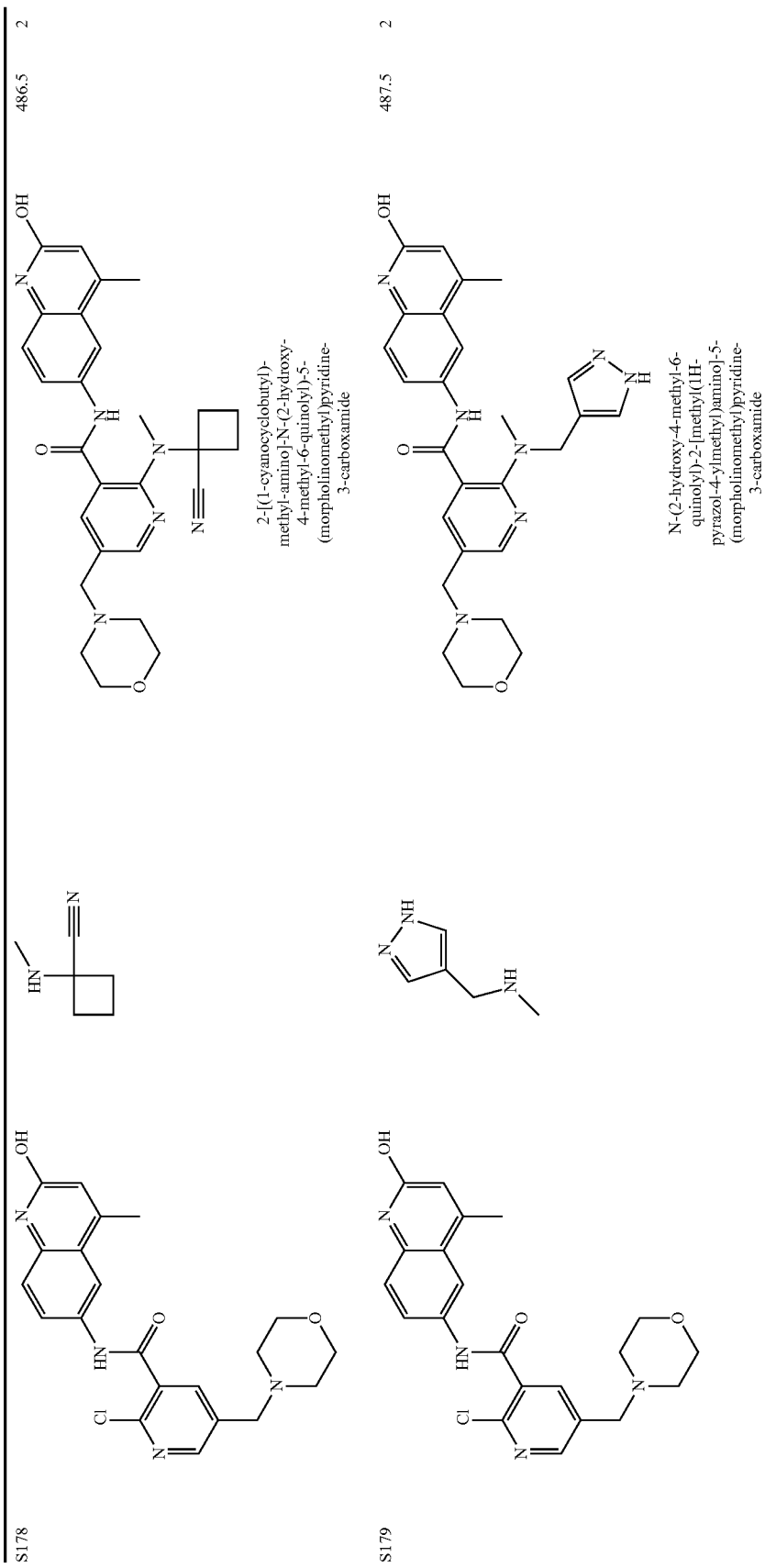

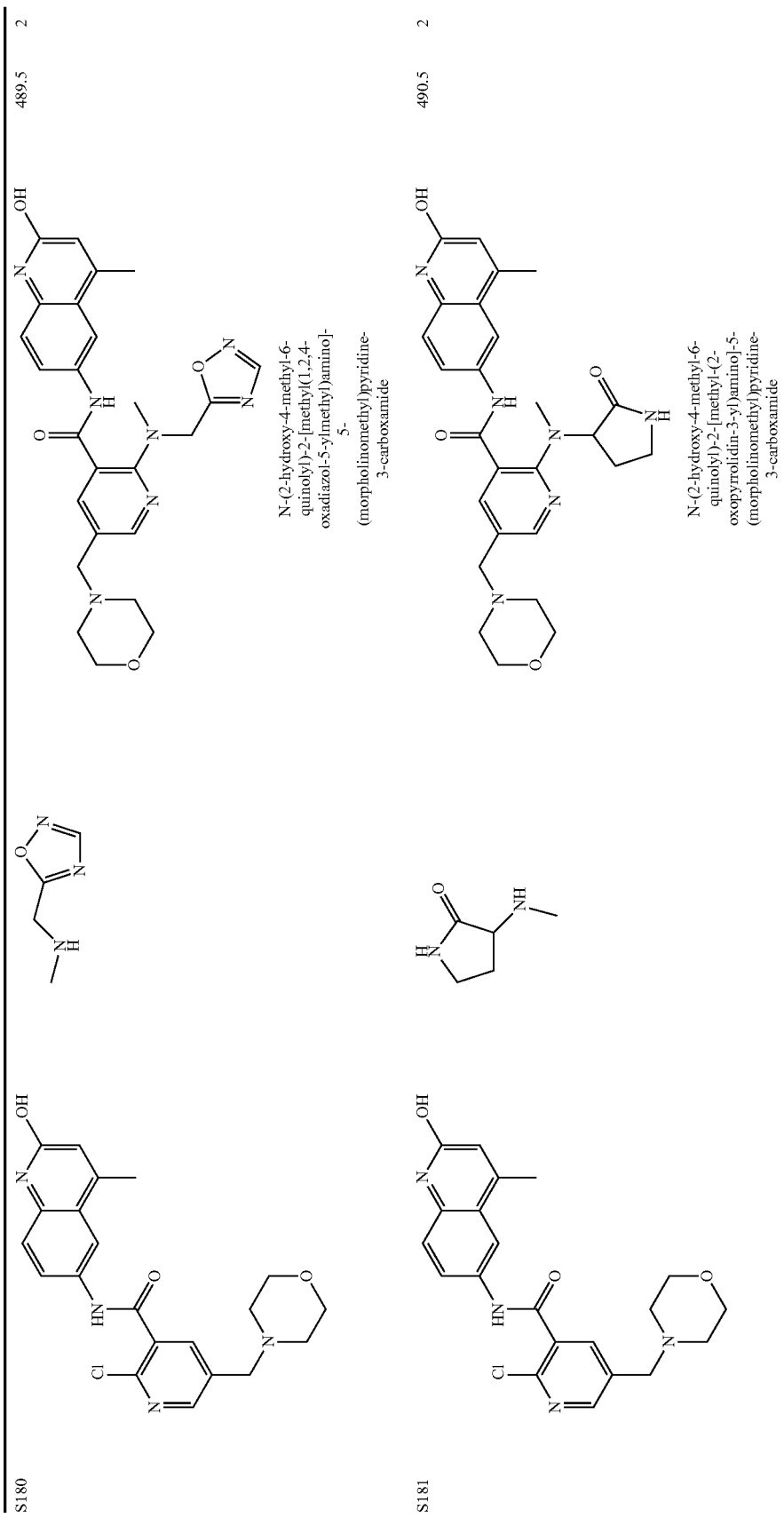

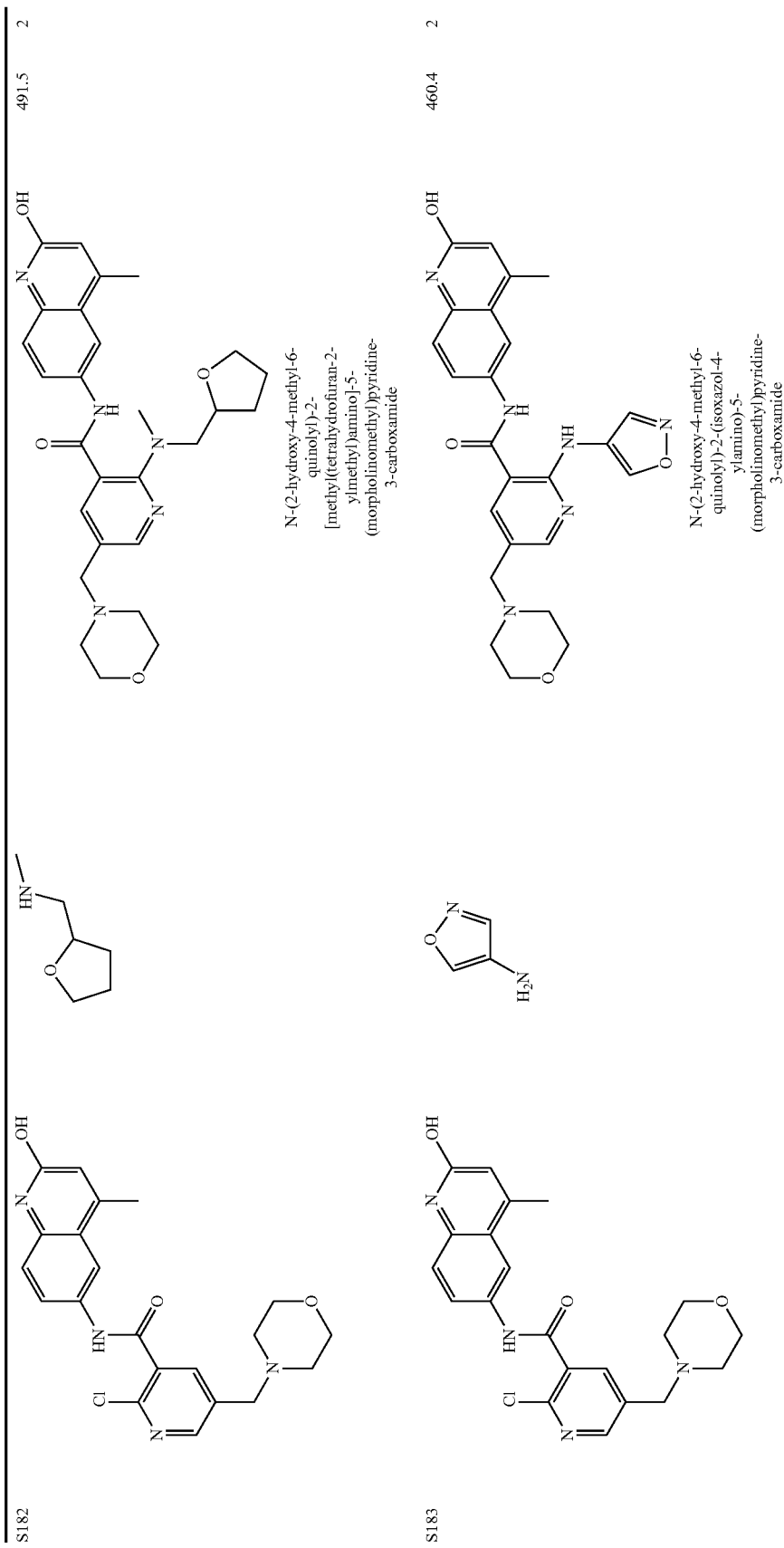

| | | | | |
|---|---|---|---|---|
| S184 | | | N-(2-hydroxy-4-methyl-6-quinolyl)-2-[(1H-imidazol-2-yl methylamino)-5-(morpholinomethyl)pyridine-3-carboxamide | 473.5 | 2 |
| S185 | | | N-(2-hydroxy-4-methyl-6-quinolyl)-2-[(5-(morpholinomethyl)-2-[(5-oxopyrrolidin-3-yl)amino]pyridine-3-carboxamide | 476.5 | 2 |

| S186 | [structure] | [structure] | [structure] | 490.5 | 2 | N-(2-hydroxy-4-methyl-6-quinolyl)-5-(morpholinomethyl)-2-[(5-oxopyrrolidin-2-yl)methylamino]pyridine-3-carboxamide |
| S187 | [structure] | [structure] | [structure] | 491.5 | 2 | 2-[[2-(hydroxymethyl)cyclopentyl]amino]-N-(2-hydroxy-4-methyl-6-quinolyl)-5-(morpholinomethyl)pyridine-3-carboxamide |

| | | | |
|---|---|---|---|
| S188 | 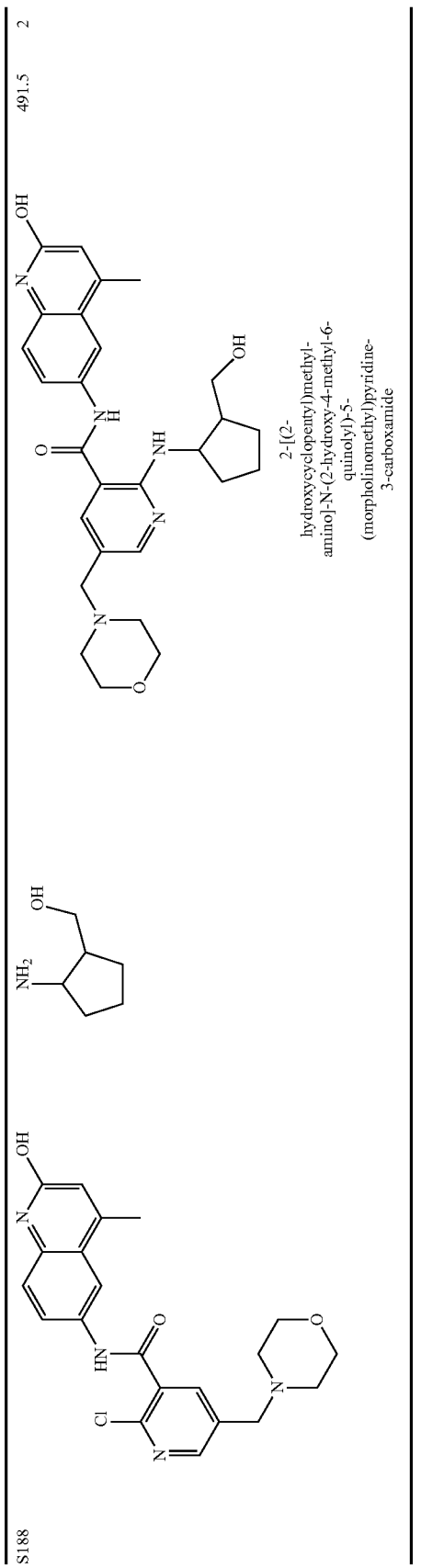 | 2-[(2-hydroxycyclopentyl)methyl-amino]-N-(2-hydroxy-4-methyl-6-quinolyl)-5-(morpholinomethyl)pyridine-3-carboxamide | 491.5 | 2 |
*comparative compound Biological Evaluation The compounds were biologically evaluated by determining the half maximal inhibitory concentration ($IC_{50}$) by FRET assay. The $IC_{50}$ is a measure of the effectiveness of a substance in inhibiting a specific biological or biochemical function.

For $IC_{50}$ determinations, dose-response curves were generated, using a top concentration of 50 μM compound in 12.5% DMSO, followed by 10-fold dilutions in 12.5% DMSO. The composition of the reaction buffer was 50 mM HEPES, pH 7.5; 100 mM NaCl, 0.05% CHAPS.

The reaction was run in a final volume of 25 μl. The BRD4 protein (16.5 μl) was added to wells of 384w white Optiplates (Perkin Elmer) (50 nM final concentration) and 1 μl of compound dilution of DMSO control. Incubation time was 30 minutes at room temperature. In the next step, 2.5 μl Biotin-H4KAc$_4$ peptide (Millipore 13-379) was added to the wells (final concentration was 12.5 nM), and the plates were incubated for 30 minutes at room temperature. Detection was performed by addition of 5 μl of a mix of mAb GST-XL665 (Cisbio 61GSTXLB) (10 nM final concentration) and Streptavidin Cryptate (Cisbio 610SAKLB) (2.4 nM final conc.) in reaction buffer with 0.4M KF and 0.05% BSA). The plates were incubated for one hour prior to reading on an Envision reader (Perkin Elmer)

Data was analyzed using GraphPad Prism, and $IC_{50}$ data was obtained using non-linear regression curve fit using log(inhibitor) vs response (variable slope). All compounds were considered active although classified (according to the half maximal inhibitory concentration ($IC_{50}$) by FRET assay) as follows:

| $IC_{50}$ ranges | Activity | Classification |
|---|---|---|
| <0.200 μM | Highly active | 1 |
| 0.2<>0.5 μM | More active | 2 |
| 0.5<>1 μM | Active | 3 |
| 1 μM<>10 μM | Moderately active | 4 |
| >10 μM | Less active | 5 |

List of Classification:

| Compound # | IUPAC_NAME | Classification |
|---|---|---|
| 1 | N-(2-hydroxy-4-methyl-6-quinolyl)-5-[(4-methylpiperazin-1-yl)methyl]-2-pyrrolidin-1-yl-benzamide | 1 |
| 2 | N-(2-hydroxy-4-methyl-6-quinolyl)-5-(piperazin-1-ylmethyl)-2-pyrrolidin-1-yl-benzamide | 1 |
| 3 | N-(2-hydroxy-4-methyl-6-quinolyl)-5-(morpholinomethyl)-2-pyrrolidin-1-yl-benzamide | 1 |
| 4 | 5-[(4-acetylpiperazin-1-yl)methyl]-N-(2-hydroxy-4-methyl-6-quinolyl)-2-pyrrolidin-1-yl-benzamide | 1 |
| 5 | N-(2-hydroxy-4-methyl-6-quinolyl)-5-(4-methylpiperazin-1-yl)sulfonyl-2-morpholino-benzamide | 1 |
| 6 | 5-[3-(dimethylamino)pyrrolidin-1-yl]sulfonyl-N-(2-hydroxy-4-methyl-6-quinolyl)-2-morpholino-benzamide | 1 |
| 7 | 5-[3-(dimethylamino)azetidin-1-yl]sulfonyl-N-(2-hydroxy-4-methyl-6-quinolyl)-2-morpholino-benzamide | 1 |
| 8 | 5-(3-aminoazetidin-1-yl)sulfonyl-N-(2-hydroxy-4-methyl-6-quinolyl)-2-morpholino-benzamide | 1 |
| 9 | N3-(2-hydroxy-4-methyl-6-quinolyl)-N1,N1-dimethyl-4-morpholino-benzene-1,3-dicarboxamide | 1 |
| 10 | N-(2-hydroxy-4-methyl-6-quinolyl)-5-(4-methylpiperazine-1-carbonyl)-2-morpholino-benzamide | 1 |
| 11 | N-(2-hydroxy-4-methyl-6-quinolyl)-5-(morpholine-4-carbonyl)-2-morpholino-benzamide | 2 |
| 12 | N3-(2-hydroxy-4-methyl-6-quinolyl)-4-morpholino-benzene-1,3-dicarboxamide | 2 |
| 13 | N-(2-hydroxy-4-methyl-6-quinolyl)-5-(methoxymethyl)-2-pyrrolidin-1-yl-benzamide | 1 |
| 14 | 5-(hydroxymethyl)-N-(2-hydroxy-4-methyl-6-quinolyl)-2-pyrrolidin-1-yl-benzamide | 2 |
| 15 | 5-(dimethylsulfamoyl)-N-(2-hydroxy-4-methyl-6-quinolyl)-2-(4-methylpiperazin-1-yl)benzamide | 1 |
| 16 | 2-[3-(dimethylamino)pyrrolidin-1-yl]-5-(dimethylsulfamoyl)-N-(2-hydroxy-4-methyl-6-quinolyl)benzamide | 2 |
| 17 | 5-(dimethylsulfamoyl)-N-(2-hydroxy-4-methyl-6-quinolyl)-2-(3-hydroxypyrrolidin-1-yl)benzamide | 1 |
| 18 | 2-(2-dimethylaminoethylamino)-5-(dimethylsulfamoyl)-N-(2-hydroxy-4-methyl-6-quinolyl)benzamide | 5 |
| 19 | 5-(dimethylsulfamoyl)-2-(2-hydroxyethylamino)-N-(2-hydroxy-4-methyl-6-quinolyl)benzamide | 5 |
| 20 | 2-[3-(dimethylamino)azetidin-1-yl]-5-(dimethylsulfamoyl)-N-(2-hydroxy-4-methyl-6-quinolyl)benzamide | 2 |
| 21 | 5-(dimethylsulfamoyl)-N-(2-hydroxy-4-methyl-6-quinolyl)-N-methyl-2-(4-methylpiperazin-1-yl)benzamide | 5 |
| 22 | N-(2-hydroxy-4-methyl-6-quinolyl)-N-methyl-5-morpholinosulfonyl-2-pyrrolidin-1-yl-benzamide | 5 |
| 23 | N-(2-hydroxy-4-methyl-6-quinolyl)-5-nitro-2-pyrrolidin-1-yl-pyridine-3-carboxamide | 4 |
| 24 | 5-amino-N-(2-hydroxy-4-methyl-6-quinolyl)-2-pyrrolidin-1-yl-pyridine-3-carboxamide | 1 |

-continued

| Compound # | IUPAC_NAME | Classification |
|---|---|---|
| 25 | 5-[(2-amino-2-oxo-ethyl)amino]-N-(2-hydroxy-4-methyl-6-quinolyl)-2-pyrrolidin-1-yl-pyridine-3-carboxamide | 2 |
| 26 | N-(2-hydroxy-4-methyl-6-quinolyl)-2-[2-(methoxymethyl)pyrrolidin-1-yl]-5-(morpholinomethyl)benzamide | 1 |
| 27 | N-(2-hydroxy-4-methyl-6-quinolyl)-5-(morpholinomethyl)-2-[2-(1H-pyrazol-3-yl)pyrrolidin-1-yl]benzamide | 4 |
| 28 | N-[2-hydroxy-4-(trifluoromethyl)-6-quinolyl]-5-(morpholinomethyl)-2-pyrrolidin-1-yl-benzamide | 3 |
| 29 | N-(2-hydroxy-4,7-dimethyl-6-quinolyl)-5-(morpholinomethyl)-2-pyrrolidin-1-yl-benzamide | 1 |
| 30 | 2-[2-(hydroxymethyl)pyrrolidin-1-yl]-N-(2-hydroxy-4-methyl-6-quinolyl)-5-(morpholinomethyl)benzamide | 1 |
| 31 | N-(2-hydroxy-4-methyl-6-quinolyl)-2-(3-hydroxypyrrolidin-1-yl)-5-(morpholinomethyl)benzamide | 1 |
| 32 | 2-[2-(dimethylaminomethyl)pyrrolidin-1-yl]-N-(2-hydroxy-4-methyl-6-quinolyl)-5-(morpholinomethyl)benzamide | 1 |
| 33 | N-(2-hydroxy-4-methyl-6-quinolyl)-3-pyrrolidin-1-yl-6-(1H-tetrazol-5-yl)pyridine-2-carboxamide | 4 |
| 34 | N-(2-hydroxy-4-methyl-6-quinolyl)-5-(morpholinomethyl)-2-(2-oxopyrrolidin-1-yl)benzamide | 3 |
| 35 | 6-cyano-N-(2-hydroxy-4-methyl-6-quinolyl)-3-pyrrolidin-1-yl-pyridine-2-carboxamide | 3 |
| 36 | 6-(aminomethyl)-N-(2-hydroxy-4-methyl-6-quinolyl)-3-pyrrolidin-1-yl-pyridine-2-carboxamide | 4 |
| 37 | 6-(dimethylaminomethyl)-N-(2-hydroxy-4-methyl-6-quinolyl)-3-pyrrolidin-1-yl-pyridine-2-carboxamide | 4 |
| 38 | 6-acetyl-N-(2-hydroxy-4-methyl-6-quinolyl)-3-pyrrolidin-1-yl-pyridine-2-carboxamide | 1 |
| 39 | 6-(1-hydroxyethyl)-N-(2-hydroxy-4-methyl-6-quinolyl)-3-pyrrolidin-1-yl-pyridine-2-carboxamide | 3 |
| 40 | N2-(2-hydroxy-4-methyl-6-quinolyl)-3-pyrrolidin-1-yl-pyridine-2,6-dicarboxamide | 2 |
| 41 | 2-cyano-N-(2-hydroxy-4-methyl-6-quinolyl)-5-pyrrolidin-1-yl-pyridine-4-carboxamide | 1 |
| 42 | 2-acetyl-N-(2-hydroxy-4-methyl-6-quinolyl)-5-pyrrolidin-1-yl-pyridine-4-carboxamide | 1 |
| 43 | 2-(1-hydroxyethyl)-N-(2-hydroxy-4-methyl-6-quinolyl)-5-pyrrolidin-1-yl-pyridine-4-carboxamide | 1 |
| 44 | N4-(2-hydroxy-4-methyl-6-quinolyl)-5-pyrrolidin-1-yl-pyridine-2,4-dicarboxamide | 1 |
| 45 | N-(2-hydroxy-4-methyl-6-quinolyl)-5-pyrrolidin-1-yl-2-(1H-tetrazol-5-yl)pyridine-4-carboxamide | 1 |
| 46 | 5-(1-hydroxyethyl)-N-(2-hydroxy-4-methyl-6-quinolyl)-2-pyrrolidin-1-yl-benzamide | 1 |
| 47 | N-(2-hydroxy-4-methyl-6-quinolyl)-5-(1-methoxyethyl)-2-pyrrolidin-1-yl-benzamide | 1 |
| 48 | 2-[2-(dimethylaminomethyl)pyrrolidin-1-yl]-N-(2-hydroxy-4-methyl-6-quinolyl)-5-(methoxymethyl)benzamide | 2 |
| 50 | N-(2-hydroxy-4-methyl-6-quinolyl)-5-(isopropoxymethyl)-2-pyrrolidin-1-yl-benzamide | 1 |
| 51 | 2-[2-(dimethylaminomethyl)pyrrolidin-1-yl]-N-(2-hydroxy-4-methyl-6-quinolyl)-5-(trifluoromethoxy)benzamide | 1 |
| 54 | 5-amino-N-(2-hydroxy-4-methyl-6-quinolyl)-2-morpholino-benzamide | 3 |
| 55 | 5-[(2-amino-2-oxo-ethyl)amino]-N-(2-hydroxy-4-methyl-6-quinolyl)-2-morpholino-benzamide | 2 |
| 67 | N-(2-hydroxy-4-methyl-6-quinolyl)-2-morpholino-5-(1-piperidylsulfonyl)benzamide | 1 |
| 68 | N-(2-hydroxy-4-methyl-6-quinolyl)-2-morpholino-5-morpholinosulfonyl-benzamide | 1 |
| 69 | N-(2-hydroxy-4-methyl-6-quinolyl)-2-methoxy-benzamide | 5 |
| 70 | N-(2-hydroxy-4-methyl-6-quinolyl)-2-morpholino-5-sulfamoyl-benzamide | 1 |
| 72 | 5-(dimethylsulfamoyl)-N-(2-hydroxy-4-methyl-6-quinolyl)-2-pyrrolidin-1-yl-benzamide | 1 |
| 73 | 5-(dimethylsulfamoyl)-N-(2-hydroxy-4-methyl-6-quinolyl)-2-morpholino-benzamide | 1 |
| 74 | N-(2-hydroxy-4-methyl-6-quinolyl)-5-morpholinosulfonyl-2-pyrrolidin-1-yl-benzamide | 1 |

| Compound # | IUPAC_NAME | Classification |
|---|---|---|
| 76 | N-(2-hydroxy-4-methyl-6-quinolyl)-2-morpholino-5-nitro-benzenesulfonamide | 4 |
| 77 | 5-amino-N-(2-hydroxy-4-methyl-6-quinolyl)-2-morpholino-benzenesulfonamide | 5 |
| 79 | 5-(dimethylsulfamoyl)-2-morpholino-N-[2-oxo-4-(trifluoromethyl)-1H-quinolin-6-yl]benzamide | 4 |
| 80 | N3-(2-hydroxy-4-methyl-6-quinolyl)-4-morpholino-benzene-1,3-disulfonamide | 5 |
| 82 | N-(2-hydroxy-4-methyl-6-quinolyl)-5-nitro-2-pyrrolidin-1-yl-benzamide | 1 |
| 84 | N-(2-hydroxy-4-methyl-6-quinolyl)-1-(oxazolidin-2-ylmethyl)-5-pyrrolidin-1-yl-indole-6-carboxamide | 1 |
| 85 | 3-(dimethylaminomethyl)-N-(2-hydroxy-4-methyl-6-quinolyl)-5-pyrrolidin-1-yl-1H-indole-6-carboxamide | 1 |
| 86 | 1-(2-amino-2-oxo-ethyl)-N-(2-hydroxy-4-methyl-6-quinolyl)-5-pyrrolidin-1-yl-indole-6-carboxamide | 1 |
| 87 | N-(2-hydroxy-4-methyl-6-quinolyl)-5-(morpholinomethyl)-2-pyrrolidin-1-yl-pyridine-3-carboxamide | 1 |
| 88 | 2-(3-fluoropyrrolidin-1-yl)-N-(2-hydroxy-4-methyl-6-quinolyl)-5-(morpholinomethyl)pyridine-3-carboxamide | 1 |
| 89 | N-(2-hydroxy-4-methyl-6-quinolyl)-2-(3-hydroxypyrrolidin-1-yl)-5-(morpholinomethyl)pyridine-3-carboxamide | 1 |
| 90 | N-(2-hydroxy-4-methyl-6-quinolyl)-2-morpholino-5-(morpholinomethyl)pyridine-3-carboxamide | 1 |
| 91 | N-(4-chloro-2-hydroxy-6-quinolyl)-2-morpholino-5-(morpholinomethyl)pyridine-3-carboxamide | 1 |
| 92 | N-(4-methyl-2-oxo-pyrido[1,2-a]pyrimidin-7-yl)-5-(morpholinomethyl)-2-pyrrolidin-1-yl-pyridine-3-carboxamide | 5 |
| 93 | N-(8-methyl-6-oxo-5H-1,5-naphthyridin-2-yl)-5-(morpholinomethyl)-2-pyrrolidin-1-yl-pyridine-3-carboxamide | 4 |
| 94 | N-(8-methyl-6-oxo-5H-1,5-naphthyridin-2-yl)-5-morpholinosulfonyl-2-pyrrolidin-1-yl-benzamide | 5 |
| 95 | N-(2-hydroxy-4-methyl-6-quinolyl)-3-pyrrolidin-1-yl-pyridine-4-carboxamide | 1 |
| 96 | N-(2-hydroxy-4-methyl-6-quinolyl)-2-pyrrolidin-1-yl-pyridine-3-carboxamide | 1 |
| 97 | 2-[2-(dimethylaminomethyl)pyrrolidin-1-yl]-N-(2-hydroxy-4-methyl-6-quinolyl)pyridine-3-carboxamide | 1 |
| 98 | N-(4-methoxy-2-oxo-1H-quinolin-6-yl)-5-[(4-methylpiperazin-1-yl)methyl]-2-pyrrolidin-1-yl-benzamide | 1 |
| 99 | 5-(dimethylsulfamoyl)-N-(2-hydroxy-4,7-dimethyl-6-quinolyl)-2-morpholino-benzamide | 1 |
| 100 | 5-morpholinosulfonyl-N-(2-oxo-3,4-dihydro-1H-quinolin-6-yl)-2-pyrrolidin-1-yl-benzamide | 3 |
| 101 | N-(4-methyl-2-oxo-3,4-dihydro-1H-quinolin-6-yl)-5-(morpholinomethyl)-2-pyrrolidin-1-yl-benzamide | 1 |
| 102 | 5-(dimethylsulfamoyl)-N-(4-methyl-2-oxo-3,4-dihydro-1H-quinolin-6-yl)-2-pyrrolidin-1-yl-benzamide | 1 |
| 103 | N-(4,4-dimethyl-2-oxo-1,3-dihydroquinolin-6-yl)-5-(morpholinomethyl)-2-pyrrolidin-1-yl-benzamide | 2 |
| 104 | N-(4,4-dimethyl-2-oxo-1,3-dihydroquinolin-6-yl)-5-(dimethylsulfamoyl)-2-pyrrolidin-1-yl-benzamide | 1 |
| 105 | 5-amino-N-(2-hydroxy-4-methyl-6-quinolyl)-2-pyrazol-1-yl-benzamide | 3 |
| 106 | 5-(dimethylsulfamoyl)-N-(8-fluoro-4,4-dimethyl-2-oxo-1,3-dihydroquinolin-6-yl)-2-pyrrolidin-1-yl-benzamide | 1 |
| 107 | 5-(dimethylsulfamoyl)-N-(2-hydroxy-4,8-dimethyl-6-quinolyl)-2-pyrrolidin-1-yl-benzamide | 1 |
| 108 | 5-(dimethylsulfamoyl)-N-(2-hydroxy-8-methoxy-4-methyl-6-quinolyl)-2-pyrrolidin-1-yl-benzamide | 1 |
| 109 | N-(2-hydroxy-4-methyl-6-quinolyl)-2-pyrrolidin-1-yl-5-(trifluoromethyl)benzamide | 1 |
| 110 | N-(2-hydroxy-4-methyl-6-quinolyl)-2-(3-hydroxypyrrolidin-1-yl)-5-morpholinosulfonyl-benzamide | 1 |
| 111 | N-(2-hydroxy-4-methyl-6-quinolyl)-2-(3-methoxypyrrolidin-1-yl)-5-morpholinosulfonyl-benzamide | 1 |
| 112 | 5-(cyanomethyl)-N-(2-hydroxy-4-methyl-6-quinolyl)-2-pyrrolidin-1-yl-benzamide | 1 |
| 113 | N-(2-hydroxy-4-methyl-6-quinolyl)-5-(1-morpholinocyclopropyl)-2-pyrrolidin-1-yl-benzamide | 1 |

| Compound # | IUPAC_NAME | Classification |
|---|---|---|
| 114 | 2-[2-(dimethylaminomethyl)pyrrolidin-1-yl]-N-(2-hydroxy-4-methyl-6-quinolyl)-5-(1-morpholinocyclopropyl)benzamide | 1 |
| 115 | 2-cyano-5-(3-fluoropyrrolidin-1-yl)-N-(2-hydroxy-4-methyl-6-quinolyl)pyridine-4-carboxamide | 1 |
| 116 | 2-cyano-N-(2-hydroxy-4-methyl-6-quinolyl)-5-morpholino-pyridine-4-carboxamide | 1 |
| 117 | N-(2-hydroxy-4-methyl-6-quinolyl)-4-pyrrolidin-1-yl-pyridine-3-carboxamide | 1 |
| 118 | N-(4-methoxy-2-oxo-1H-quinolin-6-yl)-5-[(4-methylpiperazin-1-yl)methyl]-2-pyrrolidin-1-yl-benzamide | 1 |
| 119 | N-(2-hydroxy-4-methyl-6-quinolyl)-2-pyrrolidin-1-yl-pyridine-3-carboxamide | 1 |
| 120 | N-(2-hydroxy-4-methyl-6-quinolyl)-2-(3-methylmorpholin-4-yl)pyridine-3-carboxamide | 1 |
| 121 | 2-[2-(dimethylaminomethyl)pyrrolidin-1-yl]-N-(2-hydroxy-4-methyl-6-quinolyl)pyridine-3-carboxamide | 1 |
| 122 | 5-(dimethylsulfamoyl)-N-(2-hydroxy-4,7-dimethyl-6-quinolyl)-2-morpholino-benzamide | 1 |
| 123 | N-(2-hydroxy-4-methyl-6-quinolyl)-4-morpholino-pyridine-3-carboxamide | 1 |
| 124 | N-(2-hydroxy-4-methyl-6-quinolyl)-4-pyrrolidin-1-yl-pyridine-3-carboxamide | 2 |
| 125 | N-(2-hydroxy-4,7-dimethyl-6-quinolyl)-2-morpholino-pyridine-3-carboxamide | 3 |
| 126 | 2-(3-fluoropyrrolidin-1-yl)-N-(2-hydroxy-4,7-dimethyl-6-quinolyl)pyridine-3-carboxamide | 3 |
| 127 | 2-(3,3-difluoropyrrolidin-1-yl)-N-(2-hydroxy-4,7-dimethyl-6-quinolyl)pyridine-3-carboxamide | 2 |
| 128 | N-(2-hydroxy-4-methyl-6-quinolyl)-2-morpholino-pyridine-3-carboxamide | 1 |
| 129 | N-(2-hydroxy-4-isopropyl-6-quinolyl)-2-morpholino-pyridine-3-carboxamide | 4 |
| 130 | N-(3-methyl-2-oxo-1,4-dihydroquinazolin-6-yl)-2-morpholino-pyridine-3-carboxamide | 4 |
| 131 | N-(1-methyl-2-oxo-3,4-dihydroquinolin-6-yl)-2-morpholino-pyridine-3-carboxamide | 4 |
| 132 | 2-(3-fluoropyrrolidin-1-yl)-N-(2-hydroxy-4-methyl-6-quinolyl)pyridine-3-carboxamide | 1 |
| 133 | 2-(3,3-difluoropyrrolidin-1-yl)-N-(2-hydroxy-4-methyl-6-quinolyl)pyridine-3-carboxamide | 1 |
| 134 | N-(2-hydroxy-4-methyl-6-quinolyl)-2-pyrrolidin-1-yl-6-(trifluoromethyl)pyridine-3-carboxamide | 1 |
| 135 | N-(2-hydroxy-4-methyl-6-quinolyl)-2-morpholino-6-(trifluoromethyl)pyridine-3-carboxamide | 2 |
| 136 | N-(2-hydroxy-4,8-dimethyl-6-quinolyl)-2-morpholino-pyridine-3-carboxamide | 1 |
| 137 | N-(2-hydroxy-4,7-dimethyl-6-quinolyl)-4-methyl-2-morpholino-pyridine-3-carboxamide | 4 |
| 138 | N-(2-hydroxy-4-methyl-6-quinolyl)-4-methyl-2-morpholino-pyridine-3-carboxamide | 4 |
| 139 | N-(2-hydroxy-4-methyl-6-quinolyl)-2-morpholino-5-(trifluoromethyl)pyridine-3-carboxamide | 1 |
| 140 | 5-chloro-N-(2-hydroxy-4-methyl-6-quinolyl)-2-morpholino-pyridine-3-carboxamide | 1 |
| 141 | | NT |
| 142 | 2-(3,4a,5,6,7,7a-hexahydro-2H-pyrrolo[3,4-b][1,4]oxazin-4-yl)-N-(2-hydroxy-4-methyl-6-quinolyl)pyridine-3-carboxamide | 1 |
| 143 | 2-(2,3,4a,5,7,7a-hexahydrofuro[3,4-b][1,4]oxazin-4-yl)-N-(2-hydroxy-4-methyl-6-quinolyl)pyridine-3-carboxamide | 3 |
| 144 | N-(2-hydroxy-4-methyl-6-quinolyl)-2-(3-oxa-8-azabicyclo[3.2.1]octan-8-yl)pyridine-3-carboxamide | 1 |
| 145 | 2-[3-(hydroxymethyl)morpholin-4-yl]-N-(2-hydroxy-4-methyl-6-quinolyl)pyridine-3-carboxamide | 1 |
| 146 | 2-(4,4-difluoro-1-piperidyl)-N-(2-hydroxy-4-methyl-6-quinolyl)pyridine-3-carboxamide | 1 |
| 147 | 2-(6,8-dihydro-5H-imidazo[1,2-a]pyrazin-7-yl)-N-(2-hydroxy-4-methyl-6-quinolyl)pyridine-3-carboxamide | 3 |
| 148 | N-(2-hydroxy-4-methyl-6-quinolyl)-2-(3-oxopiperazin-1-yl)pyridine-3-carboxamide | 3 |
| 149 | N-(2-hydroxy-4-methoxy-6-quinolyl)-2-morpholino-pyridine-3-carboxamide | 3 |
| 150 | N-(2-hydroxy-4-methyl-6-quinolyl)-5-iodo-2-morpholino-benzamide | NT |

| Compound # | IUPAC_NAME | Classification |
|---|---|---|
| 151 | N-(2-hydroxy-4-methyl-6-quinolyl)-5-isoxazol-4-yl-2-morpholino-benzamide | 1 |
| 152 | 5-(3,5-dimethylisoxazol-4-yl)-N-(2-hydroxy-4-methyl-6-quinolyl)-2-morpholino-benzamide | 1 |
| 153 | N-(2-hydroxy-4,7-dimethyl-6-quinolyl)-5-iodo-2-morpholino-benzamide | NT |
| 154 | N-(2-hydroxy-4,7-dimethyl-6-quinolyl)-5-(1-methylpyrazol-4-yl)-2-morpholino-benzamide | 1 |
| 155 | 5-(3,5-dimethylisoxazol-4-yl)-N-(2-hydroxy-4,7-dimethyl-6-quinolyl)-2-morpholino-benzamide | 1 |
| 156 | N-(2-hydroxy-4,8-dimethyl-6-quinolyl)-5-iodo-2-morpholino-benzamide | NT |
| 157 | 5-(3-furyl)-N-(2-hydroxy-4,8-dimethyl-6-quinolyl)-2-morpholino-benzamide | 1 |
| 158 | N-(2-hydroxy-7-methoxy-4-methyl-6-quinolyl)-5-iodo-2-morpholino-benzamide | NT |
| 159 | N-(2-hydroxy-7-methoxy-4-methyl-6-quinolyl)-5-(1-methylpyrazol-4-yl)-2-morpholino-benzamide | 1 |
| 160 | 5-(3-furyl)-N-(2-hydroxy-7-methoxy-4-methyl-6-quinolyl)-2-morpholino-benzamide | 3 |
| 161 | 5-(3,5-dimethylisoxazol-4-yl)-N-(2-hydroxy-7-methoxy-4-methyl-6-quinolyl)-2-morpholino-benzamide | 1 |
| 162 | 2-(3-fluoropyrrolidin-1-yl)-5-(3-furyl)-N-(2-hydroxy-4-methyl-6-quinolyl)pyridine-3-carboxamide | 1 |
| 163 | N-(2-hydroxy-4,7-dimethyl-6-quinolyl)-5-isoxazol-4-yl-2-morpholino-benzamide | 1 |
| 164 | 2-cyano-N-(2-hydroxy-4,7-dimethyl-6-quinolyl)-5-morpholino-pyridine-4-carboxamide | 1 |
| 165 | 5-(dimethylsulfamoyl)-N-(2-hydroxy-4-isopropyl-6-quinolyl)-2-pyrrolidin-1-yl-benzamide | 1 |
| 166 | N-(2-hydroxy-4-methyl-6-quinolyl)-5-(1-methylpyrazol-4-yl)-2-morpholino-benzamide | 1 |
| 167 | 5-(3-furyl)-N-(2-hydroxy-4-methyl-6-quinolyl)-2-morpholino-benzamide | 1 |
| 168 | 5-(1-hydroxyethyl)-N-(2-hydroxy-4-methyl-6-quinolyl)-2-morpholino-benzamide | 1 |
| 169 | N-(2-hydroxy-8-methoxy-4-methyl-6-quinolyl)-5-(1-methylpyrazol-4-yl)-2-morpholino-pyridine-3-carboxamide | 1 |
| 170 | N-(2-hydroxy-7-methoxy-4-methyl-6-quinolyl)-5-(1-methylpyrazol-4-yl)-2-morpholino-pyridine-3-carboxamide | 1 |
| 171 | N-(2-hydroxy-4,7-dimethyl-6-quinolyl)-5-(1-methylpyrazol-4-yl)-2-morpholino-pyridine-3-carboxamide | 1 |
| 172 | 5-(dimethylsulfamoyl)-2-[(3R)-3-fluoropyrrolidin-1-yl]-N-(2-hydroxy-4-methyl-6-quinolyl)benzamide | 1 |
| 173 | 5-(dimethylsulfamoyl)-2-[(3S)-3-fluoropyrrolidin-1-yl]-N-(2-hydroxy-4-methyl-6-quinolyl)benzamide | 1 |
| 174 | 5-(3-furyl)-N-(2-hydroxy-4-methyl-6-quinolyl)-2-morpholino-pyridine-3-carboxamide | 3 |
| 175 | N-(2-hydroxy-4-methyl-6-quinolyl)-5-(1-methylpyrazol-4-yl)-2-morpholino-pyridine-3-carboxamide | 1 |
| 176 | N-(2-hydroxy-4-methyl-6-quinolyl)-5-isoxazol-4-yl-2-morpholino-pyridine-3-carboxamide | 1 |
| 177 | 5-(3,5-dimethylisoxazol-4-yl)-N-(2-hydroxy-4-methyl-6-quinolyl)-2-morpholino-pyridine-3-carboxamide | 1 |
| 178 | 5-(3-furyl)-N-(2-hydroxy-4-methyl-6-quinolyl)-2-(6-oxa-2-azaspiro[3.3]heptan-2-yl)pyridine-3-carboxamide | 3 |
| 179 | 5-(3-furyl)-N-(2-hydroxy-4,8-dimethyl-6-quinolyl)-2-morpholino-pyridine-3-carboxamide | 1 |
| 180 | N-(2-hydroxy-4-methyl-6-quinolyl)-5-(5-methyl-1,3,4-oxadiazol-2-yl)-2-morpholino-benzamide | 1 |
| 181 | N-(2-hydroxy-4-methyl-6-quinolyl)-2-morpholino-5-(1H-tetrazol-5-yl)benzamide | 1 |
| 182 | 3-[(2-hydroxy-4-methyl-6-quinolyl)carbamoyl]-4-morpholino-benzoic acid | 1 |
| 183 | 5-cyano-N-(2-hydroxy-4-methyl-6-quinolyl)-2-morpholino-pyridine-3-carboxamide | 3 |
| 184 | 5-bromo-2-(3-fluoropyrrolidin-1-yl)-N-(2-hydroxy-4-methyl-6-quinolyl)pyridine-3-carboxamide | 3 |
| 185 | N-(2-hydroxy-4-methyl-6-quinolyl)-5-(4-methylpiperazin-1-yl)-2-morpholino-pyridine-3-carboxamide | 1 |

-continued

| Compound # | IUPAC_NAME | Classification |
|---|---|---|
| 186 | N-(2-hydroxy-4-methyl-6-quinolyl)-2,5-dimorpholino-pyridine-3-carboxamide | 1 |
| 187 | 5-[4-(dimethylamino)-1-piperidyl]-N-(2-hydroxy-4-methyl-6-quinolyl)-2-morpholino-pyridine-3-carboxamide | NT |
| 188 | 5-(3,5-dimethylisoxazol-4-yl)-N-(2-hydroxy-4,7-dimethyl-6-quinolyl)-2-morpholino-pyridine-3-carboxamide | 1 |
| 189 | 5-(3-furyl)-N-(2-hydroxy-8-methoxy-4-methyl-6-quinolyl)-2-morpholino-pyridine-3-carboxamide | 1 |
| 190 | 5-(3-furyl)-N-(2-hydroxy-7-methoxy-4-methyl-6-quinolyl)-2-morpholino-pyridine-3-carboxamide | 4 |
| 191 | 5-(3-furyl)-N-(2-hydroxy-4,7-dimethyl-6-quinolyl)-2-morpholino-pyridine-3-carboxamide | 1 |
| 192 | 5-(azetidin-1-yl)-N-(2-hydroxy-4-methyl-6-quinolyl)-2-morpholino-pyridine-3-carboxamide | NT |
| 193 | 5-[(3S)-3-fluoropyrrolidin-1-yl]-N-(2-hydroxy-4-methyl-6-quinolyl)-2-morpholino-pyridine-3-carboxamide | NT |
| 194 | 5-[(3R)-3-fluoropyrrolidin-1-yl]-N-(2-hydroxy-4-methyl-6-quinolyl)-2-morpholino-pyridine-3-carboxamide | NT |
| 195 | N-(2-hydroxy-4,7-dimethyl-6-quinolyl)-5-(2-methyltetrazol-5-yl)-2-morpholino-pyridine-3-carboxamide | 1 |
| 196 | N-(2-hydroxy-4,7-dimethyl-6-quinolyl)-5-(1-methyltetrazol-5-yl)-2-morpholino-pyridine-3-carboxamide | 5 |
| 197 | 2-cyano-5-(3-fluoropyrrolidin-1-yl)-N-(2-hydroxy-4-methyl-6-quinolyl)pyridine-4-carboxamide | 3 |
| 198 | 2-cyano-N-(2-hydroxy-4-methyl-6-quinolyl)-5-morpholino-pyridine-4-carboxamide | 1 |
| 199 | 5-(dimethylsulfamoyl)-2-(3-fluoropyrrolidin-1-yl)-N-(2-hydroxy-4-methyl-6-quinolyl)pyridine-3-carboxamide | 1 |
| 200 | N-(2-hydroxy-4,7-dimethyl-6-quinolyl)-5-(3-methylisoxazol-5-yl)-2-morpholino-pyridine-3-carboxamide | 2 |
| 201 | N-(2-hydroxy-7-methoxy-4-methyl-6-quinolyl)-5-(5-methyl-1,3,4-oxadiazol-2-yl)-2-morpholino-benzamide | 1 |
| 202 | N4-(2-hydroxy-4-methyl-6-quinolyl)-5-pyrrolidin-1-yl-pyridine-2,4-dicarboxamide | 1 |
| 203 | N-(2-hydroxy-4-methyl-6-quinolyl)-5-pyrrolidin-1-yl-2-(1H-tetrazol-5-yl)pyridine-4-carboxamide | 1 |
| 204 | 5-(cyanomethyl)-N-(2-hydroxy-4-methyl-6-quinolyl)-2-pyrrolidin-1-yl-benzamide | 1 |
| 205 | N-(2-hydroxy-4-methyl-6-quinolyl)-5-(1-morpholinocyclopropyl)-2-pyrrolidin-1-yl-benzamide | 1 |
| 206 | 5-(1-hydroxyethyl)-N-(2-hydroxy-4-methyl-6-quinolyl)-2-[2-(2-pyridyl)pyrrolidin-1-yl]benzamide | 1 |
| 207 | 2-acetyl-N-(2-hydroxy-4-methyl-6-quinolyl)-5-morpholino-pyridine-4-carboxamide | 1 |
| 208 | 2-(1-hydroxyethyl)-N-(2-hydroxy-4-methyl-6-quinolyl)-5-morpholino-pyridine-4-carboxamide | 1 |
| 209 | 2-acetyl-5-(3-fluoropyrrolidin-1-yl)-N-(2-hydroxy-4-methyl-6-quinolyl)pyridine-4-carboxamide | 1 |
| 210 | 5-(3-fluoropyrrolidin-1-yl)-2-(1-hydroxyethyl)-N-(2-hydroxy-4-methyl-6-quinolyl)pyridine-4-carboxamide | 1 |
| 211 | 2-cyano-5-[2-(dimethylaminomethyl)pyrrolidin-1-yl]-N-(2-hydroxy-4-methyl-6-quinolyl)pyridine-4-carboxamide | 2 |
| 212 | 2-acetyl-5-[2-(dimethylaminomethyl)pyrrolidin-1-yl]-N-(2-hydroxy-4-methyl-6-quinolyl)pyridine-4-carboxamide | 1 |
| 213 | 5-[2-(dimethylaminomethyl)pyrrolidin-1-yl]-2-(1-hydroxyethyl)-N-(2-hydroxy-4-methyl-6-quinolyl)pyridine-4-carboxamide | 1 |

A Further List of Classification:

| Compound # | IUPAC Name | Classification |
|---|---|---|
| S1 | N-(1-methyl-2-oxo-3,4-dihydroquinolin-6-yl)-2-morpholino-benzamide | 4 |

-continued

| Compound # | IUPAC Name | Classification |
|---|---|---|
| S2 | N-(2-hydroxy-4-methyl-6-quinolyl)-2-morpholino-benzamide | 2 |
| S3 | 3-(cyclopentylsulfamoyl)-4-methyl-N-(1-methyl-2-oxo-3,4-dihydroquinolin-6-yl)benzamide | 4 |
| S4 | N-(1-methyl-2-oxo-3,4-dihydroquinolin-6-yl)-2-morpholino-pyridine-3-carboxamide | 4 |
| S5 | 2-(4-methylpiperazin-1-yl)-N-(3-oxo-4H-1,4-benzoxazin-7-yl)benzamide | 5 |
| S6 | N-(1-methyl-2-oxo-3,4-dihydroquinolin-6-yl)-2-(4-methylpiperazin-1-yl)benzamide | 5 |
| S7 | N-(4-methyl-3-oxo-1,4-benzoxazin-7-yl)-2-(4-methylpiperazin-1-yl)benzamide | 5 |
| S8 | N-(1-methyl-2-oxo-3,4-dihydroquinolin-6-yl)-2-(4-pyrazin-2-ylpiperazin-1-yl)benzamide | 5 |
| S9 | N-(1-methyl-2-oxo-3,4-dihydroquinolin-6-yl)-2-morpholino-5-nitro-benzamide | 5 |
| S10 | N-(2-hydroxy-4-methyl-6-quinolyl)-2-(4-methylpiperazin-1-yl)benzamide | 4 |
| S11 | N-(2-hydroxy-4-methyl-6-quinolyl)-2-(4-pyrazin-2-ylpiperazin-1-yl)benzamide | 4 |
| S12 | N-(2-hydroxy-4-methyl-6-quinolyl)-2-morpholino-5-sulfamoyl-benzamide | 1 |
| S13 | N-(1-methyl-2-oxo-3,4-dihydroquinolin-6-yl)-2-morpholino-5-sulfamoyl-benzamide | 4 |
| S14 | 5-(2,5-dioxopyrrolidin-1-yl)-N-(2-hydroxy-4-methyl-6-quinolyl)-2-morpholino-benzamide | 2 |
| S15 | 5-(benzenesulfonamido)-N-(2-hydroxy-4-methyl-6-quinolyl)-2-(4-methylpiperazin-1-yl)benzamide | 3 |
| S16 | 5-(ethylsulfonylamino)-N-(2-hydroxy-4-methyl-6-quinolyl)-2-(4-methylpiperazin-1-yl)benzamide | 4 |
| S17 | N-(2-hydroxy-4-methyl-6-quinolyl)-2-morpholino-5-nitro-benzamide | 1 |
| S19 | N-(2-hydroxy-4-methyl-6-quinolyl)-2-morpholino-5-(1-piperidylsulfonyl)benzamide | 1 |
| S20 | N-(2-hydroxy-4-methyl-6-quinolyl)-2-morpholino-5-morpholinosulfonyl-benzamide | 1 |
| S21 | N-(2-hydroxy-4-methyl-6-quinolyl)-3-(piperazin-1-ylmethyl)benzamide | 3 |
| S22 | 2-(dimethylamino)-N-(2-hydroxy-4-methyl-6-quinolyl)-5-nitro-benzamide | 2 |
| S23 | N-(2-hydroxy-4-methyl-6-quinolyl)-3-(methylsulfamoyl)benzamide | 5 |
| S24 | N-(2-hydroxy-4-methyl-6-quinolyl)-3-[(2-oxopyrrolidin-1-yl)methyl]benzamide | 5 |
| S25 | N-(2-hydroxy-4-methyl-6-quinolyl)-5-nitro-2-pyrrolidin-1-yl-benzamide | 1 |
| S26 | 3-[(2-amino-2-oxo-ethyl)sulfamoyl]-N-(2-hydroxy-4-methyl-6-quinolyl)benzamide | 5 |
| S27 | 5-(dimethylsulfamoyl)-N-(2-hydroxy-4-methyl-6-quinolyl)-2-pyrrolidin-1-yl-benzamide | 1 |
| S28 | N-(2-hydroxy-4-methyl-6-quinolyl)-2-(methanesulfonamido)-5-morpholino-benzamide | 2 |
| S29 | N-(2-hydroxy-4-methyl-6-quinolyl)-3-pyrrolidin-1-yl-benzamide | 5 |
| S30 | 4-amino-N-(2-hydroxy-4-methyl-6-quinolyl)-3-nitro-benzamide | 5 |
| S32 | 2-morpholino-N-[2-oxo-4-(trifluoromethyl)-1H-quinolin-6-yl]-5-sulfamoyl-benzamide | 4 |
| S33 | 5-(dimethylsulfamoyl)-2-fluoro-N-(2-hydroxy-4-methyl-6-quinolyl)benzamide | 5 |
| S34 | 2-bromo-N-(2-hydroxy-4-methyl-6-quinolyl)-5-morpholinosulfonyl-benzamide | 5 |
| S35 | N-(4-hydroxy-2-oxo-1H-quinolin-6-yl)-2-morpholino-5-morpholinosulfonyl-benzamide | 1 |
| S36 | N-(2-hydroxy-4-methyl-6-quinolyl)-3-(4-methylpiperazin-1-yl)sulfonyl-benzamide | 5 |
| S37 | 5-(dimethylsulfamoyl)-N-(2,4-dioxo-1H-quinazolin-6-yl)-2-morpholino-benzamide | 5 |
| S39 | 5-(dimethylsulfamoyl)-N-(3-methyl-2-oxo-1,4-dihydroquinazolin-6-yl)-2-morpholino-benzamide | 1 |
| S41 | 5-(dimethylsulfamoyl)-N-(2-hydroxy-4-methyl-6-quinolyl)-2-(3-methylpyrrolidin-1-yl)benzamide | 3 |
| S42 | 5-(dimethylsulfamoyl)-2-(3-fluoropyrrolidin-1-yl)-N-(2-hydroxy-4-methyl-6-quinolyl)benzamide | 1 |
| S43 | 5-(dimethylsulfamoyl)-N-(2-hydroxy-4-methyl-6-quinolyl)-2-(3-methoxypyrrolidin-1-yl)benzamide | 3 |

| Compound # | IUPAC Name | Classification |
|---|---|---|
| S44 | 1-[4-(dimethylsulfamoyl)-2-[(2-hydroxy-4-methyl-6-quinolyl)carbamoyl]phenyl]pyrrolidine-3-carboxamide | 1 |
| S45 | 2-[3-(dimethylamino)pyrrolidin-1-yl]-5-(dimethylsulfamoyl)-N-(2-hydroxy-4-methyl-6-quinolyl)benzamide | 3 |
| S46 | 5-(dimethylsulfamoyl)-N-(2-hydroxy-4-methyl-6-quinolyl)-2-(3-isobutylpyrrolidin-1-yl)benzamide | 3 |
| S47 | 2-[3-(dimethylaminomethyl)pyrrolidin-1-yl]-5-(dimethylsulfamoyl)-N-(2-hydroxy-4-methyl-6-quinolyl)benzamide | 1 |
| S48 | 5-(dimethylsulfamoyl)-N-(2-hydroxy-4-methyl-6-quinolyl)-2-(3-ureidopyrrolidin-1-yl)benzamide | 1 |
| S49 | 5-(dimethylsulfamoyl)-N-(2-hydroxy-4-methyl-6-quinolyl)-2-(3-pyrrolidin-1-ylpyrrolidin-1-yl)benzamide | 3 |
| S50 | 2-[3-(2-amino-2-oxo-ethoxy)pyrrolidin-1-yl]-5-(dimethylsulfamoyl)-N-(2-hydroxy-4-methyl-6-quinolyl)benzamide | 3 |
| S51 | 5-(dimethylsulfamoyl)-N-(2-hydroxy-4-methyl-6-quinolyl)-2-(3-phenylpyrrolidin-1-yl)benzamide | 1 |
| S52 | 5-(dimethylsulfamoyl)-N-(2-hydroxy-4-methyl-6-quinolyl)-2-(2-methylpyrrolidin-1-yl)benzamide | 3 |
| S53 | 5-(dimethylsulfamoyl)-N-(2-hydroxy-4-methyl-6-quinolyl)-2-[2-(methoxymethyl)pyrrolidin-1-yl]benzamide | 1 |
| S54 | 5-(dimethylsulfamoyl)-N-(2-hydroxy-4-methyl-6-quinolyl)-2-(5-methyl-2,3,3a,4,6,6a-hexahydropyrrolo[3,4-b]pyrrol-1-yl)benzamide | 4 |
| S55 | 5-(dimethylsulfamoyl)-N-(2-hydroxy-4-methyl-6-quinolyl)-2-(2-isobutylpyrrolidin-1-yl)benzamide | 2 |
| S56 | 2-[2-(dimethylaminomethyl)pyrrolidin-1-yl]-5-(dimethylsulfamoyl)-N-(2-hydroxy-4-methyl-6-quinolyl)benzamide | 1 |
| S57 | 5-(dimethylsulfamoyl)-2-[2-(1-hydroxy-1-methyl-ethyl)pyrrolidin-1-yl]-N-(2-hydroxy-4-methyl-6-quinolyl)benzamide | 4 |
| S58 | 5-(dimethylsulfamoyl)-N-(2-hydroxy-4-methyl-6-quinolyl)-2-[2-(1H-imidazol-2-yl)pyrrolidin-1-yl]benzamide | NT |
| S59 | 5-(dimethylsulfamoyl)-N-(2-hydroxy-4-methyl-6-quinolyl)-2-[2-(1H-pyrazol-3-yl)pyrrolidin-1-yl]benzamide | 1 |
| S60 | 5-(dimethylsulfamoyl)-N-(2-hydroxy-4-methyl-6-quinolyl)-2-[2-(1H-tetrazol-5-yl)pyrrolidin-1-yl]benzamide | 1 |
| S61 | 5-(dimethylsulfamoyl)-N-(2-hydroxy-4-methyl-6-quinolyl)-2-(4-methyl-3,3a,5,6,7,7a-hexahydro-2H-pyrrolo[3,2-b]pyridin-1-yl)benzamide | 3 |
| S62 | 1-[4-(dimethylsulfamoyl)-2-[(2-hydroxy-4-methyl-6-quinolyl)carbamoyl]phenyl]-N,N-dimethyl-pyrrolidine-2-carboxamide | 1 |
| S63 | 5-(dimethylsulfamoyl)-N-(2-hydroxy-4-methyl-6-quinolyl)-2-[2-(3-pyridyl)pyrrolidin-1-yl]benzamide | NT |
| S64 | 1-[4-(dimethylsulfamoyl)-2-[(2-hydroxy-4-methyl-6-quinolyl)carbamoyl]phenyl]-4-hydroxy-pyrrolidine-2-carboxamide | NT |
| S65 | 5-(dimethylsulfamoyl)-2-(3-hydroxy-3-methyl-8-azabicyclo[3.2.1]octan-8-yl)-N-(2-hydroxy-4-methyl-6-quinolyl)benzamide | 3 |
| S66 | 5-(dimethylsulfamoyl)-2-(4-hydroxy-2,5-dimethyl-1-piperidyl)-N-(2-hydroxy-4-methyl-6-quinolyl)benzamide | 3 |
| S67 | 5-(dimethylsulfamoyl)-N-(2-hydroxy-4-methyl-6-quinolyl)-2-(2-phenyl-1-piperidyl)benzamide | 1 |
| S68 | 2-(2,3,4,4a,5,7,8,8a-octahydropyrano[4,3-b]pyridin-1-yl)-5-(dimethylsulfamoyl)-N-(2-hydroxy-4-methyl-6-quinolyl)benzamide | NT |
| S69 | 5-(dimethylsulfamoyl)-N-(2-hydroxy-4-methyl-6-quinolyl)-2-[2-(5-oxopyrrolidin-3-yl)-1-piperidyl]benzamide | NT |
| S71 | 5-(diethylsulfamoyl)-N-(2-hydroxy-4-methyl-6-quinolyl)-2-pyrrolidin-1-yl-benzamide | 3 |
| S72 | 5-(diethylsulfamoyl)-N-(2-hydroxy-4-methyl-6-quinolyl)-2-(1-piperidyl)benzamide | 3 |
| S74 | N-(2-hydroxy-4-methyl-6-quinolyl)-2-(2-methyl-1-piperidyl)-5-nitro-pyridine-3-carboxamide | 3 |

-continued

| Compound # | IUPAC Name | Classification |
|---|---|---|
| S76 | 5-nitro-N-(2-oxo-3,4-dihydro-1H-quinolin-6-yl)-2-pyrrolidin-1-yl-benzamide | 4 |
| S77 | N-(4-methyl-3-oxo-1,4-benzoxazin-7-yl)-5-nitro-2-pyrrolidin-1-yl-benzamide | 4 |
| S78 | 5-morpholinosulfonyl-N-(2-oxo-3,4-dihydro-1H-quinolin-6-yl)-2-pyrrolidin-1-yl-benzamide | 4 |
| S79 | N-(4-methyl-3-oxo-1,4-benzoxazin-7-yl)-5-morpholinosulfonyl-2-pyrrolidin-1-yl-benzamide | 4 |
| S80 | 5-[(4-methylpiperazin-1-yl)methyl]-N-(2-oxo-3,4-dihydro-1H-quinolin-6-yl)-2-pyrrolidin-1-yl-benzamide | 4 |
| S81 | 5-[[2-hydroxyethyl(methyl)amino]methyl]-N-(2-hydroxy-4-methyl-6-quinolyl)-2-pyrrolidin-1-yl-benzamide | 1 |
| S82 | N-(2-hydroxy-4-methyl-6-quinolyl)-2-pyrrolidin-1-yl-5-[(tetrahydrofuran-2-ylmethylamino)methyl]benzamide | 1 |
| S83 | 5-[[3-(dimethylamino)pyrrolidin-1-yl]methyl]-N-(2-hydroxy-4-methyl-6-quinolyl)-2-pyrrolidin-1-yl-benzamide | 1 |
| S84 | N-(2-hydroxy-4-methyl-6-quinolyl)-5-[(3-hydroxypyrrolidin-1-yl)methyl]-2-pyrrolidin-1-yl-benzamide | 1 |
| S85 | N-(2-hydroxy-4-methyl-6-quinolyl)-5-[[(2S)-2-(methoxymethyl)pyrrolidin-1-yl]methyl]-2-pyrrolidin-1-yl-benzamide | 1 |
| S86 | 5-[[4-(2-hydroxyethyl)piperazin-1-yl]methyl]-N-(2-hydroxy-4-methyl-6-quinolyl)-2-pyrrolidin-1-yl-benzamide | 1 |
| S87 | N-(2-hydroxy-4-methyl-6-quinolyl)-5-[(4-methyl-1,4-diazepan-1-yl)methyl]-2-pyrrolidin-1-yl-benzamide | 1 |
| S88 | N-(2-hydroxy-4-methyl-6-quinolyl)-5-[(3-methoxypyrrolidin-1-yl)methyl]-2-pyrrolidin-1-yl-benzamide | 1 |
| S89 | 5-[(3-hydroxyazetidin-1-yl)methyl]-N-(2-hydroxy-4-methyl-6-quinolyl)-2-pyrrolidin-1-yl-benzamide | 1 |
| S90 | N-(2-hydroxy-4-methyl-6-quinolyl)-5-[[3-(methoxymethyl)azetidin-1-yl]methyl]-2-pyrrolidin-1-yl-benzamide | 1 |
| S91 | N-(2-hydroxy-4-methyl-6-quinolyl)-5-[[3-(methoxymethyl)-1-piperidyl]methyl]-2-pyrrolidin-1-yl-benzamide | 1 |
| S93 | N-(2-hydroxy-4-methyl-6-quinolyl)-2-(3-methylpyrrolidin-1-yl)-5-(morpholinomethyl)pyridine-3-carboxamide | 1 |
| S94 | N-(2-hydroxy-4-methyl-6-quinolyl)-2-(2-methylpyrrolidin-1-yl)-5-(morpholinomethyl)pyridine-3-carboxamide | 2 |
| S97 | 2-(3-fluoro-3-methyl-pyrrolidin-1-yl)-N-(2-hydroxy-4-methyl-6-quinolyl)-5-(morpholinomethyl)pyridine-3-carboxamide | 2 |
| S98 | 2-(3-carbamoylpyrrolidin-1-yl)-N-(2-hydroxy-4-methyl-6-quinolyl)-5-(morpholinomethyl)pyridine-3-carboxamide | 3 |
| S101 | N-(2-hydroxy-4-methyl-6-quinolyl)-2-(3-isobutylpyrrolidin-1-yl)-5-(morpholinomethyl)pyridine-3-carboxamide | 4 |
| S107 | N-(2-hydroxy-4-methyl-6-quinolyl)-5-(morpholinomethyl)-2-(3-pyrrolidin-1-ylpyrrolidin-1-yl)pyridine-3-carboxamide | 4 |
| S109 | 2-[2-(dimethylcarbamoyl)pyrrolidin-1-yl]-N-(2-hydroxy-4-methyl-6-quinolyl)-5-(morpholinomethyl)pyridine-3-carboxamide | 3 |
| S111 | N-(2-hydroxy-4-methyl-6-quinolyl)-5-(morpholinomethyl)-2-[3-(4-pyridyl)pyrrolidin-1-yl]pyridine-3-carboxamide | 3 |
| S114 | 2-[2-(hydroxymethyl)morpholin-4-yl]-N-(2-hydroxy-4-methyl-6-quinolyl)-5-(morpholinomethyl)pyridine-3-carboxamide | 5 |
| S115 | 2-[2-(hydroxymethyl)-5-methyl-morpholin-4-yl]-N-(2-hydroxy-4-methyl-6-quinolyl)-5-(morpholinomethyl)pyridine-3-carboxamide | 5 |
| S116 | N-(2-hydroxy-4-methyl-6-quinolyl)-2-[2-(methoxymethyl)morpholin-4-yl]-5-(morpholinomethyl)pyridine-3-carboxamide | NT |
| S117 | 2-[2-(dimethylaminomethyl)morpholin-4-yl]-N-(2-hydroxy-4-methyl-6-quinolyl)-5-(morpholinomethyl)pyridine-3-carboxamide | 5 |

-continued

| Compound # | IUPAC Name | Classification |
|---|---|---|
| S118 | 2-[3-(hydroxymethyl)pyrrolidin-1-yl]-N-(2-hydroxy-4-methyl-6-quinolyl)-5-(morpholinomethyl)pyridine-3-carboxamide | 5 |

As can be seen from the table above, the compounds were found to show beneficial activity.

Compounds were assayed for binding affinity using a FRET assay or the Bromoscan assay, and for cellular efficacy using either a cell viability assay or a cytokine release inhibition assay and the assays are described herein and results reported in the table below.

According to some embodiments the compounds disclosed herein display a FRET inhibition of ≤10 µM, e.g. between 1 µM and 10 µM; such as ≤1 µM, e.g. between 0.5 µM and 1 µM; such as ≤0.5 µM, e.g. between 0.2 µM and 0.5 µM; such as ≤0.2 µM.

Bromoscan assays were run by DiscoveRx Corporation. The relevant assay names are BRD4(1) for the first bromodomain of BRD4 and BRD4(2) for the second bromodomain of BRD4. Further Bromoscan assays covering other bromodomains could be employed to establish the selectivity profile of a compound of interest. To run the Bromoscan assay, a T7 phage strain displaying the relevant bromodomain was grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 µm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA (bovine serum albumin), 0.05% Tween 20, 1 mM DTT (dithiothreitol)) to remove unbound ligand and to reduce non-specific phage binding. Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO and subsequently diluted 1:10 in monoethylene glycol (MEG) to create stocks at 100× the screening concentration (resulting stock solution is 10% DMSO/90% MEG). The compounds were then diluted directly into the assays such that the final concentration of DMSO and MEG were 0.1% and 0.9%, respectively. All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1x PBS, 0.05% Tween 20, 2 µM nonbiotinylated affinity ligand) and incubated at room temperature with shaking for 30 minutes. The bromodomain concentration in the eluates was measured by qPCR (quantitative real-time polymerase chain reaction).

Cell Viability Assay

Grow MV-4-11 tumor cells (ATCC CRL-9591) in suspension at 37° C. in a humidified atmosphere (5% $CO_2$, 95% air, IMDM (Iscove's Modified Dulbecco's Medium) medium supplemented with 10% FBS (fetal bovine serum))

Seed cells at a density of 10.000 cells per well of a flat-bottomed 96 well plate in 50 µL of medium. After 24 hours, add 50 µL of test compound or DMSO control from a pre-generated compound dilution series in medium. After an additional 72 hours, add 100 µL of pre-mixed CellTiter-Glo reagent (Promega G7570) to each well, shake for two minutes to allow cell lysis followed by 10 minutes of incubation at room temperature without shaking. Read luminescence on an Envision reader (Perkin Elmer). The inhibition of cell viability (IC) can be expressed as follows:

$$\% \ IC = \left(1 - \frac{OD_{compound\text{-}exposed \ wells}}{OD_{DMSO \ control \ wells}}\right) \times 100$$

IC data can be analyzed using GraphPad Prism, and $IC_{50}$ data can be obtained using non-linear regression curve fit using log(compound) vs response (variable slope). The effect of compound on the viability of other cell lines can be assayed under similar conditions, taking into account the growth requirement of the individual cell line.

Cytokine release inhibition assay: LPS-induced cytokine release from human peripheral blood mononuclear cells (PBMCs)

200,000 PBMCs were seeded per well of a 96-well plate in 160 µL of medium. Afterwards, 20 µL of ten times concentrated working dilutions of compound or DMSO control were added per well. Cells were pre-incubated with compounds for 1 h at 37° C., 5% CO2, 95% humidity and 20 µL of ten times concentrated LPS was added to cells (Sigma L4391, final concentration 1 ng/mL). Following 18 h incubation at 37° C., 5% CO2, 95% humidity, plates were centrifuged for 10 minutes at 300×g. 150 µL of supernatants were collected for IL-12p40 determination. The concentration of IL-12p40 in supernatants was determined by sandwich ELISA (enzyme-linked immunosorbent assay) using capture and detection antibodies according to the manufacturer's instructions (R&D Systems DY1240). Data can be analyzed using GraphPad Prism, and $IC_{50}$ data can be obtained using non-linear regression curve fit using log (compound) vs response (variable slope).

Table of results:

| Compound # | BromoScan BRD4_1 Kd/nM | BromoScan BRD4_2 Kd/nM | BromoScan BRD4_2/1 | Cell viability assay MV4; 11 (µM) | LPS IC50 IL12p40 µM |
|---|---|---|---|---|---|
| 107 | 3.6 | 28.0 | 7.8 | 0.7 | |
| 67 | 6.2 | 1183.3 | 190.9 | 1.2 | |
| 113 | 16.0 | 190.0 | 11.9 | 0.6 | |
| 43 | 2.4 | 79.0 | 32.9 | | 0.4 |
| 1 | 13.0 | 330.0 | 25.4 | 0.6 | 0.3 |
| 128 | 15.0 | 2500.0 | 166.7 | | 0.3 |
| 99 | 12.0 | 5600.0 | 466.7 | | 0.4 |

The table shows that compounds disclosed herein may be selective compounds, such as compounds having less than 30-fold selectivity, between 30 and 100-fold selectivity and more than 100-fold selectivity for BRD4_1 over BRD4_2. The compounds disclosed herein may also be non-selective.

The cell viability assay is used to demonstrate the compounds ability to kill cancer cells.

The LPS induced cytokine release assay demonstrates the compounds ability to inhibit the production of IL12p40 following an inflammatory stimulus (LPS), and as can be seen compounds disclosed herein are able to inhibit the production of IL12p40.

In summary, compounds disclosed herein, have been found to likely bind and thereby modulate or inhibit the function of bromodomains, and compounds disclosed herein may be selective as well as non-selective, and usefulness to treat a wide range of diseases, disorders, or conditions have been demonstrated, for example by the cell viability assay and the LPS induced cytokine release assay.

The invention claimed is:
1. A compound according to formula (I):

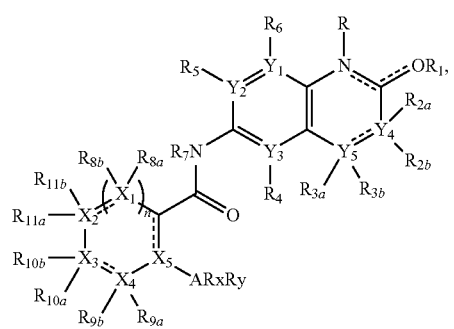

or a pharmaceutically acceptable salt thereof and tautomers thereof, wherein:

$Y_1$, $Y_2$, $Y_3$, and $Y_4$ are independently selected from the group consisting of N and C;

$Y_5$ is C;

$X_1$, $X_2$, $X_3$, and $X_4$, are independently selected from the group consisting of N, O, S and C;

$X_5$ is C;

n is 0 or 1;

R is absent or selected from the group consisting of hydrogen, and unsubstituted or substituted $C_{1-4}$ alkyl;

$R_1$ is absent, or selected from the group consisting of hydrogen, and unsubstituted or substituted $C_{1-4}$ alkyl;

$R_{2a}$, $R_{2b}$, $R_{3a}$, and $R_{3b}$ are independently absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, and —$OR_{31}$, or $R_{2a}$ and $R_{2b}$ taken together with $Y_4$, and/or $R_{3a}$ and $R_{3b}$ taken together with $Y_5$ form a ring selected from the group consisting of unsubstituted or substituted $C_{3-8}$ cycloalkyl, unsubstituted or substituted $C_{3-8}$ cycloalkenyl, and unsubstituted or substituted $C_{2-9}$ heteroalicyclyl;

$R_4$, $R_5$, $R_6$, $R_{8a}$, $R_{8b}$, $R_{9a}$, $R_{9b}$, $R_{10a}$, $R_{10b}$, $R_{11a}$, and $R_{11b}$ are independently absent or selected from the group consisting of hydrogen, halogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, —OH, —CN, —$NO_2$, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —$NR_{12}R_{13}$, —$NR_{14}C(=O)R_{15}$, —$NR_{16}C(=O)NR_{17}R_{18}$, —$NR_{28}C(=O)OR_{19}$, —$C(=O)R_{20}$, —$C(=O)OR_{21}$, —$OC(=O)R_{21}$, —$C(=O)NR_{22}R_{23}$, —$S(=O)R_{24}$, —$SO_2R_{25}$, —$SO_2NR_{26}R_{27}$, and —$OR_{31}$; or $R_5$, $R_6$, $R_{8a}$, $R_{8b}$, $R_{9a}$, $R_{9b}$, $R_{10a}$, $R_{10b}$, $R_{11a}$ and/or $R_{11b}$ are taken together with an adjacent $R_5$, $R_6$, $R_{8a}$, $R_{8b}$, $R_{9a}$, $R_{9b}$, $R_{10a}$, $R_{10b}$, $R_{11a}$ or $R_{11b}$ group to form a ring system selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl; or $R_{8a}$, $R_{8b}$ and $X_1$; $R_{9a}$, $R_{9b}$ and $X_4$; $R_{10a}$, $R_{10b}$ and $X_3$; and/or $R_{11a}$, $R_{11b}$ and $X_2$ are taken together to form a ring system selected from the group consisting of unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl; or $R_{8b}$, $R_{11b}$, $X_1$ and $X_2$; $R_{10b}$, $R_{11b}$, $X_2$ and $X_3$; and/or $R_{9b}$, $R_{10b}$, $X_3$ and $X_4$ are taken together to form a ring system selected from the group consisting of unsubstituted or substituted aryl, unsubstituted or substituted heteroaryl, unsubstituted or substituted heteroalicyclyl, unsubstituted or substituted cycloalkyl, and unsubstituted or substituted cycloalkenyl;

$R_7$ is selected from the group consisting of hydrogen, —OH, unsubstituted or substituted $C_{1-6}$ alkyl, unsubstituted or substituted $C_{3-8}$ cycloalkyl, and unsubstituted or substituted $C_{3-8}$ cycloalkenyl;

$R_{12}$, $R_{13}$, $R_{16}$, $R_{17}$, $R_{18}$, $R_{22}$, $R_{23}$, $R_{26}$, and $R_{27}$ are independently selected from the group consisting of hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl, or $R_{12}$ and $R_{13}$, $R_{16}$ and $R_{17}$, $R_{17}$ and $R_{18}$, $R_{22}$ and $R_{23}$, $R_{26}$ and $R_{27}$ are taken together with the atom to which they are attached form a ring selected from the group consisting of unsubstituted or substituted $C_{2-9}$ heteroalicyclyl and unsubstituted or substituted heteroaryl;

$R_{14}$, $R_{15}$, $R_{19}$, $R_{20}$, $R_{21}$, $R_{24}$, $R_{25}$, and $R_{28}$ are independently selected from the group consisting of hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl;

$R_{31}$ is absent or selected from the group consisting of hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl;

A is N;

$R_x$ and $R_y$ are independently selected from the group consisting of hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —C(=O)$R_{20}$ and —SO$_2$R$_{25}$; or $R_x$ and $R_y$ taken together with A form a ring system selected from the group consisting of unsubstituted or substituted $C_{2-9}$ heteroalicyclyl, and unsubstituted or substituted heteroaryl; or one of $R_x$ or $R_y$ taken together with A forms a ring system selected from the group consisting of unsubstituted or substituted $C_{2-9}$ heteroalicyclyl, and unsubstituted or substituted heteroaryl; and whenever $R_x$ and $R_y$ are independently selected from the group consisting of hydrogen, unsubstituted or substituted $C_{1-6}$ alkyl, unsubstituted or substituted $C_{1-6}$ alkenyl, substituted or unsubstituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, unsubstituted or substituted heteroaryl, —C(=O)$R_{20}$ and —SO$_2$R$_{25}$, then neither $R_{11a}$ and $R_{11b}$ are hydrogen;

whenever one or more heteroatom(s) is/are present it is/they are selected from the group consisting of O, N and S;

with the proviso that the compound of Formula (I) is not

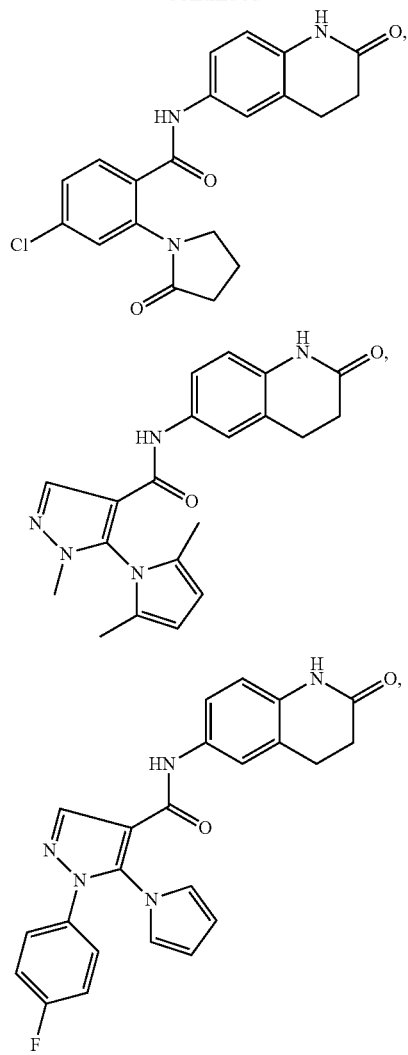

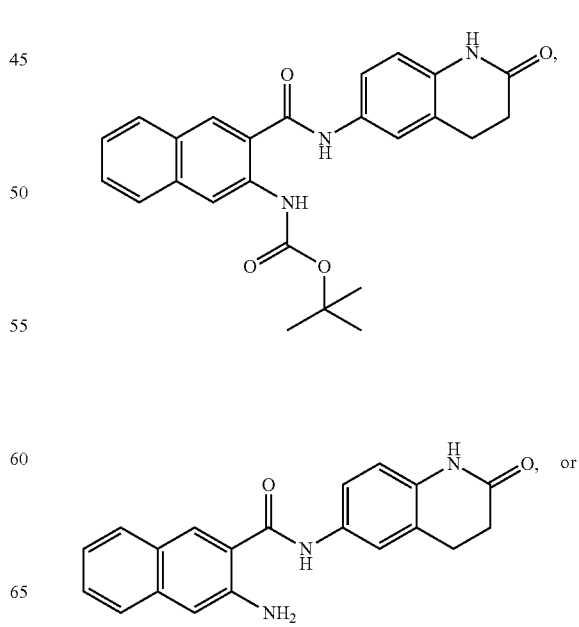

-continued

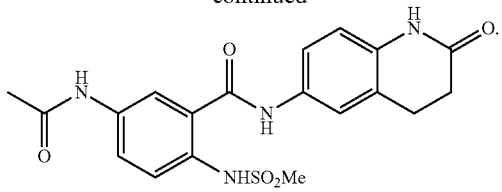

2. The compound of claim 1, wherein $Y_1$, $Y_2$, and $Y_3$ are C and $Y_4$ is C or N.

3. The compound of claim 1, wherein $Y_4$ is C.

4. The compound of claim 1, wherein R is hydrogen or methyl.

5. The compound of claim 1, wherein $R_1$ is absent or is hydrogen.

6. The compound of claim 1, wherein $R_{2a}$ and $R_{2b}$ independently are absent or selected from the group consisting of hydrogen, halogen, unsubstituted or substituted $C_{1-6}$ alkyl, unsubstituted or substituted $C_{3-6}$ cycloalkyl and unsubstituted or substituted $C_{1-6}$ alkoxy.

7. The compound of claim 1, wherein:
$R_{2a}$ is selected from the group consisting of hydrogen, methyl, ethyl, isopropyl, cyclopropyl, —$CF_3$, —$CHF_2$, —$CH_2F$, —$CH_2CH_2F$, —$CH_2CHF_2$, —$CH_2CF_3$, methoxy, ethoxy, isopropoxy, cyclopropoxy, —$OCF_3$, —$OCHF_2$, —$OCH_2F$, —$OCHFCF_3$, and halogen; and
$R_{2b}$ and $R_{3b}$ are absent.

8. The compound of claim 1, wherein $R_{3a}$ and $R_{3b}$ independently are absent or selected from the group consisting of hydrogen, halogen, unsubstituted or substituted $C_{1-6}$ alkyl, unsubstituted or substituted $C_{3-6}$ cycloalkyl, and unsubstituted or substituted $C_{1-6}$ alkoxy.

9. The compound of claim 1, wherein $R_{3a}$ is selected from the group consisting of hydrogen, methyl, ethyl, isopropyl, cyclopropyl, —$CF_3$, —$CHF_2$, —$CH_2F$, —$CH_2CH_2F$, —$CH_2CHF_2$, —$CH_2CF_3$, methoxy, ethoxy, isopropoxy, cyclopropoxy, —$OCF_3$, —$OCHF_2$, —$OCH_2F$, —$OCHFCF_3$, and halogen; and
$R_{3b}$ is absent.

10. The compound of claim 1, wherein:
$R_4$, $R_5$ and $R_6$ independently are selected from the group consisting of hydrogen, unsubstituted or substituted $C_{1-6}$ alkyl, unsubstituted or substituted $C_{1-6}$ alkoxy, —CN, —$OR_{31}$, halogen, —$NR_{12}R_{13}$, —$NR_{14}$(C=O)$R_{15}$, —$NR_{16}$(C(=O)$NR_{17}R_{18}$, —$NR_{28}$C(=O)$OR_{19}$, —$NR_{33}$(C$R_{34}R_{35}$)$_m$C(=O)$NR_{36}R_{37}$, —(C$R_{38}R_{39}$)$_m$N$R_{40}R_{41}$, —(C$R_{42}R_{43}$)$_m$C(=O)$NR_{44}R_{45}$, and —O(C=O)$R_{21}$;
$R_{12}$, $R_{13}$, $R_{14}$, $R_{15}$, $R_{16}$, $R_{17}$, $R_{18}$, $R_{19}$, $R_{21}$, $R_{28}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, and $R_{45}$ independently are selected from the group consisting of hydrogen, unsubstituted or substituted $C_{1-6}$ alkyl, unsubstituted or substituted $C_{1-6}$ alkenyl, unsubstituted or substituted $C_{1-6}$ alkynyl, unsubstituted or substituted $C_{1-6}$ alkoxy, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted aryl, and unsubstituted or substituted heteroaryl; or
$R_{12}$ and $R_{13}$, $R_{17}$ and $R_{18}$, $R_{36}$ and $R_{37}$, $R_{40}$ and $R_{41}$, and/or $R_{44}$ and $R_{45}$ taken together with the nitrogen atom to which they are attached form a ring selected from the group consisting of unsubstituted or substituted $C_{2-9}$ heteroalicyclyl and unsubstituted or substituted heteroaryl; and m is an integer selected from the group consisting of 0, 1, 2, 3 and 4.

11. The compound of claim 1, having a formula selected from the group consisting of Formulae (II)-(V):

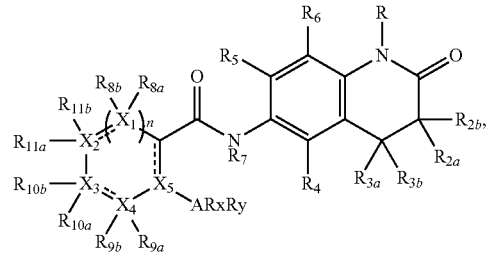

(II)

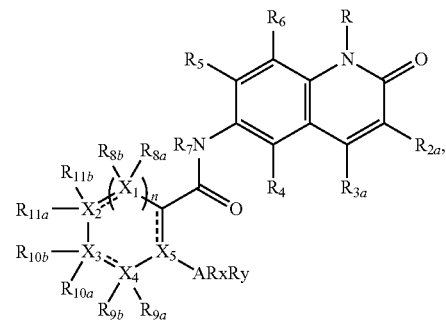

(III)

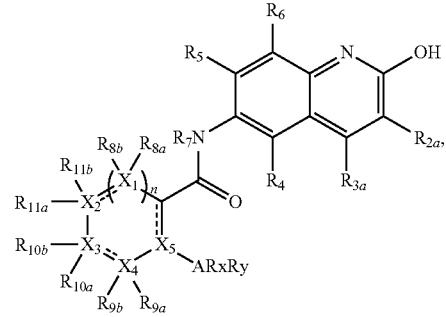

(IV)

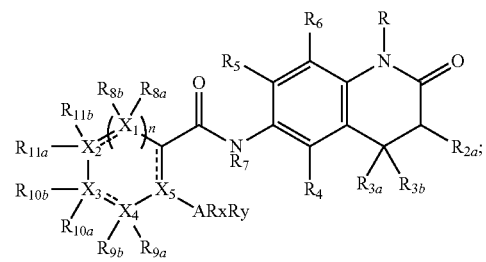

(V)

wherein:

R is selected from the group consisting of hydrogen and methyl;

$R_{2a}$, $R_{2b}$, $R_{3a}$, and $R_{3b}$ are independently selected from the group consisting of hydrogen, halogen, unsubstituted or substituted $C_{1-6}$ alkyl, unsubstituted and substituted $C_{1-6}$ alkoxy;

$R_4$, $R_5$, $R_6$ are independently selected from the group consisting of hydrogen, halogen, unsubstituted or substituted $C_{1-6}$ alkyl, unsubstituted or substituted $C_{1-6}$ alkoxy, —$OR_{31}$, —$NR_{12}R_{13}$, —$NR_{14}$(C=O)$R_{15}$, —$NR_{16}$C(=O)$NR_{17}R_{18}$, —$NR_{28}$C(=O)$OR_{19}$, —NR$_{33}$(CR$_{34}$R$_{35}$)$_m$C(=O)NR$_{36}$R$_{37}$, —(CR$_{38}$R$_{39}$)$_m$NR$_{40}$R$_{41}$, —(CR$_{42}$R$_{43}$)$_m$C(=O)NR$_{44}$R$_{45}$, and —O(C=O)R$_{21}$;

R$_{12}$, R$_{13}$, R$_{14}$, R$_{15}$, R$_{16}$, R$_{17}$, R$_{18}$, R$_{19}$, R$_{21}$, R$_{28}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$, and R$_{45}$ independently are selected from the group consisting of hydrogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, and unsubstituted or substituted heteroaryl, or R$_{12}$ and R$_{13}$, R$_{17}$ and Rig, R$_{36}$ and R$_{37}$, R$_{40}$ and R$_{41}$, and/or R$_{44}$ and R$_{45}$ taken together with the nitrogen atom to which they are attached form a ring selected from the group consisting of unsubstituted or substituted C$_{2-9}$ heteroalicyclyl and unsubstituted or substituted heteroaryl; and m is an integer selected from the group consisting of 0, 1, 2, 3 and 4.

12. The compound of claim 11, wherein the compound is a compound of Formula (II), (III) or (IV).

13. The compound of claim 10, wherein R$_{14}$, R$_{15}$, R$_{16}$, R$_{17}$, R$_{18}$, R$_{19}$, R$_{21}$ and R$_{28}$ independently are selected from the group consisting of methyl, ethyl, iso-propyl, —CF$_3$, tert-butyl, and cyclopropyl.

14. The compound of claim 1, wherein R$_7$ is hydrogen.

15. The compound of claim 1, wherein R$_{8a}$, R$_{9a}$, R$_{10a}$, and R$_{11a}$ are absent and the ring comprising X$_1$, X$_2$, X$_3$, X$_4$ and X$_5$ is a substituted aryl or substituted heteroaryl ring.

16. The compound of claim 1, wherein n is 1.

17. The compound of claim 11, wherein
X$_1$, X$_2$, X$_3$ and X$_4$ independently N or C, and
X$_5$ is C.

18. The compound of claim 11, wherein
n is 1,
one of X$_2$, X$_3$, and X$_4$ is N,
the two of X$_2$, X$_3$, and X$_4$ not being N are C; and
X$_1$ and X$_5$ are C.

19. The compound of claim 1, wherein
R$_{8a}$, R$_{8b}$, R$_{9a}$, R$_{9b}$, R$_{10a}$ and R$_{10b}$ independently are absent or selected from the group consisting of hydrogen, halogen, C$_{1-4}$ alkyl, C$_{1-4}$ alkoxy, C$_{3-5}$ cycloalkyl, —CN, —OH, —CF$_3$, and —OCF$_3$, or
R$_{8b}$, R$_{11b}$, X$_1$ and X$_2$; R$_{10b}$, R$_{11b}$, X$_2$ and X$_3$; and/or R$_{9b}$, R$_{10b}$, X$_3$ and X$_4$ are taken together to form a ring system selected from the group consisting of unsubstituted or substituted aryl, unsubstituted or substituted heteroaryl, unsubstituted or substituted heteroalicyclyl, unsubstituted or substituted cycloalkyl, and unsubstituted or substituted cycloalkenyl.

20. The compound of claim 19, wherein C$_{1-4}$ alkyl is methyl or ethyl and C$_{1-4}$ alkoxy is methoxy.

21. The compound of claim 1, wherein:
R$_{8a}$, R$_{9a}$, R$_{10a}$, and R$_{11a}$ are absent and R$_{11b}$ is selected from the group consisting of halogen, unsubstituted or substituted C$_{1-6}$ haloalkyl, unsubstituted or substituted C$_{1-6}$ hydroxyalkyl, unsubstituted or substituted C$_{1-6}$ aminoalkyl, unsubstituted or substituted C$_{1-6}$ cyanoalkyl, unsubstituted or substituted C$_{1-6}$ alkoxy-C$_{1-6}$ alkyl, unsubstituted or substituted C$_{1-6}$ alkoxy, unsubstituted or substituted C$_{1-6}$ haloalkoxy, —OH, —CN, —NO$_2$, unsubstituted or substituted C$_{2-9}$ heteroalicyclyl, unsubstituted or substituted aryl, unsubstituted or substituted heteroaryl, —NR$_{12}$R$_{13}$, —C(=O)

NR$_{22}$R$_{23}$, —SO$_2$R$_{25}$, —SO$_2$NR$_{26}$R$_{27}$, —NR$_{33}$(CR$_{34}$R$_{35}$)$_m$C(=O)NR$_{36}$R$_{37}$, —(CR$_{38}$R$_{39}$)$_m$NR$_{40}$R$_{41}$, and —(CR$_{42}$R$_{43}$)$_m$C(=O)NR$_{44}$R$_{45}$, R$_{12}$, R$_{13}$, R$_{22}$, R$_{23}$, R$_{25}$, R$_{26}$, R$_{27}$, R$_{36}$, R$_{37}$, R$_{40}$, R$_{41}$, R$_{44}$, R$_{45}$ independently are selected from the group consisting of hydrogen, unsubstituted or substituted C$_{1-6}$ alkyl, unsubstituted or substituted C$_{1-6}$ alkoxy, unsubstituted or substituted C$_{3-8}$ cycloalkyl, unsubstituted or substituted C$_{2-9}$ heteroalicyclyl, unsubstituted or substituted aryl, unsubstituted or substituted heteroaryl; or R$_{12}$ and R$_{13}$, R$_{22}$ and R$_{23}$, R$_{26}$ and R$_{27}$, R$_{36}$ and R$_{37}$, R$_{40}$ and R$_{41}$; R$_{44}$ and R$_{45}$ taken together with the nitrogen atom to which they are attached form a ring selected from the group consisting of unsubstituted or substituted C$_{3-8}$ cycloalkyl, unsubstituted or substituted C$_{2-9}$ heteroalicyclyl, unsubstituted or substituted aryl, and unsubstituted or substituted heteroaryl, R$_{33}$, R$_{34}$, R$_{35}$, R$_{38}$, R$_{39}$, R$_{42}$, and R$_{43}$ independently are selected from the group consisting of hydrogen and C$_{1-6}$ alkyl, and m is an integer selected from the group consisting of 0, 1, 2, 3 and 4.

22. The compound of claim 1, having the general Formula (XI):

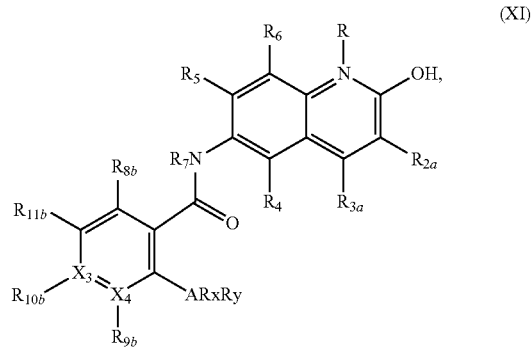

wherein R$_{2a}$ is hydrogen or methyl;
R$_{3a}$ is hydrogen or methyl;
R$_7$ is hydrogen;
R$_4$, R$_5$, R$_6$ and R$_{8b}$ independently are selected from the group consisting of hydrogen, halogen, C$_{1-4}$ alkyl, C$_{1-4}$ alkoxy, C$_{3-5}$ cycloalkyl, —CN, —OH, —CF$_3$, and —OCF$_3$;
X$_3$ and X$_4$ independently are selected from the group consisting of N and C; wherein
when X$_4$ is N, R$_{9b}$ is absent, when X$_4$ is C, R$_{9b}$ is selected from the group consisting of hydrogen, halogen, C$_{1-4}$ alkyl, C$_{1-4}$ alkoxy, C$_{3-5}$ cycloalkyl, —CN, —OH, —CF$_3$, and —OCF$_3$;
when X$_3$ is N, R$_{10b}$ is absent, and
when X$_3$ is C, R$_{10b}$ is selected from the group consisting of hydrogen, halogen, C$_{1-4}$ alkyl, C$_{1-4}$ alkoxy, C$_{3-5}$ cycloalkyl, —CN, —OH, —CF$_3$, and —OCF$_3$; and
R$_{11b}$ is selected from the group consisting of hydrogen, halogen, unsubstituted or substituted C$_{1-6}$ alkyl, unsubstituted or substituted C$_{1-6}$ alkenyl, unsubstituted or substituted C$_{1-6}$ alkynyl, unsubstituted or substituted C$_{1-6}$ alkoxy, —OH, —CN, —NO$_2$, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —NR$_{12}$R$_{13}$, —NR$_{14}$C(=O)R$_{15}$, —NR$_{16}$C(=O)NR$_{17}$R$_{18}$, —NR$_{28}$C(=O)OR$_{19}$, —C(=O)R$_{20}$, —C(=O)OR$_{21}$, —OC(=O)R$_{21}$, —C(=O)NR$_{22}$R$_{23}$, —S(=O)R$_{24}$, —SO$_2$R$_{25}$, —SO$_2$NR$_{26}$R$_{27}$, and —OR$_{31}$;

A is N;

R$_x$ and R$_y$ are independently of each other selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$, or R$_x$ and R$_y$ are both taken together with A to form a ring system selected from the group consisting of unsubstituted or substituted C$_{2-9}$ heteroalicyclyl, and unsubstituted or substituted heteroaryl, or one of R$_x$ or R$_y$ is taken together with A to form a ring system selected from the group consisting of unsubstituted or substituted C$_{2-9}$ heteroalicyclyl, and unsubstituted or substituted heteroaryl; and whenever R$_x$ and R$_y$ independently of each other are selected from hydrogen, unsubstituted or substituted C$_{1-6}$ alkyl, unsubstituted or substituted C$_{1-6}$ alkenyl, substituted or unsubstituted C$_{1-6}$ alkoxy, unsubstituted or substituted C$_{3-8}$ cycloalkyl, unsubstituted or substituted C$_{3-8}$ cycloalkenyl, unsubstituted or substituted C$_{2-9}$ heteroalicyclyl, unsubstituted or substituted aryl, unsubstituted or substituted heteroaryl, —C(=O)R$_{20}$ and —SO$_2$R$_{25}$, then R$_{11b}$ cannot be hydrogen; and whenever one or more heteroatom(s) is/are present it is/they are selected from O, N and S.

23. The compound of claim 22, wherein R$_{11b}$ is selected from the group consisting of unsubstituted or substituted C$_{2-9}$ heteroalicyclyl and unsubstituted or substituted heteroaryl.

24. The compound of claim 22, wherein R$_{11b}$ is selected from the group consisting of:

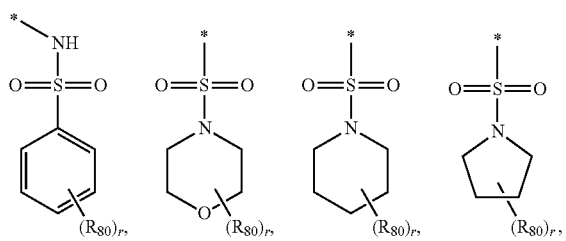

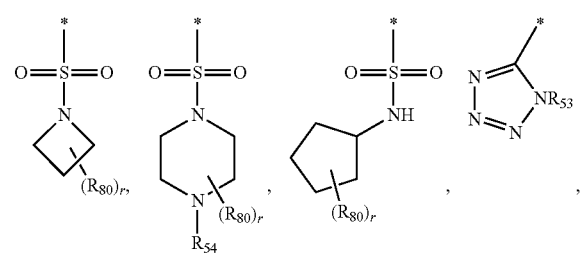

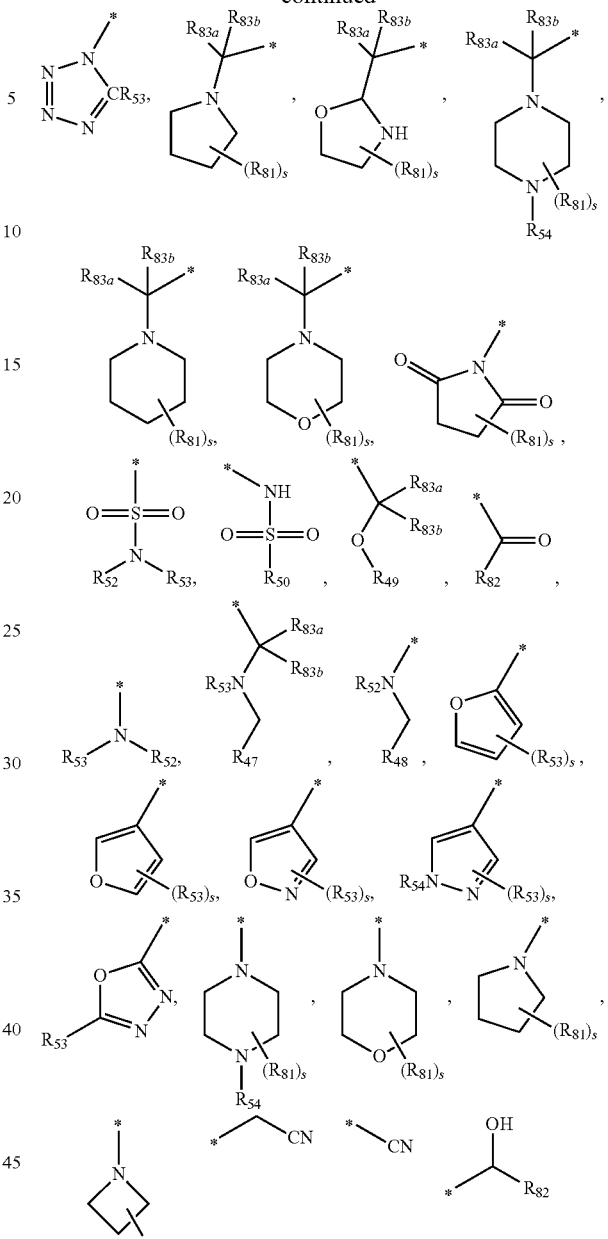

and halogen;

wherein R$_{83a}$ and R$_{83b}$ are independently selected from the group consisting of hydrogen, fluoro, C$_{1-6}$ alkyl, or R$_{83a}$ and R$_{83b}$ taken together with the carbon atom to which they are attached form a C$_{3-8}$ cycloalkyl;

R$_{80}$ and R$_{81}$ independently are selected from the group consisting of hydrogen, halogen, —CN, —OH, C$_{1-4}$ alkyl, C$_{1-4}$ haloalkyl, C$_{1-4}$ hydroxyalkyl, C$_{1-4}$ aminoalkyl, —CF$_3$, C$_{1-4}$ alkoxy, C$_{1-4}$ alkoxy-C$_{1-4}$ alkyl, —OCF$_3$, —NR$_{52}$R$_{53}$, —C(=O)NR$_{52}$R$_{53}$, —C(=O)OR$_{52}$;

r and s are integers selected from the group consisting of 0, 1 and 2;

R$_{47}$, R$_{48}$, R$_{49}$, and R$_{50}$ independently are selected from the group consisting of hydrogen, C$_{1-6}$ alkyl, C$_{1-6}$ alkoxy-C$_{1-6}$ alkyl, —NR$_{52}$R$_{53}$, C$_{1-6}$ aminoalkyl, —OH, and —C(=O)NR$_{55}$R$_{56}$;

$R_{82}$ is selected from the group consisting of $C_{1-6}$ alkyl, $C_{1-6}$ alkoxy, —$NR_{85}R_{86}$, and —OH;

$R_{52}$, $R_{53}$, and $R_{54}$ independently are selected from the group consisting of hydrogen, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-4}$ alkoxy-$C_{1-4}$ alkyl, $C_{3-8}$ cycloalkyl, and —C(=O)$R_{82}$;

$R_{55}$ and $R_{56}$ independently are selected from the group consisting of $C_{1-6}$ alkyl, unsubstituted or substituted $C_{3-8}$ cycloalkyl, unsubstituted or substituted $C_{2-9}$ heteroalicyclyl, unsubstituted or substituted aryl, and unsubstituted or substituted heteroaryl, and $R_{85}$ and $R_{86}$ independently are selected from the group consisting of hydrogen, $C_{1-6}$ alkyl, and $C_{3-8}$ cycloalkyl or $R_{85}$ and $R_{86}$ taken together with the nitrogen atom form a ring system selected from unsubstituted or substituted heteroalicyclyl.

25. The compound of claim 24, wherein $R_{80}$ and $R_{81}$ are hydrogen.

26. The compound of claim 22, wherein:
substituted $C_{1-6}$ alkyl is a $C_{1-6}$ haloalkyl selected from the group consisting of —$CF_3$, —$CHF_2$, —$CH_2F$, —$CH_2CH_2F$, —$CH_2CHF_2$, —$CHFCF_3$, and —$CH_2CF_3$;
substituted $C_{1-6}$ alkoxy is a $C_{1-6}$ haloalkoxy selected from the group consisting of —$OCF_3$, —$OCHF_2$, —$OCH_2F$, —$OCH_2CH_2F$, —$OCH_2CHF_2$, and —$OCH_2CF_3$;
unsubstituted or substituted $C_{3-8}$ cycloalkyl is selected from the group consisting of unsubstituted or substituted cyclopropyl, unsubstituted or substituted cyclobutyl, and unsubstituted or substituted cyclopentyl;
unsubstituted or substituted $C_{2-9}$ heteroalicyclyl is selected from the group consisting of unsubstituted or substituted morpholinyl, unsubstituted or substituted pyrrolidinyl, unsubstituted or substituted pyrrolidinonyl, unsubstituted or substituted piperidinyl, unsubstituted or substituted piperazinyl, unsubstituted or substituted azetidinyl, unsubstituted or substituted oxazepanyl, and unsubstituted and substituted diazepanyl;
unsubstituted or substituted aryl is unsubstituted or substituted phenyl; and
unsubstituted or substituted heteroaryl is selected from the group consisting of unsubstituted or substituted pyridinyl, unsubstituted or substituted imidazolyl, unsubstituted or substituted isoxazolyl, unsubstituted or substituted pyrazolyl, unsubstituted or substituted furanyl, and unsubstituted or substituted tetrazolyl.

27. The compound of claim 22, wherein substituted $C_{3-8}$ cycloalkyl, substituted $C_{2-9}$ heteroalicyclyl, substituted aryl and substituted heteroaryl independently are substituted by a substituent selected from the group consisting of halogen, —CN, —OH, oxo, $C_{1-4}$ alkyl, $C_{1-4}$ haloalkyl, $C_{1-4}$ hydroxyalkyl, $C_{1-4}$ alkoxy, $C_{1-4}$ haloalkoxy-$C_{1-4}$ alkyl, $C_{1-4}$ alkoxy-$C_{1-4}$ alkyl, —$NR_{52}R_{53}$, —C(=O)$NR_{52}R_{53}$, —C(=O)$OR_{52}$, —C(=O)$R_{82}$, and $C_{1-4}$ aminoalkyl.

28. The compound of claim 22, wherein:
$R_x$ and $R_y$ independently are selected from the group consisting of hydrogen, unsubstituted or substituted $C_{1-6}$ alkyl, unsubstituted or substituted $C_{3-8}$ cycloalkyl unsubstituted or substituted $C_{2-9}$ heteroalicyclyl, unsubstituted or substituted aryl, unsubstituted or substituted heteroaryl, and —C(=O)—$C_{1-6}$ alkyl, and
at least one of $R_x$ and $R_y$ is not hydrogen.

29. The compound of claim 28, wherein $C_{1-6}$ alkyl is substituted by a substituent selected from the group consisting of —OH, unsubstituted or substituted $C_{3-8}$ cycloalkyl, unsubstituted or substituted $C_{2-9}$ heteroalicyclyl, unsubstituted or substituted aryl, and unsubstituted or substituted heteroaryl.

30. The compound of claim 22, wherein $R_x$ and $R_y$ taken together with A form a ring system selected from the group consisting of unsubstituted or substituted $C_{2-9}$ heteroalicyclyl, and unsubstituted or substituted heteroaryl.

31. The compound of claim 22, wherein $R_x$ and $R_y$ taken together with A form a ring system selected from the group consisting of:

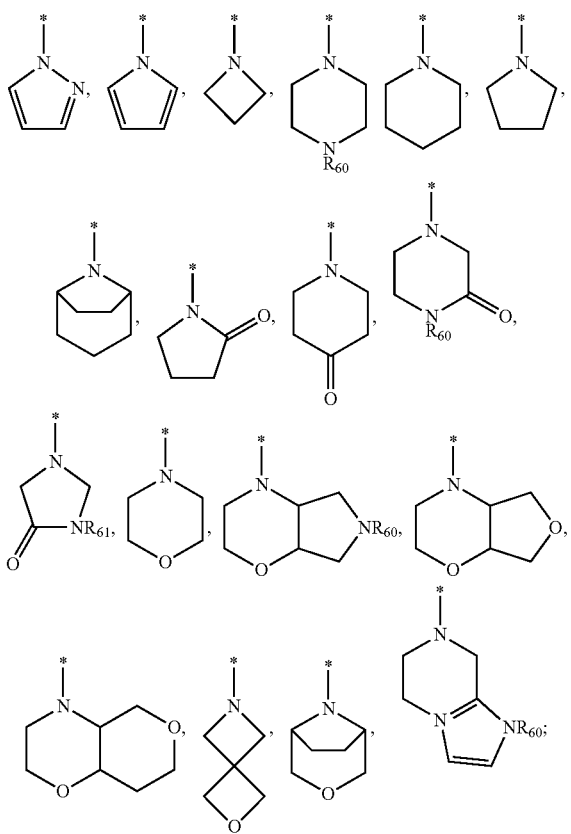

wherein the ring system is unsubstituted or substituted with 1, 2, 3 or 4 substituents selected from the group consisting of unsubstituted or substituted $C_{1-6}$ alkyl, unsubstituted or substituted $C_{1-6}$ alkoxy, unsubstituted or substituted $C_{1-6}$ haloalkyl, unsubstituted or substituted $C_{1-6}$ hydroxyalkyl, unsubstituted or substituted $C_{1-6}$ aminoalkyl, halogen, —OH, —CN, unsubstituted or substituted $C_{3-8}$ cycloalkyl, unsubstituted or substituted $C_{3-8}$ cycloalkenyl, unsubstituted or substituted $C_{2-9}$ heteroalicyclyl, unsubstituted or substituted $C_{2-9}$ heteroalicyclyl-$C_{1-6}$ alkyl, unsubstituted or substituted heteroaryl, unsubstituted or substituted heteroaryl-$C_{1-6}$ alkyl, —$(CR_{64}R_{65})_tNR_{62}R_{63}$, —$NR_{64}C(=O)NR_{65}R_{66}$, —C(=O)$NR_{67}R_{68}$, and —C(=O)$OR_{69}$;

$R_{60}$, $R_{61}$, $R_{62}$, $R_{63}$, $R_{64}$, $R_{65}$, $R_{66}$, $R_{67}$, $R_{68}$ and $R_{69}$ are independently selected from the group consisting of hydrogen and unsubstituted or substituted $C_{1-6}$ alkyl, or the ring system is part of a bicyclic ring system; and t is selected from an integer selected from 0, 1, 2 and 3.

32. The compound of claim 1, wherein:

$R_{8a}$, $R_{9a}$, $R_{10a}$, and $R_{11a}$ are absent;

$R_{11b}$ is selected from the group consisting of halogen, unsubstituted or substituted $C_{1-6}$ haloalkyl, unsubstituted or substituted $C_{1-6}$ hydroxyalkyl, unsubstituted or substituted $C_{1-6}$ aminoalkyl, unsubstituted or substituted $C_{1-6}$ cyanoalkyl, unsubstituted or substituted $C_{1-6}$ alkoxy-$C_{1-6}$ alkyl, unsubstituted or substituted $C_{1-6}$ alkoxy, unsubstituted or substituted $C_{1-6}$ haloalkoxy, —OH, —CN, —NO$_2$, unsubstituted or substituted $C_{2-9}$ heteroalicyclyl, unsubstituted or substituted aryl, unsubstituted or substituted heteroaryl, —NR$_{12}$R$_{13}$, —C(=O)NR$_{22}$R$_{23}$, —SO$_2$R$_{25}$, —SO$_2$NR$_{26}$R$_{27}$, —NR$_{33}$(CR$_{34}$R$_{35}$)$_m$C(=O)NR$_{36}$R$_{37}$, —(CR$_{38}$R$_{39}$)$_m$NR$_{40}$R$_{41}$, and —(CR$_{42}$R$_{43}$)$_m$C(=O)NR$_{44}$R$_{45}$, and $R_{12}$, $R_{13}$, $R_{22}$, $R_{23}$, $R_{25}$, $R_{26}$, $R_{27}$, $R_{36}$, $R_{37}$, $R_{40}$, $R_{41}$, $R_{44}$, and $R_{45}$ independently are selected from the group consisting of hydrogen, unsubstituted or substituted $C_{1-6}$ alkyl, unsubstituted or substituted $C_{1-6}$ alkoxy, unsubstituted or substituted $C_{3-8}$ cycloalkyl, unsubstituted or substituted $C_{2-9}$ heteroalicyclyl, unsubstituted or substituted aryl, and unsubstituted or substituted heteroaryl; or $R_{12}$ and $R_{13}$, $R_{22}$ and $R_{23}$, $R_{26}$ and $R_{27}$, $R_{36}$ and $R_{37}$, $R_{40}$ and $R_{41}$, $R_{44}$ and $R_{45}$ taken together with the atom to which they are simultaneously attached form a ring selected from the group consisting of unsubstituted or substituted $C_{3-8}$ cycloalkyl, unsubstituted or substituted $C_{2-9}$ heteroalicyclyl, unsubstituted or substituted aryl, and unsubstituted or substituted heteroaryl;

$R_{33}$, $R_{34}$, $R_{35}$, $R_{36}$, $R_{38}$, $R_{39}$, $R_{42}$, and $R_{43}$ independently are selected from the group consisting of hydrogen and $C_{1-6}$ alkyl;

m is an integer selected from the group consisting of 0, 1, 2, 3 or 4;

A is N; and $R_x$ and $R_y$ taken together with A form a ring system selected from the group consisting of unsubstituted or substituted $C_{2-9}$ heteroalicyclyl and unsubstituted or substituted heteroaryl.

33. A compound selected from the group consisting of:

N-(2-hydroxy-4-methyl-6-quinolyl)-5-[(4-methylpiperazin-1-yl)methyl]-2-pyrrolidin-1-yl-benzamide, N-(2-hydroxy-4-methyl-6-quinolyl)-5-(piperazin-1-ylmethyl)-2-pyrrolidin-1-yl-benzamide, N-(2-hydroxy-4-methyl-6-quinolyl)-5-(morpholinomethyl)-2-pyrrolidin-1-yl-benzamide, 5-[(4-acetylpiperazin-1-yl)methyl]-N-(2-hydroxy-4-methyl-6-quinolyl)-2-pyrrolidin-1-yl-benzamide, N-(2-hydroxy-4-methyl-6-quinolyl)-5-(4-methylpiperazin-1-yl)sulfonyl-2-morpholino-benzamide, 5-[3-(dimethylamino)pyrrolidin-1-yl]sulfonyl-N-(2-hydroxy-4-methyl-6-quinolyl)-2-morpholino-benzamide, 5-[3-(dimethylamino)azetidin-1-yl]sulfonyl-N-(2-hydroxy-4-methyl-6-quinolyl)-2-morpholino-benzamide, 5-(3-aminoazetidin-1-yl)sulfonyl-N-(2-hydroxy-4-methyl-6-quinolyl)-2-morpholino-benzamide, N3-(2-hydroxy-4-methyl-6-quinolyl)-N1,N1-dimethyl-4-morpholino-benzene-1,3-dicarboxamide, N-(2-hydroxy-4-methyl-6-quinolyl)-5-(4-methylpiperazine-1-carbonyl)-2-morpholino-benzamide, N-(2-hydroxy-4-methyl-6-quinolyl)-5-(morpholine-4-carbonyl)-2-morpholino-benzamide, N-3-(2-hydroxy-4-methyl-6-quinolyl)-4-morpholino-benzene-1,3-dicarboxamide, N-(2-hydroxy-4-methyl-6-quinolyl)-5-(methoxymethyl)-2-pyrrolidin-1-yl-benzamide, 5-(hydroxymethyl)-N-(2-hydroxy-4-methyl-6-quinolyl)-2-pyrrolidin-1-yl-benzamide, 5-(dimethylsulfamoyl)-N-(2-hydroxy-4-methyl-6-quinolyl)-2-(4-methylpiperazin-1-yl)benzamide, 2-[3-(dimethylamino)pyrrolidin-1-yl]-5-(dimethylsulfamoyl)-N-(2-hydroxy-4-methyl-6-quinolyl)benzamide, 5-(dimethylsulfamoyl)-N-(2-hydroxy-4-methyl-6-quinolyl)-2-(3-hydroxypyrrolidin-1-yl)benzamide, 2-(2-dimethylaminoethylamino)-5-(dimethylsulfamoyl)-N-(2-hydroxy-4-methyl-6-quinolyl)benzamide, 5-(dimethylsulfamoyl)-2-(2-hydroxyethylamino)-N-(2-hydroxy-4-methyl-6-quinolyl)benzamide, 2-[3-(dimethylamino)azetidin-1-yl]-5-(dimethylsulfamoyl)-N-(2-hydroxy-4-methyl-6-quinolyl)benzamide, 5-(dimethylsulfamoyl)-N-(2-hydroxy-4-methyl-6-quinolyl)-N-methyl-2-(4-methylpiperazin-1-yl)benzamide, N-(2-hydroxy-4-methyl-6-quinolyl)-N-methyl-5-morpholinosulfonyl-2-pyrrolidin-1-yl-benzamide, N-(2-hydroxy-4-methyl-6-quinolyl)-5-nitro-2-pyrrolidin-1-yl-pyridine-3-carboxamide, 5-amino-N-(2-hydroxy-4-methyl-6-quinolyl)-2-pyrrolidin-1-yl-pyridine-3-carboxamide, 5-[(2-amino-2-oxo-ethyl)amino]-N-(2-hydroxy-4-methyl-6-quinolyl)-2-pyrrolidin-1-yl-pyridine-3-carboxamide, N-(2-hydroxy-4-methyl-6-quinolyl)-2-[2-(methoxymethyl)pyrrolidin-1-yl]-5-(morpholinomethyl)benzamide, N-(2-hydroxy-4-methyl-6-quinolyl)-5-(morpholinomethyl)-2-[2-(1H-pyrazol-3-yl)pyrrolidin-1-yl]benzamide, N-[2-hydroxy-4-(trifluoromethyl)-6-quinolyl]-5-(morpholinomethyl)-2-pyrrolidin-1-yl-benzamide, N-(2-hydroxy-4,7-dimethyl-6-quinolyl)-5-(morpholinomethyl)-2-pyrrolidin-1-yl-benzamide, 2-[2-(hydroxymethyl)pyrrolidin-1-yl]-N-(2-hydroxy-4-methyl-6-quinolyl)-5-(morpholinomethyl)benzamide, N-(2-hydroxy-4-methyl-6-quinolyl)-2-(3-hydroxypyrrolidin-1-yl)-5-(morpholinomethyl)benzamide, 2-[2-(dimethylaminomethyl)pyrrolidin-1-yl]-N-(2-hydroxy-4-methyl-6-quinolyl)-5-(morpholinomethyl)benzamide, N-(2-hydroxy-4-methyl-6-quinolyl)-3-pyrrolidin-1-yl-6-(1H-tetrazol-5-yl)pyridine-2-carboxamide, N-(2-hydroxy-4-methyl-6-quinolyl)-5-(morpholinomethyl)-2-(2-oxopyrrolidin-1-yl)benzamide, 6-cyano-N-(2-hydroxy-4-methyl-6-quinolyl)-3-pyrrolidin-1-yl-pyridine-2-carboxamide, 6-(aminomethyl)-N-(2-hydroxy-4-methyl-6-quinolyl)-3-pyrrolidin-1-yl-pyridine-2-carboxamide, 6-(dimethylaminomethyl)-N-(2-hydroxy-4-methyl-6-quinolyl)-3-pyrrolidin-1-yl-pyridine-2-carboxamide, 6-acetyl-N-(2-hydroxy-4-methyl-6-quinolyl)-3-pyrrolidin-1-yl-pyridine-2-carboxamide, 6-(1-hydroxyethyl)-N-(2-hydroxy-4-methyl-6-quinolyl)-3-pyrrolidin-1-yl-pyridine-2-carboxamide, N2-(2-hydroxy-4-methyl-6-quinolyl)-3-pyrrolidin-1-yl-pyridine-2,6-dicarboxamide, 2-cyano-N-(2-hydroxy-4-methyl-6-quinolyl)-5-pyrrolidin-1-yl-pyridine-4-carboxamide, 2-acetyl-N-(2-hydroxy-4-methyl-6-quinolyl)-5-pyrrolidin-1-yl-pyridine-4-carboxamide, 2-(1-hydroxyethyl)-N-(2-hydroxy-4-methyl-6-quinolyl)-5-pyrrolidin-1-yl-pyridine-4-carboxamide, N4-(2-hydroxy-4-methyl-6-quinolyl)-5-pyrrolidin-1-yl-pyridine-2,4-dicarboxamide, N-(2-hydroxy-4-methyl-6-quinolyl)-5-pyrrolidin-1-yl-2-(1H-tetrazol-5-yl)pyridine-4-carboxamide,
5-(1-hydroxyethyl)-N-(2-hydroxy-4-methyl-6-quinolyl)-2-pyrrolidin-1-yl-benzamide,
N-(2-hydroxy-4-methyl-6-quinolyl)-5-(1-methoxyethyl)-2-pyrrolidin-1-yl-benzamide,
2-[2-(dimethylaminomethyl)pyrrolidin-1-yl]-N-(2-hydroxy-4-methyl-6-quinolyl)-5-(methoxymethyl)benzamide,
N-(2-hydroxy-4-methyl-6-quinolyl)-5-(methoxymethyl)-2-[2-(1H-pyrazol-3-yl)pyrrolidin-1-yl]benzamide,
N-(2-hydroxy-4-methyl-6-quinolyl)-5-(isopropoxymethyl)-2-pyrrolidin-1-yl-benzamide,
2-[2-(dimethylaminomethyl)pyrrolidin-1-yl]-N-(2-hydroxy-4-methyl-6-quinolyl)-5-(trifluoromethoxy)benzamide,
3-(dimethylaminomethyl)-N-(2-hydroxy-4-methyl-6-quinolyl)-1H-indole-7-carboxamide,
3-(dimethylaminomethyl)-N-(2-hydroxy-4-methyl-6-quinolyl)-1H-indole-4-carboxamide,
5-amino-N-(2-hydroxy-4-methyl-6-quinolyl)-2-morpholino-benzamide,
5-[(2-amino-2-oxo-ethyl)amino]-N-(2-hydroxy-4-methyl-6-quinolyl)-2-morpholino-benzamide,
5-fluoro-N-(2-hydroxy-4-methyl-6-quinolyl)-2-morpholino-benzamide,
N-(2-hydroxy-4-methyl-6-quinolyl)-2-morpholino-5-(1-piperidylsulfonyl)benzamide,
N-(2-hydroxy-4-methyl-6-quinolyl)-2-morpholino-5-morpholinosulfonyl-benzamide,
N-(2-hydroxy-4-methyl-6-quinolyl)-2-methoxy-benzamide,
N-(2-hydroxy-4-methyl-6-quinolyl)-2-morpholino-5-sulfamoyl-benzamide,
5-acetamido-N-(2-hydroxy-4-methyl-6-quinolyl)-2-morpholino-benzamide,
5-(dimethylsulfamoyl)-N-(2-hydroxy-4-methyl-6-quinolyl)-2-pyrrolidin-1-yl-benzamide,
5-(dimethylsulfamoyl)-N-(2-hydroxy-4-methyl-6-quinolyl)-2-morpholino-benzamide,
N-(2-hydroxy-4-methyl-6-quinolyl)-5-morpholinosulfonyl-2-pyrrolidin-1-yl-benzamide,
N-(2-hydroxy-4-methyl-6-quinolyl)-2-methoxy-benzenesulfonamide,
N-(2-hydroxy-4-methyl-6-quinolyl)-2-morpholino-5-nitro-benzenesulfonamide,
5-amino-N-(2-hydroxy-4-methyl-6-quinolyl)-2-morpholino-benzenesulfonamide,
2-cyano-N-(2-hydroxy-4-methyl-6-quinolyl)-5-morpholinosulfonyl-benzamide,
5-(dimethyl sulfamoyl)-2-morpholino-N-[2-oxo-4-(trifluoromethyl)-1H-quinolin-6-yl]benzamide,
N3-(2-hydroxy-4-methyl-6-quinolyl)-4-morpholino-benzene-1,3-disulfonamide,
5-(dimethylsulfamoyl)-N-(4-hydroxy-2-oxo-1H-quinolin-6-yl)-2-morpholino-benzamide,
N-(2-hydroxy-4-methyl-6-quinolyl)-5-nitro-2-pyrrolidin-1-yl-benzamide,
N-(2-hydroxy-4-methyl-6-quinolyl)-1-(oxazol-2-ylmethyl)-5-pyrrolidin-1-yl-indole-6-carboxamide,
N-(2-hydroxy-4-methyl-6-quinolyl)-1-(oxazolidin-2-ylmethyl)-5-pyrrolidin-1-yl-indole-6-carboxamide,
3-(dimethylaminomethyl)-N-(2-hydroxy-4-methyl-6-quinolyl)-5-pyrrolidin-1-yl-1H-indole-6-carboxamide,
1-(2-amino-2-oxo-ethyl)-N-(2-hydroxy-4-methyl-6-quinolyl)-5-pyrrolidin-1-yl-indole-6-carboxamide,
N-(2-hydroxy-4-methyl-6-quinolyl)-5-(morpholinomethyl)-2-pyrrolidin-1-yl-pyridine-3-carboxamide,
2-(3-fluoropyrrolidin-1-yl)-N-(2-hydroxy-4-methyl-6-quinolyl)-5-(morpholinomethyl)pyridine-3-carboxamide,
N-(2-hydroxy-4-methyl-6-quinolyl)-2-(3-hydroxypyrrolidin-1-yl)-5-(morpholinomethyl)pyridine-3-carboxamide,
N-(2-hydroxy-4-methyl-6-quinolyl)-2-morpholino-5-(morpholinomethyl)pyridine-3-carboxamide,
N-(4-chloro-2-hydroxy-6-quinolyl)-2-morpholino-5-(morpholinomethyl)pyridine-3-carboxamide,
N-(4-methyl-2-oxo-pyrido[12-a]pyrimidin-7-yl)-5-(morpholinomethyl)-2-pyrrolidin-1-yl-pyridine-3-carboxamide,
N-(8-methyl-6-oxo-5H-1,5-naphthyridin-2-yl)-5-(morpholinomethyl)-2-pyrrolidin-1-yl-pyridine-3-carboxamide,
N-(8-methyl-6-oxo-5H-1,5-naphthyridin-2-yl)-5-morpholinosulfonyl-2-pyrrolidin-1-yl-benzamide,
N-(2-hydroxy-4-methyl-6-quinolyl)-3-pyrrolidin-1-yl-pyridine-4-carboxamide,
N-(2-hydroxy-4-methyl-6-quinolyl)-2-pyrrolidin-1-yl-pyridine-3-carboxamide,
2-[2-(dimethylaminomethyl)pyrrolidin-1-yl]-N-(2-hydroxy-4-methyl-6-quinolyl)pyridine-3-carboxamide,
N-(4-methoxy-2-oxo-1H-quinolin-6-yl)-5-[(4-methylpiperazin-1-yl)methyl]-2-pyrrolidin-1-yl-benzamide,
5-(dimethylsulfamoyl)-N-(2-hydroxy-4,7-dimethyl-6-quinolyl)-2-morpholino-benzamide,
5-morpholinosulfonyl-N-(2-oxo-3,4-dihydro-1H-quinolin-6-yl)-2-pyrrolidin-1-yl-benzamide,
N-(4-methyl-2-oxo-3,4-dihydro-1H-quinolin-6-yl)-5-(morpholinomethyl)-2-pyrrolidin-1-yl-benzamide,
5-(dimethylsulfamoyl)-N-(4-methyl-2-oxo-3,4-dihydro-1H-quinolin-6-yl)-2-pyrrolidin-1-yl-benzamide,
N-(4,4-dimethyl-2-oxo-1,3-dihydroquinolin-6-yl)-5-(morpholinomethyl)-2-pyrrolidin-1-yl-benzamide,
N-(4,4-dimethyl-2-oxo-1,3-dihydroquinolin-6-yl)-5-(dimethylsulfamoyl)-2-pyrrolidin-1-yl-benzamide,
5-amino-N-(2-hydroxy-4-methyl-6-quinolyl)-2-pyrazol-1-yl-benzamide,
5-(dimethylsulfamoyl)-N-(8-fluoro-4,4-dimethyl-2-oxo-1,3-dihydroquinolin-6-yl)-2-pyrrolidin-1-yl-benzamide,
5-(dimethyl sulfamoyl)-N-(2-hydroxy-4,8-dimethyl-6-quinolyl)-2-pyrrolidin-1-yl-benzamide,
5-(dimethylsulfamoyl)-N-(2-hydroxy-8-methoxy-4-methyl-6-quinolyl)-2-pyrrolidin-1-yl-benzamide,
N-(2-hydroxy-4-methyl-6-quinolyl)-2-pyrrolidin-1-yl-5-(trifluoromethyl)benzamide,
N-(2-hydroxy-4-methyl-6-quinolyl)-2-(3-hydroxypyrrolidin-1-yl)-5-morpholinosulfonyl-benzamide,
N-(2-hydroxy-4-methyl-6-quinolyl)-2-(3-methoxypyrrolidin-1-yl)-5-morpholinosulfonyl-benzamide,
5-(cyanomethyl)-N-(2-hydroxy-4-methyl-6-quinolyl)-2-pyrrolidin-1-yl-benzamide,
N-(2-hydroxy-4-methyl-6-quinolyl)-5-(1-morpholinocyclopropyl)-2-pyrrolidin-1-yl-benzamide,
2-[2-(dimethylaminomethyl)pyrrolidin-1-yl]-N-(2-hydroxy-4-methyl-6-quinolyl)-5-(1-morpholinocyclopropyl)benzamide,
2-cyano-5-(3-fluoropyrrolidin-1-yl)-N-(2-hydroxy-4-methyl-6-quinolyl)pyridine-4-carboxamide,
2-cyano-N-(2-hydroxy-4-methyl-6-quinolyl)-5-morpholino-pyridine-4-carboxamide, N-(2-hydroxy-4-methyl-6-quinolyl)-4-pyrrolidin-1-yl-pyridine-3-carboxamide,
N-(4-methoxy-2-oxo-1H-quinolin-6-yl)-5-[(4-methylpiperazin-1-yl)methyl]-2-pyrrolidin-1-yl-benzamide,
N-(2-hydroxy-4-methyl-6-quinolyl)-2-pyrrolidin-1-yl-pyridine-3-carboxamide,
N-(2-hydroxy-4-methyl-6-quinolyl)-2-(3-methylmorpholin-4-yl)pyridine-3-carboxamide,
2-[2-(dimethylaminomethyl)pyrrolidin-1-yl]-N-(2-hydroxy-4-methyl-6-quinolyl)pyridine-3-carboxamide,
5-(dimethylsulfamoyl)-N-(2-hydroxy-4,7-dimethyl-6-quinolyl)-2-morpholino-benzamide,
N-(2-hydroxy-4-methyl-6-quinolyl)-4-morpholino-pyridine-3-carboxamide,
N-(2-hydroxy-4-methyl-6-quinolyl)-4-pyrrolidin-1-yl-pyridine-3-carboxamide,
N-(2-hydroxy-4,7-dimethyl-6-quinolyl)-2-morpholino-pyridine-3-carboxamide,
2-(3-fluoropyrrolidin-1-yl)-N-(2-hydroxy-4,7-dimethyl-6-quinolyl)pyridine-3-carboxamide,
2-(3,3-difluoropyrrolidin-1-yl)-N-(2-hydroxy-4,7-dimethyl-6-quinolyl)pyridine-3-carboxamide,
N-(2-hydroxy-4-methyl-6-quinolyl)-2-morpholino-pyridine-3-carboxamide,
N-(2-hydroxy-4-isopropyl-6-quinolyl)-2-morpholino-pyridine-3-carboxamide,
N-(3-methyl-2-oxo-1,4-dihydroquinazolin-6-yl)-2-morpholino-pyridine-3-carboxamide,
N-(1-methyl-2-oxo-3,4-dihydroquinolin-6-yl)-2-morpholino-pyridine-3-carboxamide,
2-(3-fluoropyrrolidin-1-yl)-N-(2-hydroxy-4-methyl-6-quinolyl)pyridine-3-carboxamide,
2-(3,3-difluoropyrrolidin-1-yl)-N-(2-hydroxy-4-methyl-6-quinolyl)pyridine-3-carboxamide,
N-(2-hydroxy-4-methyl-6-quinolyl)-2-pyrrolidin-1-yl-6-(trifluoromethyl)pyridine-3-carboxamide,
N-(2-hydroxy-4-methyl-6-quinolyl)-2-morpholino-6-(trifluoromethyl)pyridine-3-carboxamide,
N-(2-hydroxy-4,8-dimethyl-6-quinolyl)-2-morpholino-pyridine-3-carboxamide,
N-(2-hydroxy-4,7-dimethyl-6-quinolyl)-4-methyl-2-morpholino-pyridine-3-carboxamide,
N-(2-hydroxy-4-methyl-6-quinolyl)-4-methyl-2-morpholino-pyridine-3-carboxamide,
N-(2-hydroxy-4-methyl-6-quinolyl)-2-morpholino-5-(trifluoromethyl)pyridine-3-carboxamide,
5-chloro-N-(2-hydroxy-4-methyl-6-quinolyl)-2-morpholino-pyridine-3-carboxamide,
2-(3,4a,5,6,7,7a-hexahydro-2H-pyrrolo[3,4-b][1,4]oxazin-4-yl)-N-(2-hydroxy-4-methyl-6-quinolyl)pyridine-3-carboxamide,
2-(2,3,4a,5,7,7a-hexahydrofuro[3,4-b][1,4]oxazin-4-yl)-N-(2-hydroxy-4-methyl-6-quinolyl)pyridine-3-carboxamide,
N-(2-hydroxy-4-methyl-6-quinolyl)-2-(3-oxa-8-azabicyclo[3.2.1]octan-8-yl)pyridine-3-carboxamide,
2-[3-(hydroxymethyl)morpholin-4-yl]-N-(2-hydroxy-4-methyl-6-quinolyl)pyridine-3-carboxamide,
2-(4,4-difluoro-1-piperidyl)-N-(2-hydroxy-4-methyl-6-quinolyl)pyridine-3-carboxamide,
2-(6,8-dihydro-5H-imidazo[1,2-a]pyrazin-7-yl)-N-(2-hydroxy-4-methyl-6-quinolyl)pyridine-3-carboxamide,
N-(2-hydroxy-4-methyl-6-quinolyl)-2-(3-oxopiperazin-1-yl)pyridine-3-carboxamide,
N-(2-hydroxy-4-methoxy-6-quinolyl)-2-morpholino-pyridine-3-carboxamide,
N-(2-hydroxy-4-methyl-6-quinolyl)-5-iodo-2-morpholino-benzamide,
N-(2-hydroxy-4-methyl-6-quinolyl)-5-isoxazol-4-yl-2-morpholino-benzamide,
5-(3,5-dimethylisoxazol-4-yl)-N-(2-hydroxy-4-methyl-6-quinolyl)-2-morpholino-benzamide,
N-(2-hydroxy-4,7-dimethyl-6-quinolyl)-5-iodo-2-morpholino-benzamide,
N-(2-hydroxy-4,7-dimethyl-6-quinolyl)-5-(1-methylpyrazol-4-yl)-2-morpholino-benzamide,
5-(3,5-dimethylisoxazol-4-yl)-N-(2-hydroxy-4,7-dimethyl-6-quinolyl)-2-morpholino-benzamide,
N-(2-hydroxy-4,8-dimethyl-6-quinolyl)-5-iodo-2-morpholino-benzamide,
5-(3-furyl)-N-(2-hydroxy-4,8-dimethyl-6-quinolyl)-2-morpholino-benzamide,
N-(2-hydroxy-7-methoxy-4-methyl-6-quinolyl)-5-iodo-2-morpholino-benzamide,
N-(2-hydroxy-7-methoxy-4-methyl-6-quinolyl)-5-(1-methylpyrazol-4-yl)-2-morpholino-benzamide,
5-(3-furyl)-N-(2-hydroxy-7-methoxy-4-methyl-6-quinolyl)-2-morpholino-benzamide,
5-(3,5-dimethylisoxazol-4-yl)-N-(2-hydroxy-7-methoxy-4-methyl-6-quinolyl)-2-morpholino-benzamide,
2-(3-fluoropyrrolidin-1-yl)-5-(3-furyl)-N-(2-hydroxy-4-methyl-6-quinolyl)pyridine-3-carboxamide,
N-(2-hydroxy-4,7-dimethyl-6-quinolyl)-5-isoxazol-4-yl-2-morpholino-benzamide,
2-cyano-N-(2-hydroxy-4,7-dimethyl-6-quinolyl)-5-morpholino-pyridine-4-carboxamide,
5-(dimethylsulfamoyl)-N-(2-hydroxy-4-isopropyl-6-quinolyl)-2-pyrrolidin-1-yl-benzamide,
N-(2-hydroxy-4-methyl-6-quinolyl)-5-(1-methylpyrazol-4-yl)-2-morpholino-benzamide,
5-(3-furyl)-N-(2-hydroxy-4-methyl-6-quinolyl)-2-morpholino-benzamide,
5-(1-hydroxyethyl)-N-(2-hydroxy-4-methyl-6-quinolyl)-2-morpholino-benzamide,
N-(2-hydroxy-8-methoxy-4-methyl-6-quinolyl)-5-(1-methylpyrazol-4-yl)-2-morpholino-pyridine-3-carboxamide,
N-(2-hydroxy-7-methoxy-4-methyl-6-quinolyl)-5-(1-methylpyrazol-4-yl)-2-morpholino-pyridine-3-carboxamide,
N-(2-hydroxy-4,7-dimethyl-6-quinolyl)-5-(1-methylpyrazol-4-yl)-2-morpholino-pyridine-3-carboxamide,
5-(dimethylsulfamoyl)-2-[(3R)-3-fluoropyrrolidin-1-yl]-N-(2-hydroxy-4-methyl-6-quinolyl)benzamide,
5-(dimethylsulfamoyl)-2-[(3 S)-3-fluoropyrrolidin-1-yl]-N-(2-hydroxy-4-methyl-6-quinolyl)benzamide,
5-(3-furyl)-N-(2-hydroxy-4-methyl-6-quinolyl)-2-morpholino-pyridine-3-carboxamide,
N-(2-hydroxy-4-methyl-6-quinolyl)-5-(1-methylpyrazol-4-yl)-2-morpholino-pyridine-3-carboxamide,
N-(2-hydroxy-4-methyl-6-quinolyl)-5-isoxazol-4-yl-2-morpholino-pyridine-3-carboxamide,
5-(3,5-dimethylisoxazol-4-yl)-N-(2-hydroxy-4-methyl-6-quinolyl)-2-morpholino-pyridine-3-carboxamide,
5-(3-furyl)-N-(2-hydroxy-4-methyl-6-quinolyl)-2-(6-oxa-2-azaspiro[3.3]heptan-2-yl)pyridine-3-carboxamide,
5-(3-furyl)-N-(2-hydroxy-4,8-dimethyl-6-quinolyl)-2-morpholino-pyridine-3-carboxamide,
N-(2-hydroxy-4-methyl-6-quinolyl)-5-(5-methyl-1,3,4-oxadiazol-2-yl)-2-morpholino-benzamide,
N-(2-hydroxy-4-methyl-6-quinolyl)-2-morpholino-5-(1H-tetrazol-5-yl)benzamide, 3-[(2-hydroxy-4-methyl-6-quinolyl)carbamoyl]-4-morpholino-benzoic acid,
5-cyano-N-(2-hydroxy-4-methyl-6-quinolyl)-2-morpholino-pyridine-3-carboxamide,
5-bromo-2-(3-fluoropyrrolidin-1-yl)-N-(2-hydroxy-4-methyl-6-quinolyl)pyridine-3-carboxamide,
N-(2-hydroxy-4-methyl-6-quinolyl)-5-(4-methylpiperazin-1-yl)-2-morpholino-pyridine-3-carboxamide,
N-(2-hydroxy-4-methyl-6-quinolyl)-2,5-dimorpholino-pyridine-3-carboxamide,
5-[4-(dimethylamino)-1-piperidyl]-N-(2-hydroxy-4-methyl-6-quinolyl)-2-morpholino-pyridine-3-carboxamide,
5-(3,5-dimethylisoxazol-4-yl)-N-(2-hydroxy-4,7-dimethyl-6-quinolyl)-2-morpholino-pyridine-3-carboxamide,
5-(3-furyl)-N-(2-hydroxy-8-methoxy-4-methyl-6-quinolyl)-2-morpholino-pyridine-3-carboxamide,
5-(3-furyl)-N-(2-hydroxy-7-methoxy-4-methyl-6-quinolyl)-2-morpholino-pyridine-3-carboxamide,
5-(3-furyl)-N-(2-hydroxy-4,7-dimethyl-6-quinolyl)-2-morpholino-pyridine-3-carboxamide,
5-(azetidin-1-yl)-N-(2-hydroxy-4-methyl-6-quinolyl)-2-morpholino-pyridine-3-carboxamide,
5-[(3 S)-3-fluoropyrrolidin-1-yl]-N-(2-hydroxy-4-methyl-6-quinolyl)-2-morpholino-pyridine-3-carboxamide,
5-[(3R)-3-fluoropyrrolidin-1-yl]-N-(2-hydroxy-4-methyl-6-quinolyl)-2-morpholino-pyridine-3-carboxamide,
N-(2-hydroxy-4,7-dimethyl-6-quinolyl)-5-(2-methyltetrazol-5-yl)-2-morpholino-pyridine-3-carboxamide,
N-(2-hydroxy-4,7-dimethyl-6-quinolyl)-5-(1-methyltetrazol-5-yl)-2-morpholino-pyridine-3-carboxamide,
2-cyano-5-(3-fluoropyrrolidin-1-yl)-N-(2-hydroxy-4-methyl-6-quinolyl)pyridine-4-carboxamide,
2-cyano-N-(2-hydroxy-4-methyl-6-quinolyl)-5-morpholino-pyridine-4-carboxamide,
5-(dimethyl sulfamoyl)-2-(3-fluoropyrrolidin-1-yl)-N-(2-hydroxy-4-methyl-6-quinolyl)pyridine-3-carboxamide,
N-(2-hydroxy-4,7-dimethyl-6-quinolyl)-5-(3-methylisoxazol-5-yl)-2-morpholino-pyridine-3-carboxamide,
N-(2-hydroxy-7-methoxy-4-methyl-6-quinolyl)-5-(5-methyl-1,3,4-oxadiazol-2-yl)-2-morpholino-benzamide,
N4-(2-hydroxy-4-methyl-6-quinolyl)-5-pyrrolidin-1-yl-pyridine-2,4-dicarboxamide,
N-(2-hydroxy-4-methyl-6-quinolyl)-5-pyrrolidin-1-yl-2-(1H-tetrazol-5-yl)pyridine-4-carboxamide,
5-(cyanomethyl)-N-(2-hydroxy-4-methyl-6-quinolyl)-2-pyrrolidin-1-yl-benzamide,
N-(2-hydroxy-4-methyl-6-quinolyl)-5-(1-morpholinocyclopropyl)-2-pyrrolidin-1-yl-benzamide,
5-(1-hydroxyethyl)-N-(2-hydroxy-4-methyl-6-quinolyl)-2-[2-(2-pyridyl)pyrrolidin-1-yl]benzamide,
2-acetyl-N-(2-hydroxy-4-methyl-6-quinolyl)-5-morpholino-pyridine-4-carboxamide,
2-(1-hydroxyethyl)-N-(2-hydroxy-4-methyl-6-quinolyl)-5-morpholino-pyridine-4-carboxamide,
2-acetyl-5-(3-fluoropyrrolidin-1-yl)-N-(2-hydroxy-4-methyl-6-quinolyl)pyridine-4-carboxamide,
5-(3-fluoropyrrolidin-1-yl)-2-(1-hydroxyethyl)-N-(2-hydroxy-4-methyl-6-quinolyl)pyridine-4-carboxamide,
2-cyano-5-[2-(dimethylaminomethyl)pyrrolidin-1-yl]-N-(2-hydroxy-4-methyl-6-quinolyl)pyridine-4-carboxamide,
2-acetyl-5-[2-(dimethylaminomethyl)pyrrolidin-1-yl]-N-(2-hydroxy-4-methyl-6-quinolyl)pyridine-4-carboxamide,
5-[2-(dimethylaminomethyl)pyrrolidin-1-yl]-2-(1-hydroxyethyl)-N-(2-hydroxy-4-methyl-6-quinolyl)pyridine-4-carboxamide,
N-(1-methyl-2-oxo-3,4-dihydroquinolin-6-yl)-2-morpholino-benzamide,
N-(2-hydroxy-4-methyl-6-quinolyl)-2-morpholino-benzamide,
3-(cyclopentylsulfamoyl)-4-methyl-N-(1-methyl-2-oxo-3,4-dihydroquinolin-6-yl)benzamide,
N-(1-methyl-2-oxo-3,4-dihydroquinolin-6-yl)-2-morpholino-pyridine-3-carboxamide,
2-(4-methylpiperazin-1-yl)-N-(3-oxo-4H-1,4-benzoxazin-7-yl)benzamide,
N-(1-methyl-2-oxo-3,4-dihydroquinolin-6-yl)-2-(4-methylpiperazin-1-yl)benzamide,
N-(4-methyl-3-oxo-1,4-benzoxazin-7-yl)-2-(4-methylpiperazin-1-yl)benzamide,
N-(1-methyl-2-oxo-3,4-dihydroquinolin-6-yl)-2-(4-pyrazin-2-ylpiperazin-1-yl)benzamide,
N-(1-methyl-2-oxo-3,4-dihydroquinolin-6-yl)-2-morpholino-5-nitro-benzamide,
N-(2-hydroxy-4-methyl-6-quinolyl)-2-(4-methylpiperazin-1-yl)benzamide,
N-(2-hydroxy-4-methyl-6-quinolyl)-2-(4-pyrazin-2-ylpiperazin-1-yl)benzamide,
N-(2-hydroxy-4-methyl-6-quinolyl)-2-morpholino-5-sulfamoyl-benzamide,
N-(1-methyl-2-oxo-3,4-dihydroquinolin-6-yl)-2-morpholino-5-sulfamoyl-benzamide,
5-(2,5-dioxopyrrolidin-1-yl)-N-(2-hydroxy-4-methyl-6-quinolyl)-2-morpholino-benzamide,
5-(benzenesulfonamido)-N-(2-hydroxy-4-methyl-6-quinolyl)-2-(4-methylpiperazin-1-yl)benzamide,
5-(ethylsulfonylamino)-N-(2-hydroxy-4-methyl-6-quinolyl)-2-(4-methylpiperazin-1-yl)benzamide,
N-(2-hydroxy-4-methyl-6-quinolyl)-2-morpholino-5-nitro-benzamide,
5-(dimethylsulfamoyl)-N-(2-hydroxy-4-methyl-6-quinolyl)-2-morpholino-benzamide,
N-(2-hydroxy-4-methyl-6-quinolyl)-2-morpholino-5-(1-piperidylsulfonyl)benzamide,
N-(2-hydroxy-4-methyl-6-quinolyl)-2-morpholino-5-morpholinosulfonyl-benzamide,
N-(2-hydroxy-4-methyl-6-quinolyl)-3-(piperazin-1-ylmethyl)benzamide,
2-(dimethylamino)-N-(2-hydroxy-4-methyl-6-quinolyl)-5-nitro-benzamide,
N-(2-hydroxy-4-methyl-6-quinolyl)-3-(methyl sulfamoyl)benzamide,
N-(2-hydroxy-4-methyl-6-quinolyl)-3-[(2-oxopyrrolidin-1-yl)methyl]benzamide,
N-(2-hydroxy-4-methyl-6-quinolyl)-5-nitro-2-pyrrolidin-1-yl-benzamide,
3-[(2-amino-2-oxo-ethyl)sulfamoyl]-N-(2-hydroxy-4-methyl-6-quinolyl)benzamide,
5-(dimethylsulfamoyl)-N-(2-hydroxy-4-methyl-6-quinolyl)-2-pyrrolidin-1-yl-benzamide,
N-(2-hydroxy-4-methyl-6-quinolyl)-2-(methanesulfonamido)-5-morpholino-benzamide,
N-(2-hydroxy-4-methyl-6-quinolyl)-3-pyrrolidin-1-yl-benzamide,
4-amino-N-(2-hydroxy-4-methyl-6-quinolyl)-3-nitro-benzamide, 3-(dimethylaminomethyl)-N-(2-hydroxy-4-methyl-6-quinolyl)-1H-indole-6-carboxamide,
2-morpholino-N-[2-oxo-4-(trifluoromethyl)-1H-quinolin-6-yl]-5-sulfamoyl-benzamide,
5-(dimethylsulfamoyl)-2-fluoro-N-(2-hydroxy-4-methyl-6-quinolyl)benzamide,
2-bromo-N-(2-hydroxy-4-methyl-6-quinolyl)-5-morpholinosulfonyl-benzamide,
N-(4-hydroxy-2-oxo-1H-quinolin-6-yl)-2-morpholino-5-morpholinosulfonyl-benzamide,
N-(2-hydroxy-4-methyl-6-quinolyl)-3-(4-methylpiperazin-1-yl)sulfonyl-benzamide,
5-(dimethylsulfamoyl)-N-(2,4-dioxo-1H-quinazolin-6-yl)-2-morpholino-benzamide,
5-(dimethylsulfamoyl)-N-(2,4-dioxo-1H-quinazolin-6-yl)-2-pyrrolidin-1-yl-benzamide,
5-(dimethylsulfamoyl)-N-(3-methyl-2-oxo-1,4-dihydroquinazolin-6-yl)-2-morpholino-benzamide,
5-(dimethyl sulfamoyl)-N-(3-methyl-2-oxo-1,4-dihydroquinazolin-6-yl)-2-pyrrolidin-1-yl-benzamide,
5-(dimethylsulfamoyl)-N-(2-hydroxy-4-methyl-6-quinolyl)-2-(3-methylpyrrolidin-1-yl)benzamide,
5-(dimethylsulfamoyl)-2-(3-fluoropyrrolidin-1-yl)-N-(2-hydroxy-4-methyl-6-quinolyl)benzamide,
5-(dimethylsulfamoyl)-N-(2-hydroxy-4-methyl-6-quinolyl)-2-(3-methoxypyrrolidin-1-yl)benzamide,
1-[4-(dimethylsulfamoyl)-2-[(2-hydroxy-4-methyl-6-quinolyl)carbamoyl]phenyl]pyrrolidine-3-carboxamide,
2-[3-(dimethylamino)pyrrolidin-1-yl]-5-(dimethylsulfamoyl)-N-(2-hydroxy-4-methyl-6-quinolyl)benzamide,
5-(dimethylsulfamoyl)-N-(2-hydroxy-4-methyl-6-quinolyl)-2-(3-isobutylpyrrolidin-1-yl)benzamide,
2-[3-(dimethylaminomethyl)pyrrolidin-1-yl]-5-(dimethylsulfamoyl)-N-(2-hydroxy-4-methyl-6-quinolyl)benzamide,
5-(dimethylsulfamoyl)-N-(2-hydroxy-4-methyl-6-quinolyl)-2-(3-ureidopyrrolidin-1-yl)benzamide,
5-(dimethylsulfamoyl)-N-(2-hydroxy-4-methyl-6-quinolyl)-2-(3-pyrrolidin-1-ylpyrrolidin-1-yl)benzamide,
2-[3-(2-amino-2-oxo-ethoxy)pyrrolidin-1-yl]-5-(dimethylsulfamoyl)-N-(2-hydroxy-4-methyl-6-quinolyl)benzamide,
5-(dimethylsulfamoyl)-N-(2-hydroxy-4-methyl-6-quinolyl)-2-(3-phenylpyrrolidin-1-yl)benzamide,
5-(dimethylsulfamoyl)-N-(2-hydroxy-4-methyl-6-quinolyl)-2-(2-methylpyrrolidin-1-yl)benzamide,
5-(dimethylsulfamoyl)-N-(2-hydroxy-4-methyl-6-quinolyl)-2-[2-(methoxymethyl)pyrrolidin-1-yl]benzamide,
5-(dimethylsulfamoyl)-N-(2-hydroxy-4-methyl-6-quinolyl)-2-(5-methyl-2,3,3a,4,6,6a-hexahydropyrrolo[3,4-b]pyrrol-1-yl)benzamide,
5-(dimethylsulfamoyl)-N-(2-hydroxy-4-methyl-6-quinolyl)-2-(2-isobutylpyrrolidin-1-yl)benzamide,
2-[2-(dimethylaminomethyl)pyrrolidin-1-yl]-5-(dimethylsulfamoyl)-N-(2-hydroxy-4-methyl-6-quinolyl)benzamide,
5-(dimethylsulfamoyl)-2-[2-(1-hydroxy-1-methyl-ethyl)pyrrolidin-1-yl]-N-(2-hydroxy-4-methyl-6-quinolyl)benzamide,
5-(dimethylsulfamoyl)-N-(2-hydroxy-4-methyl-6-quinolyl)-2-[2-(1H-imidazol-2-yl)pyrrolidin-1-yl]benzamide,
5-(dimethylsulfamoyl)-N-(2-hydroxy-4-methyl-6-quinolyl)-2-[2-(1H-pyrazol-3-yl)pyrrolidin-1-yl]benzamide,
5-(dimethylsulfamoyl)-N-(2-hydroxy-4-methyl-6-quinolyl)-2-[2-(1H-tetrazol-5-yl)pyrrolidin-1-yl]benzamide,
5-(dimethylsulfamoyl)-N-(2-hydroxy-4-methyl-6-quinolyl)-2-(4-methyl-3,3a, 5,6,7,7a-hexahydro-2H-pyrrolo[3,2-b]pyridin-1-yl)benzamide,
1-[4-(dimethylsulfamoyl)-2-[(2-hydroxy-4-methyl-6-quinolyl)carbamoyl]phenyl]-N,N-dimethyl-pyrrolidine-2-carboxamide,
5-(dimethylsulfamoyl)-N-(2-hydroxy-4-methyl-6-quinolyl)-2-[2-(3-pyridyl)pyrrolidin-1-yl]benzamide,
1-[4-(dimethylsulfamoyl)-2-[(2-hydroxy-4-methyl-6-quinolyl)carbamoyl]phenyl]-4-hydroxy-pyrrolidine-2-carboxamide,
5-(dimethylsulfamoyl)-2-(3-hydroxy-3-methyl-8-azabicyclo[3.2.1]octan-8-yl)-N-(2-hydroxy-4-methyl-6-quinolyl)benzamide,
5-(dimethylsulfamoyl)-2-(4-hydroxy-2,5-dimethyl-1-piperidyl)-N-(2-hydroxy-4-methyl-6-quinolyl)benzamide,
5-(dimethylsulfamoyl)-N-(2-hydroxy-4-methyl-6-quinolyl)-2-(2-phenyl-1-piperidyl)benzamide,
2-(2,3,4,4a,5,7,8,8a-octahydropyrano[4,3-b]pyridin-1-yl)-5-(dimethylsulfamoyl)-N-(2-hydroxy-4-methyl-6-quinolyl)benzamide,
5-(dimethylsulfamoyl)-N-(2-hydroxy-4-methyl-6-quinolyl)-2-[2-(5-oxopyrrolidin-3-yl)-1-piperidyl]benzamide,
N-(2-hydroxy-4-methyl-6-quinolyl)-1H-indole-6-carboxamide,
5-(diethylsulfamoyl)-N-(2-hydroxy-4-methyl-6-quinolyl)-2-pyrrolidin-1-yl-benzamide,
5-(diethylsulfamoyl)-N-(2-hydroxy-4-methyl-6-quinolyl)-2-(1-piperidyl)benzamide,
4-chloro-N-(2-hydroxy-4-methyl-6-quinolyl)-3-nitrobenzamide,
N-(2-hydroxy-4-methyl-6-quinolyl)-2-(2-methyl-1-piperidyl)-5-nitro-pyridine-3-carboxamide,
N-(2-hydroxy-4-methyl-6-quinolyl)-2-morpholino-4-(4-piperidyl)pyrimidine-5-carboxamide,
5-nitro-N-(2-oxo-3,4-dihydro-1H-quinolin-6-yl)-2-pyrrolidin-1-yl-benzamide,
N-(4-methyl-3-oxo-1,4-benzoxazin-7-yl)-5-nitro-2-pyrrolidin-1-yl-benzamide,
5-morpholinosulfonyl-N-(2-oxo-3,4-dihydro-1H-quinolin-6-yl)-2-pyrrolidin-1-yl-benzamide,
N-(4-methyl-3-oxo-1,4-benzoxazin-7-yl)-5-morpholinosulfonyl-2-pyrrolidin-1-yl-benzamide,
5-[(4-methylpiperazin-1-yl)methyl]-N-(2-oxo-3,4-dihydro-1H-quinolin-6-yl)-2-pyrrolidin-1-yl-benzamide,
5-[[2-hydroxyethyl(methyl)amino]methyl]-N-(2-hydroxy-4-methyl-6-quinolyl)-2-pyrrolidin-1-yl-benzamide,
N-(2-hydroxy-4-methyl-6-quinolyl)-2-pyrrolidin-1-yl-5-[(tetrahydrofuran-2-ylmethylamino)methyl]benzamide,
5-[[3-(dimethylamino)pyrrolidin-1-yl]methyl]-N-(2-hydroxy-4-methyl-6-quinolyl)-2-pyrrolidin-1-yl-benzamide,
N-(2-hydroxy-4-methyl-6-quinolyl)-5-[(3-hydroxypyrrolidin-1-yl)methyl]-2-pyrrolidin-1-yl-benzamide,
N-(2-hydroxy-4-methyl-6-quinolyl)-5-[[(2S)-2-(methoxymethyl)pyrrolidin-1-yl]methyl]-2-pyrrolidin-1-yl-benzamide,
5-[[4-(2-hydroxyethyl)piperazin-1-yl]methyl]-N-(2-hydroxy-4-methyl-6-quinolyl)-2-pyrrolidin-1-yl-benzamide, N-(2-hydroxy-4-methyl-6-quinolyl)-5-[(4-methyl-1,4-diazepan-1-yl)methyl]-2-pyrrolidin-1-yl-benzamide,
N-(2-hydroxy-4-methyl-6-quinolyl)-5-[(3-methoxypyrrolidin-1-yl)methyl]-2-pyrrolidin-1-yl-benzamide,
5-[(3-hydroxyazetidin-1-yl)methyl]-N-(2-hydroxy-4-methyl-6-quinolyl)-2-pyrrolidin-1-yl-benzamide,
N-(2-hydroxy-4-methyl-6-quinolyl)-5-[[3-(methoxymethyl)azetidin-1-yl]methyl]-2-pyrrolidin-1-yl-benzamide,
N-(2-hydroxy-4-methyl-6-quinolyl)-5-[[3-(methoxymethyl)-1-piperidyl]methyl]-2-pyrrolidin-1-yl-benzamide,
N-(2-hydroxy-4-methyl-6-quinolyl)-5-(morpholinomethyl)-2-pyrrolidin-1-yl-pyridine-3-carboxamide,
N-(2-hydroxy-4-methyl-6-quinolyl)-2-(3-methylpyrrolidin-1-yl)-5-(morpholinomethyl)pyridine-3-carboxamide,
N-(2-hydroxy-4-methyl-6-quinolyl)-2-(2-methylpyrrolidin-1-yl)-5-(morpholinomethyl)pyridine-3-carboxamide,
N-(2-hydroxy-4-methyl-6-quinolyl)-2-(3-hydroxypyrrolidin-1-yl)-5-(morpholinomethyl)pyridine-3-carboxamide,
N-(2-hydroxy-4-methyl-6-quinolyl)-2-(3-methoxypyrrolidin-1-yl)-5-(morpholinomethyl)pyridine-3-carboxamide,
2-(3-fluoro-3-methyl-pyrrolidin-1-yl)-N-(2-hydroxy-4-methyl-6-quinolyl)-5-(morpholinomethyl)pyridine-3-carboxamide,
2-(3-carbamoylpyrrolidin-1-yl)-N-(2-hydroxy-4-methyl-6-quinolyl)-5-(morpholinomethyl)pyridine-3-carboxamide,
N-(2-hydroxy-4-methyl-6-quinolyl)-2-[3-(methoxymethyl)pyrrolidin-1-yl]-5-(morpholinomethyl)pyridine-3-carboxamide,
N-(2-hydroxy-4-methyl-6-quinolyl)-2-(2-isobutylpyrrolidin-1-yl)-5-(morpholinomethyl)pyridine-3-carboxamide,
N-(2-hydroxy-4-methyl-6-quinolyl)-2-(3-isobutylpyrrolidin-1-yl)-5-(morpholinomethyl)pyridine-3-carboxamide,
2-[2-(dimethylaminomethyl)pyrrolidin-1-yl]-N-(2-hydroxy-4-methyl-6-quinolyl)-5-(morpholinomethyl)pyridine-3-carboxamide,
2-[1-[3-[(2-hydroxy-4-methyl-6-quinolyl)carbamoyl]-5-(morpholinomethyl)-2-pyridyl]pyrrolidin-2-yl]acetic acid,
2-(2-carbamoyl-4-hydroxy-pyrrolidin-1-yl)-N-(2-hydroxy-4-methyl-6-quinolyl)-5-(morpholinomethyl)pyridine-3-carboxamide,
N-(2-hydroxy-4-methyl-6-quinolyl)-5-(morpholinomethyl)-2-[2-(1H-pyrazol-3-yl)pyrrolidin-1-yl]pyridine-3-carboxamide,
N-(2-hydroxy-4-methyl-6-quinolyl)-5-(morpholinomethyl)-2-[2-(1H-tetrazol-5-yl)pyrrolidin-1-yl]pyridine-3-carboxamide,
N-(2-hydroxy-4-methyl-6-quinolyl)-5-(morpholinomethyl)-2-(3-pyrrolidin-1-ylpyrrolidin-1-yl)pyridine-3-carboxamide,
N-(2-hydroxy-4-methyl-6-quinolyl)-2-(4-methyl-3,3a,5,6,7,7a-hexahydro-2H-pyrrolo[3,2-b]pyridin-1-yl)-5-(morpholinomethyl)pyridine-3-carboxamide,
2-[2-(dimethylcarbamoyl)pyrrolidin-1-yl]-N-(2-hydroxy-4-methyl-6-quinolyl)-5-(morpholinomethyl)pyridine-3-carboxamide,
N-(2-hydroxy-4-methyl-6-quinolyl)-2-(4-methyl-2,3,4a,5,7,7a-hexahydropyrrolo[3,4-b][1,4]oxazin-6-yl)-5-(morpholinomethyl)pyridine-3-carboxamide,
N-(2-hydroxy-4-methyl-6-quinolyl)-5-(morpholinomethyl)-2-[3-(4-pyridyl)pyrrolidin-1-yl]pyridine-3-carboxamide,
N-(2-hydroxy-4-methyl-6-quinolyl)-2-[2-(imidazol-1-ylmethyl)pyrrolidin-1-yl]-5-(morpholinomethyl)pyridine-3-carboxamide,
N-(2-hydroxy-4-methyl-6-quinolyl)-5-(morpholinomethyl)-2-[2-(pyrazol-1-ylmethyl)pyrrolidin-1-yl]pyridine-3-carboxamide,
2-[2-(hydroxymethyl)morpholin-4-yl]-N-(2-hydroxy-4-methyl-6-quinolyl)-5-(morpholinomethyl)pyridine-3-carboxamide,
2-[2-(hydroxymethyl)-5-methyl-morpholin-4-yl]-N-(2-hydroxy-4-methyl-6-quinolyl)-5-(morpholinomethyl)pyridine-3-carboxamide,
N-(2-hydroxy-4-methyl-6-quinolyl)-2-[2-(methoxymethyl)morpholin-4-yl]-5-(morpholinomethyl)pyridine-3-carboxamide,
2-[2-(dimethylaminomethyl)morpholin-4-yl]-N-(2-hydroxy-4-methyl-6-quinolyl)-5-(morpholinomethyl)pyridine-3-carboxamide,
2-[3-(hydroxymethyl)pyrrolidin-1-yl]-N-(2-hydroxy-4-methyl-6-quinolyl)-5-(morpholinomethyl)pyridine-3-carboxamide,
5-(dimethylsulfamoyl)-N-(2-hydroxy-4-methyl-6-quinolyl)-2-[methyl-(2-oxopyrrolidin-3-yl)amino]benzamide,
1-[4-(dimethylsulfamoyl)-2-[(2-hydroxy-4-methyl-6-quinolyl)carbamoyl]phenyl]pyrrolidine-3-carboxylic acid,
5-(dimethylsulfamoyl)-N-(2-hydroxy-4-methyl-6-quinolyl)-2-(7-oxo-2,3,3a,4,5,7a-hexahydropyrano[3,4-b]pyrrol-1-yl)benzamide,
5-(dimethylsulfamoyl)-2-[2-(hydroxymethyl)pyrrolidin-1-yl]-N-(2-hydroxy-4-methyl-6-quinolyl)benzamide,
1-[4-(dimethylsulfamoyl)-2-[(2-hydroxy-4-methyl-6-quinolyl)carbamoyl]phenyl]pyrrolidine-2-carboxamide,
(2S)-1-[4-(dimethylsulfamoyl)-2-[(2-hydroxy-4-methyl-6-quinolyl)carbamoyl]phenyl]pyrrolidine-2-carboxylic acid,
5-(dimethylsulfamoyl)-N-(2-hydroxy-4-methyl-6-quinolyl)-2-(8-oxa-4-azaspiro[4.5]decan-4-yl)benzamide,
2-(2,5-dimethyl-4-oxo-1-piperidyl)-5-(dimethylsulfamoyl)-N-(2-hydroxy-4-methyl-6-quinolyl)benzamide,
5-(dimethylsulfamoyl)-N-(2-hydroxy-4-methyl-6-quinolyl)-2-[2-(2H-tetrazol-5-yl)-1-piperidyl]benzamide,
5-(dimethylsulfamoyl)-N-(2-hydroxy-4-methyl-6-quinolyl)-2-[2-(2-methoxyphenyl)-1-piperidyl]benzamide,
1-[4-(dimethylsulfamoyl)-2-[(2-hydroxy-4-methyl-6-quinolyl)carbamoyl]phenyl]-6-methyl-piperidine-3-carboxamide,
2-(2,5-dimethylmorpholin-4-yl)-5-(dimethylsulfamoyl)-N-(2-hydroxy-4-methyl-6-quinolyl)benzamide,
5-[(2-furylmethylamino)methyl]-N-(2-hydroxy-4-methyl-6-quinolyl)-2-pyrrolidin-1-yl-benzamide,
N-(2-hydroxy-4-methyl-6-quinolyl)-5-[(isobutylamino)methyl]-2-pyrrolidin-1-yl-benzamide,
5-[(cyclopropylamino)methyl]-N-(2-hydroxy-4-methyl-6-quinolyl)-2-pyrrolidin-1-yl-benzamide,
N-(2-hydroxy-4-methyl-6-quinolyl)-5-[(3-pyridylmethylamino)methyl]-2-pyrrolidin-1-yl-benzamide,
5-[(cyanomethylamino)methyl]-N-(2-hydroxy-4-methyl-6-quinolyl)-2-pyrrolidin-1-yl-benzamide, N-(2-hydroxy-4-methyl-6-quinolyl)-5-[[isopropyl(methyl)amino]methyl]-2-pyrrolidin-1-yl-benzamide,
N-(2-hydroxy-4-methyl-6-quinolyl)-2-pyrrolidin-1-yl-5-[(2,2,2-trifluoroethylamino)methyl]benzamide,
N-(2-hydroxy-4-methyl-6-quinolyl)-5-[(3-methoxy-1-piperidyl)methyl]-2-pyrrolidin-1-yl-benzamide,
5-[[3-(dimethylamino)azetidin-1-yl]methyl]-N-(2-hydroxy-4-methyl-6-quinolyl)-2-pyrrolidin-1-yl-benzamide,
N-(2-hydroxy-4-methyl-6-quinolyl)-5-[(1H-imidazol-2-ylmethylamino)methyl]-2-pyrrolidin-1-yl-benzamide,
N-(2-hydroxy-4-methyl-6-quinolyl)-2-pyrrolidin-1-yl-5-[[1-(1H-tetrazol-5-yl)ethylamino]methyl]benzamide,
5-(dimethylaminomethyl)-N-(2-hydroxy-4-methyl-6-quinolyl)-2-pyrrolidin-1-yl-benzamide,
N-(2-hydroxy-4-methyl-6-quinolyl)-5-[[(2-methoxy-4-pyridyl)methylamino]methyl]-2-pyrrolidin-1-yl-benzamide,
5-[(3-cyano-1-piperidyl)methyl]-N-(2-hydroxy-4-methyl-6-quinolyl)-2-pyrrolidin-1-yl-benzamide,
1-[[3-[(2-hydroxy-4-methyl-6-quinolyl)carbamoyl]-4-pyrrolidin-1-yl-phenyl]methyl]-N-methyl-pyrrolidine-3-carboxamide,
N-(2-hydroxy-4-methyl-6-quinolyl)-5-[[1-(1H-imidazol-2-yl)ethylamino]methyl]-2-pyrrolidin-1-yl-benzamide,
N-(2-hydroxy-4-methyl-6-quinolyl)-2-pyrrolidin-1-yl-5-[(tetrahydrofuran-3-ylamino)methyl]benzamide,
N-(2-hydroxy-4-methyl-6-quinolyl)-5-[(isoxazol-4-ylamino)methyl]-2-pyrrolidin-1-yl-benzamide,
5-[(3-fluoropyrrolidin-1-yl)methyl]-N-(2-hydroxy-4-methyl-6-quinolyl)-2-pyrrolidin-1-yl-benzamide,
N-(2-hydroxy-4-methyl-6-quinolyl)-5-[[(1-methylpyrazol-4-yl)amino]methyl]-2-pyrrolidin-1-yl-benzamide,
N-(2-hydroxy-4-methyl-6-quinolyl)-5-(1,4-oxazepan-4-ylmethyl)-2-pyrrolidin-1-yl-benzamide,
2-(3-fluoropyrrolidin-1-yl)-N-(2-hydroxy-4-methyl-6-quinolyl)-5-(morpholinomethyl)pyridine-3-carboxamide,
2-[2-(hydroxymethyl)pyrrolidin-1-yl]-N-(2-hydroxy-4-methyl-6-quinolyl)-5-(morpholinomethyl)pyridine-3-carboxamide,
2-(2-carbamoylpyrrolidin-1-yl)-N-(2-hydroxy-4-methyl-6-quinolyl)-5-(morpholinomethyl)pyridine-3-carboxamide,
2-[3-(dimethylamino)pyrrolidin-1-yl]-N-(2-hydroxy-4-methyl-6-quinolyl)-5-(morpholinomethyl)pyridine-3-carboxamide,
(2S)-1-[3-[(2-hydroxy-4-methyl-6-quinolyl)carbamoyl]-5-(morpholinomethyl)-2-pyridyl]pyrrolidine-2-carboxylic acid,
(2R)-1-[3-[(2-hydroxy-4-methyl-6-quinolyl)carbamoyl]-5-(morpholinomethyl)-2-pyridyl]pyrrolidine-2-carboxylic acid,
2-[(2 S)-2-(difluoromethyl)pyrrolidin-1-yl]-N-(2-hydroxy-4-methyl-6-quinolyl)-5-(morpholinomethyl)pyridine-3-carboxamide,
1-[3-[(2-hydroxy-4-methyl-6-quinolyl)carbamoyl]-5-(morpholinomethyl)-2-pyridyl]pyrrolidine-3-carboxylic acid,
N-(2-hydroxy-4-methyl-6-quinolyl)-2-[2-(1H-imidazol-2-yl)pyrrolidin-1-yl]-5-(morpholinomethyl)pyridine-3-carboxamide,
N-(2-hydroxy-4-methyl-6-quinolyl)-5-(morpholinomethyl)-2-(8-oxa-4-azaspiro[4.5]decan-4-yl)pyridine-3-carboxamide,
N-(2-hydroxy-4-methyl-6-quinolyl)-5-(morpholinomethyl)-2-[2-(4-pyridyl)pyrrolidin-1-yl]pyridine-3-carboxamide,
N-(2-hydroxy-4-methyl-6-quinolyl)-5-(morpholinomethyl)-2-[2-(3-pyridyl)pyrrolidin-1-yl]pyridine-3-carboxamide,
N-(2-hydroxy-4-methyl-6-quinolyl)-2-morpholino-5-(morpholinomethyl)pyridine-3-carboxamide,
N-(2-hydroxy-4-methyl-6-quinolyl)-5-(morpholinomethyl)-2-(3-oxopiperazin-1-yl)pyridine-3-carboxamide,
N-(2-hydroxy-4-methyl-6-quinolyl)-2-(4-methylpiperazin-1-yl)-5-(morpholinomethyl)pyridine-3-carboxamide,
2-(2,5-dimethylmorpholin-4-yl)-N-(2-hydroxy-4-methyl-6-quinolyl)-5-(morpholinomethyl)pyridine-3-carboxamide,
2-[3-(hydroxymethyl)morpholin-4-yl]-N-(2-hydroxy-4-methyl-6-quinolyl)-5-(morpholinomethyl)pyridine-3-carboxamide,
2-(2-cyano-4-methyl-piperazin-1-yl)-N-(2-hydroxy-4-methyl-6-quinolyl)-5-(morpholinomethyl)pyridine-3-carboxamide,
4-[3-[(2-hydroxy-4-methyl-6-quinolyl)carbamoyl]-5-(morpholinomethyl)-2-pyridyl]morpholine-3-carboxamide,
4-[3-[(2-hydroxy-4-methyl-6-quinolyl)carbamoyl]-5-(morpholinomethyl)-2-pyridyl]morpholine-2-carboxamide,
4-[3-[(2-hydroxy-4-methyl-6-quinolyl)carbamoyl]-5-(morpholinomethyl)-2-pyridyl]morpholine-3-carboxylic acid,
2-(3,4a,5,7,8,8a-hexahydro-2H-pyrano[4,3-b][1,4]oxazin-4-yl)-N-(2-hydroxy-4-methyl-6-quinolyl)-5-(morpholinomethyl)pyridine-3-carboxamide,
N-(2-hydroxy-4-methyl-6-quinolyl)-2-[2-(1-methylpyrazol-4-yl)morpholin-4-yl]-5-(morpholinomethyl)pyridine-3-carboxamide,
N-(2-hydroxy-4-methyl-6-quinolyl)-2-(3-methyl-4-oxo-imidazolidin-1-yl)-5-(morpholinomethyl)pyridine-3-carboxamide,
N-(2-hydroxy-4-methyl-6-quinolyl)-2-[methyl(tetrahydrofuran-3-yl)amino]-5-(morpholinomethyl)pyridine-3-carboxamide,
2-[(1-cyanocyclobutyl)-methyl-amino]-N-(2-hydroxy-4-methyl-6-quinolyl)-5-(morpholinomethyl)pyridine-3-carboxamide,
N-(2-hydroxy-4-methyl-6-quinolyl)-2-[methyl(1H-pyrazol-4-ylmethyl)amino]-5-(morpholinomethyl)pyridine-3-carboxamide,
N-(2-hydroxy-4-methyl-6-quinolyl)-2-[methyl(1,2,4-oxadiazol-5-ylmethyl)amino]-5-(morpholinomethyl)pyridine-3-carboxamide,
N-(2-hydroxy-4-methyl-6-quinolyl)-2-[methyl-(2-oxopyrrolidin-3-yl)amino]-5-(morpholinomethyl)pyridine-3-carboxamide,
N-(2-hydroxy-4-methyl-6-quinolyl)-2-[methyl(tetrahydrofuran-2-ylmethyl)amino]-5-(morpholinomethyl)pyridine-3-carboxamide,
N-(2-hydroxy-4-methyl-6-quinolyl)-2-(isoxazol-4-ylamino)-5-(morpholinomethyl)pyridine-3-carboxamide,
N-(2-hydroxy-4-methyl-6-quinolyl)-2-(1H-imidazol-2-ylmethylamino)-5-(morpholinomethyl)pyridine-3-carboxamide, N-(2-hydroxy-4-methyl-6-quinolyl)-5-(morpholinomethyl)-2-[(5-oxopyrrolidin-3-yl)amino]pyridine-3-carboxamide, N-(2-hydroxy-4-methyl-6-quinolyl)-5-(morpholinomethyl)-2-[(5-oxopyrrolidin-2-yl)methylamino]pyridine-3-carboxamide, 2-[[2-(hydroxymethyl)cyclopentyl]amino]-N-(2-hydroxy-4-methyl-6-quinolyl)-5-(morpholinomethyl)pyridine-3-carboxamide, and 2-[(2-hydroxycyclopentyl)methylamino]-N-(2-hydroxy-4-methyl-6-quinolyl)-5-(morpholinomethyl)pyridine-3-carboxamide.

34. A pharmaceutical composition comprising a compound of claim 1 and at least one pharmaceutically acceptable excipient.

35. A method for treating a disease or condition selected from the group consisting of inflammatory diseases, disorders or conditions; diseases, disorders or conditions associated with lipid metabolism, fibrotic disorders or conditions, viral infections, cancer, and obesity, the method comprising administering a therapeutically effective amount of a compound of claim 1 to a patient in need thereof.

36. The method of claim 35, wherein the disease or condition is selected from the group consisting of rheumatoid arthritis, osteoarthritis, acute gout, psoriasis, psoriatic arthritis, systemic lupus erythematosus, multiple sclerosis, inflammatory bowel disease, inflammatory bowel syndrome, Crohn's disease, ulcerative colitis, colitis, asthma, chronic obstructive airways disease, pneumonitis, myocarditis, pericarditis, myositis, eczema, dermatitis, atopic dermatitis, allergy, ankylosing spondylitis, lupus erythematosus, Hashimoto's disease, pancreatitis, autoimmune ocular disease, Sjögren's disease, optic neuritis, neuromyelitis optica, Myasthenia Gravis, Guillain Barre syndrome, Graves' disease, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing, cholangitis, hypophysitis, thyroiditis, Addison's disease, type I diabetes, acute rejection of transplanted organs;

giant cell arteritis, nephritis vasculitis with organ involvement Polyarteritis nodosa, Behcet's disease, Wegener's granulomatosis, Kawasaki disease, Takayasu's Arteritis, acute rejection of transplanted organs;

sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, and malaria;

myocardial infarction, cerebrovascular ischaemia, acute coronary syndromes, renal reperfusion injury, diseases or conditions associated with organ transplantation, coronary artery bypass grafting or cardio-pulmonary bypass procedures; pulmonary, renal, hepatic, gastrointestinal or peripheral limb embolism;

idiopathic pulmonary fibrosis, renal fibrosis, post-operative stricture, keloid formation, scleroderma, cardiac fibrosis;

viral infections associated with herpes virus, human papilloma virus, human immunodeficiency virus (HIV), adenovirus, or poxvirus;

adenocarcinoma, acute lymphoblastic leukemia, acute myelogenous leukemia, adult T-cell leukemia/lymphoma, bladder cancer, blastoma, bone cancer, breast cancer, brain cancer, burkitts lymphoma, carcinoma, myeloid sarcoma, cervical cancer, chronic lymphocytic leukemia, chronic myelogenous leukemia, colorectal cancer, diffuse large B-cell lymphoma, endometrial cancer, esophageal cancer, follicular lymphoma, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, melanoma, mesothelioma, multiple myeloma, ocular cancer, optic nerve tumor, oral cancer, ovarian cancer, pituitary tumors, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor.

37. A method of modulating the activity of at least one bromodomain comprising contacting at least one bromodomain with a compound of claim 1.

38. The compound of claim 1, wherein $R_{11b}$ is hydrogen.

* * * * *

UNITED STATES PATENT AND TRADEMARK OFFICE
CERTIFICATE OF CORRECTION

PATENT NO. : 10,752,640 B2
APPLICATION NO. : 15/501058
DATED : August 25, 2020
INVENTOR(S) : Jimmi Gerner Seitzberg et al.

Page 1 of 1

It is certified that error appears in the above-identified patent and that said Letters Patent is hereby corrected as shown below:

In the Claims

Claim 11, Column 568, Line 43, replace figure for formula (V) with

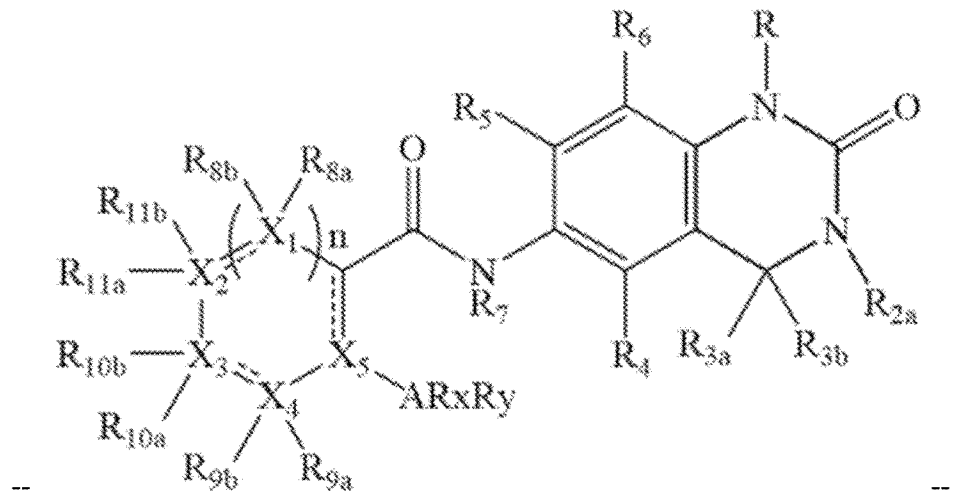

-- --

Signed and Sealed this
Eighteenth Day of April, 2023

Katherine Kelly Vidal
*Director of the United States Patent and Trademark Office*